United States Patent
Beigelman et al.

(10) Patent No.: US 11,549,110 B2
(45) Date of Patent: *Jan. 10, 2023

(54) MODIFIED SHORT INTERFERING NUCLEIC ACID (SINA) MOLECULES AND USES THEREOF

(71) Applicant: Aligos Therapeutics, Inc., South San Francisco, CA (US)

(72) Inventors: Leonid Beigelman, San Mateo, CA (US); Vivek Kumar Rajwanshi, Cupertino, CA (US); Markus Hossbach, Kulmbach (DE); Rajendra K. Pandey, Foster City, CA (US); Jin Hong, Pacifica, CA (US); Laxman Eltepu, San Ramon, CA (US); Saul Martinez Montero, San Bruno, CA (US); N. Tilani S. De Costa, South San Francisco, CA (US)

(73) Assignee: Aligos Therapeutics, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/672,268

(22) Filed: Feb. 15, 2022

(65) Prior Publication Data

US 2022/0177888 A1 Jun. 9, 2022

Related U.S. Application Data

(63) Continuation of application No. 17/194,079, filed on Mar. 5, 2021.

(60) Provisional application No. 63/109,196, filed on Nov. 3, 2020, provisional application No. 62/986,150, filed on Mar. 6, 2020.

(51) Int. Cl.
| | |
|---|---|
| *C12N 15/113* | (2010.01) |
| *A61P 31/20* | (2006.01) |
| *A61K 31/713* | (2006.01) |
| *A61K 45/06* | (2006.01) |

(52) U.S. Cl.
CPC ........ *C12N 15/1131* (2013.01); *A61K 31/713* (2013.01); *A61K 45/06* (2013.01); *A61P 31/20* (2018.01); *C12N 2310/14* (2013.01); *C12N 2310/315* (2013.01); *C12N 2310/321* (2013.01); *C12N 2310/322* (2013.01); *C12N 2310/3231* (2013.01); *C12N 2310/351* (2013.01); *C12N 2320/31* (2013.01)

(58) Field of Classification Search
CPC ............ C12N 15/1131; C12N 2310/14; C12N 2310/315; C12N 2310/321; C12N 2310/322; C12N 2310/3231; C12N 2310/351; C12N 2320/31; A61K 31/713; A61K 45/06; A61P 31/20
See application file for complete search history.

(56) References Cited

U.S. PATENT DOCUMENTS

2017/0035796 A1* 2/2017 Wooddell .................. A61P 1/16

FOREIGN PATENT DOCUMENTS

| CA | 3083968 A1 | 6/2019 |
|---|---|---|
| EP | 3 109 254 A1 | 12/2016 |
| WO | WO-2009/002944 A1 | 12/2008 |
| WO | WO-2013/003520 A1 | 1/2013 |
| WO | WO-2013/074974 A2 | 5/2013 |
| WO | WO-2018/185241 A1 | 10/2018 |
| WO | WO-2019/217397 A2 | 11/2019 |

OTHER PUBLICATIONS

Allerson et al., "Fully 2'-Modified Oligonucleotide Duplexes with Improved in Vitro Potency and Stability Compared to Unmodified Small Interfering RNA", Journal of Medicinal Chemistry, 2005, pp. 901-904, vol. 48, 2005 American Chemical Society.
Arbuthnot, Patrick, "Harnessing RNA Interference for the Treatment of Viral Infections," Drug News & Perspectives, 2010, 23(6):341-350.
Berke et al., "Capsid Assembly Modulators Have a Dual Mechanism of Action in Primary Human Hepatocytes Infected with Hepatitis B Virus," Antimicrobial Agents and Chemotherapy, Jun. 5, 2017, 61:e00560-17, 14 pages.
Boudreau et al., "RNAi Therapy for Neurodegenerative Diseases," Current Topics in Developmental Biology, 2006, 75:73-92.
Chalbatani et al., "Small interfering RNAs (siRNAs) in cancer therapy: a nano-based approach," International Journal of Nanomedicine, 2019, 14:3111-3128.
Chernikov et al., "Current Development of siRNA Bioconjugates: From Research to the Clinic," Frontiers in Pharmacology, Reviews, Apr. 26, 2019, 10(444):1-25.
Elka Yam et al., "siRNA carrying an (E)-vinylphosphonate moiety at the 5' end of the guide strand augments gene silencing by enhanced binding to human Argonaute-2", Nucleic Acids Research, 2017, pp. 3528-3536, vol. 45, No. 6, Oxford University Press.
GenBank Accession No. NM_000116.5, Jun. 26, 2021.
GenBank Accession No. NM_001253891.1, Jun. 9, 2020.
GenBank Accession No. NM_014495.4, Sep. 12, 2021.
International Search Report and Written Opinion in PCT/US2021/021199 dated Aug. 30, 2021.
Invitation to Pay Additional Fees and Partial International Search Report in PCT/US2021/021199 dated Jun. 22, 2021.

(Continued)

*Primary Examiner* — J. E. Angell
(74) *Attorney, Agent, or Firm* — Foley & Lardner LLP

(57) ABSTRACT

Disclosed herein are short interfering nucleic acid (siNA) molecules comprising modified nucleotides and uses thereof. The siNA molecules may be double stranded and comprise modified nucleotides selected from 2'-O-methyl nucleotides and 2'-fluoro nucleotides. Further disclosed herein are siNA molecules comprising (a) a phosphorylation blocker, conjugated moiety, or 5'-stabilized end cap; and (b) a short interfering nucleic acid (siNA).

30 Claims, 20 Drawing Sheets

Specification includes a Sequence Listing.

(56) References Cited

OTHER PUBLICATIONS

Jahn-Hofmann et al., "Efficient Solid Phase Synthesis of Cleavable Oligodeoxynucleotides Based on a Novel Strategy for the Synthesis of 5'-S-(4,4'-Dimethyoxytrityl)-2'-deoxy-5'-thionucleoside Phosphoramidites," Helvetica Chimica Acta, 2004, 87:2812-2828.

Klumpp et al,. "Efficacy of NVR 3-778, Alone and in Combination with Pegylated Interferon, vs Entecavir in uPA/SCID Mice with Humanized Livers and HBV infection," Gastroenterology, 2018, 154:652-662.

Matulic-Adamic et al., "Synthesis of Pyridinone Ribonucleoside 3'-O-Phosphoramidites and their Incorporation into Oligoribonucleotides," Bioorganic & Medicinal Chemistry Letters, 1996, 6(4):373-378.

Parmar et al., "Facile Synthesis, Geometry, and 2'-Substituent-Dependent in Vivo Activity of 5'-(E)- and 5'-(Z)-Vinylphosphonate-Modified siRNA Conjugates," J. Med. Chem., 2018, 61:734-744.

Prakash et al., "Comprehensive Structure-Activity Relationship of Triantennary N-Acetylgalactosamine Conjugated Antisense Oligonucleotides for Targeted Delivery to Hepatocytes", Journal of Medicinal Chemistry, 2016, pp. 2718-2733, vol. 59, 2016 American Chemical Society.

Quaedflieg et al., "Synthesis and Conformational Analysis of Phosphate-Methylated RNA Dinucleotides," J. Org. Chem., 1991, 56:5846-5859.

Rondinone, Christina M., "Therapeutic potential of RNAi in metabolic diseases," BioTechniques, Apr. 2006, 40:S31-S36.

Stout et al., "The Synthesis of Some Quinazoline Nucleosides," J. Org. Chem., Mar. 1968, 33(3):1219-1225.

Sung et al., "Genome-wide survey of recurrent HBV integration in hepatocellular carcinoma," Nature Genetics, Letters, Jul. 2012, 44(7):765-770.

Taniguchi et al., "Synthesis of 1'-phenyl-2'-OMe ribose analogues connecting the thymine base at the 1' position through a flexible linker for the formation of a stable anti-parallel triplex DNA," Tetrahedron, 2013, 69:600-606.

Wang et al., "Synthesis and Anti-Influenza Activity of Pyridine, Pyridazine, and Pyrimidine C-Nucleosides as Favipiravir (T-705) Analogues," J. Med. Chem., Apr. 27, 2016, 59:4611-4624.

* cited by examiner

- 2'-OMe
- 2'-F
- PS

Change in Serum HBsAg

Change in Serum HBsAg

Synergy Analysis
(95% confidence interval)

AAV-HBV Mouse Model Serum HBsAg

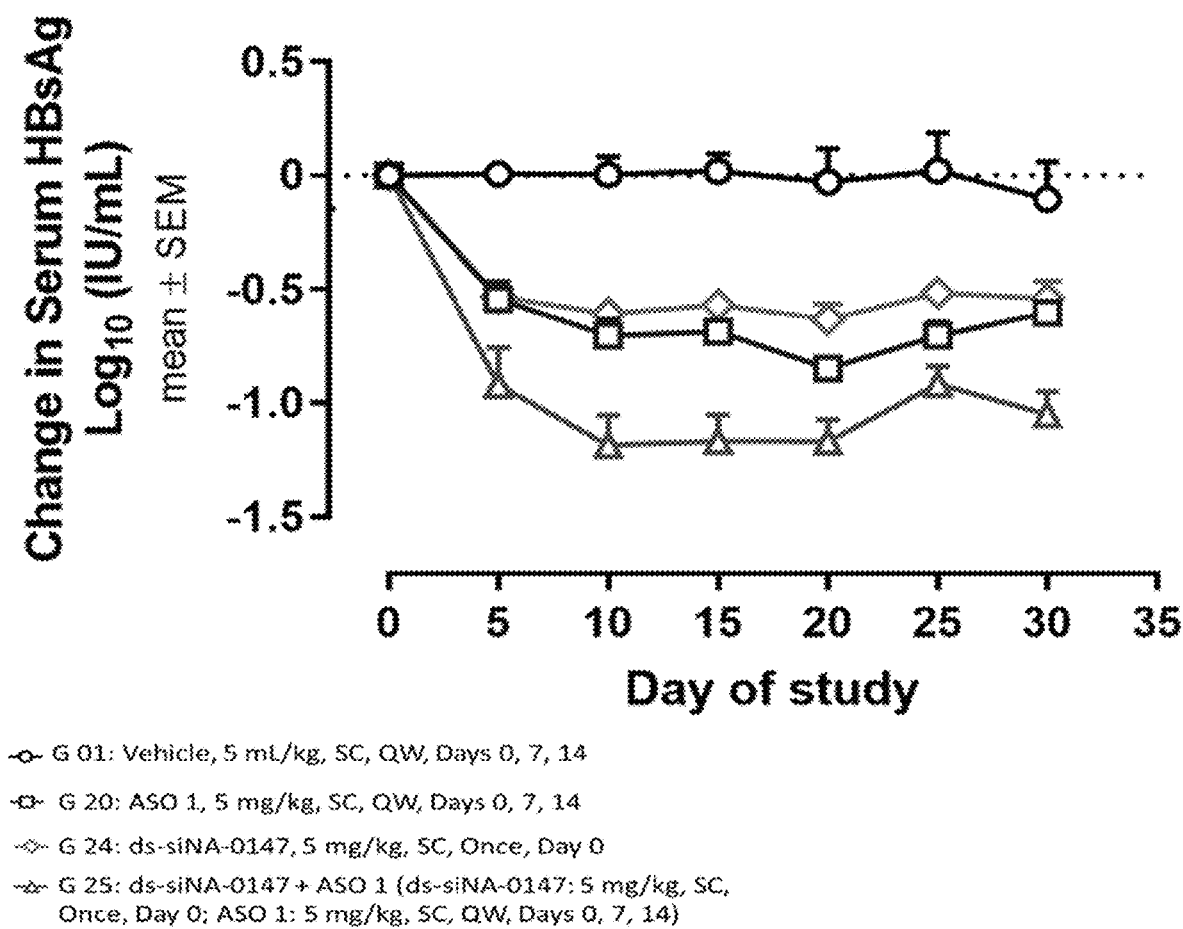

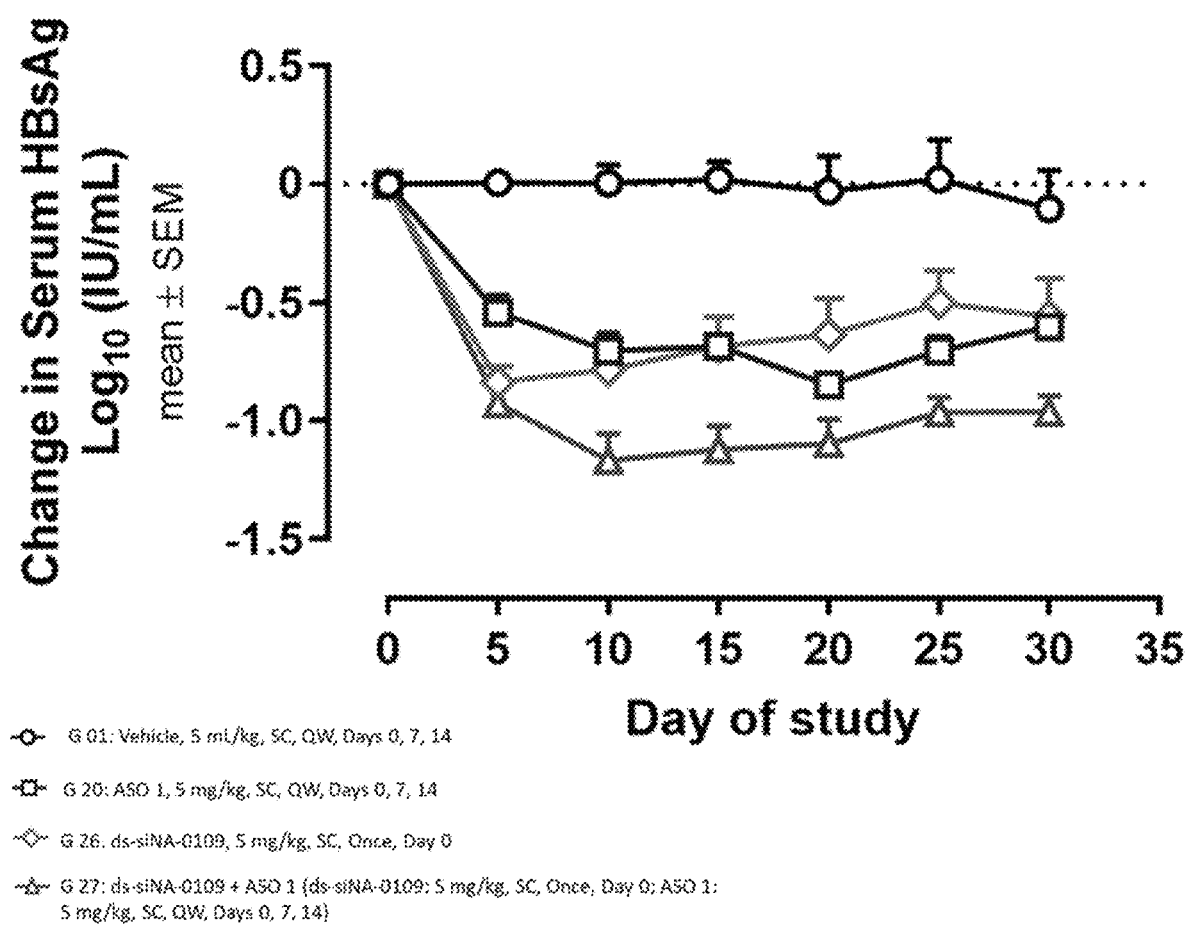

MODIFIED SHORT INTERFERING NUCLEIC ACID (SINA) MOLECULES AND USES THEREOF

CROSS-REFERENCE TO RELATED APPLICATIONS

This application is a Continuation of U.S. application Ser. No. 17/194,079, filed Mar. 5, 2021, which claims priority to U.S. Provisional Application No. 62/986,150, filed Mar. 6, 2020, and U.S. Provisional Application No. 63/109,196, filed Nov. 3, 2020, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Feb. 11, 2022, is named 122400-0259_SL.txt and is 165,787 bytes in size.

FIELD OF THE INVENTION

Described are short interfering nucleic acid (siNA) molecules comprising modified nucleotides, compositions, and uses thereof.

BACKGROUND OF THE INVENTION

RNA interference (RNAi) is a biological response to double-stranded RNA that mediates resistance to both endogenous parasitic and exogenous pathogenic nucleic acids, and regulates the expression of protein-coding genes. The short interfering nucleic acids (siNA), such as siRNA, have been developed for RNAi therapy to treat a variety of diseases. For instance, RNAi therapy has been proposed for the treatment of metabolic diseases, neurodegenerative diseases, cancer, and pathogenic infections (See e.g., Rondindone, *Biotechniques*, 2018, 40 (4S), doi.org/10.2144/000112163, Boudreau and Davidson, *Curr Top Dev Biol*, 2006, 75:73-92, Chalbatani et al., *Int J Nanomedicine*, 2019, 14:3111-3128, Arbuthnot, *Drug News Perspect*, 2010, 23(6):341-50, and Chernikov et. al., *Front. Pharmacol.*, 2019, doi.org/10.3389/fphar.2019.00444, each of which are incorporated by reference in their entirety). However, major limitations of RNAi therapy are the ability to effectively deliver siRNA to target cells and the degradation of the siRNA.

The present disclosure improves the delivery and stability of siNA molecules by providing siNA molecules comprising modified nucleotides. The siNA molecules of the present disclosure provide optimized combinations and numbers of modified nucleotides, nucleotide lengths, design (e.g., blunt ends or overhangs, internucleoside linkages, conjugates), and modification patterns for improving the delivery and stability of siNA molecules.

SUMMARY OF THE INVENTION

Disclosed herein is a short interfering nucleic acid (siNA) molecule comprising: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 3, 5, 7, 8, 9, 10, 11, 12, 14, 17, and/or 19 from the 5' end of the first nucleotide sequence is a 2'-fluoro nucleotide; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide.

Disclosed herein is a short interfering nucleic acid (siNA) molecule comprising: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 2, 5, 6, 8, 10, 14, 16, 17, and/or 18 from the 5' end of the second nucleotide sequence is a 2'-fluoro nucleotide.

In some embodiments, the first nucleotide sequence comprises 16, 17, 18, 19, 20, 21, 22, 23, or more modified nucleotides independently selected from a 2'-O-methyl nucleotide and a 2'-fluoro nucleotide. In some embodiments, 70%, 75%, 80%, 85%, 90%, 95% or 100% of the nucleotides in the first nucleotide sequence are modified nucleotides independently selected from a 2'-O-methyl nucleotide and a 2'-fluoro nucleotide. In some embodiments, between 2 to 15 modified nucleotides of the first nucleotide sequence are 2'-fluoro nucleotides. In some embodiments, between 2 to 10 modified nucleotides of the first nucleotide sequence are 2'-fluoro nucleotides. In some embodiments, between 2 to 6 modified nucleotides of the first nucleotide sequence are 2'-fluoro nucleotides. In some embodiments, at least 2, 3, 4, 5, or 6 modified nucleotides of the first nucleotide sequence are 2'-fluoro nucleotides. In some embodiments, less than or equal to 10, 9, 8, 7, 6, 5, 4, 3, or 2 modified nucleotides of the first nucleotide sequence are 2'-fluoro nucleotides. In some embodiments, between about 2 to 25 modified nucleotides of the first nucleotide sequence are 2'-O-methyl nucleotides. In some embodiments, between about 2 to 20 modified nucleotides of the first nucleotide sequence are 2'-O-methyl nucleotides. In some embodiments, between about 5 to 25 modified nucleotides of the first nucleotide sequence are 2'-O-methyl nucleotides. In some embodiments, between about 10 to 25 modified nucleotides of the first nucleotide sequence are 2'-O-methyl nucleotides. In some embodiments, between about 12 to 25 modified nucleotides of the first nucleotide sequence are 2'-O-methyl nucleotides. In some embodiments, at least 10, 11, 12, 13, 14, 15, 16, 17, 18, 19, 20, 21, or 22 modified nucleotides of the first nucleotide sequence are 2'-O-methyl nucleotides. In some embodiments, less than or equal to 25, 24, 23, 22, 21, 20, 19, 18, 17, 16, 15, 14, 13, 12, 11, 10, 9, 8, 7, 6, 5, 4, 3, or 2 modified nucleotides of the first nucleotide sequence are 2'-O-methyl nucleotides.

In some embodiments, the second nucleotide sequence comprises 16, 17, 18, 19, 20, 21, 22, 23, or more modified nucleotides independently selected from a 2'-O-methyl nucleotide and a 2'-fluoro nucleotide. In some embodiments, 70%, 75%, 80%, 85%, 90%, 95% or 100% of the nucleotides in the second nucleotide sequence are modified nucleotides independently selected from a 2'-O-methyl nucleotide and a 2'-fluoro nucleotide. In some embodiments, between 2 to 15 modified nucleotides of the second nucleotide sequence are 2'-fluoro nucleotides. In some embodiments, between 2 to 10 modified nucleotides of the second nucleotide sequence are 2'-fluoro nucleotides. In some embodiments, between 2 to 6 modified nucleotides of the second nucleotide sequence are 2'-fluoro nucleotides. In some embodiments, at least 2, 3, 4, 5, or 6 modified nucleotides of the second nucleotide sequence are 2'-fluoro nucleotides. In some embodiments, less than or equal to 10, 9, 8, 7, 6, 5, 4, 3, or 2 modified nucleotides of the second nucleotide sequence are 2'-fluoro nucleotides. In some embodiments, between about 2 to 25 modified nucleotides of the second nucleotide sequence are 2'-O-methyl nucleotides. In some embodiments, between about 2 to 20 modified nucleotides of the second nucleotide sequence are 2'-O-methyl nucleotides. In some embodiments, between about 5 to 25 modified nucleotides of the second nucleotide sequence are 2'-O-methyl nucleotides. In some embodiments, between about 10 to 25 modified nucleotides of the second nucleotide sequence are 2'-O-methyl nucleotides. In some embodiments, between about 12 to 25 modified nucleotides of the second nucleotide sequence are 2'-O-methyl nucleotides. In some embodiments, at least 10, 11, 12, 13, 14, 15, 16, 17, 18, 19, 20, 21, or 22 modified nucleotides of the second nucleotide sequence are 2'-O-methyl nucleotides. In some embodiments, less than or equal to 25, 24, 23, 22, 21, 20, 19, 18, 17, 16, 15, 14, 13, 12, 11, 10, 9, 8, 7, 6, 5, 4, 3, or 2 modified nucleotides of the second nucleotide sequence are 2'-O-methyl nucleotides.

Disclosed herein is a short interfering nucleic acid (siNA) molecule comprising: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence: (i) is 15 to 30 nucleotides in length; (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (iii) comprises 1 or more phosphorothioate internucleoside linkage; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence: (i) is 15 to 30 nucleotides in length; (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (iii) comprises 1 or more phosphorothioate internucleoside linkage.

Disclosed herein is a short interfering nucleic acid (siNA) molecule comprising: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide, wherein the siNA further comprises a phosphorylation blocker, a galactosamine, or 5'-stabilized end cap.

In some embodiments, at least 1, 2, 3, 4, 5, 6, or 7 nucleotides at position 3, 5, 7, 8, 9, 10, 11, 12, and/or 17 from the 5' end of the first nucleotide sequence is a 2'-fluoro nucleotide. In some embodiments, the nucleotide at position 3 from the 5' end of the first nucleotide sequence is a 2'-fluoro nucleotide. In some embodiments, the nucleotide at position 5 from the 5' end of the first nucleotide sequence is a 2'-fluoro nucleotide. In some embodiments, the nucleotide at position 7 from the 5' end of the first nucleotide sequence is a 2'-fluoro nucleotide. In some embodiments, the nucleotide at position 8 from the 5' end of the first nucleotide sequence is a 2'-fluoro nucleotide. In some embodiments, the nucleotide at position 9 from the 5' end of the first nucleotide sequence is a 2'-fluoro nucleotide. In some embodiments, the nucleotide at position 12 from the 5' end of the first nucleotide sequence is a 2'-fluoro nucleotide. In some embodiments, the nucleotide at position 17 from the 5' end of the first nucleotide sequence is a 2'-fluoro nucleotide. In some embodiments, nucleotide at position 10 from the 5' end of the first nucleotide sequence is a 2'-fluoro nucleotide. In some embodiments, the nucleotide at position 11 from the 5' end of the first nucleotide sequence is a 2'-fluoro nucleotide.

In some embodiments, at least 1, 2, 3, 4, 5, 6, 7, 8, or 9 nucleotides at position 2, 5, 6, 8, 10, 14, 16, 17, and/or 18 from the 5' end of the second nucleotide sequence is a 2'-fluoro nucleotide. In some embodiments, the nucleotide at position 2 from the 5' end of the second nucleotide sequence is a 2'-fluoro nucleotide. In some embodiments, the nucleotide at position 5 from the 5' end of the second nucleotide sequence is a 2'-fluoro nucleotide. In some embodiments, the nucleotide at position 6 from the 5' end of the second nucleotide sequence is a 2'-fluoro nucleotide. In some embodiments, the nucleotide at position 8 from the 5' end of the second nucleotide sequence is a 2'-fluoro nucleotide. In some embodiments, the nucleotide at position 10 from the 5' end of the second nucleotide sequence is a 2'-fluoro nucleotide. In some embodiments, the nucleotide at position 14 from the 5' end of the second nucleotide sequence is a 2'-fluoro nucleotide. In some embodiments, the nucleotides at position 16 from the 5' end of the second nucleotide sequence is a 2'-fluoro nucleotide. In some embodiments, the nucleotide at position 17 from the 5' end of the second nucleotide sequence is a 2'-fluoro nucleotide. In some embodiments, the nucleotide at position 18 from the 5' end of the second nucleotide sequence is a 2'-fluoro nucleotide.

In some embodiments, the nucleotides in the second nucleotide sequence are arranged in an alternating 1:3 modification pattern, and wherein 1 nucleotide is a 2'-fluoro nucleotide and 3 nucleotides are 2'-O-methyl nucleotides. In some embodiments, the alternating 1:3 modification pattern occurs 2-5 times. In some embodiments, at least two of the alternating 1:3 modification pattern occur consecutively. In some embodiments, at least two of the alternating 1:3 modification pattern occurs nonconsecutively. In some embodiments, at least 1, 2, 3, 4, or 5 alternating 1:3 modification pattern begins at nucleotide position 2, 6, 10, 14, and/or 18 from the 5' end of the antisense strand. In some embodiments, at least one alternating 1:3 modification pattern begins at nucleotide position 2 from the 5' end of the antisense strand. In some embodiments, at least one alternating 1:3 modification pattern begins at nucleotide position 6 from the 5' end of the antisense strand. In some embodiments, at least one alternating 1:3 modification pattern begins at nucleotide position 10 from the 5' end of the antisense strand. In some embodiments, at least one alternating 1:3 modification pattern begins at nucleotide position 14 from the 5' end of the antisense strand. In some embodiments, at least one alternating 1:3 modification pattern begins at nucleotide position 18 from the 5' end of the antisense strand.

In some embodiments, the nucleotides in the second nucleotide sequence are arranged in an alternating 1:2 modification pattern, and wherein 1 nucleotide is a 2'-fluoro nucleotide and 2 nucleotides are 2'-O-methyl nucleotides. In some embodiments, the alternating 1:2 modification pattern occurs 2-5 times. In some embodiments, at least two of the alternating 1:2 modification pattern occurs consecutively. In some embodiments, at least two of the alternating 1:2 modification pattern occurs nonconsecutively. In some embodiments, at least 1, 2, 3, 4, or 5 alternating 1:2 modification pattern begins at nucleotide position 2, 5, 8, 14, and/or 17 from the 5' end of the antisense strand. In some embodiments, at least one alternating 1:2 modification pattern begins at nucleotide position 2 from the 5' end of the antisense strand. In some embodiments, at least one alternating 1:2 modification pattern begins at nucleotide position 5 from the 5' end of the antisense strand. In some embodiments, at least one alternating 1:2 modification pattern begins at nucleotide position 8 from the 5' end of the antisense strand. In some embodiments, at least one alternating 1:2 modification pattern begins at nucleotide position 14 from the 5' end of the antisense strand. In some embodiments, at least one alternating 1:2 modification pattern begins at nucleotide position 17 from the 5' end of the antisense strand.

Disclosed herein is a short interfering nucleic acid (siNA) molecule represented by Formula (VIII):

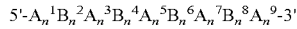

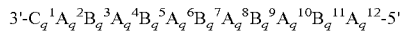

wherein:
the top strand is a sense strand comprising a first nucleotide sequence that is at least about 60%, 65%, 70%, 75%, 80%, 85%, 90%, 95%, or 100% identical to an RNA corresponding to a target gene, wherein the first nucleotide sequence comprises 15 to 30 nucleotides;
the bottom strand is an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence comprises 15 to 30 nucleotides;

each A is independently a 2'-O-methyl nucleotide or a nucleotide comprising a 5'-stabilized end cap or a phosphorylation blocker;
B is a 2'-fluoro nucleotide;
C represents overhanging nucleotides and is a 2'-O-methyl nucleotide;
$n^1$=1-4 nucleotides in length;
each $n^2$, $n^6$, $n^8$, $q^3$, $q^5$, $q^7$, $q^9$, $q^{11}$, and $q^{12}$ is independently 0-1 nucleotides in length;
each $n^3$ and $n^4$ is independently 1-3 nucleotides in length;
$n^5$ is 1-10 nucleotides in length;
$n^7$ is 0-4 nucleotides in length;
each $n^9$, $q^1$, and $q^2$ is independently 0-2 nucleotides in length;
$q^4$ is 0-3 nucleotides in length;
$q^6$ is 0-5 nucleotides in length;
$q^8$ is 2-7 nucleotides in length; and
$q^{10}$ is 2-11 nucleotides in length.

Disclosed herein is a short interfering nucleic acid (siNA) molecule represented by Formula (IX):

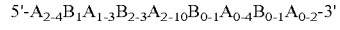

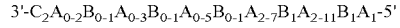

wherein:
the top strand is a sense strand comprising a first nucleotide sequence that is at least about 60%, 65%, 70%, 75%, 80%, 85%, 90%, 95%, or 100% identical to an RNA corresponding to a target gene, wherein the first nucleotide sequence comprises 15 to 30 nucleotides;
the bottom strand is an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence comprises 15 to 30 nucleotides;
each A is independently a 2'-O-methyl nucleotide or a nucleotide comprising a 5'-stabilized end cap or a phosphorylation blocker;
B is a 2'-fluoro nucleotide;
C represents overhanging nucleotides and is a 2'-O-methyl nucleotide.

Disclosed herein is a short interfering nucleic acid (siNA) molecule comprising (a) a sense strand comprising a first nucleotide sequence consisting of 17 to 23 nucleotides, wherein 2'-fluoro nucleotides are at positions 3, 7-9, 12, and 17 from the 5' end of the first nucleotide sequence, and wherein 2'-O-methyl nucleotides are at positions 1, 2, 4-6, 10, 11, and 13-16 from the 5' end of the first nucleotide sequence; and (b) an antisense strand comprising a second nucleotide sequence consisting of 17 to 23 nucleotides, wherein 2'-fluoro nucleotides are at positions 2 and 14 from the 5' end of the second nucleotide sequence, and wherein 2'-O-methyl nucleotides are at positions 1, 3-13, and 15-17 from the 5' end of the second nucleotide sequence. In some embodiments, the first nucleotide sequence consists of 19 nucleotides. In some embodiments, 2'-O-methyl nucleotides are at positions 18 and 19 from the 5' end of the first nucleotide sequence. In some embodiments, the second nucleotide sequence consists of 21 nucleotides. In some embodiments, 2'-O-methyl nucleotides are at positions 18-21 from the 5' end of the second nucleotide sequence.

Disclosed herein is a short interfering nucleic acid (siNA) molecule comprising (a) a sense strand comprising a first nucleotide sequence consisting of 17 to 23 nucleotides, wherein 2'-fluoro nucleotides are at positions 3, 7, 8, and 17 from the 5' end of the first nucleotide sequence, and wherein 2'-O-methyl nucleotides are at positions 1, 2, 4-6, and 9-16 from the 5' end of the first nucleotide sequence; and (b) an antisense strand comprising a second nucleotide sequence consisting of 17 to 23 nucleotides, wherein 2'-fluoro nucleotides are at positions 2 and 14 from the 5' end of the first nucleotide sequence; and wherein 2'-O-methyl nucleotides are at positions 1, 3-13, and 15-17 from the 5' end of the first nucleotide sequence. In some embodiments, the first nucleotide sequence consists of 19 nucleotides. In some embodiments, 2'-O-methyl nucleotides are at positions 18 and 19 from the 5' end of the first nucleotide sequence. In some embodiments, the second nucleotide sequence consists of 21 nucleotides. In some embodiments, 2'-O-methyl nucleotides are at positions 18-21 from the 5' end of the second nucleotide sequence.

Disclosed herein is a short interfering nucleic acid (siNA) molecule comprising (a) a sense strand comprising a first nucleotide sequence consisting of 17 to 23 nucleotides, wherein 2'-fluoro nucleotides are at positions 3, 7-9, 12 and 17 from the 5' end of the first nucleotide sequence, and wherein 2'-O-methyl nucleotides are at positions 1, 2, 4-6, 10, 11, and 13-16 from the 5' end of the first nucleotide sequence; and (b) an antisense strand comprising a second nucleotide sequence consisting of 17 to 23 nucleotides, wherein the nucleotides in the second nucleotide sequence are arranged in an alternating 1:3 modification pattern, and wherein 1 nucleotide is a 2'-fluoro nucleotide and 3 nucleotides are 2'-O-methyl nucleotides. In some embodiments, the first nucleotide sequence consists of 19 nucleotides. In some embodiments, 2'-O-methyl nucleotides are at positions 18 and 19 from the 5' end of the first nucleotide sequence. In some embodiments, the second nucleotide sequence consists of 21 nucleotides. In some embodiments, 2'-O-methyl nucleotides are at positions 19-21 from the 5' end of the second nucleotide sequence. In some embodiments, the alternating 1:3 modification pattern occurs 2-5 times. In some embodiments, at least two of the alternating 1:3 modification pattern occur consecutively. In some embodiments, at least two of the alternating 1:3 modification pattern occurs nonconsecutively. In some embodiments, at least 1, 2, 3, 4, or 5 alternating 1:3 modification pattern begins at nucleotide position 2, 6, 10, 14, and/or 18 from the 5' end of the antisense strand. In some embodiments, at least one alternating 1:3 modification pattern begins at nucleotide position 2 from the 5' end of the antisense strand. In some embodiments, at least one alternating 1:3 modification pattern begins at nucleotide position 6 from the 5' end of the antisense strand. In some embodiments, at least one alternating 1:3 modification pattern begins at nucleotide position 10 from the 5' end of the antisense strand. In some embodiments, at least one alternating 1:3 modification pattern begins at nucleotide position 14 from the 5' end of the antisense strand. In some embodiments, at least one alternating 1:3 modification pattern begins at nucleotide position 18 from the 5' end of the antisense strand.

Disclosed herein is a short interfering nucleic acid (siNA) molecule comprising (a) a sense strand comprising a first nucleotide sequence consisting of 17 to 23 nucleotides, wherein 2'-fluoro nucleotides are at positions 5 and 7-9 from the 5' end of the first nucleotide sequence, and wherein 2'-O-methyl nucleotides are at positions 1-4, 6, and 10-17 from the 5' end of the first nucleotide sequence; and (b) an antisense strand comprising a second nucleotide sequence consisting of 17 to 23 nucleotides, wherein the nucleotides in the second nucleotide sequence are arranged in an alternating 1:3 modification pattern, and wherein 1 nucleotide is a 2'-fluoro nucleotide and 3 nucleotides are 2'-O-methyl nucleotides. In some embodiments, the first nucleotide sequence consists of 19 nucleotides. In some embodiments, 2'-O-methyl nucleotides are at positions 18 and 19 from the 5' end of the first nucleotide sequence. In some embodiments, the second nucleotide sequence consists of 21 nucleotides. In some embodiments, 2'-O-methyl nucleotides are at positions 19-21 from the 5' end of the second nucleotide sequence. In some embodiments, the alternating 1:3 modification pattern occurs 2-5 times. In some embodiments, at least two of the alternating 1:3 modification pattern occur consecutively. In some embodiments, at least two of the alternating 1:3 modification pattern occurs nonconsecutively. In some embodiments, at least 1, 2, 3, 4, or 5 alternating 1:3 modification pattern begins at nucleotide position 2, 6, 10, 14, and/or 18 from the 5' end of the antisense strand. In some embodiments, at least one alternating 1:3 modification pattern begins at nucleotide position 2 from the 5' end of the antisense strand. In some embodiments, at least one alternating 1:3 modification pattern begins at nucleotide position 6 from the 5' end of the antisense strand. In some embodiments, at least one alternating 1:3 modification pattern begins at nucleotide position 10 from the 5' end of the antisense strand. In some embodiments, at least one alternating 1:3 modification pattern begins at nucleotide position 14 from the 5' end of the antisense strand. In some embodiments, at least one alternating 1:3 modification pattern begins at nucleotide position 18 from the 5' end of the antisense strand.

Disclosed herein is a short interfering nucleic acid (siNA) molecule comprising (a) a sense strand comprising a first nucleotide sequence consisting of 17 to 23 nucleotides, wherein 2'-fluoro nucleotides are at positions 5 and 7-9 from the 5' end of the first nucleotide sequence, and wherein 2'-O-methyl nucleotides are at positions 1-4, 6, and 10-17 from the 5' end of the first nucleotide sequence; and (b) an antisense strand comprising a second nucleotide sequence consisting of 17 to 23 nucleotides, wherein the nucleotides in the second nucleotide sequence are arranged in an alternating 1:2 modification pattern, and wherein 1 nucleotide is a 2'-fluoro nucleotide and 2 nucleotides are 2'-O-methyl nucleotides. In some embodiments, the first nucleotide sequence consists of 19 nucleotides. In some embodiments, 2'-O-methyl nucleotides are at positions 18 and 19 from the 5' end of the first nucleotide sequence. In some embodiments, the second nucleotide sequence consists of 21 nucleotides. In some embodiments, 2'-O-methyl nucleotides are at positions 18-21 from the 5' end of the second nucleotide sequence. In some embodiments, the alternating 1:2 modification pattern occurs 2-5 times. In some embodiments, at least two of the alternating 1:2 modification pattern occur consecutively. In some embodiments, at least two of the alternating 1:2 modification pattern occurs nonconsecutively. In some embodiments, at least 1, 2, 3, 4, or 5 alternating 1:2 modification pattern begins at nucleotide position 2, 5, 8, 14, and/or 17 from the 5' end of the antisense strand. In some embodiments, at least one alternating 1:2 modification pattern begins at nucleotide position 2 from the 5' end of the antisense strand. In some embodiments, at least one alternating 1:2 modification pattern begins at nucleotide position 5 from the 5' end of the antisense strand. In some embodiments, at least one alternating 1:2 modification pattern begins at nucleotide position 8 from the 5' end of the antisense strand. In some embodiments, at least one alternating 1:2 modification pattern begins at nucleotide position 14 from the 5' end of the antisense strand. In some embodiments, at least one alternating 1:2 modification pattern begins at nucleotide position 17 from the 5' end of the antisense strand.

Disclosed herein is a short interfering nucleic acid (siNA) molecule comprising (a) a sense strand comprising a first nucleotide sequence consisting of 17 to 23 nucleotides, wherein 2'-fluoro nucleotides are at positions 5 and 7-9 from the 5' end of the first nucleotide sequence, and wherein 2'-O-methyl nucleotides are at positions 1-4, 6, and 10-17 from the 5' end of the first nucleotide sequence; and (b) an antisense strand comprising a second nucleotide sequence consisting of 17 to 23 nucleotides, wherein 2'-fluoro nucleotides are at positions 2, 6, 14, and 16 from the 5' end of the second nucleotide sequence, and wherein 2'-O-methyl nucleotides are at positions 1, 3-5, 7-13, 15, and 17 from the 5' end the second nucleotide sequence. In some embodiments, the first nucleotide sequence consists of 19 nucleotides. In some embodiments, 2'-O-methyl nucleotides are at positions 18 and 19 from the 5' end of the first nucleotide sequence. In some embodiments, the second nucleotide sequence consists of 21 nucleotides. In some embodiments, 2'-O-methyl nucleotides are at positions 18-21 from the 5' end of the second nucleotide sequence.

Disclosed herein is a short interfering nucleic acid (siNA) molecule comprising: (a) a sense strand comprising a first nucleotide sequence consisting of 17 to 23 nucleotides, wherein 2'-fluoro nucleotides are at positions 5, 9-11, and 14 from the 5' end of the first nucleotide sequence, and wherein 2'-O-methyl nucleotides are at positions 1-4, 6-8, and 12-17 from the 5' end of the first nucleotide sequence; and (b) an antisense strand comprising a second nucleotide sequence consisting of 17 to 23 nucleotides, wherein 2'-fluoro nucleotides are at positions 2 and 14 from the 5' end of the second nucleotide sequence, and wherein 2'-O-methyl nucleotides are at positions 1, 3-13, and 15-17 from the 5' end the second nucleotide sequence. In some embodiments, the first nucleotide sequence consists of 21 nucleotides. In some embodiments, 2'-O-methyl nucleotides are at positions 18-21 from the 5' end of the first nucleotide sequence. In some embodiments, the second nucleotide sequence consists of 23 nucleotides. In some embodiments, 2'-O-methyl nucleotides are at positions 18-23 from the 5' end of the second nucleotide sequence.

In some embodiments, any of the sense strands disclosed herein further comprise a TT sequence adjacent to the first nucleotide sequence.

In some embodiments, any of the sense strands disclosed herein further comprise at least 1, 2, 3, 4, 5, 6, 7, 8, 9, 10, 11, 12, 13, 14, 15 or more phosphorothioate internucleoside linkages. In some embodiments, at least one phosphorothioate internucleoside linkage is between the nucleotides at positions 1 and 2 from the 5' end of the first nucleotide sequence. In some embodiments, at least one phosphorothioate internucleoside linkage is between the nucleotides at positions 2 and 3 from the 5' end of the first nucleotide sequence.

In some embodiments, any of the antisense strands disclosed herein further comprise TT sequence adjacent to the second nucleotide sequence. In some embodiments, the antisense strand further comprises at least 1, 2, 3, 4, 5, 6, 7, 8, 9, 10, 11, 12, 13, 14, 15 or more phosphorothioate internucleoside linkages. In some embodiments, at least one phosphorothioate internucleoside linkage is between the nucleotides at positions 1 and 2 from the 5' end of the second nucleotide sequence. In some embodiments, at least one phosphorothioate internucleoside linkage is between the nucleotides at positions 2 and 3 from the 5' end of the second nucleotide sequence. In some embodiments, at least one phosphorothioate internucleoside linkage is between the nucleotides at positions 1 and 2 from the 3' end of the second nucleotide sequence. In some embodiments, at least one phosphorothioate internucleoside linkage is between the nucleotides at positions 2 and 3 from the 3' end of the second nucleotide sequence.

In some embodiments, the first nucleotide from the 5' end of any of the first nucleotide sequences disclosed herein comprises a 5' stabilizing end cap.

In some embodiments, the first nucleotide from the 5' end of any of the second nucleotide sequences disclosed herein comprise a 5' stabilizing end cap.

In some embodiments, the first nucleotide from the 5' end of any of the first nucleotide sequences disclosed herein comprises a phosphorylation blocker.

In some embodiments, the first nucleotide from the 5' end of any of the second nucleotide sequences disclosed herein comprises a phosphorylation blocker.

In some embodiments, any of the first nucleotide sequences or second nucleotide sequences disclosed herein comprise at least one modified nucleotide selected from

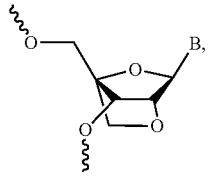

(LNA)

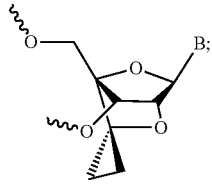

(ScpBNA or "cp")

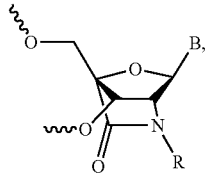

(AmNA)

where R is H or alkyl (or AmNA(N-Me)) when R is alkyl;

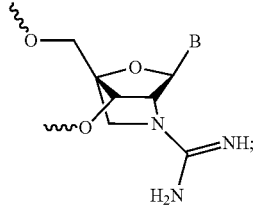

(GuNA)

and

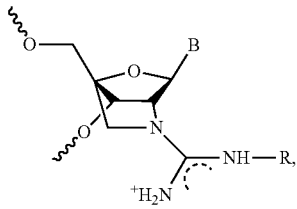

GuNA(N—R), R = Me, Et, iPr, tBu wherein B is a nucleobase.

Disclosed herein is a short-interfering nucleic acid (siNA) molecule comprising:

(a) a phosphorylation blocker of Formula (IV):

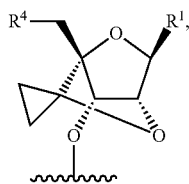

wherein $R^1$ is a nucleobase, $R^4$ is —O—$R^{30}$ or —$NR^{31}R^{32}$, $R^{30}$ is $C_1$-$C_8$ substituted or unsubstituted alkyl; and $R^{31}$ and $R^{32}$ together with the nitrogen to which they are attached form a substituted or unsubstituted heterocyclic ring; and (b) a short interfering nucleic acid (siNA). In some embodiments, the siNA is any of the siNAs disclosed herein. In some embodiments, the siNA comprises any of the sense strands, first nucleotide sequences, antisense strands, or second nucleotide sequences disclosed herein. In some embodiments, the siNA comprises any of the sense strands disclosed herein. In some embodiments, the siNA comprises any of the antisense strand disclosed herein. In some embodiments, the siNA comprises a first nucleotide sequence selected from any one of SEQ ID NOs: 1-56, 103-158, and 205-260. In some embodiments, the siNA comprises a second nucleotide sequence selected from any one of SEQ ID NOs: 57-102, 159-204, and 261-306. In some embodiments, the siNA comprises a sense sequence selected from any one of SEQ ID NOs: 307-362 and 415-444. In some embodiments, the siNA comprises an antisense sequence selected from any one of SEQ ID NOs: 363-409, 445-533, and 536-539. In some embodiments, the siNA comprises a ds-siNA sequence selected from any one of ds-siNA-001 to ds-siNA-0178. In some embodiments, the siNA further comprises any of the 5' end caps disclosed herein. In some embodiments, the siNA further comprises any of the conjugated moieties disclosed herein. In some embodiments, the siNA further comprises any of the destabilizing nucleotides disclosed herein. In some embodiments, the siNA further comprises any of the modified nucleotides disclosed herein.

Disclosed herein is a short-interfering nucleic acid (siNA) molecule comprising:

(a) a 5'-stabilized end cap of Formula (Ia):

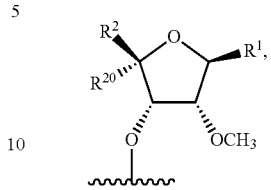

wherein $R^1$ is a nucleobase, aryl, heteroaryl, or H, $R^2$ is

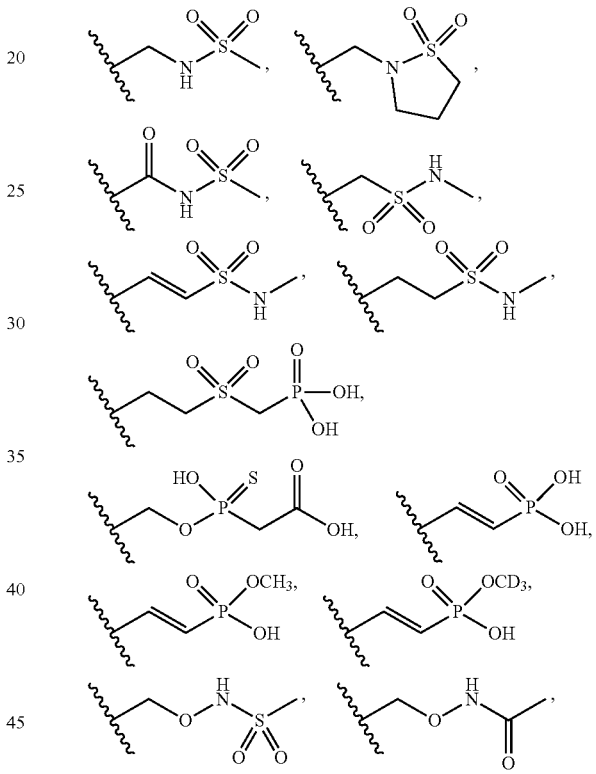

—CH=CD-Z, —CD=CH—Z, —CD=CD-Z, —($CR^{21}R^{22}$)$_n$—Z, or —($C_2$-$C_6$ alkenylene)-Z and $R^{20}$ is hydrogen; or $R^2$ and $R^{20}$ together form a 3- to 7-membered carbocyclic ring substituted with —($CR^{21}R^{22}$)$_n$—Z or —($C_2$-$C_6$ alkenylene)-Z;

n is 1, 2, 3, or 4;

Z is —$ONR^{23}R^{24}$, —OP(O)OH($CH_2$)$_m$$CO_2R^{23}$, —OP(S)OH($CH_2$)$_m$$CO_2R^{23}$, —P(O)(OH)$_2$, —P(O)(OH)(OCH$_3$), —P(O)(OH)(OCD$_3$), —SO$_2$($CH_2$)$_m$P(O)(OH)$_2$, —SO$_2$$NR^{23}R^{25}$, —$NR^{23}R^{24}$, $R^{21}$ and $R^{22}$ are independently hydrogen or $C_1$-$C_6$ alkyl; $R^{21}$ and $R^{22}$ together form an oxo group;

$R^{23}$ is hydrogen or $C_1$-$C_6$ alkyl;

$R^{24}$ is —$SO_2R^{25}$ or —C(O)$R^{25}$; or $R^{23}$ and $R^{24}$ together with the nitrogen to which they are attached form a substituted or unsubstituted heterocyclic ring;

$R^{25}$ is $C_1$-$C_6$ alkyl; and m is 1, 2, 3, or 4; and (b) a short interfering nucleic acid (siNA). In some embodiments, the siNA comprises any of the sense strands disclosed herein. In some embodiments, the siNA comprises any of the antisense strand disclosed herein. In some embodiments, the siNA comprises a first nucleotide sequence selected from any one of SEQ ID NOs: 1-56, 103-158, and 205-260. In some embodiments, the siNA comprises a second nucleotide sequence selected from any one of SEQ ID NOs: 57-102, 159-204, and 261-306. In some embodiments, the siNA comprises a sense sequence selected from any one of SEQ ID NOs: 307-362 and 415-444. In some embodiments, the siNA comprises an antisense sequence selected from any one of SEQ ID NOs: 363-409, 445-533, and 536-539. In some embodiments, the siNA comprises a ds-siNA sequence selected from any one of ds-siNA-001 to ds-siNA-0178. In some embodiments, the siNA further comprises any of the phosphorylation blockers disclosed herein. In some embodiments, the siNA further comprises any of the conjugated moieties disclosed herein. In some embodiments, the siNA further comprises any of the destabilizing nucleotides disclosed herein. In some embodiments, the siNA further comprises any of the modified nucleotides disclosed herein.

Disclosed herein is a short-interfering nucleic acid (siNA) molecule comprising:
(a) a 5'-stabilized end cap of Formula (Ib):

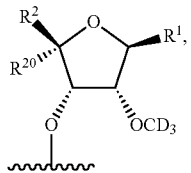

wherein
$R^1$ is a nucleobase, aryl, heteroaryl, or H,
$R^2$ is

—CH=CD-Z, —CD=CH—Z, —CD=CD-Z, —$(CR^{21}R^{22})_n$—Z, or —$(C_2$-$C_6$ alkenylene)-Z and $R^{20}$ is hydrogen;
or
$R^2$ and $R^{20}$ together form a 3- to 7-membered carbocyclic ring substituted with —$(CR^{21}R^{22})_n$—Z or —$(C_2$-$C_6$ alkenylene)-Z;
n is 1, 2, 3, or 4;
Z is —$ONR^{23}R^{24}$, —$OP(O)OH(CH_2)_mCO_2R^{23}$, —$OP(S)OH(CH_2)_mCO_2R^{23}$, —$P(O)(OH)_2$, —$P(O)(OH)(OCH_3)$, —$P(O)(OH)(OCD_3)$, —$SO_2(CH_2)_mP(O)(OH)_2$, —$SO_2NR^{23}R^{25}$, —$NR^{23}R^{24}$, $R^{21}$ and $R^{22}$ are independently hydrogen or $C_1$-$C_6$ alkyl; $R^{21}$ and $R^{22}$ together form an oxo group;
$R^{23}$ is hydrogen or $C_1$-$C_6$ alkyl;
$R^{24}$ is —$SO_2R^{25}$ or —$C(O)R^{25}$; or
$R^{23}$ and $R^{24}$ together with the nitrogen to which they are attached form a substituted or unsubstituted heterocyclic ring;
$R^{25}$ is $C_1$-$C_6$ alkyl; and
m is 1, 2, 3, or 4; and
(b) a short interfering nucleic acid (siNA). In some embodiments, the siNA comprises any of the sense strands disclosed herein. In some embodiments, the siNA comprises any of the antisense strand disclosed herein. In some embodiments, the siNA comprises a first nucleotide sequence selected from any one of SEQ ID NOs: 1-56, 103-158, and 205-260. In some embodiments, the siNA comprises a second nucleotide sequence selected from any one of SEQ ID NOs: 57-102, 159-204, and 261-306. In some embodiments, the siNA comprises a sense sequence selected from any one of SEQ ID NOs: 307-362 and 415-444. In some embodiments, the siNA comprises an antisense sequence selected from any one of SEQ ID NOs: 363-409, 445-533, and 536-539. In some embodiments, the siNA comprises a ds-siNA sequence selected from any one of ds-siNA-001 to ds-siNA-0178. In some embodiments, the siNA further comprises any of the phosphorylation blockers disclosed herein. In some embodiments, the siNA further comprises any of the conjugated moieties disclosed herein. In some embodiments, the siNA further comprises any of the destabilizing nucleotides disclosed herein. In some embodiments, the siNA further comprises any of the modified nucleotides disclosed herein.

Disclosed herein is a short-interfering nucleic acid (siNA) molecule comprising: (a) a 5'-stabilized end cap selected from the group consisting of Formula (1) to Formula (15), Formula (9X) to Formula (12X), and Formula (9Y) to Formula (12Y):

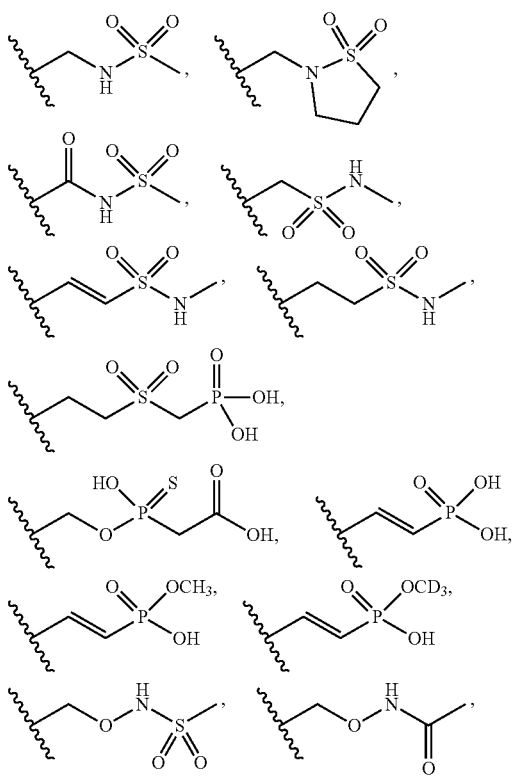

-continued
Formula (3)
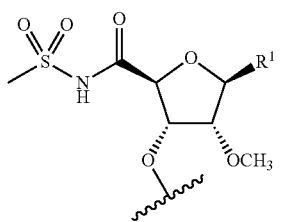
Formula (4)
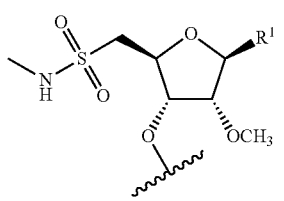
(Formula 5)
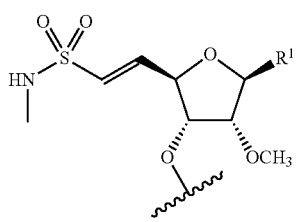
Formula (6)
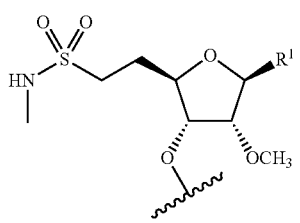
Formula (7)
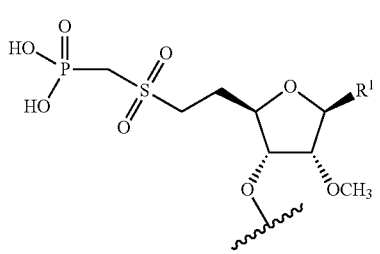
Formula (8)
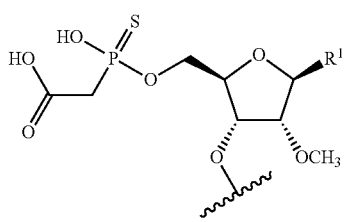
Formula (9)
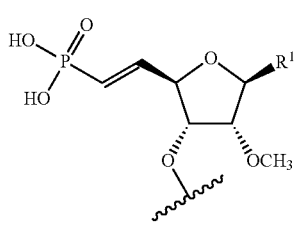
-continued
Formula (9X)
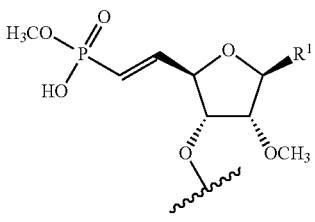
Formula (9Y)
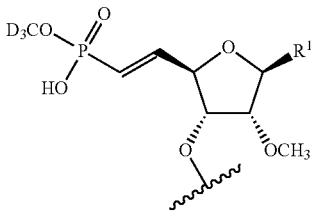
Formula (10)
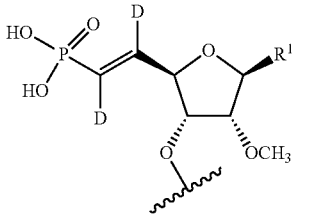
Formula (10X)
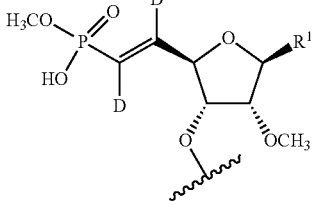
Formula (10Y)
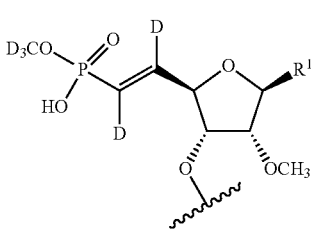
Formula (11)
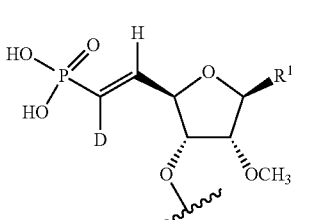
Formula (11X)
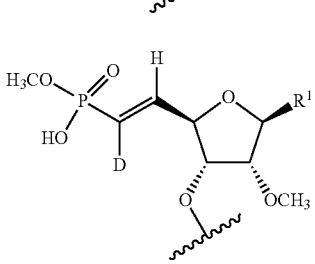

-continued

Formula (11Y)
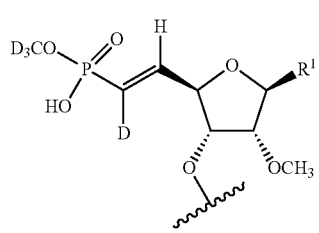

Formula (12)
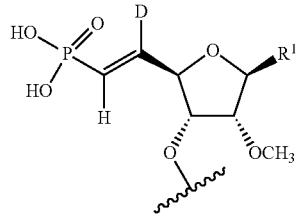

Formula (12X)
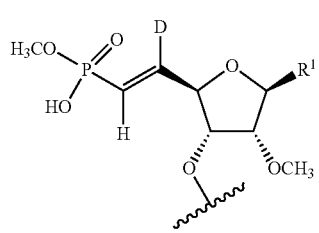

Formula (12Y)
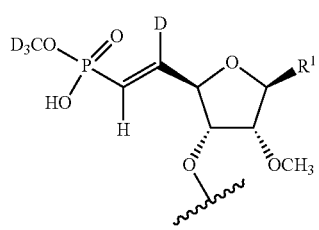

Formula (13)
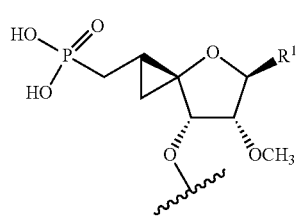

Formula (14)
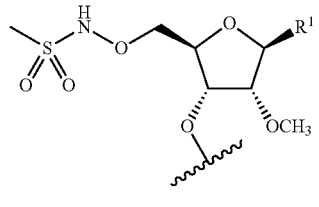

Formula (15)
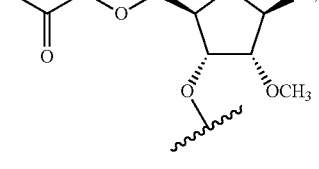

wherein $R^1$ is a nucleobase, aryl, heteroaryl, or H; and (b) a short interfering nucleic acid (siNA). In some embodiments, the siNA comprises any of the sense strands disclosed herein. In some embodiments, the siNA comprises any of the antisense strand disclosed herein. In some embodiments, the siNA comprises a first nucleotide sequence selected from any one of SEQ ID NOs: 1-56, 103-158, and 205-260. In some embodiments, the siNA comprises a second nucleotide sequence selected from any one of SEQ ID NOs: 57-102, 159-204, and 261-306. In some embodiments, the siNA comprises a sense sequence selected from any one of SEQ ID NOs: 307-362 and 415-444. In some embodiments, the siNA comprises an antisense sequence selected from any one of SEQ ID NOs: 363-409, 445-533, and 536-539. In some embodiments, the siNA comprises a ds-siNA sequence selected from any one of ds-siNA-001 to ds-siNA-0178. In some embodiments, the siNA further comprises any of the phosphorylation blockers disclosed herein. In some embodiments, the siNA further comprises any of the conjugated moieties disclosed herein. In some embodiments, the siNA further comprises any of the destabilizing nucleotides disclosed herein. In some embodiments, the siNA further comprises any of the modified nucleotides disclosed herein.

Disclosed herein is a short-interfering nucleic acid (siNA) molecule comprising: (a) a 5'-stabilized end cap selected from the group consisting of Formulas (1A)-(15A), Formulas (9B)-(12B), Formulas (9AX)-(12AX), Formulas (9AY)-(12AY), Formulas (9BX)-(12BX), and Formulas (9BY)-(12BY):

Formula (1A)
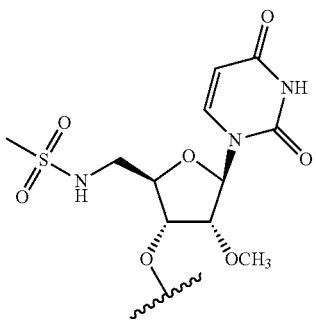

Formula (2A)
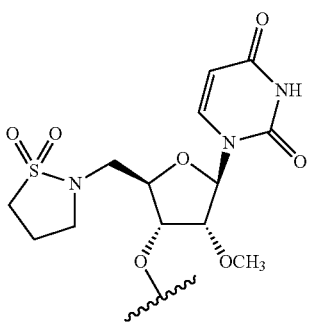

Formula (3A)
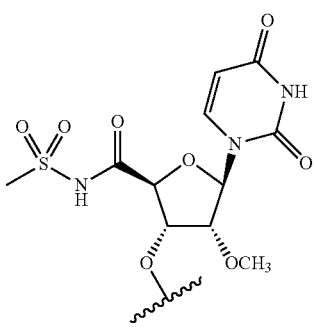

Formula (4A)
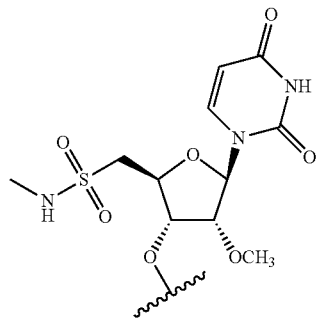
Formula (5A)
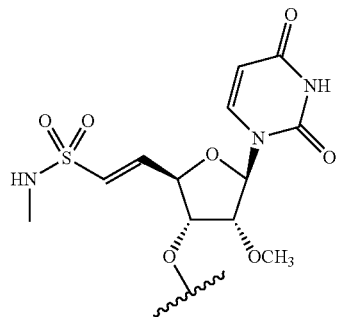
Formula (6A)
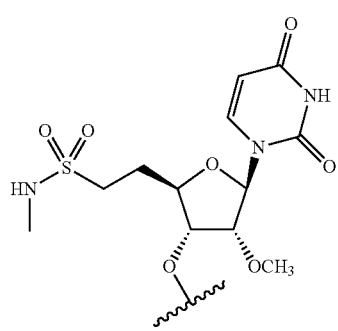
Formula (7A)
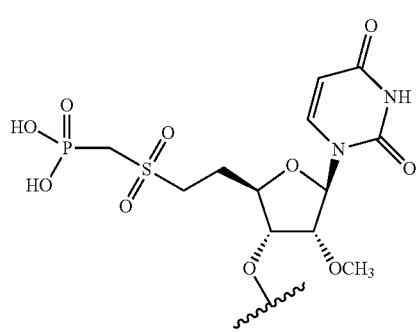
Formula (8A)
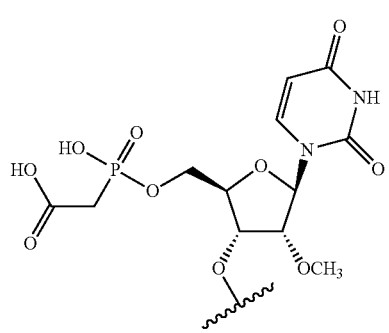
Formula (9A)
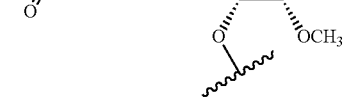
Formula (9AX)
Formula (9AY)
Formula (9B)
Formula (9BX)
Formula (9BY)

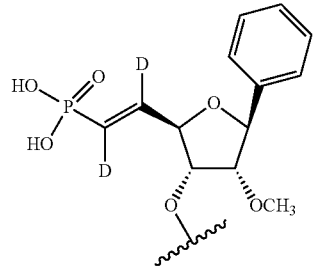
Formula (10A)
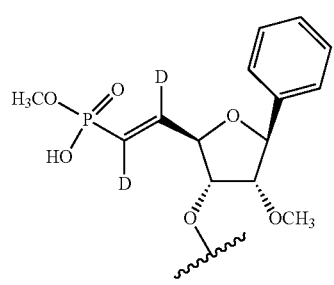
Formula (10AX)
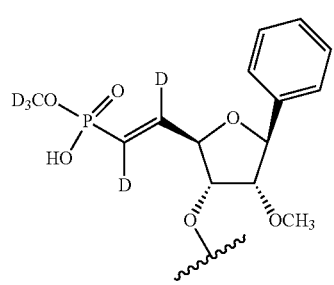
Formula (10AY)
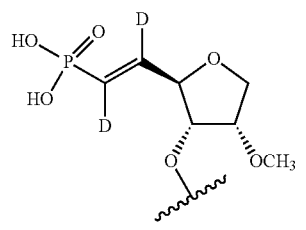
Formula (10B)
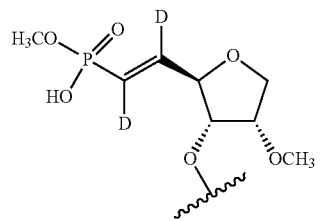
Formula (10BX)
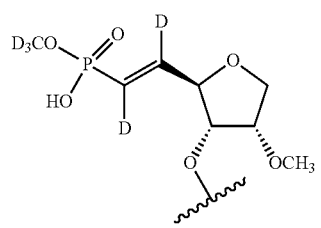
Formula (10BY)
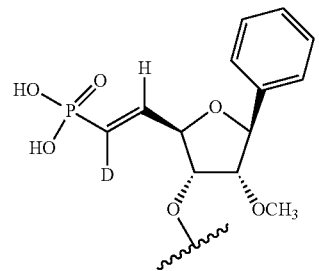
Formula (11A)
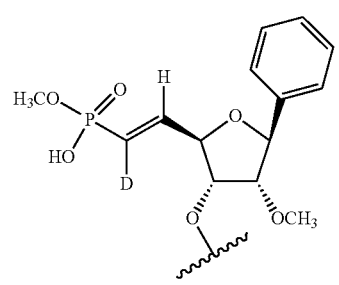
Formula (11AX)
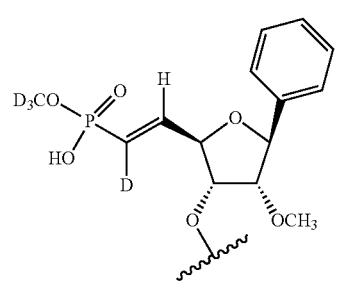
Formula (11AY)
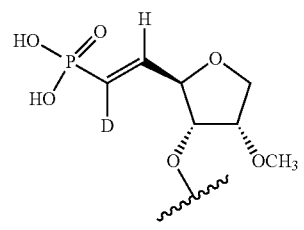
Formula (11B)
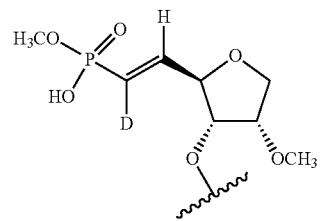
Formula (11BX)
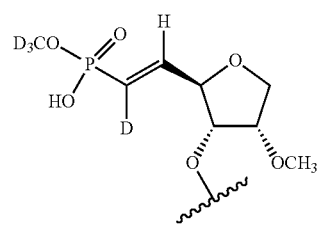
Formula (11BY)

Formula (12A)

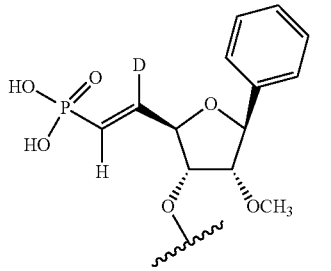

Formula (12AX)

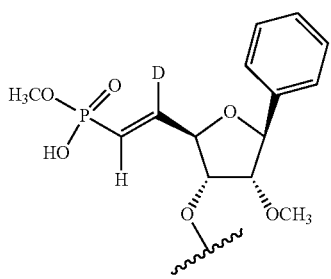

Formula (12AY)

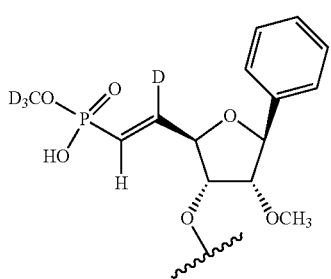

Formula (12B)

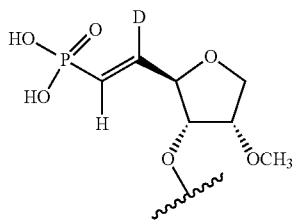

Formula (12BX)

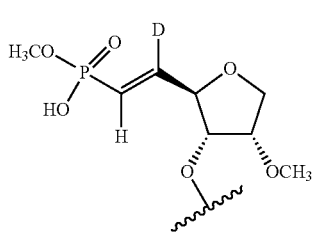

Formula (12BY)

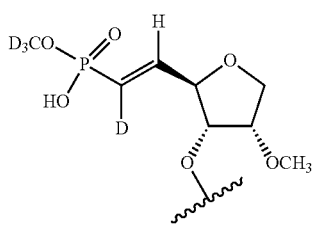

Formula (13A)

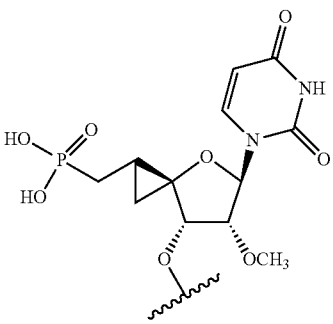

Formula (14A)

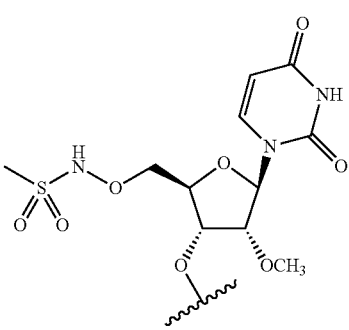

Formula (15A)

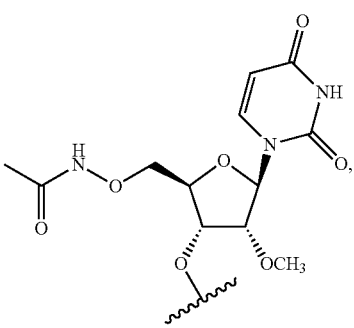

and (b) a short interfering nucleic acid (siNA). In some embodiments, the siNA comprises any of the sense strands disclosed herein. In some embodiments, the siNA comprises any of the antisense strand disclosed herein. In some embodiments, the siNA comprises a first nucleotide sequence selected from any one of SEQ ID NOs: 1-56, 103-158, and 205-260. In some embodiments, the siNA comprises a second nucleotide sequence selected from any one of SEQ ID NOs: 57-102, 159-204, and 261-306. In some embodiments, the siNA comprises a sense sequence selected from any one of SEQ ID NOs: 307-362 and 415-444. In some embodiments, the siNA comprises an antisense sequence selected from any one of SEQ ID NOs: 363-409, 445-533, and 536-539. In some embodiments, the siNA comprises a ds-siNA sequence selected from any one of ds-siNA-001 to ds-siNA-0178. In some embodiments, the siNA further comprises any of the phosphorylation blockers disclosed herein. In some embodiments, the siNA further comprises any of the conjugated moieties disclosed herein. In some embodiments, the siNA further comprises any of the destabilizing nucleotides disclosed herein. In some embodiments, the siNA further comprises any of the modified nucleotides disclosed herein.

Disclosed herein is a short-interfering nucleic acid (siNA) molecule comprising:
(a) a 5'-stabilized end cap of Formula (Ic):

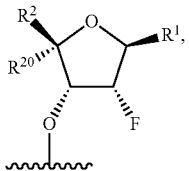

wherein
$R^1$ is a nucleobase, aryl, heteroaryl, or H,
$R^2$ is

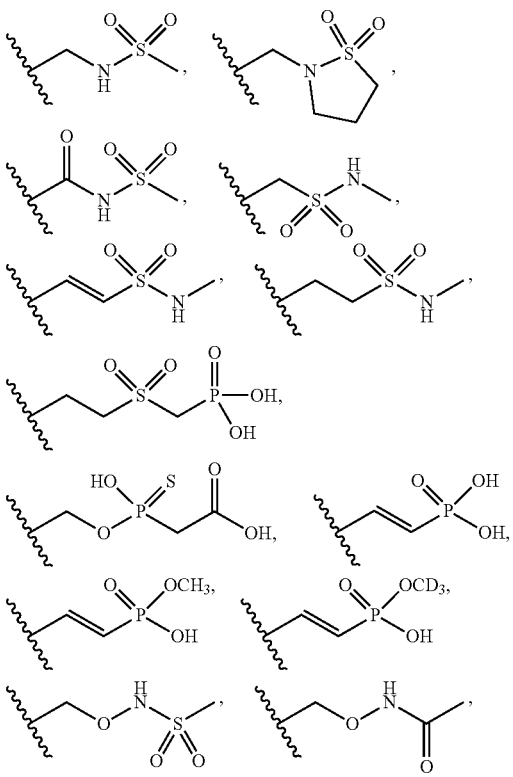

—CH=CD-Z, —CD=CH—Z, —CD=CD-Z, —($CR^{21}R^{22}$)$_n$—Z, or —($C_2$-$C_6$ alkenylene)-Z and $R^{20}$ is hydrogen; or
$R^2$ and $R^{20}$ together form a 3- to 7-membered carbocyclic ring substituted with —($CR^{21}R^{22}$)$_n$—Z or —($C_2$-$C_6$ alkenylene)-Z;
n is 1, 2, 3, or 4;
Z is —$ONR^{23}R^{24}$, —$OP(O)OH(CH_2)_mCO_2R^{23}$, —$OP(S)OH(CH_2)_mCO_2R^{23}$, —$P(O)(OH)_2$, —$P(O)(OH)(OCH_3)$, —$P(O)(OH)(OCD_3)$, —$SO_2(CH_2)_mP(O)(OH)_2$, —$SO_2NR^{23}R^{25}$, —$NR^{23}R^{24}$, or —$NR^{23}SO_2R^{24}$;
$R^{21}$ and $R^{22}$ either are independently hydrogen or $C_1$-$C_6$ alkyl, or $R^{21}$ and $R^{22}$ together form an oxo group;
$R^{23}$ is hydrogen or $C_1$-$C_6$ alkyl;
$R^{24}$ is —$SO_2R^{25}$ or —$C(O)R^{25}$; or
$R^{23}$ and $R^{24}$ together with the nitrogen to which they are attached form a substituted or unsubstituted heterocyclic ring;
$R^{25}$ is $C_1$-$C_6$ alkyl; and
m is 1, 2, 3, or 4; and
(b) a short interfering nucleic acid (siNA). In some embodiments, the siNA comprises any of the sense strands disclosed herein. In some embodiments, the siNA comprises any of the antisense strand disclosed herein. In some embodiments, the siNA comprises a first nucleotide sequence selected from any one of SEQ ID NOs: 1-56, 103-158, and 205-260. In some embodiments, the siNA comprises a second nucleotide sequence selected from any one of SEQ ID NOs: 57-102, 159-204, and 261-306. In some embodiments, the siNA comprises a sense sequence selected from any one of SEQ ID NOs: 307-362 and 415-444. In some embodiments, the siNA comprises an antisense sequence selected from any one of SEQ ID NOs: 363-409, 445-533, and 536-539. In some embodiments, the siNA comprises a ds-siNA sequence selected from any one of ds-siNA-001 to ds-siNA-0178. In some embodiments, the siNA further comprises any of the phosphorylation blockers disclosed herein. In some embodiments, the siNA further comprises any of the conjugated moieties disclosed herein. In some embodiments, the siNA further comprises any of the destabilizing nucleotides disclosed herein. In some embodiments, the siNA further comprises any of the modified nucleotides disclosed herein.

Disclosed herein is a short-interfering nucleic acid (siNA) molecule comprising:
(a) a 5'-stabilized end cap selected from the group consisting of Formula (21) to Formula (35):

Formula (21)

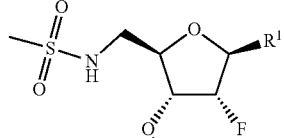

Formula (22)

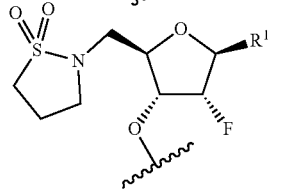

Formula (23)

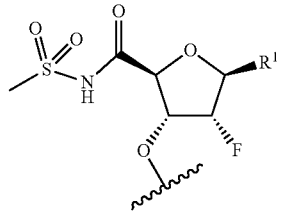

Formula (24)

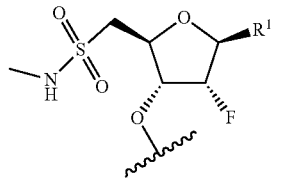

Formula (25)

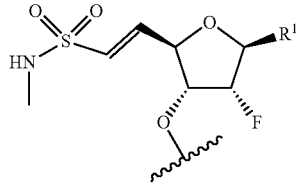

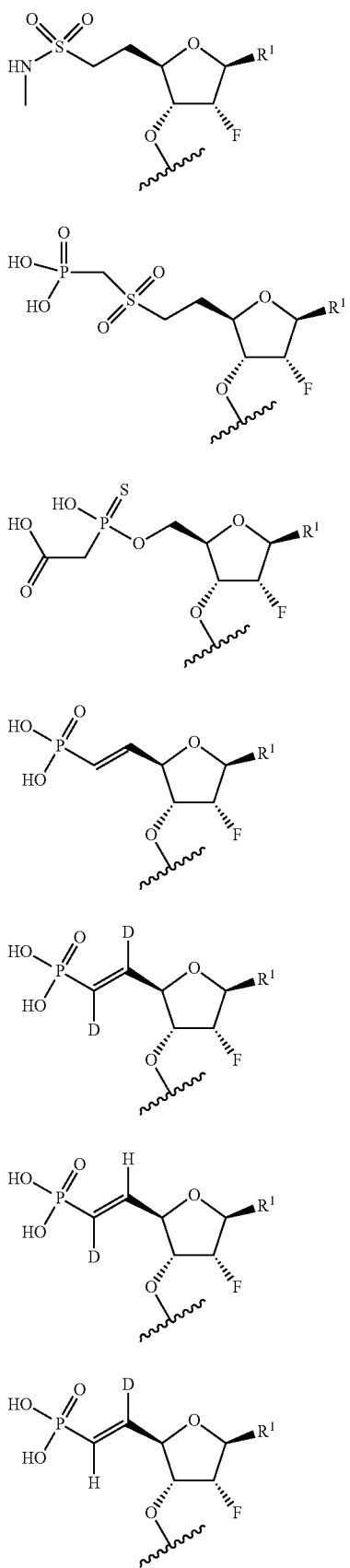

Formula (26)

Formula (27)

Formula (28)

Formula (29)

Formula (30)

Formula (31)

Formula (32)

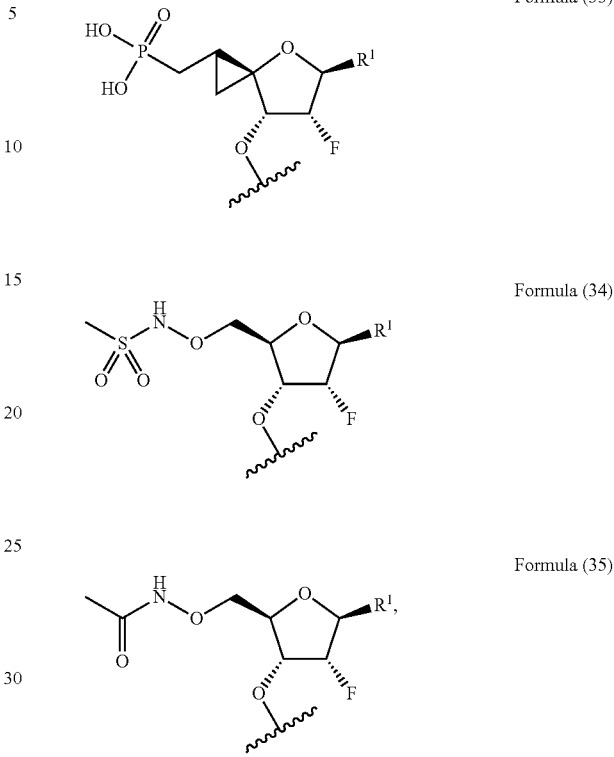

Formula (33)

Formula (34)

Formula (35)

wherein $R^1$ is a nucleobase, aryl, heteroaryl, or H; and (b) a short interfering nucleic acid (siNA). In some embodiments, the siNA comprises any of the sense strands disclosed herein. In some embodiments, the siNA comprises any of the antisense strand disclosed herein. In some embodiments, the siNA comprises a first nucleotide sequence selected from any one of SEQ ID NOs: 1-56, 103-158, and 205-260. In some embodiments, the siNA comprises a second nucleotide sequence selected from any one of SEQ ID NOs: 57-102, 159-204, and 261-306. In some embodiments, the siNA comprises a sense sequence selected from any one of SEQ ID NOs: 307-362 and 415-444. In some embodiments, the siNA comprises an antisense sequence selected from any one of SEQ ID NOs: 363-409, 445-533, and 536-539. In some embodiments, the siNA comprises a ds-siNA sequence selected from any one of ds-siNA-001 to ds-siNA-0178. In some embodiments, the siNA further comprises any of the phosphorylation blockers disclosed herein. In some embodiments, the siNA further comprises any of the conjugated moieties disclosed herein. In some embodiments, the siNA further comprises any of the destabilizing nucleotides disclosed herein. In some embodiments, the siNA further comprises any of the modified nucleotides disclosed herein.

Disclosed herein is a short-interfering nucleic acid (siNA) molecule comprising: (a) a 5'-stabilized end cap selected from the group consisting of Formulas (21A)-(35A), Formulas (29B)-(32B), Formulas (29AX)-(32AX), Formulas (29AY)-(32AY), Formulas (29BX)-(32BX), and Formulas (29BY)-(32BY):

Formula (21A)
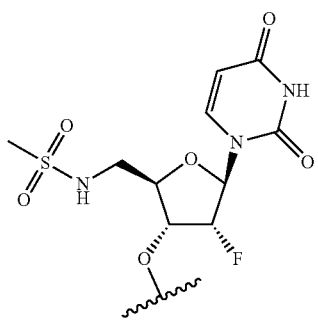
Formula (22A)
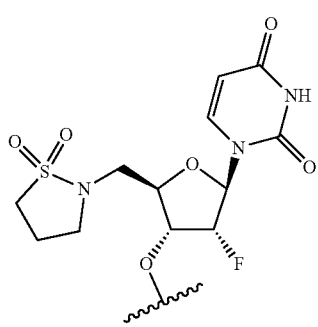
Formula (23A)
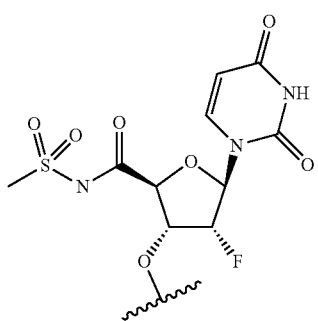
Formula (24A)
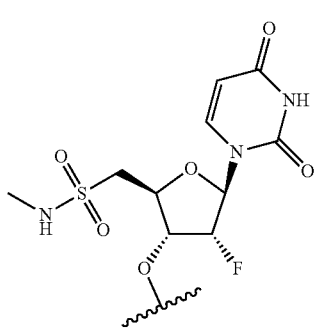
Formula (25A)
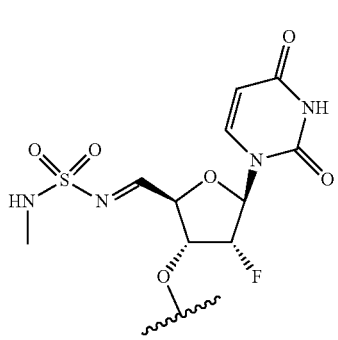
Formula (26A)
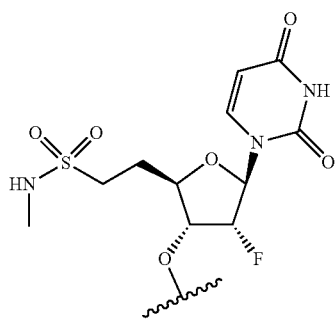
Formula (27A)
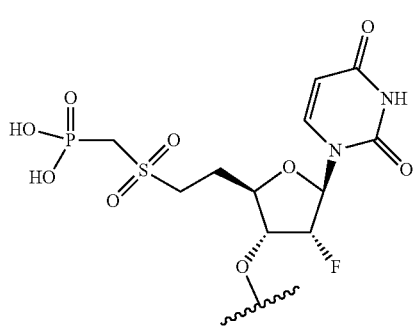
Formula (28A)
Formula (29A)
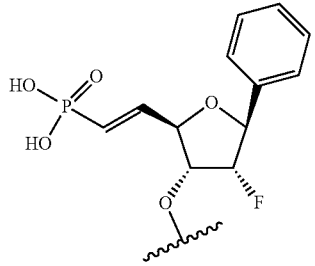
Formula (29AX)
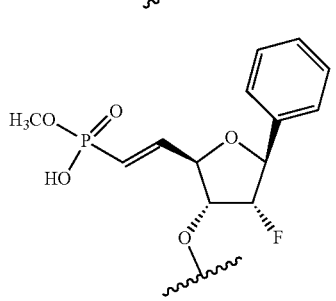

Formula (29AY)
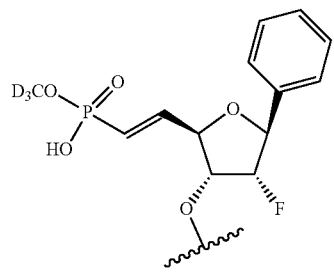
Formula (29B)
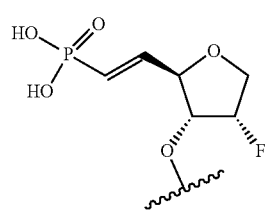
Formula (29BX)
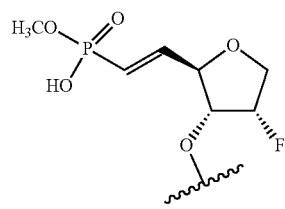
Formula (29BY)
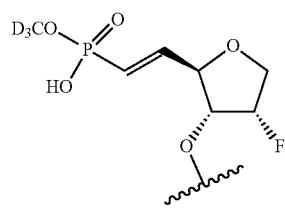
Formula (30A)
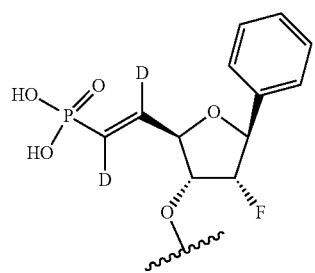
Formula (30AX)
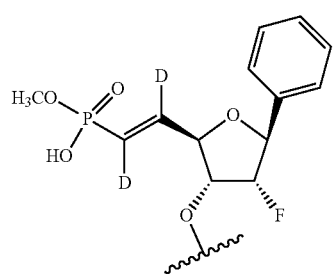
Formula (30AY)
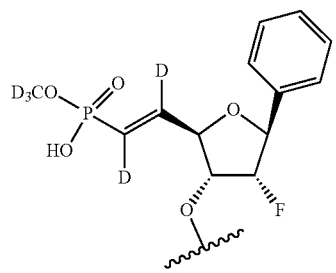
Formula (30B)
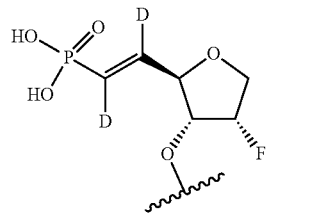
Formula (30BX)
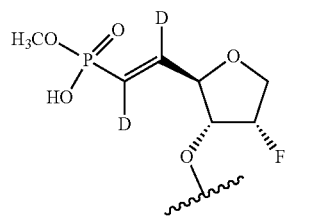
Formula (30BY)
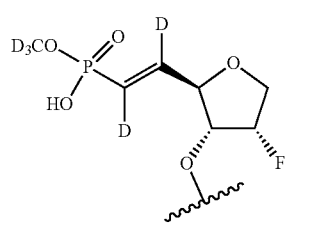
Formula (31A)
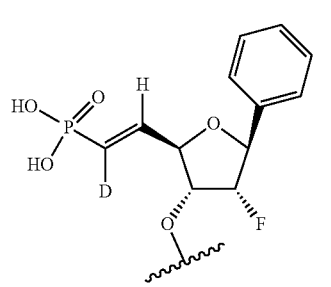
Formula (31AX)
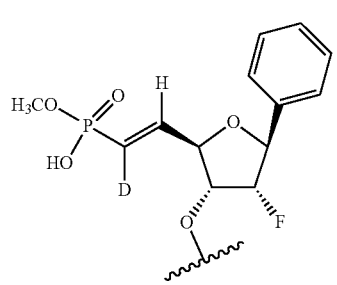

Formula (31AY)
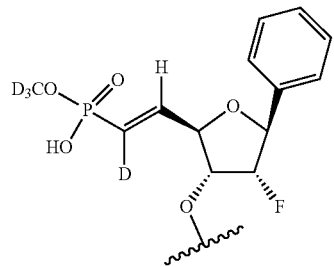
Formula (31B)
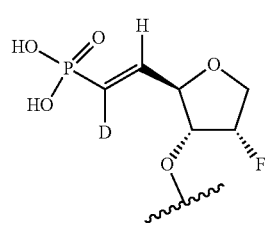
Formula (31BX)
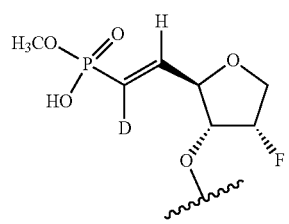
Formula (31BY)
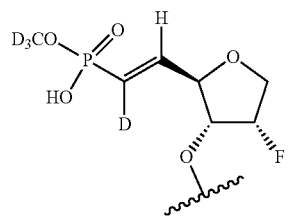
Formula (32A)
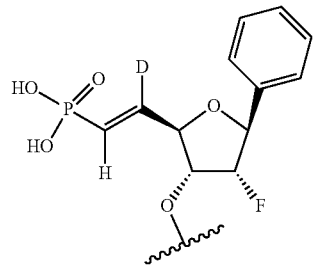
Formula (32AX)
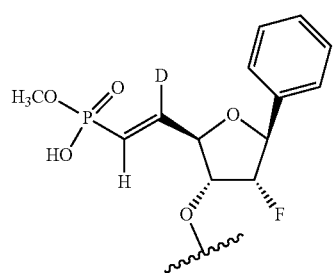
Formula (32AY)
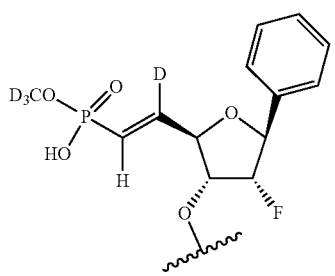
Formula (32B)
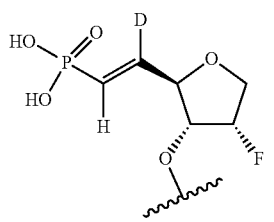
Formula (32BX)
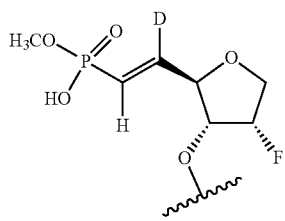
Formula (32BY)
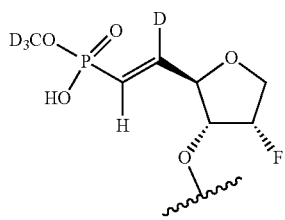
Formula (33A)
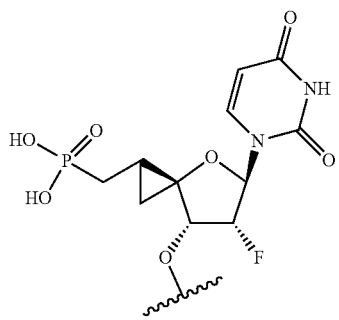
Formula (34A)
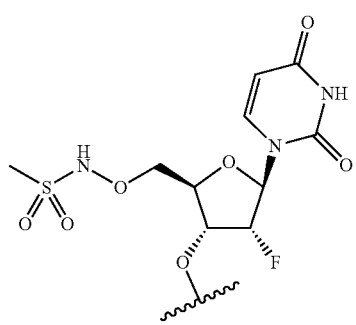

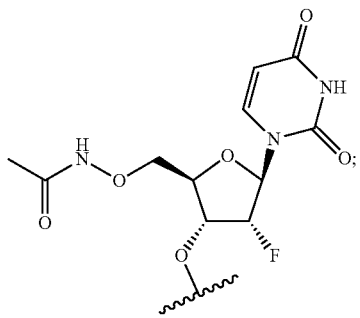

Formula (35A)

and (b) a short interfering nucleic acid (siNA). In some embodiments, the siNA comprises any of the sense strands disclosed herein. In some embodiments, the siNA comprises any of the antisense strand disclosed herein. In some embodiments, the siNA comprises a first nucleotide sequence selected from any one of SEQ ID NOs: 1-56, 103-158, and 205-260. In some embodiments, the siNA comprises a second nucleotide sequence selected from any one of SEQ ID NOs: 57-102, 159-204, and 261-306. In some embodiments, the siNA comprises a sense sequence selected from any one of SEQ ID NOs: 307-362 and 415-444. In some embodiments, the siNA comprises an antisense sequence selected from any one of SEQ ID NOs: 363-409, 445-533, and 536-539. In some embodiments, the siNA comprises a ds-siNA sequence selected from any one of ds-siNA-001 to ds-siNA-0178. In some embodiments, the siNA further comprises any of the phosphorylation blockers disclosed herein. In some embodiments, the siNA further comprises any of the conjugated moieties disclosed herein. In some embodiments, the siNA further comprises any of the destabilizing nucleotides disclosed herein. In some embodiments, the siNA further comprises any of the modified nucleotides disclosed herein.

Disclosed herein is a short interfering nucleic acid (siNA) molecule comprising: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence comprises a nucleotide sequence of any one SEQ ID NOs: 1-56, 103-158, and 205-260; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence comprises a nucleotide sequence of any one of SEQ ID NOs: 57-102, 159-204, and 261-306. In some embodiments, the siNA further comprises any of the 5' end caps disclosed herein. In some embodiments, the siNA further comprises any of the phosphorylation blockers disclosed herein. In some embodiments, the siNA further comprises any of the conjugated moieties disclosed herein. In some embodiments, the siNA further comprises any of the destabilizing nucleotides disclosed herein. In some embodiments, the siNA further comprises any of the modified nucleotides disclosed herein.

Disclosed herein is a interfering nucleic acid (siNA) molecule comprising: (a) a sense strand comprising a nucleotide sequence of any one of SEQ ID NOs: 307-362 and 415-444; and (b) an antisense strand comprising a nucleotide sequence of any one of SEQ ID NOs: 363-409, 445-533, and 536-539.

In some embodiments, any of the siNA disclosed herein further comprise a phosphorylation blocker.

In some embodiments, the phosphorylation blocker has the structure of Formula (IV):

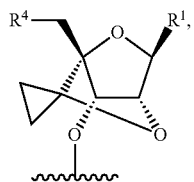

wherein
$R^1$ is a nucleobase,
$R^4$ is —O—$R^{30}$ or —$NR^{31}R^{32}$, $R^{30}$ is $C_1$-$C_8$ substituted or unsubstituted alkyl; and
$R^{31}$ and $R^{32}$ together with the nitrogen to which they are attached form a substituted or unsubstituted heterocyclic ring.

In some embodiments, $R^4$ is —$OCH_3$ or —$N(CH_2CH_2)_2O$.

In some embodiments, the phosphorylation blocker is attached to the 5' end of the sense strand.

In some embodiments, the phosphorylation blocker is attached to the 5' end of the sense strand via one or more linkers independently selected from a phosphodiester linker, phosphorothioate linker, and phosphorodithioate linker.

In some embodiments, the phosphorylation blocker is attached to the 3' end of the sense strand.

In some embodiments, the phosphorylation blocker is attached to the 3' end of the sense strand via one or more linkers independently selected from a phosphodiester linker, phosphorothioate linker, and phosphorodithioate linker.

In some embodiments, the phosphorylation blocker is attached to the 5' end of the antisense strand. In some embodiments, the phosphorylation blocker is attached to the 5' end of the antisense strand via one or more linkers independently selected from a phosphodiester linker, phosphorothioate linker, and phosphorodithioate linker. In some embodiments, the phosphorylation blocker is attached to the 3' end of the antisense strand. In some embodiments, the phosphorylation blocker is attached to the 3' end of the antisense strand via one or more linkers independently selected from a phosphodiester linker, phosphorothioate linker, and phosphorodithioate linker.

In some embodiments, any of the siNAs disclosed herein further comprise a conjugated moiety. In some embodiments, the conjugated moiety comprises a galactosamine. In some embodiments, the galactosamine is N-acetylgalactosamine (GalNAc) of Formula (VII):

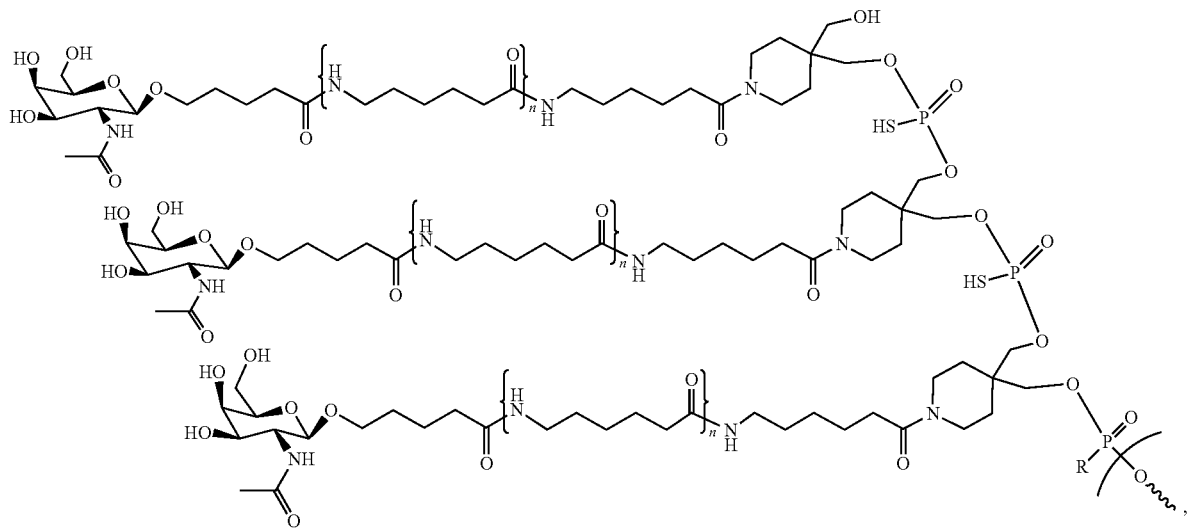

R = OH or SH wherein each n is independently 1 or 2. In some embodiments, the galactosamine is N-acetylgalactosamine (GalNAc) of Formula (VI):

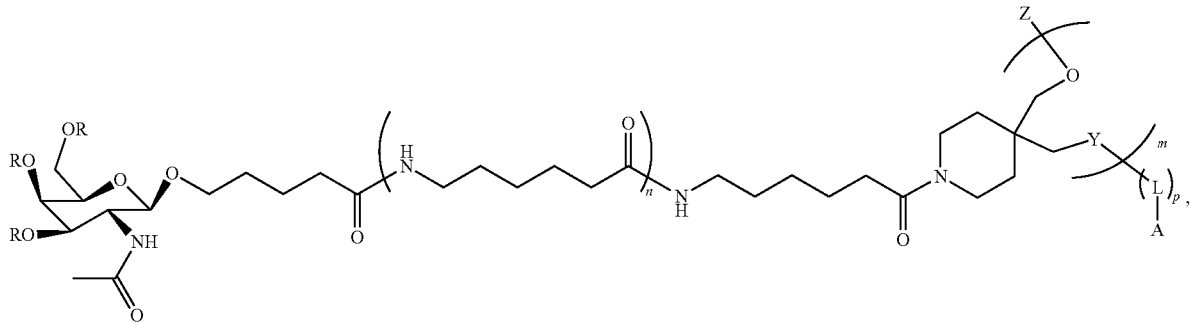

wherein
m is 1, 2, 3, 4, or 5;
each n is independently 1 or 2;
p is 0 or 1;
each R is independently H;
each Y is independently selected from —O—P(=O)(SH)—, —O—P(=O)(O)—, —O—P(=O)(OH)—, and —O—P(S)S—;
Z is H or a second protecting group;
either L is a linker or L and Y in combination are a linker; and
A is H, OH, a third protecting group, an activated group, or an oligonucleotide. In some embodiments, wherein A is an oligonucleotide. In some embodiments, A is 1-2 oligonucleotides. In some embodiments, the oligonucleotide is dTdT. In some embodiments, the galactosamine is attached to the 3' end of the sense strand. In some embodiments, the galactosamine is attached to the 3' end of the sense strand via one or more linkers independently selected from a phosphodiester linker, phosphorothioate linker, or phosphorodithioate linker. In some embodiments, the galactosamine is attached to the 5' end of the sense strand. In some embodiments, the galactosamine is attached to the 5' end of the sense strand via one or more linkers independently selected from a phosphodiester linker, phosphorothioate linker, or phosphorodithioate linker. In some embodiments, the galactosamine is attached to the 3' end of the antisense strand. In some embodiments, the galactosamine is attached to the 3' end of the antisense strand via one or more linkers independently selected from a phosphodiester linker, phosphorothioate linker, or phosphorodithioate linker. In some embodiments, the galactosamine is attached to the 5' end of the antisense strand. In some embodiments, the galactosamine is attached to the 5' end of the antisense strand via one or more linkers independently selected from a phosphodiester linker, phosphorothioate linker, or phosphorodithioate linker.

In some embodiments, any of the siNAs disclosed herein further comprise a 5'-stabilized end cap. In some embodiments, the 5'-stabilized end cap is a 5' vinyl phosphonate or deuterated 5' vinyl phosphonate. In some embodiments, the 5'-stabilized end cap has the structure of Formula (Ia):

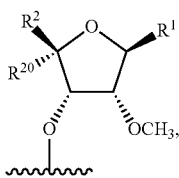

wherein
R¹ is a nucleobase, aryl, heteroaryl, or H,
R² is

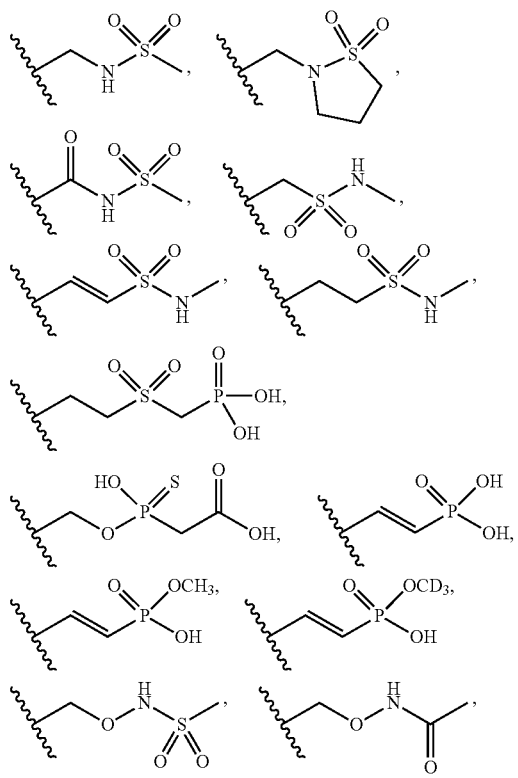

—CH=CD-Z, —CD=CH—Z, —CD=CD-Z, —(CR²¹R²²)$_n$—Z, or —(C$_2$-C$_6$ alkenylene)-Z and R²⁰ is hydrogen; or R² and R²⁰ together form a 3- to 7-membered carbocyclic ring substituted with —(CR²¹R²²)$_n$—Z or —(C$_2$-C$_6$ alkenylene)-Z;

n is 1, 2, 3, or 4;

Z is —ONR²³R²⁴, —OP(O)OH(CH$_2$)$_m$CO$_2$R²³, —OP(S)OH(CH$_2$)$_m$CO$_2$R²³, —P(O)(OH)$_2$, —P(O)(OH)(OCH$_3$), —P(O)(OH)(OCD$_3$), —SO$_2$(CH$_2$)$_m$P(O)(OH)$_2$, —SO$_2$NR²³R²⁵, —NR²³R²⁴, or —NR²³SO$_2$R²⁴;

R²¹ and R²² either are independently hydrogen or C$_1$-C$_6$ alkyl, or R²¹ and R²² together form an oxo group;

R²³ is hydrogen or C$_1$-C$_6$ alkyl;

R²⁴ is —SO$_2$R²⁵ or —C(O)R²⁵; or

R²³ and R²⁴ together with the nitrogen to which they are attached form a substituted or unsubstituted heterocyclic ring;

R²⁵ is C$_1$-C$_6$ alkyl; and m is 1, 2, 3, or 4. In some embodiments, the 5'-stabilized end cap has the structure of Formula (Ib):

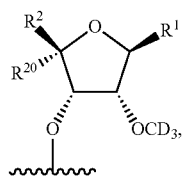

wherein
R¹ is a nucleobase, aryl, heteroaryl, or H,
R² is

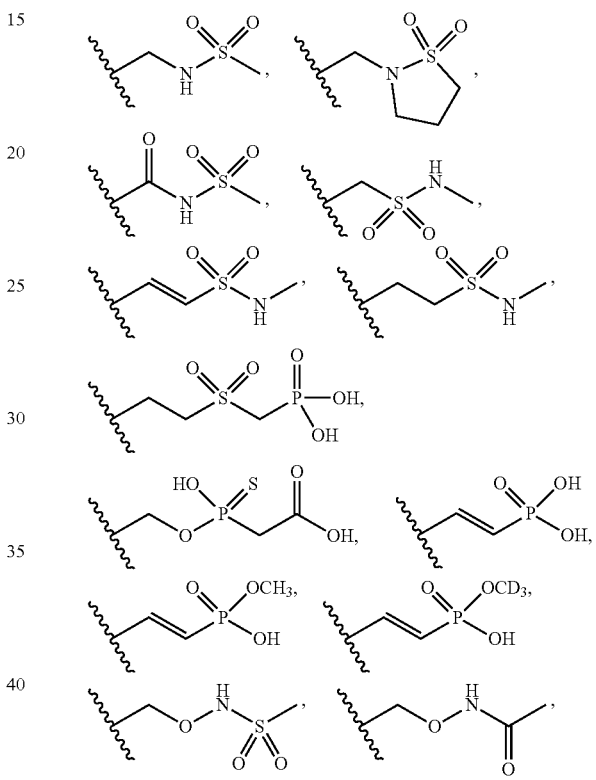

—CH=CD-Z, —CD=CH—Z, —CD=CD-Z, —(CR²¹R²²)$_n$—Z, or —(C$_2$-C$_6$ alkenylene)-Z and R²⁰ is hydrogen; or R² and R²⁰ together form a 3- to 7-membered carbocyclic ring substituted with —(CR²¹R²²)$_n$—Z or —(C$_2$-C$_6$ alkenylene)-Z;

n is 1, 2, 3, or 4;

Z is —ONR²³R²⁴, —OP(O)OH(CH$_2$)$_m$CO$_2$R²³, —OP(S)OH(CH$_2$)$_m$CO$_2$R²³, —P(O)(OH)$_2$, —P(O)(OH)(OCH$_3$), —P(O)(OH)(OCD$_3$), —SO$_2$(CH$_2$)$_m$P(O)(OH)$_2$, —SO$_2$NR²³R²⁵, —NR²³R²⁴, or —NR²³SO$_2$R²⁴;

R²¹ and R²² either are independently hydrogen or C$_1$-C$_6$ alkyl, or R²¹ and R²² together form an oxo group;

R²³ is hydrogen or C$_1$-C$_6$ alkyl;

R²⁴ is —SO$_2$R²⁵ or —C(O)R²⁵; or

R²³ and R²⁴ together with the nitrogen to which they are attached form a substituted or unsubstituted heterocyclic ring;

R²⁵ is C$_1$-C$_6$ alkyl; and m is 1, 2, 3, or 4. In some embodiments, the 5'-stabilized end cap has the structure of Formula (Ic):

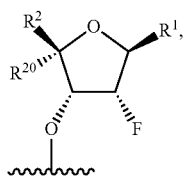

wherein
R¹ is a nucleobase, aryl, heteroaryl, or H,
R² is

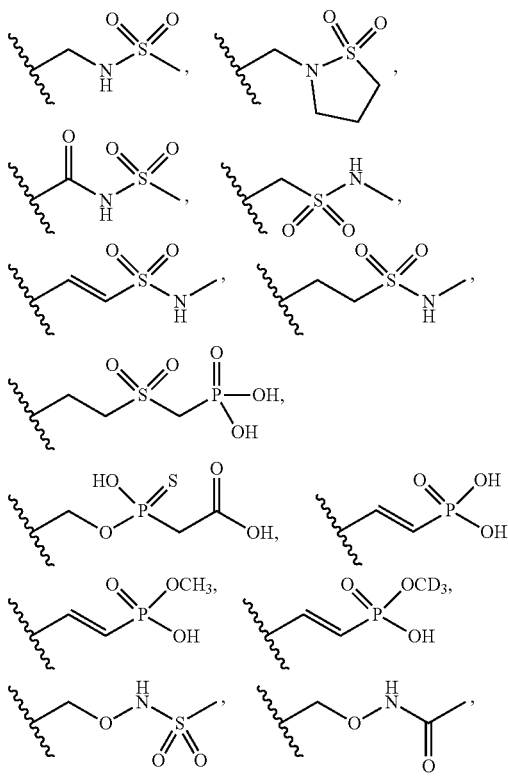

—CH═CD-Z, —CD═CH—Z, —CD═CD-Z, —(CR²¹R²²)$_n$—Z, or —(C$_2$-C$_6$ alkenylene)-Z and R²⁰ is hydrogen; or
R² and R²⁰ together form a 3- to 7-membered carbocyclic ring substituted with —(CR²¹R²²)$_n$—Z or —(C$_2$-C$_6$ alkenylene)-Z;
n is 1, 2, 3, or 4;
Z is —ONR²³R²⁴, —OP(O)OH(CH$_2$)$_m$CO$_2$R²³, —OP(S)OH(CH$_2$)$_m$CO$_2$R²³, —P(O)(OH)$_2$, —P(O)(OH)(OCH$_3$), —P(O)(OH)(OCD$_3$), —SO$_2$(CH$_2$)$_m$P(O)(OH)$_2$, —SO$_2$NR²³R²⁵, —NR²³R²⁴, or —NR²³SO$_2$R²⁴;
R²¹ and R²² either are independently hydrogen or C$_1$-C$_6$ alkyl, or R²¹ and R²² together form an oxo group;
R²³ is hydrogen or C$_1$-C$_6$ alkyl;
R²⁴ is —SO$_2$R²⁵ or —C(O)R²⁵; or
R²³ and R²⁴ together with the nitrogen to which they are attached form a substituted or unsubstituted heterocyclic ring;
R²⁵ is C$_1$-C$_6$ alkyl; and
m is 1, 2, 3, or 4. In some embodiments, R¹ is an aryl. In some embodiments, the aryl is a phenyl. In some embodiments, the 5'-stabilized end cap is selected from the group consisting of Formula (1) to Formula (15), Formula (9X) to Formula (12X), and Formula (9Y) to Formula (12Y):

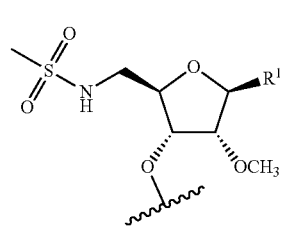

Formula (1)

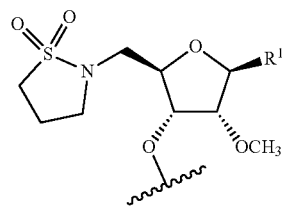

Formula (2)

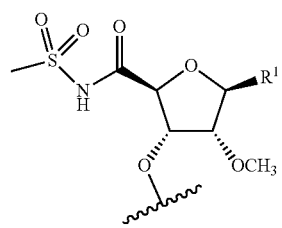

Formula (3)

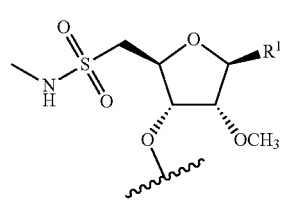

Formula (4)

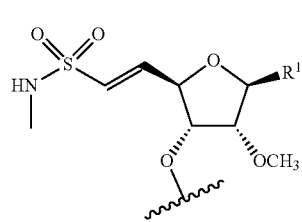

Formula (5)

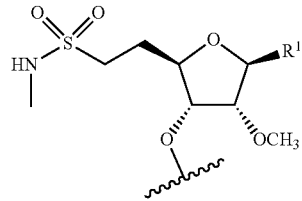

Formula (6)

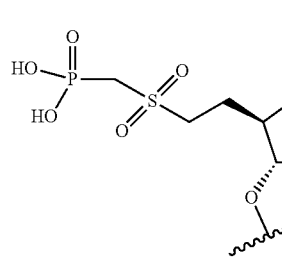

Formula (7)

Formula (8)
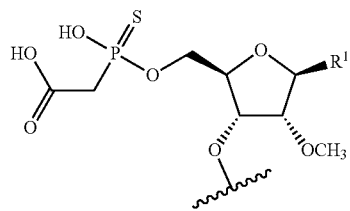
Formula (9)
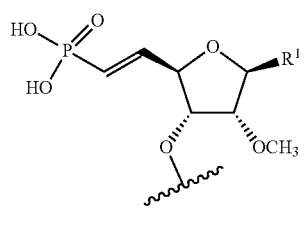
Formula (9X)
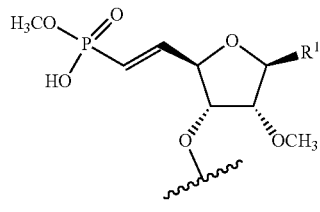
Formula (9Y)
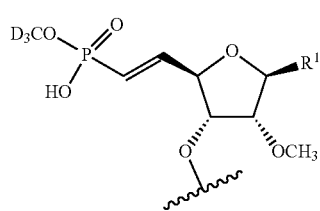
Formula (10)
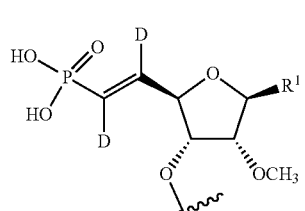
Formula (10X)
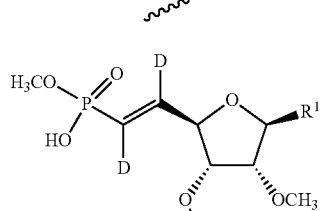
Formula (10Y)
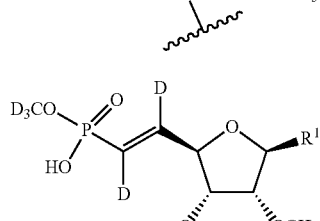
Formula (11)
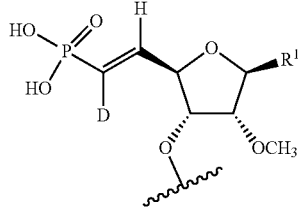
Formula (11X)
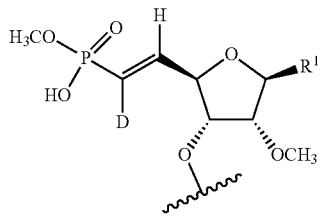
Formula (11Y)
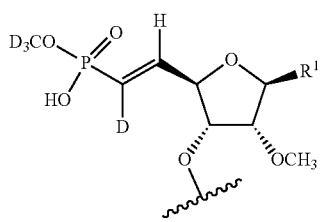
Formula (12)
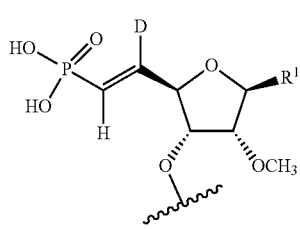
Formula (12X)
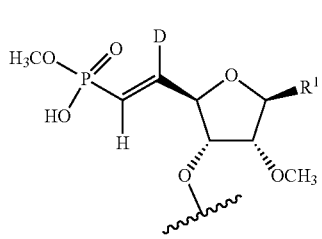
Formula (12Y)
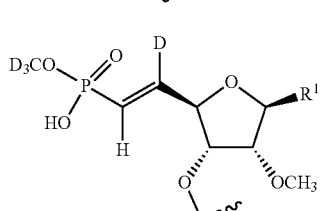
Formula (13)
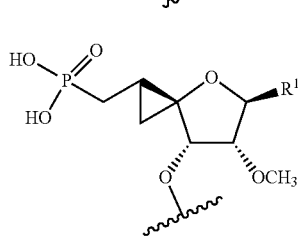

Formula (14)
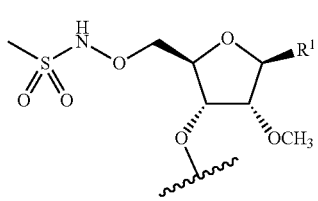
Formula (15)
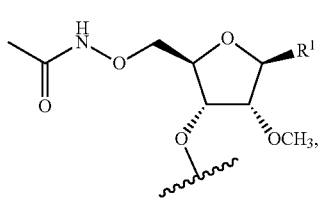
independently is a nucleobase, aryl, heteroaryl, or H. In some embodiments, the 5'-stabilized end cap is selected from the group consisting of Formulas (1A)-(15A), Formulas (9B)-(12B), Formulas (9AX)-(12AX), Formulas (9AY)-(12AY), Formulas (9BX)-(12BX), and Formulas (9BY)-(12BY):
Formula (1A)
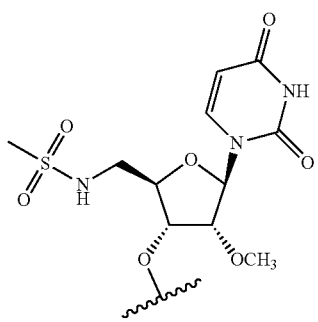
Formula (2A)
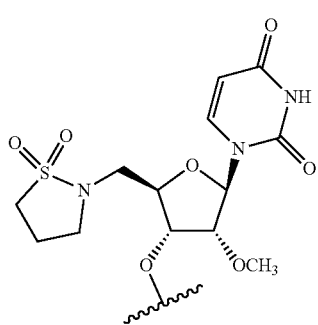
Formula (3A)
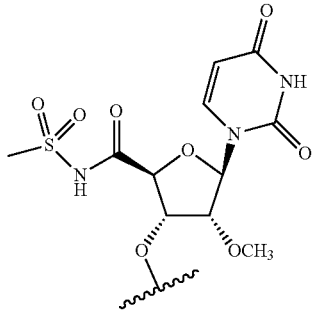
Formula (4A)
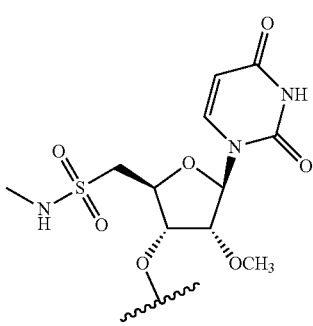
Formula (5A)
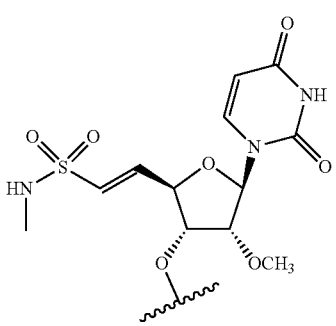
Formula (6A)
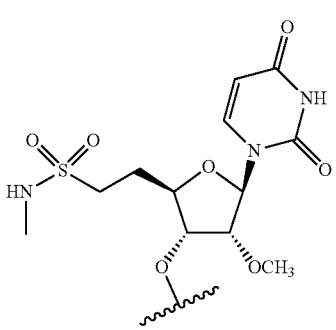
Formula (7A)
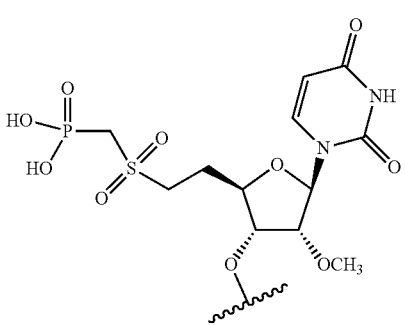
Formula (8A)
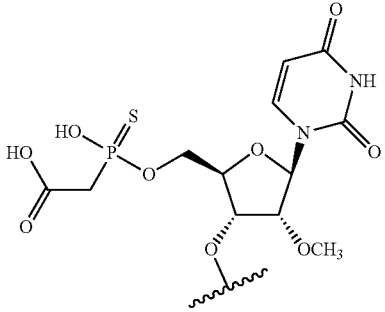

Formula (9A)
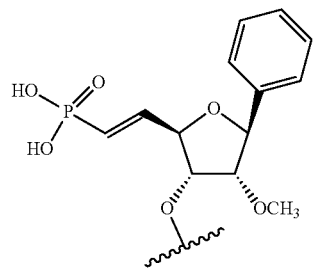
Formula (9AX)
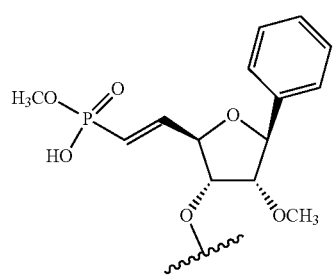
Formula (9AY)
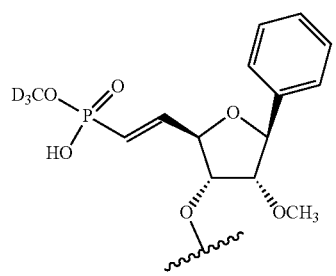
Formula (9B)
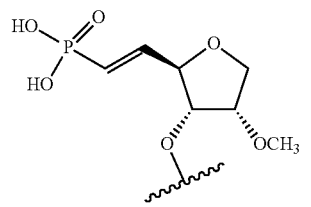
Formula (9BX)
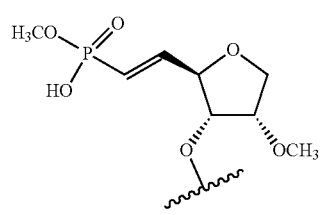
Formula (9BY)
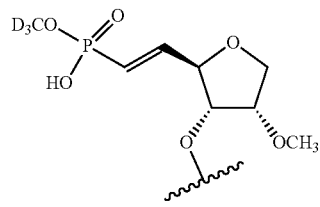
Formula (10A)
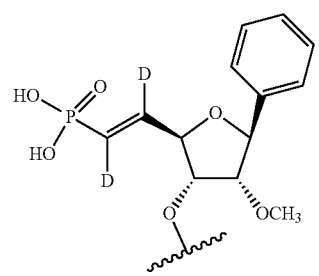
Formula (10AX)
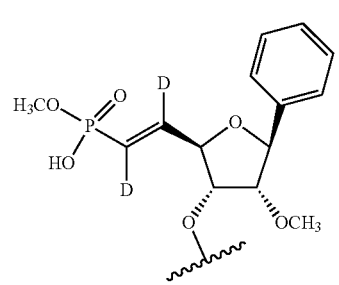
Formula (10AY)
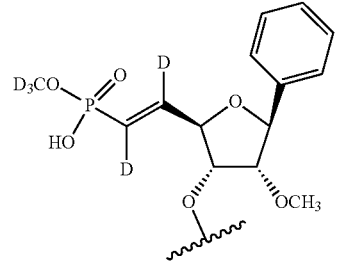
Formula (10B)
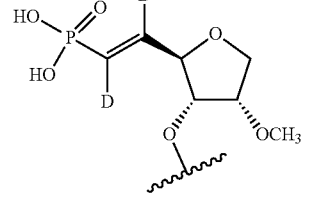
Formula (10BX)
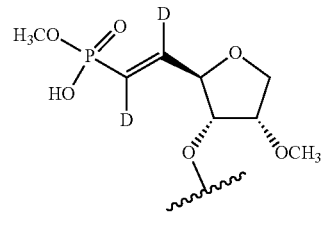
Formula (10BY)
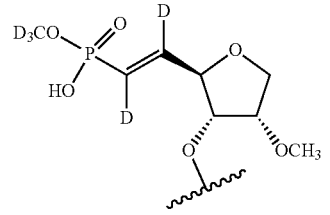

Formula (11A)
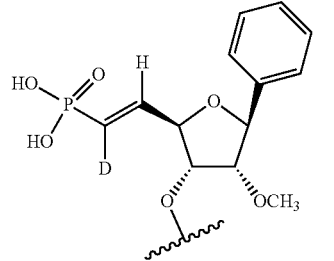
Formula (11AX)
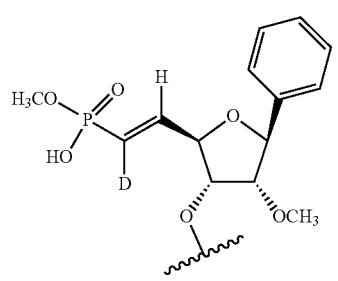
Formula (11AY)
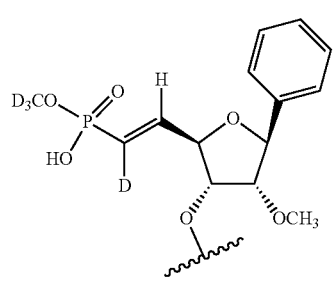
Formula (11B)
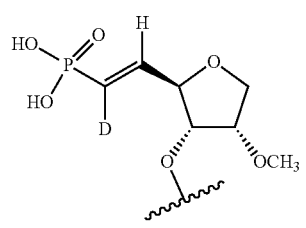
Formula (11BX)
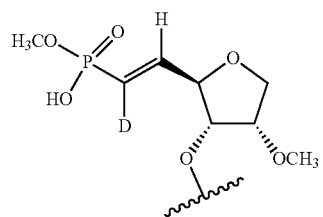
Formula (11BY)
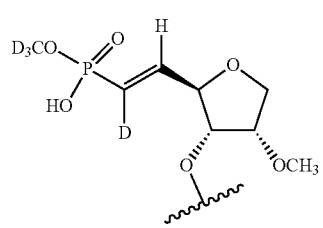
Formula (12A)
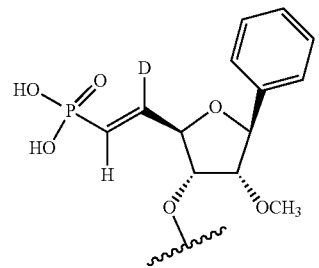
Formula (12AX)
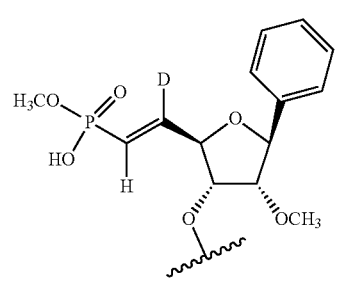
Formula (12AY)
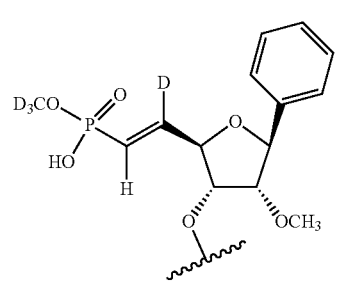
Formula (12B)
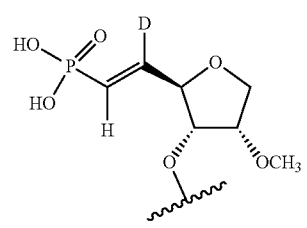
Formula (12BX)
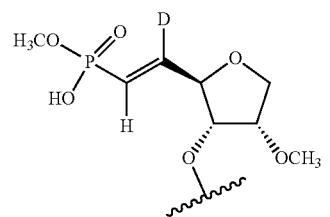
Formula (12BY)
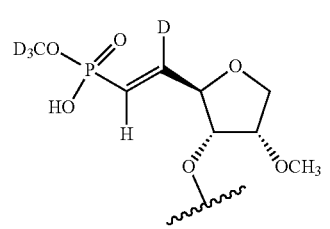

Formula (13A)
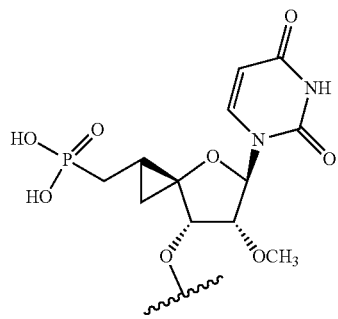
Formula (14A)
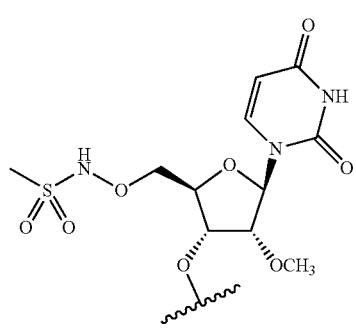
Formula (15A)
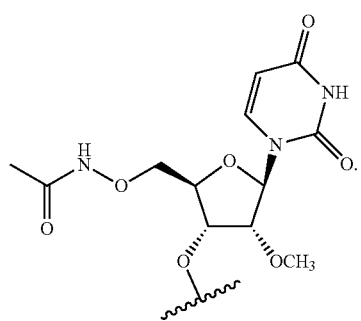
In some embodiments, the 5'-stabilized end cap is selected from the group consisting of Formula (21) to Formula (35):
Formula (21)
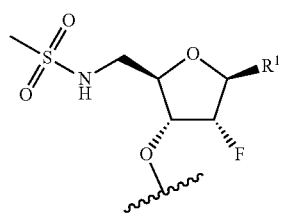
Formula (22)
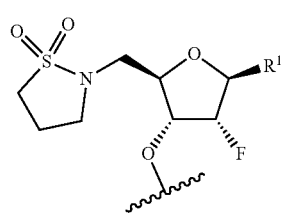
Formula (23)
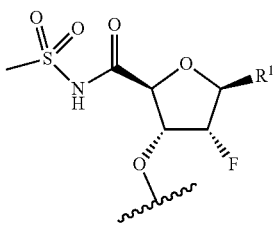
Formula (24)
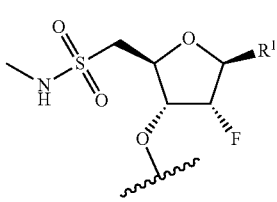
Formula (25)
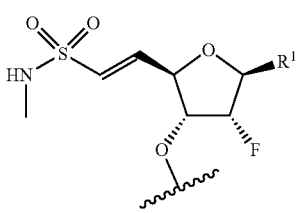
Formula (26)
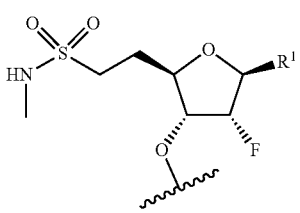
Formula (27)
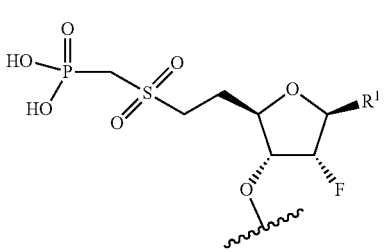
Formula (28)
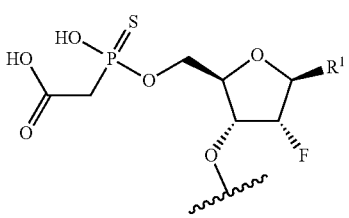
Formula (29)
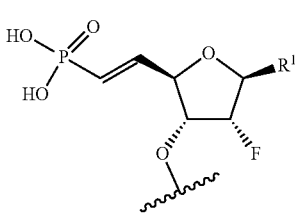

Formula (30)
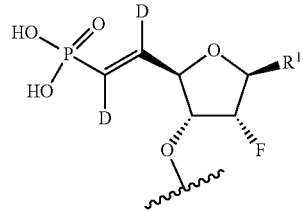
Formula (31)
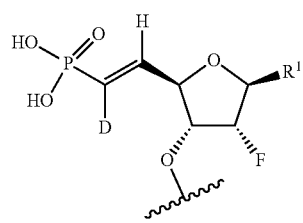
Formula (32)
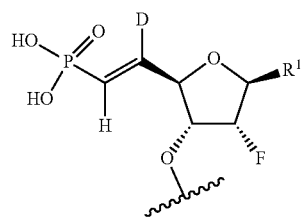
Formula (33)
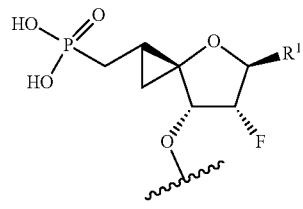
Formula (34)
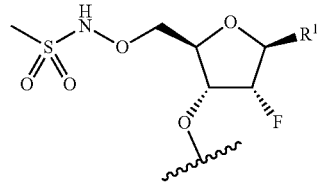
Formula (35)
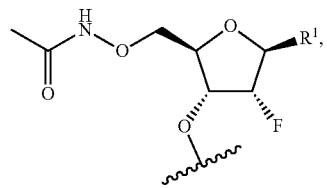
wherein $R^1$ is a nucleobase, aryl, heteroaryl, or H. In some embodiments, the 5'-stabilized end cap is selected from the group consisting of Formulas (21A)-(35A), Formulas (29B)-(32B), Formulas (29AX)-(32AX), Formulas (29AY)-(32AY), Formulas (29BX)-(32BX), and Formulas (29BY)-(32BY):
Formula (21A)
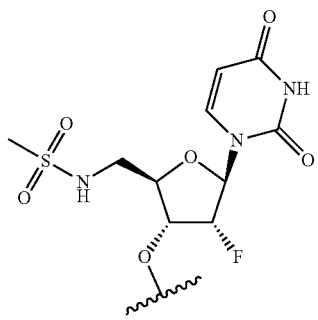
Formula (22A)
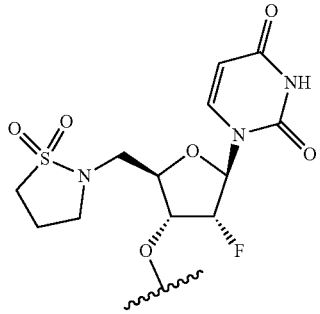
Formula (23A)
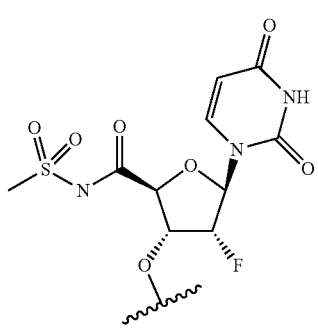
Formula (24A)
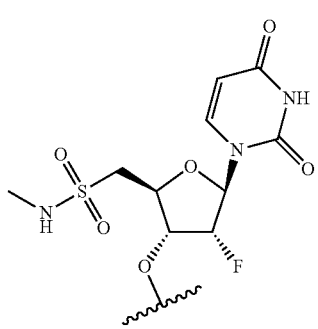
Formula (25A)
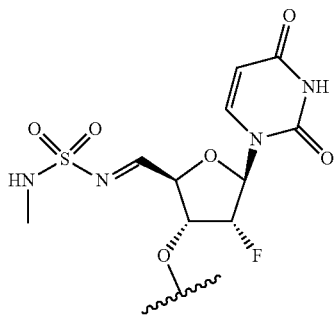

Formula (26A)
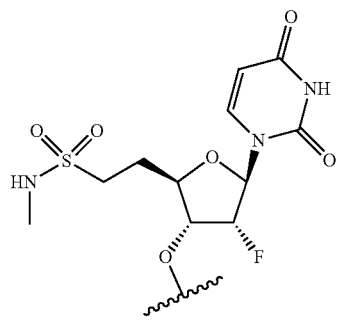
Formula (27A)
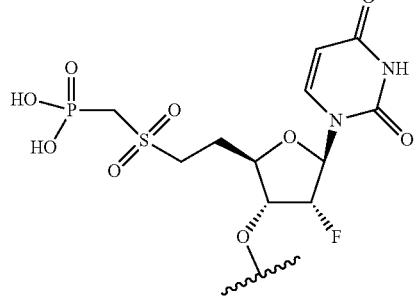
Formula (28A)
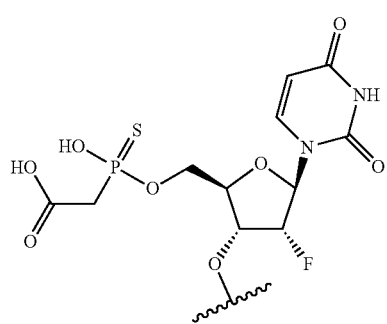
Formula (29A)
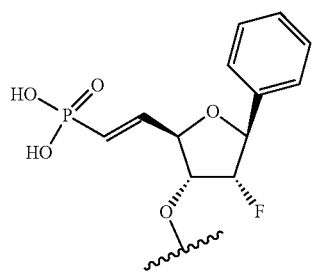
Formula (29AX)
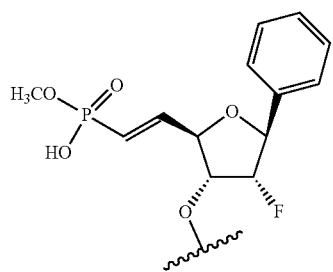
Formula (29AY)
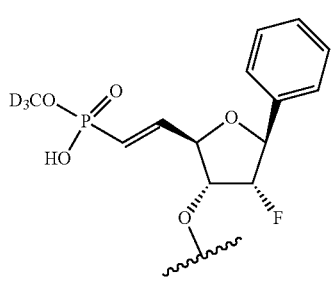
Formula (29B)
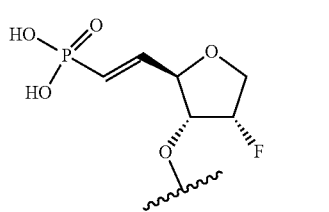
Formula (29BX)
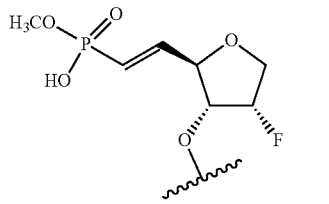
Formula (29BY)
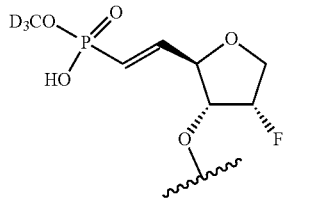
Formula (30A)
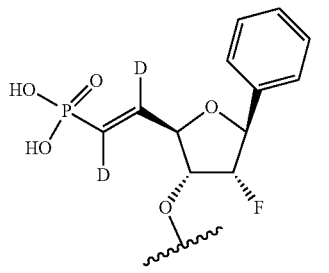
Formula (30AX)
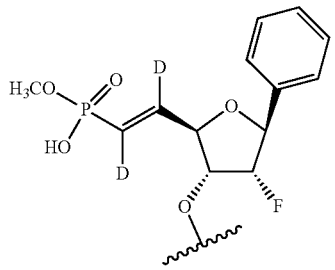

Formula (30AY)
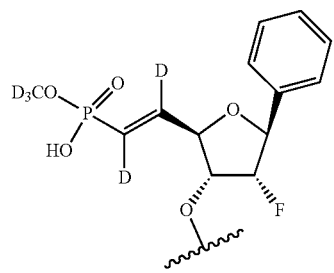
Formula (30B)
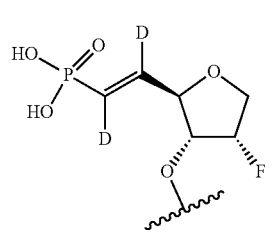
Formula (30BX)
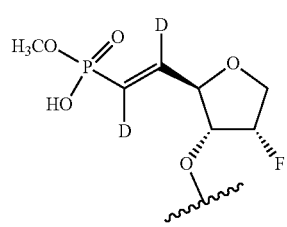
Formula (30BY)
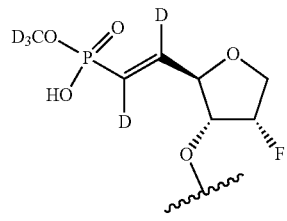
Formula (31A)
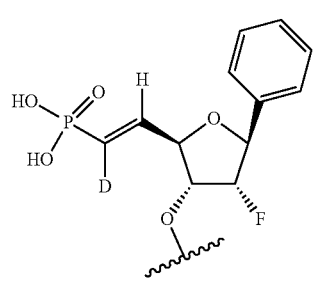
Formula (31AX)
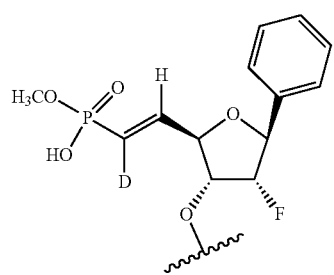
Formula (31AY)
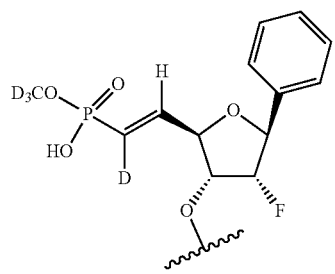
Formula (31B)
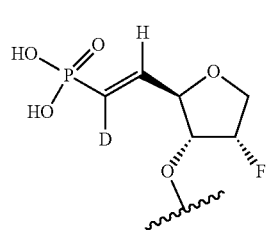
Formula (31BX)
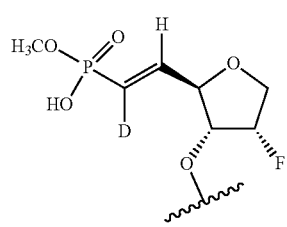
Formula (31BY)
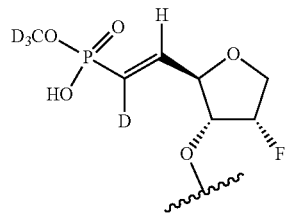
Formula (32A)
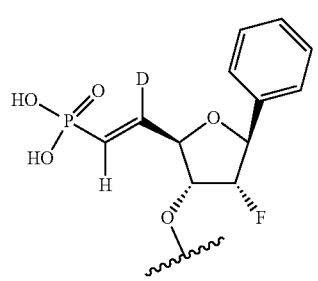
Formula (32AX)
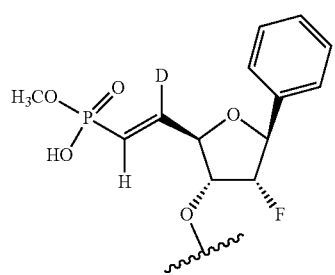

Formula (32AY)

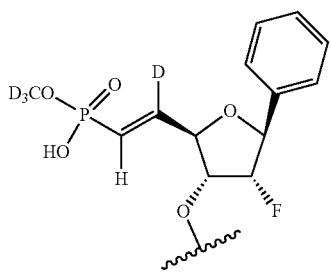

Formula (32B)

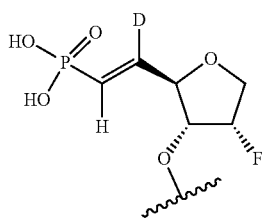

Formula (32BX)

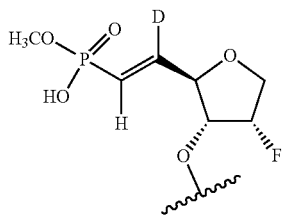

Formula (32BY)

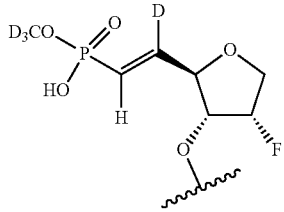

Formula (33A)

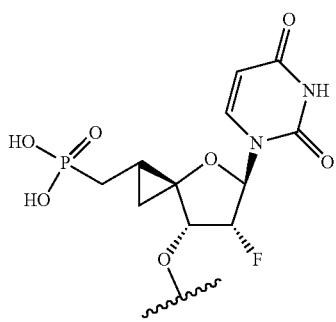

Formula (34A)

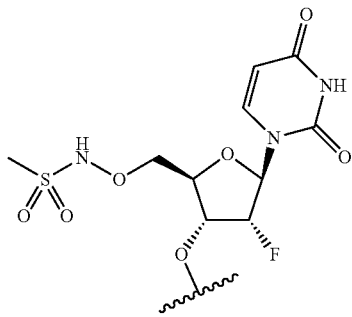

Formula (35A)

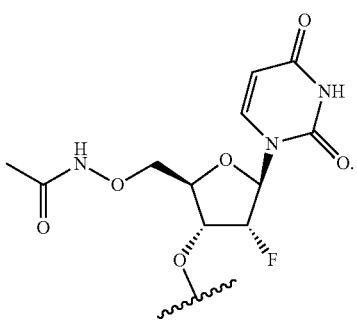

In some embodiments, the 5'-stabilized end cap is attached to the 5' end of the antisense strand. In some embodiments, the 5'-stabilized end cap is attached to the 5' end of the antisense strand via one or more linkers independently selected from a phosphodiester linker, phosphorothioate linker, or phosphorodithioate linker. In some embodiments, the 5'-stabilized end cap is attached to the 5' end of the sense strand. In some embodiments, the 5'-stabilized end cap is attached to the 5' end of the sense strand via one or more linkers independently selected from a phosphodiester linker, phosphorothioate linker, or phosphorodithioate linker.

In some embodiments, any of the siNAs, sense strands, first nucleotide sequences, antisense strands, or second nucleotide sequences disclosed herein further comprise at least one thermally destabilizing nucleotides. In some embodiments, any of the antisense strands disclosed herein further comprise at least one thermally destabilizing nucleotide selected from:

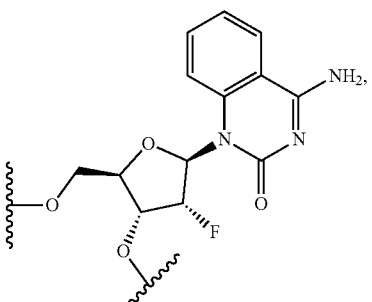

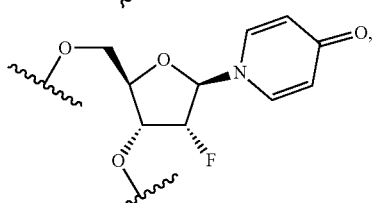

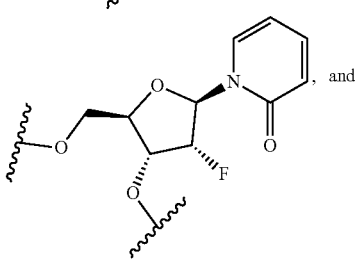

, and

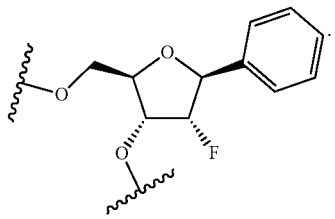

In some embodiments, any of the sense strands disclosed herein comprise at least one thermally destabilizing nucleotide selected from:

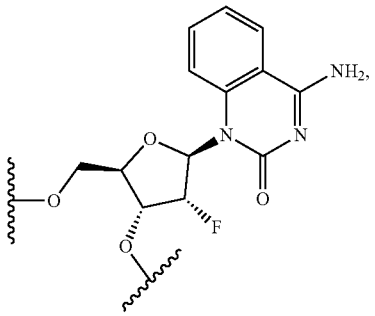

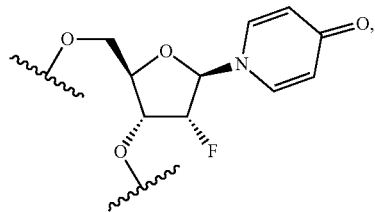

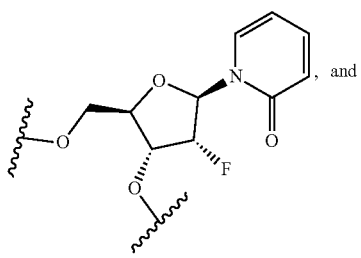

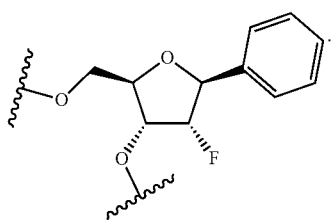

In some embodiments, any of the first nucleotide sequences disclosed herein further comprise at least one thermally destabilizing nucleotide selected

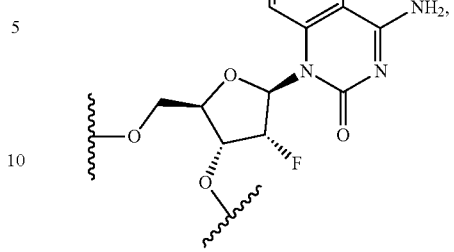

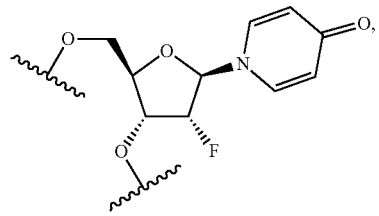

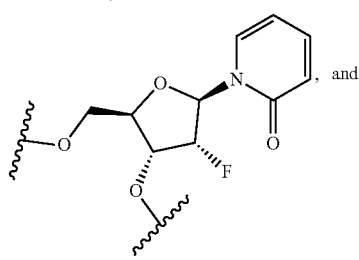

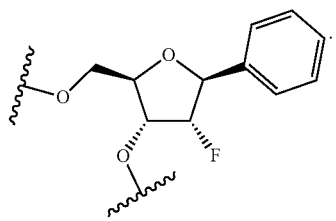

In some embodiments, any of the second nucleotide sequences disclosed herein further comprise at least one thermally destabilizing nucleotide selected from:

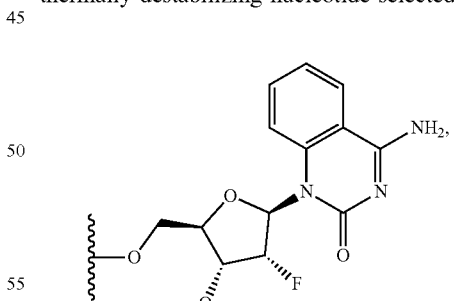

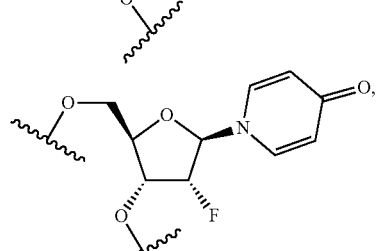

-continued

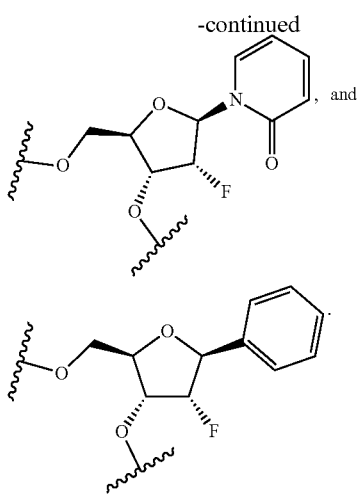

In some embodiments, any of the modified nucleotides disclosed herein is a thermally destabilizing nucleotide.

In some embodiments, any of the siNAs disclosed herein specifically downregulate or reduce expression of a target gene. In some embodiments, the target gene is a viral gene. In some embodiments, the viral gene is from a DNA virus. In some embodiments, the DNA virus is a double-stranded DNA (dsDNA) virus. In some embodiments, the dsDNA virus is a hepadnavirus. In some embodiments, the hepadnavirus is a hepatitis B virus (HBV). In some embodiments, the HBV is selected from HBV genotypes A-J. In some embodiments, the target gene is selected from the S gene or X gene of the HBV.

In some embodiments, the second nucleotide sequence is at least about 60%, 65%, 70%, 75%, 80%, 85%, 90%, 95%, or 100% complementary to 15 to 30 nucleotides within positions 200-720 or 1100-1700 of SEQ ID NO: 410. In some embodiments, the second nucleotide sequence is at least about 60%, 65%, 70%, 75%, 80%, 85%, 90%, 95%, or 100% complementary to 15 to 30 nucleotides within positions 200-280, 300-445, 460-510, 650-720, 1170-1220, 1250-1300, or 1550-1630 of SEQ ID NO: 410. In some embodiments, the second nucleotide sequence is at least about 60%, 65%, 70%, 75%, 80%, 85%, 90%, 95%, or 100% complementary to 15 to 30 nucleotides within positions 200-230, 250-280, 300-330, 370-400, 405-445, 460-500, 670-700, 1180-1210, 1260-1295, 1520-1550, or 1570-1610 of SEQ ID NO: 410. In some embodiments, the second nucleotide sequence is at least about 60%, 65%, 70%, 75%, 80%, 85%, 90%, 95%, or 100% complementary to 15 to 30 nucleotides starting at position 203, 206, 254, 305, 375, 409, 412, 415, 416, 419, 462, 466, 467, 674, 676, 1182, 1262, 1263, 1268, 1526, 1577, 1578, 1580, 1581, 1583, or 1584 of SEQ ID NO: 410.

In some embodiments, the first nucleotide sequence is at least about 60%, 65%, 70%, 75%, 80%, 85%, 90%, 95%, or 100% identical to 15 to 30 nucleotides within positions 200-720 or 1100-1700 of SEQ ID NO: 410. In some embodiments, the first nucleotide sequence is at least about 60%, 65%, 70%, 75%, 80%, 85%, 90%, 95%, or 100% identical to 15 to 30 nucleotides within positions 200-280, 300-445, 460-510, 650-720, 1170-1220, 1250-1300, or 1550-1630 of SEQ ID NO: 410. In some embodiments, the first nucleotide sequence is at least about 60%, 65%, 70%, 75%, 80%, 85%, 90%, 95%, or 100% identical to 15 to 30 nucleotides within positions 200-230, 250-280, 300-330, 370-400, 405-445, 460-500, 670-700, 1180-1210, 1260-1295, 1520-1550, or 1570-1610 of SEQ ID NO: 410. In some embodiments, the first nucleotide sequence is at least about 60%, 65%, 70%, 75%, 80%, 85%, 90%, 95%, or 100% identical to 15 to 30 nucleotides starting at position 203, 206, 254, 305, 375, 409, 412, 415, 416, 419, 462, 466, 467, 674, 676, 1182, 1262, 1263, 1268, 1526, 1577, 1578, 1580, 1581, 1583, or 1584 of SEQ ID NO: 410.

In some embodiments, the first nucleotide sequence comprises a nucleotide sequence of any one SEQ ID NOs: 1-56, 103-158, and 205-260.

In some embodiments, the second nucleotide sequence comprises a nucleotide sequence of any one of SEQ ID NOs: 57-102, 159-204, and 261-306.

In some embodiments, the sense strand comprises a nucleotide sequence of any one of SEQ ID NOs: 307-362 and 415-444.

In some embodiments, the antisense strand comprises a nucleotide sequence of any one of SEQ ID NOs: 363-409, 445-533, and 536-539.

In some embodiments, at least one end of the siNA is a blunt end.

In some embodiments, at least one end of the siNA comprises an overhang, wherein the overhang comprises at least one nucleotide.

In some embodiments, both ends of the siNA comprise an overhang, wherein the overhang comprises at least one nucleotide.

In some embodiments, the siNA is selected from ds-siNA-001 to ds-siNA-0178.

In some embodiments, at least one 2'-fluoro nucleotide or 2'-O-methyl nucleotide is a 2'-fluoro or 2-O-methyl nucleotide mimic of Formula (V):

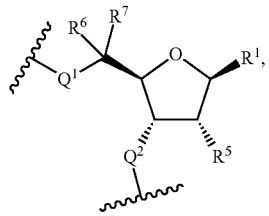

wherein
$R^1$ is independently a nucleobase, aryl, heteroaryl, or H, $Q^1$ and $Q^2$ are independently S or O,
$R^5$ is independently —OCD$_3$, —F, or —OCH$_3$, and
$R^6$ and $R^7$ are independently H, D, or CD3.

In some embodiments, the 2'-fluoro or 2'-O-methyl nucleotide mimic is a nucleotide mimic of Formula (16)-Formula (20):

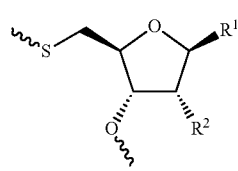

Formula (16)

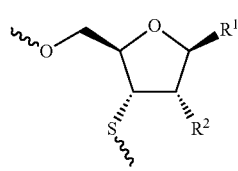

Formula (17)

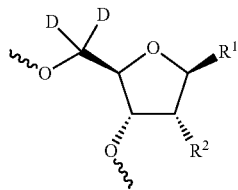

Formula (18)

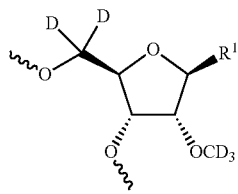

Formula (19)

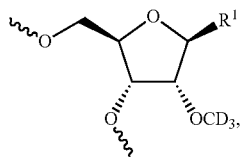

Formula (20)

wherein R¹ is a nucleobase and R² is independently F or —OCH₃.

Further disclosed herein are compositions comprising any of the siNAs disclosed herein. In some embodiments, the siNA targets an S gene of HBV. In some embodiments, the siNA specifically downregulates or reduces expression of the S gene of HBV. In some embodiments, the siNA targets an X gene of HBV. In some embodiments, the siNA specifically downregulates or reduces expression of the X gene of HBV. In some embodiments, the siNA comprises a first nucleotide sequence. In some embodiments, the first nucleotide sequence comprises a nucleotide sequence of any one SEQ ID NOs: 1-56, 103-158, and 205-260. In some embodiments, the siNA comprises a second nucleotide sequence. In some embodiments, the second nucleotide sequence comprises a nucleotide sequence of any one of SEQ ID NOs: 57-102, 159-204, and 261-306. In some embodiments, the siNA comprises a sense strand. In some embodiments, the sense strand comprises a nucleotide sequence of any one of SEQ ID NOs: 307-362 and 415-444. In some embodiments, the siNA comprises an antisense strand. In some embodiments, the antisense strand comprises a nucleotide sequence of any one of SEQ ID NOs: 363-409, 445-533, and 536-539. In some embodiments, the siNA further comprises any of the 5' end caps disclosed herein. In some embodiments, the siNA further comprises any of the phosphorylation blockers disclosed herein. In some embodiments, the siNA further comprises any of the conjugated moieties disclosed herein. In some embodiments, the siNA further comprises any of the destabilized nucleotides disclosed herein. In some embodiments, the siNA further comprises any of the modified nucleotides disclosed herein.

Further disclosed herein are compositions comprising 2, 3, 4, 5, 6, 7, 8, 9, 10 or more of any of the siNAs disclosed herein. In some embodiments, at least 1, 2, 3, 4, 5, or more siNAs target an S gene of HBV. In some embodiments, at least 1, 2, 3, 4, 5, or more siNAs specifically downregulate or reduce expression of the S gene of HBV. In some embodiments, at least 1, 2, 3, 4, 5, or more siNAs target an X gene of HBV. In some embodiments, at least 1, 2, 3, 4, 5, or more siNAs specifically downregulate or reduce expression of the X gene of HBV. In some embodiments, the siNA comprises a first nucleotide sequence. In some embodiments, the first nucleotide sequence comprises a nucleotide sequence of any one SEQ ID NOs: 1-56, 103-158, and 205-260. In some embodiments, the siNA comprises a second nucleotide sequence. In some embodiments, the second nucleotide sequence comprises a nucleotide sequence of any one of SEQ ID NOs: 57-102, 159-204, and 261-306. In some embodiments, the siNA comprises a sense strand. In some embodiments, the sense strand comprises a nucleotide sequence of any one of SEQ ID NOs: 307-362 and 415-444. In some embodiments, the siNA comprises an antisense strand. In some embodiments, the antisense strand comprises a nucleotide sequence of any one of SEQ ID NOs: 363-409, 445-533, and 536-539. In some embodiments, the siNA further comprises any of the 5' end caps disclosed herein. In some embodiments, the siNA further comprises any of the phosphorylation blockers disclosed herein. In some embodiments, the siNA further comprises any of the conjugated moieties disclosed herein. In some embodiments, the siNA further comprises any of the destabilized nucleotides disclosed herein. In some embodiments, the siNA further comprises any of the modified nucleotides disclosed herein.

In some embodiments, any of the compositions disclosed herein further comprise an additional HBV treatment agent. In some embodiments, the additional HBV treatment agent is selected from a nucleotide analog, nucleoside analog, a capsid assembly modulator (CAM), a recombinant interferon, an entry inhibitor, a small molecule immunomodulator and oligonucleotide therapy. In some embodiments, the oligonucleotide therapy is an additional siNA. In some embodiments, the additional siNA is selected from any of ds-siNA-001 to ds-siNA-0178. In some embodiments, the oligonucleotide therapy is an antisense oligonucleotide (ASO), NAPs, or STOPs. In some embodiments, the ASO is ASO 1 or ASO 2. In some embodiments, the ASO specifically targets the S gene of HBV. In some embodiments, the ASO specifically targets the X gene of HBV. In some embodiments, the additional HBV treatment agent is selected from HBV STOPS™ ALG-010133, HBV CAM ALG-000184, ASO 1, recombinant interferon alpha 2b, IFN-a, PEG-IFN-a-2a, lamivudine, telbivudine, adefovir dipivoxil, clevudine, entecavir, tenofovir alafenamide, tenofovir disoproxil, NVR3-778, BAY41-4109, JNJ-632, JNJ-3989 (ARO-HBV), RG6004, GSK3228836, REP-2139, REP-2165, AB-729, VIR-2218, RG6346 (DCR-HBVS), JNJ-6379, GLS4, ABI-HO731, JNJ-440, NZ-4, RG7907, EDP-514, AB-423, AB-506, ABI-H03733 and ABI-H2158.

In some embodiments, any of the compositions disclosed herein further comprise a liver disease treatment agent. In some embodiments, the liver disease treatment agent is selected from a peroxisome proliferator-activator receptor (PPAR) agonist, farnesoid X receptor (FXR) agonist, lipid-altering agent, and incretin-based therapy. In some embodiments, the PPAR agonist is selected from a PPARα agonist, dual PPARα/δ agonist, PPARγ agonist, and dual PPARα/γ agonist. In some embodiments, the dual PPARα agonist is a fibrate. In some embodiments, the PPARα/δ agonist is elafibranor. In some embodiments, the PPARγ agonist is a thiazolidinedione (TZD). In some embodiments, TZD is pioglitazone. In some embodiments, the dual PPARα/γ agonist is saroglitazar. In some embodiments, the FXR agonist is obeticholic acis (OCA). In some embodiments, the lipid-altering agent is aramchol. In some embodiments, the incretin-based therapy is a glucagon-like peptide 1 (GLP-1) receptor agonist or dipeptidyl peptidase 4 (DPP-4) inhibitor.

In some embodiments, the GLP-1 receptor agonist is exenatide or liraglutide. In some embodiments, the DPP-4 inhibitor is sitagliptin or vildagliptin.

Further disclosed herein are methods of treating a disease in a subject in need thereof, comprising administering to the subject any of the siNAs disclosed herein. In some embodiments, the siNA comprises a first nucleotide sequence. In some embodiments, the first nucleotide sequence comprises a nucleotide sequence of any one SEQ ID NOs: 1-56, 103-158, and 205-260. In some embodiments, the siNA comprises a second nucleotide sequence. In some embodiments, the second nucleotide sequence comprises a nucleotide sequence of any one of SEQ ID NOs: 57-102, 159-204, and 261-306. In some embodiments, the siNA comprises a sense strand. In some embodiments, the sense strand comprises a nucleotide sequence of any one of SEQ ID NOs: 307-362 and 415-444. In some embodiments, the siNA comprises an antisense strand. In some embodiments, the antisense strand comprises a nucleotide sequence of any one of SEQ ID NOs: 363-409, 445-533, and 536-539. In some embodiments, the siNA further comprises any of the 5' end caps disclosed herein. In some embodiments, the siNA further comprises any of the phosphorylation blockers disclosed herein. In some embodiments, the siNA further comprises any of the conjugated moieties disclosed herein. In some embodiments, the siNA further comprises any of the destabilized nucleotides disclosed herein. In some embodiments, the siNA further comprises any of the modified nucleotides disclosed herein.

Further disclosed herein are methods of treating a disease in a subject in need thereof, comprising administering to the subject any of the compositions disclosed herein. In some embodiments, the composition comprises at least 1, 2, 3, 4, 5, 6, 7, 8, 9, 10 or more of any of the siNAs disclosed herein. In some embodiments, the siNA comprises a first nucleotide sequence. In some embodiments, the first nucleotide sequence comprises a nucleotide sequence of any one SEQ ID NOs: 1-56, 103-158, and 205-260. In some embodiments, the siNA comprises a second nucleotide sequence. In some embodiments, the second nucleotide sequence comprises a nucleotide sequence of any one of SEQ ID NOs: 57-102, 159-204, and 261-306. In some embodiments, the siNA comprises a sense strand. In some embodiments, the sense strand comprises a nucleotide sequence of any one of SEQ ID NOs: 307-362 and 415-444. In some embodiments, the siNA comprises an antisense strand. In some embodiments, the antisense strand comprises a nucleotide sequence of any one of SEQ ID NOs: 363-409, 445-533, and 536-539. In some embodiments, the siNA further comprises any of the 5' end caps disclosed herein. In some embodiments, the siNA further comprises any of the phosphorylation blockers disclosed herein. In some embodiments, the siNA further comprises any of the conjugated moieties disclosed herein. In some embodiments, the siNA further comprises any of the destabilized nucleotides disclosed herein. In some embodiments, the siNA further comprises any of the modified nucleotides disclosed herein. In some embodiments, the composition further comprises any of the additional HBV treatment agents disclosed herein. In some embodiments, the disease is a viral disease. In some embodiments, the viral disease is caused by a DNA virus. In some embodiments, the DNA virus is a double stranded DNA (dsDNA) virus. In some embodiments, the dsDNA virus is a hepadnavirus. In some embodiments, the hepadnavirus is a hepatitis B virus (HBV). In some embodiments, the HBV is selected from HBV genotypes A-J. In some embodiments, the method further comprises administering an additional HBV treatment agent. In some embodiments, the siNA or the composition and the additional HBV treatment agent are administered concurrently. In some embodiments, the siNA or the composition and the additional HBV treatment agent are administered sequentially. In some embodiments, the siNA or the composition is administered prior to administering the additional HBV treatment agent. In some embodiments, the siNA or the composition is administered after administering the additional HBV treatment agent. In some embodiments, the additional HBV treatment agent is selected from a nucleotide analog, nucleoside analog, a capsid assembly modulator (CAM), a recombinant interferon, an entry inhibitor, a small molecule immunomodulator and oligonucleotide therapy. In some embodiments, the oligonucleotide therapy is an additional siNA. In some embodiments, the additional siNA is selected from any of ds-siNA-001 to ds-siNA-0178. In some embodiments, the oligonucleotide therapy is an antisense oligonucleotide (ASO), NAPs, or STOPs. In some embodiments, the ASO is ASO 1 or ASO 2. In some embodiments, the additional HBV treatment agent is selected from HBV STOPS™ ALG-010133, HBV CAM ALG-000184, ASO 1, recombinant interferon alpha 2b, IFN-a, PEG-IFN-a-2a, lamivudine, telbivudine, adefovir dipivoxil, clevudine, entecavir, tenofovir alafenamide, tenofovir disoproxil, NVR3-778, BAY41-4109, JNJ-632, JNJ-3989 (ARO-HBV), RG6004, GSK3228836, REP-2139, REP-2165, AB-729, VIR-2218, RG6346 (DCR-HBVS), JNJ-6379, GLS4, ABI-HO731, JNJ-440, NZ-4, RG7907, EDP-514, AB-423, AB-506, ABI-H03733 and ABI-H2158.

In some embodiments, the disease is a liver disease. In some embodiments, the liver disease is a nonalcoholic fatty liver disease (NAFLD) or hepatocellular carcinoma (HCC). In some embodiments, the NAFLD is nonalcoholic steatohepatitis (NASH). In some embodiments, the method further comprises administering to the subject a liver disease treatment agent. In some embodiments, the liver disease treatment agent is selected from a peroxisome proliferator-activator receptor (PPAR) agonist, farnesoid X receptor (FXR) agonist, lipid-altering agent, and incretin-based therapy. In some embodiments, the PPAR agonist is selected from a PPARα agonist, dual PPARα/δ agonist, PPARγ agonist, and dual PPARα/γ agonist. In some embodiments, the dual PPARα agonist is a fibrate. In some embodiments, the PPARα/δ agonist is elafibranor. In some embodiments, the PPARγ agonist is a thiazolidinedione (TZD). In some embodiments, TZD is pioglitazone. In some embodiments, the dual PPARα/γ agonist is saroglitazar. In some embodiments, the FXR agonist is obeticholic acis (OCA). In some embodiments, the lipid-altering agent is aramchol. In some embodiments, the incretin-based therapy is a glucagon-like peptide 1 (GLP-1) receptor agonist or dipeptidyl peptidase 4 (DPP-4) inhibitor. In some embodiments, the GLP-1 receptor agonist is exenatide or liraglutide. In some embodiments, the DPP-4 inhibitor is sitagliptin or vildagliptin. In some embodiments, the siNA or composition and the liver disease treatment agent are administered concurrently. In some embodiments, the siNA or composition and the liver disease treatment agent are administered sequentially. In some embodiments, the siNA or composition is administered prior to administering the liver disease treatment agent. In some embodiments, the siNA or composition is administered after administering the liver disease treatment agent.

In some embodiments, the siNA or the composition is administered at a dose of at least 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg 14 mg/kg, or 15 mg/kg. In some embodiments, the siNA or the composition is administered at a dose of between 0.5 mg/kg to 50 mg/kg, 0.5 mg/kg to 40 mg/kg 0.5 mg/kg to 30 mg/kg, 1 mg/kg to 50 mg/kg, 1 mg/kg to 40 mg/kg, 1 mg/kg to 30 mg/kg, 1 mg/kg to 20 mg/kg, 3 mg/kg to 50 mg/kg, 3 mg/kg to 40 mg/kg, 3 mg/kg to 30 mg/kg, 3 mg/kg to 20 mg/kg, 3 mg/kg to 15 mg/kg, 3 mg/kg to 10 mg/kg, 4 mg/kg to 50 mg/kg, 4 mg/kg to 40 mg/kg, 4 mg/kg to 30 mg/kg, 4 mg/kg to 20 mg/kg, 4 mg/kg to 15 mg/kg, 4 mg/kg to 10 mg/kg, 5 mg/kg to 50 mg/kg, 5 mg/kg to 40 mg/kg, 5 mg/kg to 30 mg/kg, 5 mg/kg to 20 mg/kg, 5 mg/kg to 15 mg/kg, or 5 mg/kg to 10 mg/kg.

In some embodiments, the siNA or the composition is administered at least 1, 2, 3, 4, 5, 6, 7, 8, 9, or 10 times. In some embodiments, the siNA or the composition is administered at least 1, 2, 3, 4, 5, 6, 7, 8, 9, or 10 times a day, at least 1, 2, 3, 4, 5, 6, 7, 8, 9, or 10 times a week, or at least 1, 2, 3, 4, 5, 6, 7, 8, 9, or 10 times a month. In some embodiments, the siNA or the composition are administered at least once every 1, 2, 3, 4, 5, 6, 7, 8, 9, 10, 11, 12, 13, 14, 15, 16, 17, 18, 19, 20, or 21 days. In some embodiments, the siNA or the composition is administered for a period of at least 1, 2, 3, 4, 5, 6, 7, 8, 9, 10, 11, 12, 13, 14, 15, 16, 17, 18, 19, 20, or 21 days, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 51, 52, 53, 54, or 55 weeks.

In some embodiments, the siNA or the composition is administered at a single dose of 5 mg/kg. In some embodiments, the siNA or the composition is administered at a single dose of 10 mg/kg. In some embodiments, the siNA or the composition is administered at three doses of 10 mg/kg once a week. In some embodiments, the siNA or the composition is administered at three doses of 10 mg/kg once every three days. In some embodiments, the siNA or the composition is administered at five doses of 10 mg/kg once every three days. In some embodiments, the siNA or the composition is administered at six doses of ranging from 1 mg/kg to 15 mg/kg, 1 mg/kg to 10 mg/kg, 2 mg/kg to 15 mg/kg, 2 mg/kg to 10 mg/kg, 3 mg/kg to 15 mg/kg, or 3 mg/kg to 10 mg/kg. In some embodiments, the first dose and second dose are administered at least 3 days apart. In some embodiments, the second dose and third dose are administered at least 4 days apart. In some embodiments, the third dose and fourth dose, fourth dose and fifth dose, or fifth dose and sixth dose are administered at least 7 days apart.

In some embodiments, any of the siNAs or the compositions disclosed herein are formulated as a particle or viral vector. In some embodiments, the siNA or the composition are administered in a particle or viral vector. In some embodiments, the viral vector is a vector of adenovirus, adeno-associated virus (AAV), alphavirus, flavivirus, herpes simplex virus, lentivirus, measles virus, picornavirus, poxvirus, retrovirus, or rhabdovirus. In some embodiments, the viral vector is a recombinant viral vector. In some embodiments, the viral vector is selected from AAVrh.74, AAVrh.10, AAVrh.20, AAV-1, AAV-2, AAV-3, AAV-4, AAV-5, AAV-6, AAV-7, AAV-8, AAV-9, AAV-10, AAV-11, AAV-12 and AAV-13. In some embodiments, the siNA or the composition is administered systemically. In some embodiments, the siNA or the composition is administered locally. In some embodiments, the siNA or the composition is administered intravenously, subcutaneously, or intramuscularly.

In some embodiments, any of the siRNAs or compositions disclosed herein are used in the manufacture of a medicament for treating a disease. In some embodiments, the disease is a viral disease. In some embodiments, the viral disease is caused by a DNA virus. In some embodiments, the DNA virus is a double stranded DNA (dsDNA virus). In some embodiments, the dsDNA virus is a hepadnavirus. In some embodiments, the hepadnavirus is a hepatitis B virus (HBV). In some embodiments, the HBV is selected from HBV genotypes A-J. In some embodiments, an additional HBV treatment agent is further used in the manufacture of the medicament. In some embodiments, the additional HBV treatment agent is selected from a nucleotide analog, nucleoside analog, a capsid assembly modulator (CAM), a recombinant interferon, an entry inhibitor, a small molecule immunomodulator and oligonucleotide therapy. In some embodiments, the oligonucleotide therapy is an additional siNA. In some embodiments, the additional siNA is selected from any of ds-siNA-001 to ds-siNA-0178. In some embodiments, the oligonucleotide therapy is an antisense oligonucleotide (ASO), NAPs, or STOPs. In some embodiments, the ASO is ASO 1 or ASO 2. In some embodiments, the additional HBV treatment agent is selected from HBV STOPS™ ALG-010133, HBV CAM ALG-000184, ASO 1, recombinant interferon alpha 2b, IFN-a, PEG-IFN-a-2a, lamivudine, telbivudine, adefovir dipivoxil, clevudine, entecavir, tenofovir alafenamide, tenofovir disoproxil, NVR3-778, BAY41-4109, JNJ-632, JNJ-3989 (ARO-HBV), RG6004, GSK3228836, REP-2139, REP-2165, AB-729, VIR-2218, RG6346 (DCR-HBVS), JNJ-6379, GLS4, ABI-HO731, JNJ-440, NZ-4, RG7907, EDP-514, AB-423, AB-506, ABI-H03733 and ABI-H2158.

In some embodiments, any of the siRNAs or compositions disclosed herein are used in the manufacture of a medicament for treating a disease. In some embodiments, the disease is a liver disease. In some embodiments, the liver disease is a nonalcoholic fatty liver disease (NAFLD) or hepatocellular carcinoma (HCC). In some embodiments, the NAFLD is nonalcoholic steatohepatitis (NASH). In some embodiments, the siNA comprises a first nucleotide sequence. In some embodiments, the first nucleotide sequence comprises a nucleotide sequence of any one SEQ ID NOs: 1-56, 103-158, and 205-260. In some embodiments, the siNA comprises a second nucleotide sequence. In some embodiments, the second nucleotide sequence comprises a nucleotide sequence of any one of SEQ ID NOs: 57-102, 159-204, and 261-306. In some embodiments, the siNA comprises a sense strand. In some embodiments, the sense strand comprises a nucleotide sequence of any one of SEQ ID NOs: 307-362 and 415-444. In some embodiments, the siNA comprises an antisense strand. In some embodiments, the antisense strand comprises a nucleotide sequence of any one of SEQ ID NOs: 363-409, 445-533, and 536-539. In some embodiments, the siNA further comprises any of the 5' end caps disclosed herein. In some embodiments, the siNA further comprises any of the phosphorylation blockers disclosed herein. In some embodiments, the siNA further comprises any of the conjugated moieties disclosed herein. In some embodiments, the siNA further comprises any of the destabilized nucleotides disclosed herein. In some embodiments, the siNA further comprises any of the modified nucleotides disclosed herein. In some embodiments, a liver disease treatment agent is further used in the manufacture of the medicament. In some embodiments, the liver disease treatment agent is selected from a peroxisome proliferator-activator receptor (PPAR) agonist, farnesoid X receptor (FXR) agonist, lipid-altering agent, and incretin-based therapy. In some embodiments, the PPAR agonist is selected from a PPARα agonist, dual PPARα/δ agonist, PPARγ agonist, and dual PPARα/γ agonist. In some embodiments, the dual PPARα agonist is a fibrate. In some embodiments, the PPARα/δ agonist is elafibranor. In some embodiments, the PPARγ agonist is a thiazolidinedione (TZD). In some embodiments, TZD is pioglitazone. In some embodiments, the dual PPARα/γ agonist is saroglitazar. In some embodiments, the FXR agonist is obeticholic acis (OCA). In some embodiments, the lipid-altering agent is aramchol. In some embodiments, the incretin-based therapy is a glucagon-like peptide 1 (GLP-1) receptor agonist or dipeptidyl peptidase 4 (DPP-4) inhibitor. In some embodiments, the GLP-1 receptor agonist is exenatide or liraglutide. In some embodiments, the DPP-4 inhibitor is sitagliptin or vildagliptin.

In some embodiments, any of the siNAs disclosed herein is used as a medicament. In some embodiments, the siNA comprises a first nucleotide sequence. In some embodiments, the first nucleotide sequence comprises a nucleotide sequence of any one SEQ ID NOs: 1-56, 103-158, and 205-260. In some embodiments, the siNA comprises a second nucleotide sequence. In some embodiments, the second nucleotide sequence comprises a nucleotide sequence of any one of SEQ ID NOs: 57-102, 159-204, and 261-306. In some embodiments, the siNA comprises a sense strand. In some embodiments, the sense strand comprises a nucleotide sequence of any one of SEQ ID NOs: 307-362 and 415-444. In some embodiments, the siNA comprises an antisense strand. In some embodiments, the antisense strand comprises a nucleotide sequence of any one of SEQ ID NOs: 363-409, 445-533, and 536-539. In some embodiments, the siNA further comprises any of the 5' end caps disclosed herein. In some embodiments, the siNA further comprises any of the phosphorylation blockers disclosed herein. In some embodiments, the siNA further comprises any of the conjugated moieties disclosed herein. In some embodiments, the siNA further comprises any of the destabilized nucleotides disclosed herein. In some embodiments, the siNA further comprises any of the modified nucleotides disclosed herein.

In some embodiments, any of the compositions disclosed herein are used as a medicament. In some embodiments, the composition comprises any of the siNAs disclosed herein. In some embodiments, the siNA comprises a first nucleotide sequence. In some embodiments, the first nucleotide sequence comprises a nucleotide sequence of any one SEQ ID NOs: 1-56, 103-158, and 205-260. In some embodiments, the siNA comprises a second nucleotide sequence. In some embodiments, the second nucleotide sequence comprises a nucleotide sequence of any one of SEQ ID NOs: 57-102, 159-204, and 261-306. In some embodiments, the siNA comprises a sense strand. In some embodiments, the sense strand comprises a nucleotide sequence of any one of SEQ ID NOs: 307-362 and 415-444. In some embodiments, the siNA comprises an antisense strand. In some embodiments, the antisense strand comprises a nucleotide sequence of any one of SEQ ID NOs: 363-409, 445-533, and 536-539. In some embodiments, the siNA further comprises any of the 5' end caps disclosed herein. In some embodiments, the siNA further comprises any of the phosphorylation blockers disclosed herein. In some embodiments, the siNA further comprises any of the conjugated moieties disclosed herein. In some embodiments, the siNA further comprises any of the destabilized nucleotides disclosed herein. In some embodiments, the siNA further comprises any of the modified nucleotides disclosed herein.

In some embodiments, any of the siNAs disclosed herein are used in the treatment of a disease. In some embodiments, the siNA comprises a first nucleotide sequence. In some embodiments, the first nucleotide sequence comprises a nucleotide sequence of any one SEQ ID NOs: 1-56, 103-158, and 205-260. In some embodiments, the siNA comprises a second nucleotide sequence. In some embodiments, the second nucleotide sequence comprises a nucleotide sequence of any one of SEQ ID NOs: 57-102, 159-204, and 261-306. In some embodiments, the siNA comprises a sense strand. In some embodiments, the sense strand comprises a nucleotide sequence of any one of SEQ ID NOs: 307-362 and 415-444. In some embodiments, the siNA comprises an antisense strand. In some embodiments, the antisense strand comprises a nucleotide sequence of any one of SEQ ID NOs: 363-409, 445-533, and 536-539. In some embodiments, the siNA further comprises any of the 5' end caps disclosed herein. In some embodiments, the siNA further comprises any of the phosphorylation blockers disclosed herein. In some embodiments, the siNA further comprises any of the conjugated moieties disclosed herein. In some embodiments, the siNA further comprises any of the destabilized nucleotides disclosed herein. In some embodiments, the siNA further comprises any of the modified nucleotides disclosed herein. In some embodiments, the disease is a viral disease. In some embodiments, the viral disease is caused by a DNA virus. In some embodiments, the DNA virus is a double stranded DNA (dsDNA virus). In some embodiments, the dsDNA virus is a hepadnavirus. In some embodiments, the hepadnavirus is a hepatitis B virus (HBV). In some embodiments, the HBV is selected from HBV genotypes A-J. In some embodiments, the disease is a liver disease. In some embodiments, the liver disease is a nonalcoholic fatty liver disease (NAFLD) or hepatocellular carcinoma (HCC). In some embodiments, the NAFLD is non-alcoholic steatohepatitis (NASH).

In some embodiments, any of the compositions disclosed herein are used in the treatment of a disease. In some embodiments, the composition comprises any of the siNAs disclosed herein. In some embodiments, the siNA comprises a first nucleotide sequence. In some embodiments, the first nucleotide sequence comprises a nucleotide sequence of any one SEQ ID NOs: 1-56, 103-158, and 205-260. In some embodiments, the siNA comprises a second nucleotide sequence. In some embodiments, the second nucleotide sequence comprises a nucleotide sequence of any one of SEQ ID NOs: 57-102, 159-204, and 261-306. In some embodiments, the siNA comprises a sense strand. In some embodiments, the sense strand comprises a nucleotide sequence of any one of SEQ ID NOs: 307-362 and 415-444. In some embodiments, the siNA comprises an antisense strand. In some embodiments, the antisense strand comprises a nucleotide sequence of any one of SEQ ID NOs: 363-409, 445-533, and 536-539. In some embodiments, the siNA further comprises any of the 5' end caps disclosed herein. In some embodiments, the siNA further comprises any of the phosphorylation blockers disclosed herein. In some embodiments, the siNA further comprises any of the conjugated moieties disclosed herein. In some embodiments, the siNA further comprises any of the destabilized nucleotides disclosed herein. In some embodiments, the siNA further comprises any of the modified nucleotides disclosed herein. In some embodiments, the disease is a viral disease. In some embodiments, the viral disease is caused by a DNA virus. In some embodiments, the DNA virus is a double stranded DNA (dsDNA virus). In some embodiments, the dsDNA virus is a hepadnavirus. In some embodiments, the hepadnavirus is a hepatitis B virus (HBV). In some embodiments, the HBV is selected from HBV genotypes A-J. In some embodiments, the disease is a liver disease. In some embodiments, the liver disease is a nonalcoholic fatty liver disease (NAFLD) or hepatocellular carcinoma (HCC). In some embodiments, the NAFLD is non-alcoholic steatohepatitis (NASH).

BRIEF DESCRIPTION OF THE DRAWINGS

FIG. 16 shows a graph of the change in serum HBsAg from AAV-HBV mice treated with vehicle (G 01, circle), ASO 1 (G 20, square), ds-siNA-0147 (G 24, diamond), or a combination of ASO 1 and ds-siNA-0147 (G 25, triangle).

FIG. 17 shows a graph of the change in serum HBsAg from AAV-HBV mice treated with vehicle (G 01, circle), ASO 1 (G 20, square), ds-siNA-0109 (G 26, diamond), or a combination of ASO 1 and ds-siNA-0109 (G 27, triangle).

DETAILED DESCRIPTION OF THE INVENTION

Figure 1:
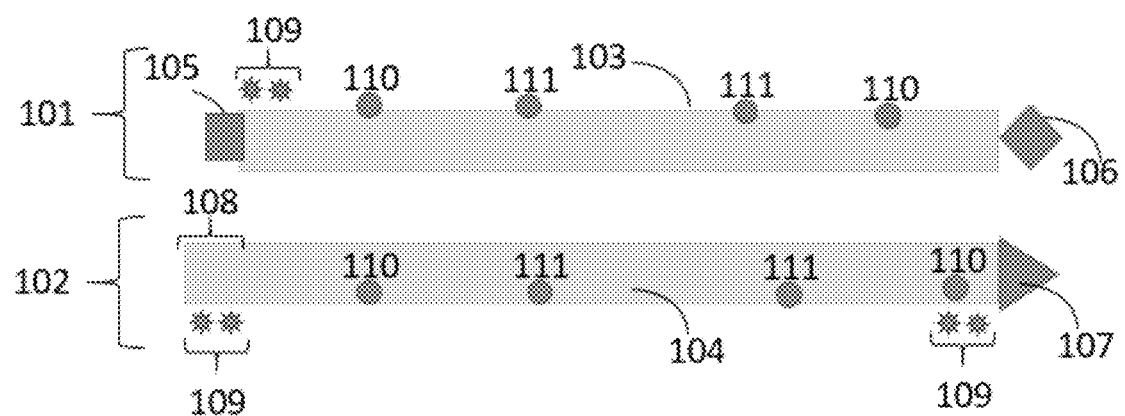
FIG. 1 illustrates an exemplary siNA molecule.

Disclosed herein are short interfering nucleic acid (siNA) molecules comprising modified nucleotides. The siNA molecules described herein may be double-stranded siNA (ds-siNA) molecules. The siNA molecules described herein may comprise modified nucleotides selected from 2'-O-methyl nucleotides and 2'-fluoro nucleotides. The siNA molecules described herein may comprise 1, 2, 3, 4, 5, 6, 7, 8, 9, or 10 or more phosphorothioate internucleoside linkages. The siNA molecules described herein may comprise a phosphorylation blocker. The siNA molecules described herein may comprise a 5'-stabilized end cap. The siNA molecules described herein may comprise a galactosamine. The siNA molecules described herein may comprise one or more blunt ends. The siNA molecules described herein may comprise one or more overhangs.

Further disclosed herein are short interfering nucleic acid (siNA) molecules comprising (a) a phosphorylation blocker; and (b) a short interfering nucleic acid (siNA). The siNA may comprise at least 5 nucleotides. The nucleotides may be modified nucleotides, non-modified nucleotides, or any combination thereof. The nucleotides may be ribonucleotides, deoxyribonucleotides, or any combination thereof. The siNA may be single-stranded. Alternatively, the siNA is double-stranded. The double-stranded siNA may comprise one or more blunt ends. The double-stranded siNA may comprise one or more overhangs. The double-stranded siNA may comprise a blunt end and an overhang.

Further disclosed herein are short interfering nucleic acid (siNA) molecules comprising (a) a conjugated moiety; and (b) a short interfering nucleic acid (siNA). The siNA may comprise at least 5 nucleotides. The nucleotides may be modified nucleotides, non-modified nucleotides, or any combination thereof. The nucleotides may be ribonucleotides, deoxyribonucleotides, or any combination thereof. The siNA may be single-stranded. Alternatively, the siNA is double-stranded. The double-stranded siNA may comprise one or more blunt ends. The double-stranded siNA may comprise one or more overhangs. The double-stranded siNA may comprise a blunt end and an overhang.

Further disclosed herein are short interfering nucleic acid (siNA) molecules comprising (a) a 5'-stabilized end cap; and (b) a short interfering nucleic acid (siNA). The siNA may comprise at least 5 nucleotides. The nucleotides may be modified nucleotides, non-modified nucleotides, or any combination thereof. The nucleotides may be ribonucleotides, deoxyribonucleotides, or any combination thereof. The siNA may be single-stranded. Alternatively, the siNA is double-stranded. The double-stranded siNA may comprise one or more blunt ends. The double-stranded siNA may comprise one or more overhangs. The double-stranded siNA may comprise a blunt end and an overhang.

Further disclosed herein are short interfering nucleic acid (siNA) molecules comprising (a) at least one phosphorylation blocker, conjugated moiety, or 5'-stabilized end cap; and (b) a short interfering nucleic acid (siNA). The siNA may comprise at least 5 nucleotides. The nucleotides may be modified nucleotides, non-modified nucleotides, or any combination thereof. The nucleotides may be ribonucleotides, deoxyribonucleotides, or any combination thereof. The siNA may be single-stranded. Alternatively, the siNA is double-stranded. The double-stranded siNA may comprise one or more blunt ends. The double-stranded siNA may comprise one or more overhangs. The double-stranded siNA may comprise a blunt end and an overhang.

An exemplary siNA molecule of the present disclosure is shown in FIG. 1. As shown in FIG. 1, an exemplary siNA molecule comprises a sense strand (101) and an antisense strand (102). The sense strand (101) may comprise a first oligonucleotide sequence (103). The first oligonucleotide sequence (103) may comprise one or more phosphorothioate internucleoside linkages (109). The phosphorothioate internucleoside linkage (109) may be between the nucleotides at the 5' or 3' terminal end of the first oligonucleotide sequence (103). The phosphorothioate internucleoside linkage (109) may be between the first three nucleotides from the 5' end of the first oligonucleotide sequence (103). The first oligonucleotide sequence (103) may comprise one or more 2'-fluoro nucleotides (110). The first oligonucleotide sequence (103) may comprise one or more 2'-O-methyl nucleotides (111). The first oligonucleotide sequence (103) may comprise 15 or more modified nucleotides independently selected from 2'-fluoro nucleotides (110) and 2'-O-methyl nucleotides (111). The sense strand (101) may further comprise a phosphorylation blocker (105). The sense strand (101) may further comprise a galactosamine (106). The antisense strand (102) may comprise a second oligonucleotide sequence (104). The second oligonucleotide sequence (104) may comprise one or more phosphorothioate internucleoside linkages (109). The phosphorothioate internucleoside linkage (109) may be between the nucleotides at the 5' or 3' terminal end of the second oligonucleotide sequence (104). The phosphorothioate internucleoside linkage (109) may be between the first three nucleotides from the 5' end of the second oligonucleotide sequence (104). The phosphorothioate internucleoside linkage (109) may be between the first three nucleotides from the 3' end of the second oligonucleotide sequence (104). The second oligonucleotide sequence (104) may comprise one or more 2'-fluoro nucleotides (110). The second oligonucleotide sequence (104) may comprise one or more 2'-O-methyl nucleotides (111). The second oligonucleotide sequence (104) may comprise 15 or more modified nucleotides independently selected from 2'-fluoro nucleotides (110) and 2'-O-methyl nucleotides (111). The antisense strand (102) may further comprise a 5'-stabilized end cap (107). The siNA may further comprise one or more blunt ends. Alternatively, or additionally, one end of the siNA may comprise an overhang (108). The overhang (108) may be part of the sense strand (101). The overhang (108) may be part of the antisense strand (102). The overhang (108) may be distinct from the first nucleotide sequence (103). The overhang (108) may be distinct from the second nucleotide sequence (104). The overhang (108) may be part of the first nucleotide sequence (103). The overhang (108) may be part of the second nucleotide sequence (104). The overhang (108) may comprise 1 or more nucleotides. The overhang (108) may comprise 1 or more deoxyribonucleotides. The overhang (108) may comprise 1 or more modified nucleotides. The overhang (108) may comprise 1 or more modified ribonucleotides. The sense strand (101) may be shorter than the antisense strand (102). The sense strand (101) may be the same length as the antisense strand (102). The sense strand (101) may be longer than the antisense strand (102).

Figure 2:
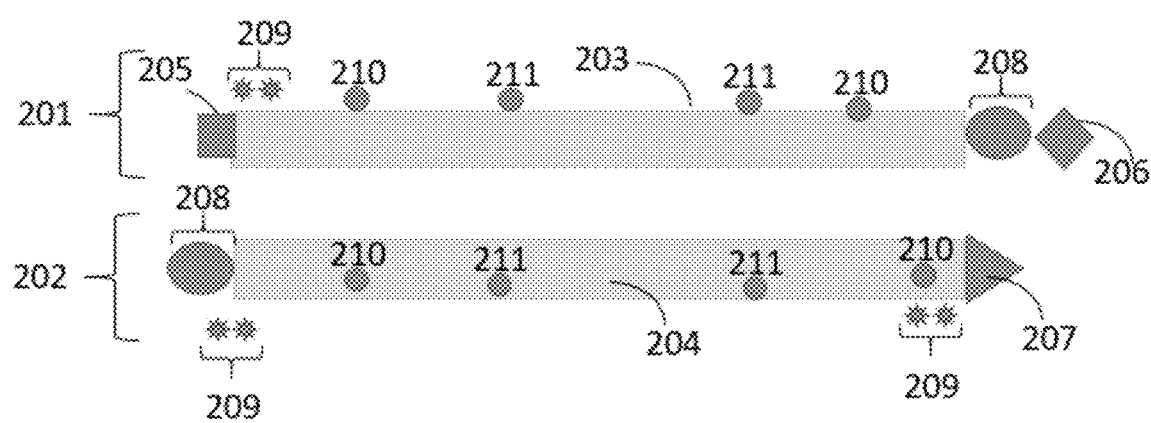
FIG. 2 illustrates an exemplary siNA molecule.

An exemplary siNA molecule of the present disclosure is shown in FIG. 2. As shown in FIG. 2, an exemplary siNA molecule comprises a sense strand (201) and an antisense strand (202). The sense strand (201) may comprise a first oligonucleotide sequence (203). The first oligonucleotide sequence (203) may comprise one or more phosphorothioate internucleoside linkages (209). The phosphorothioate internucleoside linkage (209) may be between the nucleotides at the 5' or 3' terminal end of the first oligonucleotide sequence (203). The phosphorothioate internucleoside linkage (209) may be between the first three nucleotides from the 5' end of the first oligonucleotide sequence (203). The first oligonucleotide sequence (203) may comprise one or more 2'-fluoro nucleotides (210). The first oligonucleotide sequence (203) may comprise one or more 2'-O-methyl nucleotides (211). The first oligonucleotide sequence (203) may comprise 15 or more modified nucleotides independently selected from 2'-fluoro nucleotides (210) and 2'-O-methyl nucleotides (211). The sense strand (201) may further comprise a phosphorylation blocker (205). The sense strand (201) may further comprise a galactosamine (206). The antisense strand (202) may comprise a second oligonucleotide sequence (204). The second oligonucleotide sequence (204) may comprise one or more phosphorothioate internucleoside linkages (209). The phosphorothioate internucleoside linkage (209) may be between the nucleotides at the 5' or 3' terminal end of the second oligonucleotide sequence (204). The phosphorothioate internucleoside linkage (209) may be between the first three nucleotides from the 5' end of the second oligonucleotide sequence (204). The phosphorothioate internucleoside linkage (209) may be between the first three nucleotides from the 3' end of the second oligonucleotide sequence (204). The second oligonucleotide sequence (204) may comprise one or more 2'-fluoro nucleotides (210). The second oligonucleotide sequence (204) may comprise one or more 2'-O-methyl nucleotides (211). The second oligonucleotide sequence (204) may comprise 15 or more modified nucleotides independently selected from 2'-fluoro nucleotides (210) and 2'-O-methyl nucleotides (211). The antisense strand (202) may further comprise a 5'-stabilized end cap (207). The siNA may further comprise one or more overhangs (208).

The overhang (208) may be part of the sense strand (201). The overhang (208) may be part of the antisense strand. (202). The overhang (208) may be distinct from the first nucleotide sequence (203). The overhang (208) may be distinct from the second nucleotide sequence (204). The overhang (208) may be part of the first nucleotide sequence (203). The overhang (208) may be part of the second nucleotide sequence (204). The overhang (208) may be adjacent to the 3' end of the first nucleotide sequence (203). The overhang (208) may be adjacent to the 5' end of the first nucleotide sequence (203). The overhang (208) may be adjacent to the 3' end of the second nucleotide sequence (204). The overhang (208) may be adjacent to the 5' end of the second nucleotide sequence (204). The overhang (208) may comprise 1 or more nucleotides. The overhang (208) may comprise 1 or more deoxyribonucleotides. The overhang (208) may comprise a TT sequence. The overhang (208) may comprise 1 or more modified nucleotides. The overhang (208) may comprise 1 or more modified nucleotides disclosed herein (e.g., 2-fluoro nucleotide, 2'-O-methyl nucleotide, 2'-fluoro nucleotide mimic, 2'-O-methyl nucleotide mimic, or a nucleotide comprising a modified nucleobase). The overhang (208) may comprise 1 or more modified ribonucleotides. The sense strand (201) may be shorter than the antisense strand (202). The sense strand (201) may be the same length as the antisense strand (202). The sense strand (201) may be longer than the antisense strand (202).

FIGS. 3A-3G depict exemplary ds-siNA modification patterns. As shown in FIGS. 3A-3G, an exemplary ds-siNA molecule may have the following formula:

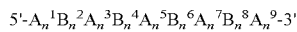

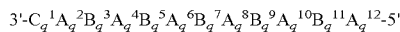

wherein:
the top strand is a sense strand comprising a first nucleotide sequence that is at least about 60%, 65%, 70%, 75%, 80%, 85%, 90%, 95%, or 100% identical to an RNA corresponding to a target gene, wherein the first nucleotide sequence comprises 15 to 30 nucleotides;
the bottom strand is an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence comprises 15 to 30 nucleotides;
each A is independently a 2'-O-methyl nucleotide or a nucleotide comprising a 5' stabilized end cap or phosphorylation blocker;
B is a 2'-fluoro nucleotide;
C represents overhanging nucleotides and is a 2'-O-methyl nucleotide;
$n^1$=1-4 nucleotides in length;
each $n^2$, $n^6$, $n^8$, $q^3$, $q^5$, $q^7$, $q^9$, $q^{11}$, and $q^{12}$ is independently 0-1 nucleotides in length;
each $n^3$ and $n^4$ is independently 1-3 nucleotides in length;
$n^5$ is 1-10 nucleotides in length;
$n^7$ is 0-4 nucleotides in length;
each $n^9$, $q^1$, and $q^2$ is independently 0-2 nucleotides in length;
$q^4$ is 0-3 nucleotides in length;
$q^6$ is 0-5 nucleotides in length;
$q^8$ is 2-7 nucleotides in length; and
$q^{10}$ is 2-11 nucleotides in length.

The ds-siNA may further comprise a conjugated moiety. The conjugated moiety may comprise any of the galactosomines disclosed herein. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. The ds-siNA may further comprise a 5'-stabilizing end cap. The 5'-stabilizing end cap may be a vinyl phosphonate. The 5'-stabilizing end cap may be attached to the 5' end of the antisense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. An exemplary ds-siNA molecule may have the following formula:

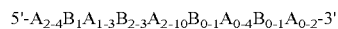

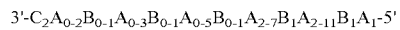

wherein:
the top strand is a sense strand comprising a first nucleotide sequence that is at least about 60%, 65%, 70%, 75%, 80%, 85%, 90%, 95%, or 100% identical to an RNA corresponding to a target gene, wherein the first nucleotide sequence comprises 15 to 30 nucleotides;
the bottom strand is an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence comprises 15 to 30 nucleotides;
each A is independently a 2'-O-methyl nucleotide or a nucleotide comprising a 5' stabilized end cap or phosphorylation blocker;
B is a 2'-fluoro nucleotide;
C represents overhanging nucleotides and is a 2'-O-methyl nucleotide.

The ds-siNA may further comprise a conjugated moiety. The conjugated moiety may comprise any of the galactosomines disclosed herein. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. The ds-siNA may further comprise a 5'-stabilizing end cap. The 5'-stabilizing end cap may be a vinyl phosphonate. The vinyl phosphonate may be a deuterated vinyl phosphonate. The deuterated vinyl phosphonate may be a mono-deuterated vinyl phosphonate. The deuterated vinyl phosphonate may be a mono-di-deuterated vinyl phosphonate. The 5'-stabilizing end cap may be attached to the 5' end of the antisense strand. The 5'-stabilizing end cap may be attached to the 3' end of the antisense strand. The 5'-stabilizing end cap may be attached to the 5' end of the sense strand. The 5'-stabilizing end cap may be attached to the 3' end of the sense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker.

The exemplary ds-siNA shown in FIGS. 3A-3G comprise (i) a sense strand comprising 19-21 nucleotides; and (ii) an antisense strand comprising 21-23 nucleotides. The ds-siNA may further comprise (iii) a conjugated moiety, wherein the conjugated moiety is attached to the 3' end of the antisense strand. The ds-siNA may comprise a 2 nucleotide overhang consisting of nucleotides at positions 20 and 21 from the 5' end of the antisense strand. The ds-siNA may comprise a 2 nucleotide overhang consisting of nucleotides at positions 22 and 23 from the 5' end of the antisense strand. The ds-siNA may further comprise 1, 2, 3, 4, 5, 6 or more phosphorothioate (ps) internucleoside linkages. At least one phosphorothioate internucleoside linkage may be between the nucleotides at positions 1 and 2 or positions 2 and 3 from the 5' end of the sense strand. At least one phosphorothioate internucleoside linkage may be between the nucleotides at positions 1 and 2 or positions 2 and 3 from the 5' end of the antisense strand. At least one phosphorothioate internucleoside linkage may be between the nucleotides at positions 19 and 20, positions 20 and 21, positions 21 and 22, or positions 22 and 23 from the 5' end of the antisense strand. As shown in FIGS. 3A-3G, 4-6 nucleotides in the sense strand may be 2'-fluoro nucleotides. As shown in FIGS. 3A-3G, 2-5 nucleotides in the antisense strand may be 2'-fluoro nucleotides. As shown in FIGS. 3A-3G, 13-15 nucleotides in the sense strand may be 2'-O-methyl nucleotides. As shown in FIGS. 3A-3G, 14-19 nucleotides in the antisense strand may be 2'-O-methyl nucleotides. As shown in FIGS. 3A-3G, the ds-siNA does not contain a base pair between 2'-fluoro nucleotides on the sense and antisense strands. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker.

Figure 3A:
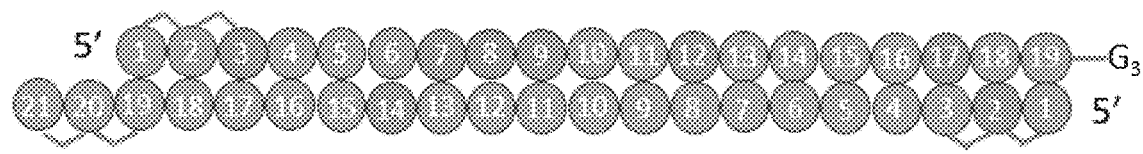
FIGS. 3A-3G illustrate exemplary double-stranded siNA molecules.

As shown in FIG. 3A, a ds-siNA may comprise (a) a sense strand consisting of 19 nucleotides, wherein 2'-fluoro nucleotides are at positions 3, 7-9, 12, and 17 from the 5' end of the sense strand, and wherein 2'-O-methyl nucleotides are at positions 1, 2, 4-6, 10, 11, 13-16, 18, and 19 from the 5' end of the sense strand; (b) an antisense strand consisting of 21 nucleotides, wherein nucleotides at positions 2 and 14 from the 5' end of the antisense strand are 2'-fluoro nucleotides; and wherein nucleotides at positions 1, 3-13, and 15-21 are 2'-O-methyl nucleotides. The ds-siNA may further comprise a conjugated moiety attached to the 3' end of the sense strand. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide. In some embodiments, the 2'-O-methyl nucleotide at position 1 from the 5' end of the antisense strand is a d2vd3 nucleotide. In some embodiments, the 2'-O-methyl nucleotide at position 1 from the 3' end of the sense strand is a d2vd3 nucleotide. In some embodiments, the 2'-O-methyl nucleotide at position 1 from the 3' end of the antisense strand is a d2vd3 nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand or antisense strand is a f4P, f2P, or fX nucleotide. In some embodiments, at least 1, 2, 3, 4 or more 2'-O-methyl nucleotide on the sense or antisense strand is a 2'-O-methyl nucleotide mimic.

Figure 3B:
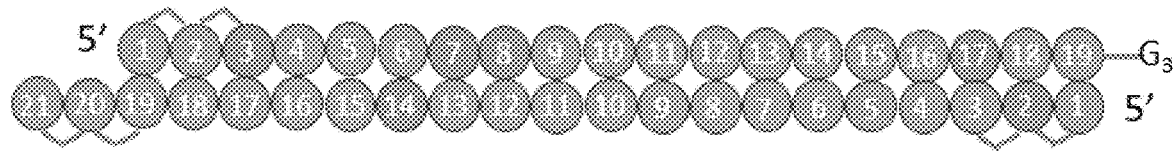

As shown in FIG. 3B, a ds-siNA may comprise (a) a sense strand consisting of 19 nucleotides, wherein 2'-fluoro nucleotides are at positions 3, 7, 8, and 17 from the 5' end of the sense strand, and wherein 2'-O-methyl nucleotides are at positions 1, 2, 4-6, 9-16, 18, and 19 from the 5' end of the sense strand; (b) an antisense strand consisting of 21 nucleotides, wherein nucleotides at positions 2 and 14 from the 5' end of the antisense strand are 2'-fluoro nucleotides; and wherein nucleotides at positions 1, 3-13, and 15-21 are 2'-O-methyl nucleotides. The ds-siNA may further comprise a conjugated moiety attached to the 3' end of the sense strand. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide. In some embodiments, the 2'-O-methyl nucleotide at position 1 from the 5' end of the antisense strand is a d2vd3 nucleotide. In some embodiments, the 2'-O-methyl nucleotide at position 1 from the 3' end of the sense strand is a d2vd3 nucleotide. In some embodiments, the 2'-O-methyl nucleotide at position 1 from the 3' end of the antisense strand is a d2vd3 nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand or antisense strand is a f4P, f2P, or fX nucleotide. In some embodiments, at least 1, 2, 3, 4 or more 2'-O-methyl nucleotide on the sense or antisense strand is a 2'-O-methyl nucleotide mimic.

Figure 3C:
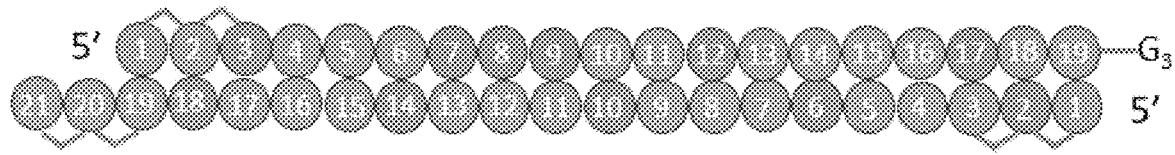

As shown in FIG. 3C, a ds-siNA may comprise (a) a sense strand consisting of 19 nucleotides, wherein 2'-fluoro nucleotides are at positions 3, 7-9, 12 and 17 from the 5' end of the sense strand, and wherein 2'-O-methyl nucleotides are at positions 1, 2, 4-6, 10, 11, 13-16, 18, and 19 from the 5' end of the sense strand; (b) an antisense strand consisting of 21 nucleotides, wherein the nucleotides in the antisense strand comprise an alternating 1:3 modification pattern, and wherein 1 nucleotide is a 2'-fluoro nucleotide and 3 nucleotides are 2'-O-methyl nucleotides. The ds-siNA may further comprise a conjugated moiety attached to the 3' end of the sense strand. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. The ds-siNA may comprise 2-5 alternating 1:3 modification patterns on the antisense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide. In some embodiments, the 2'-O-methyl nucleotide at position 1 from the 5' end of the antisense strand is a d2vd3 nucleotide. In some embodiments, the 2'-O-methyl nucleotide at position 1 from the 3' end of the sense strand is a d2vd3 nucleotide. In some embodiments, the 2'-O-methyl nucleotide at position 1 from the 3' end of the antisense strand is a d2vd3 nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand is a f4P, f2P, or fX nucleotide. In some embodiments, at least 1, 2, 3, 4 or more 2'-fluoro nucleotides on the antisense strand is a f4P, f2P, or fX nucleotide. In some embodiments, at least 1, 2, 3, 4 or more 2'-O-methyl nucleotide on the sense or antisense strand is a 2'-O-methyl nucleotide mimic.

Figure 3D:
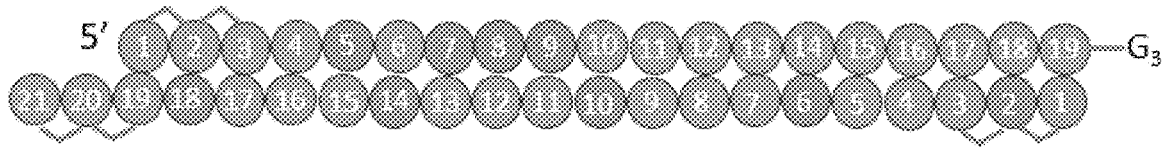

As shown in FIG. 3D, a ds-siNA may comprise (a) a sense strand consisting of 19 nucleotides, wherein 2'-fluoro nucleotides are at positions 5 and 7-9 from the 5' end of the sense strand, and wherein 2'-O-methyl nucleotides are at positions 1-4, 6, and 10-19 from the 5' end of the sense strand; (b) an antisense strand consisting of 21 nucleotides, wherein the nucleotides in the antisense strand comprise an alternating 1:3 modification pattern, and wherein 1 nucleotide is a 2'-fluoro nucleotide and 3 nucleotides are 2'-O-methyl nucleotides. The ds-siNA may further comprise a conjugated moiety attached to the 3' end of the sense strand. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. The ds-siNA may comprise 2-5 alternating 1:3 modification patterns on the antisense strand. The alternating 1:3 modification pattern may start at the nucleotide at any of positions 2, 6, 10, 14, and/or 18 from the 5' end of the antisense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide. In some embodiments, the 2'-O-methyl nucleotide at position 1 from the 5' end of the antisense strand is a d2vd3 nucleotide. In some embodiments, the 2'-O-methyl nucleotide at position 1 from the 3' end of the sense strand is a d2vd3 nucleotide. In some embodiments, the 2'-O-methyl nucleotide at position 1 from the 3' end of the antisense strand is a d2vd3 nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand is a f4P, f2P, or fX nucleotide. In some embodiments, at least 1, 2, 3, 4 or more 2'-fluoro nucleotides on the antisense strand is a f4P, f2P, or fX nucleotide. In some embodiments, at least 1, 2, 3, 4 or more 2'-O-methyl nucleotide on the sense or antisense strand is a 2'-O-methyl nucleotide mimic.

Figure 3E:
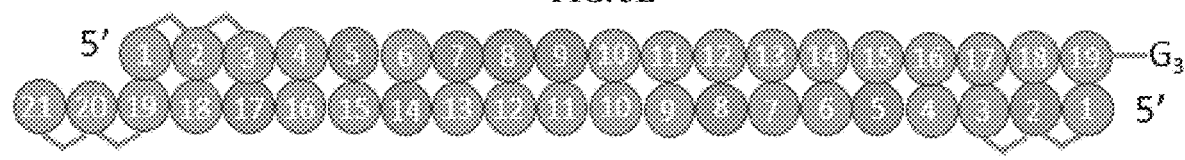

As shown in FIG. 3E, a ds-siNA may comprise (a) a sense strand consisting of 19 nucleotides, wherein 2'-fluoro nucleotides are at positions 5 and 7-9 from the 5' end of the sense strand, and wherein 2'-O-methyl nucleotides are at positions 1-4, 6, and 10-19 from the 5' end of the sense strand; (b) an antisense strand consisting of 21 nucleotides, wherein the nucleotides in the antisense strand comprise an alternating 1:2 modification pattern, and wherein 1 nucleotide is a 2'-fluoro nucleotide and 2 nucleotides are 2'-O-methyl nucleotides. The ds-siNA may further comprise a conjugated moiety attached to the 3' end of the sense strand. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. The ds-siNA may comprise 2-5 alternating 1:2 modification patterns on the antisense strand. The alternating 1:2 modification pattern may start at the nucleotide at any of positions 2, 5, 8, 14, and/or 17 from the 5' end of the antisense strand. In some embodiments, the ds-siNA comprises (a) a sense strand consisting of 19 nucleotides, wherein 2'-fluoro nucleotides are at positions 5 and 7-9 from the 5' end of the sense strand, and wherein 2'-O-methyl nucleotides are at positions 1-4, 6, and 10-19 from the 5' end of the sense strand; (b) an antisense strand consisting of 21 nucleotides, wherein 2'-fluoro nucleotides are at positions 2, 5, 8, 14, and 17 from the 5' end of the antisense strand, and wherein 2'-O-methyl nucleotides are at positions 1, 3, 4, 6, 7, 9-13, 15, 16, and 18-21 from the 5' end of the sense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide. In some embodiments, the 2'-O-methyl nucleotide at position 1 from the 5' end of the antisense strand is a d2vd3 nucleotide. In some embodiments, the 2'-O-methyl nucleotide at position 1 from the 3' end of the sense strand is a d2vd3 nucleotide. In some embodiments, the 2'-O-methyl nucleotide at position 1 from the 3' end of the antisense strand is a d2vd3 nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand is a f4P, f2P, or fX nucleotide. In some embodiments, at least 1, 2, 3, 4 or more 2'-fluoro nucleotides on the antisense strand is a f4P, f2P, or fX nucleotide. In some embodiments, at least 1, 2, 3, 4 or more 2'-O-methyl nucleotide on the sense or antisense strand is a 2'-O-methyl nucleotide mimic.

Figure 3F:
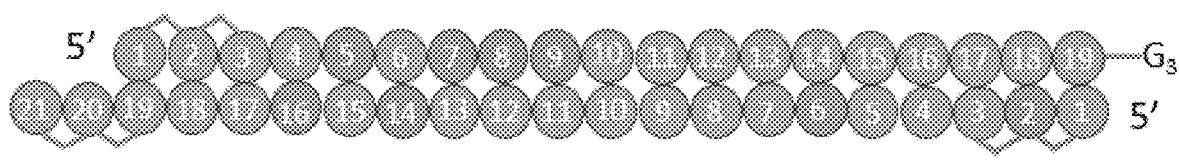

As shown in FIG. 3F, a ds-siNA may comprise (a) a sense strand consisting of 19 nucleotides, wherein 2'-fluoro nucleotides are at positions 5 and 7-9 from the 5' end of the sense strand, and wherein 2'-O-methyl nucleotides are at positions 1-4, 6, and 10-19 from the 5' end of the sense strand; (b) an antisense strand consisting of 21 nucleotides, wherein 2'-fluoro nucleotides are at positions 2, 6, 14, and 16 from the 5' end of the antisense strand, and wherein 2'-O-methyl nucleotides are at positions 1, 3-5, 7-13, 15, and 17-21 from the 5' end of the antisense strand. The ds-siNA may further comprise a conjugated moiety attached to the 3' end of the sense strand. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. In some embodiments, at least 1, 2, 3, 4 or more 2'-fluoro nucleotides on the sense strand or antisense strand is a f4P, f2P, or fX nucleotide. In some embodiments, at least 1, 2, 3, 4 or more 2'-fluoro nucleotides on the sense strand or antisense strand is a f4P nucleotide. In some embodiments, at least 1, 2, 3, or 4 of the 2'-fluoro-nucleotides at positions 2, 6, 14, and 16 from the 5' end of the antisense strand is a f4P nucleotide. In some embodiments, at least one of the 2'-fluoro-nucleotides at positions 2, 6, 14, and 16 from the 5' end of the antisense strand is a f4P nucleotide. In some embodiments, at least two of the 2'-fluoro-nucleotides at positions 2, 6, 14, and 16 from the 5' end of the antisense strand is a f4P nucleotide. In some embodiments, less than or equal to 3 of the 2'-fluoro-nucleotides at positions 2, 6, 14, and 16 from the 5' end of the antisense strand is a f4P nucleotide. In some embodiments, less than or equal to 2 of the 2'-fluoro-nucleotides at positions 2, 6, 14, and 16 from the 5' end of the antisense strand is a f4P nucleotide. In some embodiments, the 2'-fluoro-nucleotide at position 2 from the 5' end of the antisense strand is a f4P nucleotide. In some embodiments, the 2'-fluoro-nucleotide at position 6 from the 5' end of the antisense strand is a f4P nucleotide. In some embodiments, the 2'-fluoro-nucleotide at position 14 from the 5' end of the antisense strand is a f4P nucleotide. In some embodiments, the 2'-fluoro-nucleotide at position 16 from the 5' end of the antisense strand is a f4P nucleotide. In some embodiments, at least 1, 2, 3, 4 or more 2'-fluoro nucleotides on the sense strand or antisense strand is a f2P nucleotide. In some embodiments, at least 1, 2, 3, or 4 of the 2'-fluoro-nucleotides at positions 2, 6, 14, and 16 from the 5' end of the antisense strand is a f2P nucleotide. In some embodiments, at least one of the 2'-fluoro-nucleotides at positions 2, 6, 14, and 16 from the 5' end of the antisense strand is a f2P nucleotide. In some embodiments, at least two of the 2'-fluoro-nucleotides at positions 2, 6, 14, and 16 from the 5' end of the antisense strand is a f2P nucleotide. In some embodiments, less than or equal to 3 of the 2'-fluoro-nucleotides at positions 2, 6, 14, and 16 from the 5' end of the antisense strand is a f2P nucleotide. In some embodiments, less than or equal to 2 of the 2'-fluoro-nucleotides at positions 2, 6, 14, and 16 from the 5' end of the antisense strand is a f2P nucleotide. In some embodiments, the 2'-fluoro-nucleotide at position 2 from the 5' end of the antisense strand is a f2P nucleotide. In some embodiments, the 2'-fluoro-nucleotide at position 6 from the 5' end of the antisense strand is a f2P nucleotide. In some embodiments, the 2'-fluoro-nucleotide at position 14 from the 5' end of the antisense strand is a f2P nucleotide. In some embodiments, the 2'-fluoro-nucleotide at position 16 from the 5' end of the antisense strand is a f2P nucleotide. In some embodiments, at least 1, 2, 3, 4 or more 2'-fluoro nucleotides on the sense strand or antisense strand is a fX nucleotide. In some embodiments, at least 1, 2, 3, or 4 of the 2'-fluoro-nucleotides at positions 2, 6, 14, and 16 from the 5' end of the antisense strand is a fX nucleotide. In some embodiments, at least one of the 2'-fluoro-nucleotides at positions 2, 6, 14, and 16 from the 5' end of the antisense strand is a fX nucleotide. In some embodiments, at least two of the 2'-fluoro-nucleotides at positions 2, 6, 14, and 16 from the 5' end of the antisense strand is a fX nucleotide. In some embodiments, less than or equal to 3 of the 2'-fluoro-nucleotides at positions 2, 6, 14, and 16 from the 5' end of the antisense strand is a fX nucleotide. In some embodiments, less than or equal to 2 of the 2'-fluoro-nucleotides at positions 2, 6, 14, and 16 from the 5' end of the antisense strand is a fX nucleotide. In some embodiments, the 2'-fluoro-nucleotide at position 2 from the 5' end of the antisense strand is a fX nucleotide. In some embodiments, the 2'-fluoro-nucleotide at position 6 from the 5' end of the antisense strand is a fX nucleotide. In some embodiments, the 2'-fluoro-nucleotide at position 14 from the 5' end of the antisense strand is a fX nucleotide. In some embodiments, the 2'-fluoro-nucleotide at position 16 from the 5' end of the antisense strand is a fX nucleotide. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide. In some embodiments, the 2'-O-methyl nucleotide at position 1 from the 5' end of the antisense strand is a d2vd3 nucleotide. In some embodiments, the 2'-O-methyl nucleotide at position 1 from the 3' end of the sense strand is a d2vd3 nucleotide. In some embodiments, the 2'-O-methyl nucleotide at position 1 from the 3' end of the antisense strand is a d2vd3 nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand is a f4P, f2P, or fX nucleotide. In some embodiments, at least 1, 2, 3, 4 or more 2'-fluoro nucleotides on the antisense strand is a f4P, f2P, or fX nucleotide. In some embodiments, at least 1, 2, 3, 4 or more 2'-O-methyl nucleotide on the sense or antisense strand is a 2'-O-methyl nucleotide mimic.

Figure 3G:
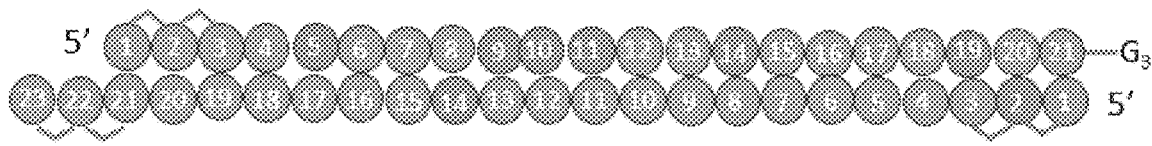

As shown in FIG. 3G, a ds-siNA may comprise (a) a sense strand consisting of 21 nucleotides, wherein 2'-fluoro nucleotides are at positions 5, 9-11, 14, and 19 from the 5' end of the sense strand, and wherein 2'-O-methyl nucleotides are at positions 1-4, 6-8, 12, 13, 15-18, 20, and 21 from the 5' end of the sense strand; and (b) an antisense strand consisting of 23 nucleotides, wherein 2'-flouro nucleotides are at positions 2 and 14 from the 5' end of the antisense strand, and wherein 2'-O-methyl nucleotides are at positions 1, 3-13, and 15-23 from the 5' end of the antisense strand. The ds-siNA may further comprise a conjugated moiety attached to the 3' end of the sense strand. The ds-siNA may further comprise (i) phosphorothioate internucleoside linkages between the nucleotides at positions 1 and 2 and positions 2 and 3 from the 5' end of the sense strand; and (ii) phosphorothioate internucleoside linkages between the nucleotides at positions 1 and 2; positions 2 and 3; positions 19 and 20; and positions 20 and 21 from the 5' end of the antisense strand. In some embodiments, the 2'-O-methyl nucleotide at position 1 from the 5' end of the sense strand is further modified to contain a 5' stabilizing end cap. In some embodiments, the 2'-O-methyl nucleotide at position 1 from the 5' end of the antisense strand is further modified to contain a 5' stabilizing end cap. In some embodiments, the 2'-O-methyl nucleotide at position 1 from the 5' end of the sense strand is further modified to contain a phosphorylation blocker. In some embodiments, the 2'-O-methyl nucleotide at position 1 from the 3' end of the sense strand is further modified to contain a phosphorylation blocker. In some embodiments, the 2'-O-methyl nucleotide at position 1 from the 5' end of the antisense strand is further modified to contain a phosphorylation blocker. In some embodiments, the 2'-O-methyl nucleotide at position 1 from the 3' end of the antisense strand is further modified to contain a phosphorylation blocker. In some embodiments, the 2'-O-methyl nucleotide at position 1 from the 5' end of the sense strand is a d2vd3 nucleotide. In some embodiments, the 2'-O-methyl nucleotide at position 1 from the 5' end of the antisense strand is a d2vd3 nucleotide. In some embodiments, the 2'-O-methyl nucleotide at position 1 from the 3' end of the sense strand is a d2vd3 nucleotide. In some embodiments, the 2'-O-methyl nucleotide at position 1 from the 3' end of the antisense strand is a d2vd3 nucleotide. In some embodiments, at least 1, 2, 3, 4 or more 2'-fluoro nucleotides on the sense strand or antisense strand is a 2'-fluoro nucleotide mimic. In some embodiments, at least 1, 2, 3, 4 or more 2'-fluoro nucleotides on the sense strand is a f4P, f2P, or fX nucleotide. In some embodiments, at least 1, 2, 3, 4 or more 2'-fluoro nucleotides on the antisense strand is a f4P, f2P, or fX nucleotide. In some embodiments, at least 1, 2, 3, 4 or more 2'-O-methyl nucleotide on the sense or antisense strand is a 2'-O-methyl nucleotide mimic.

Any of the siNAs disclosed herein may comprise a sense strand and an antisense strand. The sense strand may comprise a first nucleotide sequence that is 15 to 30 nucleotides in length. The antisense strand may comprise a second nucleotide sequence that is 15 to 30 nucleotides in length.

In some embodiments, the double-stranded short interfering nucleic acid (ds-siNA) molecule comprises: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 3, 5, 7, 8, 9, 10, 11, 12, 14, 17, and/or 19 from the 5' end of the first nucleotide sequence is a 2'-fluoro nucleotide; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide.

In some embodiments, the double-stranded short interfering nucleic acid (ds-siNA) molecule comprises: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 3, 5, 7, 8, 9, 10, 11, 12, 14, 17, and/or 19 from the 5' end of the first nucleotide sequence is a 2'-fluoro nucleotide; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide.

In some embodiments, the double-stranded short interfering nucleic acid (ds-siNA) molecule comprises: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 7 from the 5' end of the first nucleotide sequence is a 2'-fluoro nucleotide; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide.

In some embodiments, the double-stranded short interfering nucleic acid (ds-siNA) molecule comprises: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 7, 9, 10, and/or 11 from the 5' end of the first nucleotide sequence is a 2'-fluoro nucleotide; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide.

In some embodiments, the double-stranded short interfering nucleic acid (ds-siNA) molecule comprises: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 2, 5, 6, 8, 10, 14, 16, 17, and/or 18 from the 5' end of the second nucleotide sequence is a 2'-fluoro nucleotide.

In some embodiments, the double-stranded short interfering nucleic acid (ds-siNA) molecule comprises: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 2 of the second nucleotide sequence is a 2'-fluoro nucleotide.

In some embodiments, the double-stranded short interfering nucleic acid (ds-siNA) molecule comprises: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence: (i) is 15 to 30 nucleotides in length; (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (iii) comprises 1 or more phosphorothioate internucleoside linkage; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence: (i) is 15 to 30 nucleotides in length; (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (iii) comprises 1 or more phosphorothioate internucleoside linkage.

In some embodiments, the double-stranded short interfering nucleic acid (ds-siNA) molecule comprises: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide, wherein the ds-siNA may further comprise a phosphorylation blocker, a galactosamine, or 5'-stabilized end cap.

In some embodiments, the double-stranded short interfering nucleic acid (ds-siNA) molecule comprises: (I) a sense strand comprising (A) a first nucleotide sequence that is at least about 60%, 65%, 70%, 75%, 80%, 85%, 90%, 95%, or 100% identical to an RNA corresponding to a target gene, wherein the first nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (B) a phosphorylation blocker or a galactosamine; and (II) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence: (a) is 15 to 30 nucleotides in length; and (b) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide.

In some embodiments, the double-stranded short interfering nucleic acid (ds-siNA) molecule comprises: (I) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence: (a) is 15 to 30 nucleotides in length; and (b) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (II) an antisense strand comprising (A) a second nucleotide sequence that is at least about 60%, 65%, 70%, 75%, 80%, 85%, 90%, 95%, or 100% complementary to the RNA corresponding to the target gene, wherein the second nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (B) a 5'-stabilized end cap.

In some embodiments, the double-stranded short interfering nucleic acid (ds-siNA) molecule comprises: (I) a sense strand comprising (A) a first nucleotide sequence that is at least about 60%, 65%, 70%, 75%, 80%, 85%, 90%, 95%, or 100% identical to an RNA corresponding to a target gene, wherein the first nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (B) a phosphorylation blocker or a galactosamine; and (II) an antisense strand comprising (A) a second nucleotide sequence that is at least about 60%, 65%, 70%, 75%, 80%, 85%, 90%, 95%, or 100% complementary to the RNA corresponding to the target gene, wherein the second nucleotide sequence: (i) is 15 to 30 nucleotides in length; and (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (B) a 5'-stabilized end cap.

In some embodiments, the double-stranded short interfering nucleic acid (ds-siNA) molecule comprises: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence comprises a nucleotide sequence of any one SEQ ID NOs: 1-56, 103-158, and 205-260; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence comprises a nucleotide sequence of any one of SEQ ID NOs: 57-102, 159-204, and 261-306. In some embodiments, the double-stranded short interfering nucleic acid (ds-siNA) molecule comprises: (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence comprises a nucleotide sequence as shown in Tables 1-3; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence comprises a nucleotide sequence as shown in Tables 1-3.

In some embodiments, the double-stranded short interfering nucleic acid (ds-siNA) molecule comprises: (a) a sense strand comprising a nucleotide sequence of any one of SEQ ID NOs: 307-362 and 415-444; and (b) an antisense strand comprising a nucleotide sequence of any one of SEQ ID NOs: 363-409, 445-533, and 536-539. In some embodiments, the ds-siNA molecule comprises a double-stranded molecule as identified by the duplex ID (e.g., ds-siNA-001 to ds-siNA-0178) shown in Tables 6 and 10.

Further disclosed herein are compositions comprising two or more of the siNA molecules described herein.

Further disclosed herein are compositions comprising any of the siNA molecule described and a pharmaceutically acceptable carrier or diluent.

Further disclosed herein are compositions comprising two or more of the siNA molecules described herein for use as a medicament.

Further disclosed herein are compositions comprising any of the siNA molecule described and a pharmaceutically acceptable carrier or diluent for use as a medicament.

Further disclosed herein are methods of treating a disease in a subject in need thereof, the method comprising administering to the subject any of the siNA molecules described herein.

Further disclosed herein are uses of any of the siNA molecules described herein in the manufacture of a medicament for treating a disease.

Short Interfering Nucleic Acid (siNA) Molecules

As indicated above, the present disclosure provides siNA molecules comprising modified nucleotides. Any of the siNA molecules described herein may be double-stranded siNA (ds-siNA) molecules. The terms "siNA molecules" and "ds-siNA molecules" may be used interchangeably. In some embodiments, the ds-siNA molecules comprise a sense strand and an antisense strand.

Further disclosed herein are siNA molecules comprising (a) at least one phosphorylation blocker, conjugated moiety, or 5'-stabilized end cap; and (b) a short interfering nucleic acid (siNA). In some embodiments, the phosphorylation blocker is a phosphorylation blocker disclosed herein. In some embodiments, the conjugated moiety is a galactosamine disclosed herein. In some embodiments, the 5'-stabilized end cap is a 5'-stabilized end cap disclosed herein. The siNA may comprise any of the first nucleotide, second nucleotide, sense strand, or antisense strand sequences disclosed herein. The siNA may comprise 5 to 100, 5 to 90, 10 to 100, 10 to 90, 10 to 80, 10 to 70, 10 to 60, 10 to 50, 10 to 30, 10 to 25, 15 to 100, 15 to 90, 15 to 80, 15 to 70, 15 to 60, 15 to 50, 15 to 30, or 15 to 25 nucleotides. The siNA may comprise at least 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. The siNA may comprise less than or equal to 50, 45, 40, 39, 38, 37, 36, 35, 34, 33, 32, 31, 30, 29, 28, 27, 26, 25, 24, 23, 22, 21, 20, or 19 nucleotides. The nucleotides may be modified nucleotides. The siNA may be single stranded. The siNA may be double stranded. The siNA may comprise (a) a sense strand comprising 15 to 30, 15 to 25, 15 to 24, 15 to 23, 15 to 22, 15 to 21, 17 to 30, 17 to 25, 17 to 24, 17 to 23, 17 to 22, 17 to 21, 18 to 30, 18 to 25, 18 to 24, 18 to 23, 18 to 22, 18 to 21, 19 to 30, 19 to 25, 19 to 24, 19 to 23, 19 to 22, 19 to 21, 20 to 25, 20 to 24, 20 to 23, 21 to 25, 21 to 24, or 21 to 23 nucleotides; and (b) an antisense strand comprising 15 to 30, 15 to 25, 15 to 24, 15 to 23, 15 to 22, 15 to 21, 17 to 30, 17 to 25, 17 to 24, 17 to 23, 17 to 22, 17 to 21, 18 to 30, 18 to 25, 18 to 24, 18 to 23, 18 to 22, 18 to 21, 19 to 30, 19 to 25, 19 to 24, 19 to 23, 19 to 22, 19 to 21, 20 to 25, 20 to 24, 20 to 23, 21 to 25, 21 to 24, or 21 to 23 nucleotides. The siNA may comprise (a) a sense strand comprising about 15, 16, 17, 18, 19, 20, 21, 22, or 23 nucleotides; and (b) an antisense strand comprising about 15, 16, 17, 18, 19, 20, 21, 22, or 23 nucleotides. The siNA may comprise (a) a sense strand comprising about 19 nucleotides; and (b) an antisense strand comprising about 21 nucleotides. The siNA may comprise (a) a sense strand comprising about 21 nucleotides; and (b) an antisense strand comprising about 23 nucleotides.

In some embodiments, any of the siNA molecules disclosed herein further comprise one or more linkers independently selected from a phosphodiester (PO) linker, phosphorothioate (PS) linker, phosphorodithioate linker, and PS-mimic linker. In some embodiments, the PS-mimic linker is a sulfur linker. In some embodiments, the linkers are internucleoside linkers. Alternatively, or additionally, the linkers connect a nucleotide of the siNA molecule to at least one phosphorylation blocker, conjugated moiety, or 5'-stabilized end cap. In some embodiments, the linkers connect a conjugated moiety to a phosphorylation blocker or 5'-stabilized end cap.

siNA Sense Strand

Any of the siNA molecules described herein may comprise a sense strand. The sense strand may comprise a first nucleotide sequence. The first nucleotide sequence may be 15 to 30, 15 to 25, 15 to 23, 17 to 23, 19 to 23, or 19 to 21 nucleotides in length. In some embodiments, the first nucleotide sequence is 15, 16, 17, 18, 19, 20, 21, 22, 23, 24, 25, 26, 27, 28, 29, or 30 nucleotides in length. In some embodiments, the first nucleotide sequence is at least 19 nucleotides in length. In some embodiments, the first nucleotide sequence is at least 21 nucleotides in length.

In some embodiments, the sense strand is the same length as the first nucleotide sequence. In some embodiments, the sense strand is longer than the first nucleotide sequence. In some embodiments, the sense strand may further comprise 1, 2, 3, 4, or 5 or more nucleotides than the first nucleotide sequence. In some embodiments, the sense strand may further comprise a deoxyribonucleic acid (DNA). In some embodiments, the DNA is thymine (T). In some embodiments, the sense strand may further comprise a TT sequence. In some embodiments, the sense strand may further comprise one or more modified nucleotides that are adjacent to the first nucleotide sequence. In some embodiments, the one or more modified nucleotides are independently selected from any of the modified nucleotides disclosed herein (e.g., 2'-fluoro nucleotide, 2'-O-methyl nucleotide, 2'-fluoro nucleotide mimic, 2'-O-methyl nucleotide mimic, or a nucleotide comprising a modified nucleobase).

In some embodiments, the first nucleotide sequence comprises 15, 16, 17, 18, 19, 20, 21, 22, 23, or more modified nucleotides independently selected from a 2'-O-methyl nucleotide and a 2'-fluoro nucleotide. In some embodiments, 70%, 75%, 80%, 85%, 90%, 95% or 100% of the nucleotides in the first nucleotide sequence are modified nucleotides independently selected from a 2'-O-methyl nucleotide and a 2'-fluoro nucleotide. In some embodiments, 100% of the nucleotides in the first nucleotide sequence are modified nucleotides independently selected from a 2'-O-methyl nucleotide and a 2'-fluoro nucleotide. In some embodiments, the 2'-O-methyl nucleotide is a 2'-O-methyl nucleotide mimic. In some embodiments, the 2'-fluoro nucleotide is a 2'-fluoro nucleotide mimic.

In some embodiments, between about 15 to 30, 15 to 25, 15 to 24, 15 to 23, 15 to 22, 15 to 21, 17 to 30, 17 to 25, 17 to 24, 17 to 23, 17 to 22, 17 to 21, 18 to 30, 18 to 25, 18 to 24, 18 to 23, 18 to 22, 18 to 21, 19 to 30, 19 to 25, 19 to 24, 19 to 23, 19 to 22, 19 to 21, 20 to 25, 20 to 24, 20 to 23, 21 to 25, 21 to 24, or 21 to 23 modified nucleotides of the first nucleotide sequence are 2'-O-methyl nucleotides. In some embodiments, between about 2 to 20 modified nucleotides of the first nucleotide sequence are 2'-O-methyl nucleotides. In some embodiments, between about 5 to 25 modified nucleotides of the first nucleotide sequence are 2'-O-methyl nucleotides. In some embodiments, between about 10 to 25 modified nucleotides of the first nucleotide sequence are 2'-O-methyl nucleotides. In some embodiments, between about 12 to 25 modified nucleotides of the first nucleotide sequence are 2'-O-methyl nucleotides. In some embodiments, at least about 10, 11, 12, 13, 14, 15, 16, 17, 18, 19, 20, 21, or 22 modified nucleotides of the first nucleotide sequence are 2'-O-methyl nucleotides. In some embodiments, at least about 12 modified nucleotides of the first nucleotide sequence are 2'-O-methyl nucleotides. In some embodiments, at least about 13 modified nucleotides of the first nucleotide sequence are 2'-O-methyl nucleotides. In some embodiments, at least about 14 modified nucleotides of the first nucleotide sequence are 2'-O-methyl nucleotides. In some embodiments, at least about 15 modified nucleotides of the first nucleotide sequence are 2'-O-methyl nucleotides. In some embodiments, at least about 16 modified nucleotides of the first nucleotide sequence are 2'-O-methyl nucleotides. In some embodiments, at least about 17 modified nucleotides of the first nucleotide sequence are 2'-O-methyl nucleotides. In some embodiments, at least about 18 modified nucleotides of the first nucleotide sequence are 2'-O-methyl nucleotides. In some embodiments, at least about 19 modified nucleotides of the first nucleotide sequence are 2'-O-methyl nucleotides. In some embodiments, less than or equal to 25, 24, 23, 22, 21, 20, 19, 18, 17, 16, 15, 14, 13, 12, 11, 10, 9, 8, 7, 6, 5, 4, 3, or 2 modified nucleotides of the first nucleotide sequence are 2'-O-methyl nucleotides. In some embodiments, less than or equal to 21 modified nucleotides of the first nucleotide sequence are 2'-O-methyl nucleotides. In some embodiments, less than or equal to 20 modified nucleotides of the first nucleotide sequence are 2'-O-methyl nucleotides. In some embodiments, less than or equal to 19 modified nucleotides of the first nucleotide sequence are 2'-O-methyl nucleotides. In some embodiments, less than or equal to 18 modified nucleotides of the first nucleotide sequence are 2'-O-methyl nucleotides. In some embodiments, less than or equal to 17 modified nucleotides of the first nucleotide sequence are 2'-O-methyl nucleotides. In some embodiments, less than or equal to 16 modified nucleotides of the first nucleotide sequence are 2'-O-methyl nucleotides. In some embodiments, less than or equal to 15 modified nucleotides of the first nucleotide sequence are 2'-O-methyl nucleotides. In some embodiments, less than or equal to 14 modified nucleotides of the first nucleotide sequence are 2'-O-methyl nucleotides. In some embodiments, less than or equal to 13 modified nucleotides of the first nucleotide sequence are 2'-O-methyl nucleotides. In some embodiments, at least one modified nucleotide of the first nucleotide sequence is a 2'-O-methyl pyrimidine. In some embodiments, at least 5, 6, 7, 8, 9, or 10 modified nucleotides of the first nucleotide sequence are 2'-O-methyl pyrimidines. In some embodiments, at least one modified nucleotide of the first nucleotide sequence is a 2'-O-methyl purine. In some embodiments, at least 5, 6, 7, 8, 9, or 10 modified nucleotides of the first nucleotide sequence are 2'-O-methyl purines. In some embodiments, the 2'-O-methyl nucleotide is a 2'-O-methyl nucleotide mimic.

In some embodiments, between 2 to 15 modified nucleotides of the first nucleotide sequence are 2'-fluoro nucleotides. In some embodiments, between 2 to 10 modified nucleotides of the first nucleotide sequence are 2'-fluoro nucleotides. In some embodiments, between 2 to 6 modified nucleotides of the first nucleotide sequence are 2'-fluoro nucleotides. In some embodiments, 1 to 6, 1 to 5, 1 to 4, or 1 to 3 modified nucleotides of the first nucleotide sequence are 2'-fluoro nucleotides. In some embodiments, at least 1, 2, 3, 4, 5, or 6 modified nucleotides of the first nucleotide sequence are 2'-fluoro nucleotides. In some embodiments, at least 1 modified nucleotide of the first nucleotide sequence is a 2'-fluoro nucleotide. In some embodiments, at least 2 modified nucleotides of the first nucleotide sequence are 2'-fluoro nucleotides. In some embodiments, at least 3 modified nucleotides of the first nucleotide sequence are 2'-fluoro nucleotides. In some embodiments, at least 4 modified nucleotides of the first nucleotide sequence are 2'-fluoro nucleotides. In some embodiments, at least 5 modified nucleotides of the first nucleotide sequence are 2'-fluoro nucleotides. In some embodiments, at least 6 modified nucleotides of the first nucleotide sequence are 2'-fluoro nucleotides. In some embodiments, 10, 9, 8, 7, 6, 5, 4, 3 or fewer modified nucleotides of the first nucleotide sequence are 2'-fluoro nucleotides. In some embodiments, 10 or fewer modified nucleotides of the first nucleotide sequence are 2'-fluoro nucleotides. In some embodiments, 7 or fewer modified nucleotides of the first nucleotide sequence are 2'-fluoro nucleotides. In some embodiments, 6 or fewer modified nucleotides of the first nucleotide sequence are 2'-fluoro nucleotides. In some embodiments, 5 or fewer modified nucleotides of the first nucleotide sequence are 2'-fluoro nucleotides. In some embodiments, 4 or fewer modified nucleotides of the first nucleotide sequence are 2'-fluoro nucleotides. In some embodiments, 3 or fewer modified nucleotides of the first nucleotide sequence are 2'-fluoro nucleotides. In some embodiments, 2 or fewer modified nucleotides of the first nucleotide sequence are 2'-fluoro nucleotides. In some embodiments, at least one modified nucleotide of the first nucleotide sequence is a 2'-fluoro pyrimidine. In some embodiments, 1, 2, 3, 4, 5, or 6 modified nucleotides of the first nucleotide sequence are 2'-fluoro pyrimidines. In some embodiments, at least one modified nucleotide of the first nucleotide sequence is a 2'-fluoro purine. In some embodiments, 1, 2, 3, 4, 5, or 6 modified nucleotides of the first nucleotide sequence are 2'-fluoro purines. In some embodiments, the 2'-fluoro nucleotide is a 2'-fluoro nucleotide mimic.

In some embodiments, the nucleotide at position 3, 5, 7, 8, 9, 10, 11, 12, 14, 17, and/or 19 from the 5' end of the first nucleotide sequence is a 2'-fluoro nucleotide. In some embodiments, at least two nucleotides at positions 3, 5, 7, 8, 9, 10, 11, 12, 14, 17, and/or 19 from the 5' end of the first nucleotide sequence are 2'-fluoro nucleotides. In some embodiments, at least three nucleotides at positions 3, 5, 7, 8, 9, 10, 11, 12, 14, 17, and/or 19 from the 5' end of the first nucleotide sequence are 2'-fluoro nucleotides. In some embodiments, at least four nucleotides at positions 3, 5, 7, 8, 9, 10, 11, 12, 14, 17, and/or 19 from the 5' end of the first nucleotide sequence are 2'-fluoro nucleotides. In some embodiments, at least five nucleotides at positions 3, 5, 7, 8, 9, 10, 11, 12, 14, 17, and/or 19 from the 5' end of the first nucleotide sequence are 2'-fluoro nucleotides. In some embodiments, the nucleotides at positions 3, 5, 7, 8, 9, 10, 11, 12, 14, 17, and/or 19 from the 5' end of the first nucleotide sequence are 2'-fluoro nucleotides. In some embodiments, the nucleotide at position 3 from the 5' end of the first nucleotide sequence is a 2'-fluoro nucleotide. In some embodiments, the nucleotide at position 7 from the 5' end of the first nucleotide sequence is a 2'-fluoro nucleotide. In some embodiments, the nucleotide at position 8 from the 5' end of the first nucleotide sequence is a 2'-fluoro nucleotide. In some embodiments, the nucleotide at position 9 from the 5' end of the first nucleotide sequence is a 2'-fluoro nucleotide. In some embodiments, the nucleotide at position 12 from the 5' end of the first nucleotide sequence is a 2'-fluoro nucleotide. In some embodiments, the nucleotide at position 17 from the 5' end of the first nucleotide sequence is a 2'-fluoro nucleotide. In some embodiments, the 2'-fluoro nucleotide is a 2'-fluoro nucleotide mimic.

In some embodiments, at least 1, 2, 3, 4, 5, 6, or 7 nucleotides at position 3, 5, 7, 8, 9, 10, 11, 12, 14, 17, and/or 19 from the 5' end of the first nucleotide sequence is a 2'-fluoro nucleotide. In some embodiments, the nucleotide at positions 3, 5, 7, 8, 9, 10, 11, 12, 14, 17, and/or 19 from the 5' end of the first nucleotide sequence is a 2'-fluoro nucleotide. In some embodiments, at least two nucleotides at positions 3, 5, 7, 8, 9, 10, 11, 12, 14, 17, and/or 19 from the 5' end of the first nucleotide sequence are 2'-fluoro nucleotides. In some embodiments, at least three nucleotides at positions 3, 5, 7, 8, 9, 10, 11, 12, 14, 17, and/or 19 from the 5' end of the first nucleotide sequence are 2'-fluoro nucleotides. In some embodiments, the nucleotides at positions 3, 5, 7, 8, 9, 10, 11, 12, 14, 17, and/or 19 from the 5' end of the first nucleotide sequence are 2'-fluoro nucleotides. In some embodiments, the nucleotide at position 3 from the 5' end of the first nucleotide sequence is a 2'-fluoro nucleotide. In some embodiments, the nucleotide at position 5 from the 5' end of the first nucleotide sequence is a 2'-fluoro nucleotide. In some embodiments, the nucleotide at position 7 from the 5' end of the first nucleotide sequence is a 2'-fluoro nucleotide. In some embodiments, the nucleotide at position 8 from the 5' end of the first nucleotide sequence is a 2'-fluoro nucleotide. In some embodiments, the nucleotide at position 9 from the 5' end of the first nucleotide sequence is a 2'-fluoro nucleotide. In some embodiments, the nucleotide at position 10 from the 5' end of the first nucleotide sequence is a 2'-fluoro nucleotide. In some embodiments, the nucleotide at position 11 from the 5' end of the first nucleotide sequence is a 2'-fluoro nucleotide. In some embodiments, the nucleotide at position 12 from the 5' end of the first nucleotide sequence is a 2'-fluoro nucleotide. In some embodiments, the nucleotide at position 14 from the 5' end of the first nucleotide sequence is a 2'-fluoro nucleotide. In some embodiments, the nucleotide at position 17 from the 5' end of the first nucleotide sequence is a 2'-fluoro nucleotide. In some embodiments, the nucleotide at position 19 from the 5' end of the first nucleotide sequence is a 2'-fluoro nucleotide. In some embodiments, the nucleotide at position 3, 7, 8, 9, 12, and/or 17 from the 5' end of the first nucleotide sequence is a 2'-fluoro nucleotide. In some embodiments, the nucleotide at position 3, 7, 8, and/or 17 from the 5' end of the first nucleotide sequence is a 2'-fluoro nucleotide. In some embodiments, the nucleotide at position 3, 7, 8, 9, 12, and/or 17 from the 5' end of the first nucleotide sequence is a 2'-fluoro nucleotide. In some embodiments, the nucleotide at position 5, 7, 8, and/or 9 from the 5' end of the first nucleotide sequence is a 2'-fluoro nucleotide. In some embodiments, the nucleotide at position 5, 9, 10, 11, 12, and/or 19 from the 5' end of the first nucleotide sequence is a 2'-fluoro nucleotide. In some embodiments, the 2'-fluoro nucleotide is a 2'-fluoro nucleotide mimic.

In some embodiments, the 2'-fluoro nucleotide or 2'-O-methyl nucleotide is a 2'-fluoro or 2'-O-methyl nucleotide mimic. In some embodiments, the 2'-fluoro or 2'-O-methyl nucleotide mimic is a nucleotide mimic of Formula (V):

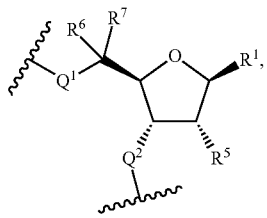

wherein $R^1$ is independently a nucleobase, aryl, heteroaryl, or H, $Q^1$ and $Q^2$ are independently S or O, $R^5$ is independently —$OCD_3$, —F, or —$OCH_3$, and $R^6$ and $R^7$ are independently H, D, or CD3. In some embodiments, the nucleobase is selected from cytosine, guanine, adenine, uracil, aryl, heteroaryl, and an analogue or derivative thereof.

In some embodiments, the 2'-fluoro or 2'-O-methyl nucleotide mimic is a nucleotide mimic of Formula (16)-Formula (20):

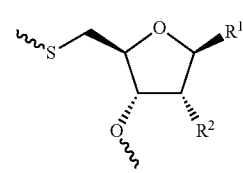

Formula (16)

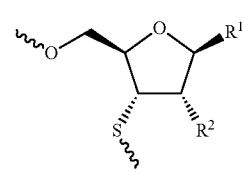

Formula (17)

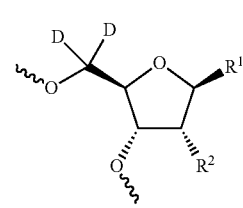

Formula (18)

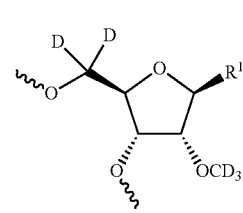

Formula (19)

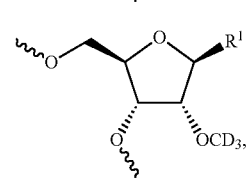

Formula (20)

wherein $R^1$ is independently a nucleobase and $R^2$ is F or —$OCH_3$. In some embodiments, the nucleobase is selected from cytosine, guanine, adenine, uracil, aryl, heteroaryl, and an analogue or derivative thereof.

In some embodiments, the first nucleotide sequence comprises, consists of, or consists essentially of ribonucleic acids (RNAs). In some embodiments, the first nucleotide sequence comprises, consists of, or consists essentially of modified RNAs. In some embodiments, the modified RNAs are selected from a 2'-O-methyl RNA and 2'-fluoro RNA. In some embodiments, 15, 16, 17, 18, 19, 20, 21, 22, or 23 modified nucleotides of the first nucleotide sequence are independently selected from 2'-O-methyl RNA and 2'-fluoro RNA.

In some embodiments, the sense strand may further comprise one or more internucleoside linkages independently selected from a phosphodiester (PO) internucleoside linkage, phosphorothioate (PS) internucleoside linkage, phosphorodithioate internucleoside linkage, and PS-mimic internucleoside linkage. In some embodiments, the PS-mimic internucleoside linkage is a sulfo internucleoside linkage.

In some embodiments, the sense strand may further comprise at least 1, 2, 3, 4, 5, 6, 7, 8, 9, 10, 11, 12, 13, 14, or 15 or more phosphorothioate internucleoside linkages. In some embodiments, the sense strand comprises 20, 19, 18, 17, 16, 15, 14, 13, 12, 11, 10, 9, 8, 7, 6, 5, 4, or 3 or fewer phosphorothioate internucleoside linkages. In some embodiments, the sense strand comprises 2 to 10, 2 to 8, 2 to 6, 1 to 5, 1 to 4, 1 to 3, or 1 to 2 phosphorothioate internucleoside linkages. In some embodiments, the sense strand comprises 1 to 2 phosphorothioate internucleoside linkages. In some embodiments, the sense strand comprises 2 to 4 phosphorothioate internucleoside linkages. In some embodiments, at least one phosphorothioate internucleoside linkage is between the nucleotides at positions 1 and 2 from the 5' end of the first nucleotide sequence. In some embodiments, at least one phosphorothioate internucleoside linkage is between the nucleotides at positions 2 and 3 from the 5' end of the first nucleotide sequence. In some embodiments, the sense strand comprises two phosphorothioate internucleoside linkages between the nucleotides at positions 1 to 3 from the 5' end of the first nucleotide sequence.

In some embodiments, any of the sense strands disclosed herein further comprise a monomer selected from Examples 21-32, 36, 37, 40-42, and 44-46 monomers. In some embodiments, any of the sense strands disclosed herein further comprise a 5' end cap monomer. In some embodiments, the 5' end cap monomer is selected from Examples 5-11, 33-35, 38, 39, 43, and 49-53 5' end cap monomers.

In some embodiments, any of the first nucleotide sequences disclosed herein further comprise a monomer selected from Examples 21-32, 36, 37, 40-42, and 44-46 monomers. In some embodiments, any of the first nucleotide sequences disclosed herein further comprise a 5' end cap monomer. In some embodiments, the 5' end cap monomer is selected from Examples 5-11, 33-35, 38, 39, 43, and 49-53 5' end cap monomers.

siNA Antisense Strand

Any of the siNA molecules described herein may comprise an antisense strand. The antisense strand may comprise a second nucleotide sequence. The second nucleotide sequence may be 15 to 30, 15 to 25, 15 to 23, 17 to 23, 19 to 23, or 19 to 21 nucleotides in length. In some embodiments, the second nucleotide sequence is 15, 16, 17, 18, 19, 20, 21, 22, 23, 24, 25, 26, 27, 28, 29, or 30 nucleotides in length. In some embodiments, the second nucleotide sequence is at least 19 nucleotides in length. In some embodiments, the second nucleotide sequence is at least 21 nucleotides in length.

In some embodiments, the antisense strand is the same length as the second nucleotide sequence. In some embodiments, the antisense strand is longer than the second nucleotide sequence. In some embodiments, the antisense strand may further comprise 1, 2, 3, 4, or 5 or more nucleotides than the second nucleotide sequence. In some embodiments, the antisense strand is the same length as the sense strand. In some embodiments, the antisense strand is longer than the sense strand. In some embodiments, the antisense strand may further comprise 1, 2, 3, 4, or 5 or more nucleotides than the sense strand. In some embodiments, the antisense strand may further comprise a deoxyribonucleic acid (DNA). In some embodiments, the DNA is thymine (T). In some embodiments, the antisense strand may further comprise a TT sequence. In some embodiments, the antisense strand may further comprise one or more modified nucleotides that are adjacent to the second nucleotide sequence. In some embodiments, the one or more modified nucleotides are independently selected from any of the modified nucleotides disclosed herein (e.g., 2'-fluoro nucleotide, 2'-O-methyl nucleotide, 2'-fluoro nucleotide mimic, 2'-O-methyl nucleotide mimic, or a nucleotide comprising a modified nucleobase).

In some embodiments, the second nucleotide sequence comprises 15, 16, 17, 18, 19, 20, 21, 22, 23, or more modified nucleotides independently selected from a 2'-O-methyl nucleotide and a 2'-fluoro nucleotide. In some embodiments, 70%, 75%, 80%, 85%, 90%, 95% or 100% of the nucleotides in the second nucleotide sequence are modified nucleotides independently selected from a 2'-O-methyl nucleotide and a 2'-fluoro nucleotide. In some embodiments, 100% of the nucleotides in the second nucleotide sequence are modified nucleotides independently selected from a 2'-O-methyl nucleotide and a 2'-fluoro nucleotide.

In some embodiments, between about 15 to 30, 15 to 25, 15 to 24, 15 to 23, 15 to 22, 15 to 21, 17 to 30, 17 to 25, 17 to 24, 17 to 23, 17 to 22, 17 to 21, 18 to 30, 18 to 25, 18 to 24, 18 to 23, 18 to 22, 18 to 21, 19 to 30, 19 to 25, 19 to 24, 19 to 23, 19 to 22, 19 to 21, 20 to 25, 20 to 24, 20 to 23, 21 to 25, 21 to 24, or 21 to 23 modified nucleotides of the second nucleotide sequence are 2'-O-methyl nucleotides. In some embodiments, between about 2 to 20 modified nucleotides of the second nucleotide sequence are 2'-O-methyl nucleotides. In some embodiments, between about 5 to 25 modified nucleotides of the second nucleotide sequence are 2'-O-methyl nucleotides. In some embodiments, between about 10 to 25 modified nucleotides of the second nucleotide sequence are 2'-O-methyl nucleotides. In some embodiments, between about 12 to 25 modified nucleotides of the second nucleotide sequence are 2'-O-methyl nucleotides. In some embodiments, at least 10, 11, 12, 13, 14, 15, 16, 17, 18, 19, 20, 21, or 22 modified nucleotides of the second nucleotide sequence are 2'-O-methyl nucleotides. In some embodiments, at least about 12 modified nucleotides of the second nucleotide sequence are 2'-O-methyl nucleotides. In some embodiments, at least about 13 modified nucleotides of the second nucleotide sequence are 2'-O-methyl nucleotides. In some embodiments, at least about 14 modified nucleotides of the second nucleotide sequence are 2'-O-methyl nucleotides. In some embodiments, at least about 15 modified nucleotides of the second nucleotide sequence are 2'-O-methyl nucleotides. In some embodiments, at least about 16 modified nucleotides of the second nucleotide sequence are 2'-O-methyl nucleotides. In some embodiments, at least about 17 modified nucleotides of the second nucleotide sequence are 2'-O-methyl nucleotides. In some embodiments, at least about 18 modified nucleotides of the second nucleotide sequence are 2'-O-methyl nucleotides. In some embodiments, at least about 19 modified nucleotides of the second nucleotide sequence are 2'-O-methyl nucleotides. In some embodiments, less than or equal to 25, 24, 23, 22, 21, 20, 19, 18, 17, 16, 15, 14, 13, 12, 11, 10, 9, 8, 7, 6, 5, 4, 3, or 2 modified nucleotides of the second nucleotide sequence are 2'-O-methyl nucleotides. In some embodiments, less than or equal to 21 modified nucleotides of the second nucleotide sequence are 2'-O-methyl nucleotides. In some embodiments, less than or equal to 20 modified nucleotides of the second nucleotide sequence are 2'-O-methyl nucleotides. In some embodiments, less than or equal to 19 modified nucleotides of the second nucleotide sequence are 2'-O-methyl nucleotides. In some embodiments, less than or equal to 18 modified nucleotides of the second nucleotide sequence are 2'-O-methyl nucleotides. In some embodiments, less than or equal to 17 modified nucleotides of the second nucleotide sequence are 2'-O-methyl nucleotides. In some embodiments, less than or equal to 16 modified nucleotides of the second nucleotide sequence are 2'-O-methyl nucleotides. In some embodiments, less than or equal to 15 modified nucleotides of the second nucleotide sequence are 2'-O-methyl nucleotides. In some embodiments, less than or equal to 14 modified nucleotides of the second nucleotide sequence are 2'-O-methyl nucleotides. In some embodiments, less than or equal to 13 modified nucleotides of the second nucleotide sequence are 2'-O-methyl nucleotides. In some embodiments, at least one modified nucleotide of the second nucleotide sequence is a 2'-O-methyl pyrimidine. In some embodiments, at least 5, 6, 7, 8, 9, or 10 modified nucleotides of the second nucleotide sequence are 2'-O-methyl pyrimidines. In some embodiments, at least one modified nucleotide of the second nucleotide sequence is a 2'-O-methyl purine. In some embodiments, at least 5, 6, 7, 8, 9, or 10 modified nucleotides of the second nucleotide sequence are 2'-O-methyl purines. In some embodiments, the 2'-O-methyl nucleotide is a 2'-O-methyl nucleotide mimic.

In some embodiments, between 2 to 15 modified nucleotides of the second nucleotide sequence are 2'-fluoro nucleotides. In some embodiments, between 2 to 10 modified nucleotides of the second nucleotide sequence are 2'-fluoro nucleotides. In some embodiments, between 2 to 6 modified nucleotides of the second nucleotide sequence are 2'-fluoro nucleotides. In some embodiments, 1 to 6, 1 to 5, 1 to 4, or 1 to 3 modified nucleotides of the second nucleotide sequence are 2'-fluoro nucleotides. In some embodiments, at least 1, 2, 3, 4, 5, or 6 modified nucleotides of the second nucleotide sequence are 2'-fluoro nucleotides. In some embodiments, at least 1 modified nucleotide of the second nucleotide sequence is a 2'-fluoro nucleotide. In some embodiments, at least 2 modified nucleotides of the second nucleotide sequence are 2'-fluoro nucleotides. In some embodiments, at least 3 modified nucleotides of the second nucleotide sequence are 2'-fluoro nucleotides. In some embodiments, at least 4 modified nucleotides of the second nucleotide sequence are 2'-fluoro nucleotides. In some embodiments, at least 5 modified nucleotides of the second nucleotide sequence are 2'-fluoro nucleotides. In some embodiments, 10, 9, 8, 7, 6, 5, 4, 3 or fewer modified nucleotides of the second nucleotide sequence are 2'-fluoro nucleotides. In some embodiments, 10 or fewer modified nucleotides of the second nucleotide sequence are 2'-fluoro nucleotides. In some embodiments, 7 or fewer modified nucleotides of the second nucleotide sequence are 2'-fluoro nucleotides. In some embodiments, 6 or fewer modified nucleotides of the second nucleotide sequence are 2'-fluoro nucleotides. In some embodiments, 5 or fewer modified nucleotides of the second nucleotide sequence are 2'-fluoro nucleotides. In some embodiments, 4 or fewer modified nucleotides of the second nucleotide sequence are 2'-fluoro nucleotides. In some embodiments, 3 or fewer modified nucleotides of the second nucleotide sequence are 2'-fluoro nucleotides. In some embodiments, 2 or fewer modified nucleotides of the second nucleotide sequence are 2'-fluoro nucleotides. In some embodiments, at least one modified nucleotide of the second nucleotide sequence is a 2'-fluoro pyrimidine. In some embodiments, 1, 2, 3, 4, 5, or 6 modified nucleotides of the second nucleotide sequence are 2'-fluoro pyrimidines. In some embodiments, at least one modified nucleotide of the second nucleotide sequence is a 2'-fluoro purine. In some embodiments, 1, 2, 3, 4, 5, or 6 modified nucleotides of the second nucleotide sequence are 2'-fluoro purines. In some embodiments, the 2'-fluoro nucleotide is a 2'-fluoro nucleotide mimic.

In some embodiments, the 2'-fluoro nucleotide or 2'-O-methyl nucleotide is a 2'-fluoro or 2'-O-methyl nucleotide mimic. In some embodiments, the 2'-fluoro or 2'-O-methyl nucleotide mimic is a nucleotide mimic of Formula (V):

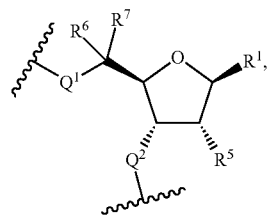

wherein $R^1$ is independently a nucleobase, aryl, heteroaryl, or H, $Q^1$ and $Q^2$ are independently S or O, $R^5$ is independently —$OCD_3$, —F, or —$OCH_3$, and $R^6$ and $R^7$ are independently H, D, or CD3. In some embodiments, the nucleobase is selected from cytosine, guanine, adenine, uracil, aryl, heteroaryl, and an analogue or derivative thereof.

In some embodiments, the 2'-fluoro or 2'-O-methyl nucleotide mimic is a nucleotide mimic of Formula (16)-Formula (20):

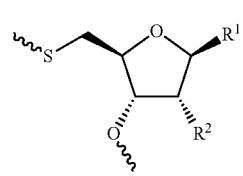
Formula (16)

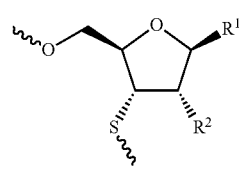
Formula (17)

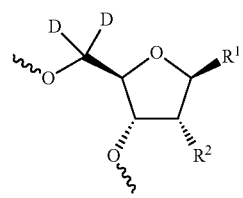
Formula (18)

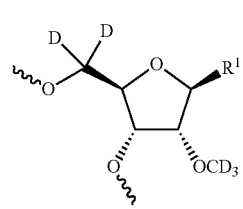
Formula (19)

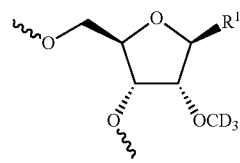
Formula (20)

wherein $R^1$ is a nucleobase and $R^2$ is independently F or —$OCH_3$. In some embodiments, the nucleobase is selected from cytosine, guanine, adenine, uracil, aryl, heteroaryl, and an analogue or derivative thereof.

In some embodiments, at least 1, 2, 3, 4, 5, 6, 7, 8, or 9 nucleotides at position 2, 5, 6, 8, 10, 14, 16, 17, and/or 18 from the 5' end of the second nucleotide sequence is a 2'-fluoro nucleotide. In some embodiments, the nucleotide at position 2, 5, 6, 8, 10, 14, 16, 17, and/or 18 from the 5' end of the second nucleotide sequence is a 2'-fluoro nucleotide. In some embodiments, at least two nucleotides at positions 2, 5, 6, 8, 10, 14, 16, 17, and/or 18 from the 5' end of the second nucleotide sequence are 2'-fluoro nucleotides. In some embodiments, at least three nucleotides at positions 2, 5, 6, 8, 10, 14, 16, 17, and/or 18 from the 5' end of the second nucleotide sequence are 2'-fluoro nucleotides. In some embodiments, at least four nucleotides at positions 2, 5, 6, 8, 10, 14, 16, 17, and/or 18 from the 5' end of the second nucleotide sequence are 2'-fluoro nucleotides. In some embodiments, at least five nucleotides at positions 2, 5, 6, 8, 10, 14, 16, 17, and/or 18 from the 5' end of the second nucleotide sequence are 2'-fluoro nucleotides. In some embodiments, the nucleotides at positions 2 and/or 14 from the 5' end of the second nucleotide sequence are 2'-fluoro nucleotides. In some embodiments, the nucleotides at positions 2, 6, and/or 16 from the 5' end of the second nucleotide sequence are 2'-fluoro nucleotides. In some embodiments, the nucleotides at positions 2, 6, 14, and/or 16 from the 5' end of the second nucleotide sequence are 2'-fluoro nucleotides. In some embodiments, the nucleotides at positions 2, 6, 10, 14, and/or 18 from the 5' end of the second nucleotide sequence are 2'-fluoro nucleotides. In some embodiments, the nucleotides at positions 2, 5, 8, 14, and/or 17 from the 5' end of the second nucleotide sequence are 2'-fluoro nucleotides. In some embodiments, the nucleotide at position 2 from the 5' end of the second nucleotide sequence is a 2'-fluoro nucleotide. In some embodiments, the nucleotide at position 5 from the 5' end of the second nucleotide sequence is a 2'-fluoro nucleotide. In some embodiments, the nucleotide at position 6 from the 5' end of the second nucleotide sequence is a 2'-fluoro nucleotide. In some embodiments, the nucleotide at position 8 from the 5' end of the second nucleotide sequence is a 2'-fluoro nucleotide. In some embodiments, the nucleotide at position 10 from the 5' end of the second nucleotide sequence is a 2'-fluoro nucleotide. In some embodiments, the nucleotide at position 14 from the 5' end of the second nucleotide sequence is a 2'-fluoro nucleotide. In some embodiments, the nucleotide at position 16 from the 5' end of the second nucleotide sequence is a 2'-fluoro nucleotide. In some embodiments, the nucleotide at position 17 from the 5' end of the second nucleotide sequence is a 2'-fluoro nucleotide. In some embodiments, the nucleotide at position 18 from the 5' end of the second nucleotide sequence is a 2'-fluoro nucleotide. In some embodiments, the 2'-fluoro nucleotide is a 2'-fluoro nucleotide mimic.

In some embodiments, the nucleotides in the second nucleotide sequence are arranged in an alternating 1:3 modification pattern, wherein 1 nucleotide is a 2'-fluoro nucleotide and 3 nucleotides are 2'-O-methyl nucleotides, and wherein the alternating 1:3 modification pattern occurs at least 2 times. In some embodiments, the alternating 1:3 modification pattern occurs 2-5 times. In some embodiments, at least two of the alternating 1:3 modification pattern occur consecutively. In some embodiments, at least two of the alternating 1:3 modification pattern occurs nonconsecutively. In some embodiments, at least 1, 2, 3, 4, or 5 alternating 1:3 modification pattern begins at nucleotide position 2, 6, 10, 14, and/or 18 from the 5' end of the antisense strand. In some embodiments, at least one alternating 1:3 modification pattern begins at nucleotide position 2 from the 5' end of the antisense strand. In some embodiments, wherein at least one alternating 1:3 modification pattern begins at nucleotide position 6 from the 5' end of the antisense strand. In some embodiments, at least one alternating 1:3 modification pattern begins at nucleotide position 10 from the 5' end of the antisense strand. In some embodiments, at least one alternating 1:3 modification pattern begins at nucleotide position 14 from the 5' end of the antisense strand. In some embodiments, at least one alternating 1:3 modification pattern begins at nucleotide position 18 from the 5' end of the antisense strand. In some embodiments, the 2'-fluoro nucleotide is a 2'-fluoro nucleotide mimic.

In some embodiments, the nucleotides in the second nucleotide sequence are arranged in an alternating 1:2 modification pattern, wherein 1 nucleotide is a 2'-fluoro nucleotide and 2 nucleotides are 2'-O-methyl nucleotides, and wherein the alternating 1:2 modification pattern occurs at least 2 times. In some embodiments, the alternating 1:2 modification pattern occurs 2-5 times. In some embodiments, at least two of the alternating 1:2 modification pattern occurs consecutively. In some embodiments, at least two of the alternating 1:2 modification pattern occurs nonconsecutively. In some embodiments, at least 1, 2, 3, 4, or 5 alternating 1:2 modification pattern begins at nucleotide position 2, 5, 8, 14, and/or 17 from the 5' end of the antisense strand. In some embodiments, at least one alternating 1:2 modification pattern begins at nucleotide position 2 from the 5' end of the antisense strand. In some embodiments, at least one alternating 1:2 modification pattern begins at nucleotide position 5 from the 5' end of the antisense strand. In some embodiments, at least one alternating 1:2 modification pattern begins at nucleotide position 8 from the 5' end of the antisense strand. In some embodiments, at least one alternating 1:2 modification pattern begins at nucleotide position 14 from the 5' end of the antisense strand. In some embodiments, at least one alternating 1:2 modification pattern begins at nucleotide position 17 from the 5' end of the antisense strand. In some embodiments, the 2'-fluoro nucleotide is a 2'-fluoro nucleotide mimic.

In some embodiments, the second nucleotide sequence comprises, consists of, or consists essentially of ribonucleic acids (RNAs). In some embodiments, the second nucleotide sequence comprises, consists of, or consists essentially of modified RNAs. In some embodiments, the modified RNAs are selected from a 2'-O-methyl RNA and 2'-fluoro RNA. In some embodiments, 15, 16, 17, 18, 19, 20, 21, 22, or 23 modified nucleotides of the second nucleotide sequence are independently selected from 2'-O-methyl RNA and 2'-fluoro RNA. In some embodiments, the 2'-fluoro nucleotide is a 2'-fluoro nucleotide mimic.

In some embodiments, the sense strand may further comprise one or more internucleoside linkages independently selected from a phosphodiester (PO) internucleoside linkage, phosphorothioate (PS) internucleoside linkage, phosphorodithioate internucleoside linkage, and PS-mimic internucleoside linkage. In some embodiments, the PS-mimic internucleoside linkage is a sulfo internucleoside linkage.

In some embodiments, the antisense strand may further comprise at least 1, 2, 3, 4, 5, 6, 7, 8, 9, 10, 11, 12, 13, 14, or 15 or more phosphorothioate internucleoside linkages. In some embodiments, the antisense strand comprises 20, 19, 18, 17, 16, 15, 14, 13, 12, 11, 10, 9, 8, 7, 6, 5, 4, or 3 or fewer phosphorothioate internucleoside linkages. In some embodiments, the antisense strand comprises 2 to 10, 2 to 8, 2 to 6, 1 to 5, 1 to 4, 1 to 3, or 1 to 2 phosphorothioate internucleoside linkages. In some embodiments, the antisense strand comprises 2 to 10, 2 to 8, 2 to 6, 1 to 5, 1 to 4, 1 to 3, or 1 to 2 phosphorothioate internucleoside linkages. In some embodiments, the antisense strand comprises 2 to 8 phosphorothioate internucleoside linkages. In some embodiments, the antisense strand comprises 3 to 8 phosphorothioate internucleoside linkages. In some embodiments, the antisense strand comprises 4 to 8 phosphorothioate internucleoside linkages. In some embodiments, at least one phosphorothioate internucleoside linkage is between the nucleotides at positions 1 and 2 from the 5' end of the second nucleotide sequence. In some embodiments, at least one phosphorothioate internucleoside linkage is between the nucleotides at positions 2 and 3 from the 5' end of the second nucleotide sequence. In some embodiments, at least one phosphorothioate internucleoside linkage is between the nucleotides at positions 1 and 2 from the 3' end of the second nucleotide sequence. In some embodiments, at least one phosphorothioate internucleoside linkage is between the nucleotides at positions 2 and 3 from the 3' end of the second nucleotide sequence. In some embodiments, the antisense strand comprises two phosphorothioate internucleoside linkages between the nucleotides at positions 1 to 3 from the 5' end of the first nucleotide sequence. In some embodiments, the antisense strand comprises two phosphorothioate internucleoside linkages between the nucleotides at positions 1 to 3 from the 3' end of the first nucleotide sequence. In some embodiments, the antisense strand comprises (a) two phosphorothioate internucleoside linkages between the nucleotides at positions 1 to 3 from the 5' end of the first nucleotide sequence; and (b) two phosphorothioate internucleoside linkages between the nucleotides at positions 1 to 3 from the 3' end of the first nucleotide sequence.

In some embodiments, at least one end of the ds-siNA is a blunt end. In some embodiments, at least one end of the ds-siNA comprises an overhang, wherein the overhang comprises at least one nucleotide. In some embodiments, both ends of the ds-siNA comprise an overhang, wherein the overhang comprises at least one nucleotide. In some embodiments, the overhang comprises 1 to 5 nucleotides, 1 to 4 nucleotides, 1 to 3 nucleotides, or 1 to 2 nucleotides. In some embodiments, the overhang consists of 1 to 2 nucleotides.

In some embodiments, the first nucleotide sequence comprises a nucleotide sequence of any one SEQ ID NOs: 1-56, 103-158, and 205-260. In some embodiments, the second nucleotide sequence comprises a nucleotide sequence of any one of SEQ ID NOs: 57-102, 159-204, and 261-306. In some embodiments, the sense strand comprises a nucleotide sequence of any one of SEQ ID NOs: 307-362 and 415-444. In some embodiments, the antisense strand comprises a nucleotide sequence of any one of SEQ ID NOs: 363-409, 445-533, and 536-539.

In some embodiments, any of the antisense strands disclosed herein further comprise a monomer selected from Examples 21-32, 36, 37, 40-42, and 44-46 monomers. In some embodiments, any of the antisense strands disclosed herein further comprise a 5' end cap monomer. In some embodiments, the 5' end cap monomer is selected from Examples 5-11, 33-35, 38, 39, 43, and 49-53 5' end cap monomers.

In some embodiments, any of the second nucleotide sequences disclosed herein further comprise a monomer selected from Examples 21-32, 36, 37, 40-42, and 44-46 monomers. In some embodiments, any of the second nucleotide sequences disclosed herein further comprise a 5' end cap monomer. In some embodiments, the 5' end cap monomer is selected from Examples 5-11, 33-35, 38, 39, 43, and 49-53 5' end cap monomers.

Modified Nucleotides

Further disclosed herein are siNA molecules comprising one or more modified nucleotides. In some embodiments, any of the siNAs disclosed herein comprise one or more modified nucleotides. In some embodiments, any of the sense strands disclosed herein comprise one or more modified nucleotides. In some embodiments, any of the first nucleotide sequences disclosed herein comprise one or more modified nucleotides. In some embodiments, any of the antisense strands disclosed herein comprise one or more modified nucleotides. In some embodiments, any of the second nucleotide sequences disclosed herein comprise one or more modified nucleotides. In some embodiments, the one or more modified nucleotides is adjacent to the first nucleotide sequence. In some embodiments, at least one modified nucleotide is adjacent to the 5' end of the first nucleotide sequence. In some embodiments, at least one modified nucleotide is adjacent to the 3' end of the first nucleotide sequence. In some embodiments, at least one modified nucleotide is adjacent to the 5' end of the first nucleotide sequence and at least one modified nucleotide is adjacent to the 3' end of the first nucleotide sequence. In some embodiments, the one or more modified nucleotides is adjacent to the second nucleotide sequence. In some embodiments, at least one modified nucleotide is adjacent to the 5' end of the second nucleotide sequence. In some embodiments, at least one modified nucleotide is adjacent to the 3' end of the second nucleotide sequence. In some embodiments, at least one modified nucleotide is adjacent to the 5' end of the second nucleotide sequence and at least one modified nucleotide is adjacent to the 3' end of the second nucleotide sequence. In some embodiments, a 2'-O-methyl nucleotide in any of sense strands or first nucleotide sequences disclosed herein is replaced with a modified nucleotide. In some embodiments, a 2'-O-methyl nucleotide in any of antisense strands or second nucleotide sequences disclosed herein is replaced with a modified nucleotide.

In some embodiments, any of the siNA molecules, siNAs, sense strands, first nucleotide sequences, antisense strands, and second nucleotide sequences disclosed herein comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more modified nucleotides. In some embodiments, 1%, 2%, 3%, 4%, 5%0, 10%, 15%, 20%, 25%, 30%, 35%, 40%, 45%, 50%, 55%, 60%0, 70%, 75%, 80%, 85%, 86%, 87%, 88%, 90%, 91%, 92%, 93%, 94%, 95%, 96%, 97%, 98%, 99% or 100% of the nucleotides in the siNA molecule, siNA, sense strand, first nucleotide sequence, antisense strand, or second nucleotide sequence are modified nucleotides.

In some embodiments, a modified nucleotide is selected from the group consisting of 2'-fluoro nucleotide, 2'-O-methyl nucleotide, 2'-fluoro nucleotide mimic, 2'-O-methyl nucleotide mimic, a locked nucleic acid, and a nucleotide comprising a modified nucleobase.

In some embodiments, any of the siRNAs disclosed herein comprise at least 1, 2, 3, 4, 5, 6, 7, 8, 9, or 10 or more 2'-fluoro or 2'-O-methyl nucleotide mimics. In some embodiments, any of the sense strands disclosed herein comprise at least 1, 2, 3, 4, 5, 6, 7, 8, 9, or 10 or more 2'-fluoro or 2'-O-methyl nucleotide mimics. In some embodiments, any of the first nucleotide sequences disclosed herein comprise at least 1, 2, 3, 4, 5, 6, 7, 8, 9, or 10 or more 2'-fluoro or 2'-O-methyl nucleotide mimics. In some embodiments, any of the antisense strand disclosed herein comprise at least 1, 2, 3, 4, 5, 6, 7, 8, 9, or 10 or more 2'-fluoro or 2'-O-methyl nucleotide mimics. In some embodiments, any of the second nucleotide sequences disclosed herein comprise at least 1, 2, 3, 4, 5, 6, 7, 8, 9, or 10 or more 2'-fluoro or 2'-O-methyl nucleotide mimics. In some embodiments, the 2'-fluoro or 2'-O-methyl nucleotide mimic is a nucleotide mimic of Formula (16)-Formula (20):

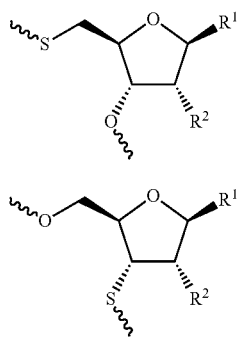

Formula (16)

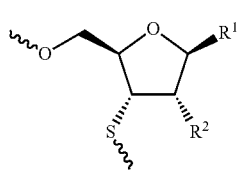

Formula (17)

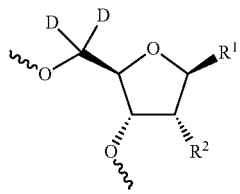

Formula (18)

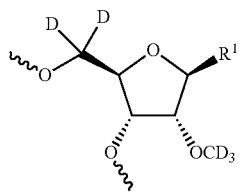

Formula (19)

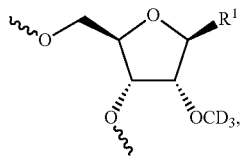

Formula (20)

wherein $R^1$ is a nucleobase and $R^2$ is independently F or —OCH$_3$. In some embodiments, the nucleobase is selected from cytosine, guanine, adenine, uracil, aryl, heteroaryl, and an analogue or derivative thereof. In some embodiments, the siNA molecules disclosed herein comprise at least one 2'-fluoro nucleotide, at least one 2'-O-methyl nucleotide, and at least one 2'-fluoro or 2'-O-methyl nucleotide mimic. In some embodiments, the at least one 2'-fluoro or 2'-O-methyl nucleotide mimic is adjacent to the first nucleotide sequence. In some embodiments, the at least one 2'-fluoro or 2'-O-methyl nucleotide mimic is adjacent to the 5' end of first nucleotide sequence. In some embodiments, the at least one 2'-fluoro or 2'-O-methyl nucleotide mimic is adjacent to the 3' end of first nucleotide sequence. In some embodiments, the at least one 2'-fluoro or 2'-O-methyl nucleotide mimic is adjacent to the second nucleotide sequence. In some embodiments, the at least one 2'-fluoro or 2'-O-methyl nucleotide mimic is adjacent to the 5' end of second nucleotide sequence. In some embodiments, the at least one 2'-fluoro or 2'-O-methyl nucleotide mimic is adjacent to the 3' end of second nucleotide sequence. In some embodiments, the first nucleotide sequence does not comprise a 2'-fluoro nucleotide mimic. In some embodiments, the first nucleotide sequence does not comprise a 2'-O-methyl nucleotide mimic. In some embodiments, the second nucleotide sequence does not comprise a 2'-fluoro nucleotide mimic. In some embodiments, the second nucleotide sequence does not comprise a 2'-O-methyl nucleotide mimic.

In some embodiments, any of the siRNAs disclosed herein comprise at least 1, 2, 3, 4, 5, 6, 7, 8, 9, or 10 or more locked nucleic acids. In some embodiments, any of the sense strands disclosed herein comprise at least 1, 2, 3, 4, 5, 6, 7, 8, 9, or 10 or more locked nucleic acids. In some embodiments, any of the first nucleotide sequences disclosed herein comprise at least 1, 2, 3, 4, 5, 6, 7, 8, 9, or 10 or more locked nucleic acids. In some embodiments, any of the antisense strand disclosed herein comprise at least 1, 2, 3, 4, 5, 6, 7, 8, 9, or 10 or more locked nucleic acids. In some embodiments, any of the second nucleotide sequences disclosed herein comprise at least 1, 2, 3, 4, 5, 6, 7, 8, 9, or 10 or more locked nucleic acids. In some embodiments, the locked nucleic acid is selected from

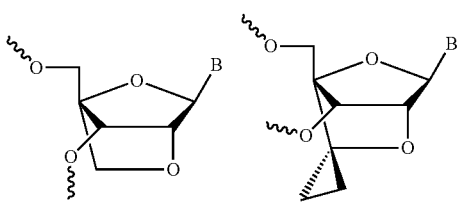

(LNA) , (ScpBNA or "cp") ;

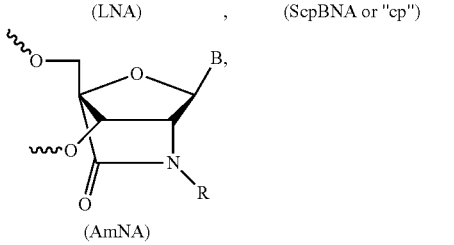

(AmNA)

where R is H or alkyl (or AmNA(N-Me)) when R is alkyl;

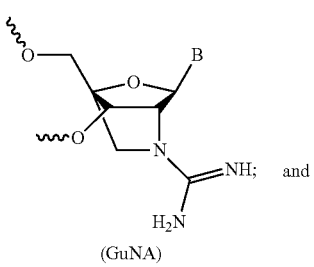

(GuNA)

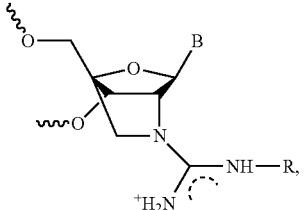

GuNA( N—R ), R = Me, Et, iPr, tBu wherein B is a nucleobase. In some embodiments, any of the siRNAs, sense strands, first nucleotide sequences, antisense strands, or second nucleotide sequences disclosed herein comprise at least modified nucleotide that is

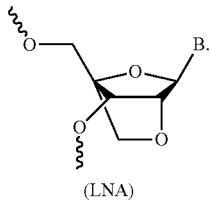

(LNA)

In some embodiments, any of the siRNAs, sense strands, first nucleotide sequences, antisense strands, or second nucleotide sequences disclosed herein comprise at least modified nucleotide that is

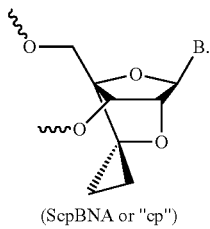

(ScpBNA or "cp")

In some embodiments, any of the siRNAs, sense strands, first nucleotide sequences, antisense strands, or second nucleotide sequences disclosed herein comprise at least modified nucleotide that is

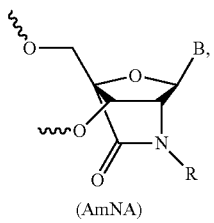

(AmNA)

where R is H or alkyl (or AmNA(N-Me)) when R is alkyl). In some embodiments, any of the siRNAs, sense strands, first nucleotide sequences, antisense strands, or second nucleotide sequences disclosed herein comprise at least modified nucleotide that is

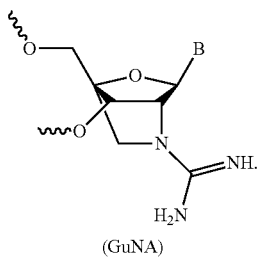

(GuNA)

In some embodiments, any of the siRNAs, sense strands, first nucleotide sequences, antisense strands, or second nucleotide sequences disclosed herein comprise at least modified nucleotide that is

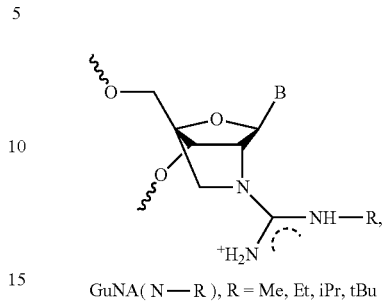

GuNA( N — R ), R = Me, Et, iPr, tBu wherein B is a nucleobase.

Phosphorylation Blocker

Further disclosed herein are siNA molecules comprising a phosphorylation blocker. In some embodiments, a 2'-O-methyl nucleotide in any of sense strands or first nucleotide sequences disclosed herein is replaced with a nucleotide containing a phosphorylation blocker. In some embodiments, a 2'-O-methyl nucleotide in any of antisense strands or second nucleotide sequences disclosed herein is replaced with a nucleotide containing a phosphorylation blocker. In some embodiments, a 2'-O-methyl nucleotide in any of sense strands or first nucleotide sequences disclosed herein is further modified to contain a phosphorylation blocker. In some embodiments, a 2'-O-methyl nucleotide in any of antisense strands or second nucleotide sequences disclosed herein is further modified to contain a phosphorylation blocker.

In some embodiments, any of the siNA molecules disclosed herein comprise a phosphorylation blocker of Formula (IV):

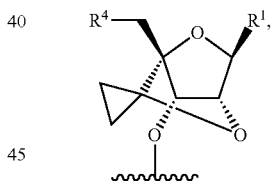

wherein $R^1$ is a nucleobase, $R^4$ is $-O-R^{30}$ or $-NR^{31}R^{32}$, $R^{30}$ is $C_1$-$C_8$ substituted or unsubstituted alkyl; and $R^{31}$ and $R^{32}$ together with the nitrogen to which they are attached form a substituted or unsubstituted heterocyclic ring.

In some embodiments, any of the siNA molecules disclosed herein comprise a phosphorylation blocker of Formula (IV):

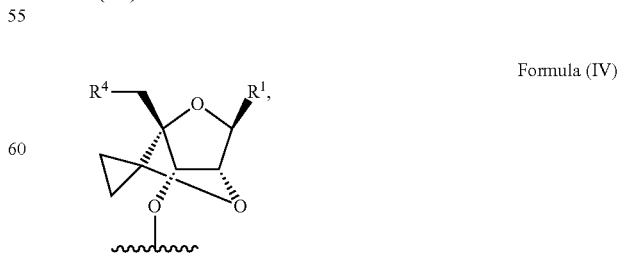

Formula (IV)

wherein $R^1$ is a nucleobase, and $R^4$ is $-OCH_3$ or $-N(CH_2CH_2)_2O$.

In some embodiments, a siNA molecule comprises (a) a phosphorylation blocker of Formula (IV):

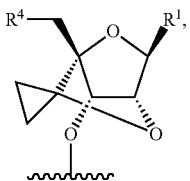

wherein $R^1$ is a nucleobase, $R^4$ is —O—$R^{30}$ or —$NR^{31}R^{32}$, $R^{30}$ is $C_1$-$C_8$ substituted or unsubstituted alkyl; and $R^{31}$ and $R^{32}$ together with the nitrogen to which they are attached form a substituted or unsubstituted heterocyclic ring; and (b) a short interfering nucleic acid (siNA), wherein the phosphorylation blocker is conjugated to the siNA.

In some embodiments, a siNA molecule comprises (a) a phosphorylation blocker of Formula (IV):

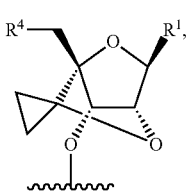

Formula (IV)

wherein $R^1$ is a nucleobase, and $R^4$ is —$OCH_3$ or —$N(CH_2CH_2)_2O$; and (b) a short interfering nucleic acid (siNA), wherein the phosphorylation blocker is conjugated to the siNA.

In some embodiments, the phosphorylation blocker is attached to the 3' end of the sense strand or first nucleotide sequence. In some embodiments, the phosphorylation blocker is attached to the 3' end of the sense strand or first nucleotide sequence via 1, 2, 3, 4, or 5 or more linkers. In some embodiments, the phosphorylation blocker is attached to the 5' end of the sense strand or first nucleotide sequence. In some embodiments, the phosphorylation blocker is attached to the 5' end of the sense strand or first nucleotide sequence. In some embodiments, the phosphorylation blocker is attached to the 5' end of the antisense strand or second nucleotide sequence via 1, 2, 3, 4, or 5 or more linkers. In some embodiments, the one or more linkers are independently selected from the group consisting of a phosphodiester linker, phosphorothioate linker, and phosphorodithioate linker.

Conjugated Moiety

Further disclosed herein are siNA molecules comprising a conjugated moiety. In some embodiments, the conjugated moiety is selected from galactosamine, peptides, proteins, sterols, lipids, phospholipids, biotin, phenoxazines, active drug substance, cholesterols, phenanthridine, anthraquinone, acridine, fluoresceins, rhodamines, coumarins, and dyes. In some embodiments, the conjugated moiety is attached to the 3' end of the sense strand or first nucleotide sequence. In some embodiments, the conjugated moiety is attached to the 3' end of the sense strand or first nucleotide sequence via 1, 2, 3, 4, or 5 or more linkers. In some embodiments, the conjugated moiety is attached to the 5' end of the sense strand or first nucleotide sequence. In some embodiments, the conjugated moiety is attached to the 5' end of the sense strand or first nucleotide sequence via 1, 2, 3, 4, or 5 or more linkers. In some embodiments, the conjugated moiety is attached to the 3' end of the antisense strand or second nucleotide sequence. In some embodiments, the conjugated moiety is attached to the 3' end of the antisense strand or second nucleotide sequence via 1, 2, 3, 4, or 5 or more linkers. In some embodiments, the conjugated moiety is attached to the 5' end of the antisense strand or second nucleotide sequence. In some embodiments, the conjugated moiety is attached to the 5' end of the antisense strand or second nucleotide sequence via 1, 2, 3, 4, or 5 or more linkers. In some embodiments, the one or more linkers are independently selected from the group consisting of a phosphodiester linker, phosphorothioate linker, and phosphorodithioate linker.

In some embodiments, the conjugated moiety is galactosamine. In some embodiments, any of the siNAs disclosed herein are attached to a conjugated moiety that is galactosamine. In some embodiments, the galactosamine is N-acetylgalactosamine (GalNAc). In some embodiments, any of the siNA molecules disclosed herein comprise GalNAc. In some embodiments, the GalNAc is of Formula (VI):

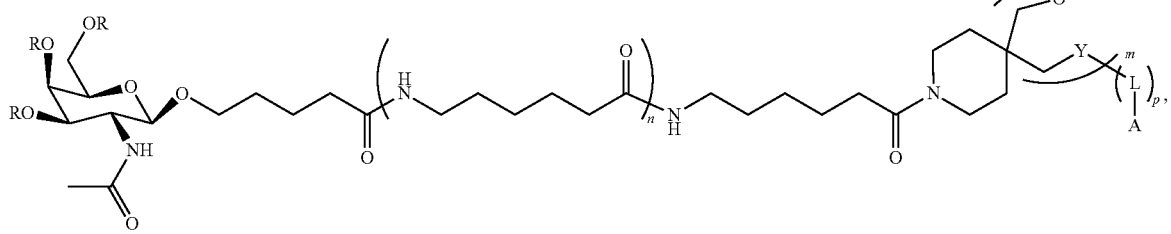

wherein m is 1, 2, 3, 4, or 5; each n is independently 1 or 2; p is 0 or 1; each R is independently H or a first protecting group; each Y is independently selected from —O—P(=O)(SH)—, —O—P(=O)(O)—, —O—P(=O)(OH)—, —O—P(S)S—, and —O—; Z is H or a second protecting group; either L is a linker or L and Y in combination are a linker; and A is H, OH, a third protecting group, an activated group, or an oligonucleotide. In some embodiments, the first protecting group is acetyl. In some embodiments, the second protecting group is trimethoxytrityl (TMT). In some embodiments, the activated group is a phosphoramidite group. In some embodiments, the phosphoramidite group is a cyanoethoxy N,N-diisopropylphosphoramidite group. In some embodiments, the linker is a C6-NH$_2$ group. In some embodiments, A is a short interfering nucleic acid (siNA) or siNA molecule. In some embodiments, m is 3. In some embodiments, R is H, Z is H, and n is 1. In some embodiments, R is H, Z is H, and n is 2.

In some embodiments, the GalNAc is of Formula (VII):

moiety. Examples of lipid moieties include, but are not limited to, a cholesterol moiety, a thioether, e.g., hexyl-S-tritylthiol, a thiocholesterol, an aliphatic chain, e.g., dodecandiol or undecyl residues a phospholipid, e.g., di-hexa-decyl-rac-glycerol or triethylammonium 1-di-O-hexadecyl-rac-glycero-S—H-phosphonate, a polyamine or a polyethylene glycol chain, adamantane acetic acid, a palmityl moiety, or an octadecylamine or hexylamino-carbonyl-oxycholesterol moiety.

In some embodiments, the conjugated moiety is an active drug substance. In some embodiments, any of the siNAs

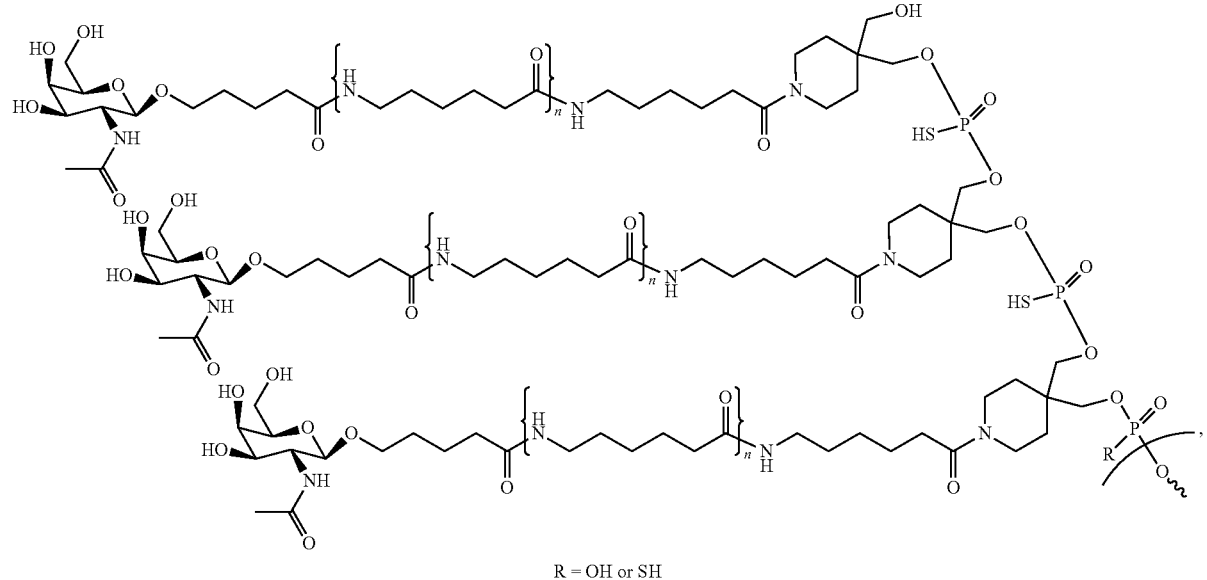

R = OH or SH wherein each n is independently 1 or 2.

In some embodiments, the galactosamine is attached to the 3' end of the sense strand or first nucleotide sequence. In some embodiments, the galactosamine is attached to the 3' end of the sense strand or first nucleotide sequence via 1, 2, 3, 4, or 5 or more linkers. In some embodiments, the galactosamine is attached to the 5' end of the sense strand or first nucleotide sequence. In some embodiments, the galactosamine is attached to the 5' end of the sense strand or first nucleotide sequence via 1, 2, 3, 4, or 5 or more linkers. In some embodiments, the galactosamine is attached to the 3' end of the antisense strand or second nucleotide sequence. In some embodiments, the galactosamine is attached to the 3' end of the antisense strand or second nucleotide sequence via 1, 2, 3, 4, or 5 or more linkers. In some embodiments, the galactosamine is attached to the 5' end of the antisense strand or second nucleotide sequence. In some embodiments, the galactosamine is attached to the 5' end of the antisense strand or second nucleotide sequence via 1, 2, 3, 4, or 5 or more linkers. In some embodiments, the one or more linkers are independently selected from the group consisting of a phosphodiester (p or po) linker, phosphorothioate (ps) linker, phosphoramidite (HEG) linker, triethylene glycol (TEG) linker, and/or phosphorodithioate linker. In some embodiments, the one or more linkers are independently selected from the group consisting of p-(PS)2, (PS)2-p-TEG-p, (PS)2-p-HEG-p, and (PS)2-p-(HEG-p)2.

In some embodiments, the conjugated moiety is a lipid moiety. In some embodiments, any of the siNAs disclosed herein are attached to a conjugated moiety that is a lipid disclosed herein are attached to a conjugated moiety that is an active drug substance. Examples of active drug substances include, but are not limited to, aspirin, warfarin phenylbutazone, ibuprofen, suprofen, fenbufen, ketoprofen, (5)-(+) pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

5'-Stabilized End Cap

Further disclosed herein are siNA molecules comprising a 5'-stabilized end cap. As used herein the terms "5'-stabilized end cap" and "5' end cap" are used interchangeably. In some embodiments, a 2'-O-methyl nucleotide in any of sense strands or first nucleotide sequences disclosed herein is replaced with a nucleotide containing a 5'-stabilized end cap. In some embodiments, a 2'-O-methyl nucleotide in any of antisense strands or second nucleotide sequences disclosed herein is replaced with a nucleotide containing a 5'-stabilized end cap. In some embodiments, a 2'-O-methyl nucleotide in any of sense strands or first nucleotide sequences disclosed herein is further modified to contain a 5'-stabilized end cap. In some embodiments, a 2'-O-methyl nucleotide in any of antisense strands or second nucleotide sequences disclosed herein is further modified to contain a 5'-stabilized end cap.

In some embodiments, the 5'-stabilized end cap is a 5' phosphate mimic. In some embodiments, the 5'-stabilized end cap is a modified 5' phosphate mimic. In some embodiments, the modified 5' phosphate is a chemically modified 5' phosphate. In some embodiments, the 5'-stabilized end cap is a 5'-vinyl phosphonate. In some embodiments, the 5'-vinyl phosphonate is a 5'-(E)-vinyl phosphonate or 5'-(Z)-vinyl phosphonate. In some embodiments, the 5'-vinyl phosphonate is a deuterated vinyl phosphonate. In some embodiments, the deuterated vinyl phosphonate is a mono-deuterated vinyl phosphonate. In some embodiments, the deuterated vinyl phosphonate is a di-deuterated vinyl phosphonate. In some embodiments, the 5'-stabilized end cap is a phosphate mimic. Examples of phosphate mimics are disclosed in Parmar et al., 2018, *J Med Chem,* 61(3):734-744, International Publication Nos. WO2018/045317 and WO2018/044350, and U.S. Pat. No. 10,087,210, each of which is incorporated by reference in its entirety.

In some embodiments, any of the siNA molecules, sense strands, first nucleotide sequences, antisense strands, or second nucleotide sequences disclosed herein comprise a 5'-stabilized end cap of Formula (Ia):

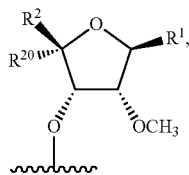

wherein $R^1$ is H, a nucleobase, aryl, or heteroaryl; $R^2$ is

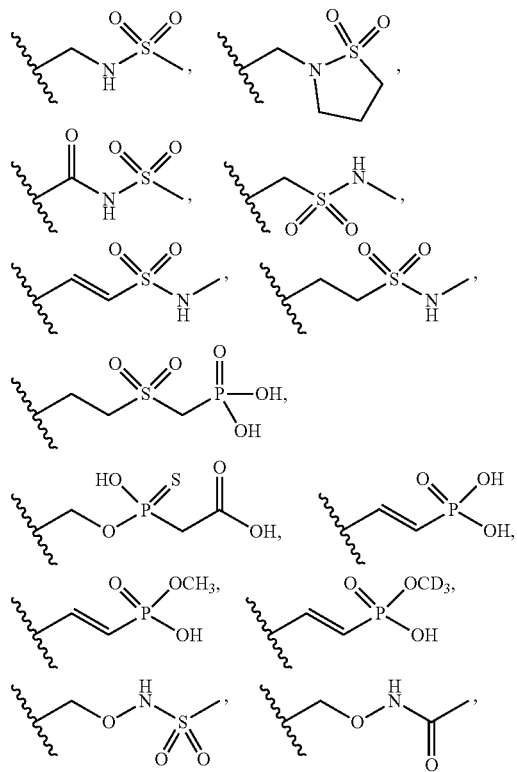

—CH=CD-Z, —CD=CH—Z, —CD=CD-Z, —(CR$^{21}$R$^{22}$)$_n$—Z, or —(C$_2$-C$_6$ alkenylene)-Z and $R^{20}$ is H; or $R^2$ and $R^{20}$ together form a 3- to 7-membered carbocyclic ring substituted with —(CR$^{21}$R$^{22}$)$_n$—Z or —(C$_2$-C$_6$alkenylene)-Z; n is 1, 2, 3, or 4; Z is —ONR$^{23}$R$^{24}$, —OP(O)OH (CH$_2$)$_m$CO$_2$R$^{23}$, —OP(S)OH(CH$_2$)$_m$CO$_2$R$^{23}$, —P(O)(OH)$_2$, —P(O)(OH)(OCH$_3$), —P(O)(OH)(OCD$_3$), —SO$_2$(CH$_2$)$_m$P(O)(OH)$_2$, —SO$_2$NR$^{23}$R$^{25}$, —NR$^{23}$R$^{24}$, —NR$^{23}$SO$_2$R$^{24}$; either $R^{21}$ and $R^{22}$ are independently hydrogen or C$_1$-C$_6$ alkyl, or $R^{21}$ and $R^{22}$ together form an oxo group; $R^{23}$ is hydrogen or C$_1$-C$_6$ alkyl; $R^{24}$ is —SO$_2$R$^{25}$ or —C(O)R$^{25}$; or $R^{23}$ and $R^{24}$ together with the nitrogen to which they are attached form a substituted or unsubstituted heterocyclic ring; $R^{25}$ is C$_1$-C$_6$ alkyl; and m is 1, 2, 3, or 4. In some embodiments, $R^1$ is an aryl. In some embodiments, the aryl is a phenyl.

In some embodiments, any of the siNA molecules, sense strands, first nucleotide sequences, antisense strands, or second nucleotide sequences disclosed herein comprise a 5'-stabilized end cap of Formula (Ib):

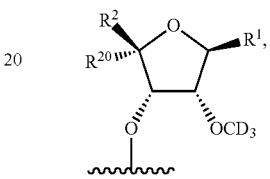

wherein $R^1$ is H, a nucleobase, aryl, or heteroaryl; $R^2$ is

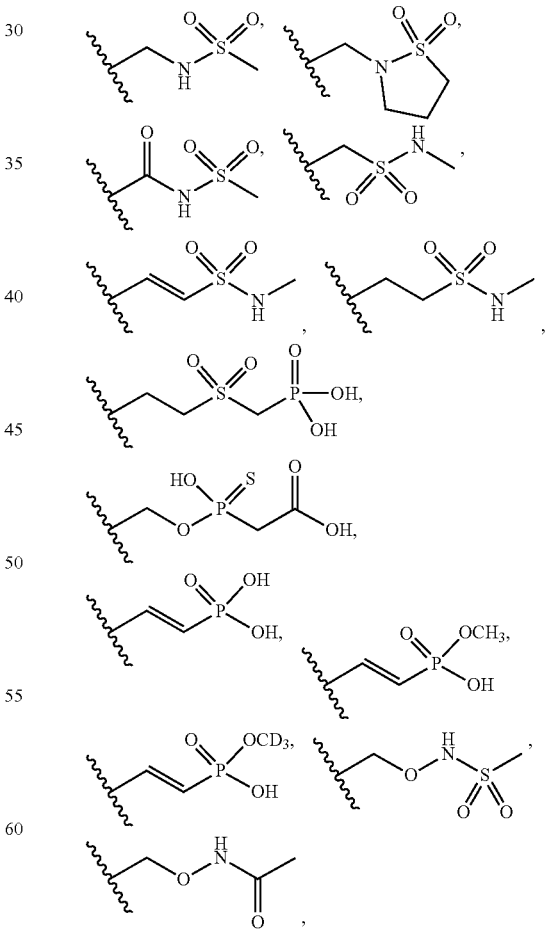

—CH=CD-Z, —CD=CH—Z, —CD=CD-Z, —(CR$^{21}$R$^{22}$)$_n$—Z, or —(C$_2$-C$_6$ alkenylene)-Z and $R^{20}$ is H; or $R^2$ and $R^{20}$ together form a 3- to 7-membered carbocyclic ring substituted with —$(CR^{21}R^{22})_n$—Z or —$(C_2$-$C_6$alkenylene)-Z; n is 1, 2, 3, or 4; Z is —$ONR^{23}R^{24}$, —OP(O)OH $(CH_2)_mCO_2R^{23}$, —OP(S)OH$(CH_2)_mCO_2R^{23}$, —P(O)(OH)$_2$, —P(O)(OH)(OCH$_3$), —P(O)(OH)(OCD$_3$), —SO$_2$(CH$_2$)$_m$P (O)(OH)$_2$, —SO$_2$NR$^{23}$R$^{25}$, —NR$^{23}$R$^{24}$, —NR$^{23}$SO$_2$R$^{24}$; either $R^{21}$ and $R^{22}$ are independently hydrogen or $C_1$-$C_6$ alkyl, or $R^{21}$ and $R^{22}$ together form an oxo group; $R^{23}$ is hydrogen or $C_1$-$C_6$ alkyl; $R^{24}$ is —SO$_2$R$^{25}$ or —C(O)R$^{25}$; or $R^{23}$ and $R^{24}$ together with the nitrogen to which they are attached form a substituted or unsubstituted heterocyclic ring; $R^{25}$ is $C_1$-$C_6$ alkyl; and m is 1, 2, 3, or 4. In some embodiments, $R^1$ is an aryl. In some embodiments, the aryl is a phenyl.

In some embodiments, any of the siNA molecules, sense strands, first nucleotide sequences, antisense strands, or second nucleotide sequences disclosed herein comprise a 5'-stabilized end cap of Formula (Ic):

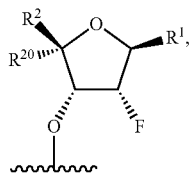

wherein $R^1$ is a nucleobase, aryl, heteroaryl, or H, $R^2$ is

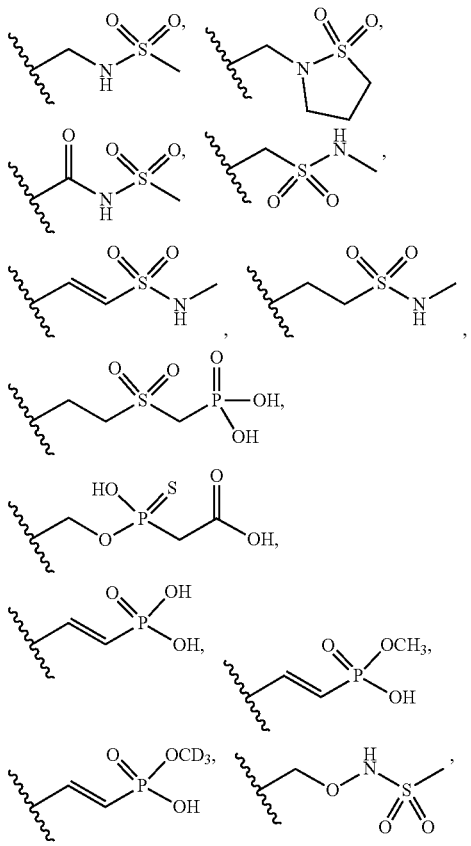

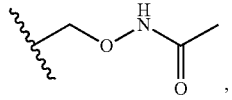

—CH=CD-Z, —CD=CH—Z, —CD=CD-Z, —$(CR^{21}R^{22})_n$—Z, or —$(C_2$-$C_6$ alkenylene)-Z and $R^{20}$ is hydrogen; or $R^2$ and $R^{20}$ together form a 3- to 7-membered carbocyclic ring substituted with —$(CR^{21}R^{22})_n$—Z or —$(C_2$-$C_6$ alkenylene)-Z; n is 1, 2, 3, or 4; Z is —ONR$^{23}$R$^{24}$, —OP(O)OH $(CH_2)_mCO_2R^{23}$, —OP(S)OH$(CH_2)_mCO_2R^{23}$, —P(O)(OH)$_2$, —P(O)(OH)(OCH$_3$), —P(O)(OH)(OCD$_3$), —SO$_2$(CH$_2$)$_m$P (O)(OH)$_2$, —SO$_2$NR$^{23}$R$^{25}$, —NR$^{23}$R$^{24}$, or —NR$^{23}$SO$_2$R$^{24}$; $R^{21}$ and $R^{22}$ either are independently hydrogen or $C_1$-$C_6$ alkyl, or $R^{21}$ and $R^{22}$ together form an oxo group; $R^{23}$ is hydrogen or $C_1$-$C_6$ alkyl; $R^{24}$ is —SO$_2$R$^{25}$ or —C(O)R$^{25}$; or $R^{23}$ and $R^{24}$ together with the nitrogen to which they are attached form a substituted or unsubstituted heterocyclic ring; $R^{25}$ is $C_1$-$C_6$ alkyl; and m is 1, 2, 3, or 4. In some embodiments, $R^1$ is an aryl. In some embodiments, the aryl is a phenyl.

In some embodiments, any of the siNA molecules, sense strands, first nucleotide sequences, antisense strands, or second nucleotide sequences disclosed herein comprise a 5'-stabilized end cap of Formula (IIa):

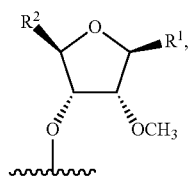

wherein $R^1$ is a nucleobase, aryl, heteroaryl, or H, $R^2$ is

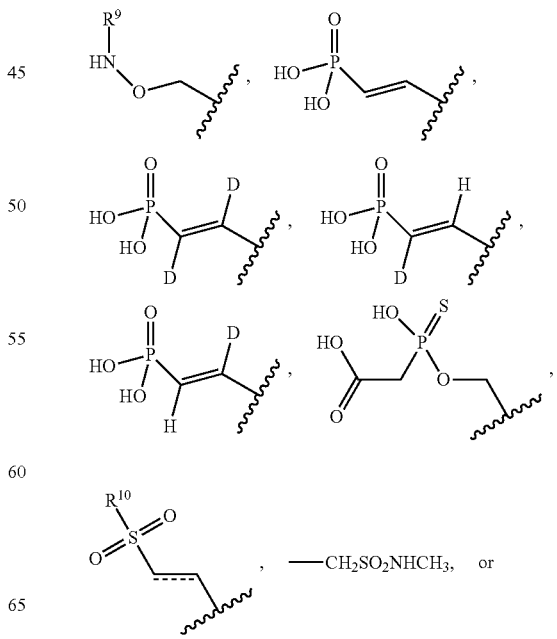

, —CH$_2$SO$_2$NHCH$_3$, or

-continued

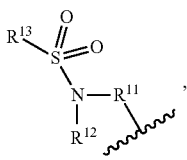

$R^9$ is —SO$_2$CH$_3$ or —COCH$_3$, ⁻⁻⁻ is a double or single bond, $R^{10}$=—CH$_2$PO$_3$H or —NHCH$_3$, $R^{11}$ is —CH$_2$— or —CO—, and $R^{12}$ is H and $R^{13}$ is CH$_3$ or $R^{12}$ and $R^{13}$ together form —CH$_2$CH$_2$CH$_2$—. In some embodiments, $R^1$ is an aryl. In some embodiments, the aryl is a phenyl.

In some embodiments, any of the siNA molecules, sense strands, first nucleotide sequences, antisense strands, or second nucleotide sequences disclosed herein comprise a 5'-stabilized end cap of Formula (IIb):

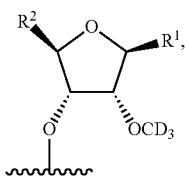

wherein $R^1$ is a nucleobase, aryl, heteroaryl, or H, $R^2$ is

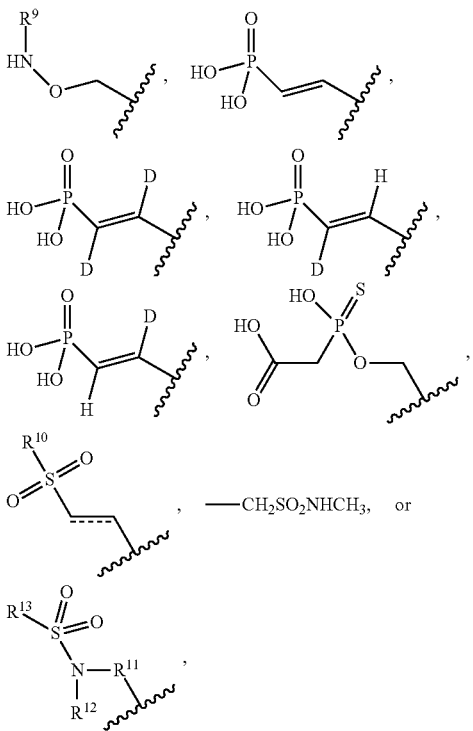

$R^9$ is —SO$_2$CH$_3$ or —COCH$_3$, ⁻⁻⁻ is a double or single bond, $R^{10}$=—CH$_2$PO$_3$H or —NHCH$_3$, $R^{11}$ is —CH$_2$— or —CO—, and $R^{12}$ is H and $R^{13}$ is CH$_3$ or $R^{12}$ and $R^{13}$ together form —CH$_2$CH$_2$CH$_2$—. In some embodiments, $R^1$ is an aryl. In some embodiments, the aryl is a phenyl.

In some embodiments, any of the siNA molecules, sense strands, first nucleotide sequences, antisense strands, or second nucleotide sequences disclosed herein comprise a 5'-stabilized end cap of Formula (III):

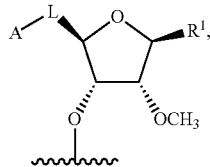

wherein $R^1$ is a nucleobase, aryl, heteroaryl, or H, L is —CH$_2$—, —CH=CH—, —CO—, or —CH$_2$CH$_2$—, and A is —ONHCOCH$_3$, —ONHSO$_2$CH$_3$, —PO$_3$H, —OP(SOH)CH$_2$CO$_2$H, —SO$_2$CH$_2$PO$_3$H, —SO$_2$NHCH$_3$, —NHSO$_2$CH$_3$, or —N(SO$_2$CH$_2$CH$_2$CH$_2$). In some embodiments, $R^1$ is an aryl. In some embodiments, the aryl is a phenyl.

In some embodiments, any of the siNA molecules, sense strands, first nucleotide sequences, antisense strands, or second nucleotide sequences disclosed herein comprise a 5'-stabilized end cap selected from Examples 5-11, 33-35, 38, 39, 43, and 49-53 5' end cap monomers.

Further disclosed herein are siNA molecules comprising (a) a 5'-stabilized end cap of Formula (Ia):

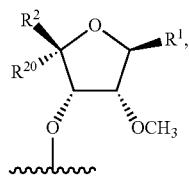

wherein $R^1$ is a nucleobase, aryl, heteroaryl, or H; $R^2$ is

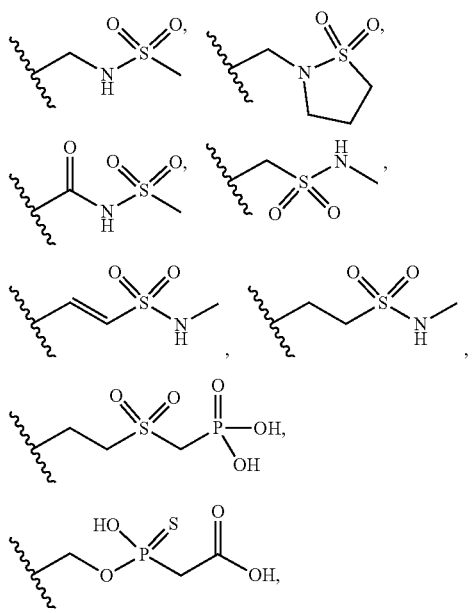

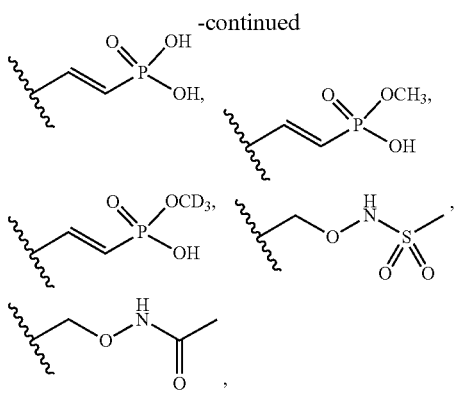

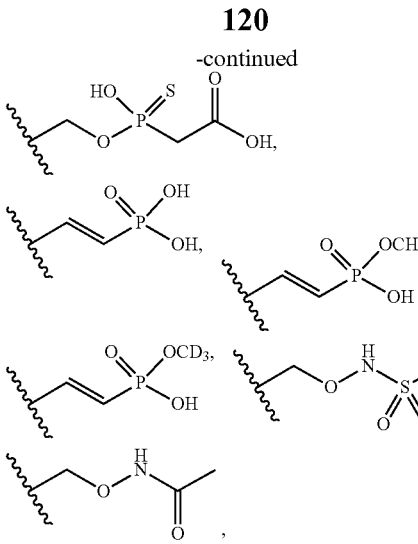

—CH=CD-Z, —CD=CH—Z, —CD=CD-Z, —(CR$^{21}$R$^{22}$)$_n$—Z, or —(C$_2$-C$_6$ alkenylene)-Z and R$^{20}$ is H; or R$^2$ and R$^{20}$ together form a 3- to 7-membered carbocyclic ring substituted with —(CR$^{21}$R$^{22}$)$_n$—Z or —(C$_2$-C$_6$ alkenylene)-Z; n is 1, 2, 3, or 4; Z is —ONR$^{23}$R$^{24}$, —OP(O)OH(CH$_2$)$_m$CO$_2$R$^{23}$, —OP(S)OH(CH$_2$)$_m$CO$_2$R$^{23}$, —P(O)(OH)$_2$, —P(O)(OH)(OCH$_3$), —P(O)(OH)(OCD$_3$), —SO$_2$(CH$_2$)$_m$P(O)(OH)$_2$, —SO$_2$NR$^{23}$R$^{25}$, —NR$^{23}$R$^{24}$, —NR$^{23}$SO$_2$R$^{24}$; either R$^{21}$ and R$^{22}$ are independently hydrogen or C$_1$-C$_6$ alkyl, or R$^{21}$ and R$^{22}$ together form an oxo group; R$^{23}$ is hydrogen or C$_1$-C$_6$ alkyl; R$^{24}$ is —SO$_2$R$^{25}$ or —C(O)R$^{25}$; or R$^{23}$ and R$^{24}$ together with the nitrogen to which they are attached form a substituted or unsubstituted heterocyclic ring; R$^{25}$ is C$_1$-C$_6$ alkyl; and m is 1, 2, 3, or 4; and (b) a short interfering nucleic acid (siNA), wherein the 5'-stabilized end cap is conjugated to the siNA. In some embodiments, R$^1$ is an aryl. In some embodiments, the aryl is a phenyl.

Further disclosed herein are siNA molecules comprising (a) a 5'-stabilized end cap of Formula (Ib):

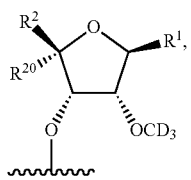

wherein R$^1$ is a nucleobase, aryl, heteroaryl, or H; R$^2$ is

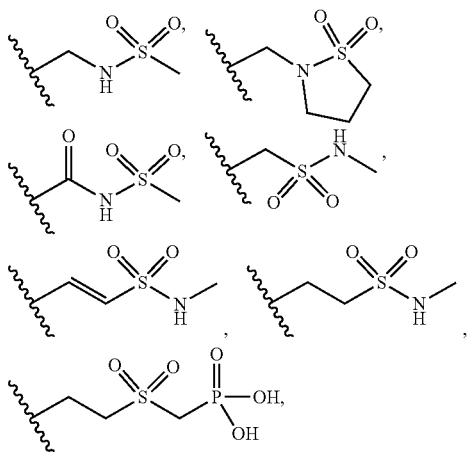

—CH=CD-Z, —CD=CH—Z, —CD=CD-Z, —(CR$^{21}$R$^{22}$)$_n$—Z, or —(C$_2$-C$_6$ alkenylene)-Z and R$^{20}$ is H; or R$^2$ and R$^{20}$ together form a 3- to 7-membered carbocyclic ring substituted with —(CR$^{21}$R$^{22}$)$_n$—Z or —(C$_2$-C$_6$ alkenylene)-Z; n is 1, 2, 3, or 4; Z is —ONR$^{23}$R$^{24}$, —OP(O)OH(CH$_2$)$_m$CO$_2$R$^{23}$, —OP(S)OH(CH$_2$)$_m$CO$_2$R$^{23}$, —P(O)(OH)$_2$, —P(O)(OH)(OCH$_3$), —P(O)(OH)(OCD$_3$), —SO$_2$(CH$_2$)$_m$P(O)(OH)$_2$, —SO$_2$NR$^{23}$R$^{25}$, —NR$^{23}$R$^{24}$, —NR$^{23}$SO$_2$R$^{24}$; either R$^{21}$ and R$^{22}$ are independently hydrogen or C$_1$-C$_6$ alkyl, or R$^{21}$ and R$^{22}$ together form an oxo group; R$^{23}$ is hydrogen or C$_1$-C$_6$ alkyl; R$^{24}$ is —SO$_2$R$^{25}$ or —C(O)R$^{25}$; or R$^{23}$ and R$^{24}$ together with the nitrogen to which they are attached form a substituted or unsubstituted heterocyclic ring; R$^{25}$ is C$_1$-C$_6$ alkyl; and m is 1, 2, 3, or 4; and (b) a short interfering nucleic acid (siNA), wherein the 5'-stabilized end cap is conjugated to the siNA. In some embodiments, R$^1$ is an aryl. In some embodiments, the aryl is a phenyl.

Further disclosed herein are siNA molecules comprising (a) a 5'-stabilized end cap of Formula (Ic):

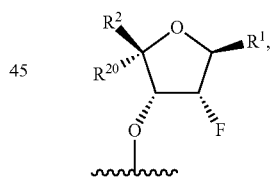

wherein R$^1$ is a nucleobase, aryl, heteroaryl, or H, R$^2$ is

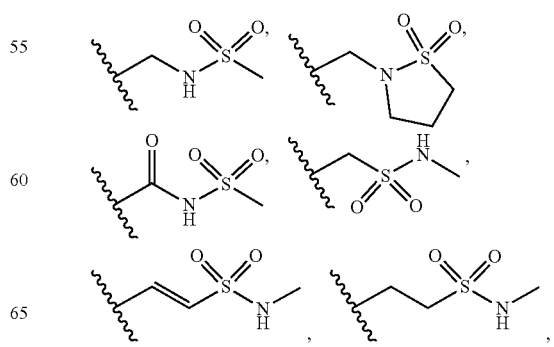

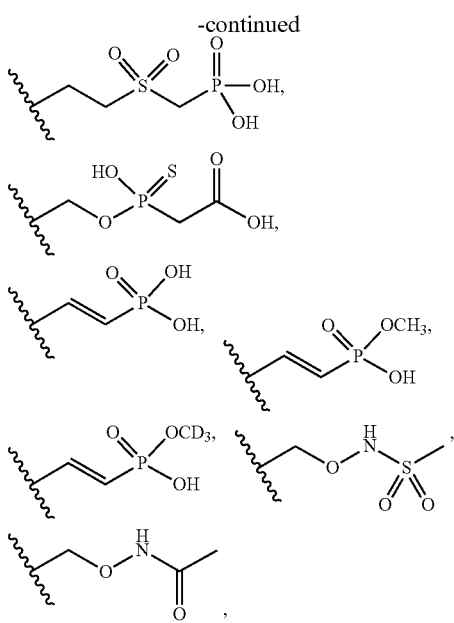

—CH=CD-Z, —CD=CH—Z, —CD=CD-Z, —(CR²¹R²²)$_n$—Z, or —(C$_2$-C$_6$ alkenylene)-Z and R²⁰ is hydrogen; or R² and R²⁰ together form a 3- to 7-membered carbocyclic ring substituted with —(CR²¹R²²)$_n$—Z or —(C$_2$-C$_6$ alkenylene)-Z; n is 1, 2, 3, or 4; Z is —ONR²³R²⁴, —OP(O)OH(CH$_2$)$_m$CO$_2$R²³, —OP(S)OH(CH$_2$)$_m$CO$_2$R²³, —P(O)(OH)$_2$, —P(O)(OH)(OCH$_3$), —P(O)(OH)(OCD$_3$), —SO$_2$(CH$_2$)$_m$P(O)(OH)$_2$, —SO$_2$NR²³R²⁵, —NR²³R²⁴, or —NR²³SO$_2$R²⁴; R²¹ and R²² either are independently hydrogen or C$_1$-C$_6$ alkyl, or R²¹ and R²² together form an oxo group; R²³ is hydrogen or C$_1$-C$_6$ alkyl; R²⁴ is —SO$_2$R²⁵ or —C(O)R²⁵; or R²³ and R²⁴ together with the nitrogen to which they are attached form a substituted or unsubstituted heterocyclic ring; R²⁵ is C$_1$-C$_6$ alkyl; and m is 1, 2, 3, or 4; and (b) a short interfering nucleic acid (siNA), wherein the 5'-stabilized end cap is conjugated to the siNA. In some embodiments, R¹ is an aryl. In some embodiments, the aryl is a phenyl.

In some embodiments, a siNA molecule comprises (a) a 5'-stabilized end cap of Formula (IIa):

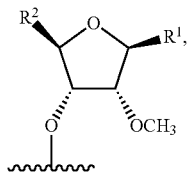

wherein R¹ is a nucleobase, aryl, heteroaryl, or H, R² is

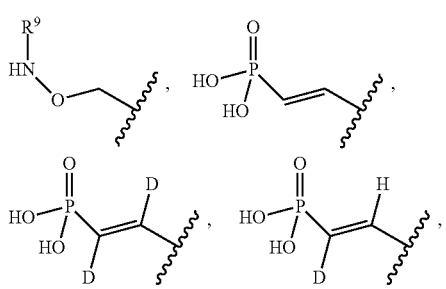

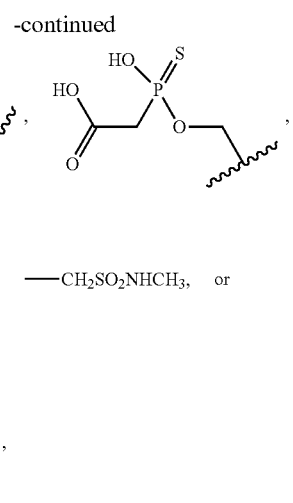

R⁹ is —SO$_2$CH$_3$ or —COCH$_3$, wherein = is a double or single bond, R¹⁰=—CH$_2$PO$_3$H or —NHCH$_3$, R¹¹ is —CH$_2$— or —CO—, and R¹² is H and R¹³ is CH$_3$ or R¹² and R¹³ together form —CH$_2$CH$_2$CH$_2$—; and (b) a short interfering nucleic acid (siNA), wherein the 5'-stabilized end cap is conjugated to the siNA. In some embodiments, R¹ is an aryl. In some embodiments, the aryl is a phenyl.

In some embodiments, a siNA molecule comprises (a) a 5'-stabilized end cap of Formula (IIb):

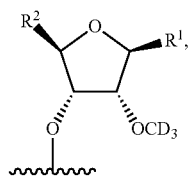

wherein R¹ is a nucleobase, aryl, heteroaryl, or H, R² is

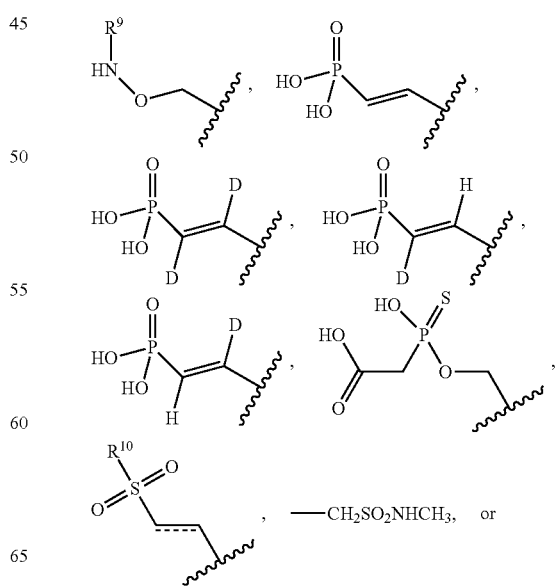

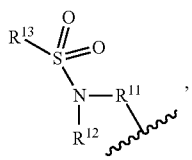

$R^9$ is —SO$_2$CH$_3$ or —COCH$_3$, wherein ═ is a double or single bond, $R^{10}$═—CH$_2$PO$_3$H or —NHCH$_3$, $R^{11}$ is —CH$_2$— or —CO—, and $R^{12}$ is H and $R^{13}$ is CH$_3$ or $R^{12}$ and $R^{13}$ together form —CH$_2$CH$_2$CH$_2$—; and (b) a short interfering nucleic acid (siNA), wherein the 5'-stabilized end cap is conjugated to the siNA. In some embodiments, $R^1$ is an aryl. In some embodiments, the aryl is a phenyl.

In some embodiments, a siNA molecule comprises (a) a 5'-stabilized end cap of Formula (III):

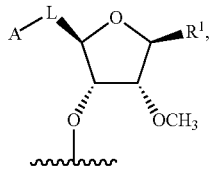

wherein $R^1$ is a nucleobase, aryl, heteroaryl, or H, L is —CH$_2$—, —CH═CH—, —CO—, or —CH$_2$CH$_2$—, and A is —ONHCOCH$_3$, —ONHSO$_2$CH$_3$, —PO$_3$H, —OP(SOH)CH$_2$CO$_2$H, —SO$_2$CH$_2$PO$_3$H, —SO$_2$NHCH$_3$, —NHSO$_2$CH$_3$, or —N(SO$_2$CH$_2$CH$_2$CH$_2$); and (b) a short interfering nucleic acid (siNA), wherein the 5'-stabilized end cap is conjugated to the siNA. In some embodiments, $R^1$ is an aryl. In some embodiments, the aryl is phenyl.

In some embodiments, any of the siNA molecules disclosed herein comprise a 5'-stabilized end cap selected from the group consisting of Formula (1) to Formula (15), Formula (9X) to Formula (12X), and Formula (9Y) to Formula (12Y):

Formula (1)

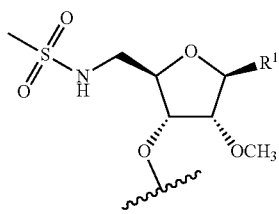

Formula (2)

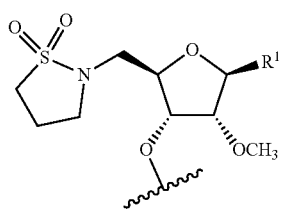

Formula (3)

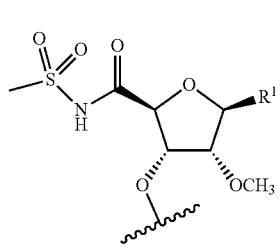

Formula (4)

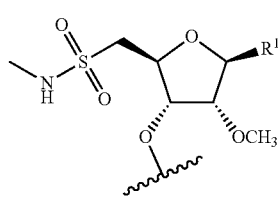

Formula (5)

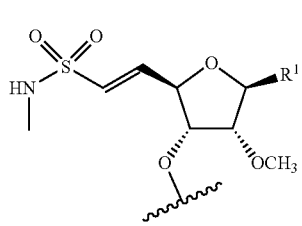

Formula (6)

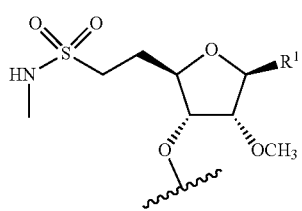

Formula (7)

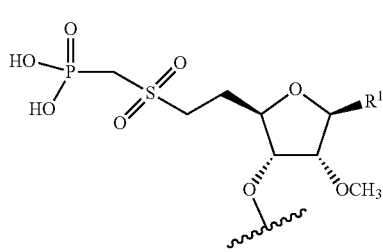

Formula (8)

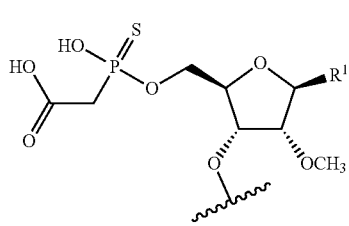

Formula (9)

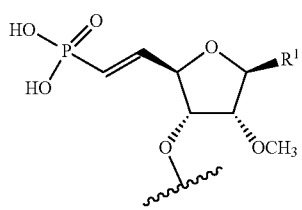

Formula (9X)
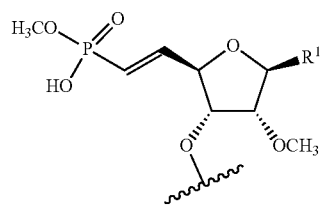

Formula (9Y)
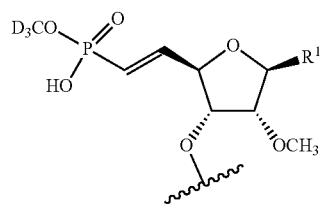

Formula (10)
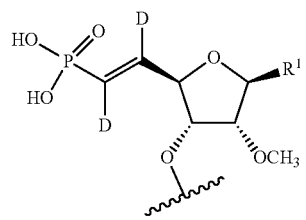

Formula (10X)
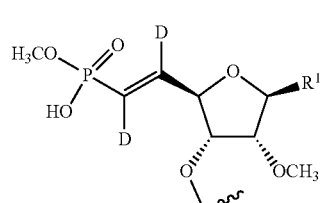

Formula (10Y)
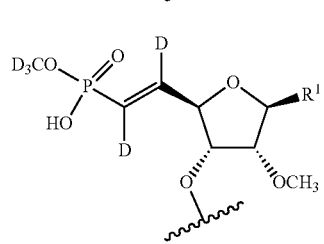

Formula (11)
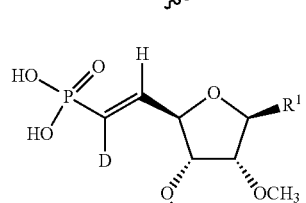

Formula (11X)
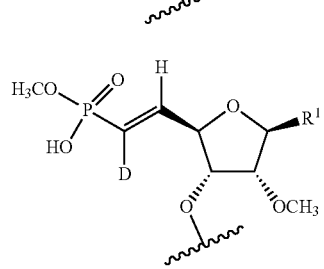

Formula (11Y)
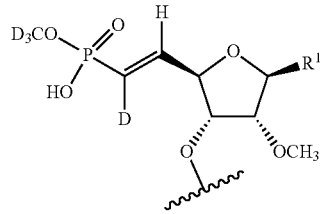

Formula (12)
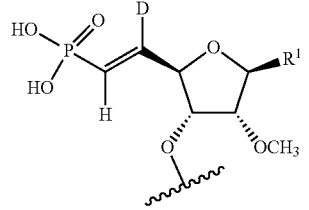

Formula (12X)
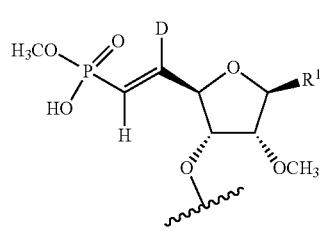

Formula (12Y)
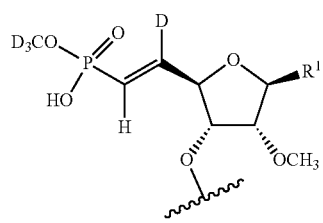

Formula (13)
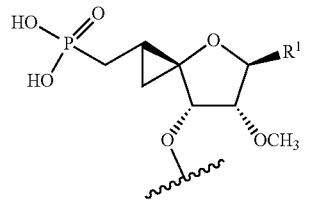

Formula (14)
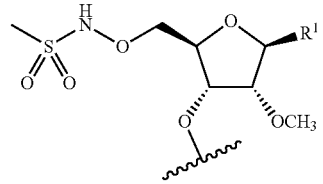

Formula (15)
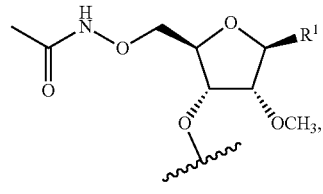

wherein $R^1$ is a nucleobase, aryl, heteroaryl, or H. In some embodiments, $R^1$ is an aryl. In some embodiments, the aryl is a phenyl.

In some embodiments, any of the siNA molecules disclosed herein comprise a 5'-stabilized end cap selected from the group consisting of Formulas (1A)-(15A), Formulas (9B)-(12B), Formulas (9AX)-(12AX), Formulas (9AY)-(12AY), Formulas (9BX)-(12BX), and Formulas (9BY)-(12BY):
Formula (1A)
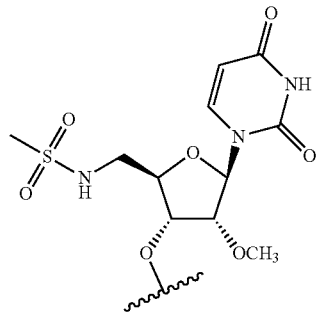
Formula (2A)
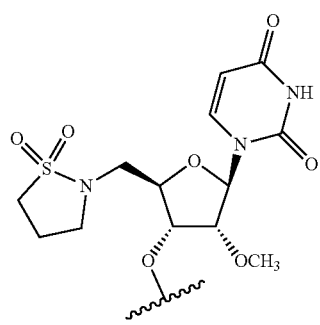
Formula (3A)
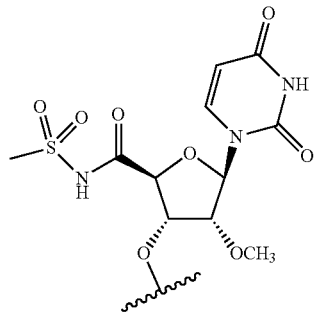
Formula (4A)
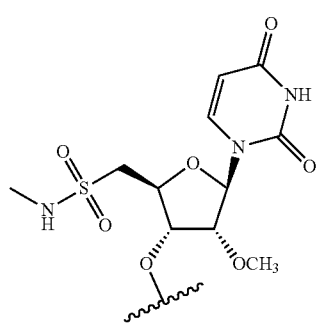
Formula (5A)
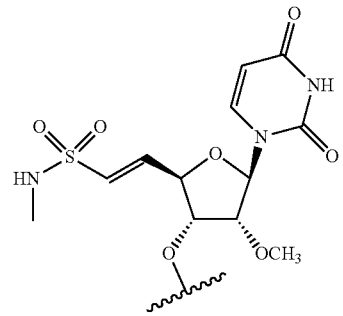
Formula (6A)
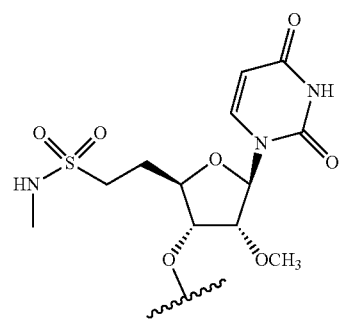
Formula (7A)
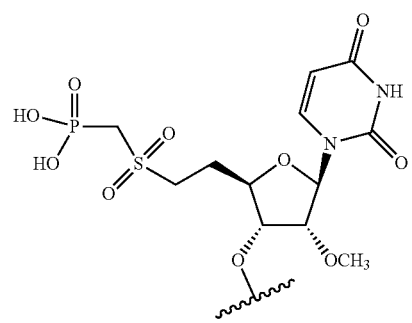
Formula (8A)
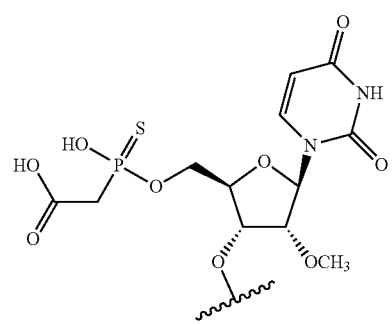
Formula (9A)
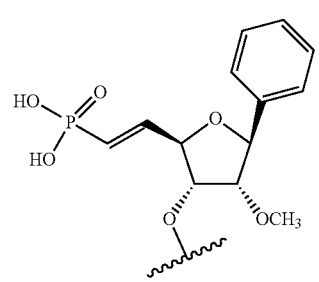

Formula (9AX)
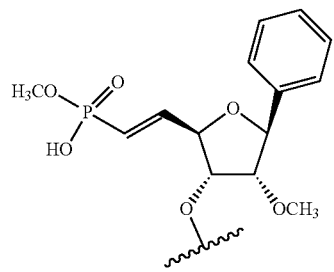
Formula (9AY)
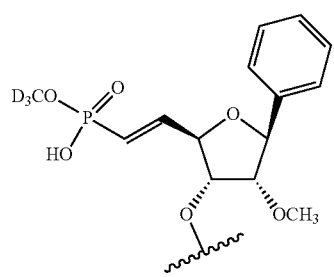
Formula (9B)
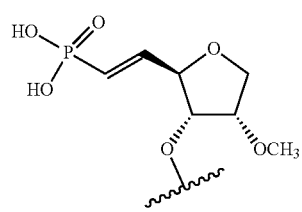
Formula (9BX)
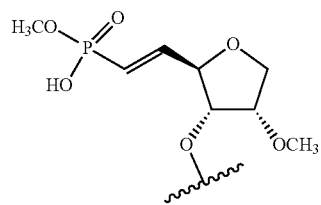
Formula (9BY)
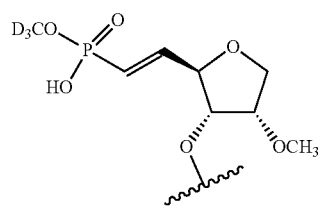
Formula (10A)
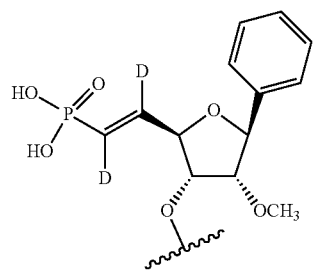
Formula (10AX)
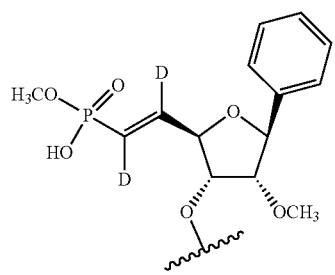
Formula (10AY)
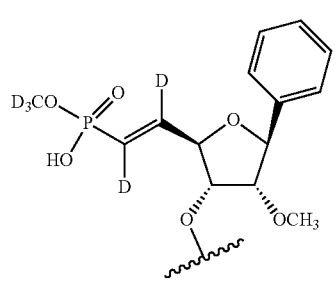
Formula (10B)
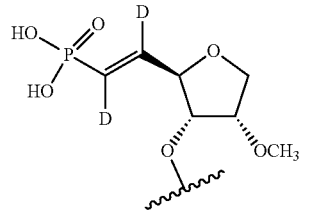
Formula (10BX)
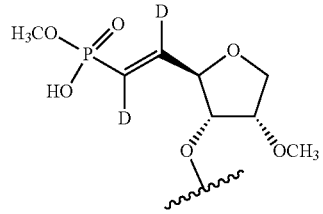
Formula (10BY)
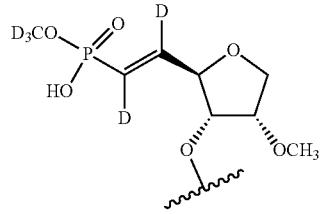
Formula (11A)
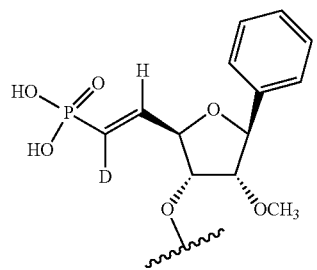

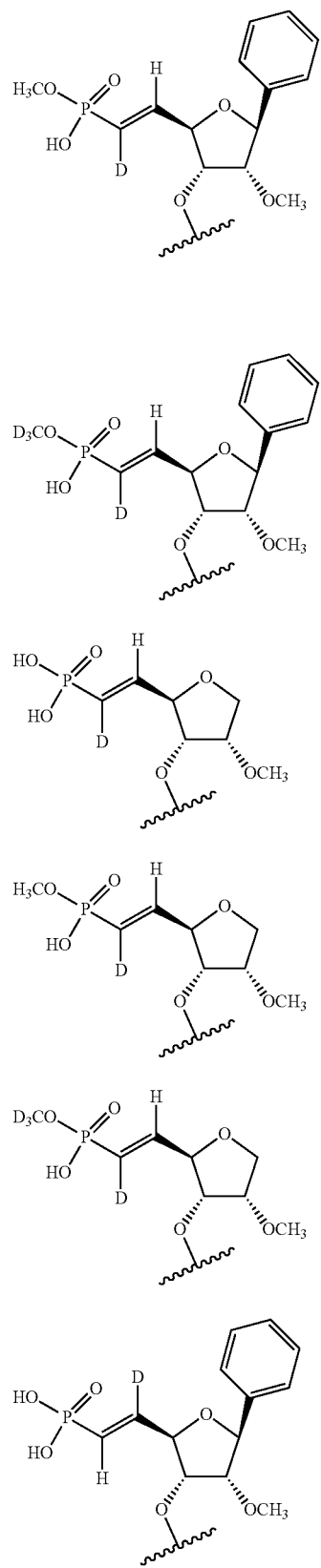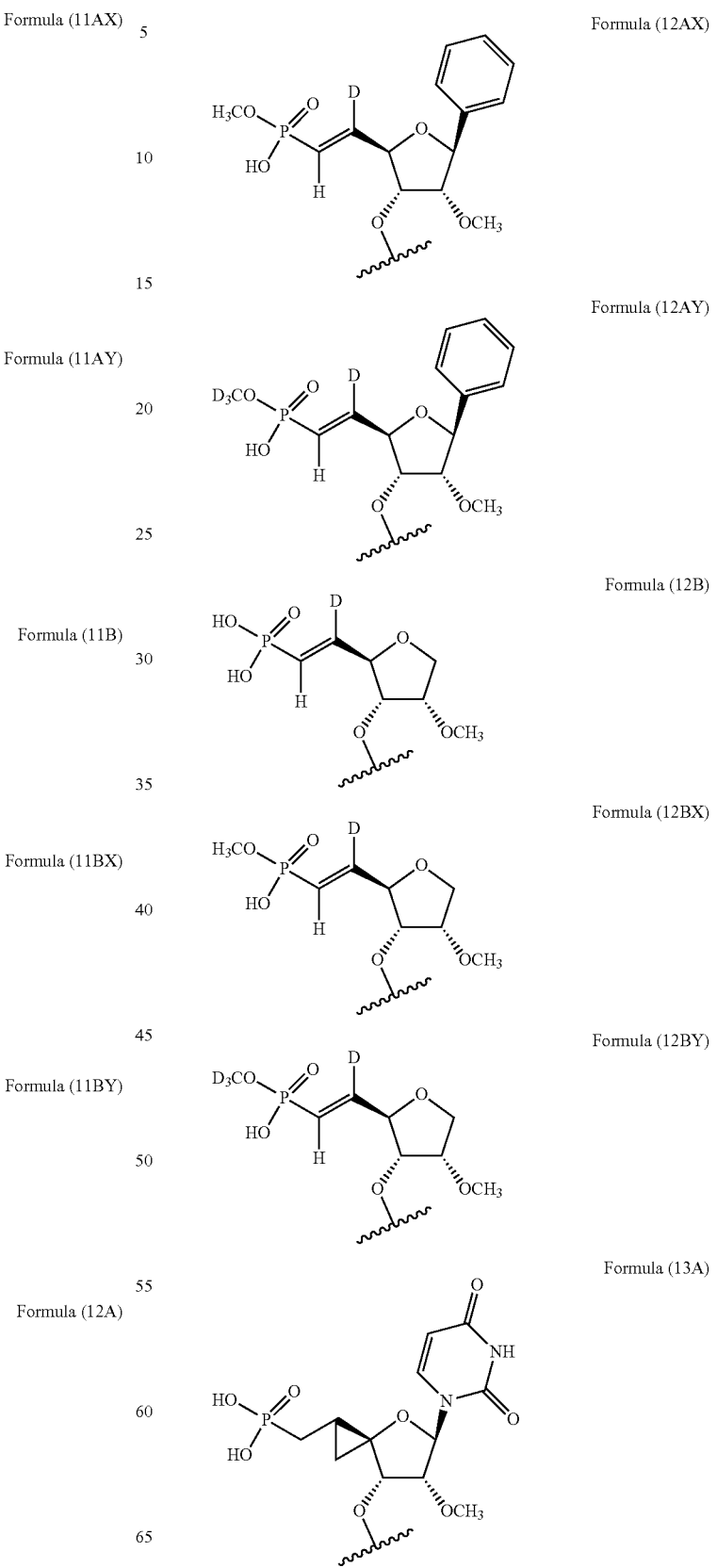

Formula (14A)
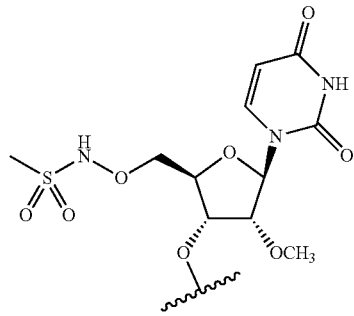
Formula (15A)
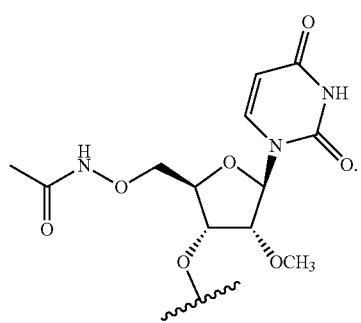
In some embodiments, any of the siNA molecules disclosed herein comprise a 5'-stabilized end cap selected from the group consisting of Formula (21) to Formula (35):
Formula (21)
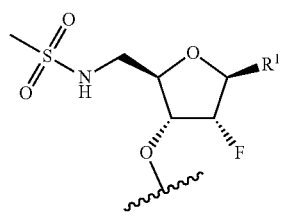
Formula (22)
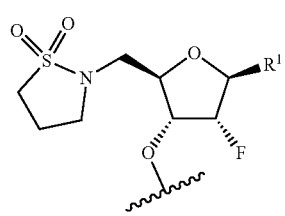
Formula (23)
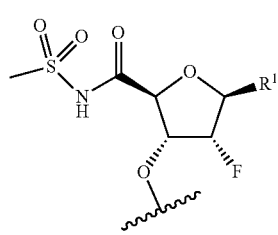
Formula (24)
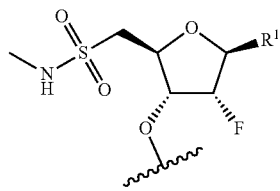
Formula (25)
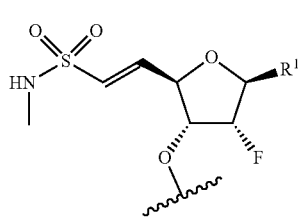
Formula (26)
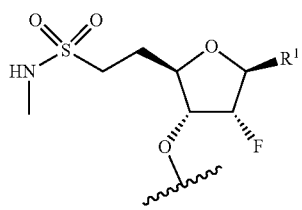
Formula (27)
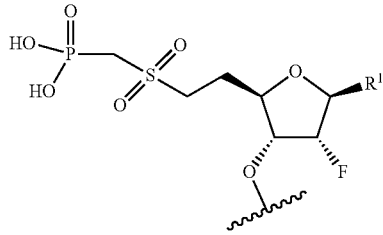
Formula (28)
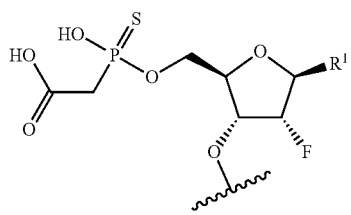
Formula (29)
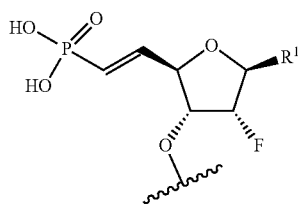
Formula (30)
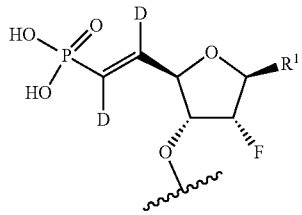

Formula (31)
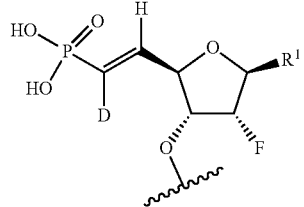

Formula (21A)
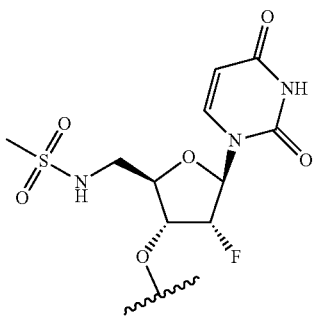

Formula (32)
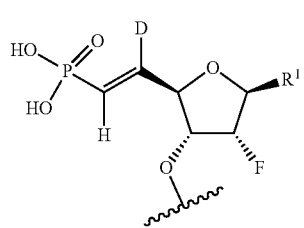

Formula (22A)
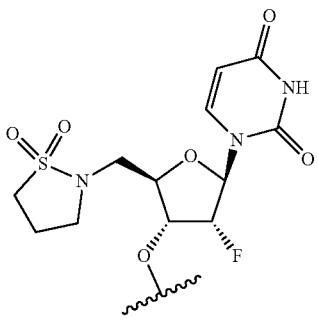

Formula (33)
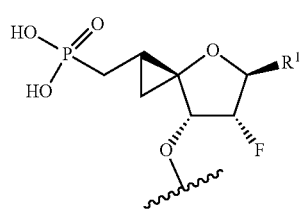

Formula (23A)
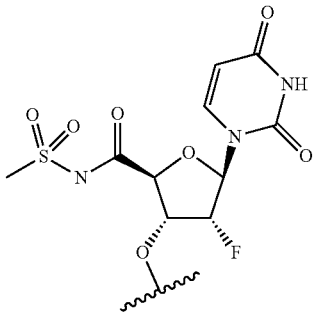

Formula (34)
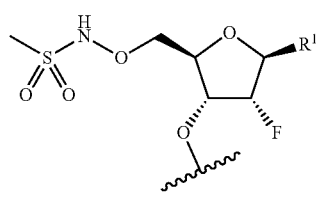

Formula (24A)
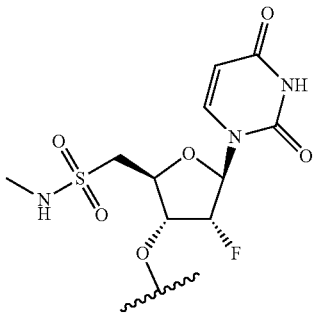

Formula (35)
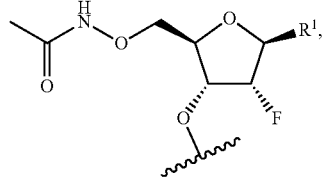

Formula (25A)
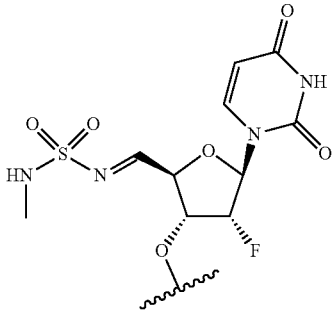

wherein $R^1$ is a nucleobase, aryl, heteroaryl, or H. In some embodiments, $R^1$ is an aryl. In some embodiments, the aryl is a phenyl.

In some embodiments, any of the siNA molecules disclosed herein comprise a 5'-stabilized end cap selected from the group consisting of Formulas (21A)-(35A), Formulas (29B)-(32B), Formulas (29AX)-(32AX), Formulas (29AY)-(32AY), Formulas (29BX)-(32BX), and Formulas (29BY)-(32BY):

Formula (26A)
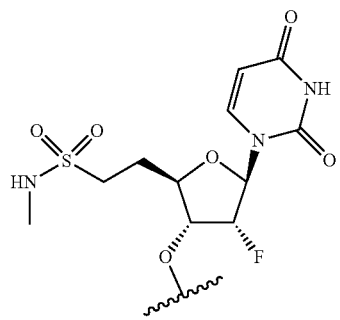
Formula (27A)
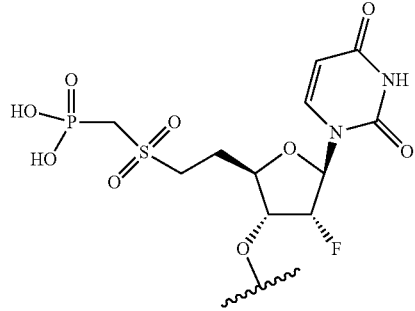
Formula (28A)
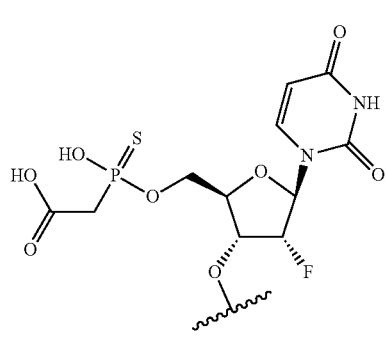
Formula (29A)
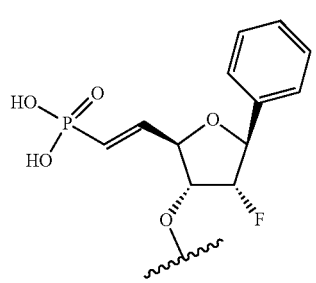
Formula (29AX)
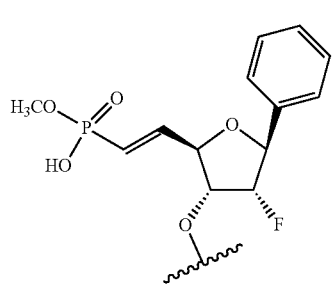
Formula (29AY)
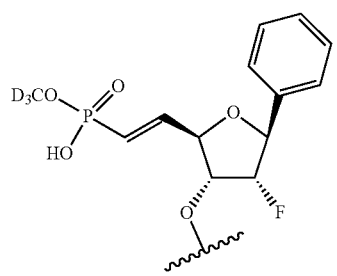
Formula (29B)
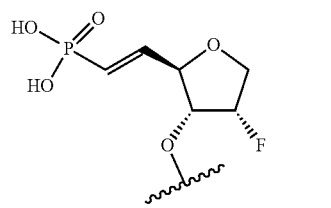
Formula (29BX)
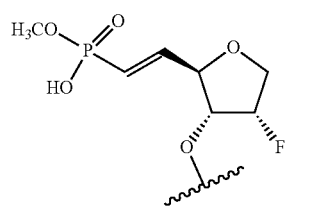
Formula (29BY)
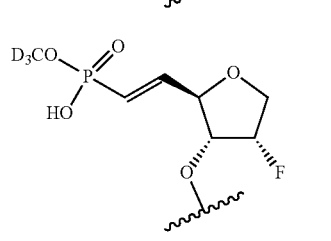
Formula (30A)
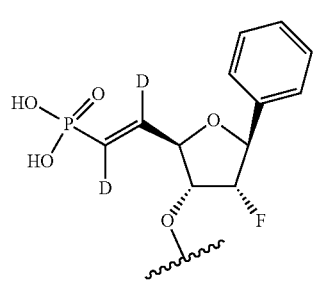
Formula (30AX)
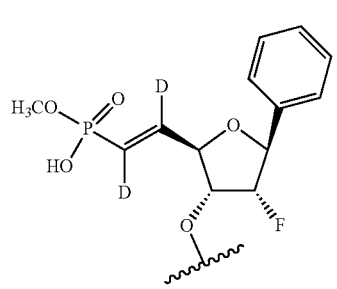

Formula (30AY)
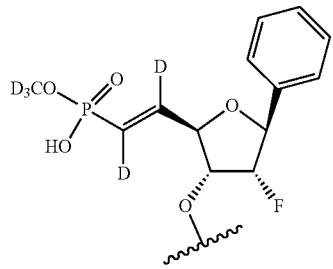
Formula (30B)
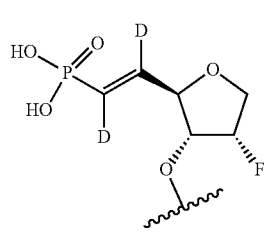
Formula (30BX)
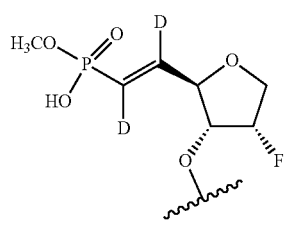
Formula (30BY)
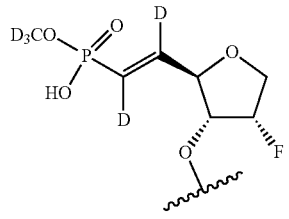
Formula (31A)
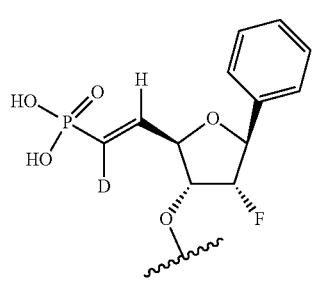
Formula (31AX)
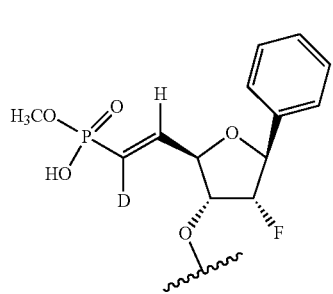
Formula (31AY)
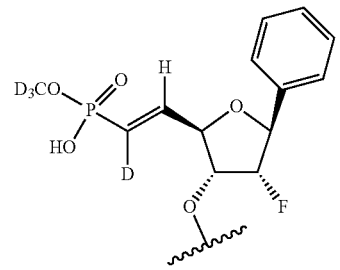
Formula (31B)
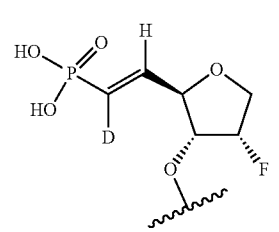
Formula (31BX)
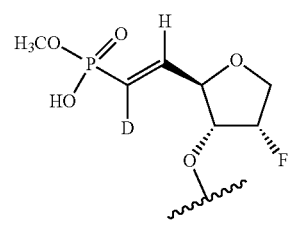
Formula (31BY)
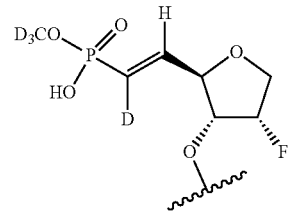
Formula (32A)
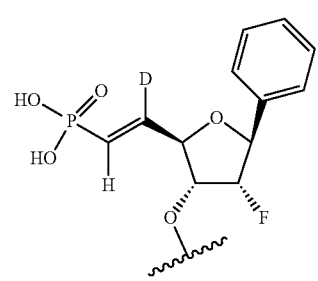
Formula (32AX)
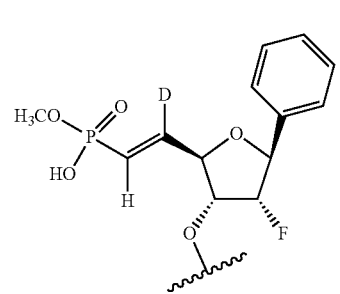

Formula (32AY)
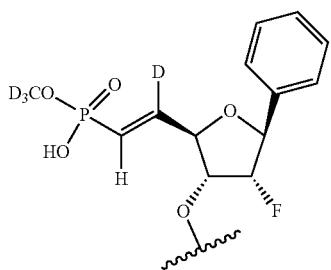

Formula (32B)
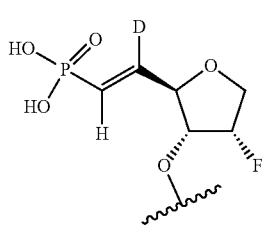

Formula (32BX)
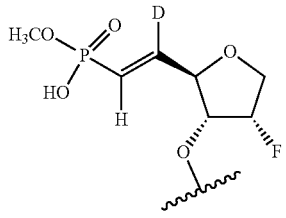

Formula (32BY)
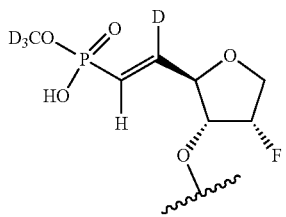

Formula (33A)
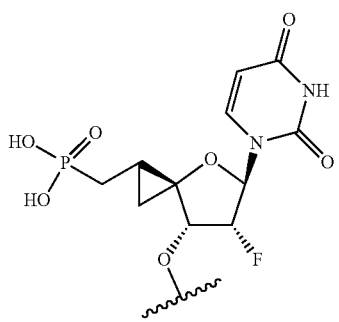

Formula (34A)
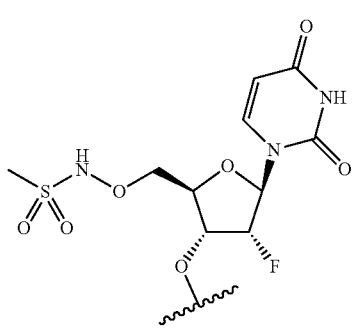

Formula (35A)
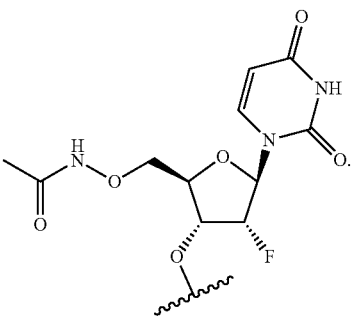

In some embodiments, the 5'-stabilized end cap is attached to the 5' end of the antisense strand. In some embodiments, the 5'-stabilized end cap is attached to the 5' end of the antisense strand via 1, 2, 3, 4, or 5 or more linkers. In some embodiments, the one or more linkers are independently selected from the group consisting of a phosphodiester (p or po) linker, phosphorothioate (ps) linker (ps), phosphoramidite (HEG) linker, triethylene glycol (TEG) linker, and/or phosphorodithioate linker. In some embodiments, the one or more linkers are independently selected from the group consisting of p-(PS)2, (PS)2-p-TEG-p, (PS)2-p-HEG-p, and (PS)2-p-(HEG-p)2.

Linker

In some embodiments, any of the siRNAs, sense strands, first nucleotide sequences, antisense strands, and/or second nucleotide sequences disclosed herein comprise 1, 2, 3, 4, 5, 6, 7, 8, 9, 10, 11, 12, 13, 14, 15, 16, 17, 18, 19, 20, 21, 22, 23 or more internucleoside linkers. In some embodiments, 1, 2, 3, 4, 5, 6, 7, 8, 9, 10 or more internucleoside linkers are independently selected from the group consisting of a phosphodiester (p or po) linker, phosphorothioate (ps) linker, or phosphorodithioate linker.

In some embodiments, any of the siRNAs, sense strands, first nucleotide sequences, antisense strands, and/or second nucleotide sequences disclosed herein further comprise 1, 2, 3, 4 or more linkers that attach a conjugated moiety, phosphorylation blocker, and/or 5' end cap to the siRNA, sense strand, first nucleotide sequence, antisense strand, and/or second nucleotide sequences. In some embodiments, the 1, 2, 3, 4 or more linkers are independently selected from the group consisting of a phosphodiester (p or po) linker, phosphorothioate (ps) linker, phosphoramidite (HEG) linker, triethylene glycol (TEG) linker, and/or phosphorodithioate linker. In some embodiments, the one or more linkers are independently selected from the group consisting of p-(PS)2, (PS)2-p-TEG-p, (PS)2-p-HEG-p, and (PS)2-p-(HEG-p)2.

Target Gene

Without wishing to be bound by theory, upon entry into a cell, any of the ds-siNA molecules disclosed herein may interact with proteins in the cell to form a RNA-Induced Silencing Complex (RISC). Once the ds-siNA is part of the RISC, the ds-siNA may be unwound to form a single-stranded siNA (ss-siNA). The ss-siNA may comprise the antisense strand of the ds-siNA. The antisense strand may bind to a complementary messenger RNA (mRNA), which results in silencing of the gene that encodes the mRNA.

The target gene may be any gene in a cell. In some embodiments, the target gene is a viral gene. In some embodiments, the viral gene is from a DNA virus. In some embodiments, the DNA virus is a double-stranded DNA (dsDNA) virus. In some embodiments, the dsDNA virus is a hepadnavirus. In some embodiments, the hepadnavirus is a hepatitis B virus (HBV). In some embodiments, the HBV is selected from HBV genotypes A-J.

In some embodiments, the target gene is selected from the S gene or X gene of the HBV. In some embodiments, the HBV has a genome sequence shown in the nucleotide sequence of SEQ ID NO: 410, which corresponds to the nucleotide sequence of GenBank Accession No. U95551.1, which is incorporated by reference in its entirety.

An exemplary HBV genome sequence is shown in SEQ ID NO: 596, corresponding to Genbank Accession No. KC315400.1, which is incorporated by reference in its entirety. Nucleotides 2307..3215, 1..1623 of SEQ ID NO: 596 correspond to the polymerase/RT gene sequence, which encodes for the polymerase protein. Nucleotides 2848..3215, 1..835 of SEQ ID NO: 596 correspond to the PreS1/S2/S gene sequence, which encodes for the large S protein. Nucleotides 3205..3215, 1..835 of SEQ ID NO: 596 correspond to the PreS2/S gene sequence, which encodes for the middle S protein. Nucleotides 155..835 of SEQ ID NO: 596 correspond to the S gene sequence, which encodes the small S protein. Nucleotides 1374..1838 of SEQ ID NO: 596 correspond to the X gene sequence, which encodes the X protein. Nucleotides 1814..2452 of SEQ ID NO: 596 correspond to the PreC/C gene sequence, which encodes the precore/core protein. Nucleotides 1901.2452 of SEQ ID NO: 596 correspond to the C gene sequence, which encodes the core protein. The HBV genome further comprises viral regulatory elements, such as viral promoters (preS2, preS1, Core, and X) and enhancer elements (ENH1 and ENH2). Nucleotides 1624..1771 of SEQ ID NO: 596 correspond to ENH2. Nucleotides 1742..1849 of SEQ ID NO: 596 correspond to the Core promoter. Nucleotides 1818..3215, 1..1930 of SEQ ID NO: 596 correspond to the pregenomic RNA (pgRNA), which encodes the core and polymerase proteins.

In some embodiments, the ASO is at least about 60%, 65%, 70%, 75%, 80%, 85%, 90%, 95%, or 100% complementary or hybridizes to a viral target RNA sequence that begins in an X region of HBV or in an S region of HBV. The viral target may, e.g., begin at the 5'-end of target-site in acc. KC315400.1 (genotype B, "gt B"), or in any one of genotypes A, C, or D. The skilled person would understand the HBV position, e.g., as described in Wing-Kin Sung, et al., *Nature Genetics* 44:765 (2012). In some embodiments, the S region is defined as from the beginning of small S protein (in genotype B KC315400.1 isolate, position #155) to before beginning of X protein (in genotype B KC315400.1 isolate, position #1373). In some embodiments, the X region is defined as from the beginning X protein (in genotype B KC315400.1 isolate, position #1374) to end of DR2 site (in genotype B KC315400.1 isolate, position #1603).

In some embodiments, the second nucleotide sequence is at least about 60%, 65%, 70%, 75%, 80%, 85%, 90%, 95%, or 100% complementary to 15 to 30, 15 to 25, 15 to 23, 15 to 22, 15 to 21, 17 to 25, 17 to 23, 17 to 22, 17 to 21, or 19 to 21 nucleotides within positions 200-720 or 1100-1700 of SEQ ID NO: 410. In some embodiments, the second nucleotide sequence is at least about 60%, 65%, 70%, 75%, 80%, 85%, 90%, 95%, or 100% complementary to 15 to 30, 15 to 25, 15 to 23, 15 to 22, 15 to 21, 17 to 25, 17 to 23, 17 to 22, 17 to 21, or 19 to 21 nucleotides within positions 200-280, 300-445, 460-510, 650-720, 1170-1220, 1250-1300, or 1550-1630 of SEQ ID NO: 410. In some embodiments, the second nucleotide sequence is at least about 60%, 65%, 70%, 75%, 80%, 85%, 90%, 95%, or 100% complementary to 15 to 30, 15 to 25, 15 to 23, 15 to 22, 15 to 21, 17 to 25, 17 to 23, 17 to 22, 17 to 21, or 19 to 21 nucleotides within positions 200-230, 250-280, 300-330, 370-400, 405-445, 460-500, 670-700, 1180-1210, 1260-1295, 1520-1550, or 1570-1610 of SEQ ID NO: 410. In some embodiments, the second nucleotide sequence is at least about 60%, 65%, 70%, 75%, 80%, 85%, 90%, 95%, or 100% complementary to 15 to 30, 15 to 25, 15 to 23, 15 to 22, 15 to 21, 17 to 25, 17 to 23, 17 to 22, 17 to 21, or 19 to 21 nucleotides starting at position 203, 206, 254, 305, 375, 409, 412, 415, 416, 419, 462, 466, 467, 674, 676, 1182, 1262, 1263, 1268, 1526, 1577, 1578, 1580, 1581, 1583, or 1584 of SEQ ID NO: 410.

In some embodiments, the first nucleotide is at least about 60%, 65%, 70%, 75%, 80%, 85%, 90%, 95%, or 100% identical to a nucleotide region within SEQ ID NO: 410, with the exception that the thymines (Ts) in SEQ ID NO: 410 are replaced with uracil (U). In some embodiments, the first nucleotide sequence is at least about 60%, 65%, 70%, 75%, 80%, 85%, 90%, 95%, or 100% identical to 15 to 30, 15 to 25, 15 to 23, 15 to 22, 15 to 21, 17 to 25, 17 to 23, 17 to 22, 17 to 21, or 19 to 21 nucleotides within positions 200-720 or 1100-1700 of SEQ ID NO: 410. In some embodiments, the first nucleotide sequence is at least about 60%, 65%, 70%, 75%, 80%, 85%, 90%, 95%, or 100% identical to 15 to 30, 15 to 25, 15 to 23, 15 to 22, 15 to 21, 17 to 25, 17 to 23, 17 to 22, 17 to 21, or 19 to 21 nucleotides within positions 200-280, 300-445, 460-510, 650-720, 1170-1220, 1250-1300, or 1550-1630 of SEQ ID NO: 410. In some embodiments, the first nucleotide sequence is at least about 60%, 65%, 70%, 75%, 80%, 85%, 90%, 95%, or 100% identical to 15 to 30, 15 to 25, 15 to 23, 15 to 22, 15 to 21, 17 to 25, 17 to 23, 17 to 22, 17 to 21, or 19 to 21 nucleotides within positions 200-230, 250-280, 300-330, 370-400, 405-445, 460-500, 670-700, 1180-1210, 1260-1295, 1520-1550, or 1570-1610 of SEQ ID NO: 410. In some embodiments, the first nucleotide sequence is at least about 60%, 65%, 70%, 75%, 80%, 85%, 90%, 95%, or 100% identical to 15 to 30, 15 to 25, 15 to 23, 15 to 22, 15 to 21, 17 to 25, 17 to 23, 17 to 22, 17 to 21, or 19 to 21 nucleotides starting at position 203, 206, 254, 305, 375, 409, 412, 415, 416, 419, 462, 466, 467, 674, 676, 1182, 1262, 1263, 1268, 1526, 1577, 1578, 1580, 1581, 1583, or 1584 of SEQ ID NO: 410.

In some embodiments, the target gene is involved in liver metabolism. In some embodiments, the target gene is an inhibitor of the electron transport chain. In some embodiments, the target gene encodes the MCJ protein (MCJ/DnaJC15 or Methylation-Controlled J protein). In some embodiments, the MCJ protein is encoded by the mRNA sequence of SEQ ID NO: 411, which corresponds to the nucleotide sequence of GenBank Accession No. NM_013238.3, which is incorporated by reference in its entirety.

In some embodiments, the target gene is TAZ. In some embodiments, TAZ comprises the nucleotide sequence of SEQ ID NO: 412, which corresponds to the nucleotide sequence of GenBank Accession No. NM_000116.5, which is incorporated by reference in its entirety.

In some embodiments, the target gene is angiopoietin like 3 (ANGPTL3). In some embodiments, ANGPTL3 comprises the nucleotide sequence of SEQ ID NO: 413, which corresponds to the nucleotide sequence of GenBank Accession No. NM_014495.4, which is incorporated by reference in its entirety.

In some embodiments, the target gene is diacylglycerol acyltransferase 2 (DGAT2). In some embodiments, DGAT2 comprises the nucleotide sequence of SEQ ID NO: 414, which corresponds to the nucleotide sequence of GenBank Accession No. NM_001253891.1, which is incorporated by reference in its entirety.

Compositions

As indicated above, the present disclosure provides compositions comprising any of the siNA molecules, sense strands, antisense strands, first nucleotide sequences, or second nucleotide sequences described herein. The compositions may comprise 1, 2, 3, 4, 5, 6, 7, 8, 9, 10, 11, 12 or more siNA molecules described herein. The compositions may comprise a first nucleotide sequence comprising a nucleotide sequence of any one SEQ ID NOs: 1-56, 103-158, and 205-260. In some embodiments, the composition comprises a second nucleotide sequence comprising a nucleotide sequence of any one of SEQ ID NOs: 57-102, 159-204, and 261-306. In some embodiments, the composition comprises a sense strand comprising a nucleotide sequence of any one of SEQ ID NOs: 307-362 and 415-444. In some embodiments, the composition comprises an antisense strand comprising a nucleotide sequence of any one of SEQ ID NOs: 363-409, 445-533, and 536-539.

Alternatively, the compositions may comprise (a) a phosphorylation blocker; and (b) a short interfering nucleic acid (siNA). In some embodiments, the phosphorylation blocker is any of the phosphorylation blockers disclosed herein. In some embodiments, the siNA is any of the siNAs disclosed herein. In some embodiments, the siNA comprises any of the sense strands, antisense strands, first nucleotide sequences, or second nucleotide sequences described herein. In some embodiments, the siNA comprises any of the sense strands, antisense strands, first nucleotide sequences, or second nucleotide sequences described herein. In some embodiments, the siNA comprises one or more modified nucleotides. In some embodiments, the one or more modified nucleotides are independently selected from a 2'-fluoro nucleotide and a 2'-O-methyl nucleotide. In some embodiments, the 2'-fluoro nucleotide or the 2'-O-methyl nucleotide is independently selected from any of the 2'-fluoro or 2'-O-methyl nucleotide mimics disclosed herein. In some embodiments, the siNA comprises a nucleotide sequence comprising any of the modification patterns disclosed herein.

In some embodiments, the composition comprises (a) a conjugated moiety; and (b) a short interfering nucleic acid (siNA). In some embodiments, the conjugated moiety is any of the galactosomines disclosed herein. In some embodiments, the siNA is any of the siNAs disclosed herein. In some embodiments, the siNA comprises any of the sense strands, antisense strands, first nucleotide sequences, or second nucleotide sequences described herein. In some embodiments, the siNA comprises any of the sense strands, antisense strands, first nucleotide sequences, or second nucleotide sequences described herein. In some embodiments, the siNA comprises one or more modified nucleotides. In some embodiments, the one or more modified nucleotides are independently selected from a 2'-fluoro nucleotide and a 2'-O-methyl nucleotide. In some embodiments, the 2'-fluoro nucleotide or the 2'-O-methyl nucleotide is independently selected from any of the 2'-fluoro or 2'-O-methyl nucleotide mimics disclosed herein. In some embodiments, the siNA comprises a nucleotide sequence comprising any of the modification patterns disclosed herein.

In some embodiments, the composition comprises (a) a 5'-stabilized end cap; and (b) a short interfering nucleic acid (siNA). In some embodiments, the 5'-stabilized end cap is any of the 5-stabilized end caps disclosed herein. In some embodiments, the siNA is any of the siNAs disclosed herein. In some embodiments, the siNA comprises any of the sense strands, antisense strands, first nucleotide sequences, or second nucleotide sequences described herein. In some embodiments, the siNA comprises one or more modified nucleotides. In some embodiments, the one or more modified nucleotides are independently selected from a 2'-fluoro nucleotide and a 2'-O-methyl nucleotide. In some embodiments, the 2'-fluoro nucleotide or the 2'-O-methyl nucleotide is independently selected from any of the 2'-fluoro or 2'-O-methyl nucleotide mimics disclosed herein. In some embodiments, the siNA comprises a nucleotide sequence comprising any of the modification patterns disclosed herein.

In some embodiments, the composition comprises (a) at least one phosphorylation blocker, conjugated moiety, or 5'-stabilized end cap; and (b) a short interfering nucleic acid (siNA). In some embodiments, the phosphorylation blocker is any of the phosphorylation blockers disclosed herein. In some embodiments, the conjugated moiety is any of the galactosomines disclosed herein. In some embodiments, the 5'-stabilized end cap is any of the 5-stabilized end caps disclosed herein. In some embodiments, the siNA is any of the siNAs disclosed herein. In some embodiments, the siNA comprises any of the sense strands, antisense strands, first nucleotide sequences, or second nucleotide sequences described herein. In some embodiments, the siNA comprises one or more modified nucleotides. In some embodiments, the one or more modified nucleotides are independently selected from a 2'-fluoro nucleotide and a 2'-O-methyl nucleotide. In some embodiments, the 2'-fluoro nucleotide or the 2'-O-methyl nucleotide is independently selected from any of the 2'-fluoro or 2'-O-methyl nucleotide mimics disclosed herein. In some embodiments, the siNA comprises a nucleotide sequence comprising any of the modification patterns disclosed herein.

The composition may be a pharmaceutical composition. In some embodiments, the pharmaceutical composition comprises an amount of one or more of the siNA molecules described herein formulated with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a siNA of the present disclosure which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound (e.g., siNA molecule) which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present disclosure comprises an excipient selected from the group consisting of cyclodextrins, celluloses, liposomes, micelle forming agents, e.g., bile acids, and polymeric carriers, e.g., polyesters and polyanhydrides; and a compound (e.g., siNA molecule) of the present disclosure. In certain embodiments, an aforementioned formulation renders orally bioavailable a compound (e.g., siNA molecule) of the present disclosure.

Methods of preparing these formulations or compositions include the step of bringing into association a compound (e.g., siNA molecule) of the present disclosure with the carrier and, optionally, one or more accessory ingredients. In general, the formulations are prepared by uniformly and intimately bringing into association a compound (e.g., siNA molecule) of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound (e.g., siNA molecule) of the present disclosure as an active ingredient. A compound (e.g., siNA molecule) of the present disclosure may also be administered as a bolus, electuary or paste.

In solid dosage forms of the disclosure for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose.

In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried.

They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds (e.g., siNA molecules) of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (I particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds (e.g., siNA molecules), may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the disclosure for rectal or vaginal administration may be presented as a suppository, which may be prepared by mixing one or more compounds (e.g., siNA molecules) of the disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound (e.g., siNA molecule).

Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of a compound (e.g., siNA molecule) of this disclosure include powders, sprays, ointments, pastes, creams, lotions, gels, solutions, patches and inhalants. The active compound (e.g., siNA molecule) may be mixed under sterile conditions with a pharmaceutically acceptable carrier, and with any preservatives, buffers, or propellants which may be required.

The ointments, pastes, creams and gels may contain, in addition to an active compound (e.g., siNA molecule) of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound (e.g., siNA molecule) of this disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound (e.g., siNA molecule) of the present disclosure to the body. Such dosage forms can be made by dissolving or dispersing the compound (e.g., siNA molecule) in the proper medium. Absorption enhancers can also be used to increase the flux of the compound (e.g., siNA molecule) across the skin. The rate of such flux can be controlled by either providing a rate controlling membrane or dispersing the compound (e.g., siNA molecule) in a polymer matrix or gel.

Ophthalmic formulations, eye ointments, powders, solutions and the like, are also contemplated as being within the scope of this invention.

Pharmaceutical compositions of this disclosure suitable for parenteral administration comprise one or more compounds (e.g., siNA molecules) of the disclosure in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds (e.g., siNA molecules) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds (e.g., siNA molecules) of the present disclosure are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Methods of Treatment and Administration

The siNA molecules of the present disclosure may be used to treat a disease in a subject in need thereof. In some embodiments, a method of treating a disease in a subject in need thereof comprises administering to the subject any of the siNA molecules disclosed herein. In some embodiments, a method of treating a disease in a subject in need thereof comprises administering to the subject any of the compositions disclosed herein.

The preparations (e.g., siNA molecules or compositions) of the present disclosure may be given orally, parenterally, topically, or rectally. They are of course given in forms suitable for each administration route. For example, they are administered in tablets or capsule form, administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds (e.g., siNA molecules) of the present disclosure, which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound (e.g., siNA molecule) of the present disclosure employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds (e.g., siNA molecules) of the disclosure employed in the pharmaceutical composition at levels lower than that required in order to achieve the desired therapeutic effect and gradually increase the dosage until the desired effect is achieved.

In general, a suitable daily dose of a compound (e.g., siNA molecule) of the disclosure is the amount of the compound that is the lowest dose effective to produce a therapeutic effect. Such an effective dose generally depends upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. In some embodiments, the compound is administered at a dose equal to or greater than 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.35, 0.40, 0.45, 0.50, 0.55, 0.60, 0.65, 0.7, 0.75, 0.8, 0.85, 0.9, 0.95, or 1 mg/kg. In some embodiments, the compound is administered at a dose equal to or less than 200, 190, 180, 170, 160, 150, 140, 130, 120, 110, 100, 95, 90, 85, 80, 75, 70, 65, 60, 55, 50, 45, 40, 35, 30, 25, 20, or 15 mg/kg. In some embodiments, the total daily dose of the compound is equal to or greater than 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 100 mg.

When the compounds (e.g., siNA molecules) described herein are co-administered with another, the effective amount may be less than when the compound is used alone.

If desired, the effective daily dose of the active compound (e.g., siNA molecule) may be administered as two, three, four, five, six or more sub-doses administered separately at appropriate intervals throughout the day, optionally, in unit dosage forms. Preferred dosing is one administration per day. In some embodiments, the compound is administered at least 1, 2, 3, 4, 5, 6, 7, 8, 9, 10, 11, 12, 13, 14, 15, 16, 17, 18, 19, 20, or 21 times a week. In some embodiments, the compound is administered at least 1, 2, 3, 4, 5, 6, 7, 8, 9, 10, 11, 12, 13, 14, 15, 16, 17, 18, 19, 20, or 21 times a month. In some embodiments, the compound is administered once every 1, 2, 3, 4, 5, 6, 7, 8, 9, 10, 11, 12, 13, 14, 15, 16, 17, 18, 19, 20, or 21 days. In some embodiments, the compound is administered once every 1, 2, 3, 4, 5, 6, 7, or 8 weeks.

Diseases

The siNA molecules and compositions described herein may be administered to a subject to treat a disease. Further disclosed herein are uses of any of the siNA molecules or compositions disclosed herein in the manufacture of a medicament for treating a disease.

In some embodiments, the disease is a viral disease. In some embodiments, the viral disease is caused by a DNA virus. In some embodiments, the DNA virus is a double stranded DNA (dsDNA virus). In some embodiments, the dsDNA virus is a hepadnavirus. In some embodiments, the hepadnavirus is a hepatitis B virus (HBV).

In some embodiments, the disease is a liver disease. In some embodiments, the liver disease is nonalcoholic fatty liver disease (NAFLD). In some embodiments, the NAFLD is nonalcoholic steatohepatitis (NASH). In some embodiments, the liver disease is hepatocellular carcinoma (HCC).

Administration of siNA

Administration of any of the siNAs disclosed herein may be conducted by methods known in the art. In some embodiments, the siNA is administered by subcutaneous (SC) or intravenous (IV) delivery. The preparations (e.g., siNAs or compositions) of the present disclosure may be given orally, parenterally, topically, or rectally. They are of course given in forms suitable for each administration route. For example, they are administered in tablets or capsule form, administration by injection, infusion or inhalation; topical by lotion or ointment; and rectal by suppositories. In some embodiments, subcutaneous administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds (e.g., siNAs) of the present disclosure, which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound (e.g., siNA) of the present disclosure employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds (e.g., siNAs) of the disclosure employed in the pharmaceutical composition at levels lower than that required in order to achieve the desired therapeutic effect and gradually increase the dosage until the desired effect is achieved.

In general, a suitable daily dose of a compound (e.g., siNA) of the disclosure is the amount of the compound that is the lowest dose effective to produce a therapeutic effect. Such an effective dose generally depends upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. In some embodiments, the compound is administered at about 1 mg/kg to about 40 mg/kg, about 1 mg/kg to about 30 mg/kg, about 1 mg/kg to about 20 mg/kg, about 1 mg/kg to about 15 mg/kg, or 1 mg/kg to about 10 mg/kg. In some embodiments, the compound is administered at a dose equal to or greater than 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.35, 0.40, 0.45, 0.50, 0.55, 0.60, 0.65, 0.7, 0.75, 0.8, 0.85, 0.9, 0.95, or 1 mg/kg. In some embodiments, the compound is administered at a dose equal to or greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mg/kg. In some embodiments, the compound is administered at a dose equal to or less than 200, 190, 180, 170, 160, 150, 140, 130, 120, 110, 100, 95, 90, 85, 80, 75, 70, 65, 60, 55, 50, 45, 40, 35, 30, 25, 20, or 15 mg/kg. In some embodiments, the total daily dose of the compound is equal to or greater than 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 100 mg.

If desired, the effective daily dose of the active compound (e.g., siNA) may be administered as two, three, four, five, six, seven, eight, nine, ten or more doses or sub-doses administered separately at appropriate intervals throughout the day, optionally, in unit dosage forms. In some embodiments, the compound is administered at least 1, 2, 3, 4, 5, 6, 7, 8, 9, 10, 11, 12, 13, 14, or 15 times. Preferred dosing is one administration per day. In some embodiments, the compound is administered at least 1, 2, 3, 4, 5, 6, 7, 8, 9, 10, 11, 12, 13, 14, 15, 16, 17, 18, 19, 20, or 21 times a week. In some embodiments, the compound is administered at least 1, 2, 3, 4, 5, 6, 7, 8, 9, 10, 11, 12, 13, 14, 15, 16, 17, 18, 19, 20, or 21 times a month. In some embodiments, the compound is administered once every 1, 2, 3, 4, 5, 6, 7, 8, 9, 10, 11, 12, 13, 14, 15, 16, 17, 18, 19, 20, or 21 days. In some embodiments, the compound is administered every 3 days. In some embodiments, the compound is administered once every 1, 2, 3, 4, 5, 6, 7, 8, 9, 10, 11, 12, 13, 14, or 15 weeks. In some embodiments, the compound is administered every month. In some embodiments, the compound is administered once every 1, 2, 3, 4, 5, 6, 7, 8, 9, 10, 11, 12, 13, 14, or 15 months. In some embodiments, the compound is administered at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 times over a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 days. In some embodiments, the compound is administered at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 times over a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 weeks. In some embodiments, the compound is administered at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 times over a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 months. In some embodiments, the compound is administered at least once a week for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 weeks. In some embodiments, the compound is administered at least once a week for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 months. In some embodiments, the compound is administered at least twice a week for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 weeks. In some embodiments, the compound is administered at least twice a week for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 months. In some embodiments, the compound is administered at least once every two weeks for a period of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 weeks. In some embodiments, the compound is administered at least once every two weeks for a period of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 months. In some embodiments, the compound is administered at least once every four weeks for a period of at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 weeks. In some embodiments, the compound is administered at least once every four weeks for a period of at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 months.

In some embodiments, any one of the siNAs or compositions disclosed herein is administered in a particle or viral vector. In some embodiments, the viral vector is a vector of adenovirus, adeno-associated virus (AAV), alphavirus, flavivirus, herpes simplex virus, lentivirus, measles virus, picornavirus, poxvirus, retrovirus, or rhabdovirus. In some embodiments, the viral vector is a recombinant viral vector. In some embodiments, the viral vector is selected from AAVrh.74, AAVrh.10, AAVrh.20, AAV-1, AAV-2, AAV-3, AAV-4, AAV-5, AAV-6, AAV-7, AAV-8, AAV-9, AAV-10, AAV-11, AAV-12 and AAV-13.

The subject of the described methods may be a mammal, and it includes humans and non-human mammals. In some embodiments, the subject is a human, such as an adult human.

Some embodiments include a method for treating an HBV virus in a subject infected with the virus comprising administering a therapeutically effective amount of one or more siNA of the present disclosure or a composition of the present disclosure to the subject in need thereof thereby reducing the viral load of the virus in the subject and/or reducing a level of a virus antigen in the subject. The siNA may be complementary or hybridize to a portion of the target RNA in the virus, e.g., an X region and/or an S region of HBV.

Combination Therapies

Any of the methods disclosed herein may further comprise administering to the subject an additional HBV treatment agent. Any of the compositions disclosed herein may further comprise an additional HBV treatment agent. In some embodiments, the additional HBV treatment agent is selected from a nucleotide analog, nucleoside analog, a capsid assembly modulator (CAM), a recombinant interferon, an entry inhibitor, a small molecule immunomodulator and oligonucleotide therapy. In some embodiments, the additional HBV treatment agent is selected from HBV STOPS™ ALG-010133, HBV CAM ALG-000184, ASO 1, recombinant interferon alpha 2b, IFN-a, PEG-IFN-a-2a, lamivudine, telbivudine, adefovir dipivoxil, clevudine, entecavir, tenofovir alafenamide, tenofovir disoproxil, NVR3-778, BAY41-4109, JNJ-632, JNJ-3989 (ARO-HBV), RG6004, GSK3228836, REP-2139, REP-2165, AB-729, VIR-2218, RG6346 (DCR-HBVS), JNJ-6379, GLS4, ABI-HO731, JNJ-440, NZ-4, RG7907, EDP-514, AB-423, AB-506, ABI-H03733 and ABI-H2158. In some embodiments, the oligonucleotide therapy is selected from Nucleic Acid Polymers or S-Antigen Transport-inhibiting Oligonucleotide Polymers (NAPs or STOPS), siRNA, and ASO. In some embodiments, the oligonucleotide therapy is an additional siNA. In some embodiments, the additional siNA is selected from any of ds-siNA-001 to ds-siNA-0178. In some embodiments, the oligonucleotide therapy is an antisense oligonucleotide (ASO). In some embodiments, the ASO is ASO 1. In some embodiments, any of the siNAs disclosed herein are co-administered with STOPS. Exemplary STOPS are described in International Publication No. WO2020/097342 and U.S. Publication No. 2020/0147124, both of which are incorporated by reference in their entirety. In some embodiments, the STOPS is ALG-010133. In some embodiments, any of the siNAs disclosed herein are co-administered with tenofovir. In some embodiments, any of the siNAs disclosed herein are co-administered with a CAM. Exemplary CAMs are described in Berke et al., *Antimicrob Agents Chemother,* 2017, 61(8):e00560-17, Klumpp, et al., Gastroenterology, 2018, 154(3):652-662.e8, International Application Nos. PCT/US2020/017974, PCT/US2020/026116, and PCT/US2020/028349 and U.S. application Ser. Nos. 16/789,298, 16/837,515, and 16/849,851, each which is incorporated by reference in its entirety. In some embodiments, the CAM is ALG-000184, ALG-001075, ALG-001024, JNJ-632, BAY41-4109, or NVR3-778. In some embodiments, the siNA and the HBV treatment agent are administered simultaneously. In some embodiments, the siNA and the HBV treatment agent are administered concurrently. In some embodiments, the siNA and the HBV treatment agent are administered sequentially. In some embodiments, the siNA is administered prior to administering the HBV treatment agent. In some embodiments, the siNA is administered after administering the HBV treatment agent. In some embodiments, the siNA and the HBV treatment agent are in separate containers. In some embodiments, the siNA and the HBV treatment agent are in the same container.

Any of the methods disclosed herein may further comprise administering to the subject a liver disease treatment agent. Any of the compositions disclosed herein may further comprise a liver disease treatment agent. In some embodiments, the liver disease treatment agent is selected from a peroxisome proliferator-activator receptor (PPAR) agonist, farnesoid X receptor (FXR) agonist, lipid-altering agent, and incretin-based therapy. In some embodiments, the PPAR agonist is selected from a PPARα agonist, dual PPARα/δ agonist, PPARγ agonist, and dual PPARα/γ agonist. In some embodiments, the dual PPARα agonist is a fibrate. In some embodiments, the PPARα/δ agonist is elafibranor. In some embodiments, the PPARγ agonist is a thiazolidinedione (TZD). In some embodiments, TZD is pioglitazone. In some embodiments, the dual PPARα/γ agonist is saroglitazar. In some embodiments, the FXR agonist is obeticholic acis (OCA). In some embodiments, the lipid-altering agent is aramchol. In some embodiments, the incretin-based therapy is a glucagon-like peptide 1 (GLP-1) receptor agonist or dipeptidyl peptidase 4 (DPP-4) inhibitor. In some embodiments, the GLP-1 receptor agonist is exenatide or liraglutide. In some embodiments, the DPP-4 inhibitor is sitagliptin or vildagliptin. In some embodiments, the siNA and the liver disease treatment agent are administered concurrently. In some embodiments, the siNA and the liver disease treatment agent are administered sequentially. In some embodiments, the siNA is administered prior to administering the liver disease treatment agent. In some embodiments, the siNA is administered after administering the liver disease treatment agent. In some embodiments, the siNA and the liver disease treatment agent are in separate containers. In some embodiments, the siNA and the liver disease treatment agent are in the same container.

Definitions

Unless defined otherwise, all technical and scientific terms used herein have the meaning commonly understood by a person skilled in the art to which this disclosure belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al., (eds.), Springer Verlag (1991); and Hale & Marham, The Harper Collins Dictionary of Biology (1991). As used herein, the following terms have the meanings ascribed to them below, unless specified otherwise. The terminology used herein is for the purpose of describing particular embodiments only and is not intended to be limiting of the disclosure.

The terms "a" and "an" as used herein mean "one or more" and include the plural unless the context is inappropriate.

As used herein, the terms "patient" and "subject" refer to organisms to be treated by the methods of the present disclosure. Such organisms are preferably mammals (e.g., marines, simians, equines, bovines, porcinis, canines, felines, and the like), and more preferably humans.

As used herein, the term "effective amount" refers to the amount of a compound (e.g., a siNA of the present disclosure) sufficient to effect beneficial or desired results. A$_n$ effective amount can be administered in one or more administrations, applications, or dosages and is not intended to be limited to a particular formulation or administration route.

As used herein, the term "treating" includes any effect, e.g., lessening, reducing, modulating, ameliorating or eliminating, that results in the improvement of the condition, disease, disorder, and the like, or ameliorating a symptom thereof.

As used herein, the terms "alleviate" and "alleviating" refer to reducing the severity of the condition, such as reducing the severity by, for example, at least 10%, 20%, 30%, 40%, 50%, 60%, 70%, 80%, 90%, or 95%.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, for example, Martin, Remington's Pharmaceutical Sciences, 15th Ed., Mack Publ. Co., Easton, Pa. [1975].

The term "about" as used herein when referring to a measurable value (e.g., weight, time, and dose) is meant to encompass variations, such as ±10%, ±5%, ±1%, or ±0.1% of the specified value.

As used herein, the term "nucleobase" refers to a nitrogen-containing biological compound that forms a nucleoside. Examples of nucleobases include, but are not limited to, thymine, uracil, adenine, cytosine, guanine, aryl, heteroaryl, and an analogue or derivative thereof.

Throughout the description, where compositions are described as having, including, or comprising specific components, or where processes and methods are described as having, including, or comprising specific steps, it is contemplated that, additionally, there are compositions of the present disclosure that consist essentially of, or consist of, the recited components, and that there are processes and methods according to the present disclosure that consist essentially of, or consist of, the recited processing steps.

As a general matter, compositions specifying a percentage are by weight unless otherwise specified. Further, if a variable is not accompanied by a definition, then the previous definition of the variable controls.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates that may need to be independently confirmed.

EXAMPLES

Example 1. siNA Synthesis

This example describes an exemplary method for synthesizing ds-siNAs, such as the siNAs disclosed in Table 6 (as identified by the ds-siNA ID).

The 2'-OMe phosphoramidite 5'-O-DMT-deoxy Adenosine (NH-Bz), 3'-O-(2-cyanoethyl-N,N-diisopropyl phosphoramidite, 5'-O-DMT-deoxy Guanosine (NH-ibu), 3'-O-(2-cyanoethyl-N,N-diisopropyl phosphoramidite, 5'-O-DMT-deoxy Cytosine (NH-Bz), 3'-O-(2-cyanoethyl-N,N-diisopropyl phosphoramidite, 5'-O-DMT-Uridine 3'-O-(2-cyanoethyl-N,N-diisopropyl phosphoramidite and solid supports were purchased from Chemgenes Corp. MA.

159
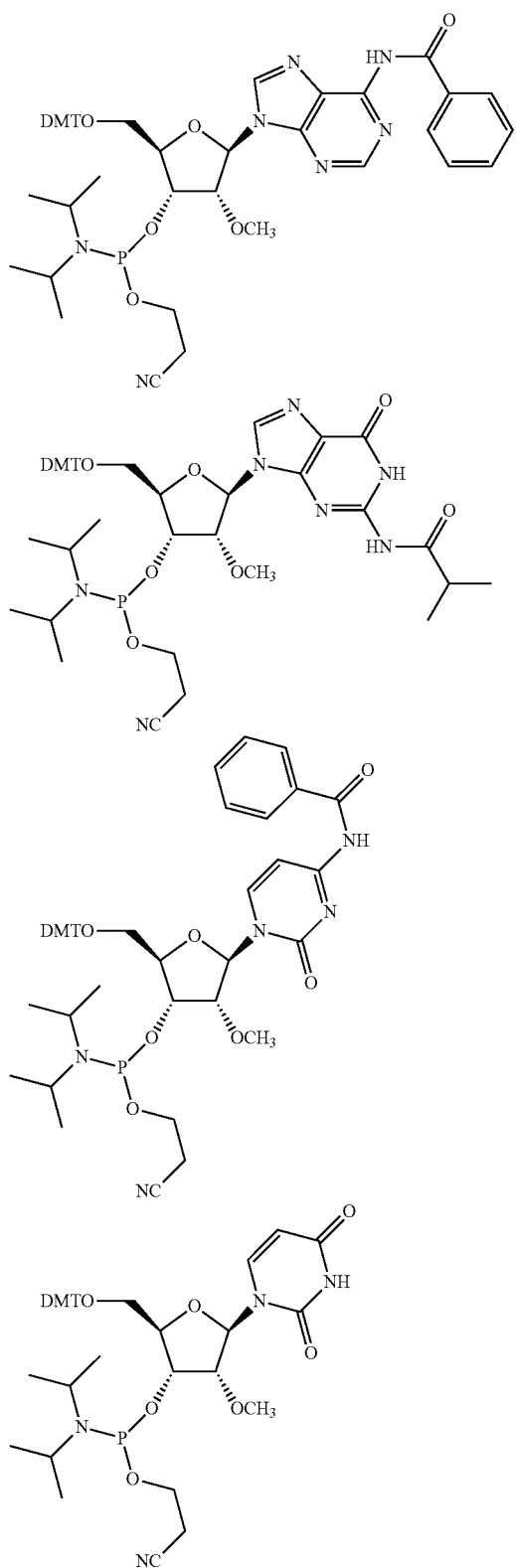
160
DMT-Uridine, 2'-F-3'-O-(2-cyanoethyl-N,N-diisopropyl phosphoramidite and solid supports were purchased from Thermo Fischer Milwaukee Wis., USA.
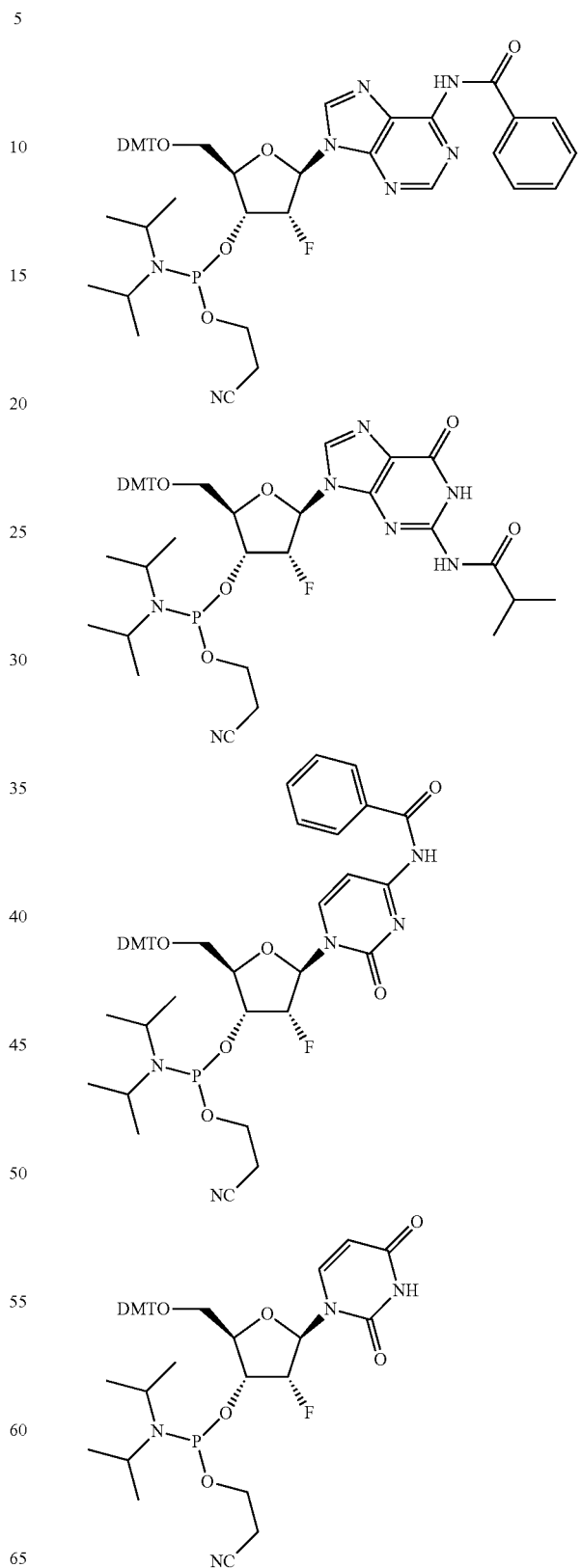
The 2'-F-5'-O-DMT-(NH-Bz) Adenosine-3'-O-(2-cyanoethyl-N,N-diisopropyl phosphoramidite, 2'-F-5'-O-DMT-(NH-ibu)-Guanosine, 3'-O-(2-cyanoethyl-N,N-diisopropyl phosphoramidite, 5'-O-DMT-(NH-Bz)-Cytosine, 2'-F-3'-O-(2-cyanoethyl-N,N-diisopropyl phosphoramidite, 5'-O-

All the monomers were dried in vacuum desiccator with desiccants ($P_2O_5$, RT 24 h). The solid supports (CPG) attached to the nucleosides and universal supports was obtained from LGC and Chemgenes. The chemicals and solvents for post synthesis workflow were purchased from commercially available sources like VWR/Sigma and used without any purification or treatment. Solvent (Acetonitrile) and solutions (amidite and activator) were stored over molecular sieves during synthesis.

The oligonucleotides were synthesized on a DNA/RNA Synthesizers (Expedite 8909 or ABI-394) using standard oligonucleotide phosphoramidite chemistry starting from the 3' residue of the oligonucleotide preloaded on CPG support. An extended coupling of 0.1 M solution of phosphoramidite in $CH_3CN$ in the presence of 5-(ethylthio)-1H-tetrazole activator to a solid bound oligonucleotide followed by standard capping, oxidation and deprotection afforded modified oligonucleotides. The 0.1 M $I_2$, THF:Pyridine; Water-7:2:1 was used as oxidizing agent while DDTT ((dimethylamino-methylidene)amino)-3H-1,2,4-dithiazaoline-3-thione was used as the sulfur-transfer agent for the synthesis of oligoribonucleotide phosphorothioates. The stepwise coupling efficiency of all modified phosphoramidites was more than 98%.

| Reagents | Detailed Description |
| --- | --- |
| Deblock Solution | 3% Dichloroacetic acid (DCA) in Dichloromethane (DCM) |
| Amidite Concentration | 0.1M in Anhydrous Acetonitrile |
| Activator | 0.25M Ethyl-thio-Tetrazole (ETT) |
| Cap-A solution | Acetic anhydride in Pyridine/THF |
| Cap-B Solution | 16% 1-Methylimidazole in THF |
| Oxidizing Solution | 0.02M $I_2$, THF: Pyridine; Water-7:2:1 |
| Sulfurizing Solution | 0.2M DDTT in Pyridine/Acetonitrile 1:1 |

Cleavage and Deprotection:

Deprotection and cleavage from the solid support was achieved with mixture of ammonia methylamine (1:1, AMA) for 15 min at 65° C., when the universal linker was used, the deprotection was left for 90 min at 65° C. or solid supports were heated with aqueous ammonia (28%) solution at 55° C. for 16 h to deprotect the base labile protecting groups.

Quantitation of Crude SiNA or Raw Analysis

Samples were dissolved in deionized water (1.0 mL) and quantitated as follows: Blanking was first performed with water alone (2 ul) on Nanodrop then Oligo sample reading obtained at 260 nm. The crude material is dried down and stored at −20° C.

Crude HPLC/LC-MS Analysis

The 0.1 OD of the crude samples were analyzed for crude HPLC and LC-MS analysis. After Confirming the crude LC-MS data then purification step was performed.

HPLC Purification

The unconjugated and GalNac modified oligonucleotides were purified by anion-exchange HPLC. The buffers were 20 mM sodium phosphate in 10% $CH_3CN$, pH 8.5 (buffer A) and 20 mM sodium phosphate in 10% $CH_3CN$, 1.0 M NaBr, pH 8.5 (buffer B). Fractions containing full-length oligonucleotides were pooled.

Desalting of Purified SiNA

The purified dry siNA was then desalted using Sephadex G-25 M (Amersham Biosciences). The cartridge was conditioned with 10 mL of deionized water thrice. Finally, the purified siNA dissolved thoroughly in 2.5 mL RNAse free water was applied to the cartridge with very slow drop wise elution. The salt free siNA was eluted with 3.5 ml deionized water directly into a screw cap vial.

IEX HPLC and Electrospray LC/MS Analysis

Approximately 0.10 OD of siNA is dissolved in water and then pipetted in special vials for IEX-HPLC and LC/MS analysis. Analytical HPLC and ES LC-MS established the integrity of the compounds.

Duplex Preparation:

Single strand oligonucleotides (Sense and Antisense strands) were annealed (1:1 by molar equivalents, heat 90° C. for 3 min followed by room temperature, 20 min) to give the duplex ds-siNA. The final compounds were analyzed on size exclusion chromatography (SEC).

Example 2. ds-siNA Activity

This example investigates the activity of the ds-siNAs synthesized in Example 1.

*Homo sapiens* HepG2.2.15 cells were cultured in Dulbecco's Modified Eagle's Medium (DMEM) (ATCC 30-2002) supplemented to also contain 10% fetal calf serum (FCS). Cells were incubated at 37° C. in an atmosphere with 5% $CO_2$ in a humidified incubator. For transfection of HepG2.2.15 cells with HBV targeting siRNAs, cells were seeded at a density of 15000 cells/well in 96-well regular tissue culture plates. Transfection of cells was carried out using RNAiMAX (Invitrogen/Life Technologies) according to the manufacturer's instructions. Dose-response experiments were done with oligo concentrations of 40, 20, 10, 5, 2.5, 1.25, 0.625, 0.3125, 0.15625 and 0.07813 nM. For each HBV targeting siRNA treatment (e.g., ds-siRNA, as identified by the ds-siNA ID in Table 6), four wells were transfected in parallel, and individual data points were collected from each well. After 24 h of incubation with siRNA, media was removed, and cells were lysed and analyzed with a QuantiGene2.0 branched DNA (bDNA) probe set specific for HBV genotype D (also called Hepatitis B virus subtype ayw, complete genome of 3182 base-pairs) as present in cell line HepG2.2.15.

For each well, the HBV on-target mRNA levels were normalized to the GAPDH mRNA level. As shown in Table 6, the activity of the HBV targeting ds-siRNAs was expressed as EC50, 50% reduction of normalized HBV RNA level from no drug control. As shown in Table 6, the cytotoxicity of the HBV targeting ds-siRNAs was expressed by CC50 of 50% reduction of GAPDH mRNA from no drug control.

Example 3. Use of ds-siNAs to Treat Hepatitis B Virus Infection

In this example, the ds-siNAs synthesized in Example 1 are used to treat a hepatitis B virus infection in a subject. Generally, a composition comprising a ds-siNA from Table 6 (as identified by the ds-siNA ID) and a pharmaceutically acceptable carrier is administered to the subject suffering from hepatitis B virus. The ds-siNA from Table 6 is conjugated to N-acetylgalactosamine. The ds-siNA is administered at a dose of 0.3 to 5 mg/kg every three weeks by subcutaneous injection or intravenous infusion.

Example 4. ds-siNA Hepatitis B Clinical Trial

In this example, the ds-siNAs from Tables 6A and 6B (as identified by the ds-siNA ID) will be evaluated for safety and efficacy in healthy volunteers and chronic hepatitis B patients.

ds-siNAs are being developed for the treatment of chronic hepatitis B (CB) in adults. The study will be conducted in 3 parts, a single ascending-dose (SAD) phase in healthy volunteers (Group A), a single-dose (SD) phase in patients with CHB (Group B), and a multiple ascending-dose (MAD) phase in patients with CHB (Group C).

Study Design

| | |
|---|---|
| Study Type: | Interventional (Clinical Trial) |
| Estimated Enrollment: | 50 participants |
| Allocation: | Randomized |
| Intervention Model: | Sequential Assignment |
| Intervention Model Description: | Progression from the SAD phase to the first cohort in the MAD phase is contingent upon the Safety Review Committee (SRC) review of a minimum of 14 days post-dose safety and tolerability data from all HV in at least the first 2 SAD cohorts. The SRC will select one (or more) well-tolerated dose(s) from the SAD phase for administration in the SD and MAD phases. In all study phases, dosing will be staggered with the use of sentinel participants to allow time for the assessment of safety before additional subjects are exposed to study drug. |
| Masking: | Triple (Participant, Care Provider, Investigator) |
| Masking Description: | This is a double-blind placebo-controlled study in which the study site team, the Sponsor, and the participants will be blinded to treatment assignment. The unblinded pharmacist will cover each syringe, prior to transport to the bedside, to ensure blinding. Participants will be centrally assigned to randomized study intervention using an Interactive Voice/Web Response System (IVRS/IWRS). |
| Primary Purpose: | Treatment |

Arms and Interventions

| Arm | Intervention/treatment |
|---|---|
| Experimental: Cohort A1 ds-siNA Single dose, Subcutaneous injection of 0.1 mg/kg of ds-siNA (HV) | Drug: ds-siNA ds-siNA is a synthetic ribonucleic acid interference (RNAi) drug that consists of double-stranded oligonucleotides conjugated to an N-acetyl-D-galactosamine (GalNAc) ligand. ds-siNA, sterile solution of the ds-siNA at a concentration of 185 mg/mL in water for injection (WFI). |
| Placebo Comparator: Cohort A1 Placebo Single dose, Subcutaneous injection of 0.1 mg/kg of Placebo for ds-siNA (HV) | Drug: Placebo for ds-siNA Sterile 9% saline for injection. Other Name: Placebo |
| Experimental: Cohort A2 ds-siNA Single dose, Subcutaneous injection of 1.5 mg/kg of ds-siNA (HV) | Drug: ds-siNA ds-siNA is a synthetic ribonucleic acid interference (RNAi) drug that consists of double-stranded oligonucleotides conjugated to an N-acetyl-D-galactosamine (GalNAc) ligand. ds-siNA, sterile solution of the ds-siNA at a concentration of 185 mg/mL in water for injection (WFI). |
| Placebo Comparator: Cohort A2 Placebo Single dose, Subcutaneous injection of 1.5 mg/kg of Placebo for ds-siNA (HV) | Drug: Placebo for ds-siNA Sterile 9% saline for injection. Other Name: Placebo |
| Experimental: Cohort A3 ds-siNA Single dose, Subcutaneous injection of 3 mg/kg of ds-siNA (HV) | Drug: ds-siNA ds-siNA is a synthetic ribonucleic acid interference (RNAi) drug that consists of double-stranded oligonucleotides conjugated to an N-acetyl-D-galactosamine (GalNAc) ligand. ds-siNA, sterile solution of the ds-siNA at a concentration of 185 mg/mL in water for injection (WFI). |
| Placebo Comparator: Cohort A3 Placebo Single dose, Subcutaneous injection of 3 mg/kg of Placebo for ds-siNA (HV) | Drug: Placebo for ds-siNA Sterile 9% saline for injection. Other Name: Placebo |
| Experimental: Cohort A4 ds-siNA Single dose, Subcutaneous injection of 6 mg/kg of ds-siNA (HV) | Drug: ds-siNA ds-siNA is a synthetic ribonucleic acid interference (RNAi) drug that consists of double-stranded oligonucleotides conjugated to an N-acetyl-D-galactosamine (GalNAc) ligand. ds-siNA, sterile solution of the ds-siNA at a concentration of 185 mg/mL in water for injection (WFI). |
| Placebo Comparator: Cohort A4 Placebo Single dose, Subcutaneous injection of 6 mg/kg of Placebo for ds-siNA (HV) | Drug: Placebo for ds-siNA Sterile 9% saline for injection. Other Name: Placebo |

| Arm | Intervention/treatment |
| --- | --- |
| Experimental: Cohort A5 ds-siNA<br>Single dose, Subcutaneous injection of<br>12 mg/kg of ds-siNA (HV) | Drug: ds-siNA<br>ds-siNA is a synthetic ribonucleic acid<br>interference (RNAi) drug that consists of double-<br>stranded oligonucleotides conjugated to an N-<br>acetyl-D-galactosamine (GalNAc) ligand. ds-<br>siNA, sterile solution of the ds-siNA at a<br>concentration of 185 mg/mL in water for<br>injection (WFI). |
| Placebo Comparator: Cohort A5<br>Placebo<br>Single dose, Subcutaneous injection of<br>12 mg/kg of Placebo for ds-siNA (HV) | Drug: Placebo for ds-siNA<br>Sterile 9% saline for injection.<br>Other Name: Placebo |
| Experimental: Cohort B ds-siNA<br>Single dose, Subcutaneous injection of<br>3 mg/kg of for ds-siNA (NUC naive,<br>CHB) | Drug: ds-siNA<br>ds-siNA is a synthetic ribonucleic acid<br>interference (RNAi) drug that consists of double-<br>stranded oligonucleotides conjugated to an N-<br>acetyl-D-galactosamine (GalNAc) ligand. ds-<br>siNA, sterile solution of the ds-siNA at a<br>concentration of 185 mg/mL in water for<br>injection (WFI). |
| Placebo Comparator: Cohort B<br>Placebo<br>Single dose, Subcutaneous injection of<br>3 mg/kg of Placebo for ds-siNA (NUC<br>naive, CHB) | Drug: Placebo for ds-siNA<br>Sterile 9% saline for injection.<br>Other Name: Placebo |
| Experimental: Cohort C1 ds-siNA<br>4 doses- Subcutaneous injection of<br>1.5 mg/kg of ds-siNA administered<br>every 28 days (NUC experienced,<br>CHB) | Drug: ds-siNA<br>ds-siNA is a synthetic ribonucleic acid<br>interference (RNAi) drug that consists of double-<br>stranded oligonucleotides conjugated to an N-<br>acetyl-D-galactosamine (GalNAc) ligand. ds-<br>siNA, sterile solution of the ds-siNA at a<br>concentration of 185 mg/mL in water for<br>injection (WFI). |
| Placebo Comparator: Cohort C1<br>Placebo<br>4 doses- Subcutaneous injection of<br>1.5 mg/kg of Placebo for ds-siNA<br>administered every 28 days (NUC<br>experienced, CHB) | Drug: Placebo for ds-siNA<br>Sterile 9% saline for injection.<br>Other Name: Placebo |
| Experimental: Cohort C2 ds-siNA<br>4 doses- Subcutaneous injection of<br>3 mg/kg of ds-siNA administered every<br>28 days (NUC experienced, CHB) | Drug: ds-siNA<br>ds-siNA is a synthetic ribonucleic acid<br>interference (RNAi) drug that consists of double-<br>stranded oligonucleotides conjugated to an N-<br>acetyl-D-galactosamine (GalNAc) ligand. ds-<br>siNA, sterile solution of the ds-siNA at a<br>concentration of 185 mg/mL in water for<br>injection (WFI). |
| Placebo Comparator: Cohort C2<br>Placebo<br>4 doses- Subcutaneous injection of<br>3 mg/kg of Placebo for ds-siNA<br>administered every 28 days (NUC<br>experienced, CHB) | Drug: Placebo for ds-siNA<br>Sterile 9% saline for injection.<br>Other Name: Placebo |
| Experimental: Cohort C3 ds-siNA<br>4 doses- Subcutaneous injection of<br>6 mg/kg of ds-siNA administered every<br>28 days (NUC experienced, CHB) | Drug: ds-siNA<br>ds-siNA is a synthetic ribonucleic acid<br>interference (RNAi) drug that consists of double-<br>stranded oligonucleotides conjugated to an N-<br>acetyl-D-galactosamine (GalNAc) ligand. ds-<br>siNA, sterile solution of the ds-siNA at a<br>concentration of 185 mg/mL in water for<br>injection (WFI). |
| Placebo Comparator: Cohort C3<br>Placebo<br>4 doses- Subcutaneous injection of<br>6 mg/kg of Placebo for ds-siNA<br>administered every 28 days (NUC<br>experienced, CHB) | Drug: Placebo for ds-siNA<br>Sterile 9% saline for injection.<br>Other Name: Placebo |

Outcome Measures

Primary Outcome Measures:

Number of healthy volunteers with Adverse Events as assessed by CTCAE v5.0 [Time Frame: 4 weeks]

Number of participants with abnormalities in vital signs, electrocardiogram (ECG), and clinically significant laboratory findings Number participants with non-cirrhotic chronic Hepatitis B with Adverse Events as assessed by CTCAE v5.0 [Time Frame: 16 weeks]

Number of participants with abnormalities in vital signs, electrocardiogram (ECG), and clinically significant laboratory findings.

Secondary Outcome Measures:

To characterize the pharmacokinetics of ds-siNA in healthy volunteers by monitoring plasma pharmacokinetics profiles of [Time Frame: 4 weeks] Measure the amount of ds-siNA excreted in urine To characterize the pharmacokinetics of ds-siNA in healthy volunteers by monitoring through concentrations of [Time Frame: 4 weeks]

Measure the amount of ds-siNA renal clearance (CLR).

To characterize the pharmacokinetics of ds-siNA in participants with non-cirrhotic CHB by monitoring plasma pharmacokinetics profiles of ds-siNA. [Time Frame: 12 weeks]

Measure the amount of ds-siNA excreted in urine

To characterize the pharmacokinetics of ds-siNA in participants with non-cirrhotic CHB by monitoring through concentrations of ds-siNA. [Time Frame: 12 weeks]

Measure ds-siNA renal clearance (CLR).

Other Outcome Measures:

To evaluate the preliminary antiviral efficacy of ds-siNA in participants with CHB by monitoring changes in serum HBsAg levels (all Group B and C participants) during and after single dose and 12 weeks of treatment with DCR HBVS. [Time Frame: 12 weeks]

Proportion of participants achieving at least a 1-log reduction in HBsAg and achieving a HBsAg level <100 IU/mL at last scheduled visit Time to HBsAg loss (Kaplan-Mayer) Time to anti-HBs seroconversion To evaluate the preliminary antiviral efficacy of ds-siNA in participants with CHB by monitoring HBeAg levels (HBeAg+ participants only) during and after single dose and 12 weeks of treatment with DCR HBVS. [Time Frame: 12 weeks]

% of participants with HBeAg loss and anti HBe at last scheduled visit (if HBeAg positive at study entry)

To evaluate the preliminary antiviral efficacy of ds-siNA in participants with CHB by monitoring HBV DNA levels (all Group B and C participants) during and after single dose and 12 weeks of treatment with DCR HBVS. [Time Frame: 12 weeks]

Proportion of participants achieving HBV DNA<2000 IU/mL (if >2,000 IU/mL at Baseline); and proportion of participants achieving PCR-nondetectable HBV DNA (if HBV DNA was detectable at Baseline).

To characterize the pharmacodynamics (PD) of ds-siNA on plasma levels of HBsAg and HBV in blood. [Time Frame: 12 weeks]

Track post-treatment duration of any observed efficacy effects.

Eligibility Criteria

| | |
|---|---|
| Ages Eligible for Study: | 18 Years to 65 Years (Adult, Older Adult) |
| Sexes Eligible for Study: | All |
| Accepts Healthy Volunteers: | Yes |

Inclusion Criteria:

Healthy at the time of screening as determined by medical evaluation.

Capable of giving informed consent.

12-lead ECG within normal limits or with no clinically significant abnormalities.

Negative screen for alcohol or drugs of abuse.

Non-smokers for at least 3 months with a negative urinary cotinine concentration at screening.

BMI within range 18.0-32.0 kg/m2 (inclusive).

Female participants not pregnant, not breastfeeding, and not of childbearing potential or willing to follow contraceptive guidance.

Chronic hepatitis B infection (Group B and C only).

Clinical history compatible with compensated liver disease with no evidence of cirrhosis (Group B and C only).

Continuously on nucleotides (NUC) therapy for at least 12 weeks prior to screening (Group C only).

Exclusion Criteria:

History of any medical condition that may interfere with the absorption, distribution, or elimination of study drug.

Poorly controlled or unstable hypertension.

History of diabetes mellitus treated with insulin or hypoglycemic agents.

History of asthma requiring hospital admission within the preceding 12 months.

Evidence of G-6-PD deficiency.

Currently poorly controlled endocrine conditions, excluding thyroid conditions.

History of multiple drug allergies or history of allergic reaction to an oligonucleotide or GalNAc.

Clinically relevant surgical history.

Use of prescription medications (excluding contraception for women) within 4 weeks prior to the administration of study intervention.

Use of clinically relevant over-the-counter medication or supplements (excluding routine vitamins) within 7 days of first dosing.

Has received an investigational agent within the 3 months prior to dosing or is in follow-up of another study.

Antiviral therapy (other than entecavir or tenofovir) within 3 months of screening or treatment with interferon in the last 3 years (Group B and C only).

Use within the last 6 months of anticoagulants or systemically administered corticosteroids, immunomodulators, or immunosuppressants (Group B and C only).

Example 5: Synthesis of 5' End Cap Monomer

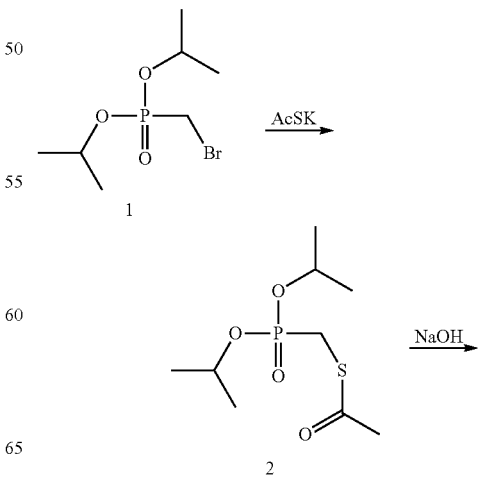

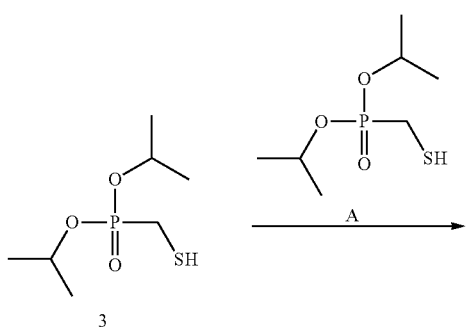

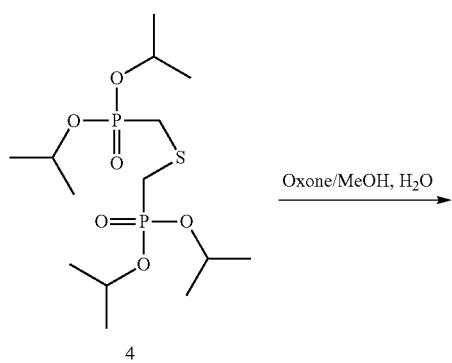

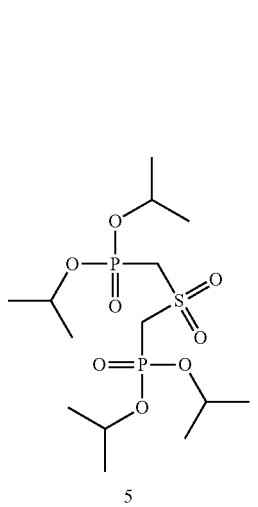

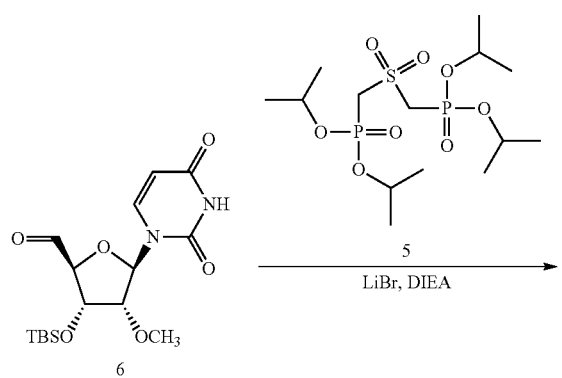

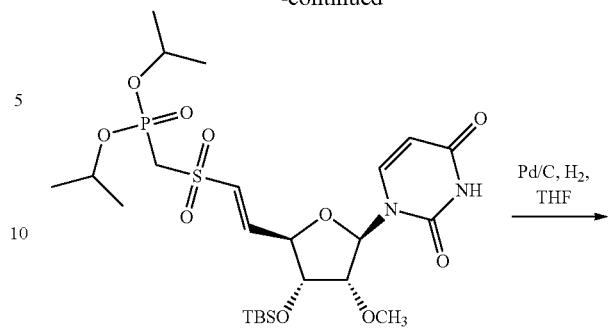

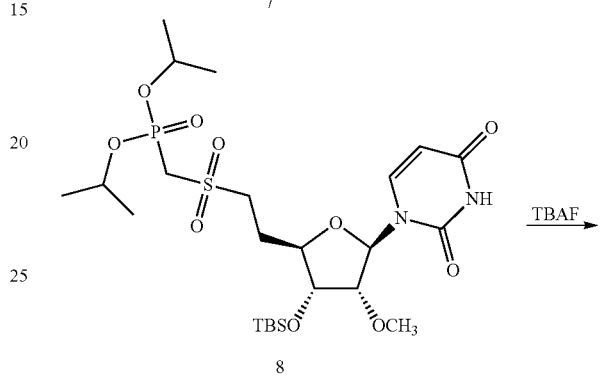

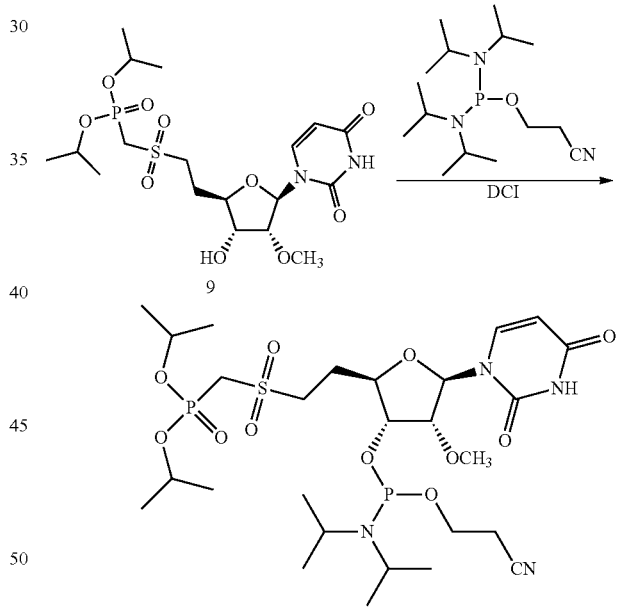

Example 5 monomer

Preparation of (2): To a solution of 1 (15 g, 57.90 mmol) in DMF (150 mL) were added AcSK (11.24 g, 98.43 mmol) and TBAI (1.07 g, 2.89 mmol), and the mixture was stirred at 25° C. for 12 h. Upon completion as monitored by LCMS, the mixture was diluted with $H_2O$ (10 mL) and extracted with EA (200 mL*3). The combined organic layers were washed with brine (200 mL*3), dried over anhydrous $Na_2SO_4$, filtered and concentrated under reduced pressure to give 2 (14.5 g, 96.52% yield, 98% purity) as a colorless oil. ESI-LCMS: 254.28 [M+H]$^+$; $^1$H NMR (400 MHz, $CDCl_3$) δ=4.78-4.65 (m, 2H), 3.19 (d, J=14.1 Hz, 2H), 2.38 (s, 3H), 1.32 (t, J=6.7 Hz, 12H); $^{31}$P NMR (162 MHz, $CDCl_3$) δ=20.59.

Preparation of (3): To a solution of 2 (14.5 g, 57.02 mmol) in CH$_3$CN (50 mL) and MeOH (25 mL) was added NaOH (3 M, 28.51 mL), and the mixture was stirred at 25° C. for 12 h under Ar. Upon completion as monitored by TLC, the reaction mixture was concentrated under reduced pressure to remove CH$_3$CN and CH$_3$OH. The residue was diluted with water (50 mL) and adjust pH=7 by 6 M HCl, and the mixture was extracted with EA (50 mL*3). The combined organic layers were washed with brine (50 mL*3), dried over anhydrous Na$_2$SO$_4$, filtered and concentrated under reduced pressure to give 3 (12.1 g, crude) as a colorless oil.

Preparation of (4): To a solution of 3 (12.1 g, 57.01 mmol) in CH$_3$CN (25 mL) and MeOH (25 mL) was added A (14.77 g, 57.01 mmol) dropwise at 25° C., and the mixture was stirred at 25° C. under Ar for 12 h. Upon completion as monitored by LCMS, the reaction mixture was concentrated under reduced pressure to give 4 (19.5 g, 78.85% yield) as a colorless oil. $^1$H NMR (400 MHz, CDCl$_3$) δ=4.80-4.66 (m, 4H), 2.93 (d, J=11.3 Hz, 4H), 1.31 (dd, J=3.9, 6.1 Hz, 24H); $^{31}$P NMR (162 MHz, CDCl$_3$) δ=22.18.

Preparation of (5): To a solution of 4 (19.5 g, 49.95 mmol) in MeOH (100 mL) and H$_2$O (100 mL) was added Oxone (61.41 g, 99.89 mmol) at 25° C. in portions, and the mixture was stirred at 25° C. for 12 h under Ar. Upon completion as monitored by LCMS, the reaction mixture was filtered, and the filtrate was concentrated under reduced pressure to remove MeOH. The residue was extracted with EA (50 mL*3). The combined organic layers were washed with brine (50 mL*3), dried over anhydrous Na$_2$SO$_4$, filtered and concentrated under reduced pressure to give a residue. The crude product was triturated with i-Pr$_2$O and n-Hexane (1:2, 100 mL) at 25° C. for 30 min to give 5 (15.6 g, 73.94% yield) as a white solid. $^1$H NMR (400 MHz, CDCl$_3$) δ=4.92-4.76 (m, 4H), 4.09 (d, J=16.1 Hz, 4H), 1.37 (dd, J=3.5, 6.3 Hz, 24H); $^{31}$P NMR (162 MHz, CDCl$_3$) δ=10.17.

Preparation of (7): To a mixture of 5 (6.84 g, 16.20 mmol) in THF (20 mL) was added LiBr (937.67 mg, 10.80 mmol) until dissolved, followed by DIEA (1.40 g, 10.80 mmol, 1.88 mL) under argon at 15° C. The mixture was stirred at 15° C. for 15 min. 6 (4 g, 10.80 mmol) were added. The mixture was stirred at 15° C. for 3 h. Upon completion as monitored by LCMS, the reaction mixture was quenched by addition of H$_2$O (40 mL) and extracted with EA (40 mL*3). The combined organic layers were washed with brine (100 mL), dried over Na$_2$SO$_4$, filtered and concentrated under reduced pressure to give a residue. The residue was purified by flash reverse-phase chromatography (120 g C-18 Column, Eluent of 0~60% ACN/H$_2$O gradient @ 80 mL/min) to give 7 (5.7 g, 61.95% yield) as a colorless oil. ESI-LCMS: 611.2 [M+H]$^+$; $^1$H NMR (400 MHz, CDCl$_3$); δ=9.26 (s, 1H), 7.50 (d, J=8.1 Hz, 1H), 7.01 (s, 2H), 5.95 (d, J=2.7 Hz, 1H), 5.80 (dd, J=2.1, 8.2 Hz, 1H), 4.89-4.72 (m, 2H), 4.66 (d, J=7.2 Hz, 1H), 4.09-4.04 (m, 1H), 3.77 (dd, J=2.7, 4.9 Hz, 1H), 3.62 (d, J=3.1 Hz, 1H), 3.58 (d, J=3.1 Hz, 1H), 3.52 (s, 3H), 1.36 (td, J=1.7, 6.1 Hz, 12H), 0.92 (s, 9H), 0.12 (s, 6H); $^{31}$P NMR (162 MHz, CDCl$_3$) δ=9.02

Preparation of (8): To a mixture of 7 (5.4 g, 8.84 mmol) in THF (80 mL) was added Pd/C (5.4 g, 10% purity) under N$_2$. The suspension was degassed under vacuum and purged with H$_2$ several times. The mixture was stirred under H$_2$ (15 psi) at 20° C. for 1 hr. Upon completion as monitored by LCMS, the reaction mixture was filtered, and the filtrate was concentrated to give 8 (5.12 g, 94.5% yield) as a white solid. ESI-LCMS: 613.3 [M+H]$^+$; H NMR (400 MHz, CD$_3$CN) δ=9.31 (s, 1H), 7.37 (d, J=8.0 Hz, 1H), 5.80-5.69 (m, 2H), 4.87-4.75 (m, 2H), 4.11-4.00 (m, 1H), 3.93-3.85 (m, 1H), 3.80-3.74 (m, 1H), 3.66-3.60 (m, 1H), 3.57-3.52 (m, 1H), 3.49 (s, 3H), 3.46-3.38 (m, 1H), 2.35-2.24 (m, 1H), 2.16-2.03 (m, 1H), 1.89-1.80 (m, 1H), 1.37-1.34 (m, 12H), 0.90 (s, 9H), 0.09 (s, 6H); $^{31}$P NMR (162 MHz, CD$_3$CN) δ=9.41.

Preparation of (9): To a solution of 8 (4.4 g, 7.18 mmol) in THF (7.2 mL) was added TBAF (1 M, 7.18 mL), and the mixture was stirred at 20° C. for 1 hr. Upon completion as monitored by LCMS, the reaction mixture was diluted with H$_2$O (50 mL) and extracted with EA (50 mL*4). The combined organic layers were washed with brine (50 mL), dried over Na$_2$SO$_4$, filtered and concentrated under reduced pressure to give a residue. The residue was purified by flash silica gel chromatography (ISCO®; 40 g SepaFlash® Silica Flash Column, Eluent of 0~5%, MeOH/DCM gradient @ 40 mL/min) to give 9 (3.2 g, 88.50% yield) as a white solid. ESI-LCMS: 499.2 [M+H]$^{+1}$; $^1$H NMR (400 MHz, CD$_3$CN) δ=9.21 (s, 1H), 7.36 (d, J=8.3 Hz, 1H), 5.81-5.72 (m, 2H), 4.88-4.74 (m, 2H), 3.99-3.87 (m, 2H), 3.84 (dd, J=1.9, 5.4 Hz, 1H), 3.66-3.47 (m, 7H), 2.98 (s, 1H), 2.44-2.15 (m, 2H), 1.36 (d, J=6.0 Hz, 12H); $^{31}$P NMR (162 MHz, CD$_3$CN) δ=9.48.

Preparation of (Example 5 monomer): To a mixture of 9 (3.4 g, 6.82 mmol, 1 eq) and 4A MS (3.4 g) in MeCN (50 mL) was added P1 (2.67 g, 8.87 mmol, 2.82 mL, 1.3 eq) at 0° C., followed by addition of 1H-imidazole-4,5-dicarbonitrile (886.05 mg, 7.50 mmol) at 0° C. The mixture was stirred at 20° C. for 2 h. Upon completion as monitored by LCMS, the reaction mixture was quenched by addition of saturated aq. NaHCO$_3$ (50 mL) and diluted with DCM (100 mL). The organic layer was washed with saturated aq. NaHCO$_3$ (50 mL*2), dried over Na$_2$SO$_4$, filtered and concentrated under reduced pressure to give a residue. The residue was purified by prep-HPLC: column: YMC-Triart Prep C18 250*50 mm*10 um; mobile phase: [water (10 mM NH$_4$HCO$_3$)-ACN]; B %: 15% to give a impure product. The impure product was further purified by a flash silica gel column (0% to 5% i-PrOH in DCM with 0.5% TEA) to give Example 5 monomer (2.1 g, 43.18% yield) as a white solid. ESI-LCMS: 721.2 [M+Na]$^+$; H NMR (400 MHz, CD$_3$CN) δ=9.29 (s, 1H), 7.45 (d, J=8.1 Hz, 1H), 5.81 (d, J=4.2 Hz, 1H), 5.65 (d, J=8.1 Hz, 1H), 4.79-4.67 (m, 2H), 4.26-4.05 (m, 2H), 4.00-3.94 (m, 1H), 3.89-3.63 (m, 6H), 3.53-3.33 (m, 5H), 2.77-2.61 (m, 2H), 2.31-2.21 (m, 1H), 2.16-2.07 (m, 1H), 1.33-1.28 (m, 12H), 1.22-1.16 (m, 1H), 1.22-1.16 (m, 11H); $^{31}$P NMR (162 MHz, CD$_3$CN) δ=149.89, 149.78, 10.07, 10.02.

Example 6. Synthesis of 5' End Cap Monomer

Example 6 Monomer Synthesis Scheme

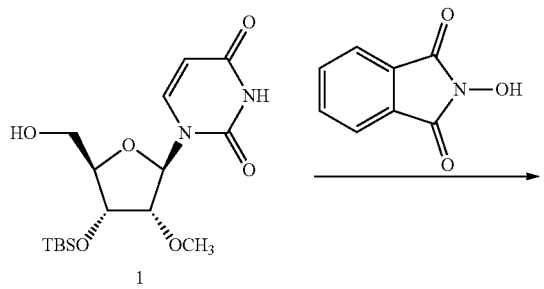

1

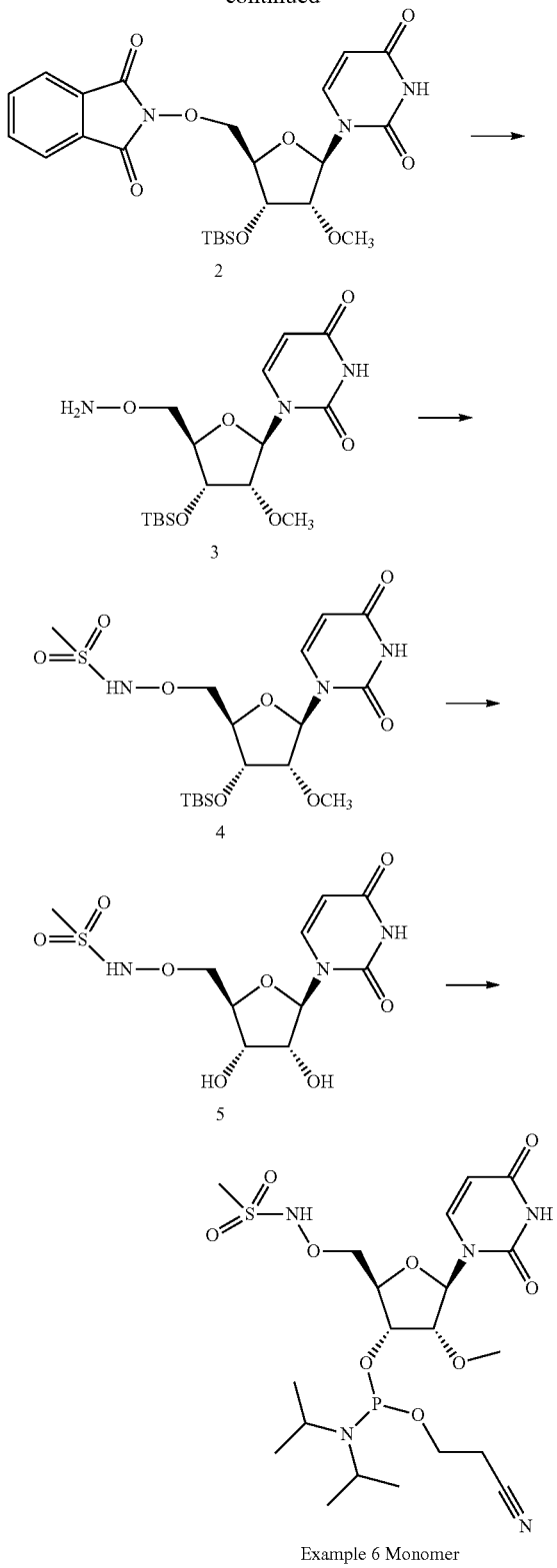

Example 6 Monomer

Preparation of (2): To a solution of 1 (5 g, 13.42 mmol) in DMF (50 mL) were added PPh₃ (4.58 g, 17.45 mmol) and 2-hydroxyisoindoline-1,3-dione (2.85 g, 17.45 mmol), followed by a solution of DIAD (4.07 g, 20.13 mmol, 3.91 mL) in DMF (10 mL) dropwise at 15° C. The resulting solution was stirred at 15° C. for 18 hr. The reaction mixture was then diluted with DCM (50 mL), washed with H₂O (60 mL*3) and brine (30 mL), dried over Na₂SO₄, filtered and evaporated to give a residue. The residue was then triturated with EtOH (55 mL) for 30 min, and the collected white powder was washed with EtOH (10 mL*2) and dried to give 2 (12.2 g, 85.16% yield) as a white powder (the reaction was set up in two batches and combined) ESI-LCMS: 518.1 [M+H]⁺.

Preparation of (3): 2 (6 g, 11.59 mmol) was suspended in MeOH (50 mL), and then NH₂NH₂.H₂O (3.48 g, 34.74 mmol, 3.38 mL, 50% purity) was added dropwise at 20° C. The reaction mixture was stirred at 20° C. for 4 hr. Upon completion, the reaction mixture was diluted with EA (20 mL) and washed with NaHCO₃ (10 mL*2) and brine (10 mL). The combined organic layers were then dried over Na₂SO₄, filtered and evaporated to give 3 (8.3 g, 92.5% yield) as a white powder. (The reaction was set up in two batches and combined). ESI-LCMS: 388.0 [M+H]⁺; ¹H NMR (400 MHz, DMSO-d₆) δ=11.39 (br s, 1H), 7.72 (d, J=8.1 Hz, 1H), 6.24-6.09 (m, 2H), 5.80 (d, J=4.9 Hz, 1H), 5.67 (d, J=8.1 Hz, 1H), 4.26 (t, J=4.9 Hz, 1H), 4.03-3.89 (m, 1H), 3.87-3.66 (m, 3H), 3.33 (s, 3H), 0.88 (s, 9H), 0.09 (d, J=1.3 Hz, 6H)

Preparation of (4): To a solution of 3 (7 g, 18.06 mmol) and Py (1.43 g, 18.06 mmol, 1.46 mL) in DCM (130 mL) was added a solution of MsCl (2.48 g, 21.68 mmol, 1.68 mL) in DCM (50 mL) dropwise at −78° C. under N₂. The reaction mixture was allowed to warm to 15° C. in 30 min and stirred at 15° C. for 3 h. The reaction mixture was quenched by addition of ice-water (70 mL) at 0° C., and then extracted with DCM (50 mL*3). The combined organic layers were washed with saturated aq. NaHCO₃ (50 mL) and brine (30 mL), dried over Na₂SO₄, filtered and concentrated under reduced pressure to give a residue. The residue was purified by flash silica gel chromatography (ISCO®; 30 g SepaFlash® Silica Flash Column, Eluent of 0~20% i-PrOH/DCM gradient @ 30 mL/min to give 4 (6.9 g, 77.94% yield) as a white solid. ESI-LCMS: 466.1 [M+H]⁺; ¹H NMR (400 MHz, DMSO-d₆) δ=11.41 (br s, 1H), 10.15 (s, 1H), 7.69 (d, J=8.1 Hz, 1H), 5.80 (d, J=4.4 Hz, 1H), 5.65 (d, J=8.1 Hz, 1H), 4.24 (t, J=5.2 Hz, 1H), 4.16-3.98 (m, 3H), 3.87 (t, J=4.8 Hz, 1H), 3.00 (s, 3H), 2.07 (s, 3H), 0.88 (s, 9H), 0.10 (d, J=1.5 Hz, 6H)

Preparation of (5): To a solution of 4 (6.9 g, 14.82 mmol) in THF (70 mL) was added TBAF (1 M, 16.30 mL) at 15° C. The reaction mixture was stirred at 15° C. for 18 hr, and then evaporated to give a residue. The residue was purified by flash silica gel chromatography (ISCO®; 24 g SepaFlash® Silica Flash Column, Eluent of 0~9% MeOH/Ethyl acetate gradient @ 30 mL/min) to give 5 (1.8 g, 50.8% yield) as a white solid. ESI-LCMS: 352.0 [M+H]⁺; ¹H NMR (400 MHz, DMSO-d₆) δ=11.40 (s, 1H), 10.13 (s, 1H), 7.66 (d, J=8.1 Hz, 1H), 5.83 (d, J=4.9 Hz, 1H), 5.65 (dd, J=1.8, 8.1 Hz, 1H), 5.36 (d, J=6.2 Hz, 1H), 4.13-4.00 (m, 4H), 3.82 (t, J=5.1 Hz, 1H), 3.36 (s, 3H), 3.00 (s, 3H)

Preparation of (Example 6 monomer): To a mixture of 5 (3 g, 8.54 mmol) and DIEA (2.21 g, 17.08 mmol, 2.97 mL) in ACN (90 mL) was added P2 (3.03 g, 12.81 mmol) dropwise at 15° C. The reaction mixture was stirred at 15° C. for 5 h. Upon completion, the reaction mixture was diluted with EA (40 mL) and quenched with 5% NaHCO₃ (20 mL). The organic layer was washed with brine (30 mL), dried over Na₂SO₄, filtered and evaporated to give a residue. The residue was purified by flash silica gel chromatography (ISCO®; 12 g SepaFlash® Silica Flash Column, Eluent of 0~15% i-PrOH/(DCM with 2% TEA) gradient @ 20 mL/min) to Example 6 monomer (2.1 g, 43.93% yield) as a white solid. ESI-LCMS: 552.3 [M+H]$^+$; $^1$H NMR (400 MHz, CD$_3$CN) δ=8.78 (br s, 1H), 7.57 (dd, J=4.6, 8.2 Hz, 1H), 5.97-5.80 (m, 1H), 5.67 (d, J=8.3 Hz, 1H), 4.46-4.11 (m, 4H), 3.95-3.58 (m, 5H), 3.44 (d, J=16.3 Hz, 3H), 3.02 (d, J=7.5 Hz, 3H), 2.73-2.59 (m, 2H), 1.23-1.15 (m, 12H); $^{31}$P NMR (162 MHz, CD$_3$CN) δ=150.30, 150.10

Example 7: Synthesis of 5' End Cap Monomer

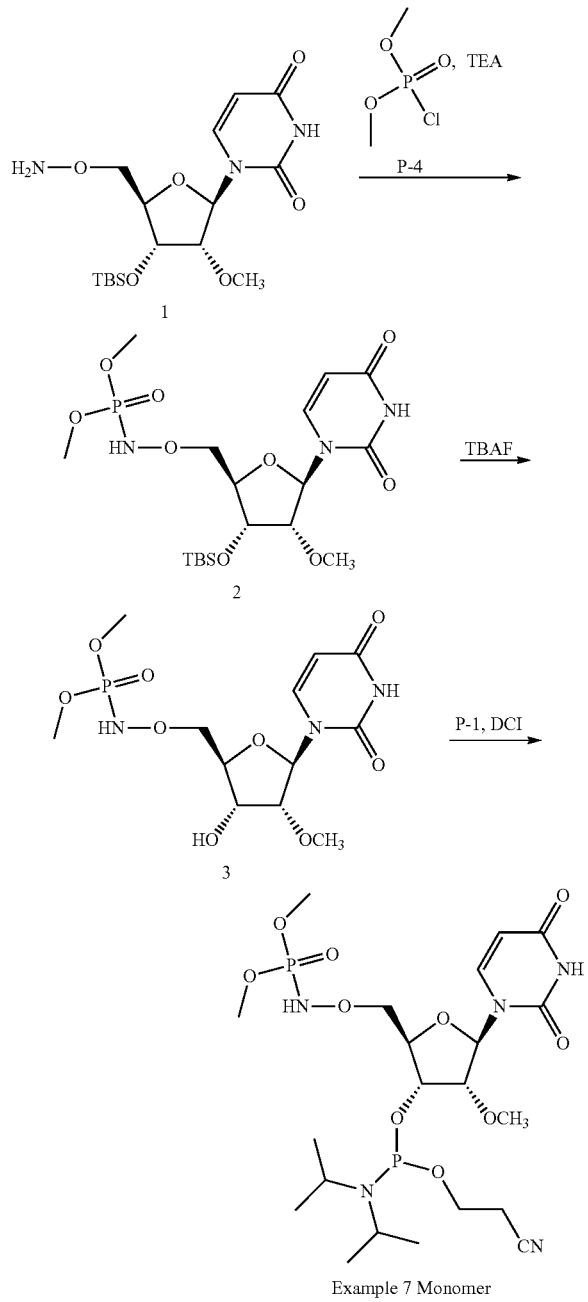

Preparation of (2): To the solution of 1 (5 g, 12.90 mmol) and TEA (1.57 g, 15.48 mmol, 2.16 mL) in DCM (50 mL) was added P-4 (2.24 g, 15.48 mmol, 1.67 mL) in DCM (10 mL) dropwise at 15° C. under N$_2$. The reaction mixture was stirred at 15° C. for 3 h. Upon completion as monitored by LCMS and TLC (PE:EtOAc=0:1), the reaction mixture was concentrated to dryness, diluted with H$_2$O (20 mL), and extracted with EA (50 mL*3). The combined organic layers were washed with brine (30 mL*3), dried over anhydrous Na$_2$SO$_4$, filtered, and the filtrate was concentrated under reduced pressure to give a residue. The residue was purified by flash silica gel chromatography (ISCO®; 40 g SepaFlash® Silica Flash Column, Eluent of 0~95% Ethyl acetate/Petroleum ether gradient @ 60 mL/min) to give 2 (5.3 g, 71.3% yield) as a white solid. ESI-LCMS: 496.1 [M+H]$^+$; H NMR (400 MHz, CDCl$_3$) δ=0.10 (d, J=4.02 Hz, 6H) 0.91 (s, 9H) 3.42-3.54 (m, 3H) 3.65-3.70 (m, 1H) 3.76-3.89 (m, 6H) 4.00 (dd, J=10.92, 2.89 Hz, 1H) 4.08-4.13 (m, 1H) 4.15-4.23 (m, 2H) 5.73 (dd, J=8.28, 2.01 Hz, 1H) 5.84 (d, J=2.76 Hz, 1H) 6.86 (d, J=15.81 Hz, 1H) 7.72 (d, J=8.03 Hz, 1H) 9.10 (s, 1H); $^{31}$P NMR (162 MHz, CD$_3$CN) δ=9.65

Preparation of (3): To a solution of 2 (8.3 g, 16.75 mmol) in THF (50 mL) were added TBAF (1 M, 16.75 mL) and CH$_3$COOH (1.01 g, 16.75 mmol, 957.95 uL). The mixture was stirred at 20° C. for 12 hr. Upon completion as monitored by LCMS, the reaction mixture was concentrated under reduced pressure. The residue was purified by column chromatography (SiO$_2$, PE:EA=0~100%; MeOH/EA=0~10%) to give 3 (5 g, 77.51% yield) as a white solid. ESI-LCMS: 382.1 [M+H]$^+$; $^1$H NMR (400 MHz, CDCl$_3$) δ=3.35 (s, 3H) 3.65 (br d, J=2.76 Hz, 3H) 3.68 (d, J=2.76 Hz, 3H) 3.77 (t, J=5.08 Hz, 1H) 3.84-4.10 (m, 4H) 5.33 (br d, J=5.52 Hz, 1H) 5.62 (d, J=7.77 Hz, 1H) 5.83 (d, J=4.94 Hz, 1H) 7.69 (d, J=7.71 Hz, 1H) 9.08 (d, J=16.81 Hz, 1H) 11.39 (br s, 1H); $^{31}$P NMR (162 MHz, CD$_3$CN) δ=15.41

Preparation of (Example 7 monomer): To a solution of 3 (2 g, 5.25 mmol) and DIPEA (2.03 g, 15.74 mmol, 2.74 mL, 3 eq) in MeCN (21 mL) and pyridine (7 mL) was added P2 (1.86 g, 7.87 mmol) dropwise at 20° C., and the mixture was stirred at 20° C. for 3 hr. Upon completion as monitored by LCMS, the reaction mixture was diluted with water (20 mL) and extracted with EA (50 mL). The combined organic layers were washed with brine (30 mL), dried over anhydrous Na$_2$SO$_4$, filtered, and the filtrate was concentrated under reduced pressure to give a residue. The residue was purified by flash silica gel chromatography (ISCO®; 25 g SepaFlash® Silica Flash Column, Eluent of 0~45% (Ethyl acetate:EtOH=4:1)/Petroleum ether gradient) to give Example 7 monomer (1.2 g, 38.2% yield) as a white solid. ESI-LCMS: 604.1 [M+H]$^+$; $^1$H NMR (400 MHz, CD$_3$CN) δ=1.12-1.24 (m, 12H) 2.61-2.77 (m, 2H) 3.43 (d, J=17.64 Hz, 3H) 3.59-3.69 (m, 2H) 3.71-3.78 (m, 6H) 3.79-4.14 (m, 5H) 4.16-4.28 (m, 1H) 4.29-4.42 (m, 1H) 5.59-5.72 (m, 1H) 5.89 (t, J=4.53 Hz, 1H) 7.48 (br d, J=12.76 Hz, 1H) 7.62-7.74 (m, 1H) 9.26 (br s, 1H); $^{31}$P NMR (162 MHz, CD$_3$CN) δ=150.57, 149.96, 9.87

Example 8: Synthesis of 5' End Cap Monomer

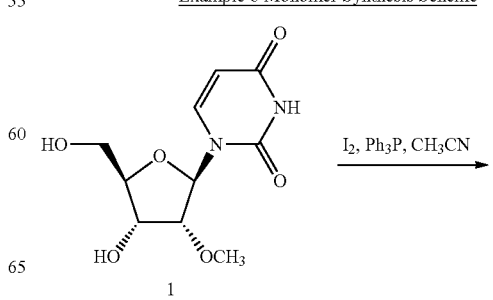

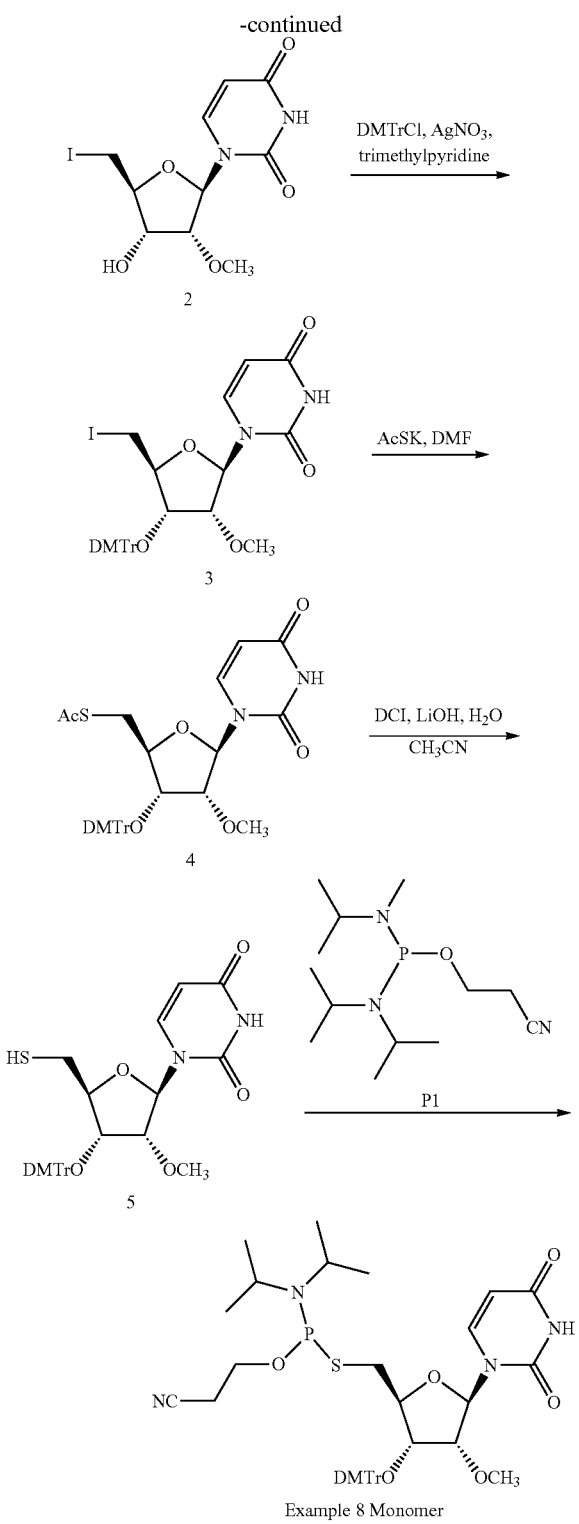

Example 8 Monomer

Preparation of (2): To a solution of 1 (30 g, 101.07 mmol, 87% purity) in CH$_3$CN (1.2 L) and Py (60 mL) were added I$_2$ (33.35 g, 131.40 mmol, 26.47 mL) and PPh$_3$ (37.11 g, 141.50 mmol) in one portion at 10° C. The reaction was stirred at 25° C. for 48 h. Upon completion, the mixture was diluted with saturated aq.Na$_2$S$_2$O$_3$ (300 mL) and saturated aq.NaHCO$_3$ (300 mL), concentrated to remove CH$_3$CN, and extracted with EtOAc (300 mL*3). The combined organic layers were washed with brine (300 mL), dried over Na$_2$SO$_4$, filtered and concentrated under reduced pressure to give a residue. The residue was purified by flash silica gel chromatography (ISCO®; 330 g SepaFlash® Silica Flash Column, Eluent of 0~60% Methanol/Dichloromethane gradient @ 100 mL/min) to give 2 (28.2 g, 72% yield) as a brown solid. ESI-LCMS: 369.1 [M+H]$^+$; H NMR (400 MHz, DMSO-d$_6$) δ=11.43 (s, 1H), 7.68 (d, J=8.1 Hz, 1H), 5.86 (d, J=5.5 Hz, 1H), 5.69 (d, J=8.1 Hz, 1H), 5.46 (d, J=6.0 Hz, 1H), 4.08-3.96 (m, 2H), 3.90-3.81 (m, 1H), 3.60-3.51 (m, 1H), 3.40 (dd, J=6.9, 10.6 Hz, 1H), 3.34 (s, 3H).

Preparation of (3): To the solution of 2 (12 g, 32.6 mmol) in DCM (150 mL) were added AgNO$_3$ (11.07 g, 65.20 mmol), 2,4,6-trimethylpyridine (11.85 g, 97.79 mmol, 12.92 mL), and DMTCl (22.09 g, 65.20 mmol) at 10° C., and the reaction mixture was stirred at 10° C. for 16 hr. Upon completion, the mixture was filtered and the filtrate was concentrated under reduced pressure. The residue was purified by flash silica gel chromatography (ISCO®; 120 g SepaFlash® Silica Flash Column, Eluent of 0~50% Ethyl acetate/Petroleum ethergradient @ 60 mL/min) to give 3 (17 g, 70.78% yield) as a yellow solid. ESI-LCMS: 693.1 [M+Na]$^1$; H NMR (400 MHz, DMSO-d$_6$) δ=11.46 (s, 1H), 7.60 (d, J=8.4 Hz, 1H), 7.49 (d, J=7.2 Hz, 2H), 7.40-7.30 (m, 6H), 7.29-7.23 (m, 1H), 6.93 (d, J=8.8 Hz, 4H), 5.97 (d, J=6.0 Hz, 1H), 5.69 (d, J=8.0 Hz, 1H), 4.05-4.02 (m, 1H), 3.75 (d, J=1.2 Hz, 6H), 3.57 (t, J=5.6 Hz, 1H), 3.27 (s, 4H), 3.06 (t, J=10.4 Hz, 1H), 2.98-2.89 (m, 1H).

Preparation of (4): To a solution of 3 (17 g, 25.35 mmol) in DMF (200 mL) was added AcSK (11.58 g, 101.42 mmol) at 25° C., and the reaction was stirred at 60° C. for 2 hr. The mixture was diluted with H$_2$O (600 mL) and extracted with EtOAc (300 mL*4). The combined organic layers were washed with brine (300 mL), dried over Na$_2$SO$_4$, filtered, and concentrated under reduced pressure to give 4 (15.6 g, crude) as a brown solid, which was used directly without further purification. ESI-LCMS: 641.3 [M+H]$^+$.

Preparation of (5): To a solution of 4 (15.6 g, 25.21 mmol) in CH$_3$CN (200 mL) were added DTT (11.67 g, 75.64 mmol, 11.22 mL) and LiOH.H$_2$O (1.06 g, 25.21 mmol) at 10° C. under Ar. The reaction was stirred at 10° C. for 1 hr. The mixture was concentrated under reduced pressure to remove CH$_3$CN, and the residue was diluted with H$_2$O (400 mL) and extracted with EtOAc (200 mL*3). The combined organic layers were washed with brine (300 mL), dried over Na$_2$SO$_4$, filtered and concentrated under reduced pressure to give a residue. The residue was purified by flash silica gel chromatography (ISCO®; 220 g SepaFlash® Silica Flash Column, Eluent of 0~60% Ethyl acetate/Petroleum ether gradient @ 100 mL/min) to give 5 (8.6 g, 56.78% yield) as a white solid. ESI-LCMS: 599.3 [M+Na]$^+$; $^1$H NMR (400 MHz, DMSO-d$_6$) δ=8.79 (s, 1H), 7.61 (d, J=8.0 Hz, 1H), 7.56-7.46 (m, 2H), 7.45-7.37 (m, 4H), 7.36-7.27 (m, 3H), 6.85 (dd, J=2.8, 8.8 Hz, 4H), 5.85 (d, J=1.3 Hz, 1H), 5.68 (dd, J=2.0, 8.2 Hz, 1H), 4.33-4.29 (m, 1H), 3.91 (dd, J=4.8, 8.2 Hz, 1H), 3.81 (d, J=1.6 Hz, 6H), 3.33 (s, 3H), 2.85-2.80 (m, 1H), 2.67-2.55 (m, 2H), 1.11 (t, J=8.8 Hz, 1H).

Preparation of (Example 8 monomer): To a solution of 5 (6 g, 10.40 mmol) in DCM (120 mL) were added P1 (4.08 g, 13.53 mmol, 4.30 mL) and DCI (1.35 g, 11.45 mmol) in one portion at 10° C. under Ar. The reaction was stirred at 10° C. for 2 hr. The reaction mixture was diluted with saturated aq.NaHCO$_3$ (50 mL) and extracted with DCM (20 mL*3). The combined organic layers were washed with brine (30 mL), dried over Na$_2$SO$_4$, filtered and concentrated under reduced pressure to give a residue. The residue was purified by prep-HPLC (column: YMC-Triart Prep C18

250*50 mm*10 um; mobile phase: [water (10 mM NH$_4$HCO$_3$)-ACN]; B %: 35%-81%, 20 min) to give Example 8 monomer (3.54 g, 43.36% yield) as a yellow solid. ESI-LCMS: 776.4 [M+H]$^+$; $^1$H NMR (400 MHz, DMSO-d$_6$) δ=7.65-7.38 (m, 7H), 7.37-7.22 (m, 3H), 6.90 (d, J=8.4 Hz, 4H), 5.92 (s, 1H), 5.66 (t, J=8.2 Hz, 1H), 4.13 (d, J=4.0 Hz, 1H), 4.00-3.88 (m, 1H), 3.87-3.59 (m, 10H), 3.33 (d, J=5.8 Hz, 3H), 3.12-2.94 (m, 1H), 2.78-2.60 (m, 3H), 2.55-2.48 (m, 1H), 1.36-0.98 (m, 12H); $^{31}$P NMR (162 MHz, DMSO-d$_6$) δ=162.69.

Example 9: Synthesis of 5' End Cap Monomer

Example 9 Monomer Synthesis Scheme

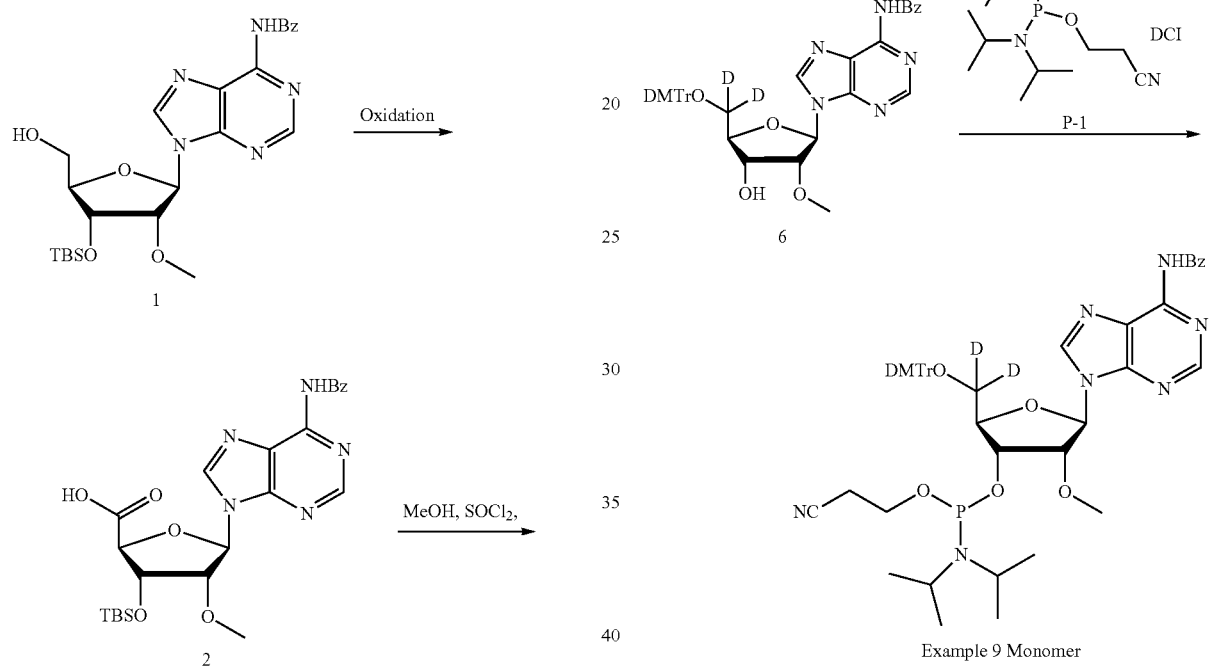

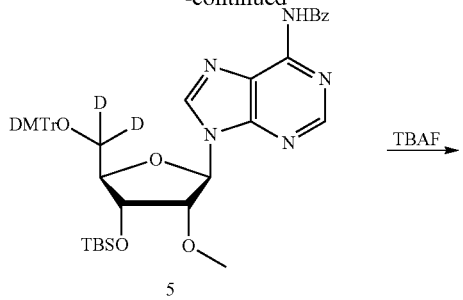

Preparation of (2): To a solution of 1 (22.6 g, 45.23 mmol) in DCM (500 mL) and H$_2$O (125 mL) were added TEMPO (6.40 g, 40.71 mmol) and DIB (29.14 g, 90.47 mmol) at 0° C. The mixture was stirred at 20° C. for 20 h. Upon completion as monitored by LCMS, saturated aq. NaHCO$_3$ was added to the mixture to adjust pH>8. The mixture was diluted with H$_2$O (200 mL) and washed with DCM (100 mL*3). The aqueous layer was collected, adjusted to pH<5 by HCl (4 M), and extracted with DCM (200 mL*3). The combined organic layers were washed with brine (300 mL), dried over Na$_2$SO$_4$, filtered, and concentrated under reduced pressure to give 2 (17.5 g, 68.55% yield) as a yellow solid. ESI-LCMS: 514.2 [M+H]$^+$; $^1$H NMR (400 MHz, DMSO-d$_6$) δ=11.27 (s, 1H), 8.86 (s, 1H), 8.78 (s, 1H), 8.06 (d, J=7.5 Hz, 2H), 7.68-7.62 (m, 1H), 7.59-7.52 (m, 2H), 6.28 (d, J=6.8 Hz, 1H), 4.82-4.76 (m, 1H), 4.54 (dd, J=4.1, 6.7 Hz, 1H), 4.48 (d, J=1.8 Hz, 1H), 3.32 (s, 3H), 0.94 (s, 9H), 0.18 (d, J=4.8 Hz, 6H).

Preparation of (3): To a solution of 2 (9.3 g, 18.11 mmol) in MeOH (20 mL) was added SOCl$_2$ (3.23 g, 27.16 mmol, 1.97 mL) dropwise at 0° C. The mixture was stirred at 20° C. for 0.5 hr. Upon completion as monitored by LCMS, the reaction mixture was quenched by addition of saturated aq. NaHCO$_3$ (80 mL) and concentrated under reduced pressure to remove MeOH. The aqueous layer was extracted with DCM (80 mL*3). The combined organic layers were washed with brine (200 mL), dried over $Na_2SO_4$, filtered and concentrated under reduced pressure to give a residue. The residue was purified by flash silica gel chromatography (ISCO®; 120 g SepaFlash® Silica Flash Column, Eluent of 0~5%, MeOH/DCM gradient @ 85 mL/min) to give 3 (5.8 g, 60% yield) as a yellow solid. ESI-LCMS: 528.3 [M+H]+; $^1$H NMR (400 MHz, DMSO-$d_6$) δ=11.28 (s, 1H), 8.79 (d, J=7.3 Hz, 2H), 8.06 (d, J=7.5 Hz, 2H), 7.68-7.62 (m, 1H), 7.60-7.53 (m, 2H), 6.28 (d, J=6.6 Hz, 1H), 4.87 (dd, J=2.4, 4.0 Hz, 1H), 4.61 (dd, J=4.3, 6.5 Hz, 1H), 4.57 (d, J=2.2 Hz, 1H), 3.75 (s, 3H), 3.32 (s, 3H), 0.94 (s, 9H), 0.17 (d, J=2.2 Hz, 6H).

Preparation of (4): To a mixture of 3 (5.7 g, 10.80 mmol) in $CD_3OD$ (120 mL) was added $NaBD_4$ (1.63 g, 43.21 mmol) in portions at 0° C., and the mixture was stirred at 20° C. for 1 hr. Upon completion as monitored by LCMS, the reaction mixture was neutralized by AcOH (~10 mL) and concentrated under reduced pressure to give a residue. The residue was purified by flash silica gel chromatography (ISCO®; 40 g SepaFlash® Silica Flash Column, Eluent of 0-5%, MeOH/DCM gradient @ 40 mL/min) to give 4 (4.15 g, 7.61 mmol, 70.45% yield) as a yellow solid. ESI-LCMS: 502.2 [M+H]+; $^1$H NMR (400 MHz, DMSO-$d_6$) δ=11.23 (s, 1H), 8.76 (s, 2H), 8.04 (d, J=7.3 Hz, 2H), 7.69-7.62 (m, 1H), 7.60-7.52 (m, 2H), 6.14 (d, J=6.0 Hz, 1H), 5.18 (s, 1H), 4.60-4.51 (m, 2H), 3.98 (d, J=3.0 Hz, 1H), 3.32 (s, 3H), 0.92 (s, 9H), 0.13 (d, J=1.5 Hz, 6H).

Preparation of (5): To a solution of 4 (4.85 g, 9.67 mmol) in pyridine (50 mL) was added DMTrCl (5.90 g, 17.40 mmol) at 25° C. and the mixture was stirred for 2 hr. Upon completion as monitored by LCMS, the reaction mixture was concentrated under reduced pressure to remove pyridine. The residue was diluted with EtOAc (150 mL) and washed with $H_2O$ (50 mL*3), dried over $Na_2SO_4$, filtered and concentrated under reduced pressure to give a residue. The residue was purified by flash silica gel chromatography (ISCO®; 80 g SepaFlash® Silica Flash Column, Eluent of 0~70%, EA/PE gradient @ 60 mL/min) to give 5 (6.6 g, 84.06% yield) as a yellow solid. ESI-LCMS: 804.3[M+H]+, $^1$H NMR (400 MHz, DMSO-$d_6$) δ=11.22 (s, 1H), 8.68 (d, J=11.0 Hz, 2H), 8.03 (d, J=7.3 Hz, 2H), 7.68-7.60 (m, 1H), 7.58-7.49 (m, 2H), 7.37-7.30 (m, 2H), 7.27-7.16 (m, 7H), 6.88-6.79 (m, 4H), 6.17 (d, J=4.2 Hz, 1H), 4.72 (t, J=5.0 Hz, 1H), 4.60 (t, J=4.5 Hz, 1H), 4.03-3.98 (m, 1H), 3.71 (s, 6H), 0.83 (s, 9H), 0.12-0.03 (m, 6H).

Preparation of (6): To a solution of 5 (6.6 g, 8.21 mmol) in THF (16 mL) was added TBAF (1 M, 8.21 mL), and the mixture was stirred at 20° C. for 2 hr. Upon completion as monitored by LCMS, the reaction mixture was diluted with EA (150 mL) and washed with $H_2O$ (50 mL*3). The organic layer was washed with brine (150 mL), dried over $Na_2SO_4$, filtered and concentrated under reduced pressure to give a residue. The residue was purified by flash silica gel chromatography (ISCO®; 80 g SepaFlash® Silica Flash Column, Eluent of 10-100%, EA/PE gradient @ 30 mL/min) to give 6 (5.4 g, 94.4% yield) as a yellow solid. ESI-LCMS: 690.3 [M+H]+; $^1$H NMR (400 MHz, DMSO-$d_6$) δ=11.24 (s, 1H), 8.69 (s, 1H), 8.62 (s, 1H), 8.05 (d, J=7.3 Hz, 2H), 7.69-7.62 (m, 1H), 7.60-7.52 (m, 2H), 7.40-7.33 (m, 2H), 7.30-7.18 (m, 7H), 6.84 (dd, J=5.9, 8.9 Hz, 4H), 6.19 (d, J=4.8 Hz, 1H), 5.36 (d, J=6.0 Hz, 1H), 4.59-4.52 (m, 1H), 4.48 (q, J=5.1 Hz, 1H), 4.11 (d, J=4.8 Hz, 1H), 3.72 (d, J=1.0 Hz, 6H), 3.40 (s, 3H).

Preparation of (Example 9 monomer): To a solution of 6 (8.0 g, 11.60 mmol) in MeCN (150 mL) was added P-1 (4.54 g, 15.08 mmol, 4.79 mL) at 0° C., followed by DCI (1.51 g, 12.76 mmol) in one portion. The mixture was warmed to 20° C. and stirred for 2 h. Upon completion as monitored by LCMS, the reaction mixture was quenched by addition of saturated aq. $NaHCO_3$ (50 mL) and diluted with DCM (250 mL). The organic layer was washed with saturated aq.$NaHCO_3$ (50 mL*2), dried over $Na_2SO_4$, filtered and concentrated under reduced pressure. The residue was purified by a flash silica gel column (0% to 60% EA in PE contain 0.5% TEA) to give Example 9 monomer (5.75 g, 55.37% yield, 99.4% purity) as a white solid. ESI-LCMS: 890.4 [M+H]+; $^1$H NMR (400 MHz, $CD_3CN$) δ=9.55 (s, 1H), 8.63-8.51 (m, 1H), 8.34-8.24 (m, 1H), 7.98 (br d, J=7.5 Hz, 2H), 7.65-7.55 (m, 1H), 7.53-7.46 (m, 2H), 7.44-7.37 (m, 2H), 7.32-7.17 (m, 7H), 6.84-6.77 (m, 4H), 6.14 (d, J=4.3 Hz, 1H), 4.84-4.73 (m, 1H), 4.72-4.65 (m, 1H), 4.34-4.27 (m, 1H), 3.91-3.61 (m, 9H), 3.50-3.43 (m, 3H), 2.72-2.61 (m, 1H), 2.50 (t, J=6.0 Hz, 1H), 1.21-1.15 (m, 10H), 1.09 (d, J=6.8 Hz, 2H); $^{31}$P NMR (162 MHz, $CD_3CN$) δ=150.01, 149.65

Example 10: Synthesis of 5' End Cap Monomer

Example 10 Monomer Synthesis Scheme

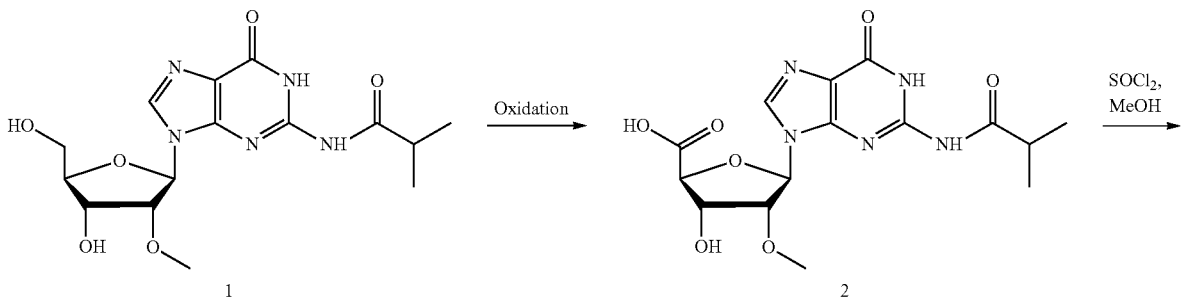

-continued

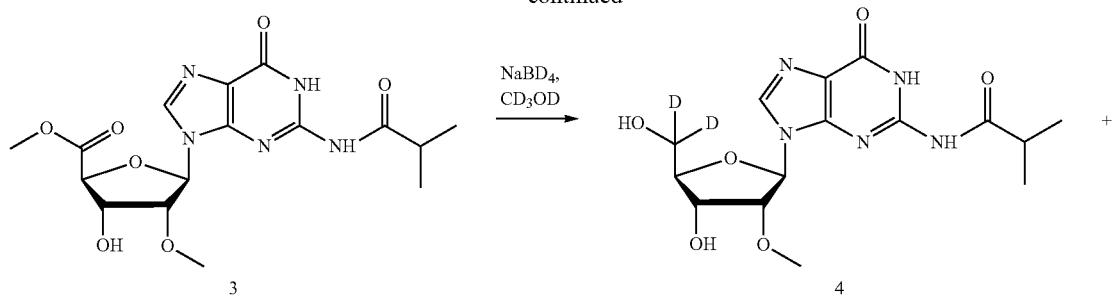

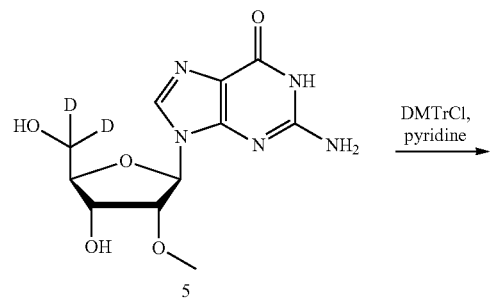

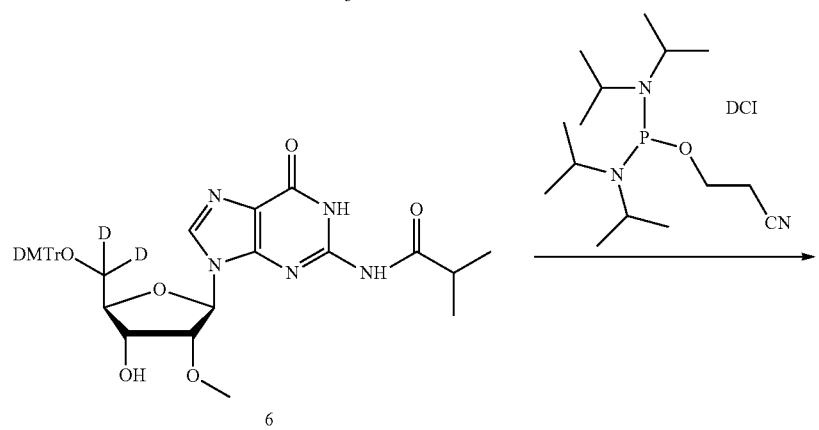

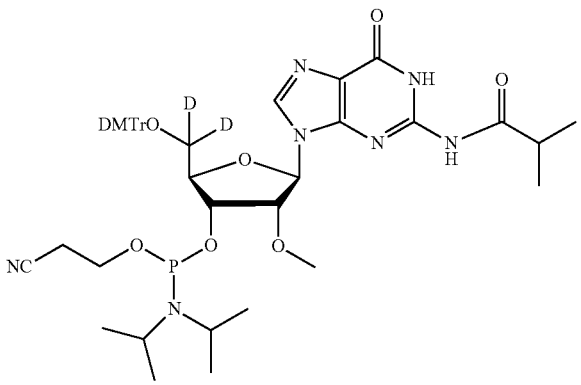

Example 10 Monomer

Preparation of (2): To a solution of 1 (10 g, 27.22 mmol) in CH$_3$CN (200 mL) and H$_2$O (50 mL) were added TEMPO (3.85 g, 24.50 mmol) and DIB (17.54 g, 54.44 mmol). The mixture was stirred at 25° C. for 12 h. Upon completion as monitored by LCMS, the reaction mixture was concentrated under reduced pressure to give a residue. The residue was triturated with EtOAc (600 mL) for 30 min. The resulting suspension was filtered and the collected solid was washed with EtOAc (300 mL*2) to give 2 (20.09 g, 91.5% yield) as a white solid. ESI-LCMS: 382.0 [M+H]$^+$.

Preparation of (3): To a solution of 2 (6 g, 15.73 mmol) in MeOH (100 mL) was added SOCl$_2$ (2.81 g, 23.60 mmol, 1.71 mL) dropwise at 0° C. The mixture was stirred at 25° C. for 12 h. Upon completion as monitored by LCMS, the reaction mixture was quenched by addition of NaHCO₃ (4 g) and stirred at 25° C. for 30 min. The reaction mixture was filtered and the filtrate was concentrated under reduced pressure to give 3 (18.8 g, 95.6% yield) as a white solid. The crude product was used for the next step without further purification. (The reaction was set up in parallel 3 batches and combined). ESI-LCMS: 396.1 [M+H]⁺; ¹H NMR (400 MHz, DMSO-d₆) δ=12.26-11.57 (m, 2H), 8.42-8.06 (m, 1H), 6.14-5.68 (m, 2H), 4.56 (s, 2H), 4.33 (dd, J=4.0, 7.3 Hz, 1H), 3.77 (m, 3H), 3.30 (s, 3H), 2.81-2.69 (m, 1H), 1.11 (s, 6H)

Preparation of (4 & 5): To a mixture of 3 (10.1 g, 25.55 mmol) in CD₃OD (120 mL) was added NaBD₄ (3.29 g, 86.86 mmol, 3.4 eq) in portions at 0° C. The mixture was stirred at 25° C. for 1 h. Upon completion as monitored by LCMS, the reaction mixture was neutralized with AcOH (~15 mL) and concentrated under reduced pressure to give a residue. The residue was purified by flash silica gel chromatography (ISCO®; 120 g SepaFlash® Silica Flash Column, Eluent of 0~7.4%, MeOH/DCM gradient @ 80 mL/min) to give 4 (2.98 g, 6.88 mmol, 27% yield) as a yellow solid. ESI-LCMS: 370.1[M+H]⁺ and 5 (10.9 g, crude) as a yellow solid. ESI-LCMS: 300.1[M+H]⁺; ¹H NMR (400 MHz, CD₃OD) δ=7.85 (s, 1H), 5.87 (d, J=6.0 Hz, 1H), 4.46-4.39 (m, 1H), 4.34 (t, J=5.4 Hz, 1H), 4.08 (d, J=3.1 Hz, 1H), 3.49-3.38 (m, 4H)

Preparation of 6: To a solution of 4 (1.9 g, 4.58 mmol, 85.7% purity) in pyridine (19 mL) was added DMTrCl (2.02 g, 5.96 mmol). The mixture was stirred at 25° C. for 2 h under N₂. Upon completion as monitored by LCMS, the reaction mixture was quenched by MeOH (10 mL) and concentrated under reduce pressure to give a residue. The residue was diluted with H₂O (10 mL*3) and extracted with EA (20 mL*3). The combined organic layers were washed with brine (20 mL), dried over anhydrous Na₂SO₄, filtered and concentrated under reduce pressure to give a residue. The residue was purified by flash silica gel chromatography (ISCO®; 25 g SepaFlash® Silica Flash Column, Eluent of 0~77%, PE: (EA with 10% EtOH): 1% TEA@ 35 mL/min) to give 6 (2.6 g, 81.71% yield, 96.71% purity) as a white foam. ESI-LCMS: 672.2 [M+H]⁺; ¹H NMR (400 MHz, CDCl₃) δ=12.02 (s, 1H), 7.96 (s, 1H), 7.83 (s, 1H), 7.51 (d, J=7.4 Hz, 2H), 7.37 (d, J=8.6 Hz, 4H), 7.25-7.17 (m, 2H), 6.80 (t, J=8.4 Hz, 4H), 5.88 (d, J=6.3 Hz, 1H), 4.69 (t, J=5.7 Hz, 1H), 4.64 (s, 1H), 4.54 (s, 1H), 4.19 (d, J=2.9 Hz, 1H), 3.77 (d, J=4.5 Hz, 6H), 3.60-3.38 (m, 3H), 2.81 (s, 1H), 1.81 (td, J=6.9, 13.7 Hz, 1H), 0.97 (d, J=6.8 Hz, 3H), 0.80 (d, J=6.9 Hz, 3H)

Preparation of Example 10 monomer: To a solution of 6 (8.4 g, 12.5 mmol) in MeCN (80 mL) was added P-1 (4.9 g, 16.26 mmol, 5.16 mL) at 0° C., followed by addition of DCI (1.624 g, 13.76 mmol) in one portion at 0° C. under Ar. The mixture was stirred at 25° C. for 2 h. Upon completion as monitored by LCMS, the reaction mixture was quenched with saturated aq.NaHCO₃ (20 mL) and extracted with DCM (50 mL*2). The combined organic layers were dried over anhydrous Na₂SO₄, filtered and concentrated under reduce pressure to give a residue. The residue was purified by flash silica gel chromatography (ISCO®; 40 g Sepa-Flash® Silica Flash Column, Eluent of 0~52% PE:EA (10% EtOH): 5% TEA, @ 80 mL/min) to give Example 10 monomer (3.4 g, 72.1% yield) as a white foam. ESI-LCMS: 872.4 [M+H]⁺; ¹H NMR (400 MHz, CD₃CN) δ=12.46-11.07 (m, 1H), 9.29 (s, 1H), 7.84 (d, J=14.6 Hz, 1H), 7.42 (t, J=6.9 Hz, 2H), 7.34-7.17 (m, 7H), 6.85-6.77 (m, 4H), 5.95-5.77 (m, 1H), 4.56-4.40 (m, 2H), 4.24 (dd, J=4.0, 13.3 Hz, 1H), 3.72 (d, J=2.0 Hz, 7H), 3.66-3.53 (m, 3H), 3.42 (d, J=11.8 Hz, 3H), 2.69-2.61 (m, 1H), 2.60-2.42 (m, 2H), 1.16-1.00 (m, 18H); ³¹P NMR (162 MHz, CD₃CN) δ=149.975, 149.9

Example 11: Synthesis of 5' End Cap Monomer

Example 11 Monomer Synthesis Scheme

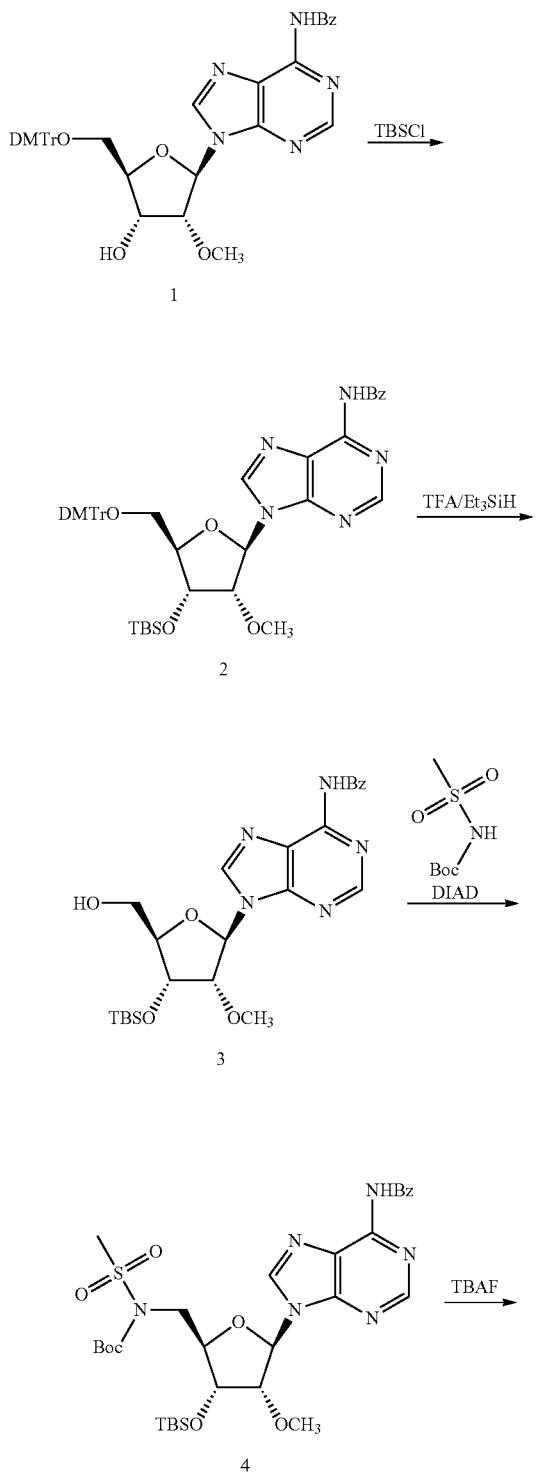

-continued

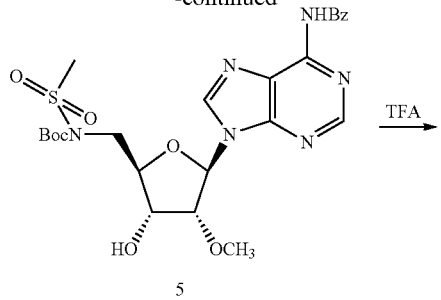

5

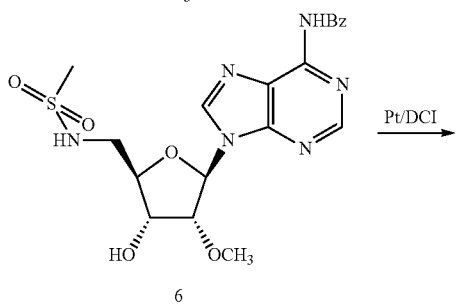

6

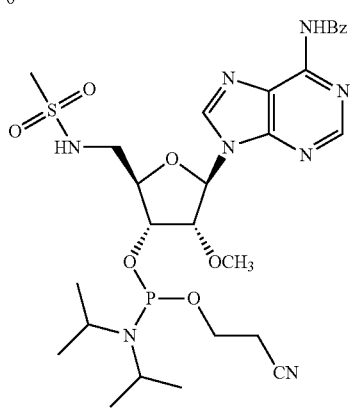

Example 11 Monomer

Preparation of (2): To a solution of 1 (40 g, 58.16 mmol) in DMF (60 mL) were added imidazole (11.88 g, 174.48 mmol), NaI (13.08 g, 87.24 mmol), and TB SCI (17.52 g, 116.32 mmol) at 20° C. in one portion. The reaction mixture was stirred at 20° C. for 12 h. Upon completion, the mixture was diluted with EA (200 mL). The organic layer was washed with brine/water (80 mL/80 mL*4), dried over $Na_2SO_4$, filtered and evaporated to give 2 (50.8 g, crude) as yellow solid. ESI-LCMS: 802.3 $[M+H]^+$ Preparation of (3): To a solution of 2 (8.4 g, 10.47 mmol) in DCM (120 mL) were added $Et_3SiH$ (3.06 g, 26.3 mmol, 4.2 mL) and TFA (1.29 g, 0.84 mL) dropwise at 0° C. The reaction mixture was stirred at 20° C. for 2 h. The reaction mixture was washed with saturated aq.$NaHCO_3$ (15 mL) and brine (80 mL). The organic layer was dried over $Na_2SO_4$, filtered and evaporated. The residue was purified by flash silica gel chromatography (ISCO®; 80 g SepaFlash® Silica Flash Column, Eluent of 0~83% EA/PE gradient @ 80 mL/min) to give 3 (2.92 g, 55.8% yield) as a white solid. ESI-LCMS: 500.2 $[M+H]^+$; $^1H$ NMR (400 MHz, $CDCl_3$) δ=8.79 (s, 1H), 8.14 (s, 1H), 8.02 (d, J=7.6 Hz, 2H), 7.64-7.58 (m, 1H), 7.56-7.49 (m, 2H), 5.98-5.93 (m, 1H), 4.63-4.56 (m, 2H), 4.23 (s, 1H), 3.98 (dd, J=1.5, 13.1 Hz, 1H), 3.75 (dd, J=1.5, 13.1 Hz, 1H), 3.28 (s, 3H), 2.06-1.99 (m, 1H), 1.00-0.90 (m, 9H), 0.15 (d, J=7.0 Hz, 6H).

Preparation of (4): 3 (6 g, 12.01 mmol) and tert-butyl N-methylsulfonylcarbamate (3.52 g, 18.01 mmol) were co-evaporated with toluene (50 mL), dissolved in dry THF (100 mL), and cooled to 0° C. $PPh_3$ (9.45 g, 36.03 mmol) was then added, followed by dropwise addition of DIAD (7.28 g, 36.03 mmol, 7.00 mL) in dry THF (30 mL). The reaction mixture was stirred at 20° C. for 18 h. Upon completion, the reaction mixture was then diluted with DCM (100 mL) and washed with water (70 mL) and brine (70 mL), dried over $Na_2SO_4$, filtered and evaporated to give a residue. The residue was purified by flash silica gel chromatography (ISCO®; 80 g SepaFlash® Silica Flash Column, Eluent of 0-100% Ethyl acetate/Petroleum ether gradient @ 60 mL/min) followed by reverse-phase HPLC (0.1% $NH_3.H_2O$ condition, eluent at 74%) to give 4 (2.88 g, 25% yield) as a white solid. ESI-LCMS: 677.1 $[M+H]^+$; $^1H$ NMR (400 MHz, $CDCl_3$) δ=9.24 (s, 1H), 8.84 (s, 1H), 8.36 (s, 1H), 8.05 (br d, J=7.3 Hz, 2H), 7.66-7.42 (m, 4H), 6.16 (d, J=5.0 Hz, 1H), 4.52 (br t, J=4.5 Hz, 1H), 4.25-4.10 (m, 1H), 3.97 (br dd, J=8.0, 14.8 Hz, 1H), 3.48 (s, 3H), 3.27 (s, 3H), 1.54 (s, 9H), 0.95 (s, 9H), 0.14 (d, J=0.8 Hz, 6H).

Preparation of (5): To a solution of 4 (2.8 g, 4.14 mmol) in THF (20 mL) was added TBAF (4 M, 1.03 mL) and the mixture was stirred at 20° C. for 12 h. The reaction mixture was then evaporated. The residue was purified by flash silica gel chromatography (ISCO®; 12 g SepaFlash® Silica Flash Column, Eluent of 0~6% MeOH/ethyl acetate gradient @ 20 mL/min) to give 5 (2.1 g, 83.92% yield) as a white solid. ESI-LCMS: 563.1$[M+H]^+$; $^1H$ NMR (400 MHz, $CDCl_3$) δ=8.85-8.77 (m, 1H), 8.38 (s, 1H), 8.11-7.99 (m, 2H), 7.64-7.50 (m, 4H), 6.19 (d, J=2.8 Hz, 1H), 4.36-4.33 (m, 1H), 4.29 (br d, J=4.3 Hz, 1H), 4.22-4.02 (m, 2H), 3.65-3.59 (m, 3H), 3.28 (s, 3H), 1.54 (s, 9H).

Preparation of (6): To a solution of 5 (2.1 g, 3.73 mmol) in DCM (20 mL) was added TFA (7.70 g, 67.53 mmol, 5 mL) at 0° C. The reaction mixture was stirred at 20° C. for 24 h. Upon completion, the reaction was quenched with saturated aq. $NaHCO_3$ to reach pH 7. The organic layer was dried over $Na_2SO_4$, filtered, and evaporated at low pressure. The residue was purified by flash silica gel chromatography (ISCO®; 12 g SepaFlash® Silica Flash Column, Eluent of 0~7% DCM/MeOH gradient @ 20 mL/min) to give 1.6 g (impure, 75% LCMS purity), followed by prep-HPLC [FA condition, column: Boston Uni C18 40*150*5 um; mobile phase: [water (0.225% FA)-ACN]; B %: 8%-38%, 7.7 min.] to give 6 (1.04 g, 63.7% yield) as a white solid. ESI-LCMS: 485.0 $[M+Na]^+$; $^1H$ NMR (400 MHz, DMSO-$d_6$) δ=11.27-11.21 (m, 1H), 8.77 (s, 1H), 8.74 (s, 1H), 8.05 (d, J=7.3 Hz, 2H), 7.68-7.62 (m, 1H), 7.59-7.53 (m, 2H), 7.39 (t, J=6.3 Hz, 1H), 6.16 (d, J=6.0 Hz, 1H), 5.48 (d, J=5.5 Hz, 1H), 4.55 (t, J=5.5 Hz, 1H), 4.43-4.37 (m, 1H), 4.08-4.02 (m, 1H), 3.41-3.36 (m, 1H), 3.35 (s, 3H), 3.31-3.22 (m, 1H), 2.91 (s, 3H).

Preparation of (Example 11 monomer): To a solution of 6 (1 g, 2.16 mmol) in DCM (30 mL) was added P1 (977.58 mg, 3.24 mmol, 1.03 mL), followed by DCI (306.43 mg, 2.59 mmol) at 0° C. in one portion under Ar atmosphere. The mixture was degassed and purged with Ar for 3 times, warmed to 20° C., and stirred for 2 hr under Ar atmosphere. Upon completion as monitored by LCMS and TLC (PE: EtOAc=4:1), the reaction mixture was diluted with sat.aq. $NaHCO_3$ (30 mL) and extracted with DCM (50 mL*2). The combined organic layers were dried over anhydrous $Na_2SO_4$, filtered, and the filtrate was concentrated under reduced pressure to give a residue. The crude product was purified by reversed-phase HPLC (40 g C18 column: neutral condition, Eluent of 0~57% of 0.3% $NH_4HCO_3$ in $H_2O$/

CH₃CN ether gradient @ 35 mL/min) to give Example 11 monomer (0.49 g, 33.7% yield) as a white solid. ESI-LCMS: 663.1[M+H]$^+$; $^1$H NMR (400 MHz, CD₃CN) δ=1.19-1.29 (m, 12H) 2.71 (q, J=5.77 Hz, 2H) 2.94 (d, J=6.27 Hz, 3H) 3.35 (d, J=15.56 Hz, 3H) 3.40-3.52 (m, 2H) 3.61-3.97 (m, 4H) 4.23-4.45 (m, 1H) 4.55-4.74 (m, 2H) 6.02 (dd, J=10.67, 6.40 Hz, 1H) 7.25 (br s, 1H) 7.47-7.57 (m, 2H) 7.59-7.68 (m, 1H) 8.01 (d, J=7.78 Hz, 2H) 8.28 (s, 1H) 8.66 (s, 1H) 9.69 (br s, 1H); $^{31}$P NMR (162 MHz, CD₃CN) δ=150.92, 149.78.

Example 12. Synthesis of 5'-Stabilized End Cap Modified Oligonucleotides

This example provides an exemplary method for synthesizing the siNAs comprising a 5'-stabilized end caps disclosed herein. The 5'-stabilized end cap and/or deuterated phosphoramidites were dissolved in anhydrous acetonitrile and oligonucleotide synthesis was performed on a Expedite 8909 Synthesizer using standard phosphoramidite chemistry. An extended coupling (12 minutes) of 0.12 M solution of phosphoramidite in anhydrous CH₃CN in the presence of Benzyl-thio-tetrazole (BTT) activator to a solid bound oligonucleotide followed by standard capping, oxidation and sulfurization produced modified oligonucleotides. The 0.02 M I2, THF:Pyridine; Water 7:2:1 was used as an oxidizing agent, while DDTT (dimethylamino-methylidene)amino)-3H-1,2,4-dithiazaoline-3-thione was used as the sulfur-transfer agent for the synthesis of oligoribonucleotide with a phosphorothioate backbone. The stepwise coupling efficiency of all modified phosphoramidites was achieved around 98%. After synthesis the solid support was heated with aqueous ammonia (28%) solution at 45° C. for 16 h or 0.05 M K₂CO₃ in methanol was used to deprotect the base labile protecting groups. The crude oligonucleotides were precipitated with isopropanol and centrifuged (Eppendorf 5810R, 3000 g, 4° C., 15 min) to obtain a pellet. The crude product was then purified using ion exchange chromatography (TSK gel column, 20 mM NaH₂PO₄, 10% CH₃CN, 1 M NaBr, gradient 20-60% B over 20 column volumes) and fractions were analyzed by ion change chromatography on an HPLC. Pure fractions were pooled and desalted by Sephadex G-25 column and evaporated to dryness. The purity and molecular weight were determined by HPLC analysis and ESI-MS analysis. Single strand RNA oligonucleotides (sense and antisense strand) were annealed (1:1 by molar equivalents) at 90° C. for 3 min followed by RT 40 min) to produce the duplexes.

Example 13. siNA Activity Assays

This example provides exemplary methods for testing the activity of the siNAs disclosed herein.

In Vitro Assay:

*Homo sapiens* HepG2.2.15 cells were cultured in Dulbecco's Modified Eagle's Medium (DMEM) (ATCC 30-2002) supplemented to also contain 10% fetal calf serum (FCS). Cells were incubated at 37° C. in an atmosphere with 5% CO2 in a humidified incubator. For transfection of HepG2.2.15 cells with HBV targeting siRNAs, cells were seeded at a density of 15000 cells/well in 96-well regular tissue culture plates. Transfection of cells was carried out using RNAiMAX (Invitrogen/Life Technologies) according to the manufacturer's instructions. Dose-response experiments were done with oligo concentrations of 40, 20, 10, 5, 2.5, 1.25, 0.625, 0.3125, 0.15625 and 0.07813 nM. For each HBV targeting siRNA treatment (e.g., ds-siRNA, as identified by the ds-siNA ID in Table 6), four wells were transfected in parallel, and individual data points were collected from each well. After 24 h of incubation with siRNA, media was removed, and cells were lysed and analyzed with a QuantiGene2.0 branched DNA (bDNA) probe set specific for HBV genotype D (also called Hepatitis B virus subtype ayw, complete genome of 3182 base-pairs) as present in cell line HepG2.2.15.

For each well, the HBV on-target mRNA levels were normalized to the GAPDH mRNA level. As shown in Table 6, the activity of the HBV targeting ds-siRNAs was expressed as EC50, 50% reduction of normalized HBV RNA level from no drug control. As shown in Table 6, the cytotoxicity of the HBV targeting ds-siRNAs was expressed by CC50 of 50% reduction of GAPDH mRNA from no drug control.

Unconjugated siRNA 1) with or without a phosphorylation blocker; and 2) with or without end caps (e.g., 5'-stabilized end cap) are transfected into in vitro disease models or in vitro toxicity models. After transfection, target reduction and/or cell viability is measured and compared after a period of incubation. For HBV, exemplary disease cell models include, but are not limited to, HepG2.2.15, HepG2.117 or live HBV infected HepG2-NTCP or Primary Human Hepatocytes.

In Vivo Assay:

GalNAc conjugated siRNA 1) with or without phosphorylation blocker; and 2) with or without 5'-end caps are dosed subcutaneously or intravenously in animal disease models. The target knockdown magnitude and duration is measured from serum or liver samples and compared to each other and/or control animals (e.g., non-treated diseased animals). In some instances, the toxicity of the siRNAs is compared through routine Clinpath or Histopath assays. For HBV, exemplary animal efficacy models include, but are not limited to, AAV-HBV mouse model, HBV transgenic mouse model, PXB or FRG mouse models.

Example 14. ds-siNA Testing in AAV-HBV Mouse Model

In this example, the efficacy of ds-siNAs in treating HBV in an adeno-associated virus (AAV)-HBV mouse model was evaluated. AAV-HBV mice were subcutaneously injected with a single dose of (a) 5 mL/kg of vehicle; or (b) 5 mg/kg a ds-siNA at day 0. The sequences of the ds-siNA tested in this example are shown in Table 7.

Figure 4:
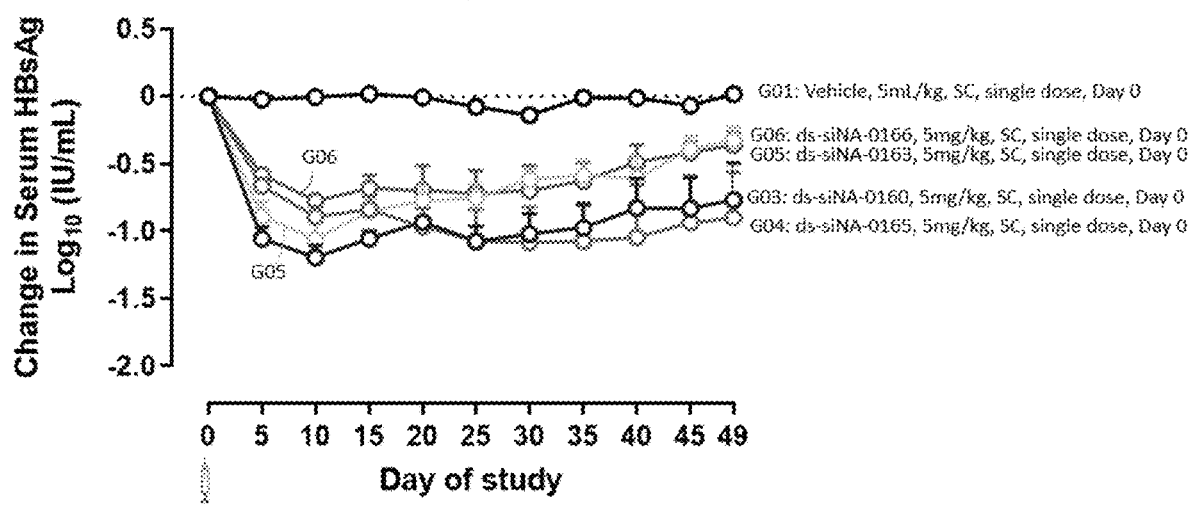
FIG. 4 shows a graph of the change in serum HBsAg from AAV-HBV mice treated with ds-siNA-0160, ds-siNA-0165, ds-siNA-0163, or ds-siNA-0166.

FIG. 4 shows a graph of the change in serum HBsAg from AAV-HBV mice treated with vehicle (G01), ds-siNA-0160 (G03), ds-siNA-0165 (G04), ds-siNA-0163 (G05), or ds-siNA-0166 (G06). These results demonstrate that the ds-siNAs containing various patterns of 2'-fluoro nucleotides and 2'-O-methyl nucleotides can effectively treated HBV.

TABLE 7 ds-siNA sequences tested in AAV-HBV mouse model

| ds-siNA ID | Sense strand sequence (5'-3') | Antisense strand sequence (5'-3') |
|---|---|---|
| ds-siNA-0160 | mCpsmCpsfGmUmGmUfGfCfAmCmUf UmCmGmCmUfUmCmA-p-(PS)2-GalNAc4 (SEQ ID NO: 600) | mUpsfGpsmAmAmGmCmGmAmAmGm UmGmCfAmCmAmCmGmGpsmUpsmC (SEQ ID NO: 272) |
| ds-siNA-0165 | mGpsmUpsfGmGmUmGfGfAfCmUmU fCmUmCmUmCfAmAmU-p-(PS)2-GalNAc4 (SEQ ID NO: 601) | mApsfUpsmUmGmAmGmAmGmAmA mGmUmCfCmAmCmCmAmCpsmGpsm A (SEQ ID NO: 292) |
| ds-siNA-0163 | mGpsmCpsmUmGmCmUfAmUfGfCfC mUmCmAmUmCmUmCmUmU-p-(PS)2-GalNAc4 (SEQ ID NO: 602) | mApsfApsmGmAmAfGmAmUmGmAm GmGmCfAmUfAmGmCmAmGm psmA psmG (SEQ ID NO: 287) |
| ds-siNA-0166 | mUpsmGpsfUmGmCmAfCfUmUmCm GmCmUmUmCmAfCmCmU-p-(PS)2-GalNAc4 (SEQ ID NO: 603) | mApsfGpsmGmUmGmAmAmGmCmGm AmAmGfUmGmCmAmCmApsmCpsmG (SEQ ID NO: 303) |

Example 15. ds-siNA Activity Assay and Testing in AAV-HBV Mouse Model

This example investigates the in vitro and in vivo activity of ds-siNAs. The sequences of the ds-siNAs tested in this example are shown in Table 8. As shown in Table 8, the ds-siNAs comprise a sense and antisense strand comprising a mixture of 2'-fluoro and 2'-O-methyl nucleotides. The total number of 2'-fluoro nucleotides in the ds-siNAs are between 6-8. The 2'-fluoro nucleotides may be at specific positions, such as nucleotide position 3, 5, 7, 8, 9, 10, 11, 12, and/or 17 from the 5' end of the sense strand or 2, 5, 6, 8, 10, 14, 16, 17, and/or 18. The 2'-fluoro nucleotides and 2'-O-methyl nucleotides might occur at specific patterns on the antisense strand, such as an alternating 1:2 or 1:3 pattern, wherein 1 nucleotide is a 2'-fluoro nucleotide and 2 or 3 nucleotides are 2-O-methyl nucleotides.

In Vitro Activity Assay

*Homo sapiens* HepG2.2.15 cells were cultured in Dulbecco's Modified Eagle's Medium (DMEM) (ATCC 30-2002) supplemented to also contain 10% fetal calf serum (FCS). Cells were incubated at 37° C. in an atmosphere with 5% $CO_2$ in a humidified incubator. For transfection of HepG2.2.15 cells with HBV targeting siRNAs, cells were seeded at a density of 15000 cells/well in 96-well regular tissue culture plates. Transfection of cells was carried out using RNAiMAX (Invitrogen/Life Technologies) according to the manufacturer's instructions. Dose-response experiments were done with oligo concentrations of 40, 20, 10, 5, 2.5, 1.25, 0.625, 0.3125, 0.15625 and 0.07813 nM. For each HBV targeting siRNA treatment (e.g., ds-siRNA, as identified by the ds-siNA ID in Table 8), four wells were transfected in parallel, and individual data points were collected from each well. After 24 h of incubation with siRNA, media was removed, and cells were lysed and analyzed with a QuantiGene2.0 branched DNA (bDNA) probe set specific for HBV genotype D (also called Hepatitis B virus subtype ayw, complete genome of 3182 base-pairs) as present in cell line HepG2.2.15.

For each well, the HBV on-target mRNA levels were normalized to the GAPDH mRNA level. Table 8 shows the activity of the HBV targeting ds-siRNAs expressed as EC50, which is 50% reduction of normalized HBV RNA level from no drug control, where A=EC50<0.5 nM; B=0.5 nM<EC50<1; and C=EC50>1.

In Vivo Testing in AAV-HBV Mouse Model:

AAV/HBV is a recombinant AAV carrying replicable HBV genome. Taking advantage of the highly hepatotropic feature of genotype 8 AAV, the HBV genome can be efficiently delivered to the mouse liver cells. Infection of immune competent mouse with AAV/HBV can result in long term HBV viremia, which mimics chronic HBV infection in patients. The AAV/HBV model can be used to evaluate the in vivo activity of various types of anti-HBV agents. Mice were infected with AAV-HBV on day −28 of the study. The test articles or negative control (PBS) were dosed subcutaneously (unless specified otherwise) as single dose on days 0 at 5 mg/kg. Serial blood collections were usually taken every 5 days on day 0, 5, 10 and 15 etc. until the termination of studies. Serum HBV S antigen (HBsAg) was assayed through ELISA.

GalNAc conjugated ds-siNAs were further tested at a single dose of 5 mg/kg at day 0 in the adeno-associated virus (AAV)-HBV mouse model. The resulting nadir $\log_{10}$ reduction in serum HBsAg is presented in Table 8, where X≥1 $\log_{10}$ reduction in HBsAg, Y is 0.5-1 $\log_{10}$ reduction in HBsAg, and Z is <0.5 $\log_{10}$ reduction in HBsAg.

Figure 5A:
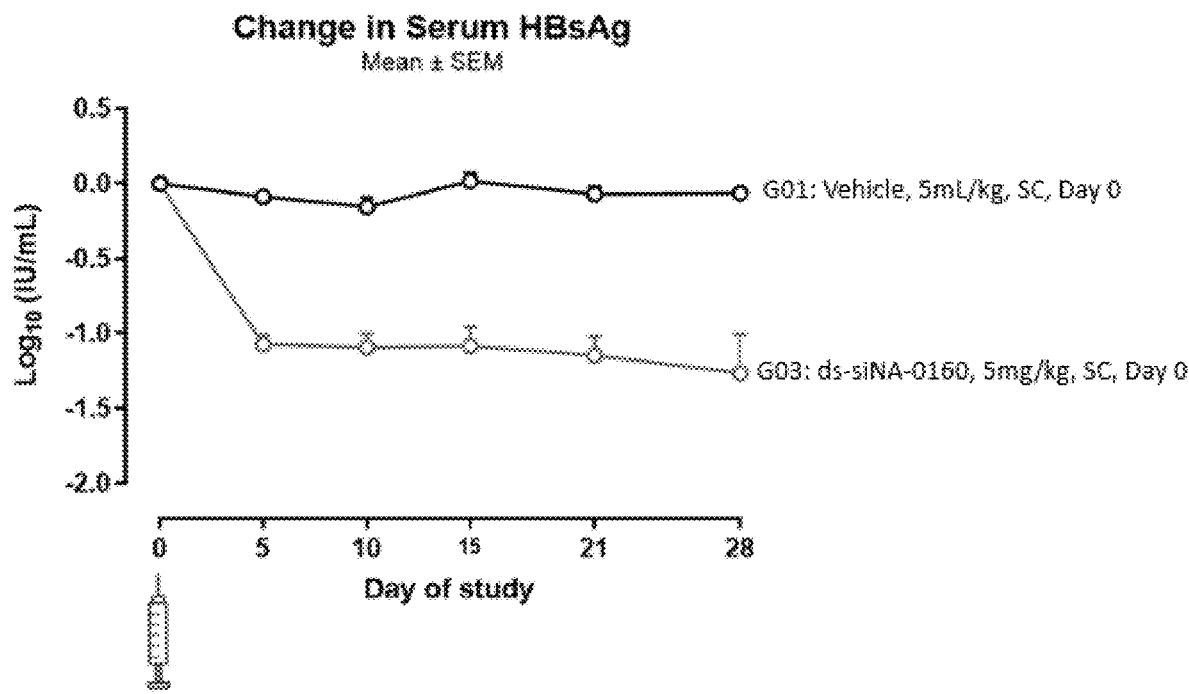
FIG. 5A shows a graph of the change in serum HBsAg from AAV-HBV mice treated with vehicle (G01) or ds-siNA-0160 (G03).

FIG. 5A shows a graph of the change in serum HBsAg from AAV-HBV mice treated with vehicle (G01) or ds-siNA-0160 (G03). AAV-HBV mice were subcutaneously injected with a single dose of 5 mL/kg of vehicle or 5 mg/kg of ds-siNA-0160 on day 0.

Figure 5B:
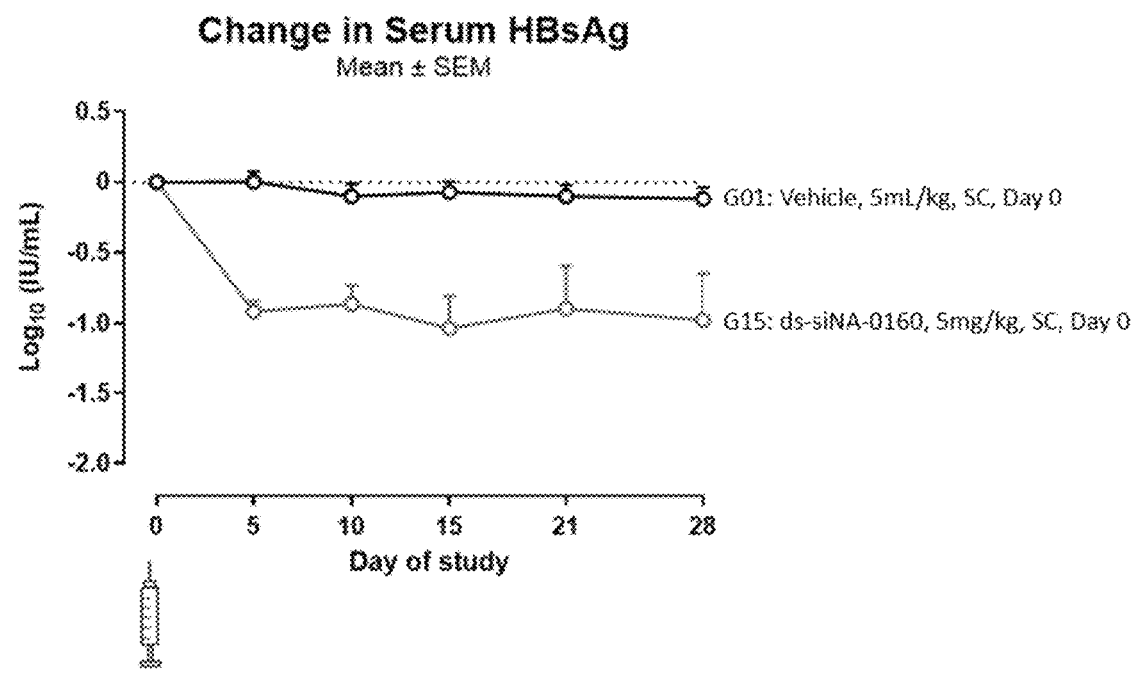
FIG. 5B shows a graph of the change in serum HBsAg from AAV-HBV mice treated with vehicle (G01) or ds-siNA-0160 (G15).

FIG. 5B shows a graph of the change in serum HBsAg from AAV-HBV mice treated with vehicle (G01) or ds-siNA-0160 (G15). AAV-HBV mice were subcutaneously injected with a single dose of 5 mL/kg of vehicle or 5 mg/kg of ds-siNA-0160 on day 0.

Figure 5C:
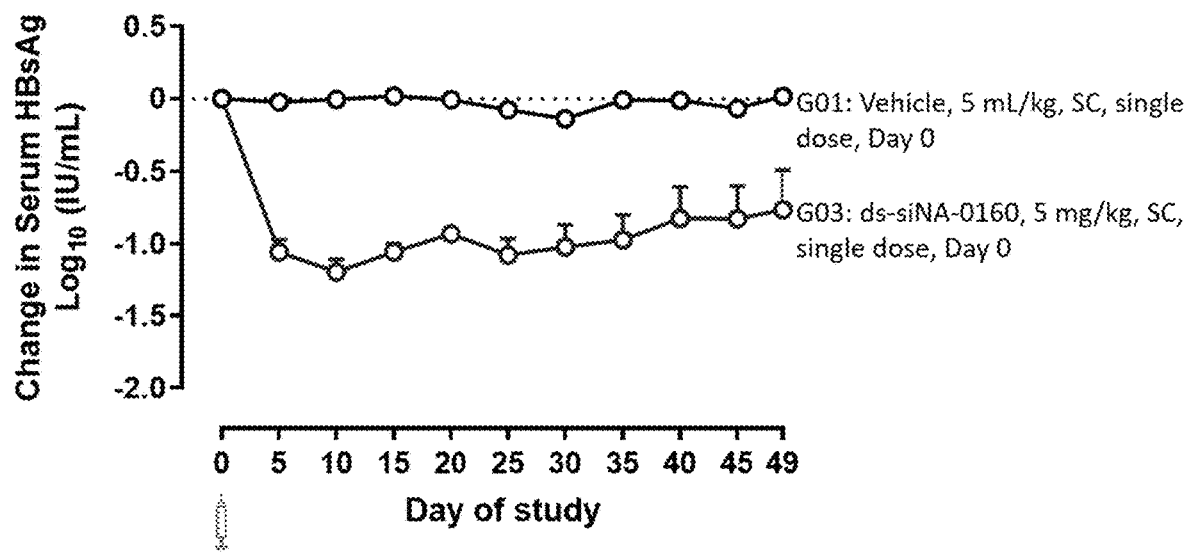
FIG. 5C shows a graph of the change in serum HBsAg from AAV-HBV mice treated with vehicle (G01) or ds-siNA-0160 (G03).

FIG. 5C shows a graph of the change in serum HBsAg from AAV-HBV mice treated with vehicle (G01) or ds-siNA-0160 (G03). AAV-HBV mice were subcutaneously injected with a single dose of 5 mL/kg of vehicle or 5 mg/kg of each ds-siNA on day 0.

Figure 5D:
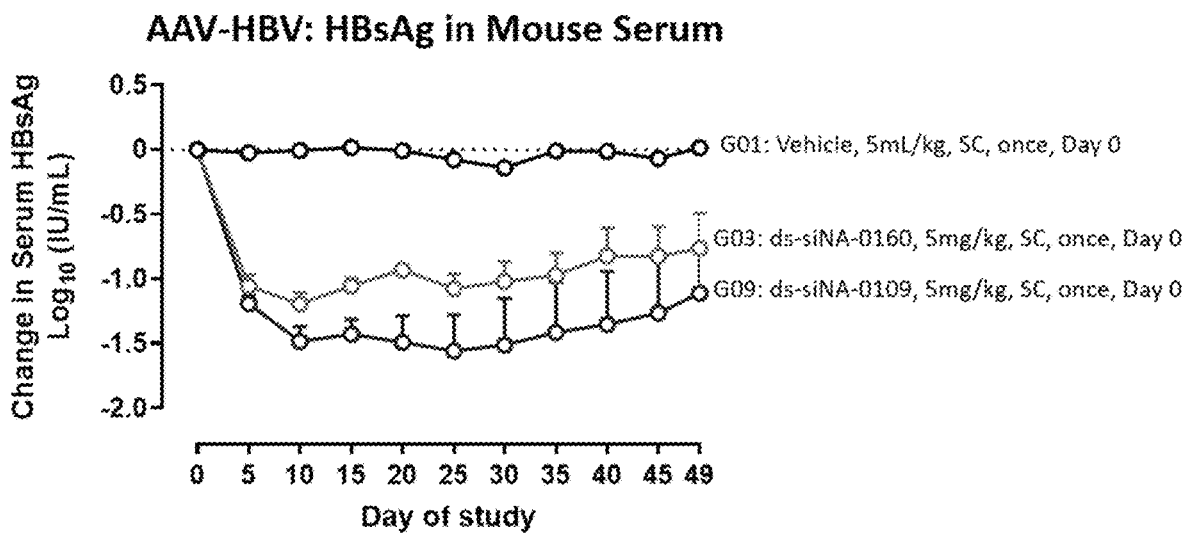
FIG. 5D shows a graph of the change in serum HBsAg from AAV-HBV mice treated with vehicle (G01), ds-siNA-0160 (G03), or ds-siNA-0109 (G09).

FIG. 5D shows a graph of the change in serum HBsAg from AAV-HBV mice treated with vehicle (G01), ds-siNA-0160 (G03), or ds-siNA-0109 (G09). AAV-HBV mice were subcutaneously injected with a single dose of 5 mL/kg of vehicle or 5 mg/kg of each ds-siNA on day 0.

Figure 5E:
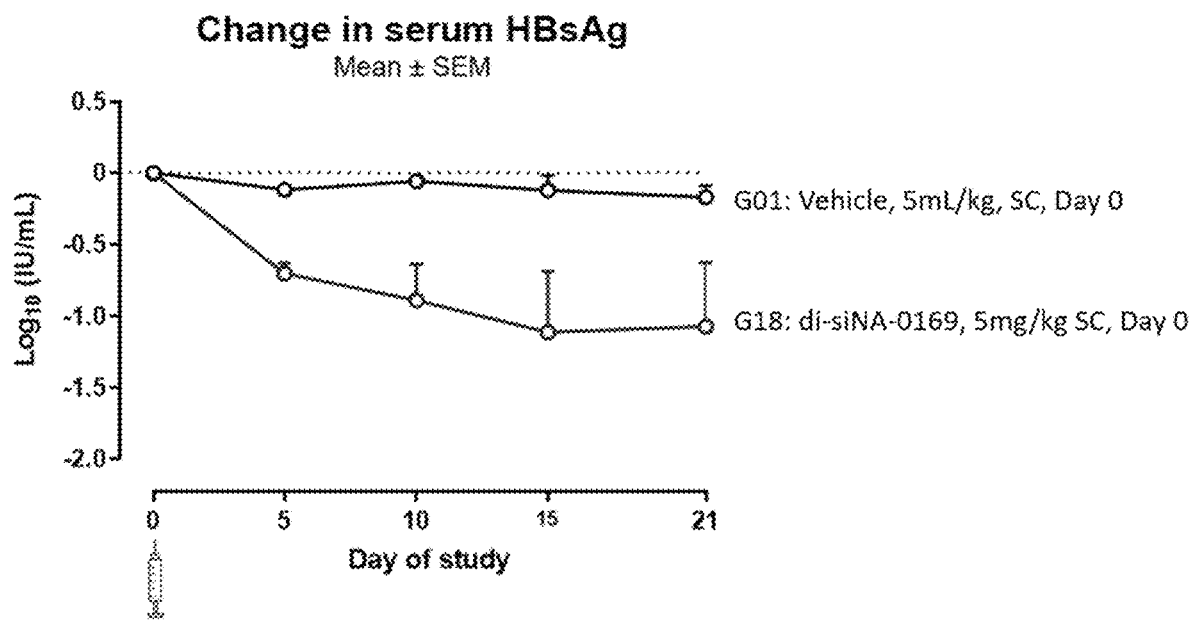
FIGS. 5E-5F show a graph of the change in serum HBsAg from AAV-HBV mice treated with vehicle (G01) or ds-siNA-0169 (G18).
Figure 5F:
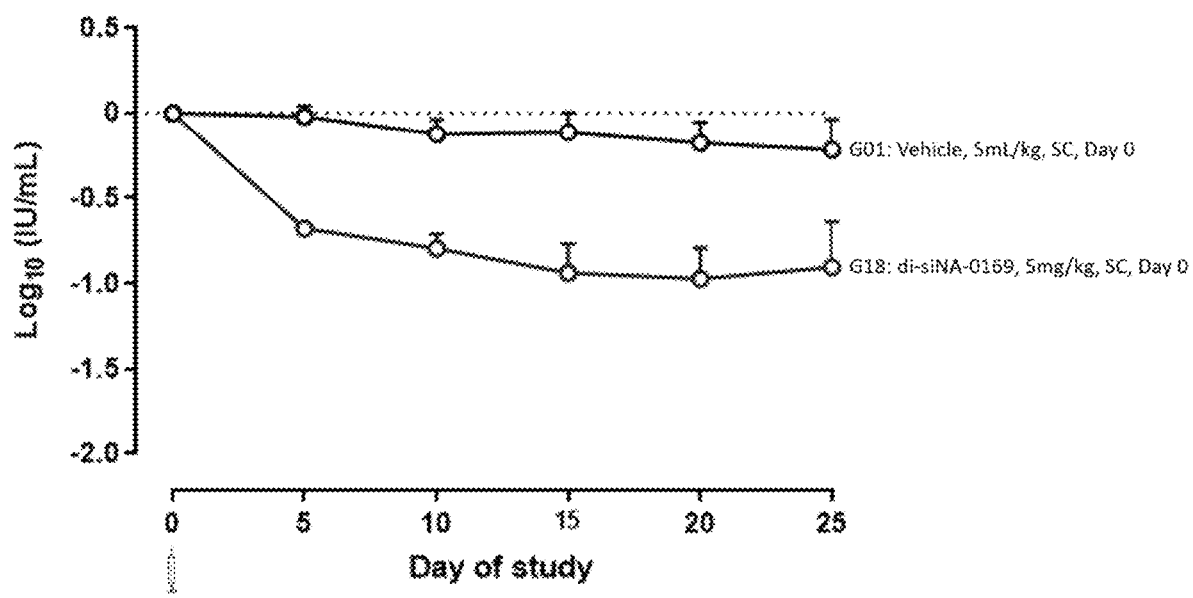

FIGS. 5E-5F show a graph of the change in serum HBsAg from AAV-HBV mice treated with vehicle (G01) or ds-siNA-0169 (G18). AAV-HBV mice were subcutaneously injected with a single dose of 5 mL/kg of vehicle or 5 mg/kg of ds-siNA-0169 on day 0.

Figure 5G:
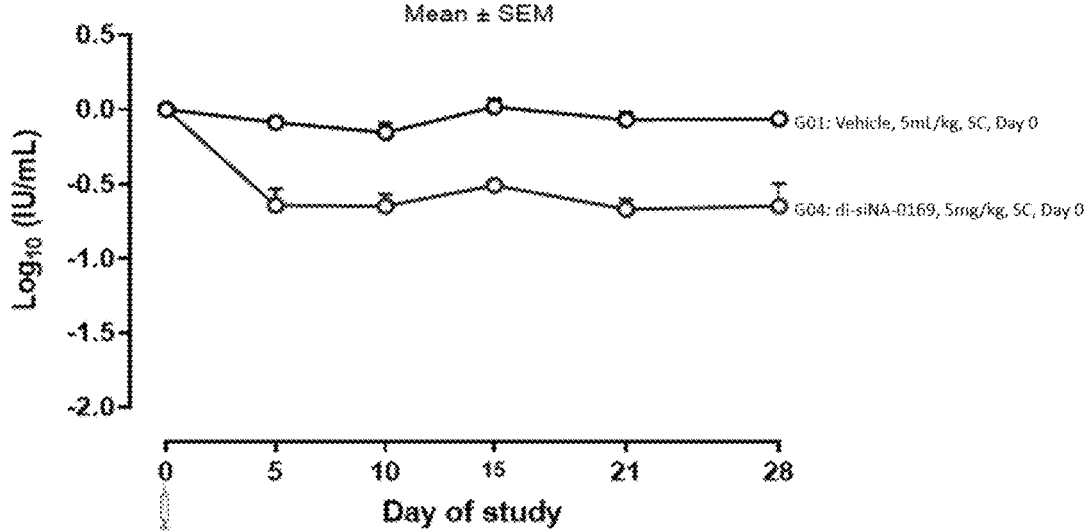
FIG. 5G shows a graph of the change in serum HBsAg from AAV-HBV mice treated with vehicle (G01) or ds-siNA-0169 (G04).

FIG. 5G shows a graph of the change in serum HBsAg from AAV-HBV mice treated with vehicle (G01) or ds-siNA-0169 (G04). AAV-HBV mice were subcutaneously injected with a single dose of 5 mL/kg of vehicle or 5 mg/kg of ds-siNA-0169 on day 0.

Figure 5H:
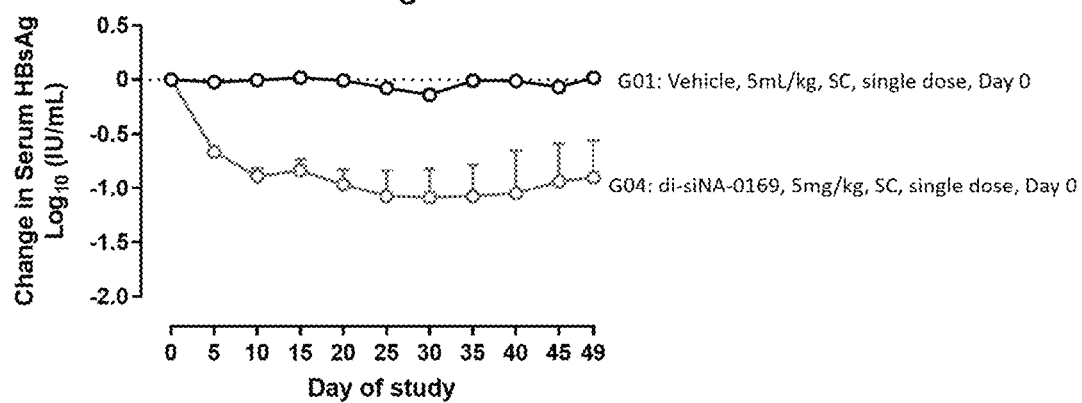
FIG. 5H shows a graph of the change in serum HBsAg from AAV-HBV mice treated with vehicle (G01) or ds-siNA-0169 (G04).

FIG. 5H shows a graph of the change in serum HBsAg from AAV-HBV mice treated with vehicle (G01) or ds-siNA-0169 (G04). AAV-HBV mice were subcutaneously injected with a single dose of 5 mL/kg of vehicle or 5 mg/kg of each ds-siNA on day 0.

Figure 5I:
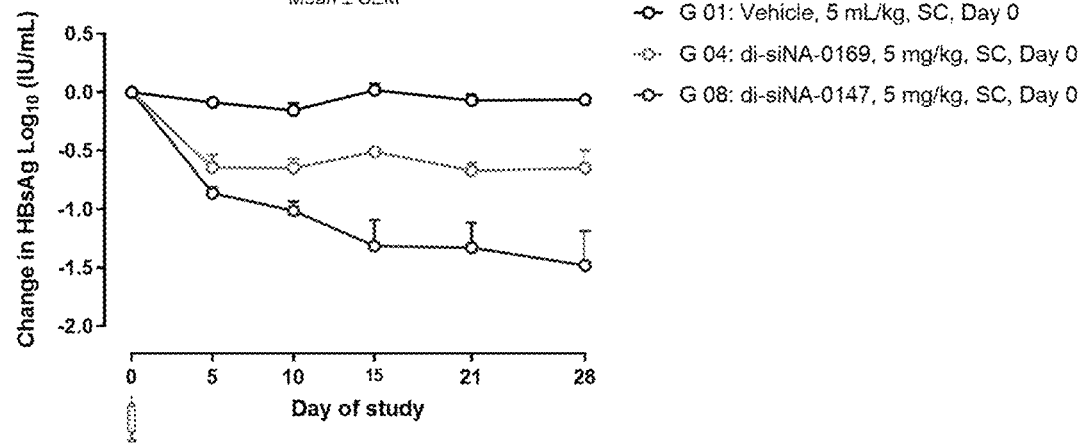
FIG. 5I shows a graph of the change in serum HBsAg from AAV-HBV mice treated with vehicle (G01), ds-siNA-0169 (G04), or ds-siNA-0147 (G08).

FIG. 5I shows a graph of the change in serum HBsAg from AAV-HBV mice treated with vehicle (G01), ds-siNA-0169 (G04) or ds-siNA-0147 (G08). AAV-HBV mice were subcutaneously injected with a single dose of 5 mL/kg of vehicle or 5 mg/kg of each ds-siNA on day 0.

Figure 5J:
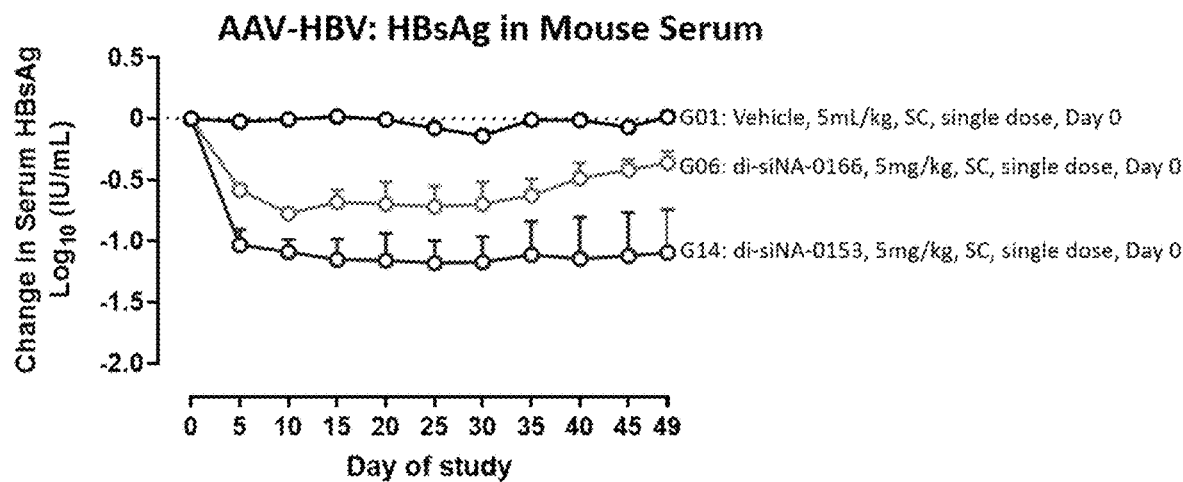
FIG. 5J shows a graph of the change in serum HBsAg from AAV-HBV mice treated with vehicle (G01), ds-siNA-0166 (G06), or ds-siNA-0153 (G14).

FIG. 5J shows a graph of the change in serum HBsAg from AAV-HBV mice treated with vehicle (G01), ds-siNA-0166 (G06), or ds-siNA-0153 (G14). AAV-HBV mice were subcutaneously injected with a single dose of 5 mL/kg of vehicle or 5 mg/kg of each ds-siNA on day 0.

Figure 5K:
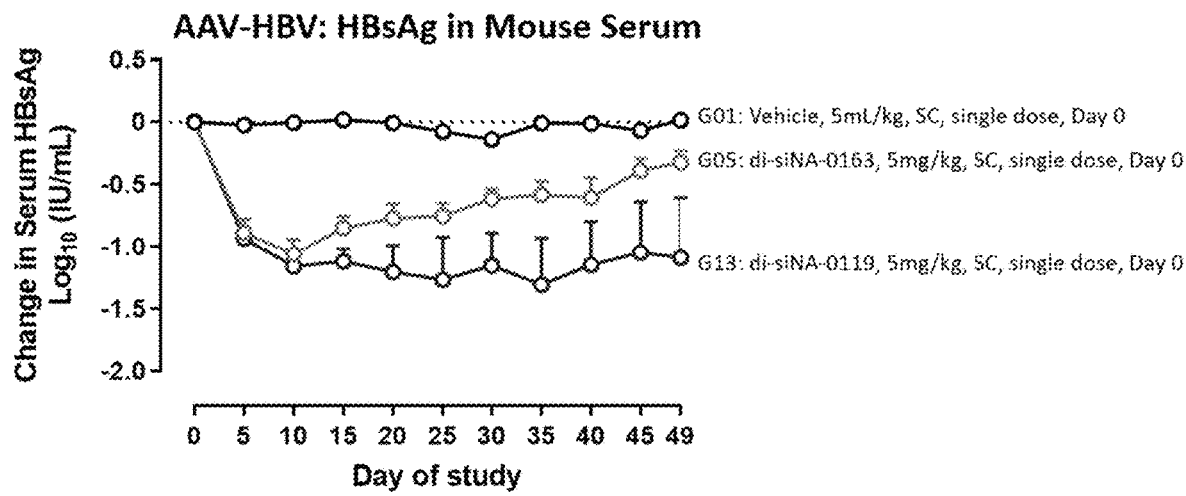
FIG. 5K shows a graph of the change in serum HBsAg from AAV-HBV mice treated with vehicle (G01), ds-siNA-0163 (G05), or ds-siNA-0119 (G13).

FIG. 5K shows a graph of the change in serum HBsAg from AAV-HBV mice treated with vehicle (G01), ds-siNA-0163 (G05), or ds-siNA-0119 (G13). AAV-HBV mice were subcutaneously injected with a single dose of 5 mL/kg of vehicle or 5 mg/kg of each ds-siNA on day 0.

These results demonstrate that ds-siNAs comprising combination of 2'-fluoro nucleotides and 2'-O-methyl nucleotides can be used to target HBV X and S gene sequences, which resulted in successful treatment of HBV.

As exemplified by ds-siNA-0160 and ds-siNA-0165, ds-siNAs comprising (a) a sense strand comprising 19 nucleotides, wherein 6 nucleotides are 2'-fluoro nucleotides and 13 nucleotides are 2'-O-methyl nucleotides; (b) an antisense strand comprising 21 nucleotides, wherein 2 nucleotides are 2'-fluoro nucleotides and 19 nucleotides are 2'-O-methyl nucleotides; and (c) a conjugated moiety, wherein the conjugated moiety is attached to the 3' end of the sense strand, resulted in successful treatment of HBV as evidenced by HBsAg reduction in serum. See FIGS. 4 and 5A-5D, and Table 8. For ds-siNA-0160 and ds-siNA-0165, the 2'-fluoro nucleotides were located at positions 3, 7-9, 12, and 17 from the 5' end of the sense strand and at positions 2 and 14 from the 5' end of the antisense strand.

As exemplified by ds-siNA-0166, ds-siNAs comprising (a) a sense strand comprising 19 nucleotides, wherein 4 nucleotides are 2'-fluoro nucleotides and 15 nucleotides are 2'-O-methyl nucleotides; (b) an antisense strand comprising 21 nucleotides, wherein 2 nucleotides are 2'-fluoro nucleotides and 19 nucleotides are 2'-O-methyl nucleotides; and (c) a conjugated moiety, wherein the conjugated moiety is attached to the 3' end of the sense strand, resulted in successful treatment of HBV as evidenced by HBsAg reduction in serum. See FIGS. 4 and 5J, and Table 8. For ds-siNA-0166, the 2'-fluoro nucleotides were located at positions 3, 7, 8, and 17 from the 5' end of the sense strand and at positions 2 and 14 from the 5' end of the antisense strand.

As exemplified by ds-siNA-0153, ds-siNAs comprising (a) a sense strand comprising 19 nucleotides; (b) an antisense strand comprising 21 nucleotides, wherein the nucleotides in the antisense strand comprise at least two alternating 1:3 modification pattern, and wherein approximate 1 nucleotide is a 2'-fluoro nucleotide and 3 nucleotides are 2'-O-methyl nucleotides in repeat pattern; and (c) a conjugated moiety, wherein the conjugated moiety is attached to the 3' end of the sense strand, resulted in successful treatment of HBV as evidenced by HBsAg reduction in serum. See FIG. 5J. For ds-siNA-0153, the sense strand comprises 6 2'-fluoro nucleotides at positions 3, 7-9, 12, and 17 from the 5' end of the sense strand. In addition, the antisense strand comprises 5 repeats of the 1:3 modification pattern starting at position 2 from the 5' end of the antisense strand.

As exemplified by ds-siNA-0109, ds-siNAs comprising (a) a sense strand comprising 19 nucleotides wherein 4 nucleotides are 2'-fluoro nucleotides and 15 nucleotides are 2'-O-methyl nucleotides; (b) an antisense strand comprising 21 nucleotides, wherein 4 nucleotides are 2'-fluoro nucleotides and 17 nucleotides are 2'-O-methyl nucleotides; and (c) a conjugated moiety, wherein the conjugated moiety is attached to the 3' end of the sense strand, resulted in successful treatment of HBV as evidenced by HBsAg reduction in serum. See FIG. 5D. For ds-siNA-0109 the sense strand comprises 4 2'-fluoro nucleotides at positions 5 and 7-9 from the 5' end of the sense strand. In addition, the antisense strand comprises 5 repeats of the 1:2 modification pattern starting at positions 2, 5, 8, 14, and 17 from the 5' end of the antisense strand.

As exemplified by ds-siNA-0147, ds-siNAs comprising (a) a sense strand comprising 19 nucleotides; (b) an antisense strand comprising 21 nucleotides, wherein the nucleotides in the antisense strand comprise at least two alternating 1:2 modification pattern, and wherein approximate 1 nucleotide is a 2'-fluoro nucleotide and 2 nucleotides are 2'-O-methyl nucleotides in repeat pattern; and (c) a conjugated moiety, wherein the conjugated moiety is attached to the 3' end of the sense strand, resulted in successful treatment of HBV as evidenced by HBsAg reduction in serum. See FIG. 5I. For ds-siNA-0147, the 2'-fluoro nucleotides were located at positions 5 and 7-9 from the 5' end of the sense strand and at positions 2, 6, 14, and 16 from the 5' end of the antisense strand.

TABLE 8 ds-siNA tested in AAV-HBV Mouse Model

| ds-siNA ID | Sense strand sequence (5'-3') | Antisense strand sequence (5'-3') | EC50 HepG2. 2.15* | HBsAg Nadir (Log)** |
|---|---|---|---|---|
| ds-siNA-0109 | mCpsmCpsmGmUfGmUfGfCf AmCmUmUmCmGmCmUmU mCmA-p-(PS)2-GalNac4 (SEQ ID NO: 604) | mUpsfGpsmAmAfGmCmGfA mAmGmUmGmCfAmCmAfC mGmGpsmUpsmC (SEQ ID NO: 605) | | |
| ds-siNA-0119 | mGpsmCpsmUmGfCmUmAm UfGfCfCmUmCfAmUmCmU mUfCmUmU-p-(PS)2-GalNac4 (SEQ ID NO: 606) | mApsfApsmGmAmAmGmA mUmGmAmGmGmCfAmUm AmGmCmAmGmCpsmApsm G (SEQ ID NO: 495) | | |

TABLE 8 -continued ds-siNA tested in AAV-HBV Mouse Model

| ds-siNA ID | Sense strand sequence (5'-3') | Antisense strand sequence (5'-3') | EC50 HepG2.2.15* | HBsAg Nadir (Log)** |
|---|---|---|---|---|
| ds-siNA-0147 | mGpsmCmUmUmCmUmUmCmA mAmU-p-(PS)2-GalNac4 (SEQ ID NO: 607) | mApsfUpsmUmGmAfGmAm GmAmAmGmUmCfCmAfCm CmAmCpsmGpsmA (SEQ ID NO: 608) | | |
| ds-siNA-0153 | mUpsmGpsfUmGmCmAfCfUf UmCmGfCmUmUmCmAfCm CmU-p-(PS)2-GalNac4 (SEQ ID NO: 609) | mApsfGpsmGmUmGfAmAm GmCfGmAmAmGfUmGmC mAfCmApsmCpsmG (SEQ ID NO: 610) | | |
| ds-siNA-0167 | mGpsmCpsfGmGmGfUfUf UmUmUfCmUmUmGmUfUm GmA-p-(PS)2-GalNac4 (SEQ ID NO: 611) | mUpsfCpsmAmAmCmAmAmGm AmAmAmAmAfCmCmCmGm CpsmCpsmU (SEQ ID NO: 285) | A | X |
| ds-siNA-0162 | mGpsmCpsfGmGmGfUfU mUmUmUmCmUmUmGmUf Um GmA-p-(PS)2-GalNac4 (SEQ ID NO: 612) | mUpsfCpsmAmAmCmAmA mGmAmAmAmAmAfCmCm CmCmGmCpsmCpsmU (SEQ ID NO: 285) | C | X |
| ds-siNA-0165 | mGpsmUpsfGmGmGfGfAf CmUmUfCmUmCmUmCfAm AmU-p-(PS)2-GalNac4 (SEQ ID NO: 601) | mApsfUpsmUmGmAmGmA mGmAmAmGmUmCfCmAm CmCmAmCpsmGpsmA (SEQ ID NO: 292) | A | X |
| ds-siNA-0168 | mUpsmCpsmGmUmGmGfUm GfGfAfCmUmUmCmUmCmU mCmAmAmU-p-(PS)2-GalNac4 (SEQ ID NO: 613) | mApsfUpsmUmGmAfGmAm GmAmAmGmUmCfCmAfCm CmAmCmGmApsmGpsmU (SEQ ID NO: 298) | A | X |
| ds-siNA-0163 | mGpsmCpsmUmGmCmUfAm UfGfCfCmUmCmAmUmCmU mUmCmUmU-p-(PS)2-GalNac4 (SEQ ID NO: 602) | mApsfApsmGmAmAfGmAm UmGmAmGmGmCfAmUfA mGmCmAmGpsmApsmG (SEQ ID NO: 287) | A | Y |
| ds-siNA-0161 | mCpsmUpsfGmCmUmAfUfGf CmCmUfCmAmUmCmUfUm CmU-p-(PS)2-GalNac4 (SEQ ID NO: 614) | mApsfGpsmAmAmGmAmU mGmAmGmGmCmAfUmAm GmCmAmGpsmCpsmA (SEQ ID NO: 277) | A | Y |
| ds-siNA-0160 | mCpsmCpsfGmUmGmUfGfCf AmCmUfUmCmGmCmUfUm CmA-p-(PS)2-GalNac4 (SEQ ID NO: 600) | mUpsfGpsmAmAmGmCmG mAmAmGmUmGmCfAmCm AmCmGmGpsmUpsmC (SEQ ID NO: 272) | A | X |
| ds-siNA-0169 | mCpsmCpsfGmUmGmUfGfCf AmCmUfUmCmGmCmUfUm CmA-p-(PS)2-GalNac4 (SEQ ID NO: 600) | mUpsfGpsmAmAmGmCmG mAmAmGmUmGmCfAmCm AmCmGmGpsTpsT (SEQ ID NO: 375) | A | X |
| ds-siNA-0170 | mUpsmGpsfUmGmCmAfCfUf UmCmGfCmUmUmCmAfCm CmU-p-(PS)2-GalNac4 (SEQ ID NO: 609) | mApsfGpsmGmUmGmAmAmGm CmGmAmAmGfUmGmCmAmCm ApsmCpsmG (SEQ ID NO: 303) | A | X |
| ds-siNA-0166 | mUpsmGpsfUmGmCmAfCfU mUmCmGmCmUmUmCmAfC mCmU-p-(PS)2-GalNAc4 (SEQ ID NO: 615) | mApsfGpsmGmUmGmAmA mGmCmGmAmAmGfUmGm CmAmCmApsmCpsmG (SEQ ID NO: 303) | A | X |
| ds-siNA-0171 | mUpsmGpsfUmGmCmAfCfU mUmCmGmCmUmUmCmAfC mCmU-p-(PS)2-GalNac4 (SEQ ID NO: 615) | mApsfGpsmGmUmGmAmAmGm CmGmAmAmGfUmGmCmAmCm ApsTpsT (SEQ ID NO: 407) | A | X | mX = 2'-O-methyl nucleotide;
fX = 2'-fluoro nucleotide;
ps = phosphorothioate linkage
*For EC50, A = EC50 < 0.5 nM; B = 0.5 nM < EC50 < 1; and C = EC50 > 1.
**For HBsAg Nadir, X ≥ 1 log$_{10}$ reduction in HBsAg, Y is 0.5-1 log$_{10}$ reduction in HBsAg, and Z is < 0.5 log$_{10}$ reduction in HBsAg.

Example 16. Testing of Ds-siNAs Having a
5'-Stabilized End Cap in AAV-HBV Mouse Model This example investigates the in vivo activity of ds-siNAs having a 5'-stabilized end cap. The sequences of the ds-siNAs tested in this example are shown in Table 9.

Figure 6A:
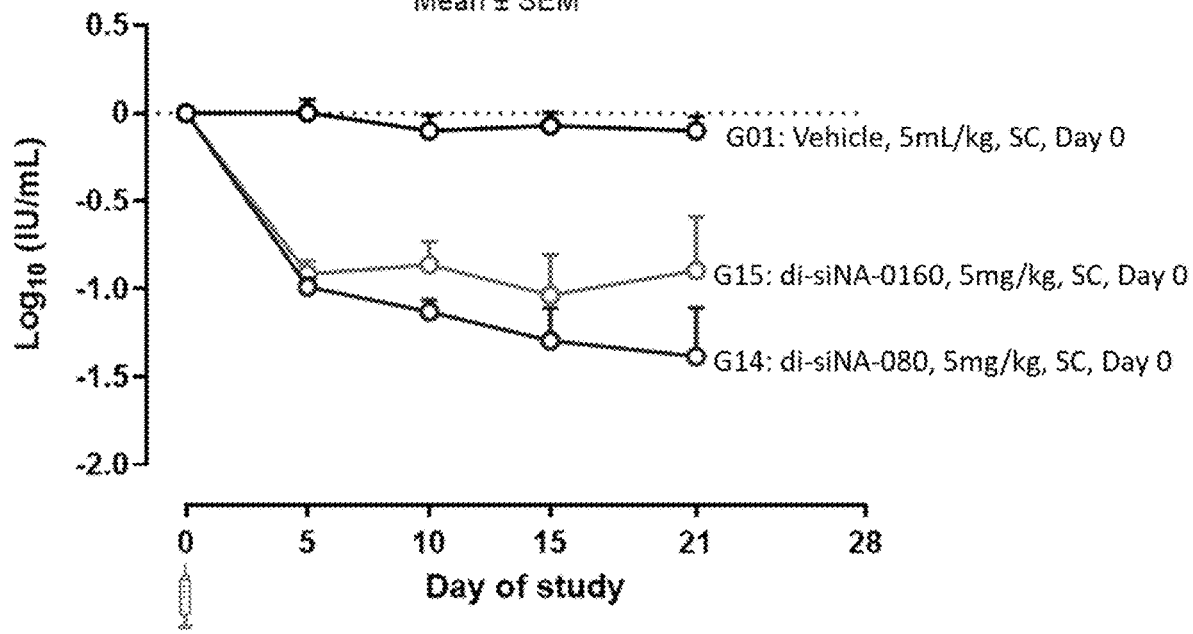
FIG. 6A shows a graph of the change in serum HBsAg from AAV-HBV mice treated with vehicle (G01), ds-siNA-0160 (G15), or ds-siNA-080 (G14).

FIG. 6A shows a graph of the change in serum HBsAg from AAV-HBV mice treated with vehicle (G01), ds-siNA-0160 (G15) (ds-siNA without a 5'-stabilized end cap, e.g., vinyl phosphonate), or ds-siNA-080 (G14) (ds-siNA with a 5'-stabilized end cap, e.g., vinyl phosphonate). AAV-HBV mice were subcutaneously injected with a single dose of 5 mL/kg of vehicle or 5 mg/kg of each ds-siNA on day 0. The resulting nadir $\log_{10}$ reduction in serum HBsAg is presented in Table 9, where X≥1 $\log_{10}$ reduction in HBsAg, Y is 0.5-1 $\log_{10}$ reduction in HBsAg, and Z is <0.5 $\log_{10}$ reduction in HBsAg.

Figure 6B:
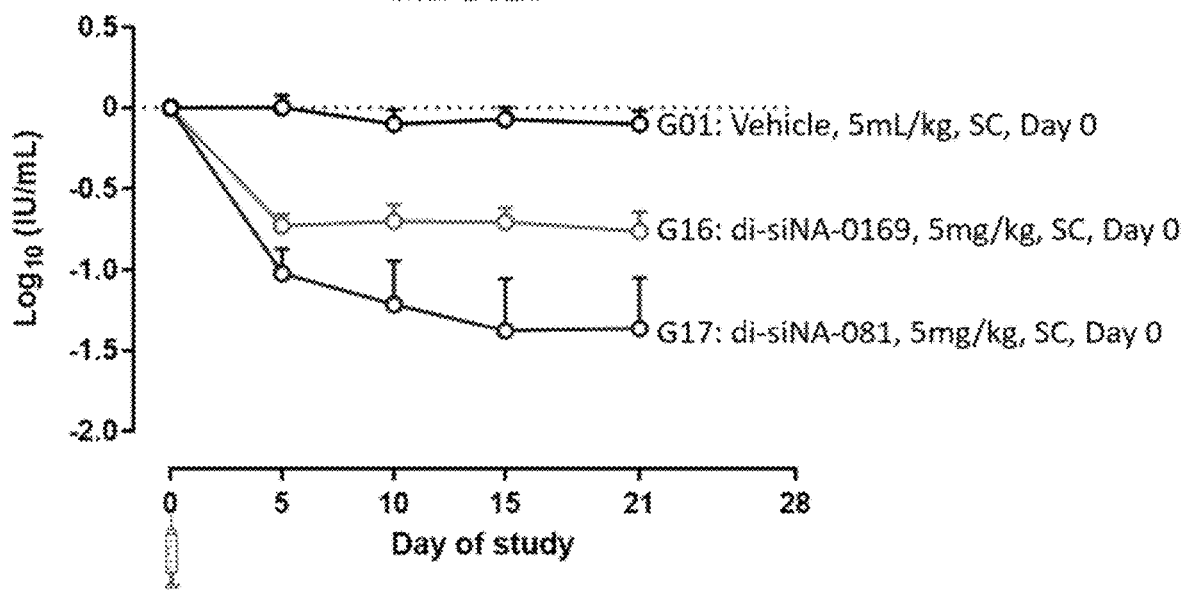
FIG. 6B shows a graph of the change in serum HBsAg from AAV-HBV mice treated with vehicle (G01), ds-siNA-0169 (G16), or ds-siNA-081 (G13).

FIG. 6B shows a graph of the change in serum HBsAg from AAV-HBV mice treated with vehicle (G01), ds-siNA-0169 (G16) (ds-siNA without a 5'-stabilized end cap, e.g., vinyl phosphonate), or ds-siNA-081 (G13) (ds-siNA with a 5'-stabilized end cap, e.g., vinyl phosphonate). AAV-HBV mice were subcutaneously injected with a single dose of 5 mL/kg of vehicle or 5 mg/kg of each ds-siNA on day 0. The resulting nadir $\log_{10}$ reduction in serum HBsAg is presented in Table 9, where X≥1 $\log_{10}$ reduction in HBsAg, Y is 0.5-1 $\log_{10}$ reduction in HBsAg, and Z is <0.5 $\log_{10}$ reduction in HBsAg.

Figure 7A:
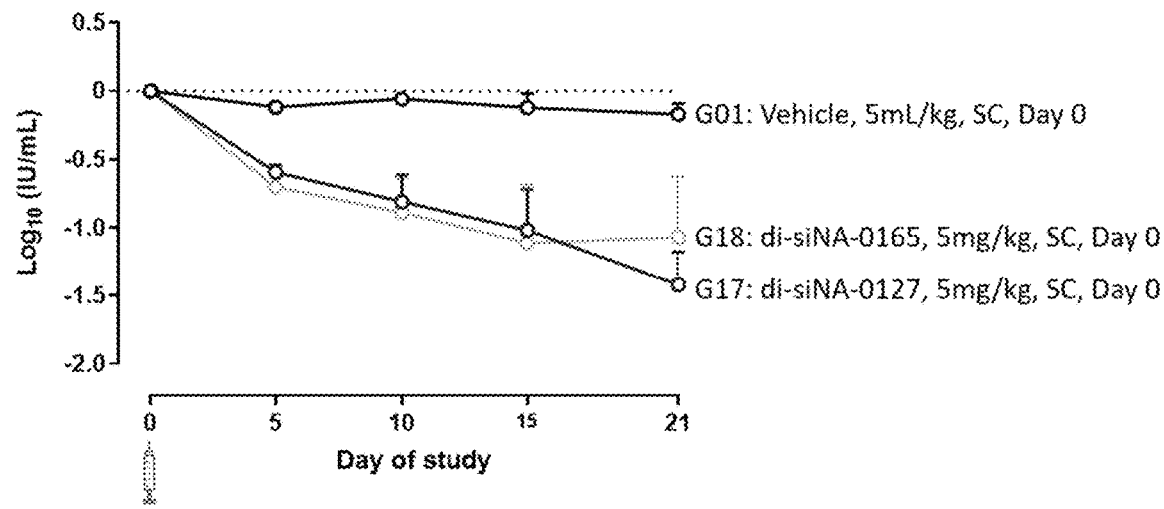
FIG. 7A shows a graph of the change in serum HBsAg from AAV-HBV mice treated with vehicle (G01), ds-siNA-0165 (G18), or ds-siNA-0127 (G17).

FIG. 7A shows a graph of the change in serum HBsAg from AAV-HBV mice treated with vehicle (G01), ds-siNA-0165 (G18) (ds-siNA without a 5'-stabilized end cap, e.g., vinyl phosphonate), or ds-siNA-0127 (G17) (ds-siNA with a 5'-stabilized end cap, e.g., vinyl phosphonate). AAV-HBV mice were subcutaneously injected with a single dose of 5 mL/kg of vehicle or 5 mg/kg of each ds-siNA on day 0. The resulting nadir $\log_{10}$ reduction in serum HBsAg is presented in Table 9, where X≥1 $\log_{10}$ reduction in HBsAg, Y is 0.5-1 $\log_{10}$ reduction in HBsAg, and Z is <0.5 $\log_{10}$ reduction in HBsAg.

Figure 7B:
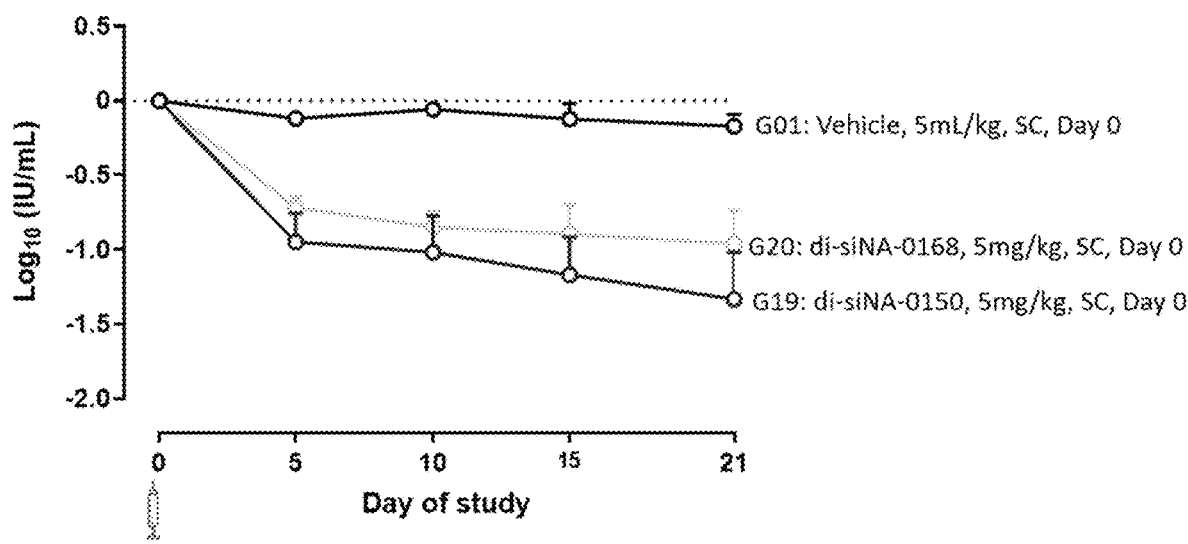
FIG. 7B shows a graph of the change in serum HBsAg from AAV-HBV mice treated with vehicle (G01), ds-siNA-0168 (G20), or ds-siNA-0150 (G19).

FIG. 7B shows a graph of the change in serum HBsAg from AAV-HBV mice treated with vehicle (G01), ds-siNA-0168 (G20) (ds-siNA without a 5'-stabilized end cap, e.g., vinyl phosphonate), or ds-siNA-0150 (G19) (ds-siNA with a 5'-stabilized end cap, e.g., vinyl phosphonate). AAV-HBV mice were subcutaneously injected with a single dose of 5 mL/kg of vehicle or 5 mg/kg of each ds-siNA on day 0. The resulting nadir $\log_{10}$ reduction in serum HBsAg is presented in Table 9, where X≥1 $\log_{10}$ reduction in HBsAg, Y is 0.5-1 $\log_{10}$ reduction in HBsAg, and Z is <0.5 $\log_{10}$ reduction in HBsAg.

These results demonstrate that the addition of a 5'-stabilized end cap can improve the efficacy of ds-siNAs without a 5'-stabilized end cap.

TABLE 9 ds-siNA sequences and HBsAg Nadir

| ds-siNA ID | Sense strand sequence (5'-3') | Antisense strand sequence (5'-3') | HBsAg Nadir (Log)* |
|---|---|---|---|
| ds-siNA-0160 | mCpsmCpsfGmUmGmUfGfC fAmCmUfUmCmGmCmUfU mCmA-(PS)2-p-GalNAc4 (SEQ ID NO: 616) | mUpsfGpsmAmAmGmCmGmAmAm GmUmGmCfAmCmAmCmGmGpsm UpsmC (SEQ ID NO: 272) | Y |
| ds-siNA-080 | mCpsmCpsfGmUmGmUfGfC fAmCmUfUmCmGmCmUfU mCmA-(PS)2-p-GalNAc4 (SEQ ID NO: 616) | vmUpsfGpsmAmAmGmCmGmAmA mGmUmGmCfAmCmAmCmGmGps mUpsmC (SEQ ID NO: 462) | X |
| ds-siNA-0169 | mCpsmCpsfGmUmGmUfGfC fAmCmUfUmCmGmCmUfU mCmA-(PS)2-p-GalNAc4 (SEQ ID NO: 616) | mUpsfGpsmAmAmGmCmGmAmAm GmUmGmCfAmCmAmCmGmGpsTp sT (SEQ ID NO: 375) | Y |
| ds-siNA-081 | mCpsmCpsfGmUmGmUfGfC fAmCmUfUmCmGmCmUfU mCmA-(PS)2-p-GalNAc4 (SEQ ID NO: 616) | vmUpsfGpsmAmAmGmCmGmAmA mGmUmGmCfAmCmAmCmGmGpsT psT (SEQ ID NO: 463) | X |
| ds-siNA-0165 | mGpsmUpsfGmGmUmGfGfA fCmUmUfCmUmCmUmCfA mAmU-(PS)2-p-GalNAc4 (SEQ ID NO: 617) | mApsfUpsmUmGmAmGmAmGmAm AmGmUmCfCmAmCmCmAmCpsmG psmA (SEQ ID NO: 292) | X |
| ds-siNA-0127 | mGpsmUpsfGmGmUmGfGfA fCmUmUfCmUmCmUmCfA mAmU-(PS)2-p-GalNAc4 (SEQ ID NO: 617) | vmApsfUpsmUmGmAmGmAmGmA mAmGmUmCfCmAmCmCmAmCpsm GpsmA (SEQ ID NO: 503) | X |
| ds-siNA-0168 | mUpsmCpsmGmUmGmGfUm GfGfAfCmUmUmCmUmCm UmCmAmAmU-(PS)2-p- GalNAc4 (SEQ ID NO: 618) | mApsfUpsmUmGmAfGmAmGmAmA mGmUmCfCmAfCmCmAmCmGmAp smGpsmU (SEQ ID NO: 298) | Y |

TABLE 9-continued ds-siNA sequences and HBsAg Nadir

| ds-siNA ID | Sense strand sequence (5'-3') | Antisense strand sequence (5'-3') | HBsAg Nadir (Log)* |
|---|---|---|---|
| ds-siNA-0150 | mUpsmCpsmGmUmGmGfUm GfGfAfCmUmUmCmUmCm UmCmAmAmU-(PS)2-p-GalNAc4 (SEQ ID NO: 618) | vmApsfUpsmUmGmAfGmAmGmAm AmGmUmCfCmAfCmCmAmCmGm ApsmGpsmU (SEQ ID NO: 523) | X | mX = 2'-O-methyl nucleotide;
fX = 2'-fluoro nucleotide;
ps = phosphorothioate linkage;
VP = vinyl phosphonate
*For HBsAg Nadir, X ≥ 1 logio reduction in HBsAg, Y is 0.5-1 log$_{10}$ reduction in HBsAg, and Z is < 0.5 logio reduction in HBsAg.

Example 17. Efficacy of a Combination Therapy in AAV-HBV Mouse Model

This example investigates the efficacy of a combination therapy comprising an antisense oligonucleotide (ASO 1, 5' GalNAc4-ps-GalNAc4-ps-GalNAc4-po-mA-po-lnGpslnApslnTpslnApslnApsApsAps(5OH)CpsGps(5m) Cps(5m)CpsGps(5m)CpslnApslnG pslnApscp(5m)C-3' (SEQ ID NO: 534)) and a ds-siNA-0160 for treating HBV in an AAV-HBV mouse model.

Figure 8A:
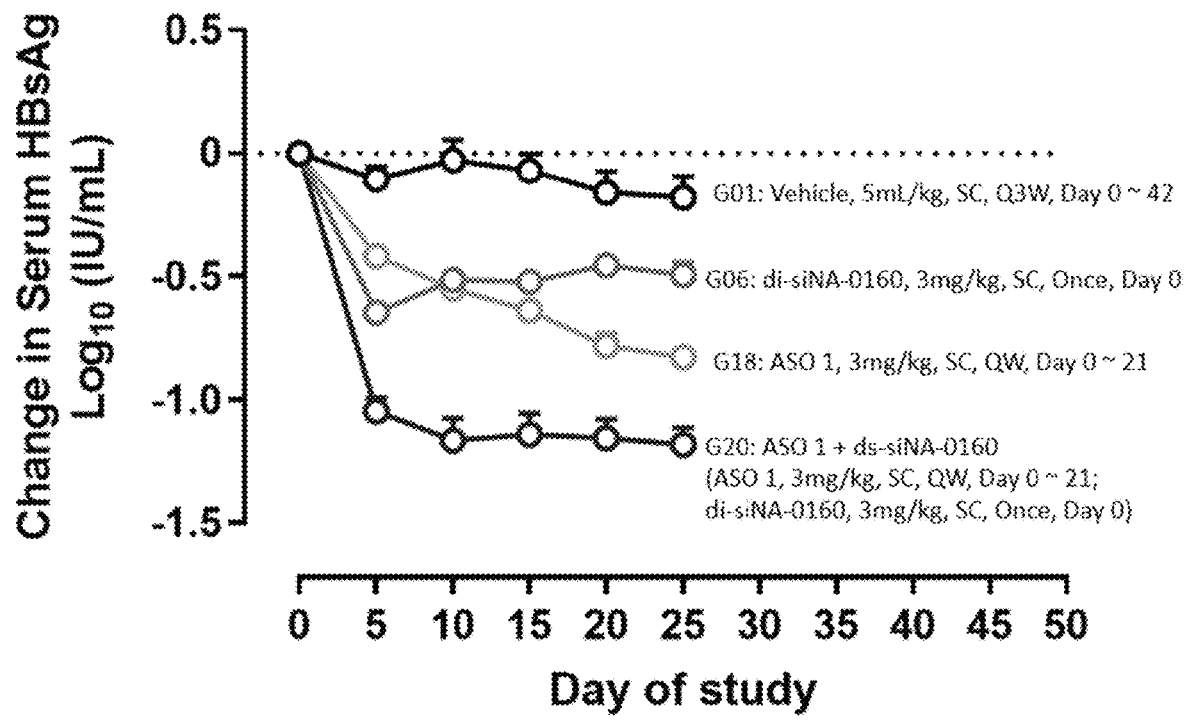
FIG. 8A shows a graph of the change in serum HBsAg from AAV-HBV mice treated with vehicle (G01), ds-siNA-0160 (G06), ASO 1 (G18), or a combination of ds-siNA-0160 and ASO 1 (G20).

FIG. 8A shows a graph of the change in serum HBsAg from AAV-HBV mice treated with vehicle (G01), ds-siNA-0160 (G06), ASO 1 (G18), or a combination of ds-siNA-0160 and ASO 1 (G20). AAV-HBV mice were subcutaneously injected with (a) 5 mL/kg of vehicle, three times a week, from days 0-42 (G01); (b) a single dose of 3 mg/kg of ds-siNA-0160 on day 0 (G06); (c) 3 mg/kg of ASO 1 on a weekly basis, from days 0-21 (G18); or (d) a combination of ASO 1 and ds-siNA-0160, wherein ASO 1 was administered at a dose of 3 mg/kg on a weekly basis, from days 0-21; and ds-siNA-0160 was administered as a single dose of 3 mg/kg at day 0.

Figure 8B:
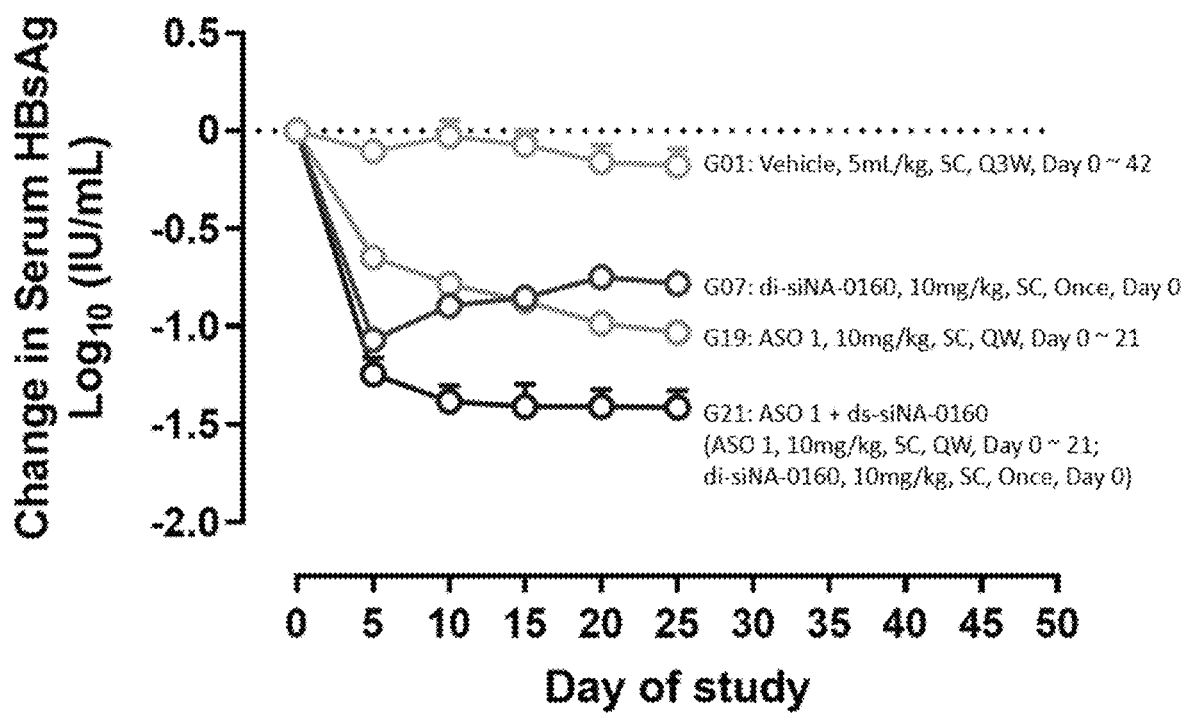
FIG. 8B shows a graph of the change in serum HBsAg from AAV-HBV mice treated with vehicle (G01), ds-siNA-0160 (G06), ASO 1 (G18), or a combination of ds-siNA-0160 and ASO 1 (G20).

FIG. 8B shows a graph of the change in serum HBsAg from AAV-HBV mice treated with vehicle (G01), ds-siNA-0160 (G06), ASO 1 (G18), or a combination of ds-siNA-0160 and ASO 1 (G20). AAV-HBV mice were subcutaneously injected with (a) 5 mL/kg of vehicle, three times a week, from days 0-42 (G01); (b) a single dose of 10 mg/kg of ds-siNA-0160 on day 0 (G06); (c) 10 mg/kg of ASO 1 on a weekly basis, from days 0-21 (G18); or (d) a combination of ASO 1 and ds-siNA-0160, wherein ASO 1 was administered at a dose of 10 mg/kg on a weekly basis, from days 0-21; and ds-siNA-0160 was administered as a single dose of 3 mg/kg at day 0.

Figure 8C:
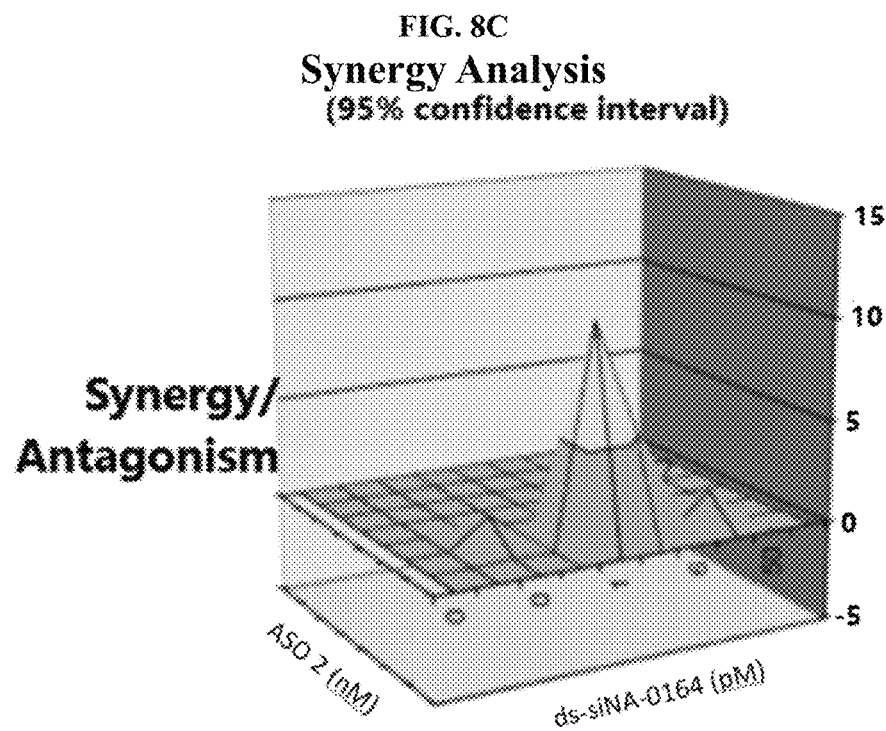
FIG. 8C shows a graph of a synergy analysis of a combination therapy with unconjugated forms of ds-siNA-0164 and ASO 2 (e.g., ds-siNA-0160 and ASO 1 without GalNac).

FIG. 8C shows a graph of a synergy analysis of an in vitro combination therapy with the ASO 2 and ds-siNA-0164. For the ds-siNA-0164 combination studies with ASO 2, 35,000 cells per well were reverse transfected in a collagen I-coated 96-well plate (Corning, Biocoat; Catalog 356698). Test articles ds-siNA-0164 and ASO 2 were diluted in Opti-MEM™ I Reduced Serum Medium (Thermo Fisher Scientific; Catalog 31985088) to 40× the desired final test concentration then serially diluted (1:3) up to 5 or 9 distinct concentrations, respectively. A 3.25-µL aliquot of each diluted compound was combined in a checkerboard fashion. This combination of compounds was mixed with 0.3 µL Lipofectamine© RNAiMAX Transfection Reagent (Thermo Fisher Scientific, Catalog 13778150) and 6.2 µL of Opti-MEM™ I Reduced Serum Medium. After incubating for 20 minutes, the mixture was added to the cells. Space was also allotted for titrations of each compound alone as reference controls. Cells were incubated with compounds for 3 days at 37° C. in a 5% CO$_2$ atmosphere. After that, HBsAg in the supernatant of cell culture was assayed by ELISA and cell viability was measured with Cell Titer Glow, the same procedures as in HepG2.2.15 in vitro assay section. The HBsAg reduction synergy between two test articles were analyzed using MacSynergy Software.

These results demonstrate that a combination therapy with ASO 1 and ds-siNA-0160 resulted in a greater reduction in serum HBsAg as compared to treatment with ASO 1 or ds-siNA-0160 alone.

Example 18. siNA Activity Assays

This example evaluates the activity of the siNAs disclosed in Table 10 (as identified by the ds-siNA ID). siRNAs were synthesized as described in Example 1. A conjugated moiety (e.g., ligand monomer) was further conjugated to the 3' end of the sense strand (note: for ds-siNA-067 and ds-siNA-083, the ligand monomer was conjugated to the 5' end of the sense strand). A 5'-stabilized end cap was further attached to the 5' end of the antisense strand of some siRNAs.

In Vitro Assay:

*Homo sapiens* HepG2.2.15 cells were cultured in Dulbecco's Modified Eagle's Medium (DMEM) (ATCC 30-2002) supplemented to also contain 10% fetal calf serum (FCS). Cells were incubated at 37° C. in an atmosphere with 5% CO2 in a humidified incubator. For transfection of HepG2.2.15 cells with HBV targeting siRNAs, cells were seeded at a density of 15000 cells/well in 96-well regular tissue culture plates. Transfection of cells was carried out using RNAiMAX (Invitrogen/Life Technologies) according to the manufacturer's instructions. Dose-response experiments were done with oligo concentrations of 40, 20, 10, 5, 2.5, 1.25, 0.625, 0.3125, 0.15625 and 0.07813 nM. For each HBV targeting siRNA treatment (e.g., ds-siRNA, as identified by the ds-siNA ID in Table 6), four wells were transfected in parallel, and individual data points were collected from each well. After 24 h of incubation with siRNA, media was removed, and cells were lysed and analyzed with a QuantiGene2.0 branched DNA (bDNA) probe set specific for HBV genotype D (also called Hepatitis B virus subtype ayw, complete genome of 3182 base-pairs) as present in cell line HepG2.2.15.

For each well, the HBV on-target mRNA levels were normalized to the GAPDH mRNA level. As shown in Table 10, the activity of the HBV targeting ds-siRNAs was expressed as EC50, 50% reduction of normalized HBV RNA level from no drug control, where A=EC50≤5 nM; B=5 nM<EC50<10; C=EC50≥10. As shown in Table 10, the cytotoxicity of the HBV targeting ds-siRNAs was expressed by CC50 of 50% reduction of GAPDH mRNA from no drug control.

In Vivo Assay:

GalNAc conjugated siRNA with or without 5'-stabilized end caps were subcutaneously injected at a single dose of 5 mg/kg into AAV-HBV mice. The target knockdown magnitude was measured from serum. The resulting max HBsAg knockdown ($\log_{10}$) is presented in Table 10, where X≥1 $\log_{10}$ reduction in HBsAg, Y is 0.5-1 $\log_{10}$ reduction in HBsAg, and Z is <0.5 $\log_{10}$ reduction in HBsAg.

Example 19: Analysis of 5'-Stabilized End Cap on the Efficacy of siNAs

Figure 9:
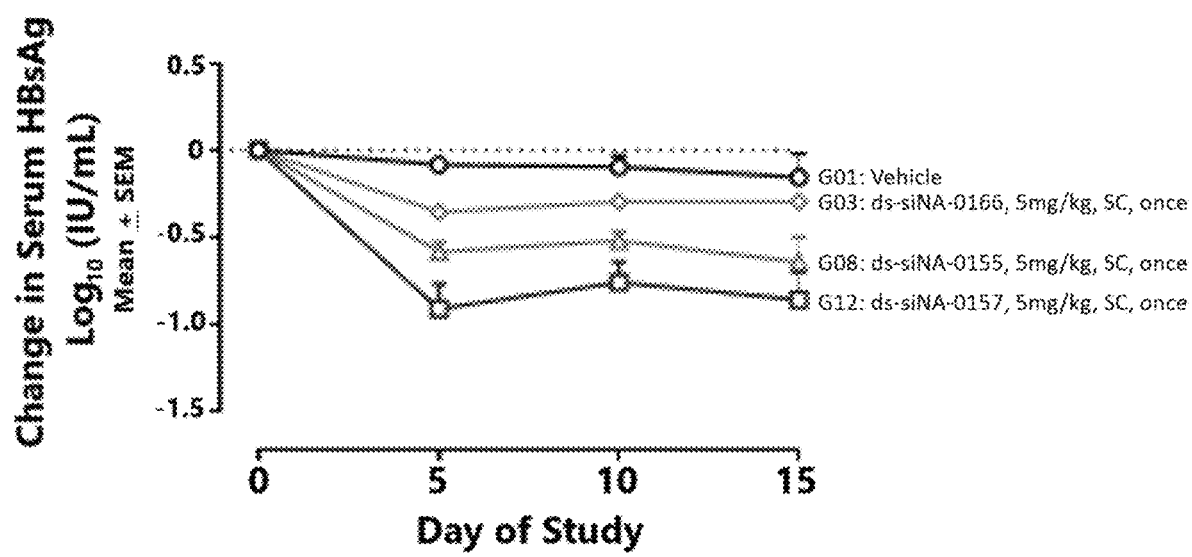
FIG. 9 shows a graph of the change in serum HBsAg from AAV-HBV mice treated with vehicle (G01), ds-siNA-0166 (G03), ds-siNA-0155 (G08), or ds-siNA-0157.

In this example, the role of a 5'-stabilized end cap on the efficacy of siNAs was investigated. Specifically, the first nucleotide on the 5' end of the antisense strand was modified to contain a 5'-stabilized end cap. The ds-siNAs investigated in this example are shown in the table below:

| ds-siNA ID | Sense Strand Sequence (5'→3') | Antisense Strand Sequence (5'→3') |
| --- | --- | --- |
| ds-siNA-0166 | mUpsmGpsfUmGmCmAfCfUmUmCmG mCmUmUmCmAfCmCmU-p-(PS)2- GalNAc4 (SEQ ID NO: 615) | mApsfGpsmGmUmGmAmAmGmCm GmAmAmGfUmGmCmAmCmApsm CpsmG (SEQ ID NO: 303) |
| ds-siNA-0155 | mUpsmGpsfUmGmCmAfCfUmUmCmG mCmUmUmCmAfCmCmU-p-(PS)2- GalNAc4 (SEQ ID NO: 615) | vmApsfGpsmGmUmGmAmAmGmC mGmAmAmGfUmGmCmAmCmAps mCpsmG (SEQ ID NO: 525) |
| ds-siNA-0157 | mUpsmGpsfUmGmCmAfCfUmUmCmG mCmUmUmCmAfCmCmU-p-(PS)2- GalNAc4 (SEQ ID NO: 615) | d2vmApsfGpsmGmUmGmAmAmG mCmGmAmAmGfUmGmCmAmCm ApsmCpsmG (SEQ ID NO: 529) | mX = 2'-O-methyl nucleotide;
fX = 2'-fluoro nucleotide;
vmA = 5'-vinyl phosphonate 2'-O-methyl adenosine;
d2vmA = deuterated 5' vinyl phosphonate adenosine;
ps = phosphorothioate linkage AAV-HBV mice were subcutaneously injected with vehicle or ds-siNAs. ds-siNA-0166, ds-siNA-0155, or ds-siNA-0157 were subcutaneously injected at a single dose of 5 mg/kg into AAV-HBV mice. The target knockdown magnitude is measured from serum. As shown in FIG. 9, the presence of the 5' stabilized end cap in the first nucleotide from the 5' end of the antisense strand in ds-siNA-0155 (triangle) and ds-siNA-0157 (square) improved the efficacy of the siNA (squares and triangles) as compared to the siNA without the 5' stabilized end cap (ds-siNA-0166, diamond). In addition, the presence of the deuterated 5' vinyl phosphonate in ds-siNA-0157 resulted in a greater improvement in efficacy of a ds-siNA as compared to the presence of the 5' vinylphosphanate in ds-siNA-0155. These results demonstrate that a 5' stabilized end cap improves the efficacy of siNAs, with the greatest improvement seen in siNAs containing deuterated 5' vinyl phosphonate.

Example 20: Analysis of HBV siRNA S and X Combination Therapy

Figure 10:
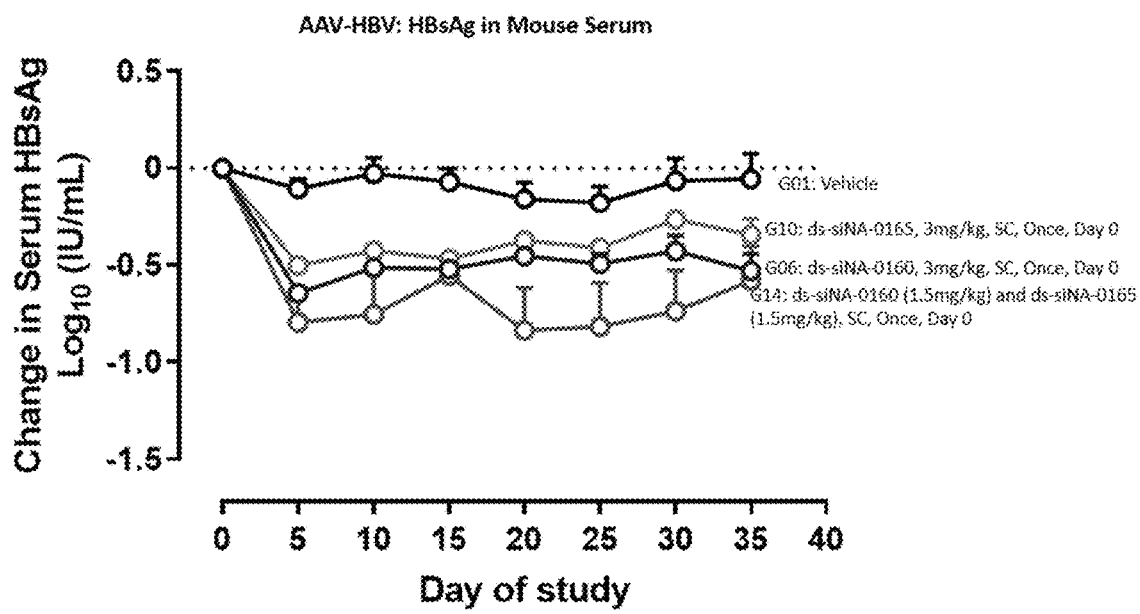
FIG. 10 shows a graph of the change in serum HBsAg from AAV-HBV mice treated with vehicle (G01), ds-siNA-0165 (G10), ds-siNA-0160 (G06), or a combination therapy with ds-siNA-0160 and ds-siNA-0165 (G14).

In this example, combination therapy using an siNA targeting the S gene of HBV and an siNA targeting the X gene of HBV was examined. AAV-HBV mice were treated with vehicle, a single siNA therapy, or a combination siNA therapy targeting the S gene and X gene of HBV. AAV-HBV mice were subcutaneously injected with a single dose of ds-siNA-0160 or ds-siNA-0165 on day 0. For the combination siNA therapy, AAV-HBV mice were subcutaneously injected with a single dose of 1.5 mg/kg of ds-siNA-0165 (S trigger) and 1.5 mg/kg of ds-siNA-0160 (X trigger) on day 0. As shown in FIG. 10, the combination therapy with a siNA targeting the S gene and a siNA targeting the X gene was more potent than the single therapy with ds-siNA-0165 or ds-siNA-0160.

Example 21. Synthesis of Monomer

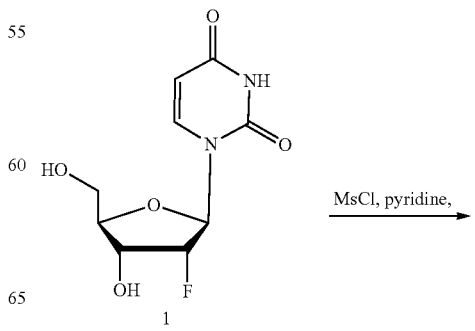

Scheme 1

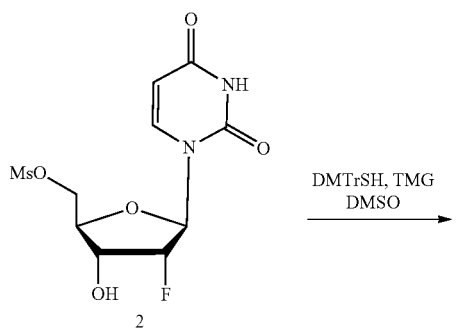

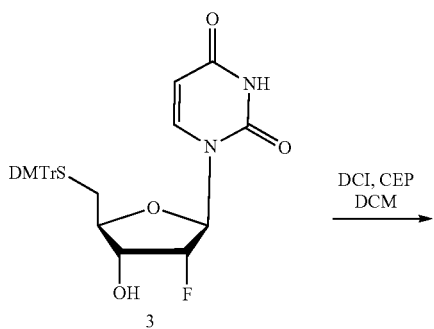

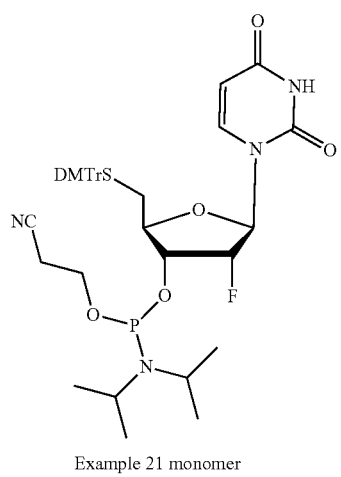

Example 21 monomer

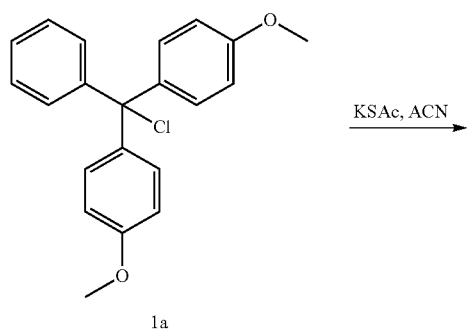

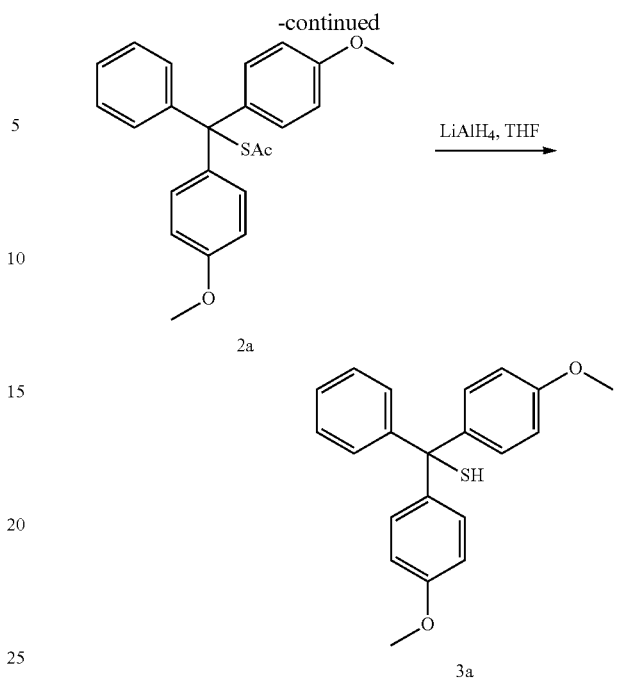

Preparation of (2a): To a solution of 1a (10.0 g, 29.5 mmol) in ACN (200.0 mL), KSAc (13.5 g, 118.6 mmol) was added at r.t., the mixture was stirred at r.t. for 15 h, TLC showed 1a was consumed completely. Mixture was filtered by silica gel and filter cake was washed with DCM (100.0 mL), the filtrate was concentrated to give crude 2a (11.1 g) as an oil. $^1$H-NMR (400 MHz, CDCl$_3$): δ 7.32-7.24 (m, 5H), 7.16 (d, J=8.9 Hz, 4H), 6.82 (d, J=8.9 Hz, 4H), 3.82 (s, 6H), 2.28 (s, 3H).

Preparation of (3a): To a solution of crude 2a (11.1 g, 29.2 mmol) in THF (290.0 mL), LiAlH$_4$ (2.0 g, 52.6 mmol) was added at 0° C. and kept for 10 min, reaction was stirred at r.t. for 5 h under N$_2$, TLC showed 2a was consumed completely. Mixture was put into aqueous NaHCO$_3$ solution and extracted with EA (500.0 mL*2), organic phase was concentrated to give crude which was purified by column chromatography (SiO$_2$, PE/EA=30:1 to 10:1) to give 3a (8.1 g, 95% purity) as a white solid. ESI-LCMS: m/z 335.3 [M−H]$^-$; $^1$H-NMR (400 MHz, CDCl$_3$): δ 7.33-7.24 (m, 5H), 7.19 (d, J=8.8 Hz, 4H), 6.82 (d, J=8.8 Hz, 4H), 3.83 (s, 6H), 3.09 (s, 1H).

Preparation of (2): To a solution of 1 (20.0 g, 81.3 mmol) in pyridine (400.0 mL), MsCl (10.23 g, 89.43 mmol) was added dropwise at −10° C., reaction was stirred at −10° C. for 1 h, LCMS showed 1 was consumed completely, 100.0 mL aqueous NaHCO$_3$ solution was added and extracted with DCM (100.0 mL*2), organic phase was concentrated to give crude which was purified by column chromatography (SiO$_2$, DCM/MeOH=30:1 to 10:1) to give 2 (9.5 g, 97% purity) as a white solid. ESI-LCMS: m/z 325.3 [M+H]$^+$; $^1$H-NMR (400 MHz, DMSO-d$_6$): δ 11.45 (s, 1H), 7.64-7.62 (d, J=8.0 Hz, 1H), 5.92-5.85 (m, 2H), 5.65-5.63 (d, J=8.0 Hz, 1H), 5.26-5.11 (m, 1H), 4.53-4.37 (m, 2H), 4.27-4.16 (m, 1H), 4.10-4.04 (m, 1H), 3.23 (s, 3H).

Preparation of (3): Intermediate 3 was prepared by prepared according to reaction condition described in reference *Helvetica Chimica Acta*, 2004, 87. 2812. To a solution of 2 (9.2 g, 28.3 mmol) in dry DMSO (130.0 mL). DMTrSH (14.31 g, 42.5 mmol) was added, followed by tetramethylguanidine (3.6 g, 31.2 mmol) was added under N$_2$, reaction was stirred at r.t. for 3 h, LCMS showed 2 was consumed completely. 100.0 mL H$_2$O was added and extracted with EA (100.0 mL*2), organic phase was concentrated to give crude which was purified by column chromatography (SiO$_2$, PE/EA=5:1 to 1:1) to give 3 (12.0 g, 97% purity) as a white solid. ESI-LCMS: m/z 563.2 [M−H]$^-$; $^1$H-NMR (400 MHz, DMSO-d$_6$): δ 11.43-11.42 (d, J=4.0 Hz, 1H), 7.57-7.55 (d, J=8.0 Hz, 1H), 7.33-7.17 (m, 9H), 6.89-6.86 (m, 4H), 5.80-5.74 (m, 1H), 5.65-5.62 (m, 1H), 5.58-5.57 (d, J=4.0 Hz, 1H), 5.16-5.01 (m, 1H), 3.98-3.90 (m, 1H), 3.73 (s, 6H), 3.73-3.67 (m, 1H), 2.50-2.37 (m, 2H).

Preparation of Example 21 monomer: To a solution of 3 (10.0 g, 17.7 mmol) in dichloromethane (120.0 mL) with an inert atmosphere of nitrogen was added CEOP[N(iPr)$_2$]$_2$ (6.4 g, 21.2 mmol) and DCI (1.8 g, 15.9 mmol) in order at room temperature. The resulting solution was stirred for 1.0 h at room temperature and diluted with 50 mL dichloromethane and washed with 2×50 mL of saturated aqueous sodium bicarbonate and 1×50 mL of saturated aqueous sodium chloride respectively. The organic phase was dried over anhydrous sodium sulfate, filtered and concentrated till no residual solvent left under reduced pressure. The residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=6/1; Detector, UV 254 nm. This resulted in to give Example 21 monomer (12.8 g, 98% purity, 93% yield) as an oil. ESI-LCMS: m/z 765.2 [M+H]$^+$; $^1$H-NMR (400 MHz, DMSO-d$_6$): δ 11.44 (s, 1H), 7.70-7.66 (m, 1H), 7.32-7.18 (m, 9H), 6.89-6.85 (m, 4H), 5.80-5.64 (m, 2H), 5.38-5.22 (m, 1H), 4.38-4.15 (m, 1H), 3.81-3.70 (m, 8H), 3.61-3.43 (m, 3H), 2.76-2.73 (m, 1H), 2.66-2.63 (m, 1H), 2.50-2.41 (m, 2H), 1.12-1.05 (m, 9H), 0.97-0.95 (m, 3H); $^{31}$P-NMR (162 MHz, DMSO-d$_6$): δ 149.01, 148.97, 148.74, 148.67; $^{19}$F-NMR (376 MHz, DMSO-d$_6$): δ 149.01, 148.97, 148.74, 148.67.

Example 22. Synthesis of Monomer

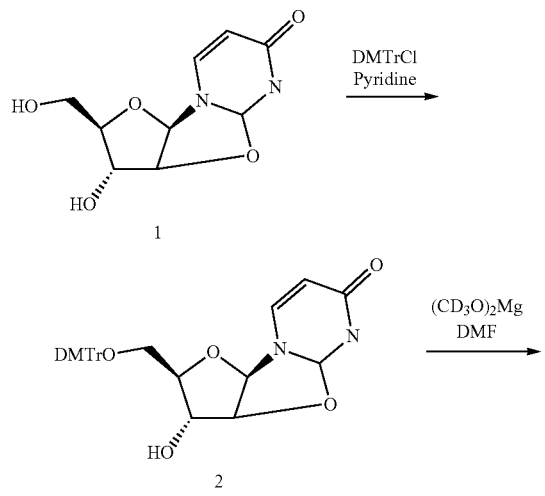

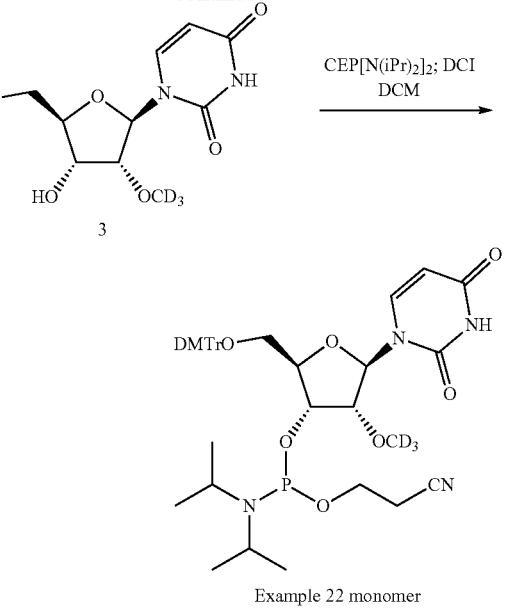

Example 22 monomer

Preparation of (2): To a stirred solution of 1 (2.0 g, 8.8 mmol) in pyridine (20 mL) were added DMTrCl (3.3 g, 9.7 mmol) at r.t. The reaction mixture was stirred at r.t. for 2.5 hrs. With ice-bath cooling, the reaction was quenched with water and the product was extracted with EA (100 mL). The organic phase was evaporated to dryness under reduced pressure to give a residue which was purified by silica gel column chromatography (eluent, DCM:MeOH=50:1-20:1) to give 2 (3.7 g, 7.2 mmol, 80.1%) as a white solid. ESI-LCMS: m/z 527 [M−H]$^-$.

Preparation of (3): To the solution of 2 (2.8 g, 5.3 mmol) in dry DMF (56 mL) was added (CD$_3$O)$_2$Mg (2.9 g, 31.8 mmol) at r.t. under N$_2$ atmosphere. The reaction mixture was stirred at 100° C. for 15 hrs. With ice-bath cooling, the reaction was quenched with saturated aq. NH$_4$Cl and extracted with EA (300 mL). The combined organic layer was washed with water and brine, dried over Na$_2$SO$_4$, and concentrated to give a residue which was purified by Flash-Prep-HPLC with the following conditions (IntelFlash-1): Column, C18 silica gel; mobile phase, CH$_3$CN/H$_2$O (0.5% NH$_4$HCO$_3$)=2/3 increasing to CH$_3$CN/H$_2$O (0.5% NH$_4$HCO$_3$)=3/2 within 20 min, the eluted product was collected at CH$_3$CN/H$_2$O (0.5% NH$_4$HCO$_3$)=1/1; Detector, UV 254 nm. This resulted in to give 3 (2.0 g, 3.6 mmol, 67.9%) as a white solid. ESI-LCMS: m/z 562 [M−H]$^-$; $^1$H-NMR (400 MHz, DMSO-d$_6$): δ 11.38 (s, 1H), 7.73 (d, J=8 Hz, 1H), 7.46-7.19 (m, 9H), 6.91 (d, J=7.4 Hz, 4H), 5.81-5.76 (AB, J=20 Hz, 1H), 5.30 (d, J=8 Hz, 1H), 5.22 (s, 1H), 4.25-4.15 (m, 1H), 3.99-3.92 (m, 1H), 3.85-3.79 (m, 1H), 3.74 (s, 6H), 3.34-3.18 (m, 31H).

Preparation of Example 22 monomer: To a suspension of 3 (2.0 g, 3.5 mmol) in DCM (20 mL) was added DCI (357 mg, 3.0 mmol) and CEP[N(iPr)$_2$]$_2$ (1.3 g, 4.3 mmol). The mixture was stirred at r.t. for 1 h. LC-MS showed 3 was consumed completely. The solution was washed with water twice and washed with brine and dried over Na$_2$SO$_4$. Then concentrated to give a residue which was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give Example 22 monomer (2.1 g, 2.7 mmol, 77.1%) as a white solid. ESI-LCMS: m/z 764 [M+H]$^+$; $^1$H-NMR (400 MHz, ACN-d$_3$): δ 9.45-8.90 (m, 1H, exchanged with D$_2$O), 7.88-7.66 (m, 1H), 7.50-7.18 (m, 9H), 6.93-6.80 (m, 4H), 5.85 (d, J=8.2 Hz, 1H), 5.29-5.16 (m, 1H), 4.57-4.37 (m, 1H), 4.18-4.09 (m, 1H), 3.98-3.90 (m, 1H), 3.90-3.74 (m, 7H), 3.74-3.50 (m, 3H), 3.48-3.31 (m, 2H), 2.70-2.61 (m, 1H), 2.56-2.46 (m, 1H), 1.24-1.12 (m, 9H), 1.09-0.99 (m, 3H). $^{31}$P-NMR (162 MHz, ACN-d$_3$): δ=149.87, 149.55.

Example 23. Synthesis of Monomer

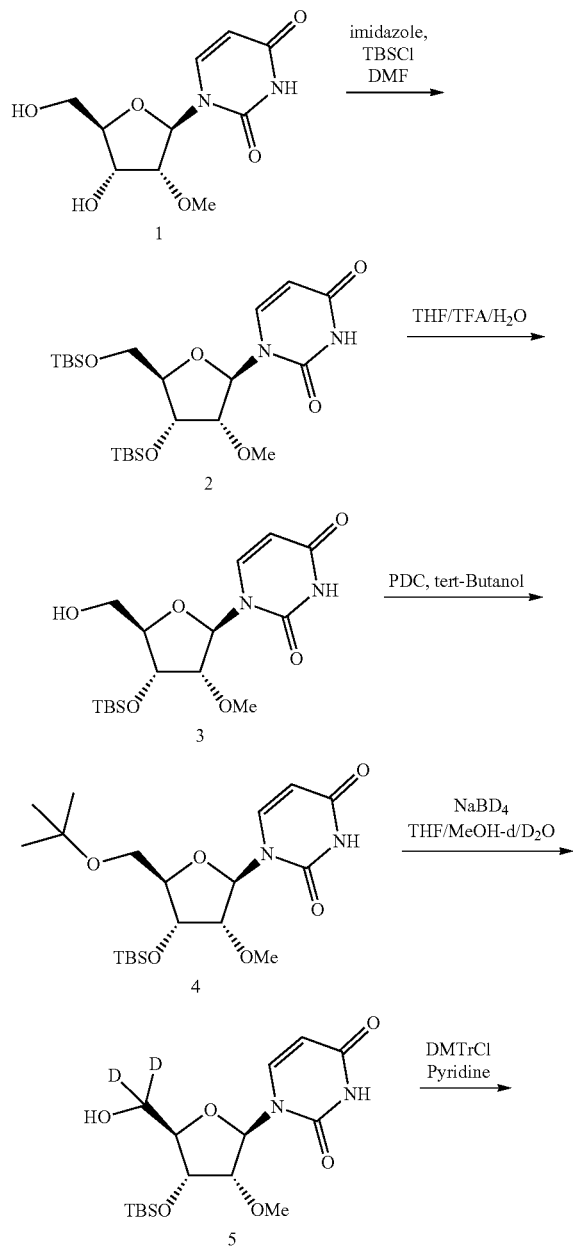

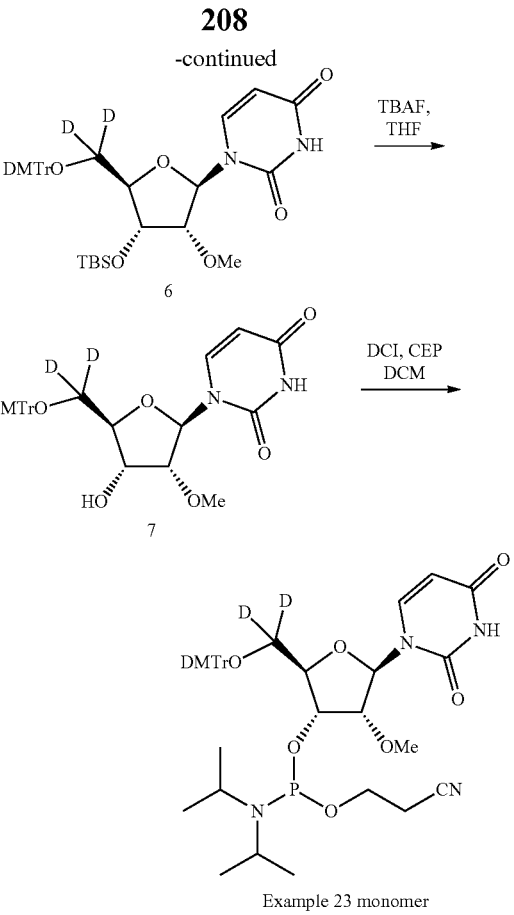

Preparation of (2): To the solution of 1 (39.2 g, 151.9 mmol) in DMF (390.0 mL) was added imidazole (33.0 g, 485.3 mmol) and TBSCl (57.2 g, 379.6 mmol) at 0° C. The reaction mixture was stirred at room temperature for 15 hrs under N$_2$ atmosphere. After addition of water, the resulting mixture was extracted with EA (500.0 mL). The combined organic layer was washed with water and brine, dried over Na$_2$SO$_4$, concentrated to give the crude 2 (85.6 g) as a white solid which was used directly for next step. ESI-LCMS: m/z 487.7 [M+H]$^+$.

Preparation of (3): A solution of crude 2 (85.6 g) in a mixture solvent of TFA/H$_2$O=1/1 (400.0 mL) and THF (400.0 mL) was stirred at 0° C. for 30 min. After completion of reaction, the resulting mixture was added con.NH$_3$*H$_2$O to pH=7, and then extracted with EA (500.0 mL). The organic layer was washed with brine, dried over sodium sulfate and removed to give the residue was purified by Flash-Prep-HPLC with the following conditions (IntelFlash-1): Column, C18 silica gel; mobile phase, CH$_3$CN/H$_2$O (0.5% NH$_4$HCO$_3$)=2/3 increasing to CH$_3$CN/H$_2$O (0.5% NH$_4$HCO$_3$)=3/2 within 20 min, the eluted product was collected at CH$_3$CN/H$_2$O (0.5% NH$_4$HCO$_3$)=1/1; Detector, UV 254 nm. This resulted in to give 3 (36.6 g, 98.4 mmol, 64.7% over two step) as a white solid. ESI-LCMS: m/z 372.5 [M+H]$^+$; $^1$H-NMR (400 MHz, DMSO-d$_6$): δ 11.36 (d, J=1 Hz, 1H), 7.92 (d, J=8 Hz, 1H), 5.83 (d, J=5 Hz, 1H), 5.67-5.65 (m, 1H), 5.19 (s, 1H), 4.30 (t, J=5 Hz, 1H), 3.85-3.83 (m, 2H), 3.68-3.52 (m, 2H), 0.88 (s, 9H), 0.09 (s, 6H).

Preparation of (4): To the solution of 3 (36.6 g, 98.4 mmol) in dry DCM (200.0 mL) and DMF (50.0 mL) was added PDC (73.9 g, 196.7 mmol), tert-butyl alcohol (188.0 mL) and Ac₂O (93.0 mL) at r.t under N₂ atmosphere, the reaction mixture was stirred at r.t for 2 hrs. The solvent was removed to give a residue which was purified by silica gel column chromatography (eluent, PE/EA=4:1~2:1) to give a residue which was purified by Flash-Prep-HPLC with the following conditions (IntelFlash-1): Column, C18 silica gel; mobile phase, CH₃CN/H₂O (0.5% NH₄HCO₃)=1/1 increasing to CH₃CN/H₂O (0.5% NH₄HCO₃)=1/0 within 20 min, the eluted product was collected at CH₃CN/H₂O (0.5% NH₄HCO₃)=1/0; Detector, UV 254 nm. This resulted in to give 4 (24.3 g, 54.9 mmol, 55.8%) as a white solid. ESI-LCMS: m/z 443.2 [M+H]⁺; ¹H-NMR (400 MHz, DMSO-d₆): δ 11.30 (d, J=1 Hz, 1H), 7.92 (d, J=8 Hz, 1H), 5.86 (d, J=6 Hz, 1H), 5.67-5.65 (m, 1H), 4.33-4.31 (m, 1H), 4.13 (d, J=3 Hz, 1H), 3.73-3.70 (m, 1H), 1.34 (s, 9H), 0.77 (s, 9H), 0.08 (s, 6H).

Preparation of (5): To the solution of 4 (18.0 g, 40.7 mmol) in dry THF/MeOD/D₂O=10/2/1 (145.0 mL) was added NaBD₄ (5.1 g, 122.1 mmol) three times during an hour at 50° C., the reaction mixture was stirred at r.t. for 2 hrs. After completion of reaction, adjusted pH value to 7 with CH₃COOD, after addition of water, the resulting mixture was extracted with EA (300.0 mL). The combined organic layer was washed with water and brine, dried over Na₂SO₄, concentrated to give a residue which was purified by Flash-Prep-HPLC with the following conditions (IntelFlash-1): Column, C18 silica gel; mobile phase, CH₃CN/H₂O (0.5% NH₄HCO₃)=2/3 increasing to CH₃CN/H₂O (0.5% NH₄HCO₃)=3/2 within 20 min, the eluted product was collected at CH₃CN/H₂O (0.5% NH₄HCO₃)=1/1; Detector, UV 254 nm. This resulted in to give 5 (10.4 g, 27.8 mmol, 68.3%) as a white solid. ESI-LCMS: m/z 375.2 [M+H]⁺; ¹H-NMR (400 MHz, DMSO-d₆): δ 11.36 (d, J=1 Hz, 1H), 7.92 (d, J=8 Hz, 1H), 5.83 (d, J=5 Hz, 1H), 5.67-5.65 (m, 1H), 5.19 (s, 1H), 4.30 (t, J=5 Hz, 1H), 3.85-3.83 (m, 2H), 0.88 (s, 9H), 0.09 (s, 6H).

Preparation of (6): To a stirred solution of 5 (10.4 g, 27.8 mmol) in pyridine (100.0 mL) was added DMTrCl (12.2 g, 36.1 mmol) at r.t., The reaction mixture was stirred at r.t. for 2.5 hrs, the reaction was quenched with water and extracted with EA (200.0 mL). The organic phase was evaporated to dryness under reduced pressure to give a residue which was purified by Flash-Prep-HPLC with the following conditions (IntelFlash-1): Column, C18 silica gel; mobile phase, CH₃CN/H₂O (0.5% NH₄HCO₃)=1/1 increasing to CH₃CN/H₂O (0.5% NH₄HCO₃)=1/0 within 20 min, the eluted product was collected at CH₃CN/H₂O (0.5% NH₄HCO₃)=1/0; Detector, UV 254 nm. This resulted in to give 6 (13.5 g, 19.9 mmol, 71.6%) as a white solid. ESI-LCMS: m/z 677.8 [M+H]⁺; ¹H-NMR (400 MHz, DMSO-d₆): δ 11.39 (d, J=1 Hz, 1H), 7.86 (d, J=4 Hz, 1H), 7.35-7.21 (m, 9H), 6.90-6.88 (m, 4H), 5.78 (d, J=2 Hz, 1H), 5.30-5.27 (m, 1H), 4.33-4.30 (m, 1H), 3.91 (d, J=7 Hz, 1H), 3.85-3.83 (m, 1H), 3.73 (s, 6H), 3.38 (s, 3H), 0.77 (s, 9H), 0.03 (s, 3H), 0.01 (s, 3H).

Preparation of (7): To a solution of 6 (13.5 g, 19.9 mmol) in THF (130.0 mL) was added 1 M TBAF solution (19.0 mL). The reaction mixture was stirred at r.t. for 1.5 hrs. LC-MS showed 6 was consumed completely. Water (500.0 mL) was added and extracted with EA (300.0 mL), the organic layer was washed with brine and dried over Na₂SO₄. Then the organic layer was concentrated to give a residue which was purified by Flash-Prep-HPLC with the following conditions (IntelFlash-1): Column, C18 silica gel; mobile phase, CH₃CN/H₂O (0.5% NH₄HCO₃)=2/3 increasing to CH₃CN/H₂O (0.5% NH₄HCO₃)=3/2 within 20 min, the eluted product was collected at CH₃CN/H₂O (0.5% NH₄HCO₃)=1/1; Detector, UV 254 nm. This resulted in to give 7 (10.9 g, 19.4 mmol, 97.5%) as a white solid. ESI-LCMS: m/z 563.6 [M+H]⁺; ¹H-NMR (400 MHz, DMSO-d₆): δ 11.39 (s, 1H), 7.23 (d, J=8 Hz, 1H), 7.73 (d, J=8 Hz, 1H), 7.36-7.23 (m, 9H), 6.90 (d, J=8 Hz, 4H), 5.81 (d, J=3 Hz, 1H), 5.30-5.28 (m, 1H), 5.22 (d, J=7 Hz, 1H), 4.20 (q, J=7 Hz, 1H), 3.93 (d, J=7 Hz, 1H), 3.81 (t, J=5 Hz, 1H), 3.74 (s, 6H), 3.41 (s, 3H).

Preparation of Example 23 monomer: To a suspension of 7 (10.9 g, 19.4 mmol) in DCM (100.0 mL) was added DCI (1.8 g, 15.7 mmol) and CEP[N(iPr)₂]₂ (6.1 g, 20.4 mmol). The mixture was stirred at r.t. for 1 h. LC-MS showed 7 was consumed completely. The mixture was washed with water twice and brine, dried over Na₂SO₄. Then concentrated to give a residue which was purified by Flash-Prep-HPLC with the following conditions (IntelFlash-1): Column, C18 silica gel; mobile phase, CH₃CN/H₂O (0.5% NH₄HCO₃)=1/1 increasing to CH₃CN/H₂O (0.5% NH₄HCO₃)=1/0 within 20 min, the eluted product was collected at CH₃CN/H₂O (0.5% NH₄HCO₃)=1/0; Detector, UV 254 nm. This resulted in to give Example 23 monomer (12.5 g, 14.5 mmol, 74.7%) as a white solid. ESI-LCMS: m/z 863.6 [M+H]⁺; ¹H-NMR (400 MHz, DMSO-d₆): δ 11.39 (s, 1H), 7.81-7.55 (m, 1H), 7.40-7.22 (m, 9H), 6.92-6.87 (m, 4H), 5.83-5.80 (m, 1H), 5.32-5.25 (m, 1H), 4.46-4.34 (m, 1H), 4.10-3.98 (m, 2H), 3.84-3.73 (m, 7H), 3.60-3.50 (m, 3H), 3.42, 3.40 (s, 3H), 2.78 (t, J=6 Hz, 1H), 2.62-2.59 (m, 1H), 2.07 (s, 1H), 1.17-0.96 (m, 12H); ³¹P-NMR (162 MHz, DMSO-d₆): δ 149.37, 149.06.

Example 24. Synthesis of Monomer

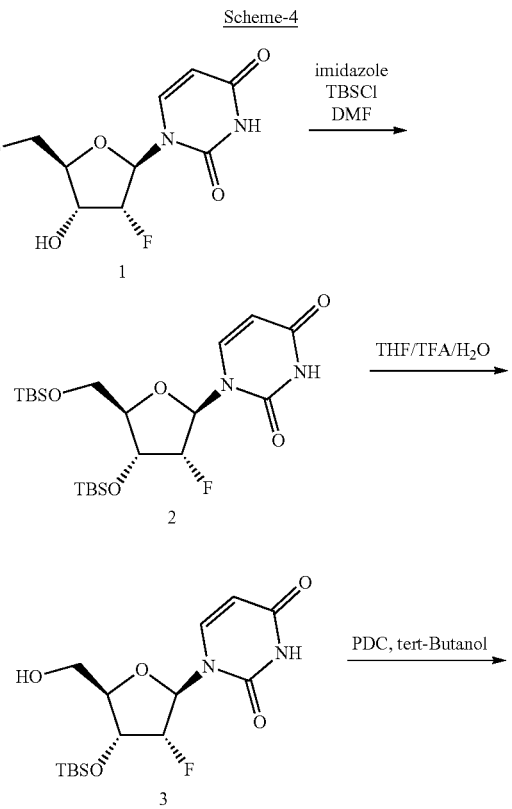

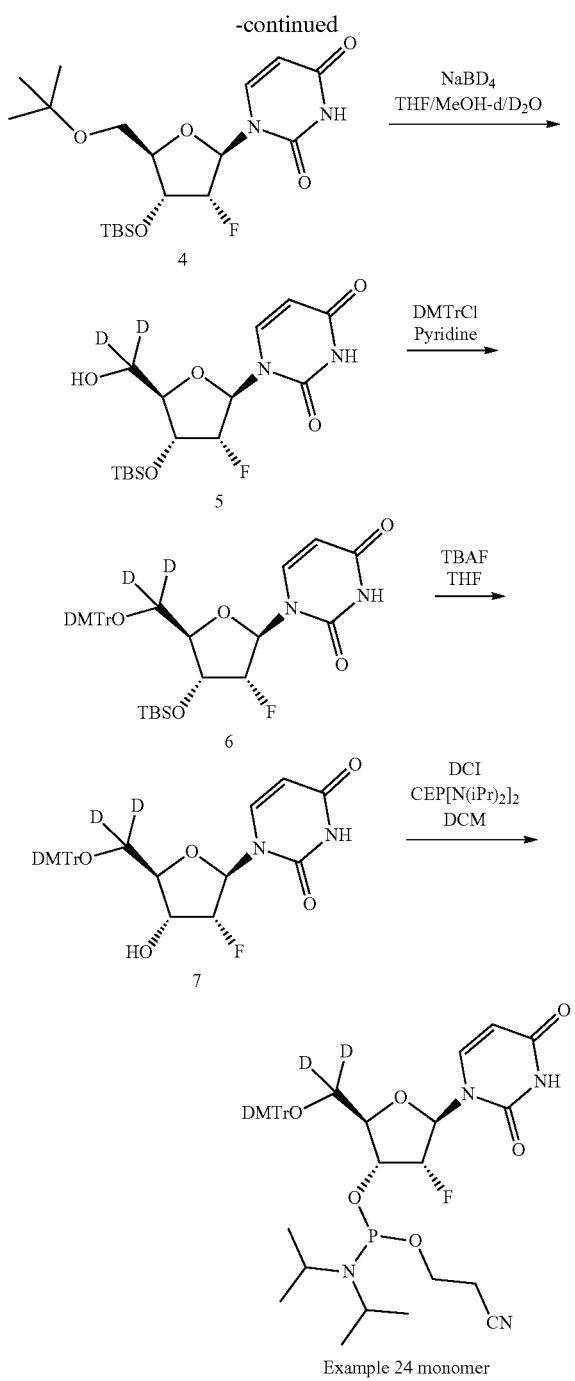

Example 24 monomer

Preparation of (2): To the solution of 1 (13.0 g, 52.8 mmol) in DMF (100 mL) was added imidazole (12.6 g, 184.8 mmol) and TBSCl (19.8 g, 132.0 mmol) at 0° C., and the reaction mixture was stirred at room temperature for 15 h under $N_2$ atmosphere. After addition of water, the resulting product was extracted with EA (500 mL). The combined organic layer was washed with water and brine, dried over $Na_2SO_4$, and concentrated to give the crude 2 (30.6 g) as a white solid which was used directly for next step. ESI-LCMS: m/z 475 [M+H]$^+$. WO2017106710A1

Preparation of (3): A solution of crude 2 (30.6 g) in a mixture solvent of TFA/$H_2O$=1/1 (100 mL) and THF (100 mL) was stirred at 0° C. for 30 min. After completion of reaction, the resulting mixture was added con.$NH_3$*$H_2O$ to pH=7.5, and then the mixture was extracted with EA (500 mL), the organic layer was washed with brine, dried over $Na_2SO_4$ and removed to give the residue was purified by Flash-Prep-HPLC with the following conditions (IntelFlash-1): Column, C18 silica gel; mobile phase, $CH_3CN/H_2O$ (0.5% $NH_4HCO_3$)=2/3 increasing to $CH_3CN/H_2O$ (0.5% $NH_4HCO_3$)=3/2 within 20 min, the eluted product was collected at $CH_3CN/H_2O$ (0.5% $NH_4HCO_3$)=1/1; Detector, UV 254 nm. This resulted in to give 3 (12.0 g, 33.3 mmol, 65.8% over two step) as a white solid. ESI-LCMS: m/z 361 [M+H]$^+$; $^1$H-NMR (400 MHz, DMSO-$d_6$): δ 11.39 (s, J=1 Hz, 1H, exchanged with $D_2O$), 7.88 (d, J=8 Hz, 1H), 5.91-5.86 (m, 1H), 5.66-5.62 (m, 1H), 5.21 (t, J=5.2 Hz, 1H, exchanged with $D_2O$), 5.18-5.03 (m, 1H), 4.37-4.29 (m, 1H), 3.87-3.83 (m, 1H), 3.78-3.73 (m, 1H), 3.56-3.51 (m, 1H), 0.87 (s, 9H), 0.09 (s, 6H). WO2017106710A1.

Preparation of (4): To the solution of 3 (11.0 g, 30.5 mmol) in dry DCM (60 mL) and DMF (15 mL) was added PDC (21. g, 61.0 mmol), tert-butyl alcohol (45 mL) and $Ac_2O$ (32 mL) at r.t under $N_2$ atmosphere. And the reaction mixture was stirred at r.t for 2 h. The solvent was removed to give a residue which was purified by silica gel column chromatography (eluent, PE:EA=4:1~2:1) to give a residue which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give 4 (9.5 g, 22.0 mmol, 72.3%) as a white solid. ESI-LCMS: m/z 431 [M+H]$^+$; $^1$H-NMR (400 MHz, DMSO-$d_6$): δ 11.45 (s, J=1 Hz, 1H, exchanged with $D_2O$), 7.93 (d, J=8.5 Hz, 1H), 6.02-5.97 (m, 1H), 5.76-5.74 (m, 1H), 5.29-5.14 (m, 1H), 4.59-4.52 (m, 1H), 4.29-4.27 (m, 1H), 1.46 (s, 9H), 0.89 (s, 9H), 0.12 (s, 6H).

Preparation of (5): To the solution of 4 (8.5 g, 19.7 mmol) in dry THF/MeOD/$D_2O$=10/2/1 (80 mL) was added $NaBD_4$ (2.5 g, 59.1 mmol) three times per an hour at 50° C. And the reaction mixture was stirred at r.t for 2 h. After completion of reaction, adjusted pH value to 7 with $CH_3COOD$, after addition of water, the resulting mixture was extracted with EA (300 mL). The combined organic layer was washed with water and brine, dried over $Na_2SO_4$, and concentrated to give a residue which was purified by Flash-Prep-HPLC with the following conditions (IntelFlash-1): Column, C18 silica gel; mobile phase, $CH_3CN/H_2O$ (0.5% $NH_4HCO_3$)=2/3 increasing to $CH_3CN/H_2O$ (0.5% $NH_4HCO_3$)=3/2 within 20 min, the eluted product was collected at $CH_3CN/H_2O$ (0.5% $NH_4HCO_3$)=1/1; Detector, UV 254 nm. This resulted in to give 5 (3.5 g, 9.7 mmol, 50.3%) as a white solid. ESI-LCMS: m/z 363 [M+H]$^+$; $^1$H-NMR (400 MHz, DMSO-$d_6$): δ 11.41 (s, J=1 Hz, 1H, exchanged with $D_2O$), 7.88 (d, J=8 Hz, 1H), 5.91-5.86 (m, 1H), 5.66-5.62 (m, 1H), 5.19 (t, J=5.2 Hz, 1H, exchanged with $D_2O$), 5.18-5.03 (m, 1H), 4.37-4.29 (m, 1H), 3.87-3.83 (m, 1H), 0.88 (s, 9H), 0.10 (s, 6H).

Preparation of (6): To a stirred solution of 5 (3.4 g, 9.7 mmol) in pyridine (35 mL) were added DMTrCl (3.4 g, 10.1 mmol) at r.t. And the reaction mixture was stirred at r.t for 2.5 h. With ice-bath cooling, the reaction was quenched with water and the product was extracted with EA (200 mL). The organic phase was evaporated to dryness under reduced pressure to give a residue which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at CH$_3$CN/H$_2$O (0.5% NH$_4$HCO$_3$)=1/0; Detector, UV 254 nm. This resulted in to give 6 (PCT Int. Appl., 2019173602), (5.5 g, 8.3 mmol, 85.3%) as a white solid. ESI-LCMS: m/z 665 [M+H]$^+$; $^1$H-NMR (400 MHz, DMSO-d$_6$): δ 11.50 (d, J=1 Hz, 1H, exchanged with D$_2$O), 7.92 (d, J=4 Hz, 1H), 7.44-7.27 (m, 9H), 6.96-6.93 (m, 4H), 5.94 (d, J=20.5 Hz, 1H), 5.39-5.37 (m, 1H), 5.32-5.17 (m, 1H), 4.60-4.51 (m, 1H), 4.01 (d, J=8.8 Hz, 1H), 3.80 (s, 6H), 0.80 (s, 9H), 0.09 (s, 3H), −0.05 (s, 3H).

Preparation of (7): To a solution of 6 (5.5 g, 8.3 mmol) in THF (50 mL) was added 1 M TBAF solution (9 mL). The reaction mixture was stirred at r.t. for 1.5 h. LC-MS showed 6 was consumed completely. Water (500 mL) was added. The product was extracted with EA (300 mL) and the organic layer was washed with brine and dried over Na$_2$SO$_4$. Then the organic layer was concentrated to give a residue which was purified by Flash-Prep-HPLC with the following conditions (IntelFlash-1): Column, C18 silica gel; mobile phase, CH$_3$CN/H$_2$O (0.5% NH$_4$HCO$_3$)=2/3 increasing to CH$_3$CN/H$_2$O (0.5% NH$_4$HCO$_3$)=3/2 within 20 min, the eluted product was collected at CH$_3$CN/H$_2$O (0.5% NH$_4$HCO$_3$)=1/1; Detector, UV 254 nm. This resulted in to give 7 (4.1 g, 7.5 mmol, 90.0%) as a white solid. ESI-LCMS: m/z 551 [M+H]$^+$; $^1$H-NMR (400 MHz, DMSO-d$_6$): δ 11.42 (s, 1H, exchanged with D$_2$O), 7.76 (d, J=8.2 Hz, 1H), 7.39-7.22 (m, 9H), 6.90-6.88 (m, 4H), 5.83 (d, J=20.5 Hz, 1H), 5.65 (d, J=7.0 Hz, 1H, exchanged with D$_2$O), 5.29 (d, J=7.2 Hz, 1H), 5.18-5.03 (m, 1H), 4.40-4.28 (m, 1H), 4.01 (d, J=8.8 Hz, 1H), 3.74 (s, 6H).

Preparation of Example 24 monomer: To a suspension of 7 (4.1 g, 7.5 mmol) in DCM (40 mL) was added DCI (0.7 g, 6.4 mmol) and CEP[N(iPr)$_2$]$_2$ (2.9 g, 9.7 mmol). The mixture was stirred at r.t. for 1 h. LC-MS showed 7 was consumed completely. The solution was washed with water twice and washed with brine and dried over Na$_2$SO$_4$. Then concentrated to give a residue which was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give Example 24 monomer (5.0 g, 6.6 mmol, 90.0%) as a white solid. ESI-LCMS: m/z 751 [M+H]$^+$; $^1$H-NMR (400 MHz, DMSO-d$_6$): δ 11.43 (s, 1H), 7.85-7.82 (m, 1H), 7.40-7.23 (m, 9H), 6.90-6.85 (m, 4H), 5.94-5.86 (m, 1H), 5.40-5.24 (m, 2H), 4.74-4.49 (m, 1H), 4.12-4.09 (m, 2H), 3.79-3.47 (m, 10H), 2.78-2.59 (m, 2H), 1.14-0.93 (m, 12H). $^{31}$P-NMR (162 MHz, DMSO-d$_6$): δ 149.67, 149.61, 149.32, 149.27.

Example 25. Synthesis of Monomer

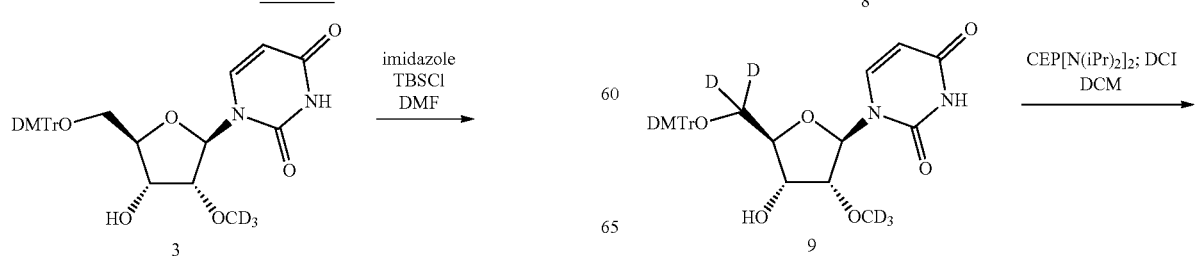

-continued

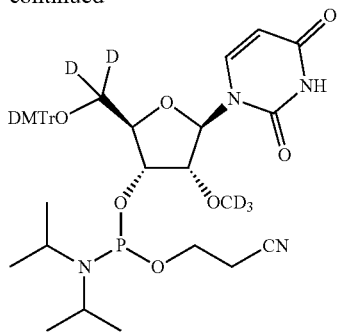

Preparation of (4): To the solution of 3 (14.3 g, 25.4 mmol, Scheme 2) in pyridine (150 mL) was added imidazole (4.5 g, 66.6 mmol) and TBSCl (6.0 g, 40.0 mmol) at 0° C., and the reaction mixture was stirred at room temperature for 15 h under $N_2$ atmosphere. After addition of water, the resulting mixture was extracted with EA (500 mL). The combined organic layer was washed with water and brine, dried over $Na_2SO_4$, and concentrated to give the crude 4 (18.0 g) as a white solid which was used directly for next step. ESI-LCMS: m/z 676 [M−H]⁻.

Preparation of (5): To the solution of crude 4 (18.0 g) in the solution of DCA (6%) in DCM (200 mL) was added TES (50 mL) at r.t, and the reaction mixture was stirred at room temperature for 5-10 min. After completion of reaction, the resulting mixture was added pyridine to pH=7, and then the solvent was removed and the residue was purified by Flash-Prep-HPLC with the following conditions (IntelFlash-1): Column, C18 silica gel; mobile phase, $CH_3CN/H_2O$ (0.5% $NH_4HCO_3$)=2/3 increasing to $CH_3CN/H_2O$ (0.5% $NH_4HCO_3$)=3/2 within 20 min, the eluted product was collected at $CH_3CN/H_2O$ (0.5% $NH_4HCO_3$)=1/1; Detector, UV 254 nm. This resulted in to give 5 (6.5 g, 17.2 mmol, 67.7% for two step) as a white solid. ESI-LCMS: m/z 376 [M+H]⁺; ¹H-NMR (400 MHz, DMSO-$d_6$): δ 7.92 (d, J=8 Hz, 1H), 5.82 (d, J=5.2 Hz, 1H), 5.68-5.63 (m, 1H), 5.20-5.15 (m, 1H), 4.32-4.25 (m, 1H), 3.87-3.80 (m, 2H), 3.69-3.61 (m, 1H), 3.57-3.49 (m, 1H), 0.88 (s, 9H), 0.09 (s, 6H).

Preparation of (6): To the solution of 5 (6.5 g, 17.2 mmol) in dry DCM (35 mL) and DMF (9 mL) was added PDC (12.9 g, 34.3 mmol), tert-butyl alcohol (34 mL) and $Ac_2O$ (17 mL) at r.t under $N_2$ atmosphere. And the reaction mixture was stirred at r.t for 2 hrs. The solvent was removed to give a residue which was purified by silica gel column chromatography (eluent, PE:EA=4:1~2:1) to give a residue which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give 6 (5.5 g, 12.3 mmol, 70.1%) as a white solid. ESI-LCMS: m/z 446 [M+H]⁺; ¹H-NMR (400 MHz, DMSO-$d_6$): δ=11.29 (s, 1H), 7.91 (d, J=8.4 Hz, 1H), 5.85 (d, J=6.4 Hz, 1H), 5.71-5.61 (m, 1H), 4.35-4.28 (m, 1H), 4.12 (d, J=3.2 Hz, 1H), 3.75-3.67 (m, 1H), 1.33 (s, 9H), 0.76 (s, 9H), 0.00 (d, J=1.6 Hz, 6H).

Preparation of (7): To the solution of 6 (5.4 g, 12.1 mmol) in THF/MeOD/$D_2O$=10/2/1 (44 mL) was added $NaBD_4$ (1.5 g, 36.3 mmol) at r.t. and the reaction mixture was stirred at 50° C. for 2 hrs. After completion of reaction, adjusted pH value to 7 with $CH_3COOD$. Water was added, the resulting mixture was extracted with EA (500 mL). The combined organic layer was washed with water and brine, dried over $Na_2SO_4$, and concentrated to give a residue which was purified by Flash-Prep-HPLC with the following conditions (IntelFlash-1): Column, C18 silica gel; mobile phase, $CH_3CN/H_2O$ (0.5% $NH_4HCO_3$)=2/3 increasing to $CH_3CN/H_2O$ (0.5% $NH_4HCO_3$)=3/2 within 20 min, the eluted product was collected at $CH_3CN/H_2O$ (0.5% $NH_4HCO_3$)=1/1; Detector, UV 254 nm. This resulted in to give 7 (2.6 g, 6.8 mmol, 56.1%) as a white solid. ESI-LCMS: m/z 378 [M+H]⁺; ¹H-NMR (400 MHz, DMSO-$d_6$): δ 11.35 (s, 1H), 7.91 (d, J=8.0 Hz, 1H), 5.82 (d, J=5.2 Hz, 1H), 5.69-5.60 (m, 1H), 5.14 (s, 1H), 4.34-4.20 (m, 1H), 3.88-3.76 (m, 2H), 0.87 (s, 9H), 0.08 (s, 6H).

Preparation of (8): To a stirred solution of 7 (2.6 g, 6.8 mmol) in pyridine (30 mL) were added DMTrCl (3.5 g, 10.3 mmol) at r.t. And the reaction mixture was stirred at r.t. for 2.5 hrs. With ice-bath cooling, the reaction was quenched with water and the product was extracted into EA (200 mL). The organic phase was evaporated to dryness under reduced pressure to give a residue which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give 8 (4.3 g, 6.3 mmol, 90.1%) as a white solid. ESI-LCMS: m/z 678 [M−H]⁻; ¹H-NMR (400 MHz, DMSO-$d_6$): δ 11.39 (s, 1H), 7.86 (d, J=8.0 Hz, 1H), 7.42-7.17 (m, 9H), 6.96-6.83 (m, 4H), 5.82-5.69 (m, 2H), 5.29 (d, J=8.4 Hz, 1H), 4.36-4.25 (m, 1H), 3.90 (d, J=7.2 Hz, 1H), 3.86-3.80 (m, 1H), 3.73 (s, 6H), 0.75 (s, 9H), 0.02 (s, 3H), −0.04 (s, 3H).

Preparation of (9): To a solution of 8 (4.3 g, 6.3 mmol) in THF (45 mL) was added 1 M TBAF solution (6 mL). The reaction mixture was stirred at r.t. for 1.5 hrs. LCMS showed 8 was consumed completely. Water (200 mL) was added. The product was extracted with EA (200 mL) and the organic layer was washed with brine and dried over $Na_2SO_4$. Then the organic layer was concentrated to give a residue which was purified by Flash-Prep-HPLC with the following conditions (IntelFlash-1): Column, C18 silica gel; mobile phase, $CH_3CN/H_2O$ (0.5% $NH_4HCO_3$)=2/3 increasing to $CH_3CN/H_2O$ (0.5% $NH_4HCO_3$)=3/2 within 20 min, the eluted product was collected at $CH_3CN/H_2O$ (0.5% $NH_4HCO_3$)=1/1; Detector, UV 254 nm. This resulted in to give 8 (3.5 g, 6.1 mmol, 90.1%) as a white solid. ESI-LCMS: m/z 678 [M−H]⁻; ¹H-NMR (400 MHz, DMSO-$d_6$): δ 11.38 (d, J=2.0 Hz, 1H), 7.23 (d, J=8.0 Hz, 1H), 7.41-7.19 (m, 9H), 6.94-6.85 (m, 4H), 5.81 (d, J=4.0 Hz, 1H), 5.33-5.26 (m, 1H), 5.21 (d, J=7.2 Hz, 1H), 4.06-3.90 (m, 2H), 3.83-3.77 (m, 1H), 3.74 (s, 6H).

Preparation of Example 25 monomer: To a suspension of 9 (2.1 g, 3.7 mmol) in DCM (20 mL) was added DCI (373 mg, 3.1 mmol) and CEP[N(iPr)$_2$]$_2$ (1.3 g, 4.4 mmol). The mixture was stirred at r.t. for 1 h. LC-MS showed 9 was consumed completely. The solution was washed with water twice and washed with brine and dried over $Na_2SO_4$. Then concentrated to give a residue which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give Example 25 monomer (2.2 g, 3.5 mmol, 80%) as a white solid. ESI-LCMS: m/z 766 [M+H]⁺; ¹H-NMR (400 MHz, ACN-$d_3$): δ 9.65-8.86 (m, 1H, exchanged with $D_2O$), 7.93-7.68 (m, 1H), 7.52-7.19 (m, 9H), 6.94-6.78 (m, 4H), 5.95-5.77 (m, 1H), 5.31-5.17

(m, 1H), 4.61-4.37 (m, 1H), 4.20-4.07 (m, 1H), 4.01-3.51 (m, 10H), 2.74-2.59 (m, 1H), 2.57-2.43 (m, 1H), 1.27-1.10 (m, 9H), 1.09-0.95 (m, 3H). $^{31}$P-NMR (162 MHz, ACN-d$_3$): δ=149.88, 149.55.

Example 26. Synthesis of Monomer

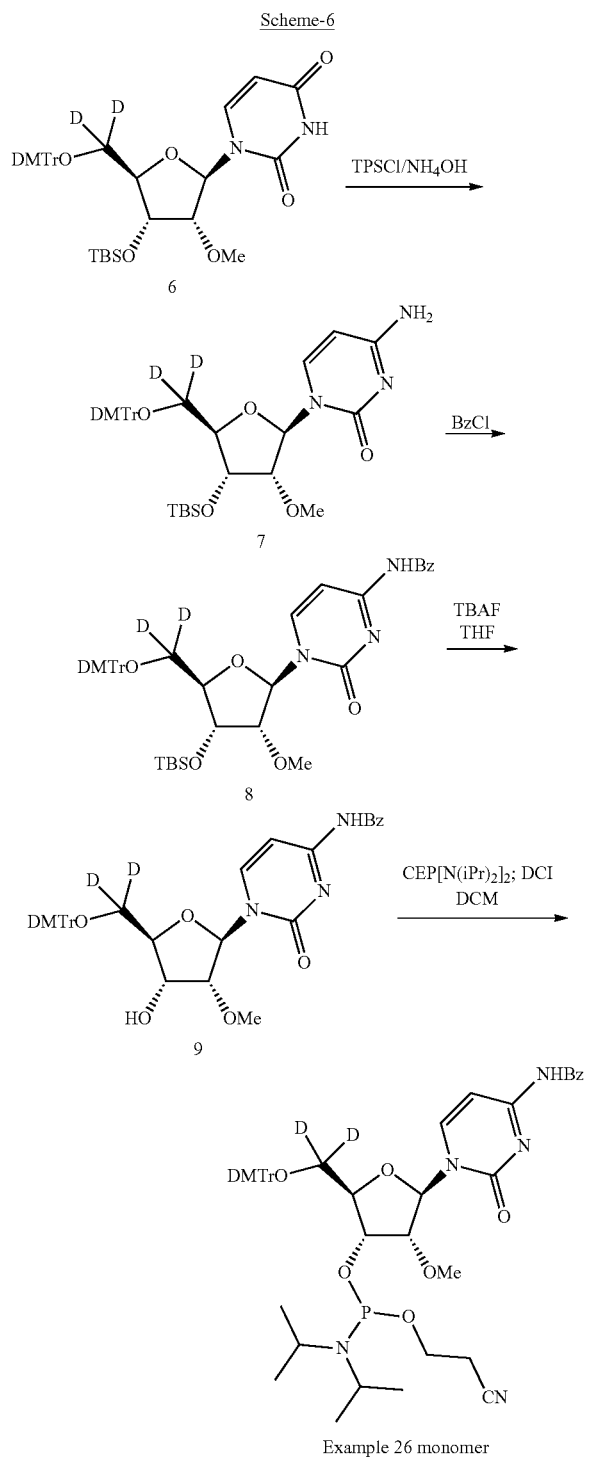

Preparation of (7): To a solution of 6 (17 g, 25.1 mmol, Scheme 3) in ACN (170 mL) was added DMAP (6.13 g, 50.3 mmol) and TEA (5.1 g, 50.3 mmol, 7.2 mL), Then added TPSCl (11.4 g, 37.7 mmol) at 0° C. under N$_2$ atmosphere and the mixture was stirred at r.t. for 3 h under N$_2$ atmosphere. Then con. NH$_3$.H$_2$O (27.3 g, 233.7 mmol) was added at r.t. and the mixture was stirred at r.t. for 16 h. The reaction was quenched with water and the product was extracted with EA (200 mL). The organic phase was concentrated to give the crude 7 (17.0 g) as a white solid which was used directly for next step.

Preparation of (8): To a stirred solution of 7 (17.0 g, 25.1 mmol) in pyridine (170 mL) were added BzCl (4.3 g, 30.1 mmol) 0° C. under N$_2$ atmosphere. And the reaction mixture was stirred at r.t for 2.5 h. With ice-bath cooling, the reaction was quenched with water and the product was extracted with EA (200 mL). The organic phase was evaporated to dryness under reduced pressure to give a residue which was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give 8 (19.0 g, 24.3 mmol, 95.6% over two step) as a white solid. ESI-LCMS: m/z 780 [M+H]$^+$.

Preparation of (9): To a solution of 8 (19.0 g, 24.3 mmol) in THF (190 mL) was added 1 M TBAF solution (24 mL). The reaction mixture was stirred at r.t. for 1.0 h. LC-MS showed 8 was consumed completely. Water (500 mL) was added. The product was extracted with EA (300 mL) and the organic layer was washed with brine and dried over Na$_2$SO$_4$. Then the organic layer was concentrated to give a residue which was purified by Flash-Prep-HPLC with the following conditions (IntelFlash-1): Column, C18 silica gel; mobile phase, CH$_3$CN/H$_2$O (0.5% NH$_4$HCO$_3$)=2/3 increasing to CH$_3$CN/H$_2$O (0.5% NH$_4$HCO$_3$)=3/2 within 20 min, the eluted product was collected at CH$_3$CN/H$_2$O (0.5% NH$_4$HCO$_3$)=1/1; Detector, UV 254 nm. This resulted in to give 9 (15.2 g, 23.1 mmol, 95.5%) as a white solid. ESI-LCMS: m/z 666 [M+H]$^+$; $^1$H-NMR (400 MHz, DMSO-d$_6$): δ 11.28 (s, 1H), 8.41 (m, 1H), 8.00-7.99 (m, 2H), 7.63-7.15 (m, 13H), 6.93-6.89 (m, 4H), 5.87 (s, 1H), 5.20 (d, J=7.4 Hz, 1H), 4.30 (m, 1H), 4.02 (m, 1H), 3.75 (s, 7H), 3.53 (s, 3H).

Preparation of Example 26 monomer: To a suspension of 9 (10.0 g, 15.0 mmol) in DCM (100 mL) was added DCI (1.5 g, 12.7 mmol) and CEP[N(iPr)$_2$]$_2$ (5.4 g, 18.0 mmol). The mixture was stirred at r.t. for 1 h. LC-MS showed 9 was consumed completely. The solution was washed with water twice and washed with brine and dried over Na$_2$SO$_4$. Then concentrated to give a residue which was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give Example 26 monomer (11.5 g, 13.5 mmol, 90.7%) as a white solid. ESI-LCMS: m/z 866 [M+H]$^+$; $^1$H-NMR (400 MHz, DMSO-d$_6$): δ=11.28 (s, 1H), 8.48-8.41 (m, 1H), 8.00-7.99 (m, 2H), 7.63-7.11 (m, 13H), 6.93-6.89 (m, 4H), 5.92 (m, 1H), 4.55-4.44 (m, 1H), 4.17 (m, 1H), 3.95 (m, 1H), 3.80-3.62 (m, 7H), 3.57-3.46 (m, 5H), 3.32 (s, 1H), 2.78 (m, 1H), 2.62-2.59 (m, 1H), 1.19-0.94 (m, 12H); $^{31}$P-NMR (162 MHz, DMSO-d$_6$): δ=149.52, 148.82.

Example 27. Synthesis of Monomer

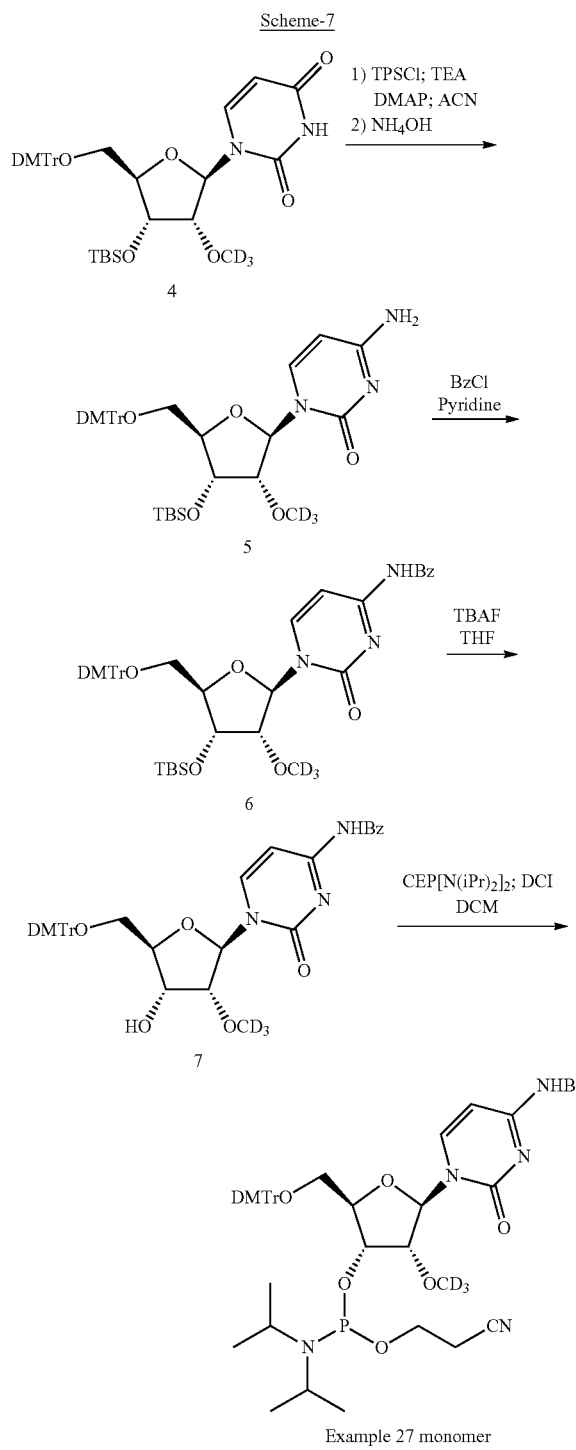

Preparation of (5): To the solution of 4 (18.8 g, Scheme 5) in dry ACN (200 mL) was added TPSCl (16.8 g, 65.2 mmol) and TEA (5.6 g, 65.2 mmol) and DMAP (6.8 g, 65.2 mmol), and the reaction mixture was stirred at room temperature for 3.5 hrs under $N_2$ atmosphere. After addition of water, the resulting mixture was extracted with EA (300 mL). The combined organic layer was washed with water and brine, dried over $Na_2SO_4$, and concentrated to give the crude 5 (22.0 g) as a white solid which was used directly for next step. ESI-LCMS: m/z 677 $[M-H]^+$.

Preparation of (6): To a solution of 5 (22.0 g) in pyridine (150 mL) was added BzCl (6.8 g, 48.9 mmol) under ice bath. The reaction mixture was stirred at r.t. for 2.5 hrs. LCMS showed 5 was consumed. The mixture was diluted with EA and water was added. The product was extracted with EA. The crude was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 25 min, the eluted product was collected at $CH_3CN/H_2O$ (0.5% $NH_4HCO_3$)=1/0; Detector, UV 254 nm. This resulted in to give the crude 6 (20.8 g, 26.7 mmol, 82% yield over two steps) as a white solid. ESI-LCMS: m/z 781 $[M+H]^+$; $^1$H-NMR (400 MHz, DMSO-$d_6$): δ 11.30 (s, 1H), 8.55 (d, J=8.0 Hz, 1H), 8.00-7.98 (m, 2H), 7.74-7.66 (m, 1H), 7.60-7.50 (m, 2H), 7.47-7.31 (m, 4H), 7.30-7.2 (m, 5H), 7.20-7.1 (m, 1H), 6.91 (d, J=7.4 Hz, 4H), 5.91-5.86 (AB, J=20.0 Hz, 1H), 4.30 (d, J=8.0 Hz, 1H), 3.87-3.78 (s, 1H), 3.78-3.70 (m, 6H), 3.62-3.51 (m, 1H), 3.28-3.2 (m, 1H), 2.15-2.05 (m, 3H), 0.73 (s, 9H), 0.00 (m, 6H).

Preparation of (7): To a solution of 6 (20.8 g, 26.7 mmol) in THF (210 mL) was added 1 M TBAF solution (32 mL). The reaction mixture was stirred at r.t. for 1.5 hrs. LCMS showed 6 was consumed completely. Water (600 mL) was added. The product was extracted with EA (400 mL) and the organic layer was washed with brine and dried over $Na_2SO_4$. Then the organic layer was concentrated to give a residue which was purified by Flash-Prep-HPLC with the following conditions (IntelFlash-1): Column, C18 silica gel; mobile phase, $CH_3CN/H_2O$ (0.5% $NH_4HCO_3$)=2/3 increasing to $CH_3CN/H_2O$ (0.5% $NH_4HCO_3$)=3/2 within 20 min, the eluted product was collected at $CH_3CN/H_2O$ (0.5% $NH_4HCO_3$)=1/1; Detector, UV 254 nm. This resulted in to give 7 (12.4 g, 18.6 mmol, 70%) as a white solid. ESI-LCMS: m/z 667 $[M+H]^+$; $^1$H-NMR (400 MHz, DMSO-$d_6$): δ 11.03 (m, 1H), 8.51-8.48 (m, 1H), 8.08-7.95 (m, 2H), 7.63-7.54 (m, 1H), 7.52-7.19 (m, 9H), 7.16-7.07 (m, 1H), 6.94-6.89 (m, 3H), 5.95-5.87 (m, 1H), 5.31-5.17 (m, 1H), 4.61-4.37 (m, 1H), 4.20-4.07 (m, 1H), 3.82-3.47 (m, 7H), 2.57-2.42 (m, 2H).

Preparation of Example 27 monomer: To a suspension of 7 (12.4 g, 18.6 mmol) in DCM (120 mL) was added DCI (1.7 g, 15.8 mmol) and CEP[N(iPr)$_2$]$_2$ (7.3 g, 24.2 mmol). The mixture was stirred at r.t. for 2 hrs. LC-MS showed 7 was consumed completely. The solution was washed with water twice and washed with brine and dried over $Na_2SO_4$. Then concentrated to give a residue which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give Example 27 monomer (13.6 g, 15.7 mmol, 84.0%) as a white solid. ESI-LCMS: m/z 867 $[M+H]^+$; $^1$H-NMR (400 MHz, DMSO-$d_6$): δ 11.03 (m, 1H), 8.51-8.48 (m, 1H), 8.08-7.95 (m, 2H), 7.63-7.54 (m, 1H), 7.52-7.19 (m, 9H), 7.16-7.07 (m, 1H), 6.94-6.89 (m, 3H), 5.95-5.87 (m, 1H), 5.31-5.17 (m, 1H), 4.61-4.37 (m, 1H), 4.20-4.07 (m, 1H), 3.82-3.47 (m, 10H), 2.74-2.59 (m, 1H), 2.57-2.43 (m, 1H), 1.27-1.10 (m, 9H), 1.09-0.95 (m, 3H). $^{31}$P-NMR (162 MHz, DMSO-$d_6$): δ 149.59, 148.85.

Example 28. Synthesis of Monomer

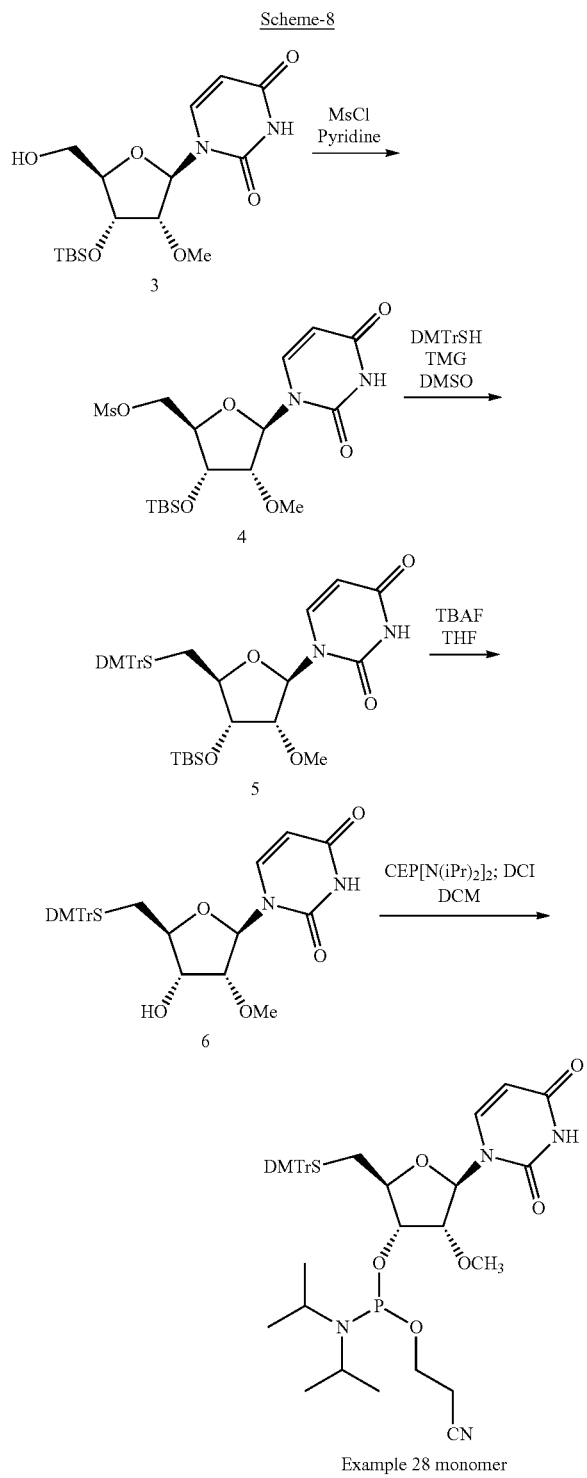

Example 28 monomer

Preparation of (4): To a solution of 3 (13.1 g, 35.2 mmol, Scheme 3) in pyridine (130 mL) was added MsCl (4.8 g, 42.2 mmol) under −10~0° C. The reaction mixture was stirred at r.t. for 2.5 h under $N_2$ atmosphere. TLC (DCM/MeOH=15:1) showed the reaction was consumed. The mixture was diluted with EA and water was added. The product was extracted with EA. The organic layer was washed with brine and dried over $Na_2SO_4$ and concentrated to give the crude. This resulted in to give the product 4 (14.2 g) which was used directly for the next step. ESI-LCMS: m/z 451 $[M+H]^+$; $^1$H-NMR (400 MHz, DMSO-$d_6$) δ 11.43 (m, 1H), 7.67-7.65 (m, 1H), 5.90-5.80 (m, 1H), 5.75-5.64 (m, 1H), 4.52-4.21 (m, 3H), 4.12-3.90 (m, 2H), 3.48-3.21 (m, 6H), 0.95-0.78 (s, 9H), 0.13-0.03 (s, 6H).

Preparation of (5): To a solution of 4 (14.2 g) in DMSO (200 mL) was added DMTrSH (19.6 g, 63.2 mmol) and tetramethylguanidine (5.1 g, 47.4 mmol) at r.t. The reaction mixture was stirred at r.t. for 3.5 h under $N_2$ atmosphere. LCMS showed 4 the reaction was consumed. The mixture was diluted with EA and water was added. The product was extracted with EA. The organic layer was washed with brine and dried over $Na_2SO_4$ and concentrated to give the crude. The crude was purified by silica gel column ($SiO_2$, PE/EA=10:1~1:1) to give 5 (14.2 g, 20.6 mmol, 58.5% yield over two steps) as a white solid. ESI-LCMS: m/z 689 $[M+H]^-$; $^1$H-NMR (400 MHz, DMSO-$d_6$) δ 11.39 (m, 1H), 7.63-7.61 (d, J=8.0 Hz, 1H), 7.45-7.1 (m, 9H), 6.91-6.81 (m, 4H), 5.80-5.70 (m, 2H), 4.01-3.91 (m, 1H), 3.85-3.78 (m, 1H), 3.78-3.65 (m, 6H), 3.60-3.51 (m, 1H), 3.43-3.2 (m, 3H), 2.50-2.32 (m, 2H), 0.95-0.77 (s, 9H), −0.00-0.02 (s, 6H).

Preparation of (6): To a solution of 5 (14.2 g, 20.6 mmol) in THF (140 mL) was added 1 M TBAF solution (20 mL). The reaction mixture was stirred at r.t. under $N_2$ atmosphere for 2.5 h. LCMS showed 5 was consumed completely. Water was added. The product was extracted with EA and the organic layer was washed with brine and dried over $Na_2SO_4$. Then the organic layer was concentrated to give a residue which was purified by Flash-Prep-HPLC with the following conditions (IntelFlash-1): Column, C18 silica gel; mobile phase, $CH_3CN/H_2O$ (0.5% $NH_4HCO_3$)=2/3 increasing to $CH_3CN/H_2O$ (0.5% $NH_4HCO_3$)=3/2 within 20 min, the eluted product was collected at $CH_3CN/H_2O$ (0.5% $NH_4HCO_3$)=1/1; Detector, UV 254 nm. This resulted in to give 6 (10.5 g, 18.2 mmol, 88.5%) as a white solid. ESI-LCMS: m/z 576 $[M+H]^+$; $^1$H-NMR (400 MHz, DMSO-$d_6$) δ 11.38 (m, 1H), 7.56-7.54 (d, J=8.0 Hz, 1H), 7.45-7.1 (m, 9H), 6.91-6.81 (m, 4H), 5.80-5.70 (m, 2H), 4.05-4.00 (m, 1H), 3.81-3.79 (m, 1H), 3.74 (m, 2H), 3.78-3.65 (m, 6H), 3.60-3.51 (m, 1H), 3.43-3.2 (m, 3H), 2.40-2.32 (m, 1H).

Preparation of Example 28 monomer: To a suspension of 9 (10.5 g, 18.2 mmol) in DCM (100 mL) was added DCI (1.7 g, 15.5 mmol) and $CEP[N(iPr)_2]_2$ (7.2 g, 23.7 mmol). The mixture was stirred at r.t. for 1 h. LC-MS showed 9 was consumed completely. The solution was washed with water twice and washed with brine and dried over $Na_2SO_4$. Then concentrated to give a residue which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give Example 28 monomer (12.5 g, 16.1 mmol, 88%) as a white solid. ESI-LCMS: m/z 776 $[M+H]^+$; $^1$H-NMR (400 MHz, DMSO-$d_6$) δ 11.41 (m, 1H), 7.64-7.59 (m, 1H), 7.40-7.25 (m, 4H), 7.25-7.10 (m, 5H), 6.89-6.86 (m, 4H), 5.72-5.67 (m, 2H), 4.02-4.00 (m, 2H), 3.76-3.74 (m, 8H), 3.74-3.73 (m, 3H), 3.51-3.49 (d, J=8 Hz, 1H), 3.33-3.29 (m, 1H), 2.77-2.73 (m, 1H), 2.63-2.60 (m, 1H), 2.50-2.47 (m, 1H), 1.12-0.99 (m, 12H). $^{31}$P-NMR (162 MHz, DMSO-$d_6$): δ 148.92, 148.84.

Example 29. Synthesis of Monomer

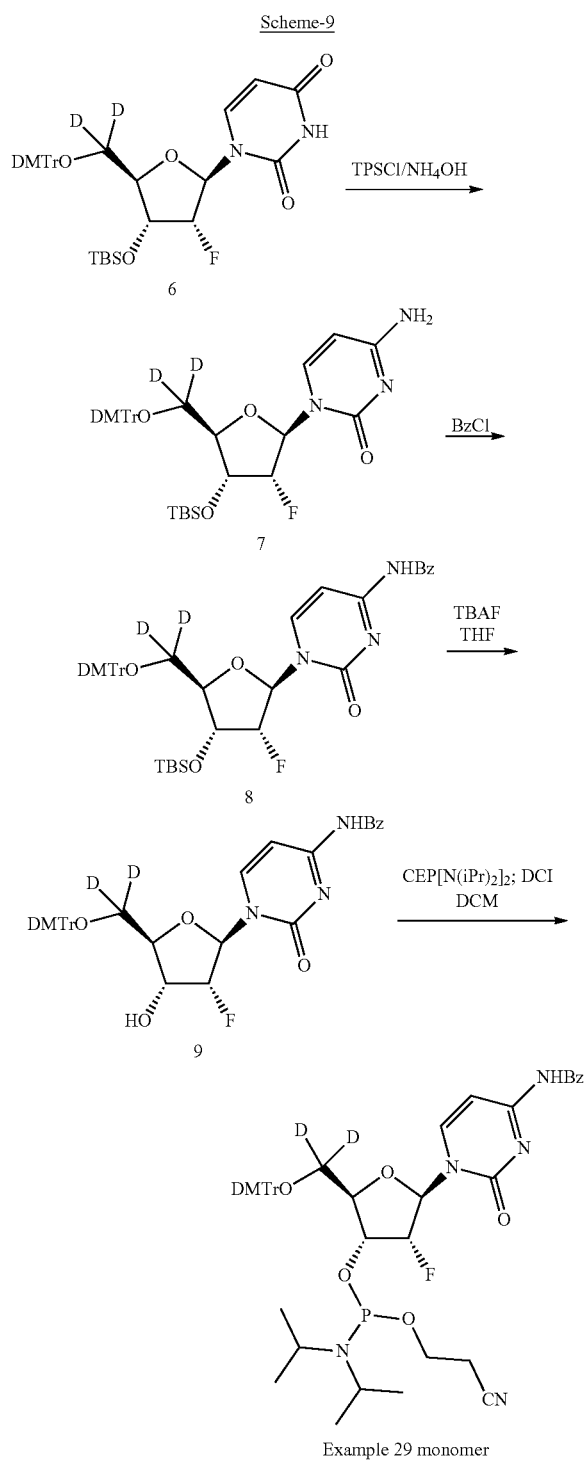

Example 29 monomer

Preparation of (7): To a solution of 6 (16 g, 24.1 mmol, Scheme 4) in ACN (160 mL) was added DMAP (5.9 g, 48.2 mmol) and TEA (4.8 g, 48.2 mmol), then added TPSCl (10.9 g, 36.1 mmol) at 0° C. under $N_2$ atmosphere and the mixture was stirred at r.t. for 5 hrs under $N_2$ atmosphere. Then con. $NH_3 \cdot H_2O$ (30 mL) was added at r.t. and the mixture was stirred at r.t. for 16 h. The reaction was quenched with water and the product was extracted with EA (200 mL). The organic phase was concentrated to give the crude 7 (16.0 g) as a white solid which was used directly for next step.

Preparation of (8): To a stirred solution of 7 (16.0 g, 24.1 mmol) in pyridine (160 mL) were added BzCl (4.1 g, 28.9 mmol) 0° C. under $N_2$ atmosphere. And the reaction mixture was stirred at r.t. for 2.5 h. With ice-bath cooling, the reaction was quenched with water and the product was extracted with EA (200 mL). The organic phase was evaporated to dryness under reduced pressure to give a residue which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give 8 (18.0 g, 23.4 mmol, 97.0%) as a white solid. ESI-LCMS: m/z 768 [M+H]$^+$; $^1$H-NMR (400 MHz, DMSO-d$_6$): δ 11.31 (s, 1H), 8.47 (d, J=7.2 Hz, 1H), 7.99 (d, J=7.6 Hz, 2H), 7.65-7.16 (m, 13H), 6.92 (d, J=8.8 Hz, 4H), 6.01 (d, J=18.4 Hz, 1H), 5.18-5.04 (dd, 1H), 4.58-4.52 (m, 1H), 4.07 (d, J=9.6 Hz, 1H), 3.75 (s, 6H), 0.73 (s, 9H), 0.05 (s, 3H), −0.06 (s, 3H).

Preparation of (9): To a solution of 8 (18.0 g, 23.4 mmol) in THF (180 mL) was added 1 M TBAF solution (23 mL). The reaction mixture was stirred at r.t. for 1.5 h. LC-MS showed 8 was consumed completely. Water (500 mL) was added. The product was extracted with EA (300 mL) and the organic layer was washed with brine and dried over $Na_2SO_4$. Then the organic layer was concentrated to give a residue which was purified by Flash-Prep-HPLC with the following conditions (IntelFlash-1): Column, C18 silica gel; mobile phase, $CH_3CN/H_2O$ (0.5% $NH_4HCO_3$)=2/3 increasing to $CH_3CN/H_2O$ (0.5% $NH_4HCO_3$)=3/2 within 20 min, the eluted product was collected at $CH_3CN/H_2O$ (0.5% $NH_4HCO_3$)=1/1; Detector, UV 254 nm. This resulted in to give 7 (13.7 g, 21.1 mmol, 90.5%) as a white solid. ESI-LCMS: m/z 654.2 [M+H]$^+$; $^1$H-NMR (400 MHz, DMSO-d$_6$): δ 11.31 (s, 1H), 8.35 (d, J=7.4 Hz, 1H), 8.01 (m, 2H), 7.65-7.16 (m, 13H), 6.92 (d, J=8.8 Hz, 4H), 5.94 (d, J=18.0 Hz, 1H), 5.71 (d, J=7.0 Hz, 1H), 5.12-4.98 (dd, 1H), 4.51-4.36 (m, 1H), 4.09 (d, J=9.6 Hz, 1H), 3.75 (s, 6H).

Preparation of Example 29 monomer: To a suspension of 9 (10.6 g, 16.2 mmol) in DCM (100 mL) was added DCI (1.6 g, 13.7 mmol) and CEP[N(iPr)$_2$]$_2$ (5.8 g, 19.4 mmol). The mixture was stirred at r.t. for 1 h. LC-MS showed 9 was consumed completely. The solution was washed with water twice and washed with brine and dried over $Na_2SO_4$. Then concentrated to give a residue which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give Example 29 monomer (10.5 g, 14.5 mmol, 75.9%) as a white solid. ESI-LCMS: m/z 854.3 [M+H]$^+$; $^1$H-NMR (400 MHz, DMSO-d$_6$): δ 11.31 (s, 1H), 8.41-8.37 (m, 1H), 8.01 (d, J=7.7 Hz, 2H), 7.65-7.16 (m, 13H), 6.92-6.88 (m, 4H), 6.06-5.98 (m, 1H), 5.33-5.15 (m, 1H), 4.78-4.58 (m, 1H), 4.23-4.19 (m, 1H), 3.81-3.73 (m, 6H), 3.60-3.50 (m, 3H), 3.32 (s, 1H), 2.76 (t, J=6.0 Hz, 1H), 2.60 (t, J=5.8 Hz, 1H), 1.15-0.94 (m, 12H); $^{31}$P-NMR (162 MHz, DMSO-d$_6$): δ 150.23, 150.18, 149.43, 149.38.

Example 30. Synthesis of Monomer

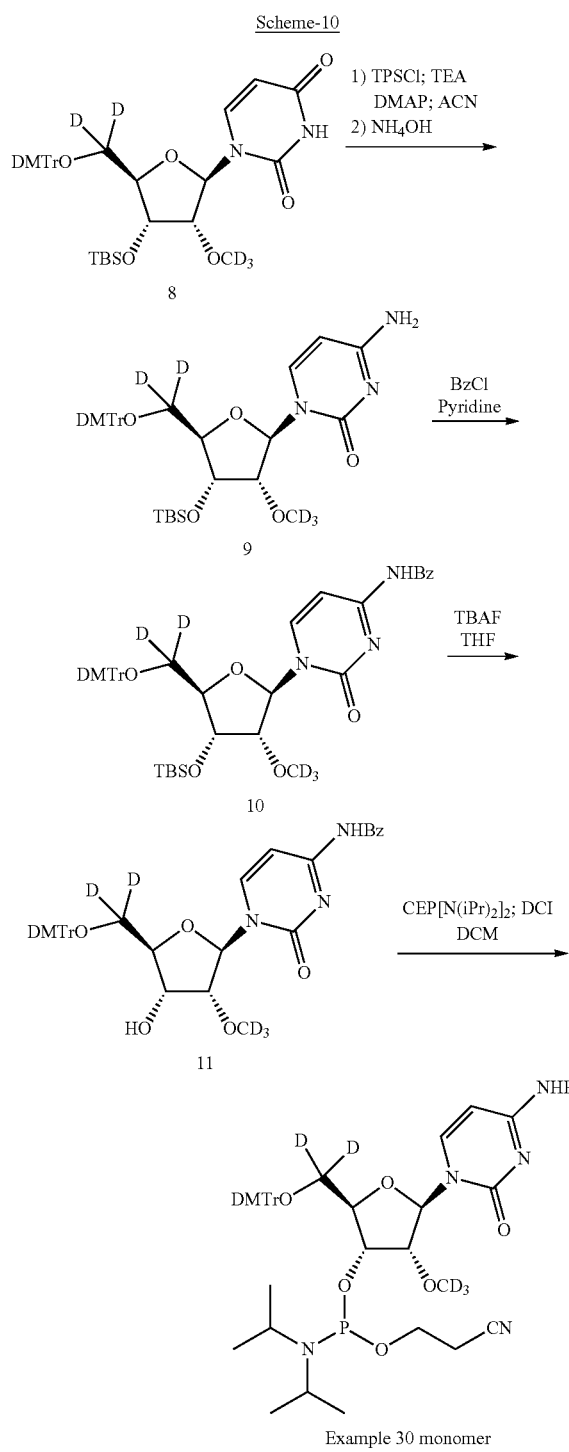

Preparation of (9): To a solution of 8 (18.8 g, 26.4 mmol, Scheme 5) in ACN (200 mL) was added TPSCl (16.8 g, 55.3 mmol) and DMAP (5.6 g, 55.3 mmol) and TEA (6.8 g, 55.3 mmol). The reaction mixture was stirred at r.t. for 3.5 hrs. LCMS showed the reaction was consumed. The mixture was diluted with con. NH$_4$OH (28 mL). The mixture was diluted with water and EA. The product was extracted with EA. The organic layer was washed with brine and dried over Na$_2$SO$_4$ and concentrated to give the crude 9 (18.5 g) which was used directly for the next step.

Preparation of (10): To a solution of 9 (18.8 g, 27.69 mmol) in pyridine (200 mL) was added BzCl (5.8 g, 41.5 mmol) under ice bath. The reaction mixture was stirred at r.t. for 2.5 hrs. LCMS showed 9 was consumed. The mixture was diluted with EA and water was added. The product was extracted with EA. The crude was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 25 min, the eluted product was collected at CH$_3$CN/H$_2$O (0.5% NH$_4$HCO$_3$)=1/0; Detector, UV 254 nm. This resulted in to give 10 (19.8 g, 25.3 mmol, 91% yield) as a white solid. ESI-LCMS: m/z 783 [M−H]$^-$; $^1$H-NMR (400 MHz, DMSO-d$_6$): δ 11.29 (d, J=2.0 Hz, 1H), 8.42 (d, J=8.0 Hz, 1H), 8.02-8.00 (m, 2H), 7.64-7.62 (m, 1H), 7.60-7.41 (m, 2H), 7.47.41-7.19 (m, 9H), 6.94-6.85 (m, 4H), 5.81 (d, J=4.0 Hz, 1H), 5.33-5.26 (m, 1H), 5.21 (d, J=7.2 Hz, 1H), 4.06-3.90 (m, 2H), 3.83-3.77 (m, 1H), 3.74 (s, 6H).

Preparation of (11): To a solution of 10 (18.8 g, 26.4 mmol) in THF (190 mL) was added 1 M TBAF solution (28 mL). The reaction mixture was stirred at r.t. for 1.5 hrs. LCMS showed 10 was consumed completely. Water (200 mL) was added. The product was extracted with EA (200 mL) and the organic layer was washed with brine and dried over Na$_2$SO$_4$. Then the organic layer was concentrated to give a residue which was purified by Flash-Prep-HPLC with the following conditions (IntelFlash-1): Column, C18 silica gel; mobile phase, CH$_3$CN/H$_2$O (0.5% NH$_4$HCO$_3$)=2/3 increasing to CH$_3$CN/H$_2$O (0.5% NH$_4$HCO$_3$)=3/2 within 20 min, the eluted product was collected at CH$_3$CN/H$_2$O (0.5% NH$_4$HCO$_3$)=1/1; Detector, UV 254 nm. This resulted in to give 11 (17.1 g, 25.6 mmol, 96%) as a white solid. ESI-LCMS: m/z 669 [M−H]$^-$; $^1$H-NMR (400 MHz, DMSO-d$_6$): δ 11.29 (d, J=2.0 Hz, 1H), 8.42 (d, J=8.0 Hz, 1H), 8.02-8.00 (m, 2H), 7.64-7.62 (m, 1H), 7.60-7.41 (m, 2H), 7.47.41-7.19 (m, 9H), 6.94-6.85 (m, 4H), 5.81 (d, J=4.0 Hz, 1H), 5.33-5.26 (m, 1H), 5.21 (d, J=7.2 Hz, 1H), 4.06-3.90 (m, 2H), 3.83-3.77 (m, 1H), 3.74 (s, 6H).

Preparation of Example 30 monomer: To a suspension of 11 (10.8 g, 16.2 mmol) in DCM (100 mL) was added DCI (1.5 g, 13.7 mmol) and CEP[N(iPr)$_2$]$_2$ (5.8 g, 19.3 mmol). The mixture was stirred at r.t. for 2 hrs. LC-MS showed 11 was consumed completely. The solution was washed with water twice and washed with brine and dried over Na$_2$SO$_4$. Then concentrated to give a residue which was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give Example 30 monomer (11.3 g, 13 mmol, 80%) as a white solid. ESI-LCMS: m/z 868 [M+H]$^+$; H-NMR (400 MHz, DMSO-d$_6$): δ 11.03 (m, 1H), 8.51-8.48 (m, 1H), 8.08-7.95 (m, 2H), 7.63-7.54 (m, 1H), 7.52-7.19 (m, 9H), 7.16-7.07 (m, 1H), 6.94-6.89 (m, 3H), 5.95-5.87 (m, 1H), 5.31-5.17 (m, 1H), 4.61-4.37 (m, 1H), 4.20-4.07 (m, 1H), 3.82-3.47 (m, 10H), 2.74-2.59 (m, 1H), 2.57-2.43 (m, 1H), 1.27-1.10 (m, 9H), 1.09-0.95 (m, 3H). $^{31}$P-NMR (162 MHz, DMSO-d$_6$): δ 149.52, 148.81.

Example 31. Synthesis of Monomer

Scheme-11

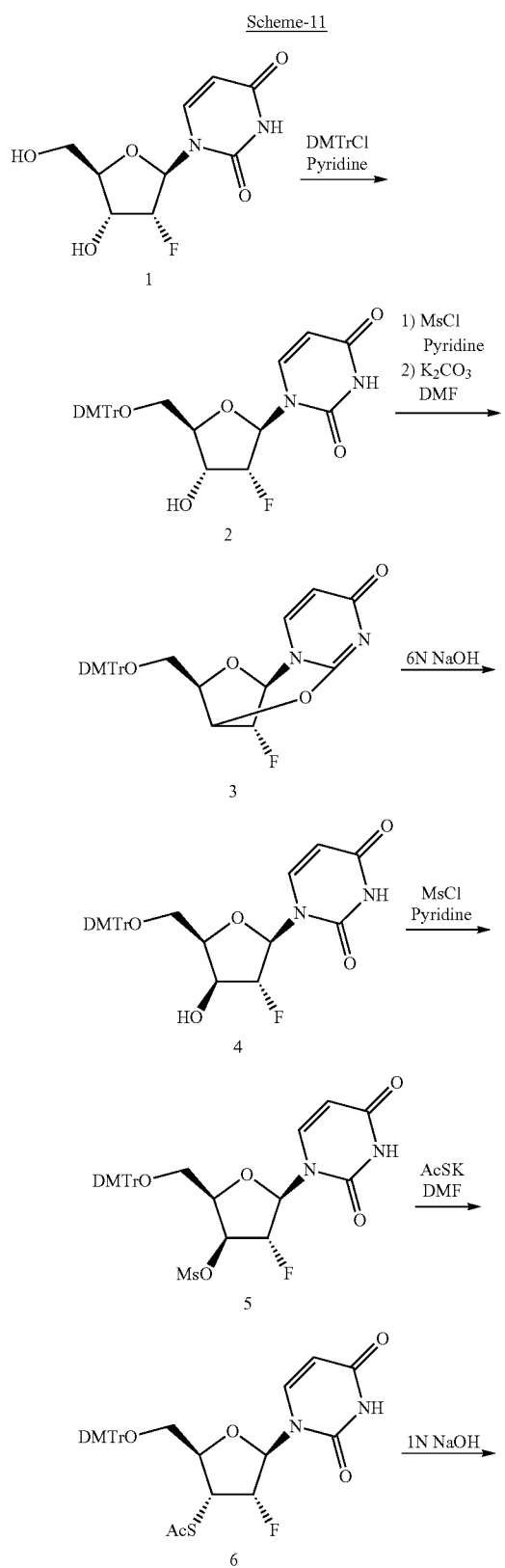

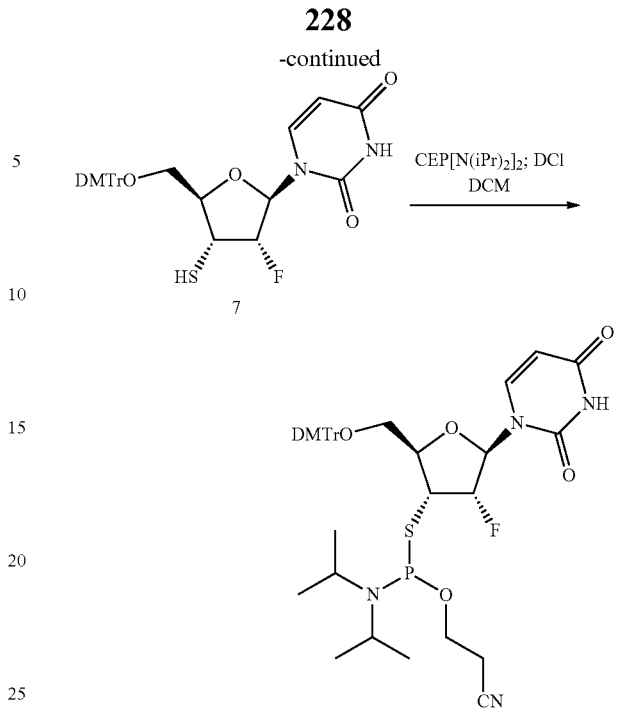

Example 31 monomer

Preparation of (2): To a stirred solution of 1 (100.0 g, 406.5 mmol) in pyridine (1000 mL) were added DMTrCl (151.2 g, 447.1 mmol) at r.t. And the reaction mixture was stirred at r.t. for 2.5 hrs. With ice-bath cooling, the reaction was quenched with water and the product was extracted with EA (3000 mL). The organic phase was evaporated to dryness under reduced pressure to give a residue which was purified by silica gel column chromatography (SiO$_2$, dichloromethane:methanol=100:1) to give 2 (210.0 g, 90%) as a white solid. ESI-LCMS: m/z 548.2 [M+H]$^+$; $^1$H-NMR (400 MHz, DMSO-d$_6$): δ 11.43 (d, J=1.8 Hz, 1H), 7.77 (d, J=8.0 Hz, 1H), 7.40-7.21 (m, 9H), 6.92-6.88 (m, 4H), 5.89 (d, J=20.0 Hz, 1H), 5.31-5.29 (m, 1H), 5.19-5.04 (dd, 1H), 4.38-4.31 (m, 1H), 4.02-3.98 (m, 1H), 3.74 (s, 6H), 3.30 (d, J=3.2 Hz, 2H); $^{19}$F-NMR (376 MHz, DMSO-d$_6$): δ−199.51.

Preparation of (3): To a stirred solution of 2 (100.0 g, 182.8 mmol) in pyridine (1000 mL) were added MsCl (31.2 g, 274.2 mmol) at 0° C. under N$_2$ atmosphere. And the reaction mixture was stirred at r.t for 2.5 h. With ice-bath cooling, the reaction was quenched with water and the product was extracted with EA (200 mL). The organic phase was evaporated to dryness under reduced pressure to give the crude (114.0 g) as a white solid which was used directly for next step. To the solution of the crude (114.0 g, 187.8 mmol) in DMF (2000 mL) was added K$_2$CO$_3$ (71.5 g, 548.4 mmol), and the reaction mixture was stirred at 90° C. for 15 h under N$_2$ atmosphere. After addition of water, the resulting mixture was extracted with EA (500 mL). The combined organic layer was washed with water and brine, dried over Na$_2$SO$_4$, and concentrated to give a residue which was purified by silica gel column chromatography (SiO$_2$, dichloromethane:methanol=30:1) to give 3 (100.0 g, 90%) as a white solid. ESI-LCMS: m/z 531.2 [M+H]$^+$; $^1$H-NMR (400 MHz, DMSO-d$_6$): δ 7.79 (d, J=8.0 Hz, 1H), 7.40-7.21 (m, 9H), 6.89-6.83 (m, 4H), 6.14 (d, J=5.4 Hz, 1H), 6.02-5.90 (dd, 1H), 5.87 (d, J=20.0 Hz, 1H), 5.45 (m, 1H), 4.61 (m, 1H), 3.73 (d, J=1.9 Hz, 6H), 3.30-3.15 (m, 2H), 1.24-1.16 (m, 1H); $^{19}$F-NMR (376 MHz, DMSO-d$_6$): δ−204.23.

Preparation of (4): A solution of 3 (100 g, 187.8 mmol) in THF (1000 mL) was added 6N NaOH (34 mL, 206.5 mmol). The mixture was stirred at r.t. for 6 h. After completion of reaction, the resulting mixture was added H$_2$O, and then the mixture was extracted with EA, the organic layer was washed with brine, dried over sodium sulfate and removed to give the residue was purified by silica gel column chromatography (SiO$_2$, dichloromethane:methanol=30:1) to give 4 (90.4 g, 90%) as a white solid. ESI-LCMS: m/z 548.2 [M+H]$^+$; $^{19}$F-NMR (376 MHz, DMSO-d$_6$): δ−184.58.

Preparation of (5): To a stirred solution of 4 (90.4 g, 165.2 mmol) in pyridine (1000 mL) were added MsCl (61.5 g, 495.6 mmol) at 0° C. under N$_2$ atmosphere. And the reaction mixture was stirred at r.t for 16 hrs. With ice-bath cooling, the reaction was quenched with water and the product was extracted with EA. the organic layer was washed with brine, dried over sodium sulfate and removed to give the residue was purified by silica gel column chromatography (SiO$_2$, PE:EA=1:1) to give 5 (75.0 g, 90%) as a white solid. ESI-LCMS: m/z 626.2 [M+H]$^+$; $^1$H-NMR (400 MHz, DMSO-d$_6$): δ 11.51 (d, J=1.6 Hz, 1H), 7.43-7.23 (m, 10H), 6.92-6.88 (m, 4H), 6.08 (d, J=20.0 Hz, 1H), 5.55-5.39 (m, 2H), 4.59 (m, 1H), 3.74 (s, 6H), 3.48-3.28 (m, 2H), 3.17 (s, 3H); $^{19}$F-NMR (376 MHz, DMSO-d$_6$): δ−187.72.

Preparation of (6): To the solution of 5 (75.0 g, 120.4 mmol) in DMF (1500 mL) was added KSAc (71.5 g, 548.4 mmol) at 110° C. under N$_2$ atmosphere, After the reaction mixture was stirred at 110° C. for 3 h were added KSAc (71.5 g, 548.4 mmol) under N$_2$ atmosphere. And the reaction mixture was stirred at r.t for 16 h. After addition of water, the resulting mixture was extracted with EA. The combined organic layer was washed with water and brine, dried over Na$_2$SO$_4$, and concentrated to give a residue which was purified by silica gel column chromatography (SiO$_2$, PE:EA=1:1) to give 6 (29.0 g, 90%) as a white solid. ESI-LCMS: m/z 605.2 [M+H]$^+$; $^1$H-NMR (400 MHz, DMSO-d$_6$): δ 11.45 (d, J=1.9 Hz, 1H), 7.95 (d, J=8.0 Hz, 1H), 7.38-7.21 (m, 9H), 6.92-6.87 (m, 4H), 5.93 (m, 1H), 5.50-5.36 (dd, 1H), 5.25-5.23 (dd, 1H), 4.54-4.42 (m, 1H), 4.17-4.12 (m, 1H), 3.74 (m, 7H), 3.35-3.22 (m, 2H), 2.39 (s, 1H); $^{19}$F-NMR (376 MHz, DMSO-d$_6$): δ−181.97.

Preparation of (7): A solution of 6 (22 g, 36.3 mmol) in a mixture solvent of THF/MeOH (1:1, 200 mL) was added 1N NaOMe (70 mL, 72.6 mmol) was stirred at 20° C. for 4 h. After completion of reaction, the resulting mixture was added H$_2$O, and then the mixture was extracted with EA, the organic layer was washed with brine, dried over sodium sulfate and removed to give the residue was purified by Flash-Prep-HPLC with the following conditions (IntelFlash-1): Column, C18 silica gel; mobile phase, CH$_3$CN/H$_2$O (0.5% NH$_4$HCO$_3$)=2/3 increasing to CH$_3$CN/H$_2$O (0.5% NH$_4$HCO$_3$)=3/2 within 25 min, the eluted product was collected at CH$_3$CN/H$_2$O (0.5% NH$_4$HCO$_3$)=4/3; Detector, UV 254 nm. This resulted in to give 7 (10.5 g, 14.5 mmol, 75.9%) as a white solid. ESI-LCMS: m/z 565.1 [M+]H$^+$; $^1$H-NMR (400 MHz, DMSO-d$_6$): δ 11.45 (s, 1H), 7.83 (d, J=8.0 Hz, 1H), 7.40-7.23 (m, 9H), 6.90 (d, J=8.8 Hz, 4H), 5.88 (m, 1H), 5.29-5.15 (m, 2H), 3.72 (m, 7H), 3.43 (m, 2H), 2.78 (d, J=10.6 Hz, 1H).

Preparation of Example 31 monomer: To a suspension of 7 (10.5 g, 18.6 mmol) in DCM (100 mL) was added DCI (1.8 g, 15.7 mmol) and CEP[N(iPr)$_2$]$_2$ (6.7 g, 22.3 mmol). The mixture was stirred at r.t. for 1 h. LC-MS showed 8 was consumed completely. The solution was washed with water twice and washed with brine and dried over Na$_2$SO$_4$. Then concentrated to give a residue which was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give Example 31 monomer (10.5 g, 14.5 mmol, 75.9%) as a white solid. ESI-LCMS: m/z 765.3 [M+H]$^+$; $^1$H-NMR (400 MHz, DMSO-d$_6$): δ 11.40 (d, J=12.2 Hz, 1H), 7.90-7.86 (m, 1H), 7.41-7.24 (m, 9H), 6.91-6.89 (m, 4H), 5.97 (m, 1H), 5.33-5.10 (m, 2H), 4.18-4.16 (m, 1H), 3.91-3.39 (m, 17H), 2.81 (t, J=5.6 Hz, 1H), 2.66 (t, J=6.0 Hz, 1H), 1.33-0.97 (m, 12H); $^{31}$P-NMR (162 MHz, DMSO-d$_6$): δ 164.57, 160.13.

Example 32. Synthesis of Monomer

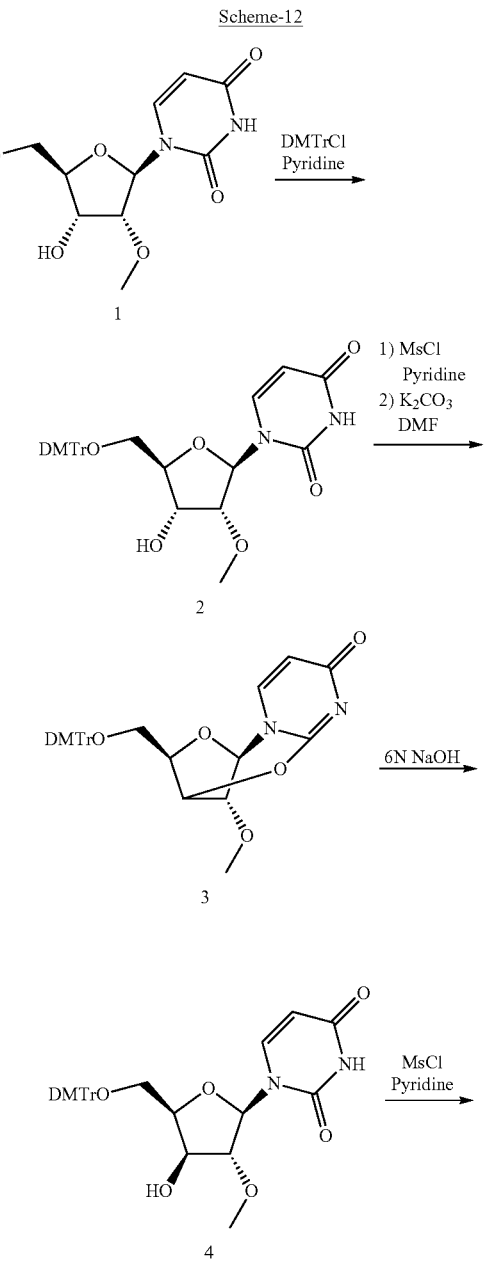

Scheme-12

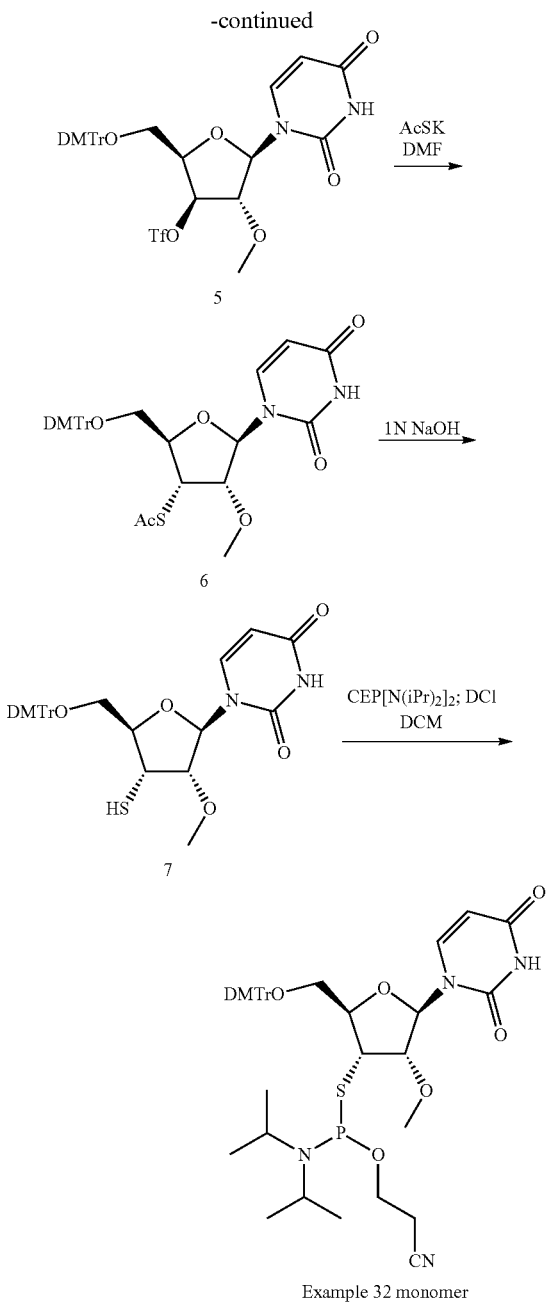

Example 32 monomer

Preparation of (2): To a stirred solution of 1 (100.0 g, 387.5 mmol) in pyridine (1000 mL) was added DMTrCl (151.2 g, 447.1 mmol) at r.t. And the reaction mixture was stirred at r.t. for 2.5 hrs. With ice-bath cooling, the reaction was quenched with water and the product was extracted with EA (3000 mL). The organic phase was evaporated to dryness under reduced pressure to give a residue which was purified by silica gel column chromatography ($SiO_2$, dichloromethane:methanol=100:1) to give 2 (200.0 g, 90%) as a white solid. ESI-LCMS: m/z 561 [M+H]$^+$.

Preparation of (3): To a stirred solution of 2 (730.0 g, 1307.3 mmol) in pyridine (730 mL) were added MsCl (19.5 g, 169.2 mmol) at 0° C. und $N_2$ atmosphere. And the reaction mixture was stirred at r.t for 2.5 h. With ice-bath cooling, the reaction was quenched with water and the product was extracted with EA (200 mL). The organic phase was evaporated to dryness under reduced pressure to give the crude (80.0 g) as a white solid which was used directly for next step. To the solution of the crude (8.0 g, 130.3 mmol) in n DMF (1600 mL) was added $K_2CO_3$ (71.5 g, 390.9 mmol), and the reaction mixture was stirred at 90° C. for 15 h under $N_2$ atmosphere. After addition of water, the resulting mixture was extracted with EA (500 mL). The combined organic layer was washed with water and brine, dried over $Na_2SO_4$, and concentrated to give a residue which was purified by silica gel column chromatography ($SiO_2$, dichloromethane:methanol=30:1) to give 3 (55.0 g, 90%) as a white solid. ESI-LCMS: m/z 543. [M+H]$^+$; $^1$H-NMR (400 MHz, DMSO-$d_6$): δ 7.68 (d, J=8.0 Hz, 1H), 7.40-7.21 (m, 9H), 6.89-6.83 (m, 4H), 5.96 (s, 1H), 5.83 (d, J=5.4 Hz, 1H), 5.26 (s, 1H), 4.59 (s, 1H), 4.46 (t, J=6.0 Hz, 1H), 3.72 (s, 6H), 3.44 (s, 3H), 3.18-3.12 (m, 2H).

Preparation of (4): A solution of 3 (55 g, 101.8 mmol) in THF (550 mL) was added 6N NaOH (34 mL, 206.5 mmol). The mixture was stirred at 20° C. for 6 hrs. After completion of reaction, the resulting mixture was added $H_2O$, and then the mixture was extracted with EA, the organic layer was washed with brine, dried over sodium sulfate and removed to give the residue was purified by silica gel column chromatography ($SiO_2$, dichloromethane:methanol=30:1) to give 4 (57.4 g, 87%) as a white solid. ESI-LCMS: m/z 561 [M+H]$^+$.

Preparation of (5): To a stirred solution of 4 (57.4 g, 101.8 mmol) in pyridine (550 mL) were added MsCl (61.5 g, 495.6 mmol) at 0° C. under $N_2$ atmosphere. And the reaction mixture was stirred at r.t for 16 h. With ice-bath cooling, the reaction was quenched with water and the product was extracted with EA. the organic layer was washed with brine, dried over sodium sulfate and removed to give the residue was purified by silica gel column chromatography ($SiO_2$, PE:EA=1:1) to give 5 (57.0 g, 90%) as a white solid. ESI-LCMS: m/z 639 [M+H]$^+$.

Preparation of (6): To the solution of 5 (57.0 g, 89.2 mmol) in DMF (600 mL) was added KSAc (71.5 g, 448.4 mmol) at 110° C. under $N_2$ atmosphere, After the reaction mixture was stirred at 110° C. for 3 h were added KSAc (71.5 g, 448.4 mmol) under $N_2$ atmosphere. And the reaction mixture was stirred at r.t for 16 h. After addition of water, the resulting mixture was extracted with EA. The combined organic layer was washed with water and brine, dried over $Na_2SO_4$, and concentrated to give a residue which was purified by silica gel column chromatography ($SiO_2$, PE:EA=1:1) to give 6 (29.0 g, 47%) as a white solid. ESI-LCMS: m/z 619.2 [M+H]$^+$; $^1$H-NMR (400 MHz, DMSO-$d_6$): δ 11.41 (s, 1H), 8.06 (s, 1H), 7.40-7.23 (m, 9H), 6.90 (d, J=8.8 Hz, 4H), 5.82 (s, 1H), 5.10-5.08 (dd, 1H), 4.38-4.34 (m, 1H), 4.08-4.02 (m, 3H), 3.74 (s, 6H), 3.45 (s, 3H), 3.25 (m, 2H), 2.37 (s, 3H); ESI-LCMS: m/z 619 [M+H]$^+$.

Preparation of (7): A solution of 6 (22 g, 35.3 mmol) in a mixture solvent of THF/MeOH (1:1, 200 mL) was added 1N NaOMe (70 mL, 72.6 mmol) was stirred at 20° C. for 4 h. After completion of reaction, the resulting mixture was added $H_2O$, and then the mixture was extracted with EA, the organic layer was washed with brine, dried over sodium sulfate and removed to give the residue was purified by Flash-Prep-HPLC with the following conditions (IntelFlash-1): Column, C18 silica gel; mobile phase, $CH_3CN/H_2O$ (0.5% $NH_4HCO_3$)=2/3 increasing to $CH_3CN/H_2O$ (0.5% $NH_4HCO_3$)=3/2 within 25 min, the eluted product was collected at $CH_3CN/H_2O$ (0.5% $NH_4HCO_3$)=4/3; Detector, UV 254 nm. This resulted in to give 7 (14.0 g, 70.9%) as a white solid. ESI-LCMS: m/z 576.1 [M+H]$^+$; $^1$H-NMR (400

MHz, DMSO-d$_6$): δ 11.38 (s, 1H), 7.90 (d, J=8.0 Hz, 1H), 7.40-7.23 (m, 9H), 6.90 (d, J=8.8 Hz, 4H), 5.80 (s, 1H), 5.15-5.13 (dd, 1H), 3.93 (m, 1H), 3.87 (d, J=5.0 Hz, 1H), 3.74 (s, 6H), 3.59 (m, 2H), 3.49 (s, 3H), 3.39 (d, J=2.2 Hz, 2H), 2.40 (d, J=10.2 Hz, 1H).

Preparation of Example 32 monomer: To a suspension of 7 (10.5 g, 18.6 mmol) in DCM (100 mL) was added DCI (1.8 g, 15.7 mmol) and CEP[N(iPr)$_2$]$_2$ (6.7 g, 22.3 mmol). The mixture was stirred at r.t. for 1 h. LC-MS showed 7 was consumed completely. The solution was washed with water twice and washed with brine and dried over Na$_2$SO$_4$. Then concentrated to give a residue which was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give Example 32 monomer (10.5 g, 14.5 mmol, 75.9%) as a white solid. ESI-LCMS: m/z 776.3 [M+H]$^+$, $^1$H-NMR (400 MHz, DMSO-d$_6$): δ 11.40 (d, J=12.2 Hz, 1H), 8.04-7.96 (dd, 1H), 7.43-7.24 (m, 9H), 6.92-6.87 (m, 4H), 5.84 (m, 1H), 4.93 (m, 1H), 4.13 (m, 1H), 3.91-3.39 (m, 17H), 2.82 (t, J=5.6 Hz, 1H), 2.68 (t, J=6.0 Hz, 1H), 1.22-0.97 (m, 12H); $^{31}$P-NMR (162 MHz, DMSO-d$_6$): δ 165.06, 157.59.

Example 33. Synthesis of 5' End Cap Monomer

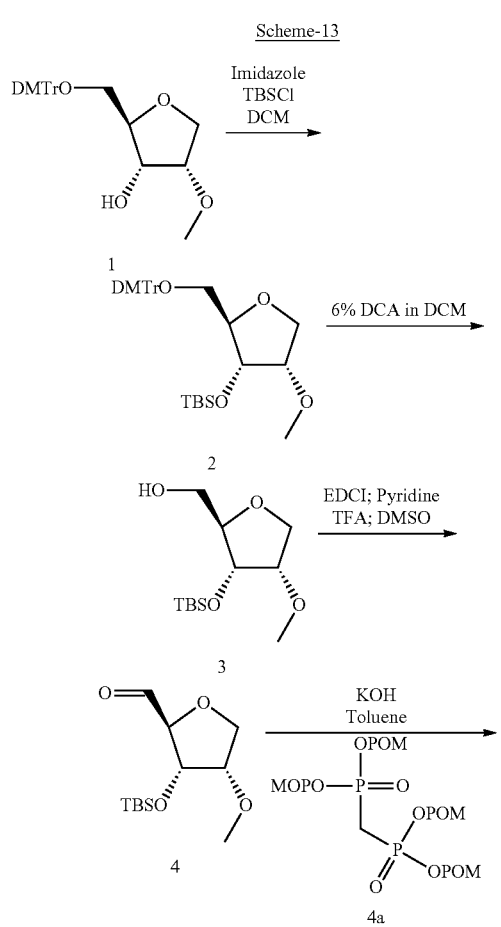

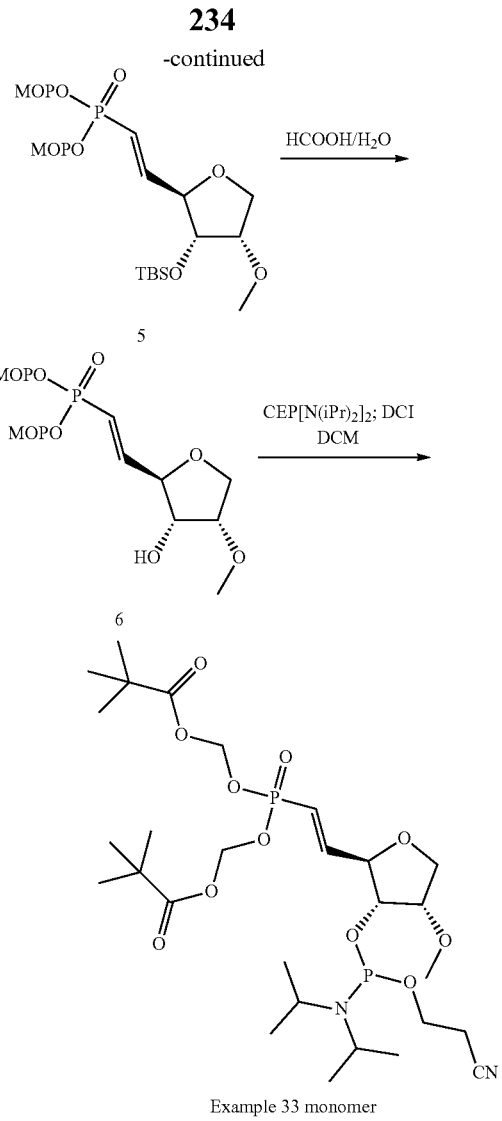

Example 33 monomer

Preparation of (2): To a solution of 1 (11.2 g, 24.7 mmol) in DCM (120 mL), imidazole (4.2 g, 61.9 mmol) and TBSCl (5.6 g, 37.1 mmol) were added at r.t., mixture was stirred at r.t. for 15 hrs, LCMS showed 1 was consumed completely. Mixture was added water (500 mL) and extracted with DCM (50 mL*2). The organic phase was dried over Na$_2$SO$_4$ and concentrated to give 2 (16.0 g) as an oil for the next step.

Preparation of (3): To a solution of 2 (16.0 g, 28.4 mmol) was added 6% DCA in DCM (160 mL) and triethylsilane (40 mL) at r.t. The reaction mixture was stirred at r.t. for 2 hrs. TLC showed 2 was consumed completely. Water (300 mL) was added, mixture was extracted with DCM (50 mL*4), organic phase was dried by Na$_2$SO$_4$, concentrated by reduce pressure to give crude which was purified by column chromatography (SiO$_2$, PE/EA=10:1 to 1:1) to give 3 (4.9 g, 65.9% yield) as an oil. ESI-LCMS: m/z 263 [M+H]$^+$; $^1$H-NMR (400 MHz, DMSO-d$_6$) δ 4.84-4.50 (m, 1H), 4.3-4.09 (m, 1H), 3.90-3.80 (m, 1H), 3.75-3.67 (m, 1H), 3.65-3.57 (m, 2H), 3.50-3.44 (m, 1H), 3.37-3.28 (m, 4H), 0.95-0.78 (s, 9H), 0.13-0.03 (s, 6H).

Preparation of (4): To a solution of 3 (3.3 g, 12.6 mmol) in DMSO (33 mL) was added EDCI (7.2 g, 37.7 mmol). The mixture was added pyridine (1.1 g, 13.8 mmol) and TFA (788.6 mg, 6.9 mmol). The reaction mixture was stirred at r.t. for 3 hrs. TLC (PE/EA=4:1) showed 3 was consumed. The mixture was diluted with EA and water was added. The product was extracted with EA. The organic layer was washed with brine and dried over $Na_2SO_4$ and concentrated to give the crude. This resulted in to give 4 (3.23 g) as an oil for the next step.

Preparation of (5): To a solution of 4 (3.3 g, 12.6 mmol) in toluene (30 mL) was added POM ester 4a (reference for 4a Journal of Medicinal Chemistry, 2018, 61 (3), 734-744) (7.9 g, 12.6 mmol) and KOH (1.3 g, 22.6 mmol) at r.t. The reaction mixture was stirred at 40° C. for 8 hrs. LCMS showed 4 was consumed. The mixture was diluted with water and EA was added. The product was extracted with EA. The organic layer was washed with brine and dried over $Na_2SO_4$ and concentrated to give the crude. The crude was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=91/9 Detector, UV 254 nm. This resulted in to give 5 (5.4 g, 9.5 mmol, 75.9% yield) as an oil. ESI-LCMS: m/z 567.2 $[M+H]^+$; $^1$H-NMR (400 MHz, $CDCl_3$) δ 6.89-6.77 (m, 1H), 6.07-5.96 (m, 1H), 5.86-5.55 (m, 4H), 4.85-4.73 (m, 1H), 4.36-4.27 (m, 1H), 4.05-3.96 (m, 1H), 3.95-3.85 (m, 1H), 3.73-3.65 (m, 1H), 3.44-3.35 (m, 3H), 1.30-1.25 (s, 18H), 0.94-0.84 (s, 9H), 0.14-0.05 (s, 6H). $^{31}$P-NMR (162 MHz, $CDCl_3$) δ 18.30, 15.11.

Preparation of (6): To a solution of 5 (5.4 g, 9.5 mmol) in HCOOH (30 mL)/$H_2O$ (30 mL)=1:1 at r.t. The reaction mixture was stirred at r.t. for 15 hrs. LCMS showed the reaction was consumed. The mixture was diluted with con. $NH_4OH$ till pH=7.5. The product was extracted with EA. The organic layer was washed with brine and dried over $Na_2SO_4$ and concentrated to give the crude. The crude was purified by Flash-Prep-HPLC with the following conditions (IntelFlash-1): Column, C18 silica gel; mobile phase, $CH_3CN/H_2O$ (0.5% HCOOH)=30/70 increasing to $CH_3CN/H_2O$ (0.5% HCOOH)=70/30 within 45 min, the eluted product was collected at $CH_3CN/H_2O$ (0.5% HCOOH)=59/41 Detector, UV 220 nm. This resulted in to give 6 (2.4 g, 5.7 mmol, 59.4% yield) as an oil. ESI-LCMS: m/z 453.2 $[M+H]^+$; $^1$H-NMR (400 MHz, DMSO-$d_6$) δ 6.84-6.68 (m, 1H), 6.07-5.90 (m, 1H), 5.64-5.55 (m, 4H), 5.32-5.24 (m, 1H), 4.23-4.15 (m, 1H), 4.00-3.90 (m, 1H), 3.89-3.80 (m, 1H), 3.78-3.69 (m, 2H), 3.37-3.30 (s, 3H), 1.30-1.10 (s, 18H). $^{31}$P-NMR (162 MHz, DMSO-$d_6$) δ 18.14.

Preparation of Example 33 monomer: To a solution of 6 (2.1 g, 4.5 mmol) in DCM (21 mL) were added DCI (452.5 mg, 3.8 mmol) and CEP[N(iPr)$_2$]$_2$ (1.8 g, 5.9 mmol) at r.t. The reaction mixture was stirred at r.t. for 15 hrs under $N_2$ atmosphere. LCMS showed 6 was consumed. The mixture was diluted with water. The product was extracted with DCM (30 mL). The organic layer was washed with brine and dried over $Na_2SO_4$ and concentrated to give the crude. The crude was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 28 min, the eluted product was collected at $CH_3CN/H_2O$ (0.5% $NH_4HCO_3$)=80/20 Detector, UV 254 nm. This resulted in to give Example 33 monomer (2.8 g, 4.3 mmol, 95.2% yield) as an oil. ESI-LCMS: m/z 653.2 $[M+H]^+$; $^1$H-NMR (400 MHz, DMSO-$d_6$) δ 6.89-6.77 (m, 1H), 6.11-5.96 (m, 1H), 5.65-5.50 (m, 4H), 4.39-4.34 (d, J=20 Hz, 1H), 4.18-3.95 (m, 2H), 3.94-3.48 (s, 6H), 3.40-3.28 (m, 4H), 2.84-2.75 (m, 2H), 1.26-1.98 (s, 30H). $^{31}$P-NMR (162 MHz, DMSO-$d_6$) δ 149.018, 148.736, 17.775, 17.508.

Example 34. Synthesis of 5' End Cap Monomer

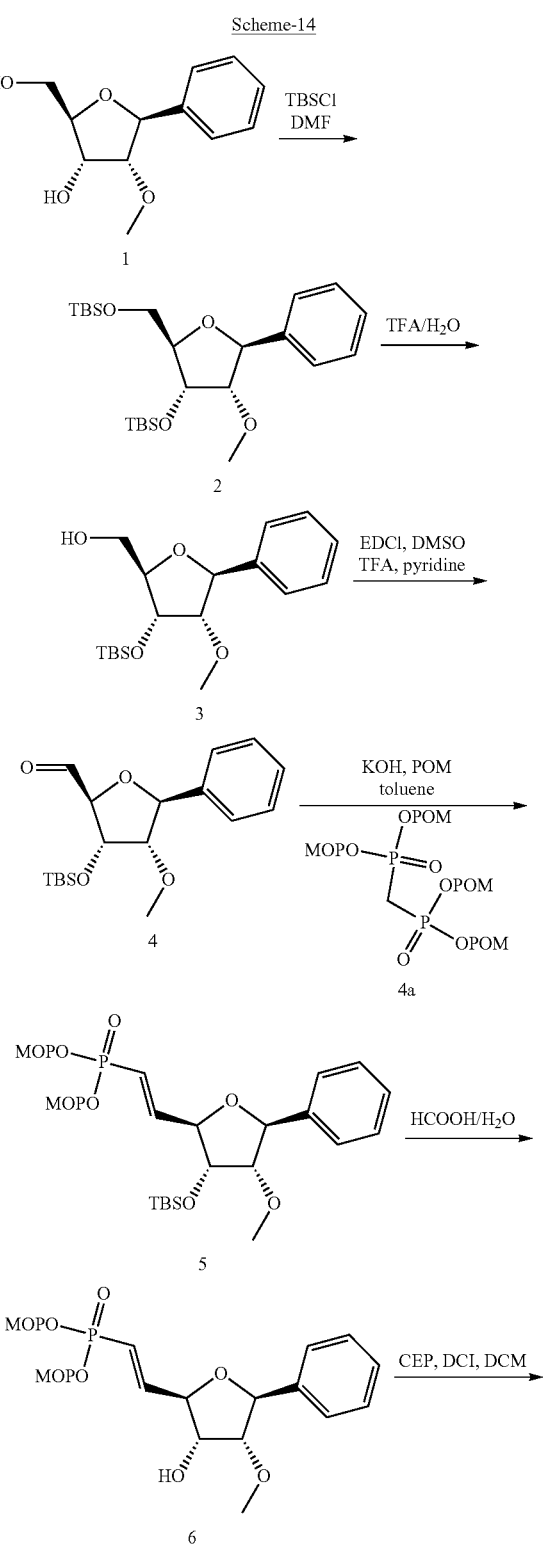

Scheme-14

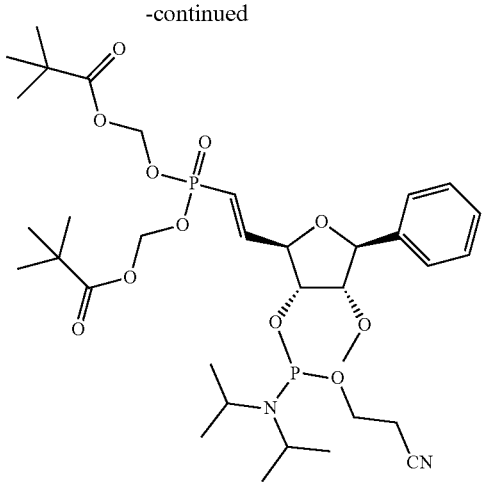

Example 34 monomer

Preparation of (2): To a solution of 1 (ref for 1 *Tetrahedron*, 2013, 69, 600-606) (10.60 g, 47.32 mmol) in DMF (106 mL), imidazole (11.26 g, 165.59 mmol) and TBSCl (19.88 g, 132.53 mmol) were added. The mixture was stirred at r.t. for 3.5 hrs, LCMS showed 1 was consumed completely. Water was added and extracted with EA, dried over by $Na_2SO_4$. The filtrate was evaporated under reduced pressure to give 2 (20.80 g, 45.94 mmol, 97.19% yield) for the next step.

Preparation of (3): To a solution of 2 (20.80 g, 45.94 mmol) in THF (248 mL), was added TFA (124 mL) and $H_2O$ (124 mL) at 0° C., reaction mixture was stirred for 30 min. LCMS showed 2 was consumed completely. Then was extracted with EA, washed with sat. NaCl (aq.), dried over by $Na_2SO_4$. The filtrate was evaporated under reduced pressure to give the crude product which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give 3 (10.00 g, 29.59 mmol, 64.31% yield). $^1$H-NMR (400 MHz, DMSO-$d_6$): δ 7.33-7.18 (m, 5H), 4.83-4.80 (m, 1H), 4.61-4.59 (m, 1H), 4.21-4.19 (m, 1H), 3.75-3.74 (m, 1H), 3.23 (m, 3H), 3.13 (m, 3H), 2.41-2.40 (m, 1H), 0.81 (m, 9H), 0.00 (m, 6H).

Preparation of (4): To a solution of 3 (3.70 g, 10.95 mmol) in DMSO (37 mL) was added EDCI (6.30 g, 32.84 mmol). Then pyridine (0.95 g, 12.05 mmol) and TFA (0.69 g, 6.02 mmol) was added in $N_2$ atmosphere. The mixture was stirred for 3 hrs at r.t. LCMS showed 3 was consumed completely. Water was poured into and extracted with EA, washed with sat. NaCl (aq.), dried over by $Na_2SO_4$. The filtrate was evaporated under reduced pressure to give the crude product which was directly used for next step.

Preparation of (5): To a solution of 4 in toluene (100.00 mL), was added 4a (6.93 g, 10.97 mmol) and KOH (1.11 g, 19.78 mmol). It was stirred for 3.5 hrs at 40° C. in $N_2$ atmosphere. TLC and LCMS showed 4 was consumed completely. Then was extracted with EA, washed with water and sat. NaCl (aq.), dried over by $Na_2SO_4$. The filtrate was evaporated under reduced pressure to give the crude product which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give 5 (4.30 g, 6.70 mmol, 61.17% yield). $^1$H-NMR (400 MHz, CDCl$_3$): δ 7.27-7.26 (m, 4H), 7.17 (m, 1H), 6.94-6.82 (m, 1H), 6.13-6.02 (m, 1H), 5.63-5.56 (m, 4H), 4.90-4.89 (m, 1H), 4.45-4.41 (m, 1H), 3.98-3.95 (m, 1H), 3.39-3.29 (m, 4H), 1.90 (m, 1H), 1.12-0.83 (m, 29H), 0.00 (m, 7H); $^{31}$P-NMR (162 MHz, CDCl$_3$): δ 18.021, 14.472.

Preparation of (6): To a solution of 5 (4.30 g, 6.70 mmol) in THF (43.00 mL) was added HCOOH (100 mL) and $H_2O$ (100 mL). It was stirred overnight at r.t. LCMS showed 5 was consumed completely. $NH_4OH$ was poured into it and was extracted with EA, washed with sat. NaCl (aq.), dried over by $Na_2SO_4$. The filtrate was evaporated under reduced pressure to give the crude product which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give 6 (2.10 g, 3.98 mmol, 59.32% yield). $^1$H-NMR (400 MHz, CDCl$_3$): δ 7.40-7.28 (m, 5H), 7.11-7.00 (m, 1H), 6.19-6.14 (m, 1H), 5.71-5.68 (m, 4H), 4.95-4.94 (m, 1H), 4.48-4.47 (m, 1H), 4.05-4.03 (m, 1H), 3.62-3.61 (m, 1H), 3.46 (m, 3H), 3.00-2.99 (m, 1H), 1.22 (m, 18H); $^{31}$P-NMR (162 MHz, CDCl$_3$): δ 18.134.

Preparation of Example 34 monomer: To a solution of 6 (2.10 g, 3.98 mmol) in DCM (21 mL) was added DCI (410 mg, 3.47 mmol). CEP (1.40 g, 4.65 mmol) was added in a $N_2$ atmosphere. LCMS showed 6 was consumed completely. DCM and $H_2O$ was poured, the organic phase was washed with water and sat. NaCl (aq.), dried over by $Na_2SO_4$. The filtrate was evaporated under reduced pressure at 40° C. to give the crude product which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give Example 34 monomer (2.10 g, 2.88 mmol). $^1$H-NMR (400 MHz, DMSO-$d_6$): δ 7.39-7.32 (m, 6H), 6.21-6.11 (m, 1H), 5.64-5.61 (m, 4H), 4.91-4.85 (m, 1H), 4.59 (m, 1H), 4.28-4.25 (m, 1H), 3.84-3.60 (m, 5H), 3.36-3.36 (m, 2H), 2.83-2.79 (m, 2H), 1.18-1.14 (m, 29H); $^{31}$P-NMR (162 MHz, DMSO-$d_6$): δ 149.588, 148.920, 17.355, 17.010.

Example 35. Synthesis of 5' End Cap Monomer

Scheme-15

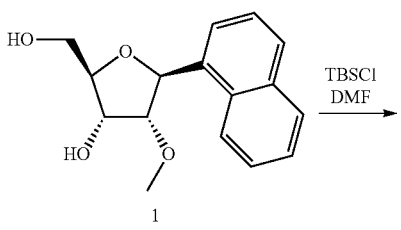

1

-continued

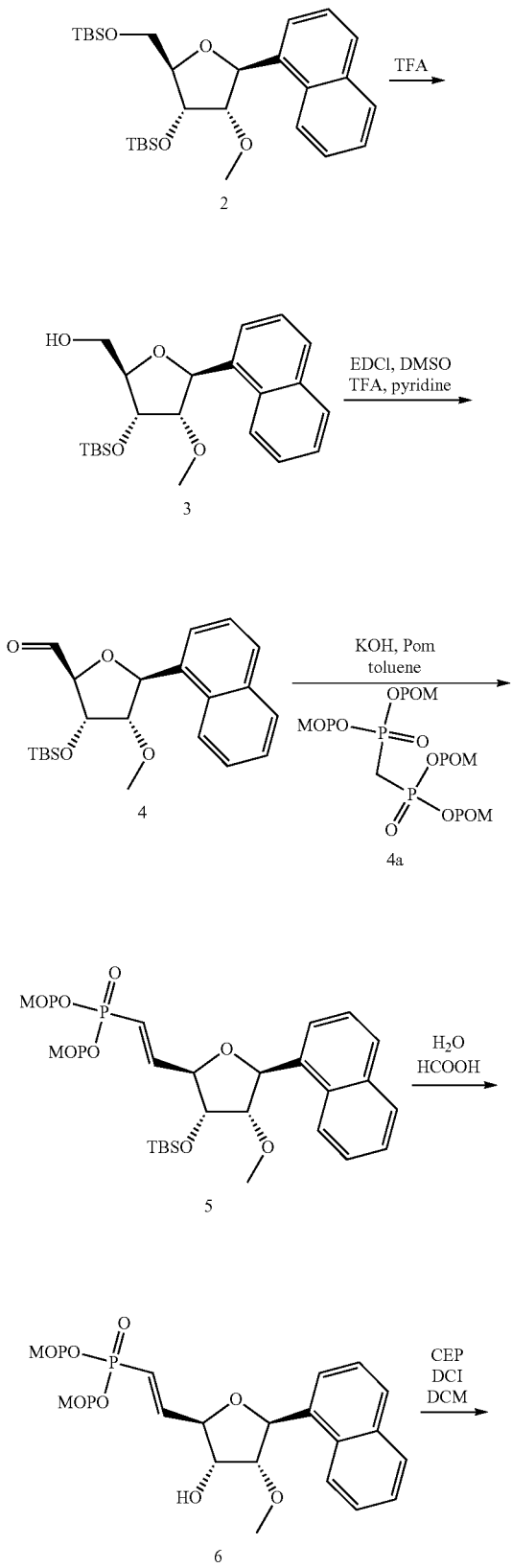

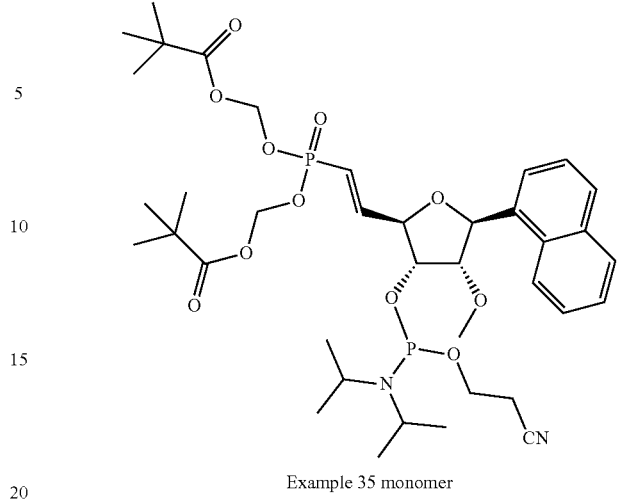

Example 35 monomer

Preparation of (2): To a solution of 1 (5.90 g, 21.50 mmol) in DMF (60.00 mL), imidazole (4.39 g, 64.51 mmol) and TBSCl (7.63 g, 49.56 mmol) were added. The mixture was stirred at r.t. for 3.5 hrs, LCMS showed 1 was consumed completely. Water was added and extracted with EA, dried over by $Na_2SO_4$. The filtrate was evaporated under reduced pressure to give 2 (11.00 g, 21.91 mmol, 98.19% yield) for the next step. ESI-LCMS: m/z 225.1 $[M+H]^+$.

Preparation of (3): To a solution of 2 (11.00 g, 21.91 mmol) in THF (55.00 mL) was added TFA (110.00 mL) and $H_2O$ (55.00 mL) at 0° C., reaction mixture was stirred for 30 min. LCMS showed 2 was consumed completely. Then was extracted with EA, washed with sat. NaCl (aq.), dried over by $Na_2SO_4$. The filtrate was evaporated under reduced pressure to give the crude product which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give 3 (6.20 g, 16.32 mmol, 72.94% yield). ESI-LCMS: m/z 411.2 $[M+H]^+$.

Preparation of (4): To a solution of 3 (3.50 g, 9.02 mmol) in DMSO (35.00 mL) was added EDCI (5.19 g, 27.06 mmol). Then pyridine (0.78 g, 9.92 mmol) and TFA (0.57 g, 4.96 mmol) was added in $N_2$ atmosphere. The mixture was stirred for 3 h at r.t. Water was poured into it and was extracted with EA, washed with sat. NaCl (aq.), dried over by $Na_2SO_4$. The filtrate was evaporated under reduced pressure to give the crude product which was directly used for next step. ESI-LCMS: m/z 406.2 $[M+H]^+$.

Preparation of (5): To a solution of 4 in toluene (100.00 mL) was added 4a (5.73 g, 9.07 mmol) and KOH (916.3 g, 16.33 mmol). It was stirred for 3.5 h at 40° C. in $N_2$ atmosphere. Then was extracted with EA, washed with water and sat. NaCl (aq.), dried over by $Na_2SO_4$. The filtrate was evaporated under reduced pressure to give the crude product which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give 5 (5.02 g, 7.25 mmol, 80.44% yield). ESI-LCMS: m/z 693.2 $[M+H]^+$; $^{31}$P-NMR (162 MHz, DMSO-$d_6$): δ 17.811

Preparation of (6): To a solution of 5 (4.59 g, 6.63 mmol) in THF (46.00 mL) was added HCOOH (92.00 mL) and H$_2$O (92.00 mL). It was stirred overnight at r.t. NH$_4$OH was poured into it and extracted with EA, washed with sat. NaCl (aq.), dried over by Na$_2$SO$_4$. The filtrate was evaporated under reduced pressure to give the crude product which was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give 6 (2.52 g, 4.36 mmol, 65.80% yield).

Preparation of Example 35 monomer: To a solution of 6 (2.00 g, 3.46 mmol) in DCM (21.00 mL) was added DCI (370.00 mg, 3.11 mmol) and CEP (1.12 g, 4.15 mmol) was added in N$_2$ atmosphere. DCM and H$_2$O was poured, the organic phase was washed with water and sat. NaCl (aq.), dried over by Na$_2$SO$_4$. The filtrate was evaporated under reduced pressure at 38° C. to give the crude product which was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give Example 35 monomer (2.10 g, 2.70 mmol, 78.07% yield). $^1$H-NMR (400 MHz, DMSO-d$_6$): δ 7.39-7.32 (m, 6H), 6.21-6.11 (m, 1H), 5.64-5.61 (m, 4H), 4.91-4.85 (m, 1H), 4.59 (m, 1H), 4.28-4.25 (m, 1H), 3.84-3.60 (m, 5H), 3.36-3.36 (m, 2H), 2.83-2.79 (m, 2H), 1.18-1.14 (m, 29H). $^{31}$P-NMR (162 MHz, DMSO-d$_6$): δ 149.588, 148.920, 17.355, 17.010.

Example 36. Synthesis of Monomer

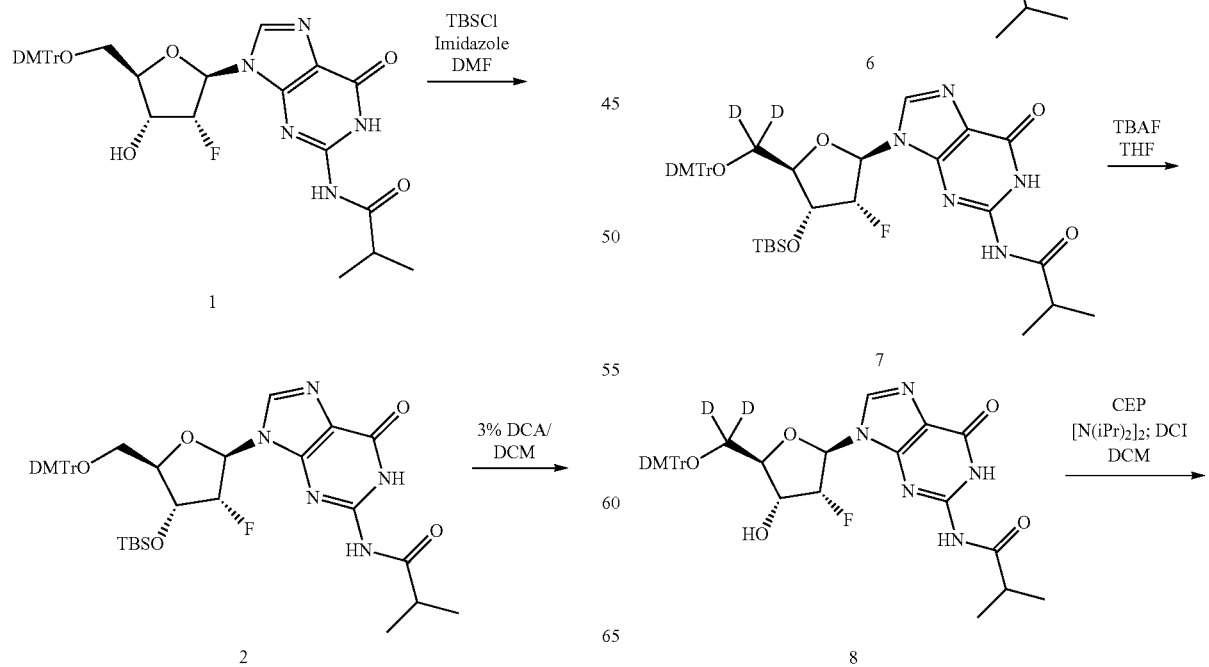

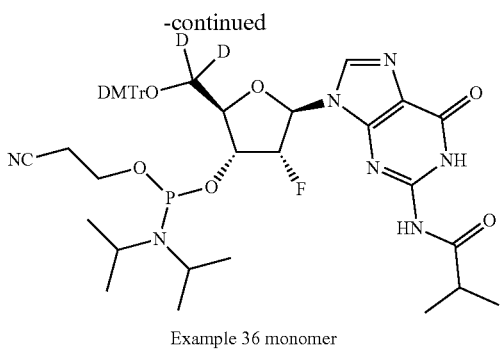

Example 36 monomer

Preparation of (2): To a solution of 1 (35.0 g, 53.2 mmol) in DMF (350 mL) was added imidazole (9.0 g, 133.0 mmol) then added TBSCl (12.0 g, 79.8 mmol) at 0° C. The mixture was stirred at r.t. for 14 hrs. TLC showed 1 was consumed completely. Water was added to the reaction. The product was extracted with EA, The organic layer was washed with NaHCO$_3$ and brine. Then the solution was concentrated under reduced pressure the crude 2 (41.6 g) as a white solid which was used directly for next step. ESI-LCMS: m/z 772 [M+H]$^+$.

Preparation of (3): To a solution of 2 (41.0 g, 53.1 mmol) in 3% DCA (53.1 mmol, 350 mL) and Et$_3$SiH (53.1 mmol, 100 mL) at 0° C. The mixture was stirred at 0° C. for 0.5 h. TLC showed 2 was consumed completely. NaHCO$_3$ was added to the reaction. The product was extracted with EA, The organic layer was washed with NaHCO$_3$ and brine. Then the solution was concentrated under reduced pressure. The residue silica gel column chromatography (eluent, DCM/MeOH=100:1-20:1). This resulted in to give 3 (20.0 g, 41.7 mmol, 78.6% over two step) as a white solid. ESI-LCMS: m/z 470 [M+H]$^+$; $^1$H-NMR (400 MHz, DMSO-d$_6$): δ 12.12 (s, 1H), 11.67 (s, 1H), 8.28 (s, 1H), 6.12-6.07 (dd, J=15 Hz, 1H), 5.75 (d, J=5 Hz, 1H), 5.48-5.24 (m, 2H), 4.55-4.49 (m, 1H), 3.97 (s, 1H), 3.75-3.55 (m, 2H), 2.79-2.76 (m, 1H), 1.12 (d, J=6 Hz, 6H), 0.88 (s, 9H), 0.11 (d, J=6 Hz, 6H).

Preparation of (4): To the solution of 3 (20 g, 42.6 mmol) in dry DCM (100 mL) and DMF (60 mL) was added PDC (20. g, 85.1 mmol), tert-butyl alcohol (63.1 g, 851.8 mmol) and Ac$_2$O (43.4 g, 425.9 mmol) at r.t. under N$_2$ atmosphere. And the reaction mixture was stirred at r.t. for 2 h. The solvent was removed to give a residue which was purified by silica gel column chromatography (eluent, PE:EA=4:1-2:1) to give a residue which was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give 4 (16.0 g, 29.0 mmol, 68.2% yield) as a white solid. ESI-LCMS: m/z 540 [M+H]$^+$; $^1$H-NMR (400 MHz, DMSO-d$_6$): δ 12.12 (s, 1H), 11.69 (s, 1H), 8.28 (s, 1H), 6.21-6.17 (dd, J=15 Hz, 1H), 5.63-5.55 (m, 1H), 4.75-4.72 (m, 1H), 4.41 (d, J=5 Hz, 1H), 2.79-2.76 (m, 1H), 1.46 (s, 9H), 1.13-1.11 (m, 6H), 0.90 (s, 9H), 0.14 (d, J=2 Hz, 6H).

Preparation of (5): To the solution of 4 (16.0 g, 29.6 mmol) in dry THF/MeOD/D$_2$O=10/2/1 (195 mL) was added NaBD$_4$ (3.4 g, 88.9 mmol) at r.t. and the reaction mixture was stirred at 50° C. for 2 h. After completion of reaction, adjusted pH value to 7 with CH$_3$COOD, after addition of water, the resulting mixture was extracted with EA (300 mL). The combined organic layer was washed with water and brine, dried over Na$_2$SO$_4$, Then the solution was concentrated under reduced pressure the crude 5 (11.8 g) as a white solid which was used directly for next step. ESI-LCMS: m/z 402 [M+H]$^+$.

Preparation of (6): To a solution of 5 (5.0 g, 12.4 mmol) in pyridine (50 mL) was added iBuCl (2.6 g, 24.9 mmol) at 0° C. under N$_2$ atmosphere. The mixture was stirred at r.t. for 14 h. TLC showed 5 was consumed completely. Then the solution diluted with EA. The organic layer was washed with NaHCO$_3$ and brine. Then the solution was concentrated under reduced pressure to give the crude. To a solution of the crude in pyridine (50 mL) was added 2N NaOH (MeOH/H$_2$O=4:1, 15 mL) at 0° C. The mixture was stirred at 0° C. for 10 min. Then the solution diluted with EA. The organic layer was washed with NH$_4$Cl and brine. Then the solution was concentrated under reduced pressure the residue was purified by Flash-Prep-HPLC with the following conditions (IntelFlash-1): Column, C18 silica gel; mobile phase, CH$_3$CN/H$_2$O (0.5% NH$_4$HCO$_3$)=1/3 increasing to CH$_3$CN/H$_2$O (0.5% NH$_4$HCO$_3$)=4/1 within 25 min, the eluted product was collected at CH$_3$CN/H$_2$O (0.5% NH$_4$HCO$_3$)=3/2; Detector, UV 254 nm. This resulted in to give 6 (6 g, 10.86 mmol, 87.17% yield) as a white solid. ESI-LCMS: m/z 472.2 [M+H]$^+$; $^1$H-NMR (400 MHz, DMSO-d$_6$): δ 12.12 (s, 1H), 11.67 (s, 1H), 8.28 (s, 1H), 6.12-6.07 (dd, J=15 Hz, 1H), 5.48-5.24 (m, 2H), 5.22 (s, 1H), 4.55-4.49 (m, 1H), 3.97 (d, J=5 Hz, 1H), 2.79-2.76 (m, 1H), 1.12 (d, J=6 Hz, 6H), 0.88 (s, 9H), 0.11 (d, J=6 Hz, 6H).

Preparation of (7): To a solution of 6 (3.8 g, 8.1 mmol) in pyridine (40 mL) was added DMTrCl (4.1 g, 12.1 mmol) at 20° C. The mixture was stirred at 20° C. for 1 h. TLC showed 7 was consumed completely. Water was added to the reaction. The product was extracted with EA, The organic layer was washed with NaHCO$_3$ and brine. Then the solution was concentrated under reduced pressure to give the crude product of 7 (6 g, 7.6 mmol, 94.3% yield) as a yellow solid. ESI-LCMS: m/z 775 [M+H]$^+$.

Preparation of (8): To a solution of 7 (6.0 g, 7.75 mmol) in THF (60 mL) was added TBAF (2.4 g, 9.3 mmol). The mixture was stirred at r.t. for 1 h. TLC showed 7 was consumed completely. Water was added to the reaction. The product was extracted with EA, The organic layer was washed with NaHCO$_3$ and brine. Then the solution was concentrated under reduced pressure, the residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 25 min, the eluted product was collected at CH$_3$CN/H$_2$O (0.5% NH$_4$HCO$_3$)=4/1; Detector, UV 254 nm. This resulted in to give 8 (4.0 g, 5.9 mmol, 76.6% yield) as a white solid. ESI-LCMS: m/z 660 [M+H]$^+$; $^1$H-NMR (400 MHz, DMSO-d$_6$): δ 12.12 (s, 1H), 11.67 (s, 1H), 8.12 (s, 1H), 7.34-7.17 (m, 9H), 6.83-6.78 (m, 4H), 6.23-6.18 (m, 1H), 5.66 (d, J=7 Hz, 1H), 5.48-5.35 (m, 1H), 4.65-4.54 (m, 1H), 3.72 (d, J=2 Hz, 6H), 2.79-2.73 (m, 1H), 1.19-1.06 (m, 6H).

Preparation of Example 36 monomer: To a solution of 9 (4.0 g, 6.1 mmol) in DCM (40 mL) was added DCI (608 mg, 5.1 mmol) and CEP (2.2 g, 7.3 mmol) under N$_2$ pro. The mixture was stirred at 20° C. for 0.5 h. TLC showed 9 was consumed completely. The product was extracted with DCM, The organic layer was washed with H$_2$O and brine. Then the solution was concentrated under reduced pressure and the residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 25 min, the eluted product was collected at CH$_3$CN/H$_2$O (0.5% NH$_4$HCO$_3$)=1/0; Detector, UV 254 nm. This resulted in to give Example 36 monomer (5.1 g, 5.81 mmol, 95.8% yield) as a white solid. ESI-LCMS: m/z 860 [M+H]$^+$; $^1$H-NMR (400 MHz, DMSO-d$_6$): δ 12.12 (s, 1H), 11.67 (s, 1H), 8.12 (s, 1H), 7.34-7.17 (m, 9H), 6.83-6.78 (m, 4H), 6.23-6.18 (m, 1H), 5.67-5.54 (m, 1H), 4.70-4.67 (m, 1H), 4.23-4.20 (m, 1H), 3.72 (m, 6H), 3.60-3.48 (m, 3H), 2.79-2.58 (m, 3H), 1.13-0.94 (m, 18H); $^{31}$P-NMR (162 MHz, DMSO-d$_6$): δ 150.31, 150.26, 140.62, 149.57.

Example 37: Synthesis of Monomer

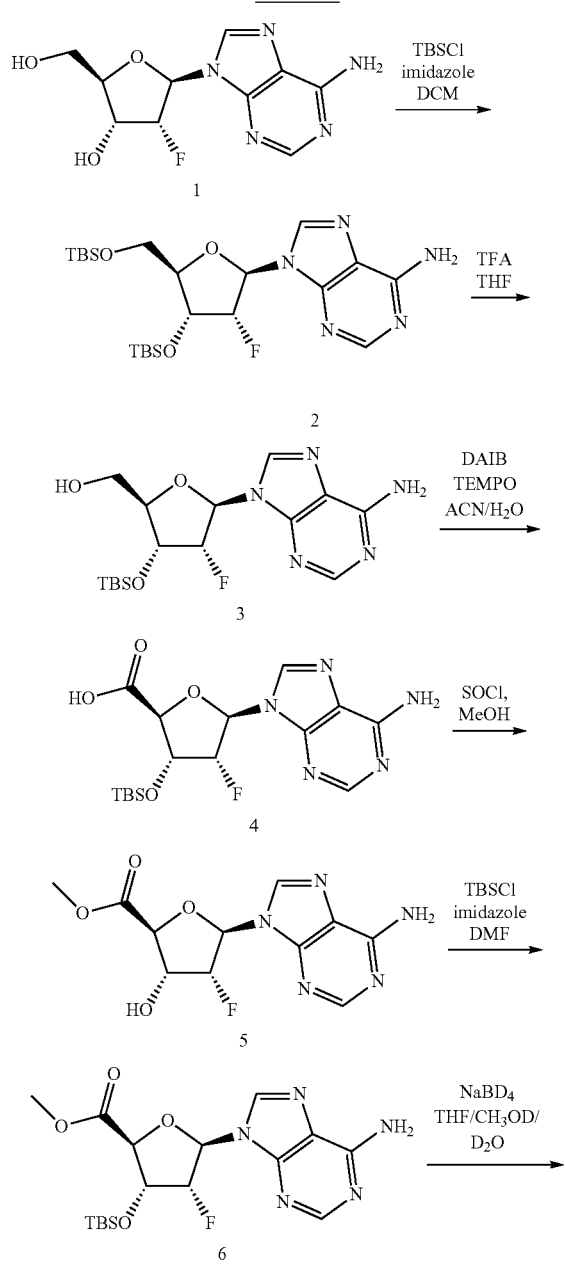

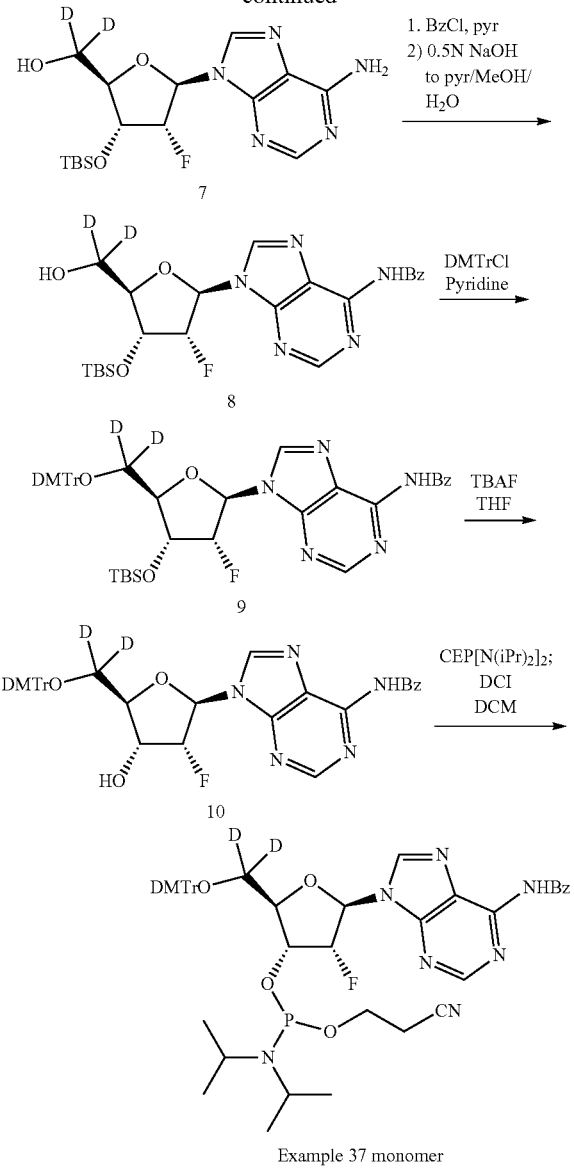

Example 37 monomer

Preparation of (2): To a solution of 1 (35 g, 130.2 mmol) in DMF (350 mL) was added imidazole (26.5 g, 390.0 mmol) then added TBSCl (48.7 g, 325.8 mmol) at 0° C. The mixture was stirred at r.t. for 14 h. TLC showed 1 was consumed completely. Water was added to the reaction. The product was extracted with EA, The organic layer was washed with NaHCO$_3$ and brine. Then the solution was concentrated under reduced pressure the crude 2 (64.6 g) as a white solid which was used directly for next step. ESI-LCMS: m/z 498 [M+H]$^+$.

Preparation of (3): To a solution of 2 (64.6 g, 130.2 mmol) in THF (300 mL) and added TFA/H$_2$O (1:1, 300 mL) at 0° C. The mixture was stirred at 0° C. for 2 h. TLC showed 2 was consumed completely. NaHCO$_3$ was added to the reaction. The product was extracted with EA, The organic layer was washed with NaHCO$_3$ and brine. Then the solution was concentrated under reduced pressure. The residue was purified by silica gel column chromatography (eluent, DCM: MEOH=100:1~20:1). This resulted in to give 3 (31.3 g, 81.7 mmol, 62.6% over two step) as a white solid. ESI-LCMS: m/z 384 [M+H]$^+$.

Preparation of (4): To a solution of 3 (31.3 g, 81.7 mmol) in ACN/H₂O (1:1, 350 mL) was added DAIB (78.0 g, 244.0 mmol) and Tempo (3.8 g, 24.4 mmol). The mixture was stirred at 40° C. for 2 h. TLC showed 3 was consumed completely. Then filtered to give 4 (22.5 g, 55.5 mmol, 70.9%) as a white solid. ESI-LCMS: m/z 398 [M+H]⁺.

Preparation of (5): To a solution of 4 (22.5 g, 55.5 mmol) in MeOH (225 mL) held at −15° C. with an ice/MeOH bath was added SOCl₂ (7.6 mL, 94.5 mmol), dropwise at such a rate that the reaction temp did not exceed 7° C. After the addition was complete, cooling was removed, the reaction was allowed to stir at room temp. The mixture was stirred at r.t. for 14 h. TLC showed 4 was consumed completely. Then the solution was concentrated under reduced pressure to get crude 5 (23.0 g) as a white solid which was used directly for next step. ESI-LCMS: m/z 298 [M+H]⁺.

Preparation of (6): To a solution of 5 (23 g, 55.5 mmol) in DMF (220 mL) was added imidazole (11.6 g, 165.0 mmol) then added TBSCl (12.3 g, 82.3 mmol) at 0° C. The mixture was stirred at 20° C. for 14 h. TLC showed 1 was consumed completely. Water was added to the reaction. The product was extracted with EA, The organic layer was washed with NaHCO₃ and brine. Then the solution was concentrated under reduced pressure. The residue was purified by silica gel column chromatography (eluent, DCM: MEOH=100:1~20:1). This resulted in to give 6 (21.3 g, 51.1 mmol, 90% over two step) as a white solid. ESI-LCMS: m/z 412 [M+H]⁺.

Preparation of (7): To the solution of 6 (21.0 g, 51.0 mmol) in dry THF/MeOD/D₂O=10/2/1 (260.5 mL) was added NaBD₄ (6.4 g, 153.1 mmol) at r.t. and the reaction mixture was stirred at 50° C. for 2 h. After completion of reaction, the resulting mixture was added CH₃COOD to pH=7, after addition of water, the resulting mixture was extracted with EA (300 mL). The combined organic layer was washed with water and brine, dried over Na₂SO₄. Then the solution was concentrated under reduced pressure and the residue was used for next step without further purification. ESI-LCMS: m/z 386 [M+H]⁺.

Preparation of (8): To a stirred solution of 7 (14.0 g, 35 mmol) in pyridine (50 mL) were added BzCl (17.2 g, 122.5 mmol) at 0° C. under N₂ atmosphere. The mixture was stirred at r.t. for 14 h. TLC showed 7 was consumed completely. Then the solution diluted with EA. The organic layer was washed with NaHCO₃ and brine. Then the solution was concentrated under reduced pressure and the residue was used for next step without further purification. To a solution of the crude in pyridine (300 mL) then added 2 M NaOH (MeOH: H₂O=4:1, 60 mL) at 0° C. The mixture was stirred at 0° C. for 10 min. Then the solution diluted with EA. The organic layer was washed with NH₄Cl and brine. Then the solution was concentrated under reduced pressure and the residue was purified by Flash-Prep-HPLC with the following conditions (IntelFlash-1): Column, C18 silica gel; mobile phase, CH₃CN/H₂O (0.5% NH₄HCO₃)=1/3 increasing to CH₃CN/H₂O (0.5% NH₄HCO₃)=4/1 within 25 min, the eluted product was collected at CH₃CN/H₂O (0.5% NH₄HCO₃)=3/2; Detector, UV 254 nm. This resulted in to give 8 (14 g, 28.02 mmol, 69.21% yield) as a white solid. ESI-LCMS: m/z 490 [M+H]⁺; ¹H-NMR (400 MHz, DMSO-d₆): δ 11.24 (s, 1H), 8.76 (s, 1H), 8.71 (m, 1H), 8.04 (d, J=7 Hz, 2H), 7.66-7.10 (m, 5H), 6.40-6.35 (dd, 1H), 5.71-5.56 (m, 1H), 5.16 (s, 1H), 4.79-4.72 (m, 1H), 4.01 (m, 1H), 0.91 (s, 9H), 0.14 (m, 6H).

Preparation of (9): To a solution of 8 (5.1 g, 10.4 mmol) in pyridine (50 mL) was added DMTrCl (5.3 g, 15.6 mmol). The mixture was stirred at r.t. for 1 h. TLC showed 8 was consumed completely. Water was added to the reaction. The product was extracted with EA, The organic layer was washed with NaHCO₃ and brine. Then the solution was concentrated under reduced pressure and the residue was used for next step without further purification. ESI-LCMS: m/z 792 [M+H]⁺.

Preparation of (10): To a solution of 9 (7.9 g, 10.0 mmol) in THF (80 mL) was added 1 M TBAF in THF (12 mL). The mixture was stirred at r.t. for 1 h. TLC showed 9 was consumed completely. Water was added to the reaction. The product was extracted with EA, The organic layer was washed with NaHCO₃ and brine. Then the solution was concentrated under reduced pressure the residue was purified by Flash-Prep-HPLC with the following conditions (IntelFlash-1): Column, C18 silica gel; mobile phase, CH₃CN/H₂O (0.5% NH₄HCO₃)=1/1 increasing to CH₃CN/H₂O (0.5% NH₄HCO₃)=1/0 within 25 min, the eluted product was collected at CH₃CN/H₂O (0.5% NH₄HCO₃)=4/1; Detector, UV 254 nm. This resulted in to give 10 as a white solid. ESI-LCMS: m/z 678 [M+H]⁺; ¹H-NMR (400 MHz, DMSO-d₆): δ 11.25 (s, 1H), 8.74 (s, 1H), 8.62 (s, 1H), 8.04 (d, J=7 Hz, 2H), 7.66-7.53 (m, 3H), 7.33-7.15 (m, 9H), 6.82-6.78 (m, 4H), 6.43 (d, J=20 Hz, 1H), 5.76-5.60 (m, 1H), 4.88-4.80 (m, 1H), 4.13 (d, J=8 Hz, 1H), 3.71 (m, 6H).

Preparation of Example 37 monomer: To a solution of 10 (6.2 g, 9.1 mmol) in DCM (60 mL) was added DCI (1.1 g, 9.4 mmol) and CEP (3.3 g, 10.9 mmol) under N₂ pro. The mixture was stirred at 20° C. for 0.5 h. TLC showed 10 was consumed completely. The product was extracted with DCM, The organic layer was washed with H₂O and brine. Then the solution was concentrated under reduced pressure and the residue was purified by Flash-Prep-HPLC with the following conditions (IntelFlash-1): Column, C18 silica gel; mobile phase, CH₃CN/H₂O (0.5% NH₄HCO₃)=1/1 increasing to CH₃CN/H₂O (0.5% NH₄HCO₃)=1/0 within 20 min, the eluted product was collected at CH₃CN/H₂O (0.5% NH₄HCO₃)=1/0; Detector, UV 254 nm. This resulted in to give Example 37 monomer (7.5 g, 8.3 mmol, 90.7%) as a white solid. ESI-LCMS: m/z 878 [M+H]⁺; ¹H-NMR (400 MHz, DMSO-d₆): δ 11.25 (s, 1H), 8.68-8.65 (dd, 2H), 8.04 (m, 2H), 7.66-7.53 (m, 3H), 7.33-7.15 (m, 9H), 6.82-6.78 (m, 4H), 6.53-6.43 (m, 1H), 5.96-5.81 (m, 1H), 5.36-5.15 (m, 1H), 4.21 (m, 1H), 3.86-3.52 (m, 10H), 2.79-2.61 (m, 2H), 1.21-0.99 (m, 12H); ³¹P-NMR (162 MHz, DMSO-d₆): δ 149.60, 149.56, 149.48.

Example 38. Synthesis of End Cap Monomer

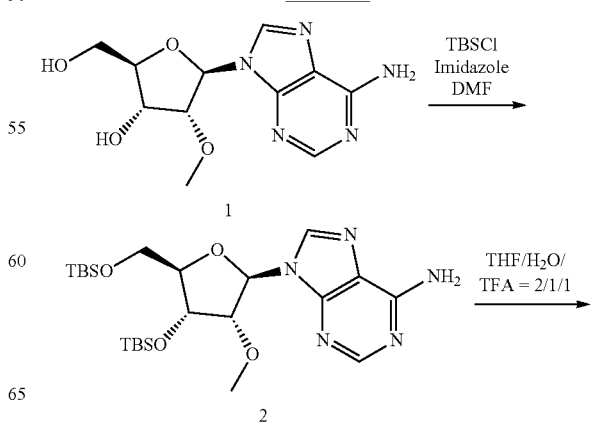

Scheme-18

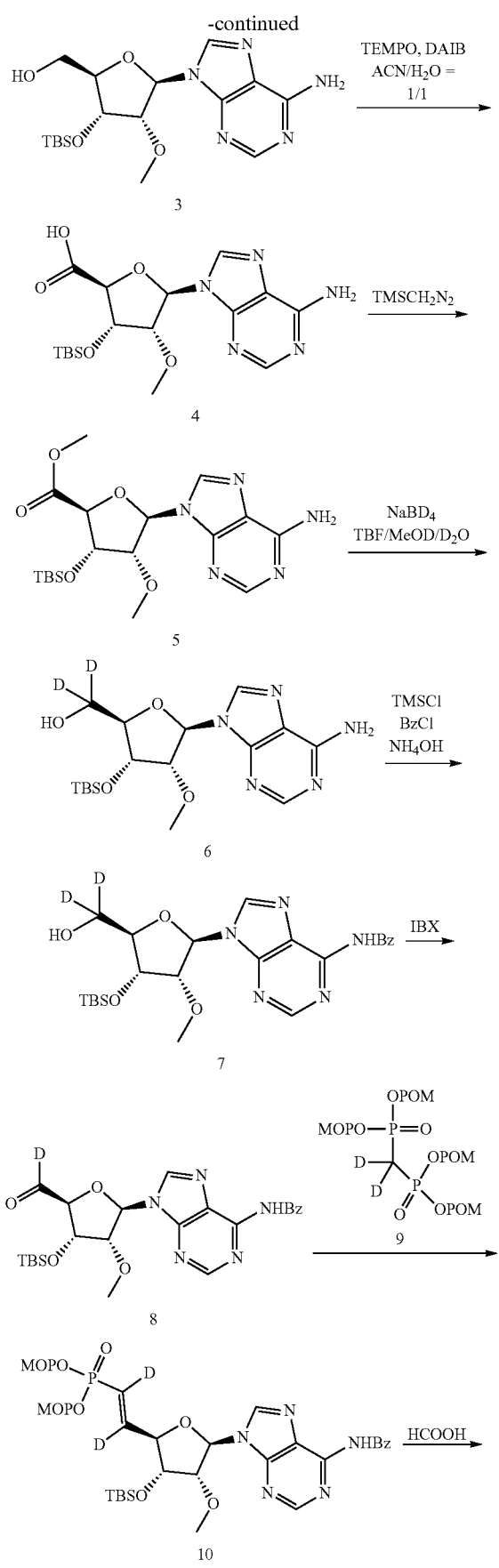
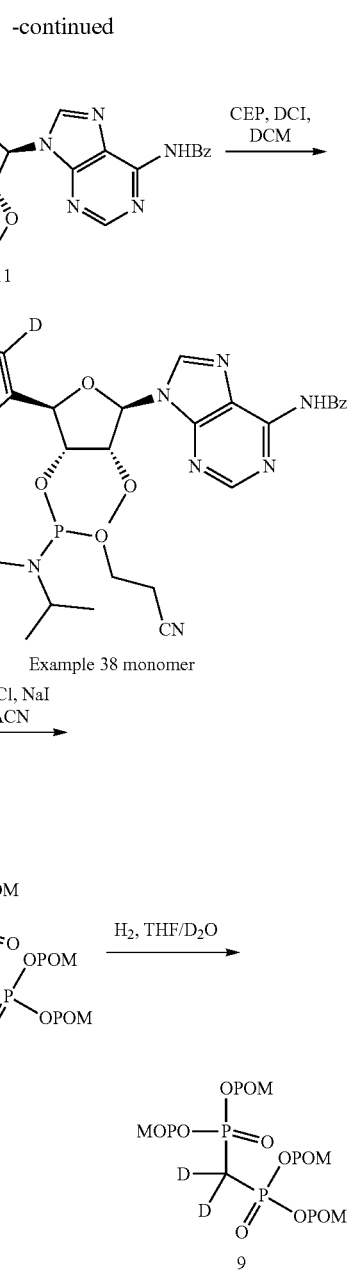

Preparation of (2): To a solution of 1 (20.0 g, 71.2 mmol) in dry pyridine (200.0 mL) was added TBSCl (26.8 g, 177.9 mmol) and imidazole (15.6 g, 227.8 mmol). The mixture was stirred at r.t. for 15 h. TLC showed 1 was consumed completely. The reaction mixture was concentrated to give residue. The residue was quenched with DCM (300.0 mL). The DCM layer was washed with $H_2O$ (100.0 mL*2) and brine. The DCM layer concentrated to give crude 2 (45.8 g) as a yellow oil. The crude used to next step directly. ESI-LCMS m/z 510.5 $[M+H]^+$.

Preparation of (3): To a mixture solution of 2 (45.8 g) in THF (300.0 mL) was added mixture of $H_2O$ (100.0 mL) and TFA (100.0 mL) at 0° C. over 30 min. Then the reaction mixture was stirred at 0° C. for 4 h. TLC showed the 2 was consumed completely. The reaction mixture pH was adjusted to 7-8 with $NH_3 \cdot H_2O$ (100 mL). Then the mixture was extracted with EA (500.0 mL*2). The combined EA layer was washed with brine and concentrated to give crude which was purified by c.c. (PE:EA=5:1~1:0) to give compound 3 (21.0 g, 53.2 mmol, 74.7% yield over 2 steps) as a white solid. ESI-LCMS m/z 396.2 [M+H]$^+$.

Preparation of (4): To a solution of 3 (21.0 g, 53.2 mmol) in ACN (100.0 mL) and water (100.0 mL) were added (diacetoxyiodo)benzene (51.0 g, 159.5 mmol) and TEMPO (2.5 g, 15.9 mmol), The reaction mixture was stirred at 40° C. for 1 h. TLC showed the 3 was consumed completely. The reaction mixture was cooled down to r.t. and filtered, the filtrate was concentrated to give crude which was purified by crystallization (ACN) to give 4 (14.5 g, 35.4 mmol, 66.2% yield). ESI-LCMS m/z 410.1[M+H]$^+$.

Preparation of (5): To a solution of 4 (14.5 g, 35.4 mmol) in toluene (90.0 mL) and MeOH (60.0 mL) was added trimethylsilyldiazomethane (62.5 mL, 2.0 M, 141.8 mmol) at 0° C., then stirred at r.t. for 2 h. TLC showed the 4 was consumed completely. The solvent was removed under reduce pressure, the residue was purified by crystallization (ACN) to give 5 (10.0 g, 23.6 mmol, 66.6% yield). ESI-LCMS m/z 424.2 [M+H]$^+$ Preparation of (6): To the solution of 5 (10.0 g, 23.6 mmol) in dry THF/MeOD/D$_2$O=10/2/1 (100.0 mL) was added NaBD$_4$ (2.98 g, 70.9 mmol) three times during an hour at 40° C., the reaction mixture was stirred at r.t. for 2.0 h. The resulting mixture was added CH$_3$COOD change pH=7.5, after addition of water, the resulting mixture was extracted with EA (50.0 mL*3). The combined organic layer was washed with water and brine, dried over Na$_2$SO$_4$, concentrated to give a residue which was purified by c.c. (PE/EA=1:1~1:0). This resulted in to give 6 (6.1 g, 15.4 mmol, 65.3% yield) as a white solid. ESI-LCMS m/z 398.1 [M+H]$^+$; $^1$H-NMR (400 MHz, DMSO-d$_6$) δ 8.28 (s, 1H), 8.02 (s, 1H), 7.23 (s, 2H), 5.86 (d, J=6.4 Hz, 1H), 5.26 (s, 1H), 4.42-4.41 (m, 1H), 4.35-4.32 (m, 1H), 3.82 (d, J=2.6 Hz, 1H), 3.14 (s, 3H), 0.78 (s, 9H), 0.00 (d, J=0.9 Hz, 6H).

Preparation of (7): To a solution of 6 (6.1 g, 15.4 mmol) in pyridine (60.0 mL) was added the benzoyl chloride (6.5 g, 46.2 mmol) drop wise at 5° C. The reaction mixture was stirred at r.t. for 2 h. TLC showed the 6 was consumed completely. The reaction mixture was cooled down to 10° C. and quenched with H$_2$O (20.0 mL), extracted with EA (200.0 mL*2), combined the EA layer. The organic phase was washed with brine and dried over Na$_2$SO$_4$, concentrated to give the crude (12.0 g) which was dissolved in pyridine (60.0 mL), cooled to 0° C., 20.0 mL NaOH (2 M in methanol:H$_2$O=4:1) was added and stirred for 10 min. The reaction was quenched by saturated solution of ammonium chloride, the aqueous layer was extracted with EA (200.0 mL*2), combined the EA layer, washed with brine and dried over Na$_2$SO$_4$, concentrated. The residue was purified by c.c. (PE/EA=10:1~1:1) to give 7 (7.0 g, 13.9 mmol, 90.2% yield). ESI-LCMS m/z 502.2 [M+H]$^+$; $^1$H-NMR (400 MHz, DMSO-d$_6$) δ 11.24 (s, 1H, exchanged with D$_2$O) 8.77 (s, 2H), 8.04-8.06 (m, 2H), 7.64-7.66 (m, 2H), 7.54-7.58 (m, 2H), 6.14-6.16 (d, J=5.9 Hz, 1H), 5.20-5.23 (m, 1H), 4.58-4.60 (m, 1H), 4.52-4.55 (m, 1H), 3.99-4.01 (m, 1H), 3.34 (s, 4H), 0.93 (s, 9H), 0.14-0.15 (d, J=1.44 Hz, 6H).

Preparation of (8): To a stirred solution of 7 (5.5 g, 10.9 mmol) in DMSO (55.0 mL) was added EDCI (6.3 g, 32.9 mmol), pyridine (0.9 g, 10.9 mmol) and TFA (0.6 g, 5.5 mmol), the reaction mixture was stirred at r.t. for 15 h. The reaction was quenched with water and extracted with EA (100.0 mL). The organic phase was washed by brine, dried over Na$_2$SO$_4$, The organic phase was evaporated to dryness under reduced pressure to give a residue 8 (4.8 g) which was used directly to next step. ESI-LCMS: m/z 517.1 [M+H$_2$O]$^+$.

Preparation of (9b): A solution of 9a (35.0 g, 150.8 mmol) and NaI (90.5 g, 603.4 mmol) in dry ACN (180.0 mL) was added chloromethyl pivalate (113.6 g, 754.3 mmol) at r.t., the reaction was stirred at 80° C. for 4 h. The reaction was cooled to r.t. and quenched by water, then the mixture was extracted with EA (500.0 mL*3), combined the organic layer was washed with saturated solution of ammonium chloride, followed by with brine and dried over Na$_2$SO$_4$. Then the organic layer was concentrated to give a residue which was purified by c.c., this resulted in to give 9b (38.0 g, 60.1 mmol, 39.8% yield) as a white solid. ESI-LCMS m/z 655.2 [M+Na]$^+$; $^1$H-NMR (400 MHz, CDCl$_3$): δ 5.74-5.67 (m, 8H), 2.67 (t, J=21.6 Hz, 2H), 1.23 (s, 36H).

Preparation of (9): 3.8 g 10% Pd/C was washed with dry THF (30.0 mL) three times. Then transferred into a round-bottom flask charged with 9b (38.0 g, 60.1 mmol) and solvent (dry THF:D$_2$O=5:1, 400.0 mL), the mixture was stirred at 80° C. under 1 L H$_2$ balloon for 15 h. The reaction was cooled to r.t. and extracted with EA (500.0 mL*3), combined the organic layer was washed with brine and dried over Na$_2$SO$_4$. The residue 9 (3.0 g, 3.7 mmol, 38.8% yield) as a white solid was used directly to next step without further purification. ESI-LCMS m/z 657.2 [M+Na]$^+$; $^1$H-NMR (400 MHz, CDCl$_3$): δ 5.74-5.67 (m, 8H), 1.23 (s, 36H).

Preparation of (10): A solution of 8 (4.8 g, 9.6 mmol), 9 (7.3 g, 11.5 mmol) and K$_2$CO$_3$ (4.0 g, 38.8 mmol) in dry THF (60.0 mL) and D20 (20.0 mL) was stirred at r.t. 18 h. LC-MS showed 8 was consumed completely. The product was extracted with EA (300.0 mL) and the organic layer was washed with brine and dried over Na$_2$SO$_4$. Then the organic layer was concentrated to give a residue which was purified by c.c. (PE/EA=5:1~1:1) and MPLC. This resulted in to give 10 (3.0 g, 3.7 mmol, 38.8% yield) as a white solid. ESI-LCMS m/z 806.4[M+H]$^+$; $^1$H-NMR (400 MHz, DMSO-d$_6$): δ 11.25 (s, 1H, exchanged with D$_2$O) 8.75 (s, 2H), 8.07-8.05 (d, J=8.0 Hz, 2H), 7.67-7.54 (m, 3H), 6.05 (d, J=5.1 Hz, 1H), 5.65-5.58 (m, 4H), 4.80-4.70 (m, 2H), 4.59-4.57 (m, 1H), 3.36 (s, 3H), 1.11 (s, 9H), 1.10 (s, 9H), 0.94 (s, 9H), 0.17-0.16 (m, 6H); $^{31}$P NMR (162 MHz, DMSO-d$_6$) δ 17.02.

Preparation of (11): To a round-bottom flask was added 10 (3.0 g, 3.7 mmol) in a mixture of H$_2$O (30.0 mL), HCOOH (30.0 mL). The reaction mixture was stirred at 40° C. for 15 hrs. LC-MS showed the 10 was consumed completely. The reaction mixture was adjusted the pH=6-7 with con. NH$_3$.H$_2$O (100.0 mL). Then the mixture was extracted with DCM (100.0 mL*3). The combined DCM layer was dried over Na$_2$SO$_4$. Filtered and filtrate was concentrated to give crude which was purified by Flash-Prep-HPLC with the following conditions (IntelFlash-1): Column, C18 silica gel; mobile phase, CH$_3$CN/H$_2$O (0.5% NH$_4$HCO$_3$)=1/2 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=3/2; Detector, UV 254 nm. To give product 11 (1.8 g, 2.6 mmol, 70.3% yield). ESI-LCMS m/z=692.2[M+H]$^+$; $^1$H-NMR (400 MHz, DMSO-d$_6$): δ 11.11 (s, 1H, exchanged with D$_2$O) 8.71-8.75 (d, J=14.4, 2H), 8.04-8.06 (m, 2H), 7.64-7.65 (m, 1H), 7.54-7.58 (m, 2H), 6.20-6.22 (d, J=5.4, 2H), 5.74-5.75 (d, J=5.72, 2H), 5.56-5.64 (m, 4H), 4.64-4.67 (m, 1H), 4.58-4.59 (m, 1H), 4.49-4.52 (m, 1H), 3.37 (s, 3H), 1.09-1.10 (d, J=1.96, 18H); $^{31}$P NMR (162 MHz, DMSO-d$_6$) δ 17.46.

Preparation of Example 38 monomer: To a solution of 11 (1.8 g, 2.6 mmol) in DCM (18.0 mL) was added the DCI (276.0 mg, 2.3 mmol), then CEP[N(ipr)$_2$]$_2$ (939.5 mg, 3.1 mmol) was added. The mixture was stirred at r.t. for 1 h. TLC showed 11 consumed completely. The reaction mixture was washed with H₂O (50.0 mL*2) and brine (50.0 mL*2), dried over Na₂SO₄ and concentrated to give crude which was purified by Flash-Prep-HPLC with the following conditions (IntelFlash-1): Column, C18 silica gel; mobile phase, CH₃CN/H₂O (0.5% NH₄HCO₃)=1/1 increasing to CH₃CN/H₂O (0.5% NH₄HCO₃)=1/0 within 20 min, the eluted product was collected at CH₃CN/H₂O (0.5% NH₄HCO₃)=9/1; Detector, UV 254 nm. The product was concentrated to give Example 38 monomer (2.0 g, 2.2 mmol, 86.2% yield) as a white solid. ESI-LCMS m/z 892.3[M+H]⁺; ¹H-NMR (400 MHz, DMSO-d₆): δ 11.27 (s, 1H, exchanged with D₂O) 8.72-8.75 (m, 2H), 8.04-8.06 (m, 2H), 7.54-7.68 (m, 3H), 6.20-6.26 (m, 1H), 5.57-5.64 (m, 4H), 4.70-4.87 (m, 3H), 3.66-3.88 (m, 4H), 3.37-3.41 (m, 3H), 2.82-2.86 (m, 2H), 1.20-1.21 (m, 12H), 1.08-1.09 (m, 18H); ³¹P-NMR (162 MHz, DMSO-d₆): δ 150.03, 149.19, 17.05, 16.81.

Example 39. Synthesis of 5' End Cap Monomer

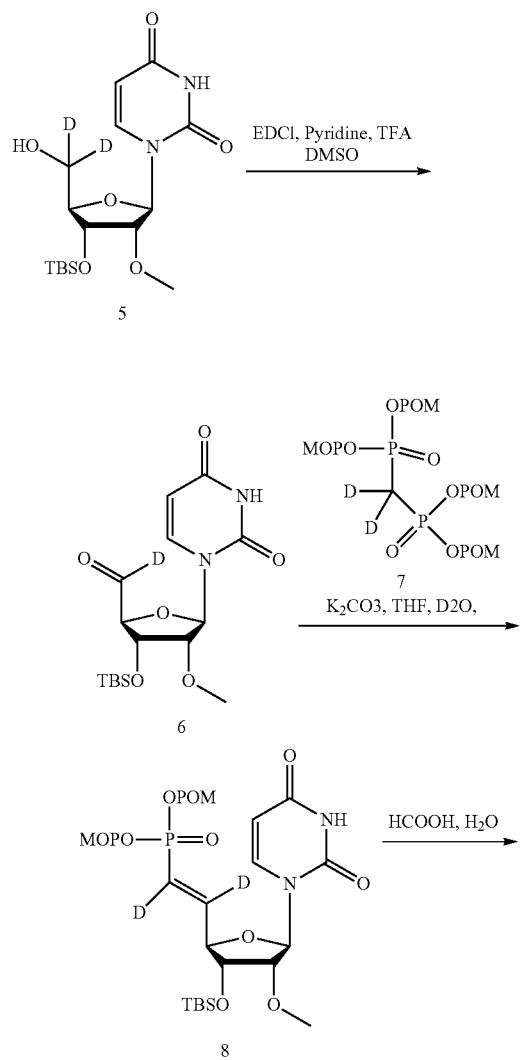

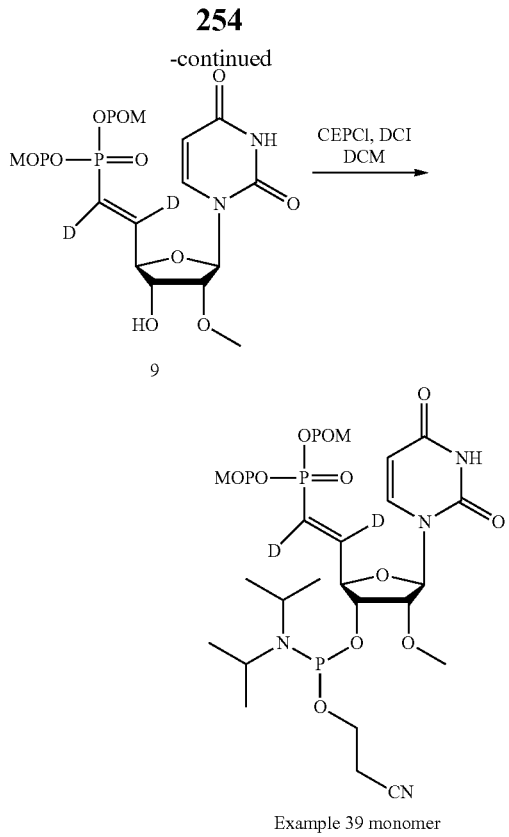

Example 39 monomer

Preparation of (6): To a stirred solution of 5 (8.0 g, 21.3 mmol, Scheme 3) in DMSO (80.0 mL) were added EDCI (12.2 g, 63.9 mmol), pyridine (1.7 g, 21.3 mmol), TFA (1.2 g, 10.6 mmol) at r.t. And the reaction mixture was stirred at r.t. for 1.5 h. The reaction was quenched with water and extracted with EA (200.0 mL). The organic phase was washed by brine, dried over Na₂SO₄, The organic phase was evaporated to dryness under reduced pressure to give a residue 6 which was used directly to next step. ESI-LCMS: m/z 372.3 [M+H]⁺.

Preparation of (8): To a solution of K₂CO₃ (5.5 g, 8.3 mmol) in dry THF (60.0 mL) and D2O (20.0 mL) was added a solution of 6 (8.0 g, 21.5 mmol) in dry THF (10.0 mL). The reaction mixture was stirred at r.t. overnight. LC-MS showed 6 was consumed completely. The product was extracted with EA (300.0 mL) and the organic layer was washed with brine and dried over Na₂SO₄. Then the organic layer was concentrated to give a residue which was purified by Flash-Prep-HPLC with the following conditions (IntelFlash-1): Column, C18 silica gel; mobile phase, CH₃CN/H₂O (0.5% NH₄HCO₃)=2/3 increasing to CH₃CN/H₂O (0.5% NH₄HCO₃)=3/2 within 20 min, the eluted product was collected at CH₃CN/H₂O (0.5% NH₄HCO₃)=1/1; Detector, UV 254 nm. This resulted in to give 8 (5.0 g, 7.3 mmol, 40.0%) as a white solid. ESI-LCMS: m/z 679.3 [M+H]⁺; ¹H-NMR (400 MHz, Chloroform-d): δ 9.91 (s, 1H), 7.29 (d, J=8.1 Hz, 1H), 5.82 (d, J=2.7 Hz, 1H), 5.72 (d, J=8.1 Hz, 1H), 5.65-5.54 (m, 4H), 4.43 (dd, J=7.2, 3.2 Hz, 1H), 3.92 (dd, J=7.2, 5.0 Hz, 1H), 3.65 (dd, J=5.1, 2.7 Hz, 1H), 3.44 (s, 3H), 1.13 (s, 18H), 0.82 (s, 9H), 0.01 (d, J=4.8 Hz, 6H); ³¹P NMR (162 MHz, Chloroform-d): δ 16.40.

Preparation of (9): To a solution of HCOOH (50.0 mL) and H₂O (50.0 mL) was added 8 (5.0 g, 7.3 mmol). The reaction mixture was stirred at 40° C. overnight. LC-MS showed 8 was consumed completely. A solution of NaHCO₃

(500.0 mL) was added. The product was extracted with EA (300.0 mL) and the organic layer was washed with brine and dried over Na$_2$SO$_4$. Then the organic layer was concentrated to give a residue which was purified by Flash-Prep-HPLC with the following conditions (IntelFlash-1): Column, C18 silica gel; mobile phase, CH$_3$CN/H$_2$O (0.5% NH$_4$HCO$_3$)=2/3 increasing to CH$_3$CN/H$_2$O (0.5% NH$_4$HCO$_3$)=3/2 within 20 min, the eluted product was collected at CH$_3$CN/H$_2$O (0.5% NH$_4$HCO$_3$)=1/1; Detector, UV 254 nm. This resulted in to give 9 (3.0 g, 5.4 mmol, 73.2%) as a white solid. ESI-LCMS: m/z 565.2 [M+H]$^+$; $^1$H-NMR (400 MHz, DMSO-d$_6$): δ 11.43 (s, 1H), 7.64 (d, J=8.1 Hz, 1H), 5.83 (d, J=4.3 Hz, 1H), 5.69-5.56 (m, 5H), 5.54 (d, J=6.7 Hz, 1H), 4.37 (dd, J=6.1, 2.9 Hz, 1H), 4.12 (q, J=6.1 Hz, 1H), 3.96 (dd, J=5.4, 4.3 Hz, 1H), 3.39 (s, 3H), 1.16 (s, 18H); $^{31}$P NMR (162 MHz, DMSO-d$_6$): δ 17.16.

Preparation of Example 39 monomer: To a suspension of 9 (2.6 g, 4.6 mmol) in DCM (40.0 mL) was added DCI (0.5 g, 5.6 mmol) and CEP[N(iPr)$_2$]$_2$ (1.7 g, 5.6 mmol). The mixture was stirred at r.t. for 1.0 h. LC-MS showed 9 was consumed completely. The solution was washed with water twice and washed with brine and dried over Na$_2$SO$_4$. Then concentrated to give a residue which was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give Example 39 monomer (3.0 g, 3.9 mmol, 85.2%) as a white solid. ESI-LCMS: m/z 765.3 [M+H]$^+$; $^1$H-NMR (400 MHz, DMSO-d$_6$): δ 11.44 (s, 1H), 7.71 (dd, J=8.1, 3.8 Hz, 1H), 5.81 (dd, J=4.4, 2.5 Hz, 1H), 5.74-5.53 (m, 5H), 4.59-4.33 (m, 2H), 4.20-4.14 (m, 1H), 3.88-3.53 (m, 4H), 3.39 (d, J=16.2 Hz, 3H), 2.80 (td, J=5.9, 2.9 Hz, 2H), 1.16 (d, J=1.9 Hz, 30H); $^{31}$P-NMR (162 MHz, DMSO-d$_6$): δ 147.68, 149.16, 16.84, 16.55.

Example 40. Synthesis of Monomer

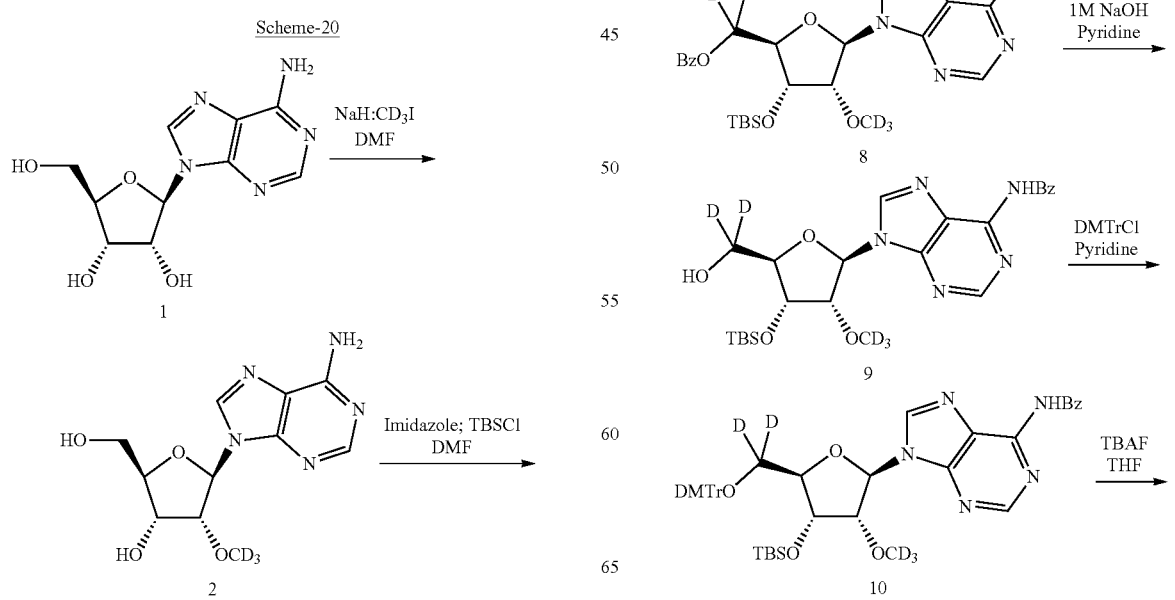

-continued

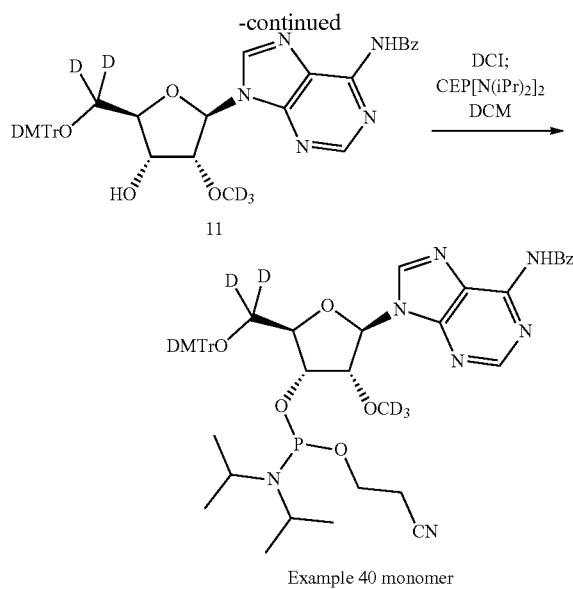

Example 40 monomer

Preparation of (2): To a solution of 1 (26.7 g*2, 0.1 mol) in DMF (400 mL) was added sodium hydride (4.8 g, 0.1 mol) for 30 min, then was added CD₃I (16 g, 0.1 mol) at 0° C. for 2.5 hr (ref. for selective 2'-O-alkylation reaction conditions, J. Org. Chem. 1991, 56, 5846-5859). The mixture was stirring at r.t. for another 1 h. LCMS showed the reaction was consumed. The mixture was filtered and the clear solution was evaporated to dryness and was evaporated with CH₃OH. The crude was purified by silica gel column (SiO₂, DCM/MeOH=50:1~15:1). This resulted in to give the product 2 (35.5 g, 124.6 mmol, 62% yield) as a solid. ESI-LCMS: m/z 285 [M+H].

Preparation of (3): To a solution of 2 (35.5 g, 124.6 mmol) in pyridine (360 mL) was added imidazole (29.7 g, 436.1 mmol) and TBSCl (46.9 g, 311.5 mmol). The mixture was stirred at r.t. over night. LCMS showed 2 was consumed completely. The reaction was quenched with water (500 mL). The product was extracted into ethyl acetate (1 L). The organic layer was washed with brine and dried over anhydrous Na₂SO₄. The crude was purified by silica gel column (SiO₂, PE/EA=4:1~1:1). This resulted in to give the product 3 (20.3 g, 39.6 mmol, 31.8% yield) as a solid. ESI-LCMS: m/z 513 [M+H]⁺; ¹H-NMR (400 MHz, DMSO-d₆): δ 8.32 (m, 1H), 8.13 (m, 1H), 7.31 (m, 2H), 6.02-6.01 (d, J=4.0 Hz, 1H), 4.60-4.58 (m, 1H), 4.49-4.47 (m, 1H), 3.96-3.86 (m, 2H), 3.72-3.68 (m, 1H), 0.91-0.85 (m, 18H), 0.13-0.01 (m, 12H).

Preparation of (4): To a solution of 3 (20.3 g, 39.6 mmol) in THF (80 mL) was added TFA (20 mL) and water (20 mL) at 0° C. The reaction mixture was stirred at 0° C. for 5 h. LC-MS showed 3 was consumed completely. Con. NH₄OH was added to the mixture at 0° C. to quench the reaction until the pH=7.5. The product was extracted into ethyl acetate (200 mL). The organic layer was washed with brine and dried over anhydrous Na₂SO₄. The solution was then concentrated under reduced pressure and the residue was washed by PE/EA=5:1. This resulted in to give 4 (10.5 g, 26.4 mmol, 66.6% yield) as a white solid. ESI-LCMS: m/z 399 [M+H]⁺; ¹H-NMR (400 MHz, DMSO-d₆): δ 8.41 (m, 1H), 8.14 (m, 1H), 7.37 (m, 2H), 5.99-5.97 (d, J=8.0 Hz, 1H), 5.43 (m, 1H), 4.54-4.44 (m, 2H), 3.97-3.94 (m, 1H), 3.70-3.53 (m, 2H), 0.91 (m, 9H), 0.13-0.12 (m, 6H).

Preparation of (5): To a solution of 4 (10.5 g, 26.4 mmol) in ACN/H₂O=1:1 (100 mL) was added DAIB (25.4 g, 79.2 mmol) and TEMPO (1.7 g, 7.9 mmol). The reaction mixture was stirred at 40° C. for 2 h. LCMS showed 4 was consumed. The mixture was diluted with EA and water was added. The product was extracted with EA. The organic layer was washed with brine and dried over anhydrous Na₂SO₄. The solution was then concentrated under reduced pressure and the residue was washed by ACN. This resulted in to give 5 (6.3 g, 15.3 mmol, 57.9% yield) as a white solid. ESI-LCMS: m/z 413 [M+H]⁺; ¹H-NMR (400 MHz, DMSO-d₆): δ=8.48 (m, 1H), 8.16 (m, 1H), 7.41 (m, 2H), 6.12-6.10 (d, J=8.0 Hz, 1H), 4.75-4.73 (m, 1H), 4.42-4.36 (m, 2H), 3.17 (m, 6H), 2.07 (m, 2H), 0.93 (m, 9H), 0.17-0.15 (m, 6H).

Preparation of (6): To a solution of 5 (6.3 g, 15.3 mmol) in toluene (36 mL) and methanol (24 mL) was added (trimethylsilyl)diazomethane (7.0 g, 61.2 mmol) till the yellow color not disappear at r.t. for 2 min. LCMS showed the reaction was consumed. The solvent was removed to give the cured 6 (6.0 g) as a solid which used for the next step. ESI-LCMS: m/z 427 [M+H]⁺; ¹H-NMR (400 MHz, DMSO-d₆): δ 8.45 (m, 1H), 8.15 (m, 1H), 7.35 (m, 2H), 6.12-6.10 (d, J=8.0 Hz, 1H), 4.83-4.81 (m, 1H), 4.50-4.46 (m, 1H), 3.73 (m, 3H), 3.31 (m, 1H), 0.93 (m, 9H), 0.15-0.14 (m, 6H).

Preparation of (7): To the solution of 6 (6 g) in dry THF/MeOD/D₂O=10/2/1 (78 mL) was added NaBD₄ (2.3 g, 54.8 mmol) at r.t. And the reaction mixture was stirred at r.t for 2.5 hr. After completion of reaction, adjusted pH value to 7 with CH₃COOD, after addition of water, the resulting mixture was extracted with EA (100 mL). The combined organic layer was washed with water and brine, dried over Na₂SO₄, and concentrated to give 7 (5.7 g) which was used for the next step. ESI-LCMS: m/z 401 [M+H].

Preparation of (8): To a solution of 7 (5.7 g) in pyridine (60 mL) was added BzCl (10.0 g, 71.3 mmol) under ice bath. The reaction mixture was stirred at r.t. for 2.5 hrs. LCMS showed 7 was consumed. The mixture was diluted with EA and water was added. The product was extracted with EA. The crude was purified by Flash-Prep-HPLC with the following conditions (IntelFlash-1): Column, C18 silica gel; mobile phase, CH₃CN/H₂O (0.5% NH₄HCO₃)=1/1 increasing to CH₃CN/H₂O (0.5% NH₄HCO₃)=1/0 within 25 min, the eluted product was collected at CH₃CN/H₂O (0.5% NH₄HCO₃)=7/3; Detector, UV 254 nm. This resulted in to give the crude 8 (6.2 g, 8.7 mmol, 57% yield, over two steps) as a white solid. ESI-LCMS: n/z 713 [M+H]⁺.

Preparation of (9): To a solution of 8 (6.2 g, 8.7 mmol) in pyridine (70 mL) and was added 1 M NaOH (MeOH/H₂O=4/1) (24 mL). LCMS showed 8 was consumed. The mixture was added saturated NH₄Cl till pH=7.5. The mixture was diluted with water and EA. The organic layer was washed with brine and dried over Na₂SO₄ and concentrated to give the crude. The crude was purified by Flash-Prep-HPLC with the following conditions (IntelFlash-1): Column, C18 silica gel; mobile phase, CH₃CN/H₂O (0.5% NH₄HCO₃)=1/1 increasing to CH₃CN/H₂O (0.5% NH₄HCO₃)=1/0 within 25 min, the eluted product was collected at CH₃CN/H₂O (0.5% NH₄HCO₃)=67/33 Detector, UV 254 nm. This resulted in to give the product 10 (4.3 g, 8.5 mmol, 98% yield) as a white solid. ESI-LCMS: m/z 505 [M+H]⁺; ¹H-NMR (400 MHz, DMSO-d₆): δ 11.23 (m, 1H), 8.77 (m, 2H), 8.06-8.04 (m, 2H), 7.66-7.63 (m, 2H), 7.57-7.53 (m, 3H), 6.16-6.14 (d, J=8.0 Hz, 1H), 5.17 (m, 1H), 4.60-4.52 (m, 2H), 3.34 (m, 1H), 0.93 (m, 9H), 0.14 (m, 6H).

Preparation of (10): To a stirred solution of 9 (4.3 g, 8.5 mmol) in pyridine (45 mL) were added DMTrCl (3.3 g, 9.8 mmol) at r.t. And the reaction mixture was stirred at r.t for 2.5 hr. With ice-bath cooling, the reaction was quenched with water and the product was extracted into EA. The organic layer was washed with brine and dried over $Na_2SO_4$ and concentrated to give the crude. The crude was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 25 min, the eluted product was collected at $CH_3CN/H_2O$ (0.5% $NH_4HCO_3$)=97/3 Detector, UV 254 nm. This resulted in to give the product 10 (6.5 g, 8.1 mmol, 95% yield) as a white solid. ESI-LCMS: m/z 807 [M+H]$^+$; $^1$H-NMR (400 MHz, DMSO-d$_6$): δ 11.23 (m, 1H), 8.70-8.68 (m, 2H), 8.04-8.02 (m, 2H), 7.66-7.62 (m, 1H), 7.56-7.52 (m, 2H), 7.35-7.26 (m, 2H), 7.25-7.17 (m, 7H), 6.85-6.82 (m, 4H), 6.18-6.16 (d, J=8.0 Hz, 1H), 4.73-4.70 (m, 1H), 4.61-4.58 (m, 1H), 3.71 (m, 6H), 3.32 (m, 1H), 0.83 (m, 9H), 0.09-0.03 (m, 6H).

Preparation of (11): To a solution of 10 (3.5 g, 4.3 mmol) in THF (35 mL) was added 1 M TBAF solution (5 mL). The reaction mixture was stirred at r.t. for 1.5 h. LCMS showed 10 was consumed completely. Water (100 mL) was added. The product was extracted with EA (100 mL) and the organic layer was washed with brine and dried over Na2SO4. Then the organic layer was concentrated to give a residue which was purified by Flash-Prep-HPLC with the following conditions (IntelFlash-1): Column, C18 silica gel; mobile phase, $CH_3CN/H_2O$ (0.5% $NH_4HCO_3$)=2/3 increasing to $CH_3CN/H_2O$ (0.5% $NH_4HCO_3$)=1/0 within 20 min, the eluted product was collected at $CH_3CN/H_2O$ (0.5% $NH_4HCO_3$)=62/38; Detector, UV 254 nm. This resulted in to give 11 (2.7 g, 3.9 mmol, 90.7%) as a white solid. ESI-LCMS: m/z 693 [M+H]$^+$.

Preparation of Example 40 monomer: To a suspension of 11 (2.7 g, 3.9 mmol) in DCM (30 mL) was added DCI (0.39 g, 3.3 mmol) and CEP[N(iPr)$_2$]$_2$ (1.4 g, 4.7 mmol). The mixture was stirred at r.t. for 2 h. LC-MS showed 11 was consumed completely. The solution was washed with water twice and washed with brine and dried over $Na_2SO_4$. Then concentrated to give a residue which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=73/27; Detector, UV 254 nm. This resulted in to give Example 40 monomer (3.3 g, 3.7 mmol, 94.9%) as a white solid. ESI-LCMS: m/z 893 [M+H]$^+$; $^1$H-NMR (400 MHz, DMSO-d$_6$): δ=11.24 (m, 1H), 8.66-8.64 (m, 2H), 8.06-8.03 (m, 2H), 7.65-7.53 (m, 3H), 7.42-7.38 (m, 2H), 7.37-7.34 (m, 2H), 7.25-7.19 (m, 7H), 6.86-6.80 (m, 4H), 6.20-6.19 (d, J=4.0 Hz, 1H), 4.78 (m, 2H), 4.22-4.21 (m, 1H), 3.92-3.83 (m, 1H), 3.72 (m, 6H), 3.62-3.57 (m, 3H), 2.81-2.78 (m, 1H), 2.64-2.61 (m, 1H), 1.17-1.04 (m, 12H); $^{31}$P-NMR (162 MHz, DMSO-d$_6$): δ 149.51, 149.30.

Example 41. Synthesis of Monomer

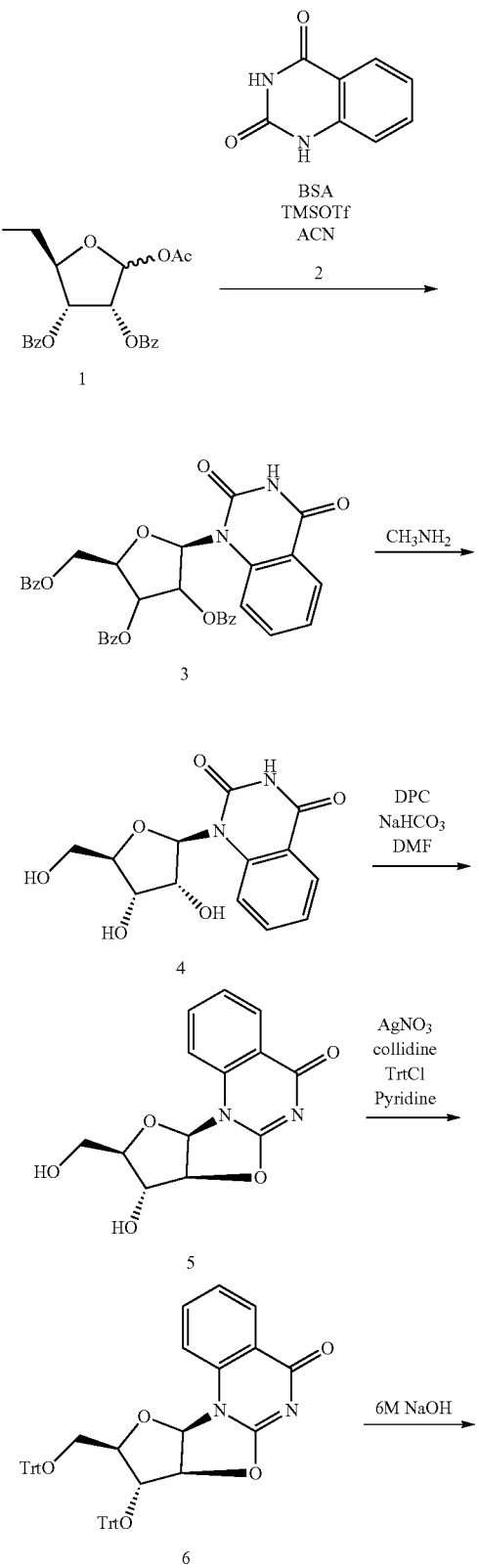

Scheme-21

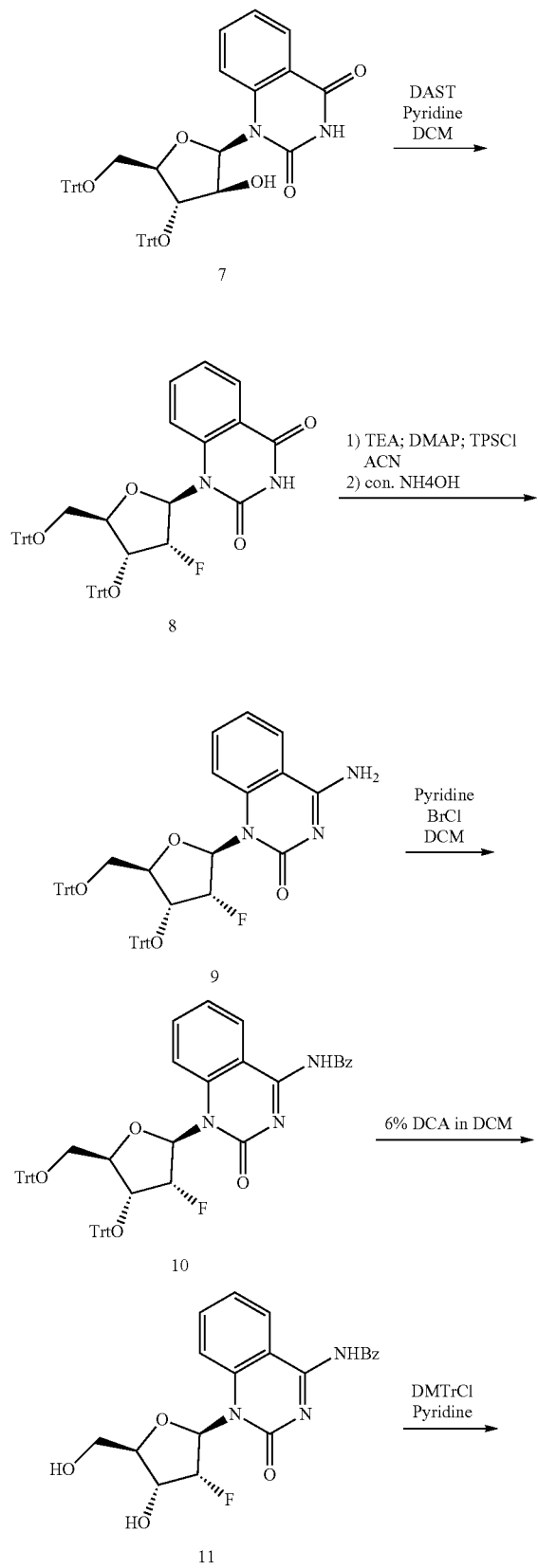

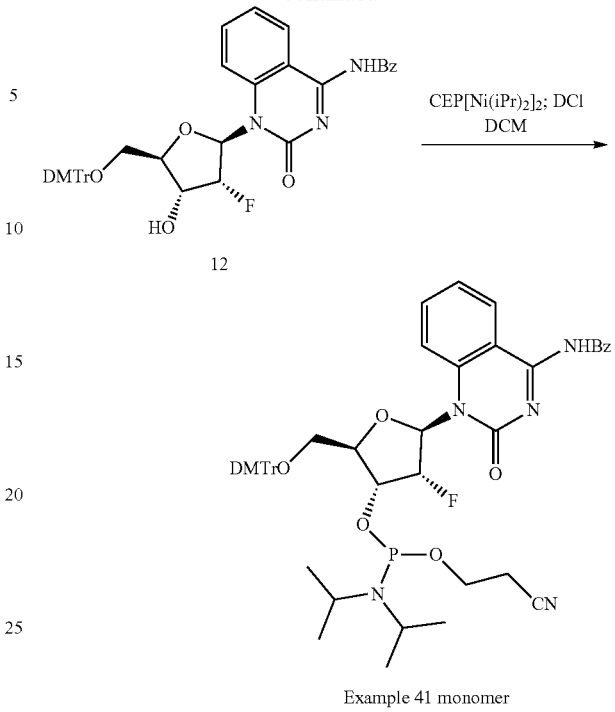

Example 41 monomer

Preparation of (3): To the solution of 1 (70 g, 138.9 mmol) in dry acetonitrile (700 mL) was added 2 (27.0 g, 166.7 mmol), BSA (112.8 g, 555.5 mmol). The mixture was stirred at 50° C. for 1 h. Then the mixture was cooled to −5° C. and TMSOTf (46.2 g, 208.3 mmol) slowly added to the mixture. Then the reaction mixture was stirred at r.t for 48 h. Then the solution was cooled to 0° C. and saturated aq. NaHCO$_3$ was added and the resulting mixture was extracted with EA. The combined organic layer was washed with water and brine, dried over Na$_2$SO$_4$, and concentrated under reduced pressure to give a residue which was purified by silica gel column chromatography (eluent, PE:EA=3:1~1:1) to give 3 (70 g, 115.3 mmol, 81.6%) as a white solid. ESI-LCMS: m/z 605 [M−H]$^+$.

Preparation of (4): To the solution of 3 (70.0 g, 115.3 mmol) in methylammonium solution (1 M, 700 mL), and the reaction mixture was stirred at 40° C. for 15 h. After completion of reaction, the resulting mixture was concentrated. The residue was crystallized from EA. Solid was isolated by filtration, washed with PE and dried overnight at 45° C. in vacuum to give 4 (31.0 g, 105.4 mmol, 91.1%) as a white solid. ESI-LCMS: m/z 295 [M+H]$^+$; $^1$H-NMR (400 MHz, DMSO): δ 11.63 (s, 1H), 8.07-7.99 (m, 1H), 7.81 (d, J=8.4 Hz, 1H), 7.72-7.63 (m, 1H), 7.34-7.26 (m, 1H), 6.18 (d, J=6.4 Hz, 1H), 5.24 (s, 1H), 5.00 (s, 2H), 4.58-4.47 (m, 1H), 4.19-4.10 (m, 1H), 3.85-3.77 (m, 1H), 3.75-3.66 (m, 1H), 3.66-3.57 (m, 1H).

Preparation of (5): To the solution of 4 (20.0 g, 68.0 mmol) in dry DMF (200 mL) was added DPC (18.9 g, 88.0 mmol) and NaHCO$_3$ (343 mg, 4 mmol) at r.t, and the reaction mixture was stirred at 150° C. for 35 min. After completion of reaction, the resulting mixture was poured into tert-Butyl methyl ether (4 L). Solid was isolated by filtration, washed with PE and dried in vacuum to give crude 5 (21.0 g) as a brown solid which was used directly for next step (ref for 5, *Journal of Organic Chemistry*, 1989, vol. 33, p. 1219-1225). ESI-LCMS: m/z 275 [M−H]$^−$.

Preparation of (6): To the solution of 5 (crude, 21.0 g) in Pyridine (200 mL) was added AgNO$_3$ (31.0 g, 180.0 mmol) and collidine (88.0 g, 720 mmol) and TrtCl (41.5 g, 181 mmol) at r.t, and the reaction mixture was stirred at r.t for 15 h. After addition of water, the resulting mixture was extracted with EA. The combined organic layer was washed with water and brine, dried over Na$_2$SO$_4$, and concentrated to give the crude. The crude was by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give 6 (10.0 g, 13.1 mmol, 20% yield over 3 steps) as a white solid. ESI-LCMS: m/z 761 [M+H]$^+$.

Preparation of (7): To the solution of 6 (10.0 g, 13.1 mmol) in THF (100 mL) was added 6N NaOH (30 mL) at r.t, and the reaction mixture was stirred at r.t for 1 hr. After addition of NH$_4$Cl, the resulting mixture was extracted with EA. The combined organic layer was washed with water and brine, dried over Na$_2$SO$_4$, and concentrated under reduced pressure and the residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=9/1; Detector, UV 254 nm. This resulted in to give 7 (9.3 g, 11.9 mmol, 90%) as a white solid. ESI-LCMS: m/z 777 [M−H]$^-$; $^1$H-NMR (400 MHz, DMSO-d$_6$): δ 11.57 (s, 1H), 8.02 (d, J=8.7 Hz, 1H), 7.88-7.81 (m, 1H), 7.39-7.18 (m, 30H), 7.09-6.99 (m, 30H), 6.92-6.84 (m, 30H), 6.44 (d, J=4.0 Hz, 1H), 4.87 (d, J=4.0 Hz, 1H), 4.37-4.29 (m, 1H), 4.00-3.96 (m, 1H), 3.76-3.70 (m, 1H), 3.22-3.13 (m, 1H), 3.13-3.04 (m, 1H).

Preparation of (8): To the solution of 7 (8.3 g, 10.7 mmol) in dry DCM (80 mL) was added Pyridine (5.0 g, 64.2 mmol) and DAST (6.9 g, 42.8 mmol) at 0° C., and the reaction mixture was stirred at r.t for 15 hr. After addition of NH$_4$Cl, the resulting mixture was extracted with DCM. The combined organic layer was washed with water and brine, dried over Na$_2$SO$_4$, and concentrated under reduced pressure and the residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give 8 (6.8 g, 8.7 mmol, 81.2%) as a white solid. ESI-LCMS: m/z 779 [M−H]$^+$; $^{19}$F-NMR (376 MHz, DMSO-d$_6$): δ−183.05.

Preparation of (9): To the solution of 8 (5.8 g, 7.5 mmol) in dry ACN (60 mL) was added TEA (1.5 g, 15.1 mmol), DMAP (1.84 g, 15.1 mmol) and TPSCl (4.1 g, 13.6 mmol) at r.t, and the reaction mixture was stirred at room temperature for 3 h under N$_2$ atmosphere. After completion of reaction, the mixture was added NH$_3$.H$_2$O (12 mL). After addition of water, the resulting mixture was extracted with EA. The combined organic layer was washed with water and brine, dried over Na$_2$SO$_4$, and concentrated under reduced pressure and the residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give 9 (5.5 g, 7 mmol, 90.2%) as a white solid. ESI-LCMS: m/z 780 [M+H]$^+$.

Preparation of (10): To a solution of 9 (5.5 g, 7 mmol) in DCM (50 mL) with an inert atmosphere of nitrogen was added pyridine (5.6 g, 70.0 mmol) and BzCl (1.2 g, 8.5 mmol) in order at 0° C. The reaction solution was stirred for 30 minutes at room temperature. The solution was diluted with DCM (100 mL) and the combined organic layer was washed with water and brine, dried over Na$_2$SO$_4$, and concentrated under reduced pressure to give a residue which was purified by silica gel column chromatography (eluent, PE:EA=5:1~2:1) to give 10 (5.4 g, 6.1 mmol, 90.6%) as a white solid. ESI-LCMS: m/z 884 [M+H]$^+$; $^{19}$F-NMR (376 MHz, DMSO-d$_6$): δ−183.64.

Preparation of (11): To the solution of 10 (5.4 g, 6.1 mmol) in the solution of DCA (6%) in DCM (60 mL) was added TES (15 mL) at r.t, and the reaction mixture was stirred at room temperature for 5-10 min. After completion of reaction, the resulting mixture was added NaHCO$_3$, the resulting mixture was extracted with DCM. The combined organic layer was washed with water and brine, dried over Na$_2$SO$_4$, and concentrated under reduced pressure and the residue was crystallized from EA. Solid was isolated by filtration, washed with PE and dried overnight at 450 in vacuum to give 11 (2.0 g, 5.0 mmol, 83.2%) as a white solid. ESI-LCMS: m/z 400 [M+H]$^+$.

Preparation of (12): To a solution of 11 (2.0 g, 5.0 mmol) in dry Pyridine (20 mL) was added DMTrCl (2.0 g, 6.0 mmol). The reaction mixture was stirred at r.t. for 2.5 h. LCMS showed 11 was consumed and water (200 mL) was added. The product was extracted with EA (200 mL) and the organic layer was washed with brine and dried over Na$_2$SO$_4$ and concentrated to give the crude. The crude was purified by c.c. (PE:EA=4:1~1:1) to give crude 12. The crude was further purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give 12 (2.1 g, 3 mmol, 60%) as a white solid. ESI-LCMS: m/z 702 [M+H]$^+$; $^1$H-NMR (400 MHz, DMSO-d$_6$): δ 12.63 (s, 1H), 8.54 (d, J=7.8 Hz, 1H), 8.25 (d, J=7.2 Hz, 2H), 7.82 (d, J=3.6 Hz, 2H), 7.67-7.58 (m, 1H), 7.57-7.49 (m, 2H), 7.49-7.39 (m, 1H), 7.39-7.31 (m, 2H), 7.27-7.09 (m, 7H), 6.82-6.69 (m, 4H), 6.23 (d, J=26.1 Hz, 1H), 5.59-5.49 (m, 1H), 4.83-4.61 (m, 1H), 4.15-4.01 (m, 1H), 3.74-3.59 (m, 6H), 3.33-3.28 (m, 1H), 3.16-3.05 (m, 1H). $^{19}$F-NMR (376 MHz, DMSO-d$_6$): δ−191.66.

Preparation of Example 41 monomer: To a suspension of 12 (2.1 g, 3.0 mmol) in DCM (20 mL) was added DCI (310 mg, 2.6 mmol) and CEP[N(iPr)$_2$]$_2$ (1.1 g, 3.7 mmol). The mixture was stirred at r.t. for 1 h. LC-MS showed 12 was consumed completely. The solution was washed with water twice and washed with brine and dried over Na$_2$SO$_4$. Then concentrated to give the crude. The crude was by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in to give Example 41 monomer (2.1 g, 2.3 mmol, 80.0%) as a white solid. ESI-LCMS: m/z 902 [M+H]$^+$; $^1$H-NMR (400 MHz, DMSO-d$_6$): δ 12.64 (s, 1H), 8.54 (d, J=7.6 Hz, 1H), 8.24 (d, J=7.7 Hz, 2H), 7.93-7.88 (m, 2H), 7.67-7.58 (m, 1H), 7.56-7.42 (m, 3H), 7.41-7.29 (m, 2H), 7.27-7.08 (m, 7H), 6.82-6.64 (m, 4H), 6.37-6.18 (m, 1H), 6.03-5.72 (m, 1H), 5.26-4.83 (m, 1H), 4.28-4.12 (m, 1H), 3.88-3.72 (m, 1H), 3.71-3.37 (m, 9H), 3.15-3.00 (m, 1H), 2.83-2.75 (m, 1H), 2.66-2.57 (m, 1H), 1.21-0.88 (m, 12H). $^{19}$F-NMR (376 MHz, DMSO-$d_6$): δ −189.71. $^{31}$P-NMR (162 MHz, DMSO-$d_6$): δ 149.48, 149.50, 148.95, 148.88.

Example 42. Synthesis of Monomer

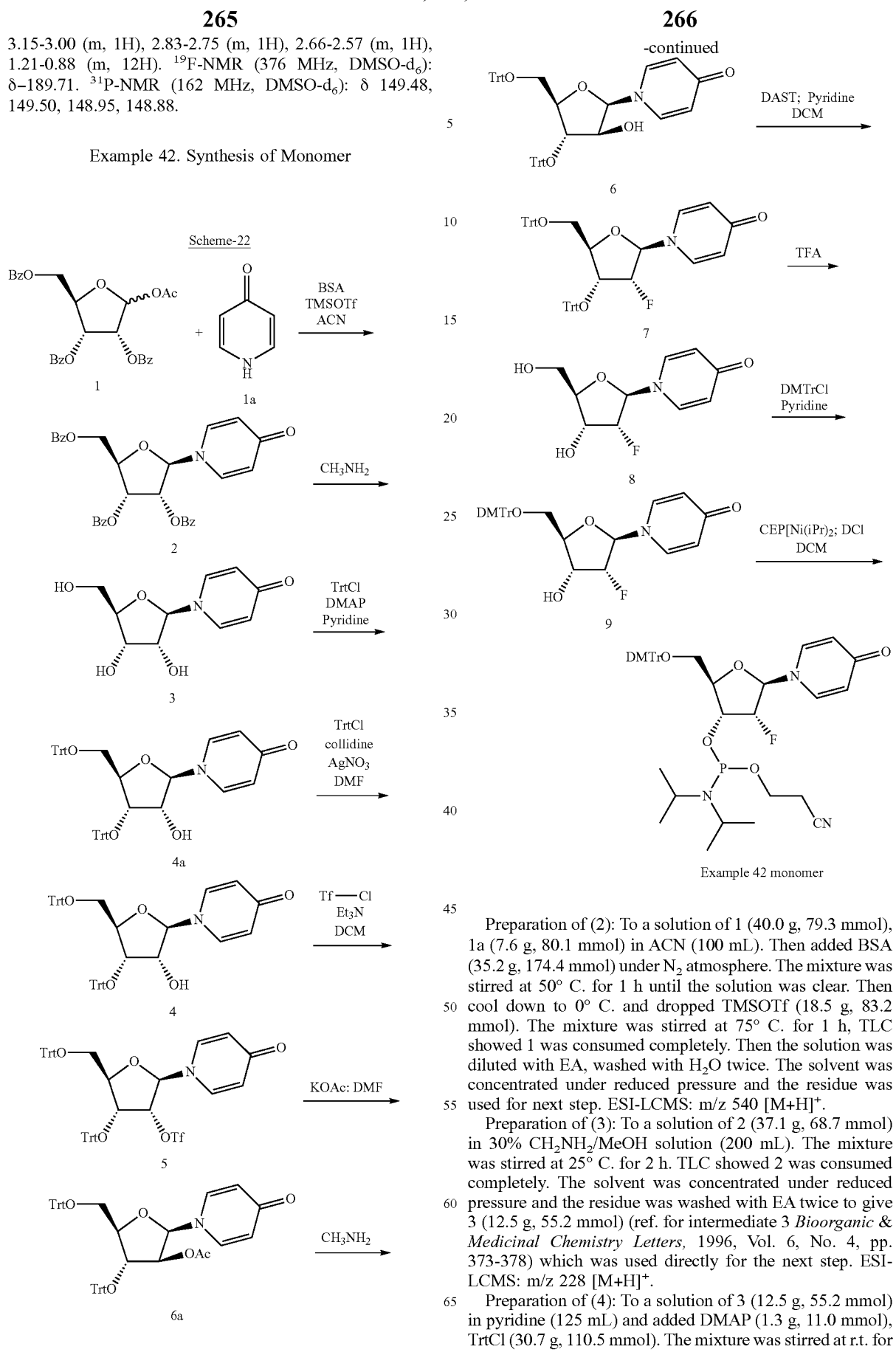

Preparation of (2): To a solution of 1 (40.0 g, 79.3 mmol), 1a (7.6 g, 80.1 mmol) in ACN (100 mL). Then added BSA (35.2 g, 174.4 mmol) under $N_2$ atmosphere. The mixture was stirred at 50° C. for 1 h until the solution was clear. Then cool down to 0° C. and dropped TMSOTf (18.5 g, 83.2 mmol). The mixture was stirred at 75° C. for 1 h, TLC showed 1 was consumed completely. Then the solution was diluted with EA, washed with $H_2O$ twice. The solvent was concentrated under reduced pressure and the residue was used for next step. ESI-LCMS: m/z 540 [M+H]$^+$.

Preparation of (3): To a solution of 2 (37.1 g, 68.7 mmol) in 30% $CH_2NH_2$/MeOH solution (200 mL). The mixture was stirred at 25° C. for 2 h. TLC showed 2 was consumed completely. The solvent was concentrated under reduced pressure and the residue was washed with EA twice to give 3 (12.5 g, 55.2 mmol) (ref. for intermediate 3 *Bioorganic & Medicinal Chemistry Letters*, 1996, Vol. 6, No. 4, pp. 373-378) which was used directly for the next step. ESI-LCMS: m/z 228 [M+H]$^+$.

Preparation of (4): To a solution of 3 (12.5 g, 55.2 mmol) in pyridine (125 mL) and added DMAP (1.3 g, 11.0 mmol), TrtCl (30.7 g, 110.5 mmol). The mixture was stirred at r.t. for 24 h. TLC showed 3 was consumed completely. H$_2$O was added to the mixture. Then filtered and the solution diluted with EA. The organic layer was washed with NaHCO$_3$ and brine. The solvent was concentrated under reduced pressure and then added ACN, filtered to give 4a (17.0 g, 35.4 mmol, 64% yield) as a white solid.

To a solution of 4a (17.0 g, 35.4 mmol) in DMF (200 mL), collidine (5.2 g, 43.5 mmol), TrCl (13.1 g, 47.1 mmol) were added after 2 h and then again after 3 h TrCl (13.1 g, 47.1 mmol), AgNO$_3$ (8.0 g, 47.1 mmol). The mixture was stirred at 25° C. for 24 h. TLC showed 4a was consumed completely. Then filtered and the solution diluted with EA. The organic layer was washed with NaHCO$_3$ and brine. The solvent was concentrated under reduced pressure and then added ACN, filtered to get 4 (14.2 g, 19.5 mmol, 54% yield) as a white solid. ESI-LCMS: m/z 712 [M+H]$^+$; $^1$H-NMR (400 MHz, DMSO-d$_6$): δ 7.83 (d, J=8 Hz, 2H), 7.42-7.20 (m, 30H), 6.18 (d, J=7 Hz, 1H), 6.09 (d, J=8 Hz, 2H), 5.60 (d, J=7 Hz, 1H), 4.22 (m, 1H), 3.90 (d, J=5 Hz, 1H), 2.85 (d, J=10 Hz, 1H), 2.76 (s, 1H), 2.55-2.50 (dd, 1H).

Preparation of (5): To a solution of 4 (14.2 g, 19.9 mmol) in DCM (150 mL), DMAP (2.4 g, 19.9 mmol), TEA (4.0 g, 39.9 mmol, 5.6 mL) were added. Then cool down to 0° C., TfCl (6.7 g, 39.9 mmol) dissolved in DCM (150 mL) were dropped. The mixture was stirred at 25° C. for 1 h. TLC showed 4 was consumed completely. Then filtered and the solution diluted with EA. The organic layer was washed with NaHCO$_3$ and brine. The solvent was concentrated under reduced pressure to get 5 (16.8 g, 19.9 mmol) as a brown solid. ESI-LCMS: m/z 844 [M+H]$^+$.

Preparation of (6): To a solution of 5 (16.8 g, 19.9 mmol) in DMF (200 mL), KOAc (9.7 g, 99.6 mmol) were added, The mixture was stirred at 25° C. for 14 h and 50° C. for 3 h, TLC showed 5 was consumed completely. Then filtered and the solution diluted with EA. The organic layer was washed with H$_2$O and brine. The solvent was concentrated under reduced pressure to get 6a (15.0 g, 18.9 mmol, 90% yield) as a brown solid. To a solution of 6a (15.0 g, 19.9 mmol) in 30% CH$_3$NH$_2$/MeOH solution (100 mL) were added. The mixture was stirred at 25° C. for 2 h, TLC showed 6a was consumed completely. Then the solvent was concentrated under reduced pressure and the residue was purified by cc (0-5% MeOH in DCM) to give 6 (11.6 g, 16.3 mmol, 82% yield) as a yellow solid. ESI-LCMS: m/z 712 [M+H]$^+$; $^1$H-NMR (400 MHz, DMSO-d$_6$): δ 7.59 (d, J=8 Hz, 2H), 7.37-7.22 (m, 30H), 6.01 (d, J=8 Hz, 2H), 5.84 (d, J=3 Hz, 1H), 5.42 (d, J=4 Hz, 1H), 3.78-3.70 (m, 3H), 3.10 (t, J=9 Hz, 1H), 2.53 (d, J=4 Hz, 6H), 1.77 (s, 6H).

Preparation of (7): To a solution of 6 (11.6 g, 16.32 mmol) in DCM (200 mL), DAST (7.9 g, 48.9 mmol) were added at 0° C., The mixture was stirred at 25° C. for 16 h, TLC showed 6 was consumed completely. Then the solution was diluted with EA, washed with NaHCO$_3$ twice, The solvent was concentrated under reduced pressure the residue purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 25 min, the eluted product was collected at CH$_3$CN/H$_2$O (0.5% NH$_4$HCO$_3$)=4/1; Detector, UV 254 nm. This resulted in to give 7 (11.6 g, 13.8 mmol, 84% yield) as a white solid. ESI-LCMS: m/z 714 [M+H].

Preparation of (8): To a solution of 7 (11.6 g, 16.2 mmol) in DCM (100 mL) was added TFA (10 mL). The mixture was stirred at 20° C. for 1 h. TLC showed 7 was consumed completely. Then the solution was concentrated under reduced pressure the residue was purified by silica gel column (0~20% MeOH in DCM) and Flash-Prep-HPLC with the following conditions (IntelFlash-1): Column, C18 silica gel; mobile phase, CH$_3$CN/H$_2$O (0.5% NH$_4$HCO$_3$) =0/1 increasing to CH$_3$CN/H$_2$O (0.5% NH$_4$HCO$_3$)=1/3 within 25 min, the eluted product was collected at CH$_3$CN/H$_2$O (0.5% NH$_4$HCO$_3$)=0/1; Detector, UV 254 nm. This resulted in to give 9 (1.7 g, 7.2 mmol, 45% yield) as a white solid. ESI-LCMS: m/z 229.9 [M+H]$^+$; $^1$H-NMR (400 MHz, DMSO-d$_6$): δ 7.91 (d, J=8 Hz, 2H), 6.14 (d, J=8 Hz, 2H), 5.81-5.76 (m, 2H), 5.28 (t, J=5 Hz, 1H), 5.13-4.97 (t, J=4 Hz, 1H), 4.23 (m, 1H), 3.97 (m, 1H), 3.74-3.58 (m, 2H); $^{19}$F-NMR (376 MHz, DMSO-d$_6$): δ–206.09.

Preparation of (9): To a solution of 8 (1.4 g, 6.1 mmol) in pyridine (14 mL) was added DMTrCl (2.5 g, 7.3 mmol) at 20° C. The mixture was stirred at 20° C. for 1 h. TLC showed 8 was consumed completely. Water was added to the reaction. The product was extracted with EA, The organic layer was washed with NaHCO$_3$ and brine. Then the solution was concentrated under reduced pressure and the residue was purified by Flash-Prep-HPLC with the following conditions (IntelFlash-1): Column, C18 silica gel; mobile phase, CH$_3$CN/H$_2$O (0.5% NH$_4$HCO$_3$)=1/3 increasing to CH$_3$CN/H$_2$O (0.5% NH$_4$HCO$_3$)=4/1 within 25 min, the eluted product was collected at CH$_3$CN/H$_2$O (0.5% NH$_4$HCO$_3$)=1/1; Detector, UV 254 nm. This resulted in to give 9 (2.5 g, 4.6 mmol, 76 yield) as a white solid. ESI-LCMS: m/z 532.2 [M+H]$^+$; $^1$H-NMR (400 MHz, DMSO-d$_6$): δ 7.87-7.84 (m, 2H), 7.40-7.22 (m, 9H), 6.91-6.87 (m, 4H), 5.98-5.95 (m, 2H), 5.88-5.77 (m, 2H), 5.16-5.02 (m, 1H), 4.42 (m, 1H), 4.05 (m, 1H), 3.74 (s, 6H), 3.35 (m, 2H); $^{19}$F-NMR (376 MHz, DMSO-d$_6$): δ–202.32.

Preparation of Example 42 monomer: To a solution of 9 (2.2 g, 4.1 mmol) in DCM (20 mL) was added DCI (415 mg, 3.5 mmol) and CEP (1.5 g, 4.9 mmol) under N$_2$ pro. The mixture was stirred at 20° C. for 0.5 h. TLC showed 9 was consumed completely. The product was extracted with DCM, The organic layer was washed with H$_2$O and brine. Then the solution was concentrated under reduced pressure and the residue was purified by Flash-Prep-HPLC with the following conditions (IntelFlash-1): Column, C18 silica gel; mobile phase, CH$_3$CN/H$_2$O (0.5% NH$_4$HCO$_3$)=1/3 increasing to CH$_3$CN/H$_2$O (0.5% NH$_4$HCO$_3$)=1/0 within 25 min, the eluted product was collected at CH$_3$CN/H$_2$O (0.5% NH$_4$HCO$_3$)=1/0; Detector, UV 254 nm. This resulted in to give Example 42 monomer (2.6 g, 3.5 mmol, 85% yield) as a white solid. ESI-LCMS: m/z 732.2 [M+H]$^+$; $^1$H-NMR (400 MHz, DMSO-d$_6$): δ 7.87-7.84 (m, 2H), 7.40-7.22 (m, 9H), 6.91-6.87 (m, 4H), 5.98-5.95 (m, 2H), 5.90-5.88 (m, 1H), 5.30-5.17 (m, 1H), 4.62 (m, 1H), 4.19 (m, 1H), 3.78-3.73 (m, 7H), 3.62-3.35 (m, 5H), 2.78 (t, J=5 Hz, 1H), 2.63 (t, J=6 Hz, 1H), 1.14-0.96 (m, 12H); $^{19}$F-NMR (376 MHz, DMSO-d$_6$): δ–200.77, 200.80, 201.62, 201.64. $^{31}$P-NMR (162 MHz, DMSO-d$_6$): δ 150.31, 150.24, 149.66, 149.60.

Example 43. Synthesis of End Cap Monomer

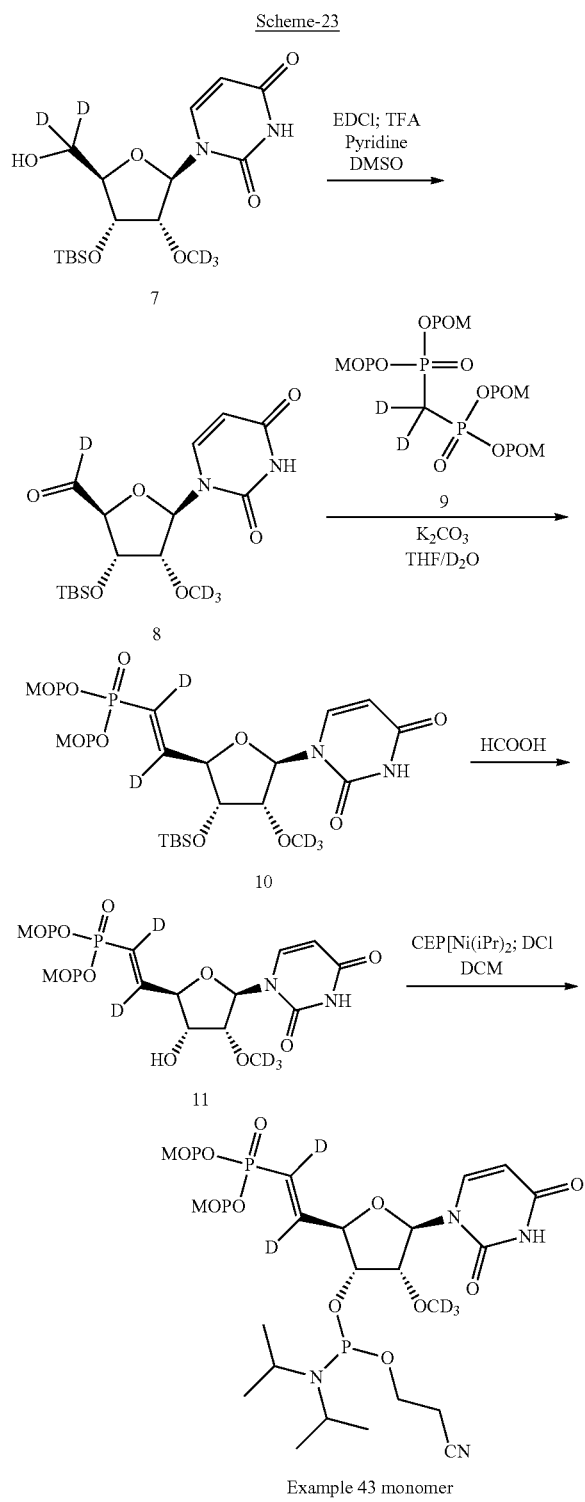

Scheme-23

Example 43 monomer

Preparation of (8): To a stirred solution of 7 (13.4 g, 35.5 mmol, Scheme 5) in DMSO (135 mL) were added EDCI (6.3 g, 32.9 mmol) and pyridine (0.9 g, 10.9 mmol), TFA (0.6 g, 5.5 mmol) at r.t. And the reaction mixture was stirred at r.t for 2 h. LCMS showed 7 consumed completely. The reaction was quenched with water and the product was extracted with EA (1800 mL). The organic phase was washed by brine, dried over $Na_2SO_4$, The organic phase was evaporated to dryness under reduced pressure to give a residue 8 (13.2 g, 35.3 mmol, 99.3% yield). Which was used directly to next step. ESI-LCMS: m/z=375 $[M+H_2O]^+$ Preparation of (10): A solution of 8 (13.2 g, 35.3 mmol), 9 (26.8 g, 42.3 mmol, Scheme 18) and $K_2CO_3$ (19.5 g, 141.0 mmol) in dry THF (160 mL) and D2O (53 mL) was stirred at r.t. 17 h. LCMS showed most of 8 was consumed. The product was extracted with EA (2500 mL) and the organic layer was washed with brine and dried over $Na_2SO_4$. Then the organic layer was concentrated to give a residue which was purified by c.c. (PE:EA=10:1~1:2) to give product 10 (8.1 g, 11.8 mmol, 33.4% yield) as a white solid. ESI-LCMS m/z=682 $[M+H]^+$; $^1$H-NMR (400 MHz, DMSO-$d_6$): δ 11.42 (s, 1H), 7.69-7.71 (d, J=8.1 Hz, 1H), 5.78-5.79 (d, J=3.7 Hz, 1H), 5.65-5.67 (m, 1H), 5.59-5.63 (m, 4H), 4.29-4.35 (m, 2H), 3.97-3.99 (m, 1H), 1.15 (s, 18H), 0.87 (s, 9H), 0.07-0.08 (d, J=5.1 Hz, 6H). $^{31}$P-NMR (162 MHz, DMS O-$d_6$) δ 16.62.

Preparation of (11): To a round-bottom flask was added 10 (7.7 g, 11.1 mmol) in a mixture of HCOOH (80 mL) and $H_2O$ (80 mL). The reaction mixture was stirred at 40° C. for 3 h. LCMS showed the 10 was consumed completely. The reaction mixture was adjusted the pH=7.0 with con.$NH_3.H_2O$ (100 mL). Then the mixture was extracted with DCM (100 mL*3). The combined DCM layer was dried over $Na_2SO_4$. Filtered and filtrate was concentrated to give crude which was purified by Flash-Prep-HPLC with the following conditions (IntelFlash-1): Column, C18 silica gel; mobile phase, $CH_3CN/H_2O$ (0.5% $NH_4HCO_3$)=1/2 increasing to $CH_3CN/H_2O$ (0.5% $NH_4HCO_3$)=1/1 within 20 min, the eluted product was collected at $CH_3CN/H_2O$ (0.5% $NH_4HCO_3$)=1/0; Detector, UV 254 nm. To give product 11 (5.5 g, 9.6 mmol, 86.1% yield) as a white solid. ESI-LCMS m/z=568 $[M+H]v$; $^1$H-NMR (400 MHz, DMSO-$d_6$): δ 11.42 (s, 1H, exchanged with $D_2O$), 7.62-7.64 (d, J=8.1, 1H), 5.81-5.82 (d, J=4.3, 1H), 5.58-5.66 (m, 5H), 5.52-5.53 (d, J=6.6, 1H), 4.34-4.37 (m, 1H), 4.09-4.13 (m, 1H), 3.94-3.96 (t, J=9.7, 1H), 1.15 (s, 18H), 0 (s, 1H). $^{31}$P NMR (162 MHz, DMSO-$d_6$) δ 17.16.

Preparation of Example 43 monomer: To a solution of 11 (5.3 g, 9.3 mmol) in DCM (40 mL) was added the DCI (1.1 g, 7.9 mmol), then $CEP[N(ipr)_2]_2$ (3.4 g, 11.2 mmol) was added. The mixture was stirred at r.t. for 1 h. LCMS showed 11 consumed completely. The reaction mixture was washed with $H_2O$ (50 mL*2) and brine (50 mL*1). Dried over $Na_2SO_4$ and concentrated to give crude which was purified by Flash-Prep-HPLC with the following conditions (IntelFlash-1): Column, C18 silica gel; mobile phase, $CH_3CN/H_2O$ (0.5% $NH_4HCO_3$)=1/3 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. The product was concentrated to give Example 43 monomer (6.2 g, 8.0 mmol, 85.6% yield) as a white solid. ESI-LCMS m/z=768 $[M+H]^+$; $^1$H-NMR (400 MHz, DMSO-$d_6$): δ 11.43 (s, 1H), 7.68-7.71 (m, 1H), 5.79-5.81 (m, 1H), 5.58-5.67 (m, 5H), 4.34-4.56 (m, 2H), 4.14-4.17 (m, 1H), 3.54-3.85 (m, 4H), 2.78-2.81 (m, 2H), 1.13-1.17 (m, 30H). $^{31}$P-NMR (162 MHz, DMSO-$d_6$): δ 149.66, 149.16, 16.84, 16.56.

Example 44. Synthesis of Monomer
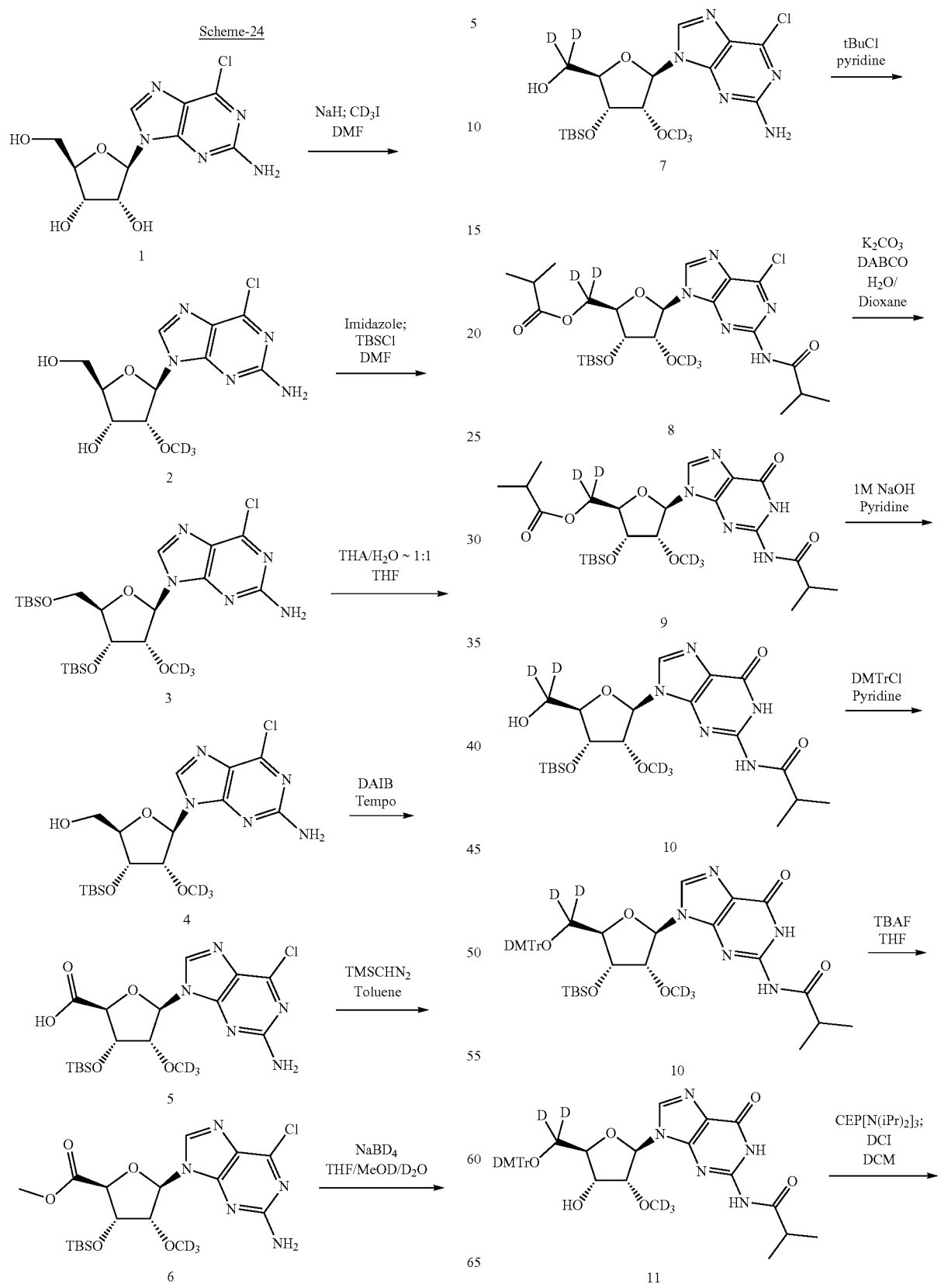

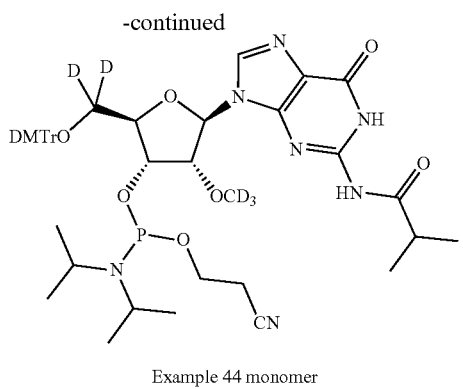

Example 44 monomer

Preparation of (2): To a solution of 1 (20.0 g, 66.4 mmol) in dry DMF (400 mL) was added sodium hydride (1.9 g, 79.7 mmol) for 30 min, then was added $CD_3I$ (9.1 g, 79.7 mmol) in dry DCM (40 mL) at −20° C. for 5.5 hr. LCMS showed the reaction was consumed. The mixture was filtered and the clear solution was evaporated to dryness and was evaporated with $CH_3OH$. The crude was purified by silica gel column ($SiO_2$, DCM/MeOH=50:1~10:1). This resulted in to give the product 2 (7.5 g, 23.5 mmol, 35.5% yield) as a solid. ESI-LCMS: m/z 319 $[M+H]^+$; $^1$H-NMR (400 MHz, DMSO-$d_3$): δ=8.38 (m, 1H), 6.97 (m, 2H), 5.93-5.81 (m, 1H), 5.27-5.26 (d, J=4 Hz, 1H), 5.13-5.11 (m, 1H), 4.39-4.31 (m, 1H), 4.31-4.25 (m, 1H), 3.96-3.94 (m, 1H), 3.66-3.63 (m, 1H), 3.63-3.56 (m, 1H).

Preparation of (3): To a solution of 2 (7.5 g, 23.5 mmol) in dry DMF (75 mL) was added Imidazole (5.6 g, 82.3 mmol) and TBSCl (8.9 g, 58.8 mmol). The mixture was stirred at r.t. over night. LCMS showed 2 was consumed completely. The reaction was quenched with water (300 mL). The product was extracted into ethyl acetate (100 mL). The organic layer was washed with brine and dried over anhydrous $Na_2SO_4$. The solvent was removed to give the cured 3 (9.8 g) as a solid which used for the next step. ESI-LCMS: m/z 547 $[M+H]^+$.

Preparation of (4): To a solution of 3 (9.8 g) in THF (40 mL) was added TFA (10 mL) and water (10 mL) at 0° C. The reaction mixture was stirred at 0° C. for 5 h. LC-MS showed 3 was consumed completely. Con. $NH_4OH$ was added to the mixture at 0° C. to quench the reaction until the pH=7.5. The product was extracted into ethyl acetate (200 mL). The organic layer was washed with brine and dried over anhydrous $Na_2SO_4$. The solvent was removed to give the cured 4 (8.4 g) as a solid which used for the next step. ESI-LCMS: m/z 433 $[M+H]^+$.

Preparation of (5): To a solution of 4 (8.4 g) in DCM/$H_2O$=2:1 (84 mL) was added DAIB (18.8 g, 58.4 mmol) and TEMPO (0.87 g, 5.8 mmol). The reaction mixture was stirred at 40° C. for 2 h. LCMS showed 4 was consumed. The mixture was diluted with DCM and water was added. The product was extracted with DCM. The organic layer was washed with brine and dried over anhydrous $Na_2SO_4$. The solution was then concentrated under reduced pressure. This resulted in to give 5 (14.4 g) as a white solid. ESI-LCMS: m/z 447 $[M+H]^+$.

Preparation of (6): To a solution of 5 (14.4 g) in toluene (90 mL) and methanol (60 mL) was added 2 M $TMSCHN_2$ (8.9 g, 78.1 mmol) till the yellow color not disappear at r.t. for 10 min. LCMS showed 5 was consumed. The crude was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 25 min, the eluted product was collected at $CH_3CN/H_2O$ (0.5% $NH_4HCO_3$)=65/35 Detector, UV 254 nm. This resulted in to give the product 6 (3.5 g, 7.6 mmol, 32.3% yield over three steps, 70% purity) as a white solid. ESI-LCMS: m/z 461 $[M+H]^+$.

Preparation of (7): To the solution of 6 (3.5 g, 7.6 mmol) in dry THF/MeOD/$D_2O$=10/2/1 (45 mL) was added $NaBD_4$ (0.96 g, 22.8 mmol). And the reaction mixture was stirred at r.t for 2.5 hr. After completion of reaction, the resulting mixture was added $CH_3COOD$ to pH=7, after addition of water, the resulting mixture was extracted with EA (100 mL). The combined organic layer was washed with water and brine, dried over $Na_2SO_4$, and concentrated to give 7 (3.3 g) which was used for the next step. ESI-LCMS: m/z 435 $[M+H]^+$.

Preparation of (8): To a solution of 7 (3.3 g) in dry DCM (30 mL) was added pyridine (5.9 g, 74.5 mmol) and iBuCl (2.4 g, 22.4 mmol) in DCM (6 mL) under ice bath. The reaction mixture was stirred at 0° C. for 2.5 hr. LCMS showed 7 was consumed. The mixture was diluted with EA and water was added. The product was extracted with EA. The crude was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 25 min, the eluted product was collected at $CH_3CN/H_2O$ (0.5% $NH_4HCO_3$)=87/13; Detector, UV 254 nm. This resulted in to give the crude 8 (1.6 g, 2.8 mmol, 36.8% yield over two steps) as a white solid. ESI-LCMS: m/z 575 $[M+H]^+$.

Preparation of (9): To a solution of 8 (1.6 g, 2.8 mmol) in $H_2O$/dioxane=1:1 (30 ml) was added $K_2CO_3$ (772.8 mg, 5.6 mmol) and DABCO (739.2 mg, 2.9 mmol). The reaction mixture was stirred at 50° C. for 3 hr. LCMS showed 8 was consumed. The mixture was diluted with EA and water was added. The product was extracted with EA. The combined organic layer was washed with water and brine, dried over $Na_2SO_4$, and concentrated to give 9 (1.8 g) which was used for the next step. ESI-LCMS: m/z 557 $[M+H]^+$.

Preparation of (10): To a solution of 9 (1.8 g) in pyridine (20 mL) and was added 2 M NaOH (MeOH/$H_2O$=4/1) (5 mL) at 0° C. for 1 h. LCMS showed 9 was consumed. The mixture was added saturated $NH_4Cl$ till pH=7.5. The mixture was diluted with water and EA. The organic layer was washed with brine and dried over $Na_2SO_4$ and concentrated to give the crude. This resulted in to give the product 10 (1.5 g) as a white solid which was used for the next step. ESI-LCM S: m/z 487 $[M+H]^+$.

Preparation of (11): To a stirred solution of 10 (1.5 g) in pyridine (20 mL) were added DMTrCl (1.1 g, 3 mmol) at r.t. And the reaction mixture was stirred at r.t for 2.5 hr. With ice-bath cooling, the reaction was quenched with water and the product was extracted into EA. The organic layer was washed with brine and dried over $Na_2SO_4$ and concentrated to give the crude. The crude was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 25 min, the eluted product was collected at $CH_3CN/H_2O$ (0.5% $NH_4HCO_3$)=7/3 Detector, UV 254 nm. This resulted in to give the product 11 (1.9 g, 2.4 mmol, 85.7% yield over two steps) as a white solid. ESI-LCMS: m/z 789.3 $[M+H]^+$; $^1$H-NMR (400 MHz, DMSO-$d_6$): δ 12.10 (m, 1H), 11.63 (m, 1H), 8.20 (m, 1H), 7.35-7.33 (m, 2H), 7.29-7.19 (m, 7H), 6.86-6.83 (m, 4H), 5.89-5.88 (d, J=4 Hz, 1H), 4.40-4.28 (m, 2H), 3.72 (m, 6H), 2.81-2.76 (m, 1H), 1.13-1.11 (m, 6H), 0.80 (m, 9H), 0.05-0.01 (m, 7H).

Preparation of (12): To a solution of 11 (1.9 g, 2.4 mmol) in THF (20 mL) was added 1 M TBAF solution (3 mL). The reaction mixture was stirred at r.t. for 1.5 h. LCMS showed 11 was consumed completely. Water (100 mL) was added. The product was extracted with EA (50 mL) and the organic layer was washed with brine and dried over $Na_2SO_4$. Then the organic layer was concentrated to give a residue which was purified by Flash-Prep-HPLC with the following conditions (IntelFlash-1): Column, C18 silica gel; mobile phase, $CH_3CN/H_2O$ (0.5% $NH_4HCO_3$)=2/3 increasing to $CH_3CN/H_2O$ (0.5% $NH_4HCO_3$)=1/0 within 20 min, the eluted product was collected at $CH_3CN/H_2O$ (0.5% $NH_4HCO_3$)=58/42; Detector, UV 254 nm. This resulted in to give 12 (1.5 g, 2.2 mmol, 91.6% yield) as a white solid. ESI-LCMS: m/z 675.3 $[M+H]^+$; $^1$H-NMR (400 MHz, DMSO-$d_6$): δ 12.09 (m, 1H), 11.60 (m, 1H), 8.14 (m, 1H), 7.35-7.27 (m, 2H), 7.25-7.20 (m, 7H), 6.85-6.80 (m, 4H), 5.96-5.94 (d, J=8 Hz, 1H), 5.26-5.24 (m, 1H), 4.35-4.28 (m, 2H), 3.72 (m, 6H), 3.32 (m, 1H), 2.79-2.72 (m, 1H), 1.13-1.11 (m, 6H).

Preparation of Example 44 monomer: To a suspension of 11 (1.5 g, 2.2 mmol) in DCM (15 mL) was added DCI (220.8 mg, 1.9 mmol) and $CEP[N(iPr)_2]_2$ (795.7 mg, 2.6 mmol) under $N_2$ pro. The mixture was stirred at r.t. for 2 h. LCMS showed 11 was consumed completely. The solution was washed with water twice and washed with brine and dried over $Na_2SO_4$. Then concentrated to give a residue which was purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=4/1; Detector, UV 254 nm. This resulted in to give Example 44 monomer (1.6 g, 1.8 mmol, 83% yield) as a white solid. ESI-LCMS: m/z 875 $[M+H]^+$; $^1$H-NMR (400 MHz, DMSO-$d_6$): δ 12.12 (m, 1H), 11.60 (m, 1H), 8.15 (m, 1H), 7.37-7.29 (m, 2H), 7.27-7.20 (m, 7H), 6.86-6.81 (m, 4H), 5.94-5.88 (m, 1H), 4.54-4.51 (m, 2H), 4.21-4.20 (m, 1H), 3.73-3.54 (m, 10H), 2.80-2.75 (m, 1H), 2.61-2.58 (m, 1H), 1.19-1.11 (m, 19H). $^{31}$P-NMR (162 MHz, DMSO-$d_6$): δ=149.77, 149.71.

Example 45. Synthesis of Monomer

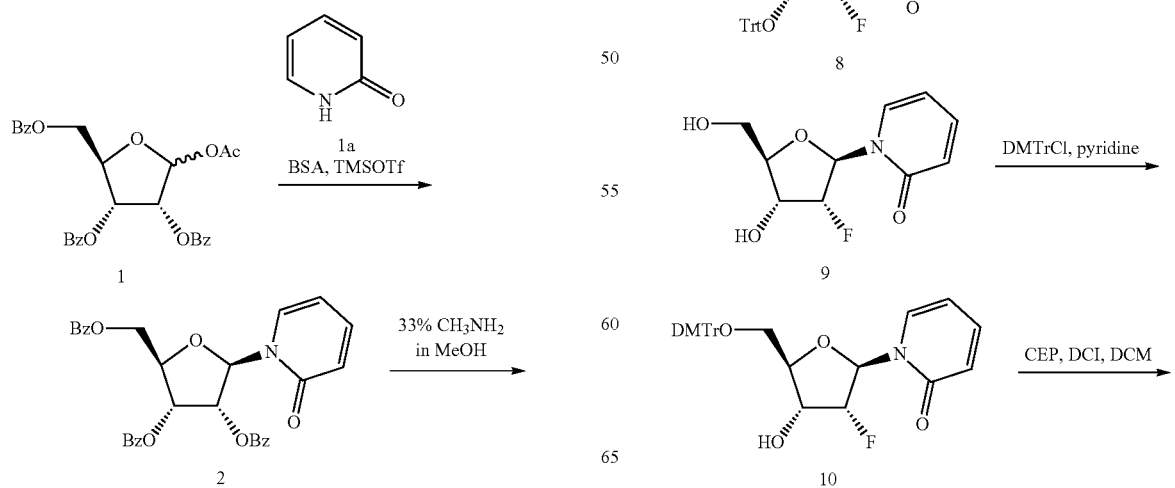

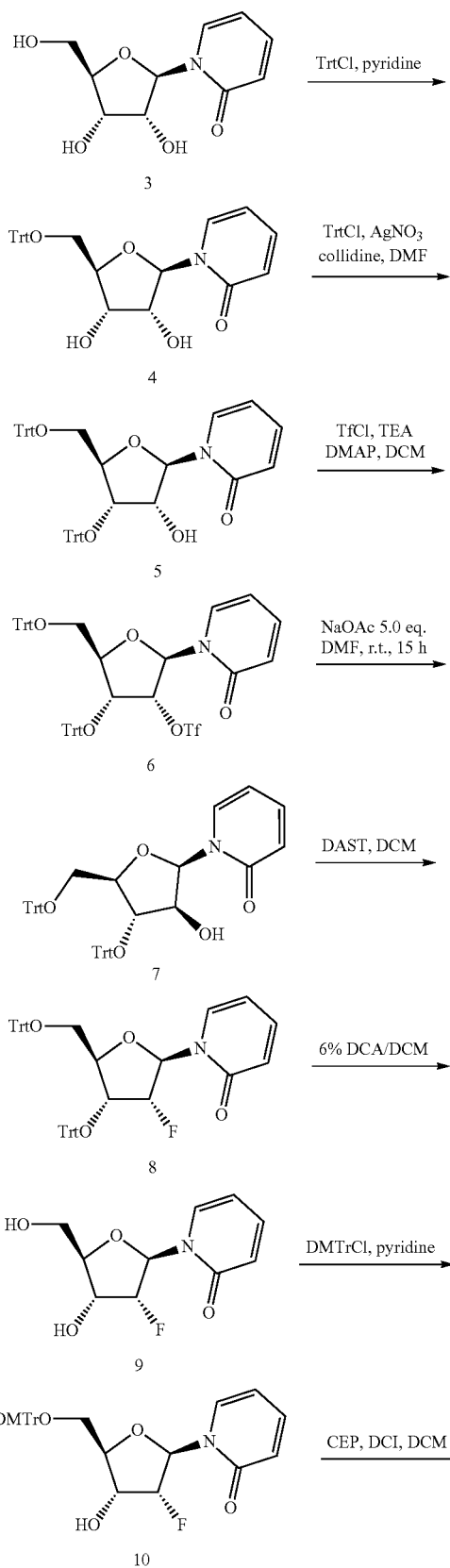

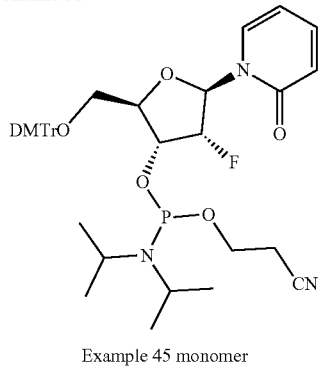

Example 45 monomer

Preparation of (2): To a solution of 1 (50.0 g, 99.2 mmol) and 1a (11.3 g, 119.0 mmol) in ACN (500.0 mL). Then added BSA (53.2 g, 218.0 mmol) under $N_2$ Pro. The mixture was stirred at 50° C. for 1 h until the solution was clear. Then cool down to 0° C. and dropped TMSOTf (26.4 g, 119.0 mmol). The mixture was stirred at 75° C. for 1 h, TLC showed 1 was consumed completely. The reaction was quenched by sodium bicarbonate solution at 0° C., then the solution was diluted with EA, washed with $H_2O$ twice. The solvent was concentrated under reduced pressure and the crude 2 (60.1 g) was used for next step. ESI-LCMS: m/z 540.2 $[M+H]^+$.

Preparation of (3): To a solution of 2 (60.1 g) in $CH_3NH_2$/ethanol (500.0 mL). The mixture was stirred at 25° C. for 2 h. TLC showed 2 was consumed completely. The solvent was concentrated under reduced pressure and the residue was purified by c.c. (MeOH:DCM=50:1~10:1) to give 3 (22.0 g, 96.9 mmol, 97.3% yield over two steps). ESI-LCMS: m/z 228.0 $[M+H]^+$; $^1$H-NMR (400 MHz, DMSO-$d_6$): δ 8.01-7.98 (m, 1H), 7.43-7.38 (m, 1H), 6.37-6.35 (m, 1H), 6.27-6.23 (m, 1H), 6.03 (d, J=3.5 Hz, 1H), 5.39 (d, J=4.2 Hz, 1H), 5.11 (t, J=5.1 Hz, 1H), 5.03 (d, J=5.1 Hz, 1H), 3.98-3.95 (m, 2H), 3.91-3.88 (m, 1H), 3.74-3.57 (m, 2H).

Preparation of (4): To a solution of 3 (22.0 g, 96.9 mmol) in pyridine (250.0 mL), TrtCl (30.7 g, 110.5 mmol) was added. The mixture was stirred at 25° C. for 24 h. TLC showed 3 was consumed completely, $H_2O$ was added to the mixture. Then filtered and the filtrate diluted with EA, the organic layer was washed with $NaHCO_3$ and brine. The solvent was concentrated under reduced pressure and then purified by c.c. (PE/EA=5:1~0:1) to give 4 (38.8 g, 82.5 mmol, 85.1% yield) as a white solid. ESI-LCMS: m/z 470.1 $[M+H]^+$.

Preparation of (5): To a solution of 4 (38.8 g, 82.5 mmol) in DMF (500.0 mL), collidine (10.0 g, 107.3 mmol), TrtCl (27.6 g, 99.1 mmol) were added followed by $AgNO_3$ (18.0 g, 105.1 mmol). The mixture was stirred at 25° C. for 4 h. TLC showed 4 was consumed completely. Then filtered and the filtrate diluted with EA. The organic layer was washed with $NaHCO_3$ and brine. The solvent was concentrated under reduced pressure and then purified by c.c. (PE/EA=5:1~1:1) to give a mixture of 5 (52.3 g, 73.5 mmol, 86.3% yield) as white solid. ESI-LCMS: m/z 711.1 $[M+H]^+$.

Preparation of (6): To a solution of 5 (52.3 g, 73.5 mmol) in DCM (500.0 mL), DMAP (8.9 g, 73.5 mmol), TEA (14.9 g, 147.3 mmol, 20.6 mL) were added, cool down to 0° C., TfCl (16.1 g, 95.6 mmol) dissolved in DCM (100.0 mL) were dropped. The mixture was stirred at 25° C. for 1 h. TLC showed 5 was consumed completely. Then filtered and the solution diluted with EA. The organic layer was washed with $NaHCO_3$ and brine. The solvent was concentrated under reduced pressure to get crude 6 (60.2 g) as a brown solid. ESI-LCMS: m/z 844.2 $[M+H]^+$.

Preparation of (7): To a solution of 6 (60.2 g) in DMF (500.0 mL), KOAc (36.1 g, 367.8 mmol) were added, The mixture was stirred at 25° C. for 14 h and 50° C. for 3 h, TLC showed 6 was consumed completely. Then filtered and the solution diluted with EA. The organic layer was washed with $H_2O$ and brine. The solvent was concentrated under reduced pressure, residue was purified by c.c. (PE/EA=5:1~1:1) to give 7 (28.0 g, 39.3 mmol, 53.5% yield) as yellow solid. ESI-LCMS: m/z 710.2 $[M-H]^-$; $^1$H-NMR (400 MHz, DMSO-$d_6$): δ 7.37-7.25 (m, 33H), 6.34-6.31 (m, 2H), 6.13-6.10 (m, 1H), 5.08 (d, J=4.2 Hz, 1H), 3.99 (d, J=7.6 Hz, 1H), 3.74 (s, 1H), 3.12 (t, J=9.2 Hz, 1H), 2.72-2.69 (m, 1H).

Preparation of (8): To a solution of 7 (28.0 g, 39.3 mmol) in DCM (300.0 mL), DAST (31.6 g, 196.6 mmol) was added at 0° C., the mixture was stirred at 25° C. for 16 h, TLC showed 7 was consumed completely. Then the solution was diluted with EA, washed with $NaHCO_3$ twice, the solvent was removed under reduced pressure, residue was purified by c.c. (PE/EA=5:1~3:1) to give 8 (5.0 g, 7.0 mmol, 17.8% yield) as a white solid. ESI-LCMS: m/z 748.2 $[M+2NH_4]^+$; $^1$H-NMR (400 MHz, DMSO-$d_6$): δ 7.57-7.18 (m, 35H), 6.30 (d, J=8.8 Hz, 1H), 6.00 (d, J=19.5 Hz, 1H), 5.92-5.88 (m, 1H), 4.22-4.17 (m, 2H), 3.94 (s, 0.5H), 3.80 (s, 0.5H), 3.35-3.31 (m, 1H), 3.14-3.10 (m, 1H); $^{19}$F-NMR (376 MHz, DMSO-$d_6$): δ−193.54.

Preparation of (9): To a solution of 8 (5.0 g, 7.0 mmol) in DCM (60.0 mL) was added DCA (3.6 mL) and TES (15.0 mL). The mixture was stirred at 20° C. for 1 h, TLC showed 8 was consumed completely. Then the solution was concentrated under reduced pressure, the residue was purified by Flash-Prep-HPLC with the following conditions (IntelFlash-1): Column, C18 silica gel; mobile phase, $CH_3CN/H_2O$ (0.5% $NH_4HCO_3$)=0/1 increasing to $CH_3CN/H_2O$ (0.5% $NH_4HCO_3$)=1/3 within 25 min, the eluted product was collected at $CH_3CN/H_2O$ (0.5% $NH_4HCO_3$)=0/1; Detector, UV 254 nm. This resulted in to give 9 (1.6 g, 6.9 mmol, 98.5% yield) as a white solid. ESI-LCMS: m/z 229.9 $[M+H]^+$; $^1$H-NMR (400 MHz, DMSO-$d_6$): δ 8.06-8.04 (m, 1H), 7.48-7.43 (m, 1H), 6.39 (d, J=9.0 Hz, 1H), 6.31-6.27 (m, 1H), 6.16-6.11 (m, 1H), 5.63 (s, 1H), 5.26 (s, 1H), 4.95-4.81 (m, 1H), 4.20-411 (m, 1H), 3.95 (d, J=8.2 Hz, 1H), 3.84 (d, J=12.4 Hz, 1H), 3.64 (d, J=12.1 Hz, 1H); $^{19}$F-NMR (376 MHz, DMSO-$d_6$): δ−201.00.

Preparation of (10): To a solution of 9 (1.6 g, 6.9 mmol) in pyridine (20.0 mL) was added DMTrCl (3.5 g, 10.5 mmol) at 20° C. and stirred for 1 h. TLC showed 9 was consumed completely. Water was added and extracted with EA, the organic layer was washed with $NaHCO_3$ and brine. Then the solution was concentrated under reduced pressure and the residue was purified by Flash-Prep-HPLC with the following conditions (IntelFlash-1): Column, C18 silica gel; mobile phase, $CH_3CN/H_2O$ (0.5% $NH_4HCO_3$)=1/3 increasing to $CH_3CN/H_2O$ (0.5% $NH_4HCO_3$)=4/1 within 25 min, the eluted product was collected at $CH_3CN/H_2O$ (0.5% $NH_4HCO_3$)=1/1; Detector, UV 254 nm. This resulted in to give 10 (2.2 g, 4.2 mmol, 60.8% yield) as a white solid. ESI-LCMS: m/z 530.1 $[M-H]^-$; $^1$H-NMR (400 MHz, DMSO-$d_6$): δ 7.93-7.91 (m, 1H), 7.47-7.23 (m, 10H), 6.91-6.89 (m, 4H), 6.41 (d, J=8.8 Hz, 1H), 6.13 (d, J=18.8 Hz, 1H), 6.00-5.96 (m, 1H), 5.68 (d, J=6.6 Hz, 1H), 5.01 (d, J=4.2 Hz, 0.5H), 4.88 (d, J=4.2 Hz, 0.5H), 4.42-4.31 (m, 1H), 4.10-4.08 (m, 1H), 3.74 (s, 6H), 3.40-3.34 (m, 2H); $^{19}$F-NMR (376 MHz, DMSO-$d_6$): δ−199.49.

Preparation of Example 45 monomer: To a solution of 10 (2.2 g, 4.2 mmol) in DCM (20.0 mL) was added DCI (415 mg, 3.5 mmol) and CEP (1.5 g, 4.9 mmol) under N₂ pro. The mixture was stirred at 20° C. for 0.5 h. TLC showed 10 was consumed completely. The product was extracted with DCM, the organic layer was washed with H₂O and brine. Then the solution was concentrated under reduced pressure and the residue was purified by cc (PE/EA=5:1~1:1) and Flash-Prep-HPLC with the following conditions (IntelFlash-1): Column, C18 silica gel; mobile phase, CH₃CN/H₂O (0.5% NH₄HCO₃)=1/3 increasing to CH₃CN/H₂O (0.5% NH₄HCO₃)=1/0 within 25 min, the eluted product was collected at CH₃CN/H₂O (0.5% NH₄HCO₃)=1/0; Detector, UV 254 nm. This resulted in to give Example 45 monomer (2.1 g, 3.0 mmol, 73.1% yield) as a white solid. ESI-ESI-LCMS: m/z 732.2 [M+H]⁺; ¹H-NMR (400 MHz, DMSO-d₆): δ 7.98-7.92 (m, 1H), 7.42-7.24 (m, 10H), 6.91-6.85 (m, 4H), 6.43-6.39 (m, 1H), 6.18-6.11 (m, 1H), 6.01-5.97 (m, 1H), 5.22-5.19 (m, 0.5H), 5.09-5.06 (m, 0.5H), 4.73-4.52 (m, 1H), 4.21-4.19 (m, 1H), 3.79-3.62 (m, 7H), 3.57-3.47 (m, 4H), 3.32-3.28 (m, 1H), 2.75-2.58 (m, 1H), 1.13-0.92 (m, 12H); ¹⁹F-NMR (376 MHz, DMSO-d₆): δ-196.82, -196.84, -197.86, -197.88; ³¹P-NMR (162 MHz, DMSO-d₆): δ 149.88, 149.83, 149.39, 149.35.

Example 46. Synthesis of Monomer

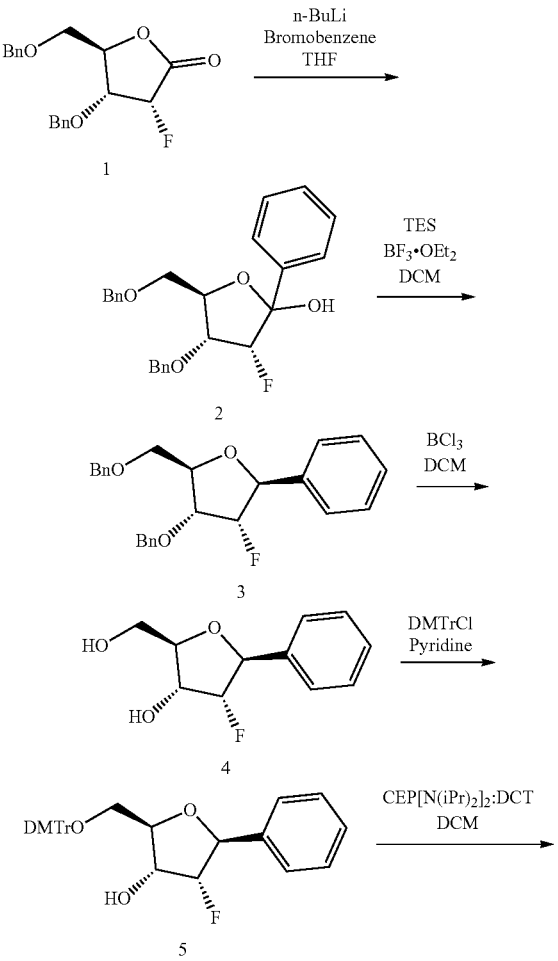

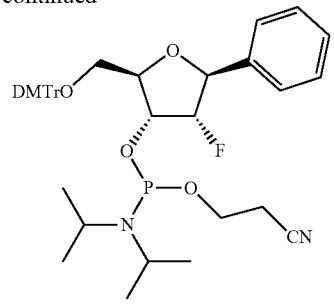

Example 46 monomer

Preparation of (2): To the solution of Bromobenzene (2.1 g, 13.6 mmol) in dry THF (15 mL) was added 1.6 M n-BuLi (7 mL, 11.8 mmol) drop wise at −78° C. The mixture was stirred at −78° C. for 0.5 h. Then the 1 (3.0 g, 9.1 mmol, Wang, Guangyi et al, Journal of Medicinal Chemistry, 2016, 59(10), 4611-4624) was dissolved in THF (15 mL) and added to the mixture drop wise with keeping at −78° C. Then the reaction mixture was stirred at −78° C. for 1 hr. LC-MS showed 1 was consumed completely. Then the solution was added to saturated aq. NH₄Cl and the resulting mixture was extracted with EA. The combined organic layer was washed with water and brine, dried over Na₂SO₄, and concentrated under reduced pressure to give a residue which was purified by Flash-Prep-HPLC with the following conditions (IntelFlash-1): Column, C18 silica gel; mobile phase, CH₃CN/H₂O (0.5% NH₄HCO₃)=2/3 increasing to CH₃CN/H₂O (0.5% NH₄HCO₃)=4/1 within 25 min, the eluted product was collected at CH₃CN/H₂O (0.5% NH₄HCO₃)=3/2; Detector, UV 254 nm. This resulted in to give 2 (3.0 g, 7.3 mmol, 80.0%) as a white solid. ESI-LCMS: m/z 391 [M−OH]⁻.

Preparation of (3): To the solution of 2 (4.0 g, 9.8 mmol) in DCM (40 mL) was added TES (1.9 g, 11.7 mmol) at −78° C., and the mixture was added BF₃.OEt₂ (2.1 g, 14.7 mmol) drop wise at −78° C. The mixture was stirred at −40° C. for 1 hr. LC-MS showed 2 was consumed completely. Then the solution was added to saturated aq. NaHCO₃ and the resulting mixture was extracted with DCM. The combined organic layer was washed with water and brine, dried over Na₂SO₄, and concentrated under reduced pressure to give a residue which was purified by Flash-Prep-HPLC with the following conditions (IntelFlash-1): Column, C18 silica gel; mobile phase, CH₃CN/H₂O (0.5% NH₄HCO₃)=2/3 increasing to CH₃CN/H₂O (0.5% NH₄HCO₃)=4/1 within 25 min, the eluted product was collected at CH₃CN/H₂O (0.5% NH₄HCO₃)=7/3; Detector, UV 254 nm. This resulted in to give 3 (3.1 g, 5.3 mmol, 54.0%) as a water clear oil. ESI-LCMS: m/z 410 [M+H₂O]⁺; ¹H-NMR (400 MHz, CDCl₃): δ 7.48-7.25 (m, 15H), 5.24-5.13 (m, 1H), 4.93-4.74 (m, 1H), 4.74-4.46 (m, 4H), 4.37-4.25 (m, 1H), 4.19-4.05 (m, 1H), 4.00-3.80 (m, 1H), 3.77-3.63 (m, 1H). ¹⁹F-NMR (376 MHz, CDCl₃): δ-196.84.

Preparation of (4): To the solution of 3 (2.1 g, 5.3 mmol) in dry DCM (20 mL) was added 1 M BCl₃ (25 mL, 25.5 mmol) drop wise at −78° C., and the reaction mixture was stirred at −78° C. for 0.5 hr. LC-MS showed 3 was consumed completely. After completion of reaction, the resulting mixture was poured into water (50 mL). The solution was extracted with DCM and the combined organic layer was concentrated under reduced pressure to give a crude. The crude in MeOH (4 mL) was added 1 M NaOH (15 mL), and the mixture was stirred at r.t for 5~10 min. The mixture was extracted with EA. The combined organic layer was washed with brine, dried over $Na_2SO_4$, and concentrated under reduced pressure to give a residue which was purified by silica gel column chromatography (eluent, DCM: MeOH=40:1~15:1) to give 4 (1.0 g, 4.7 mmol, 88.6%) as a water clear oil. ESI-LCMS: m/z 211 [M−H]$^-$; $^1$H-NMR (400 MHz, DMSO-d$_6$): δ 7.58-7.19 (m, 5H), 5.41 (d, J=6.1 Hz, 1H), 5.09-5.95 (m, 1H), 5.95-4.84 (m, 1H), 4.82-4.59 (m, 1H), 4.14-3.94 (m, 1H), 3.89-3.80 (m, 1H), 3.78-3.67 (m, 1H), 3.65-3.53 (m, 1H). $^{19}$F-NMR (376 MHz, DMSO-d$_6$): δ−196.46.

Preparation of (5): To a solution of 4 (1.0 g, 4.7 mmol) in Pyridine (10 mL) was added DMTrCl (2.0 g, 5.7 mmol). The reaction mixture was stirred at r.t. for 2 hr. LCMS showed 4 was consumed and water (100 mL) was added. The product was extracted with EA (100 mL) and the organic layer was washed with brine and dried over $Na_2SO_4$ and concentrated to give the crude. The crude was further purified by Flash-Prep-HPLC with the following conditions (IntelFlash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=9/1; Detector, UV 254 nm. This resulted in to give 5 (2.1 g, 4.1 mmol, 87.0%) as a red oil. ESI-LCMS: m/z 513 [M−H]$^-$; $^1$H-NMR (400 MHz, DMSO-d$_6$): δ 7.56-7.16 (m, 14H), 6.94-9.80 (m, 4H), 5.45 (d, J=6.3 Hz, 1H), 5.21-5.09 (m, 1H), 4.89-4.68 (m, 1H), 4.18-4.03 (m, 2H), 3.74 (s, 6H), 3.33-3.29 (m, 1H), 3.26-3.17 (m, 1H). $^{19}$F-NMR (376 MHz, DMSO-d$_6$): δ−194.08.

Preparation of Example 46 monomer: To a suspension of 5 (2.1 g, 4.1 mmol) in DCM (20 mL) was added DCI (410 mg, 3.4 mmol) and CEP[N(iPr)$_2$]$_2$ (1.5 g, 4.9 mmol). The mixture was stirred at r.t. for 1 h. LC-MS showed 5 was consumed completely. The solution was washed with water twice and washed with brine and dried over $Na_2SO_4$. Then concentrated to give the crude. The crude was purification by Flash-Prep-HPLC with the following conditions (Intel-Flash-1): Column, C18 silica gel; mobile phase, $CH_3CN/H_2O$ (0.5% $NH_4HCO_3$)=1/1 increasing to $CH_3CN/H_2O$ (0.5% $NH_4HCO_3$)=1/0 within 20 min, the eluted product was collected at $CH_3CN/H_2O$ (0.5% $NH_4HCO_3$)=1/0; Detector, UV 254 nm. This resulted in to give Example 46 monomer (2.1 g, 2.9 mmol, 70.0%) as a white solid. ESI-LCMS: m/z 715 [M+H]$^+$; $^1$H-NMR (400 MHz, DMSO-d$_6$): δ 7.59-7.16 (m, 14H), 6.94-9.80 (m, 4H), 5.26-5.12 (m, 1H), 5.06-4.77 (m, 1H), 4.50-4.20 (m, 1H), 4.20-4.10 (m, 1H), 3.83-3.63 (m, 7H), 3.59-3.37 (m, 4H), 3.25-3.13 (m, 1H), 2.80-2.66 (m, 1H), 2.63-2.53 (m, 1H), 1.18-0.78 (m, 12H). $^{19}$F-NMR (376 MHz, DMSO-d$_6$): δ−194.40, −194.42, −194.50, −194.53. $^{31}$P-NMR (162 MHz, DMSO-d$_6$): δ 149.38, 149.30, 149.02, 148.98.

Example 47. Deuterated Vinyl Phosphonate Improves Potency of siNA

Figure 11:
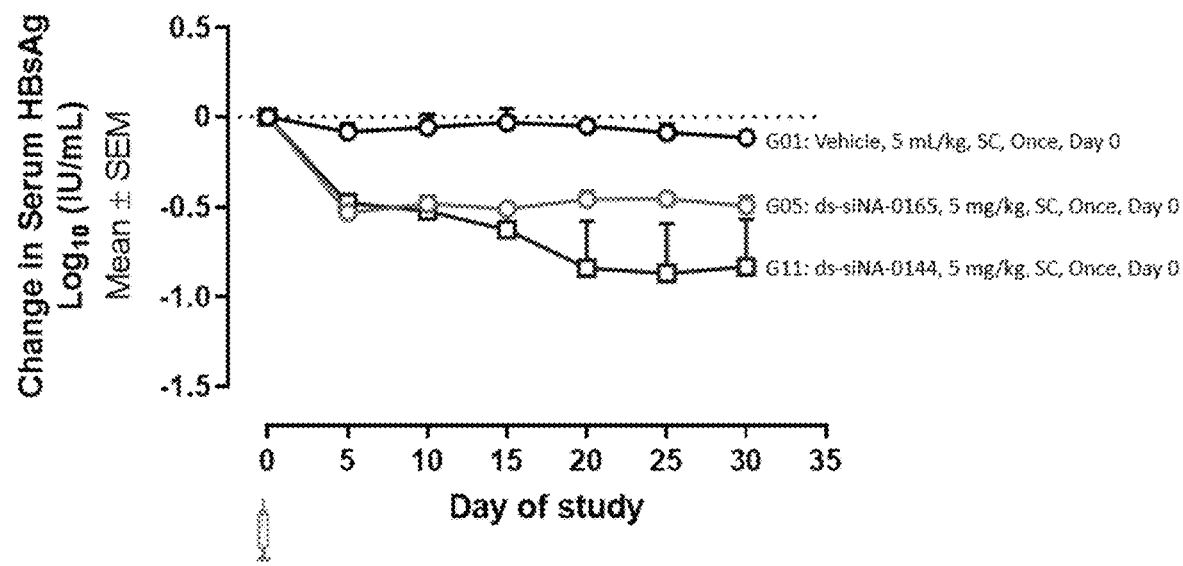
FIG. 11 shows a graph of the change in serum HBsAg from AAV-HBV mice treated with vehicle (G01), ds-siNA-0165 (G05), or ds-siNA-0144 (G11).

This example investigates whether a deuterated vinyl phosphonate improves potency of siNA in an AAV-HBV mouse. AAV-HBV mice were subcutaneously injected with vehicle, ds-siNA-0165 (e.g., siNA without a deuterated vinyl phosphonate), or ds-siNA-0144 (e.g., siNA with a deuterated vinyl phosphonate). For siNA-treated AAV-HBV mice, AAV-HBV mice were subcutaneously injected with a single dose of 5 mg/kg of siNA. As shown in FIG. 11, siNA molecules having 2'-fluoro nucleotides at positions 3, 7-9, 12, and 17 from the 5' end of the sense strand and 2'-fluoro nucleotides at positions 2 and 14 from the 5' end of the antisense strand resulted in at least a 0.5-log reduction in HBsAg, with the greatest reduction in HBsAg found in mice treated with the deuterated vinylphosphonate siNA (ds-siNA-0165). Thus, FIG. 11 demonstrates that the presence of a deuterated vinyl phosphonate improves potency of the siNA.

Figure 12:
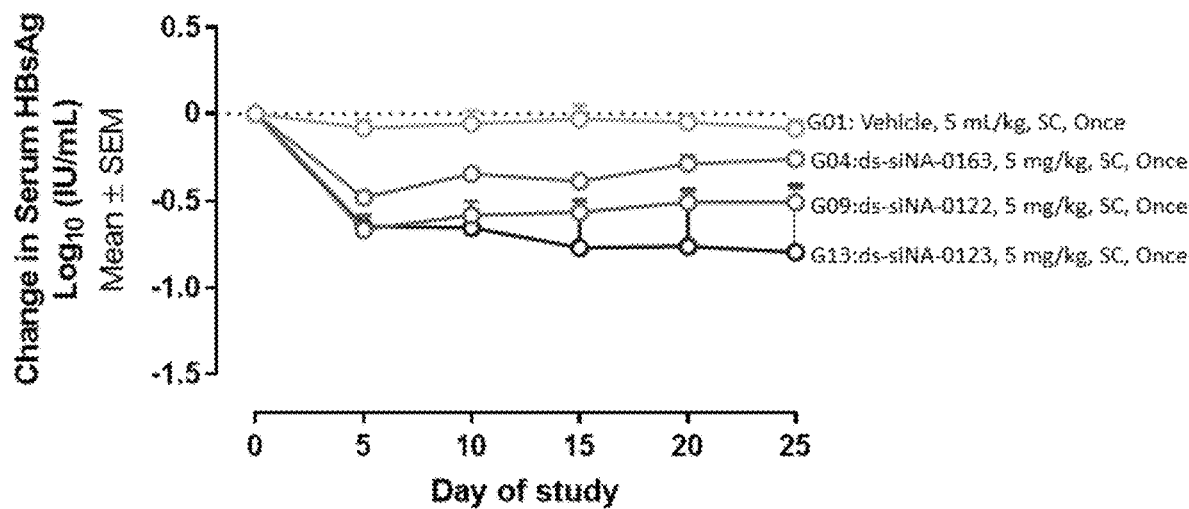
FIG. 12 shows a graph of the change in serum HBsAg from AAV-HBV mice treated with vehicle (G01), ds-siNA-0163 (G04), ds-siNA-0122 (G09), or ds-siNA-0123 (G13).

Example 48. Deuterated Vinyl Phosphonate Results in a Greater Reduction in Serum HBsAg AAV-HBV mice were subcutaneously injected with vehicle, ds-siNA-0163 (e.g., siNA without a vinyl phosphonate), ds-siNA-0122 (e.g., siNA with a vinyl phosphonate), or ds-siNA-0123 (e.g., siNA with a deuterated vinyl phosphonate). For siNA-treated AAV-HBV mice, AAV-HBV mice were subcutaneously injected with a single dose of 5 mg/kg of siNA. As shown in FIG. 12, siNA molecules having 2'-fluoro nucleotides at positions 7, 9-11 from the 5' end of the sense strand and 2'-fluoro nucleotides at positions 2 and 14 from the 5' end of the antisense strand resulted in at least a 0.5-log reduction in HBsAg, with the greatest reduction in HBsAg found in mice treated with the deuterated vinylphosphonate siNA (ds-siNA-0165). Thus, FIG. 12 demonstrates that the presence of a deuterated vinyl phosphonate improves potency of the siNA, as compared to the siNA without a vinyl phosphonate and the siNA with the vinyl phosphonate.

Example 49: Synthesis of 5' End Cap Monomer

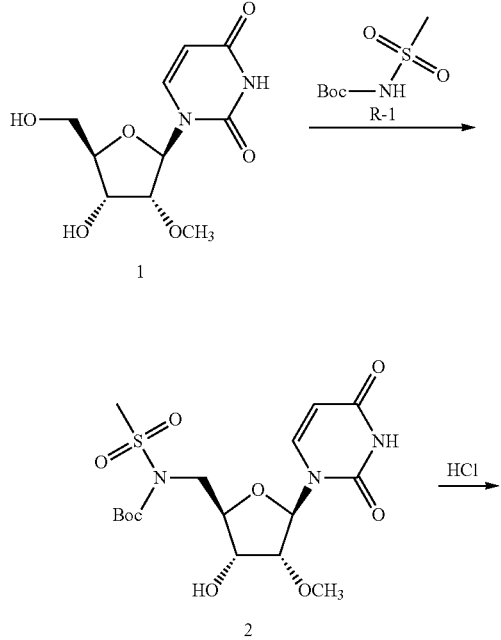

Example 49 Monomer Synthesis Scheme

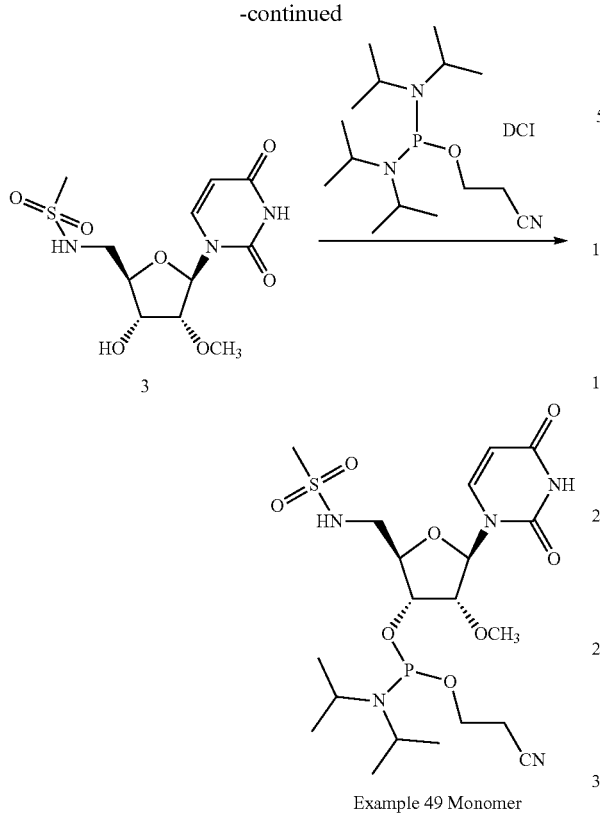

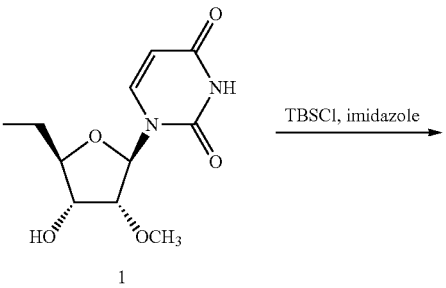

Example 49 Monomer

Preparation of (2): 1 (15 g, 58.09 mmol) and tert-butyl N-methylsulfonylcarbamate (17.01 g, 87.13 mmol) were dissolved in THF (250 mL), and PPh$_3$ (30.47 g, 116.18 mmol) was added followed by dropwise addition of DIAD (23.49 g, 116.18 mmol, 22.59 mL) at 0° C. The reaction mixture was stirred at 15° C. for 12 h. Upon completion as monitored by TLC (DCM/MeOH=10/1), the reaction mixture was evaporated to give a residue. The residue was purified by flash silica gel chromatography (ISCO®; 120 g SepaFlash® Silica Flash Column, Eluent of 0~20% MeOH/DCM gradient @ 60 mL/min) to give 2 (6.9 g, 24.28% yield) as a white solid. ESI-LCMS: m/z 457.9 [M+Na]$^+$; $^1$H NMR (400 MHz, CDCl$_3$) δ=8.64 (br s, 1H), 7.64 (d, J=8.2 Hz, 1H), 5.88 (d, J=1.9 Hz, 1H), 5.80 (dd, J=2.2, 8.2 Hz, 1H), 4.19-4.01 (m, 3H), 3.90 (dt, J=5.5, 8.2 Hz, 1H), 3.82-3.78 (m, 1H), 3.64 (s, 3H), 3.32 (s, 3H), 2.75 (d, J=8.9 Hz, 1H), 1.56 (s, 9H).

Preparation of (3): 2 (6.9 g, 15.85 mmol) was dissolved in MeOH (40 mL), and a solution of HCl/MeOH (4 M, 7.92 mL) was added dropwise. The reaction mixture was stirred at 15° C. for 12 h, and then evaporated to give a residue. The residue was purified by flash silica gel chromatography (ISCO®; 40 g SepaFlash® Silica Flash Column, Eluent of 0-10% MeOH/DCM gradient @ 40 mL/min) to give 3 (2.7 g, 50.30% yield) as a white solid. ESI-LCMS: m/z 336.0 [M+H]$^+$; $^1$H NMR (400 MHz, CD$_3$CN) δ=9.20 (br s, 1H), 7.52 (d, J=8.1 Hz, 1H), 5.75 (d, J=3.8 Hz, 1H), 5.64 (dd, J=2.0, 8.1 Hz, 1H), 5.60-5.52 (m, 1H), 4.15-3.99 (m, 1H), 3.96-3.81 (m, 2H), 3.46 (s, 3H), 3.44-3.35 (m, 1H), 3.34-3.26 (m, 1H), 2.92 (s, 3H).

Preparation of (Example 49 monomer): To a solution of 3 (2.14 g, 6.38 mmol) in DCM (20 mL) was added dropwise 3-bis(diisopropylamino)phosphanyloxypropanenitrile (2.50 g, 8.30 mmol, 2.63 mL) at 0° C., followed by 1H-imidazole-4, 5-dicarbonitrile (829 mg, 7.02 mmol), and the mixture was purged under Ar for 3 times. The reaction mixture was stirred at 15° C. for 2 h. Upon completion, the mixture was quenched with 5% NaHCO$_3$ (20 mL), extracted with DCM (20 mL*2), washed with brine (15 mL), dried over Na$_2$SO$_4$, filtered, and evaporated to give a residue. The residue was purified by flash silica gel chromatography (ISCO®; 40 g SepaFlash® Silica Flash Column, Eluent of 0~10% (Phase B: i-PrOH/DCM=1/2)/Phase A: DCM with 5% TEA gradient @ 40 mL/min) to give Example 49 monomer (1.73 g, 48.59% yield) as a white solid. ESI-LCMS: m/z 536.3 [M+H]$^+$; $^1$H NMR (400 MHz, CD$_3$CN) δ=7.58-7.48 (m, 1H), 5.83-5.78 (m, 1H), 5.71-5.64 (m, 1H), 4.40-4.29 (m, 1H), 4.19-4.07 (m, 1H), 3.98 (td, J=5.3, 13.3 Hz, 1H), 3.90-3.78 (m, 2H), 3.73-3.59 (m, 3H), 3.41 (d, J=14.8 Hz, 4H), 2.92 (br d, J=7.0 Hz, 3H), 2.73-2.63 (m, 2H), 1.23-1.11 (m, 12H); $^{31}$P NMR (162 MHz, CD$_3$CN) δ=149.81, 150.37.

Example 50: Synthesis of 5' End Cap Monomer

Example 50 Monomer Synthesis Scheme

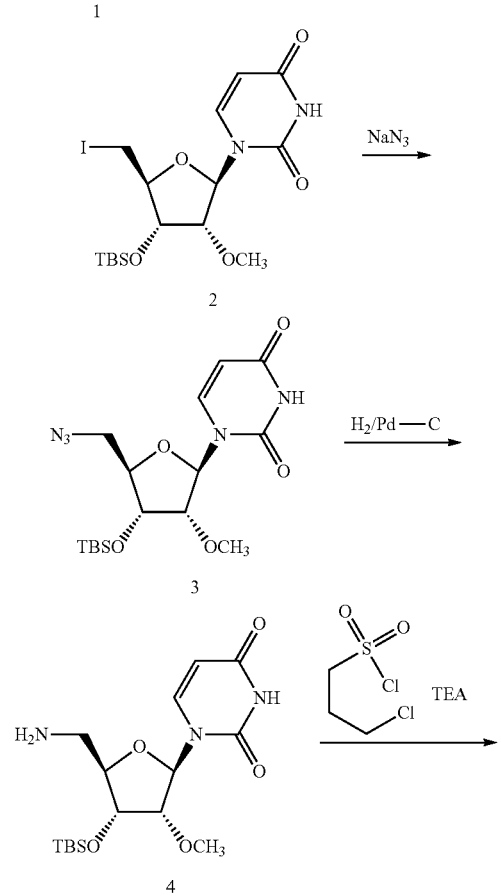

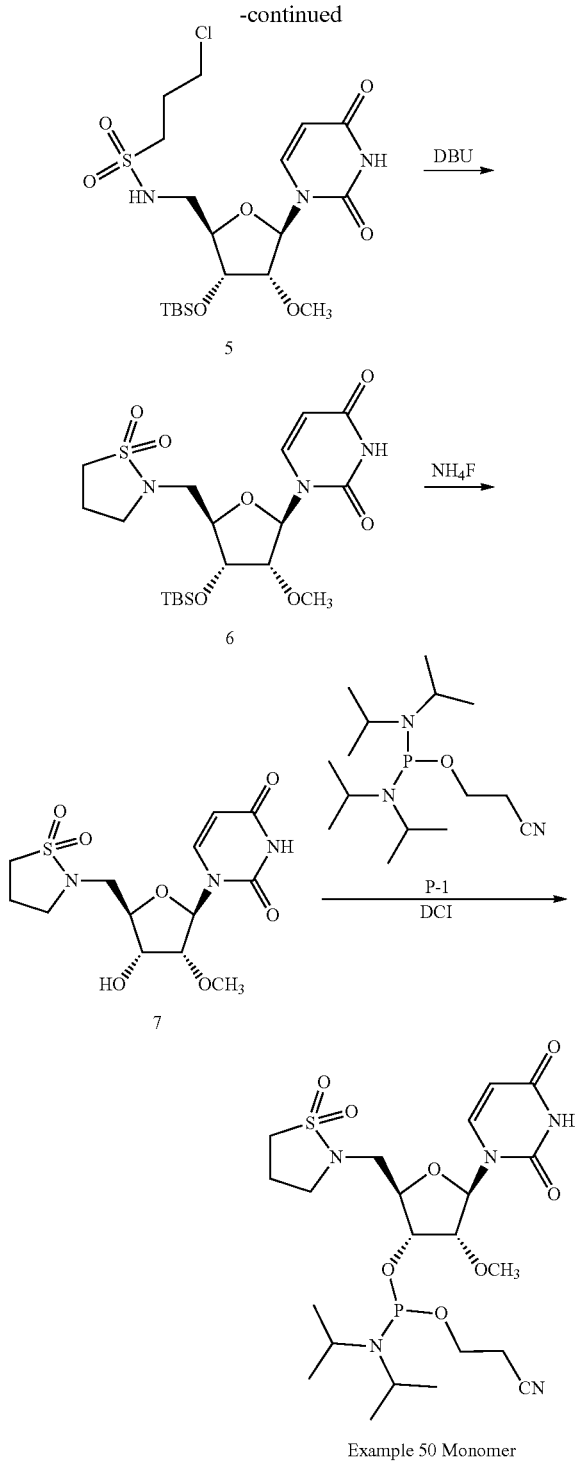

Example 50 Monomer

Preparation of (2): To a solution of t (10 g, 27.16 mmol) in DMF (23 mL) were added imidazole (3.70 g, 54.33 mmol) and TBSCl (8.19 g, 54.33 mmol) at 25° C. The mixture was stirred at 25° C. for 2 hr. Upon completion, the reaction mixture was diluted with H$_2$O (20 mL) and extracted with EA (30 mL*2). The combined organic layers were washed with brine (20 mL*2), dried over Na$_2$SO$_4$, filtered and concentrated under reduced pressure to give 2 (13 g, 99.2 yield) as a white solid. ES-LCMS: m/z 482.9 [M+H]$^+$.

Preparation of (3): To a solution of 2 (35.00 g, 72.56 mmol) in DMF (200 mL) was added NaN$_3$ (14.15 g, 217.67 mmol). The mixture was stirred at 60° C. for 17 h. Upon completion, the reaction mixture was diluted with H$_2$O (200 mL) and extracted with EA (200 mL*2). The combined organic layers were washed with brine (100 mL*2), dried over Na$_2$SO$_4$, filtered and concentrated under reduced pressure to give 3 (31.8 g, crude) as a yellow solid. ESI-LCMS: m/z 398.1 [M+H]$^+$; $^1$H NMR (400 MHz, DMSO-d$_6$) δ=11.21 (d, J=1.3 Hz, 1H), 7.50 (d, J=8.1 Hz, 1H), 5.57 (d, J=4.5 Hz, 1H), 5.46 (dd, J=2.1, 8.0 Hz, 1H), 4.06 (t, J=5.2 Hz, 1H), 3.81-3.64 (m, 2H), 3.44-3.30 (m, 2H), 2.31-2.25 (m, 3H), 0.65 (s, 9H), −0.13 (s, 6H).

Preparation of (4): To a solution of 3 (7 g, 17.61 mmol) in THF (60 mL) was added Pd/C (2 g) at 25° C. The reaction mixture was stirred at 25° C. for 3 h under H$_2$ atmosphere (15 PSI). The reaction mixture was filtered, and the filtrate was concentrated to give 4 (5.4 g, 75.11% yield) as a gray solid. ESI-LCMS: m/z 372.1 [M+H]$^+$; $^1$H NMR (400 MHz, DMSO-d$_6$) δ=7.93 (d, J=8.0 Hz, 1H), 5.81 (d, J=5.5 Hz, 1H), 5.65 (d, J=8.3 Hz, 1H), 4.28 (t, J=4.6 Hz, 1H), 3.88 (t, J=5.3 Hz, 1H), 3.74 (q, J=4.6 Hz, 1H), 3.31 (s, 3H), 2.83-2.66 (m, 2H), 0.88 (s, 9H), 0.09 (s, 6H).

Preparation of (5): To a solution of 4 (3 g, 8.08 mmol) in DCM (30 mL) was added TEA (2.45 g, 24.23 mmol, 3.37 mL) followed by dropwise addition of 3-chloropropane-1-sulfonyl chloride (1.50 g, 8.48 mmol, 1.03 mL) at 25° C. The reaction mixture was stirred at 25° C. for 18 h under N$_2$ atmosphere. Upon completion, the reaction mixture was diluted with H$_2$O (50 mL) and extracted with DCM (50 mL*2). The combined organic layers were washed with brine (50 mL*2), dried over Na$_2$SO$_4$, filtered and concentrated under reduced pressure. The residue was purified by flash silica gel chromatography (ISCO®; 24 g SepaFlash® Silica Flash Column, Eluent of 0~30% MeOH/DCM @ 50 mL/min) to give 5 (3.6 g, 84.44% yield) as a white solid. ESI-LCMS: m/z 512.1 [M+H]$^+$; $^1$H NMR (400 MHz, DMSO-d$_6$) δ=11.42 (s, 1H), 7.75 (d, J=8.1 Hz, 1H), 7.49 (t, J=6.2 Hz, 1H), 5.83 (d, J=5.8 Hz, 1H), 5.70-5.61 (m, 1H), 4.33-4.23 (m, 1H), 3.95 (t, J=5.5 Hz, 1H), 3.90-3.78 (m, 1H), 3.73 (t, J=6.5 Hz, 2H), 3.30 (s, 3H), 3.26-3.12 (m, 4H), 2.14-2.02 (m, 2H), 0.88 (s, 9H), 0.11 (d, J=3.3 Hz, 6H).

Preparation of (6): To a solution of 5 (5 g, 9.76 mmol) in DMF (45 mL) was added DBU (7.43 g, 48.82 mmol, 7.36 mL). The mixture was stirred at 25° C. for 16 h. The reaction mixture was concentrated to give a residue, diluted with H$_2$O (50 mL) and extracted with EA (50 mL*2). The combined organic layers were washed with brine (50 mL*2), dried over Na$_2$SO$_4$, filtered and concentrated under reduced pressure. The residue was purified by flash silica gel chromatography (ISCO®; 24 g SepaFlash® Silica Flash Column, Eluent of 0~80% EA/PE @ 40 mL/min) to give 6 (4.4 g, 89.06% yield) as a white solid. ESI-LCMS: m/z 476.1 [M+H]$^+$; $^1$H NMR (400 MHz, DMSO-d$_6$) δ=11.43 (d, J=1.7 Hz, 1H), 7.72 (d, J=8.1 Hz, 1H), 5.82 (d, J=4.8 Hz, 1H), 5.67 (dd, J=2.1, 8.1 Hz, 1H), 4.22 (t, J=5.1 Hz, 1H), 3.99-3.87 (m, 2H), 3.33-3.27 (m, 6H), 3.09 (dd, J=6.6, 14.7 Hz, 1H), 2.26-2.16 (m, 2H), 0.88 (s, 9H), 0.10 (d, J=3.8 Hz, 6H).

Preparation of (7): To a solution of 6 (200 mg, 420.49 umol) in MeOH (2 mL) was added NH$_4$F (311.48 mg, 8.41 mmol, 20 eq), and the mixture was stirred at 80° C. for 2 h. The reaction mixture was filtered and concentrated to give a residue, which was purified by flash silica gel chromatography (ISCO®; 4 g SepaFlash® Silica Flash Column, Eluent of 0~50% MeOH/DCM @ 20 mL/min) to give 7 (120 mg, 76.60% yield) as a white solid. ESI-LCMS: m/z 362.1 [M+H]$^+$; $^1$H NMR (400 MHz, DMSO-d$_6$) δ=11.37 (br s, 1H), 7.68 (d, J=8.1 Hz, 1H), 5.81 (d, J=4.6 Hz, 1H), 5.65 (d, J=8.0 Hz, 1H), 4.02 (q, J=5.6 Hz, 1H), 3.95-3.83 (m, 2H), 3.34 (s, 9H), 3.09 (dd, J=6.9, 14.6 Hz, 1H), 2.26-2.14 (m, 2H).

Preparation of (Example 50 monomer): To a solution of 7 (1.5 g, 4.15 mmol) in CH$_3$CN (12 mL) were added 3-bis(diisopropylamino)phosphanyloxypropanenitrile (1.63 g, 5.40 mmol, 1.71 mL) and 1H-imidazole-4,5-dicarbonitrile (539.22 mg, 4.57 mmol) in one portion at 0° C. The reaction mixture was gradually warmed to 25° C. The reaction mixture was stirred at 25° C. for 2 h under N$_2$ atmosphere. Upon completion, the reaction mixture was diluted with NaHCO$_3$ (20 mL) and extracted with DCM (20 mL*2). The combined organic layers were washed with brine (20 mL*2), dried over Na$_2$SO$_4$, filtered and concentrated under reduced pressure to give a residue, which was purified by flash silica gel chromatography (ISCO®; 12 g SepaFlash® Silica Flash Column, Eluent of 0~85% EA/PE with 0.5% TEA @ 30 mL/min to give Example 50 monomer (800 mg, 33.6% yield) as a white solid. ESI-LCMS: m/z 562.3 [M+H]$^+$; $^1$H NMR (400 MHz, CD$_3$CN) δ=9.28 (br s, 1H), 7.55 (br dd, J=8.3, 12.8 Hz, 1H), 5.86 (br d, J=3.9 Hz, 1H), 5.65 (br d, J=8.0 Hz, 1H), 4.33-4.06 (m, 2H), 4.00-3.89 (m, 1H), 4.08-3.86 (m, 1H), 3.89-3.72 (m, 4H), 3.43 (br d, J=15.1 Hz, 6H), 3.23-3.05 (m, 3H), 2.69 (br s, 2H), 2.36-2.24 (m, 2H), 1.26-1.10 (m, 12H); $^{31}$P NMR (162 MHz, CD$_3$CN) δ=149.94, 149.88.

Example 51: Synthesis of 5' End Cap Monomer

Example 51 Monomer Synthesis Scheme

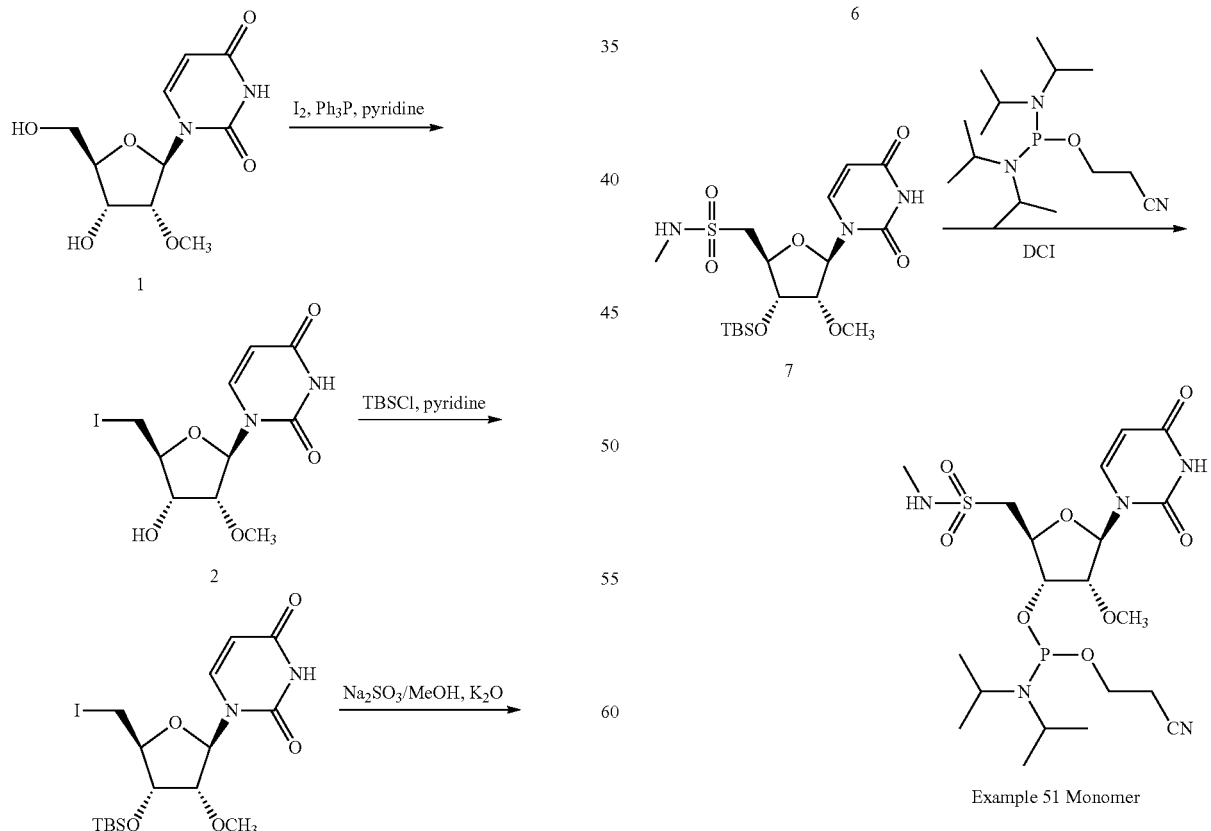

Example 51 Monomer

Preparation of (2): To a solution of 1 (30 g, 101.07 mmol, 87% purity) in CH$_3$CN (1.2 L) and Py (60 mL) were added 12 (33.35 g, 131.40 mmol, 26.47 mL) and PPh₃ (37.11 g, 141.50 mmol) in one portion at 10° C. The reaction was stirred at 25° C. for another 48 h. The mixture was diluted with aq.Na₂S₂O₃ (300 mL) and aq.NaHCO₃ (300 mL), concentrated to remove CH₃CN, and then extracted with EtOAc (300 mL*3). The combined organic layers were washed with brine (300 mL), dried over Na₂SO₄, filtered and concentrated under reduced pressure to give a residue. The residue was purified by flash silica gel chromatography (ISCO®; 330 g SepaFlash® Silica Flash Column, Eluent of 0~60% Methanol/Dichloromethane gradient @ 100 mL/min) to give 2 (28.2 g, 72.00% yield, 95% purity) as a brown solid. ESI-LCMS: m/z 369.1 [M+H]$^+$; $^1$H NMR (400 MHz, DMSO-d₆) δ=11.43 (s, 1H), 7.68 (d, J=8.1 Hz, 1H), 5.86 (d, J=5.5 Hz, 1H), 5.69 (d, J=8.1 Hz, 1H), 5.46 (d, J=6.0 Hz, 1H), 4.08-3.96 (m, 2H), 3.90-3.81 (m, 1H), 3.60-3.51 (m, 1H), 3.40 (dd, J=6.9, 10.6 Hz, 1H), 3.34 (s, 3H).

Preparation of (3): To a solution of 2 in DMF (90 mL) were added imidazole (4.25 g, 62.48 mmol) and TBSCl (6.96 g, 46.18 mmol) in one portion at 15° C. The mixture was stirred at 15° C. for 6 h. The reaction mixture was quenched by addition of H₂O (300 mL) and extracted with EtOAc (300 mL*2). The combined organic layers were washed with brine (300 mL), dried over Na₂SO₄, filtered and concentrated under reduced pressure to give 3 (13.10 g, crude) as a white solid. ESI-LCMS: m/z 483.0 [M+H]$^+$.

Preparation of (4): To a solution of 3 (10 g, 20.73 mmol) in MeOH (20 mL), H₂O (80 mL), and dioxane (20 mL) was added Na₂SO₃ (15.68 g, 124.38 mmol), and the mixture was stirred at 80° C. for 24 h. The reaction mixture was concentrated under reduced pressure to remove MeOH. The aqueous layer was extracted with EtOAc (80 mL*2) and concentrated under reduced pressure to give a residue. The residue was triturated with MeOH (100*3 mL) to give 4 (9.5 g, 94.48% yield, 90% purity) as a white solid. ESI-LCMS: m/z 437.0 [M+H]$^+$.

Preparation of (5): To a solution of 4 (11 g, 21.42 mmol, 85% purity) in DCM (120 mL) was added DMF (469.65 mg, 6.43 mmol, 494.37 uL) at 0° C., followed by dropwise addition of oxalyl dichloride (13.59 g, 107.10 mmol, 9.37 mL). The mixture was stirred at 20° C. for 2 h. The reaction mixture was quenched by addition of water (60 mL) and the organic layer 5 (0.1125 M, 240 mL DCM) was used directly for next step. (This reaction was set up for two batches and combined) ESI-LCMS: m/z 455.0 [M+H]$^+$.

Preparation of (6): 5 (186.4 mL, 0.1125 M in DCM) was diluted with DCM (60 mL) and treated with methylamine (3.26 g, 41.93 mmol, 40% purity). The mixture was stirred at 20° C. for 2 h. The reaction mixture was concentrated under reduced pressure to give a residue. The residue was purified by flash silica gel chromatography (ISCO®; 40 g SepaFlash® Silica Flash Column, Eluent of 0~10%, MeOH/DCM gradient @ 40 mL/min) to give AGS-9-3-008 (1.82 g, 18.53% yield, 96% purity) as a yellow solid. ESI-LCMS: m/z 472.0 [M+Na]$^+$; $^1$H NMR (400 MHz, CDCl₃) δ=9.08 (s, 1H), 7.31 (d, J=8.1 Hz, 1H), 5.78 (d, J=8.1 Hz, 1H), 5.57 (d, J=3.8 Hz, 1H), 4.61-4.48 (m, 1H), 4.41-4.27 (m, 2H), 4.13-4.03 (m, 1H), 3.46 (s, 3H), 3.43-3.33 (m, 2H), 2.78 (d, J=5.2 Hz, 3H), 0.92 (s, 9H), 0.13 (s, 6H).

Preparation of (7): To a solution of 6 (2.3 g, 5.12 mmol) in MeOH (12 mL) was added HCl/MeOH (4 M, 6.39 mL). The mixture was stirred at 20° C. for 2 h. The reaction mixture was concentrated under reduced pressure to give a residue. The residue was purified by flash silica gel chromatography (ISCO®; 24 g SepaFlash® Silica Flash Column, Eluent of 0~15%, MeOH/DCM gradient @ 30 mL/min) to give 7 (1.4 g, 79.98% yield) as a pink solid. ESI-LCMS: m/z 336.1 [M+H]$^+$; $^1$H NMR (400 MHz, CDCl₃) δ=9.12 (s, 1H), 7.39 (d, J=8.0 Hz, 1H), 5.79 (d, J=3.3 Hz, 1H), 5.66 (dd, J=2.1, 8.2 Hz, 1H), 5.13 (s, 1H), 4.13 (t, J=4.0, 7.4 Hz, 1H), 4.07-4.02 (m, 1H), 3.87 (dd, J=3.3, 5.5 Hz, 1H), 3.47 (s, 3H), 3.43-3.37 (m, 2H), 2.65 (d, J=4.5 Hz, 3H).

Preparation of (Example 51 monomer): To a mixture of 7 (1.7 g, 5.07 mmol) and 4Å MS (1.4 g) in MeCN (18 mL) was added 3-bis(diisopropylamino)phosphanyloxypropanenitrile (1.99 g, 6.59 mmol, 2.09 mL) at 0° C., followed by addition of 1H-imidazole-4,5-dicarbonitrile (658.57 mg, 5.58 mmol) in one portion at 0° C. The mixture was stirred at 20° C. for 2 h. Upon completion, the reaction mixture was quenched by addition of sat. NaHCO₃ solution (20 mL) and diluted with DCM (40 mL). The organic layer was washed with sat. NaHCO₃ (20 mL*2), dried over Na₂SO₄, filtered and concentrated under reduced pressure to give a residue. The residue was purified by a flash silica gel column (0% to 5% i-PrOH in DCM with 5% TEA) to give Example 51 monomer (1.30 g, 46.68% yield) as a white solid. ESI-LCMS: m/z 536.2 [M+H]$^+$; $^1$H NMR (400 MHz, CD₃CN) δ=9.00 (s, 1H), 7.40 (d, J=8.0 Hz, 1H), 5.85-5.76 (m, 1H), 5.64 (d, J=8.0 Hz, 1H), 5.08 (d, J=5.0 Hz, 1H), 4.42-4.21 (m, 2H), 4.00 (td, J=4.6, 9.3 Hz, 1H), 3.89-3.61 (m, 4H), 3.47-3.40 (m, 4H), 3.37-3.22 (m, 1H), 2.71-2.60 (m, 5H), 1.21-1.16 (m, 11H), 1.21-1.16 (m, 1H); $^{31}$P NMR (162 MHz, CD₃CN) δ=150.07, 149.97

Example 52: Synthesis of 5' End Cap Monomer

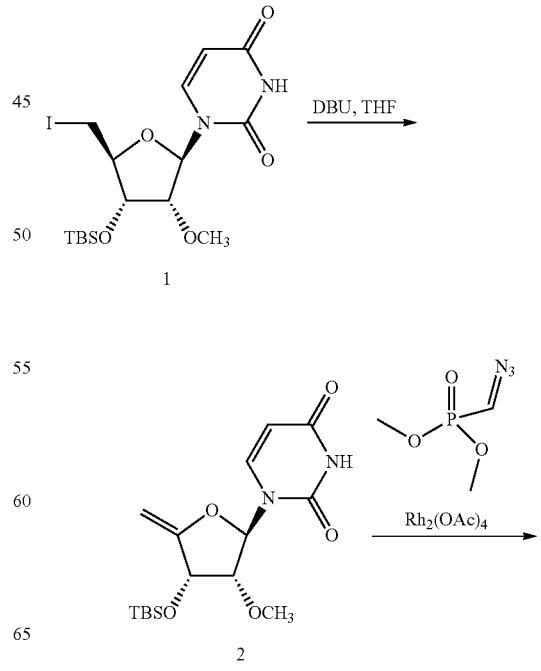

Example 52 Monomer Synthesis Scheme

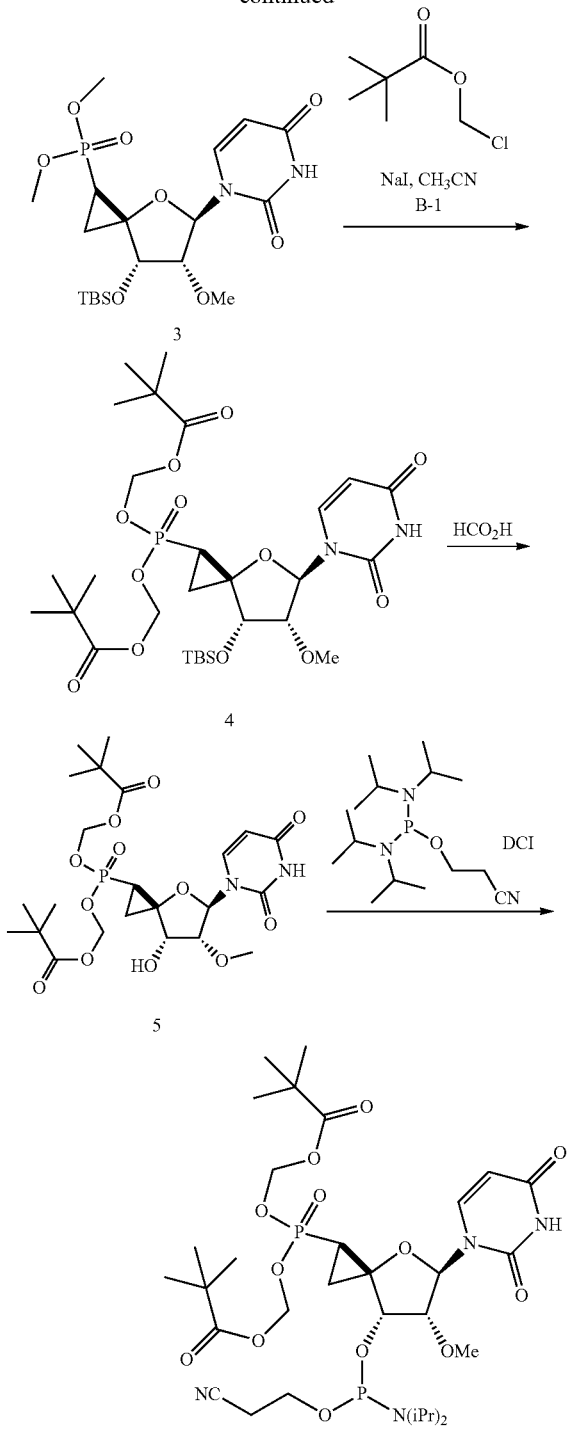

A: petroleum ethergradient@ 45 mL/min) to give 2 (5.9 g, 60.1% yield) as a white solid. ESI-LCMS: m/z 355.1 [M+H]$^+$; $^1$H NMR (400 MHz, DMSO-d$_6$) δ=11.61-11.30 (m, 1H), 7.76-7.51 (m, 1H), 6.04 (d, J=5.4 Hz, 1H), 5.75 (s, 1H), 5.73-5.67 (m, 1H), 4.78 (d, J=4.9 Hz, 1H), 4.41 (d, J=1.1 Hz, 1H), 4.30 (t, J=4.8 Hz, 1H), 4.22 (d, J=1.4 Hz, 1H), 4.13 (t, J=5.1 Hz, 1H), 4.06-3.97 (m, 1H), 3.94-3.89 (m, 1H), 3.82-3.75 (m, 1H), 3.33 (s, 3H), 3.30 (s, 2H), 1.17 (t, J=7.2 Hz, 1H), 0.89 (s, 9H), 0.16-0.09 (m, 6H).

Preparation of (3): To a solution of 2 (4 g, 11.28 mmol) in DCM (40 mL) was added Ru(II)-Pheox (214.12 mg, 338.53 umol) in one portion followed by addition of diazo (dimethoxyphosphoryl)methane (2.54 g, 16.93 mmol) dropwise at 0° C. under N$_2$. The reaction was stirred at 20° C. for 16 h. Upon completion, the reaction mixture was filtered and concentrated under reduced pressure to give a residue. The residue was purified by flash silica gel chromatography (ISCO®; 80 g SepaFlash® Silica Flash Column, Eluent of 0~4% MeOH/DCM@ 60 mL/min) to give 3 (5 g, 86.47% yield) as a red liquid. ESI-LCMS: m/z 477.1 [M+H]$^+$; $^1$H NMR (400 MHz, DMSO-d$_6$) δ=11.46 (s, 1H), 7.49 (d, J=8.0 Hz, 1H), 6.01-5.87 (m, 1H), 5.75 (dd, J=2.0, 8.0 Hz, 1H), 4.58 (d, J=3.8 Hz, 1H), 4.23 (dd, J=3.8, 7.8 Hz, 1H), 3.80-3.68 (m, 6H), 3.30 (s, 3H), 1.65-1.46 (m, 2H), 1.28-1.16 (m, 1H), 0.91 (s, 9H), 0.10 (d, J=4.3 Hz, 6H); $^{31}$P NMR (162 MHz, DMSO-d$_6$) δ=27.5

Preparation of (4): To a mixture of 3 (2.8 g, 5.88 mmol) and NaI (1.76 g, 11.75 mmol) in CH$_3$CN (30 mL) was added chloromethyl 2,2-dimethylpropanoate (2.21 g, 14.69 mmol, 2.13 mL) at 25° C. The mixture was stirred at 80° C. for 40 h under Ar. The reaction mixture was filtered and concentrated under reduced pressure to give a residue. The residue was purified by flash silica gel chromatography (ISCO®; 40 g SepaFlash® Silica Flash Column, Eluent of 0~50% Ethylacetate/Petroleum ether gradient @ 40 mL/min) to give 4 (2.1 g, 51.23% yield, 97% purity) as a yellow solid. ESI-LCMS: 677.3 [M+H]$^+$.

Preparation of (5): A mixture of 4 (2.09 g, 3.09 mmol) in H$_2$O (1.5 mL) and HCOOH (741.81 mg, 15.44 mmol, 6 mL) was stirred at 15° C. for 40 h. Upon completion, the reaction mixture was quenched by saturated aq.NaHCO$_3$ (300 mL) and extracted with EA (300 mL*2). The combined organic layers were washed with brine (300 mL), dried over Na$_2$SO$_4$, filtered and concentrated under reduced pressure to give a residue. The residue was purified by flash silica gel chromatography (ISCO®; 20 g SepaFlash® Silica Flash Column, Eluent of 0~5% Methanol/Dichloromethane@ 45 mL/min) to give 5 (1.51 g, 85.19% yield) as a yellow solid. ESI-LCMS: 585.1 [M+Na]$^+$; $^1$H NMR (400 MHz, DMSO-d$_6$) δ=11.45 (d, J=1.8 Hz, 1H), 7.44 (d, J=8.2 Hz, 1H), 6.04 (d, J=7.5 Hz, 1H), 5.78-5.51 (m, 6H), 4.39 (t, J=4.4 Hz, 1H), 4.15 (dd, J=4.3, 7.4 Hz, 1H), 4.03 (q, J=7.1 Hz, 1H), 1.99 (s, 1H), 1.66 (dd, J=8.6, 10.8 Hz, 1H), 1.55-1.29 (m, 2H), 1.18 (d, J=2.0 Hz, 18H).

Preparation of (Example 52 monomer): To a solution of 5 (2.5 g, 4.44 mmol) in MeCN (30 mL) was added 3-bis (diisopropylamino)phosphanyloxypropanenitrile (1.74 g, 5.78 mmol, 1.84 mL) at 0° C., followed by 1H-imidazole-4,5-dicarbonitrile (577.36 mg, 4.89 mmol) in one portion under Ar. The mixture was gradually warmed to 20° C. and stirred at 20° C. for 1 h. The reaction mixture was quenched by addition of sat.NaHCO$_3$ solution (50 mL) and diluted with DCM (250 mL). The organic layer was washed with sat.NaHCO$_3$ solution (50 mL*2), dried over Na$_2$SO$_4$, filtered and concentrated under reduced pressure to give a residue. The residue was purified by a flash silica gel column (0% to 50% EA/PE with 0.5% TEA) to give Example 52

Preparation of (2): To a solution of 1 (13.10 g, 27.16 mmol) in THF (100 mL) was added DBU (20.67 g, 135.78 mmol, 20.47 mL). The mixture was stirred at 60° C. for 6 h. Upon completion, the reaction mixture was quenched by addition of sat.NH$_4$Cl solution (600 mL) and extracted with EA (600 mL*2). The combined organic layers were washed with brine (100 ml), dried over Na$_2$SO$_4$, filtered and concentrated under reduced pressure to give a residue. The residue was purified by flash silica gel chromatography (ISCO®; 120 g SepaFlash® Silica Flash Column, Eluent of 0~50% (Phase B: ethyl acetate:dichloromethane=1:1)/Phase monomer (1.85 g, 54.1% yield) as a white solid. ESI-LCMS: 785.2 [M+Na]$^+$; $^1$H NMR (400 MHz, CD$_3$CN) δ=9.18 (s, 1H), 7.31 (d, J=8.3 Hz, 1H), 6.06 (d, J=7.8 Hz, 1H), 5.72-5.60 (m, 5H), 4.85-4.76 (m, 1H), 4.27 (m, 1H), 3.93-3.64 (m, 4H), 3.41 (d, J=16.6 Hz, 3H), 2.80-2.62 (m, 2H), 1.76-1.49 (m, 3H), 1.23-1.19 (m, 30H); $^{31}$P NMR (162 MHz, CD$_3$CN) δ=150.66 (s), 150.30, 24.77, 24.66.

Example 53: Synthesis of 5' End Cap Monomer

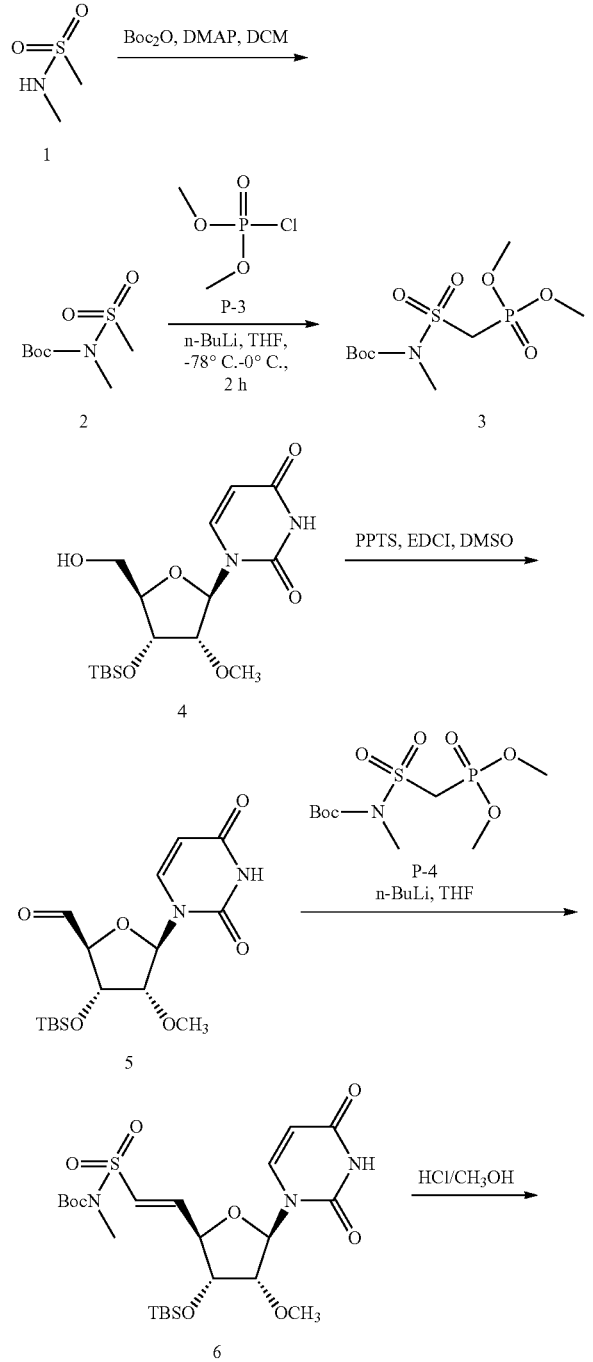

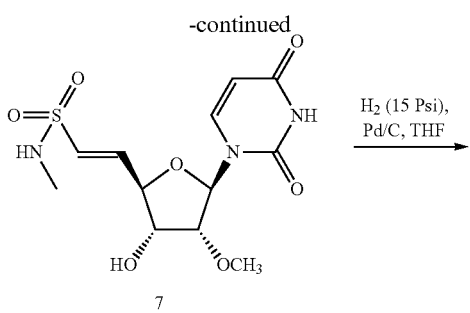

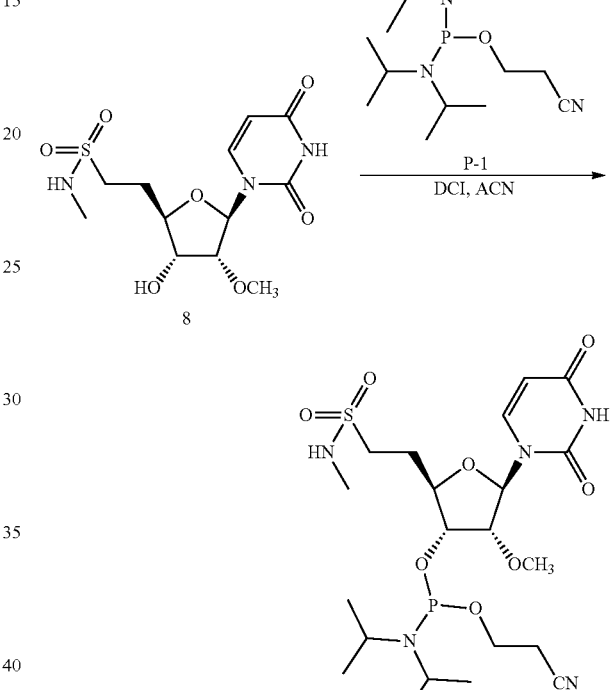

Example 53 Monomer

Preparation of (2): To a solution oft (15 g, 137.43 mmol) in DCM (75 mL) were added BOC$_2$O (31.49 g, 144.30 mmol, 33.15 mL) and DMAP (839.47 mg, 6.87 mmol, 0.05 eq) at 0° C. The mixture was stirred at 20° C. for 16 hr, and concentrated under reduced pressure to give 2 (29.9 g, crude) as a yellow oil. $^1$H NMR (400 MHz, CDCl$_3$) δ=3.23 (s, 3H), 3.16 (s, 3H), 1.51 (s, 9H).

Preparation of (3): To a solution of 2 (24.9 g, 118.99 mmol) in THF (250 mL) was added n-BuLi (2.5 M, 47.60 mL) dropwise at −78° C. under Ar and stirred at −78° C. for 1 hr. P-3 (17.19 g, 118.99 mmol, 12.83 mL) was added at 0° C. and stirred for 1 hr. The reaction mixture was quenched by saturated aq. NH$_4$Cl (100 mL), and then extracted with EA (100 mL*2). The combined organic layers were washed with brine (100 mL*2), dried over Na$_2$SO$_4$, filtered and concentrated under reduced pressure to give a residue. The residue was purified by flash silica gel chromatography (ISCO®; 80 g SepaFlash® Silica Flash Column, Eluent of 0~50 Ethyl acetate/Petroleum ethergradient @ 65 mL/min) to give 3 (7.1 g, 18.62% yield) as a yellow oil. ESI-LCMS: 339.9 [M+Na]$^+$; $^1$H NMR (400 MHz, CDCl$_3$) δ=4.12 (s, 1H), 4.08 (s, 1H), 3.83 (s, 3H), 3.81 (s, 3H), 3.22 (s, 3H), 1.51 (s, 9H).

Preparation of (5): To a mixture of 4 (15 g, 40.27 mmol) and PPTS (10.12 g, 40.27 mmol) in DMSO (75 mL) was added EDCI (23.16 g, 120.81 mmol) at 20° C. The mixture was stirred at 20° C. for 4 hr. The reaction mixture was diluted with water (150 mL) and extracted with EA (150 mL*2). The combined organic layers were washed with brine (150 mL*2), dried over $Na_2SO_4$, filtered and concentrated under reduced pressure to give 5 (12 g, crude) as a white solid. ESI-LCMS: 371.2[M+H]$^+$; $^1$H NMR (400 MHz, CDCl$_3$) δ=9.77 (s, 1H), 7.62 (d, J=8.1 Hz, 1H), 5.83-5.76 (m, 2H), 4.53 (d, J=4.3 Hz, 1H), 4.43 (br t, J=4.4 Hz, 1H), 3.95 (br t, J=4.7 Hz, 1H), 3.47-3.35 (m, 5H), 0.92 (s, 9H), 0.13 (d, J=5.8 Hz, 6H).

Preparation of (6): To a solution of P4 (8.02 g, 25.27 mmol) in THF (40 mL) was added n-BuLi (2.5 M, 8.42 mL) dropwise under Ar at −78° C., and the mixture was stirred at −78° C. for 0.5 hr. A solution of 4 (7.8 g, 21.05 mmol) in THF (40 mL) was added dropwise. The mixture was allowed to warm to 0° C. and stirred for another 2 hr. The reaction mixture was quenched by saturated aq. NH$_4$Cl solution (80 mL) and extracted with EA (80 mL). The combined organic layers were washed with brine (80 mL*2), dried over Na$_2$SO$_4$, filtered and concentrated under reduced pressure to give a residue. The residue was purified by flash silica gel chromatography (ISCO®; 80 g SepaFlash® Silica Flash Column, Eluent of 0~38% ethylacetate/petroleum ether gradient @ 60 mL/min) to give 7 (7.7 g, 13.43 mmol, 63.8% yield) as a white solid. ESI-LCMS: 506.2 [M-tBu]$^+$; $^1$H NMR (400 MHz, CDCl$_3$) δ=8.97 (s, 1H), 7.25 (d, J=8.3 Hz, 1H), 6.95-6.88 (m, 1H), 6.87-6.81 (m, 1H), 5.83-5.77 (m, 2H), 4.58 (dd, J=4.4, 6.7 Hz, 1H), 4.05 (dd, J=5.0, 7.5 Hz, 1H), 3.82-3.77 (m, 1H), 3.53 (s, 3H), 3.20 (s, 3H), 1.50 (s, 9H), 0.91 (s, 9H), 0.11 (d, J=2.5 Hz, 6H).

Preparation of (7): To a solution of 6 (7.7 g, 13.71 mmol) in MeOH (10 mL) was added HCl/MeOH (4 M, 51.40 mL) at 20° C. The mixture was stirred at 20° C. for 16 hr. Upon completion, the reaction mixture was concentrated under reduced pressure to remove MeOH. The residue was purified by flash silica gel chromatography (ISCO®; 80 g SepaFlash® Silica Flash Column, Eluent of 0~4% MeOH/DCM @ 60 mL/min) to give 7 (4.1 g, 86.11% yield) as a white solid. ESI-LCMS: 369.9 [M+Na]$^+$; $^1$H NMR (400 MHz, DMSO-d$_6$) δ=11.44 (s, 1H), 7.66 (d, J=8.3 Hz, 1H), 7.11 (q, J=4.9 Hz, 1H), 6.69 (dd, J=6.0, 15.1 Hz, 1H), 6.56-6.47 (m, 1H), 5.82 (d, J=4.0 Hz, 1H), 5.67 (dd, J=2.0, 8.0 Hz, 1H), 5.56 (br s, 1H), 4.42 (t, J=6.1 Hz, 1H), 4.13 (t, J=5.8 Hz, 1H), 3.97 (t, J=4.8 Hz, 1H), 3.39 (s, 3H), 2.48 (d, J=5.3 Hz, 3H)

Preparation of (8): To a solution of 7 (2.5 g, 7.20 mmol) in THF (25 mL) was added Pd/C (2.5 g, 10% purity) under H$_2$ atmosphere, and the suspension was degassed and purged with H$_2$ for 3 times. The mixture was stirred under H$_2$ (15 Psi) at 20° C. for 1 hr. Upon completion, the reaction mixture was filtered and concentrated under reduced pressure to give a residue. The residue was purified by flash silica gel chromatography (ISCO®; 25 g SepaFlash® Silica Flash Column, Eluent of 0~5% Ethylacetate/Petroleum ethergradient @ 50 mL/min) to give 8 (2.2 g, 87.49% yield) as a white solid. ESI-LCMS: 372.1 [M+Na]$^+$; $^1$H NMR (400 MHz, DMSO-d$_6$) δ=11.40 (s, 1H), 7.62 (d, J=8.0 Hz, 1H), 6.93 (q, J=4.9 Hz, 1H), 5.76 (d, J=4.5 Hz, 1H), 5.66 (d, J=8.0 Hz, 1H), 5.26 (d, J=6.3 Hz, 1H), 3.97 (q, J=5.9 Hz, 1H), 3.91-3.79 (m, 2H), 3.36 (s, 3H), 3.14-3.00 (m, 2H), 2.56 (d, J=5.0 Hz, 3H), 2.07-1.87 (m, 2H).

Preparation of (Example 53 monomer): To a solution of 8 (2.2 g, 6.30 mmol, 1 eq) in CH$_3$CN (25 mL) was added P-1 (2.47 g, 8.19 mmol, 2.60 mL, 1.3 eq) at 0° C., and then 1H-imidazole-4,5-dicarbonitrile (818.07 mg, 6.93 mmol, 1.1 eq) was added in one portion at 0° C. under Ar. The mixture was stirred at 20° C. for 2 hr. Upon completion, the reaction mixture was quenched by saturated aq. NaHCO$_3$ (25 mL), and extracted with DCM (25 mL*2). The combined organic layers were washed with brine (25 mL*2), dried over Na$_2$SO$_4$, filtered and concentrated under reduced pressure to give a residue. The residue was purified by flash silica gel chromatography (ISCO®; 40 g SepaFlash® Silica Flash Column, Eluent of 40~85% ethylacetate/petroleum ether gradient @ 40 mL/min) to give Example 53 monomer (2.15 g, 61.32% yield) as a white solid. ESI-LCMS: 572.2 [M+Na]$^+$; $^1$H NMR (400 MHz, CD$_3$CN) δ=9.32 (br s, 1H), 7.39 (d, J=8.1 Hz, 1H), 5.82-5.75 (m, 1H), 5.66 (dd, J=0.7, 8.1 Hz, 1H), 5.14 (qd, J=4.9, 9.4 Hz, 1H), 4.24-4.02 (m, 2H), 3.99-3.93 (m, 1H), 3.90-3.60 (m, 4H), 3.43 (d, J=17.5 Hz, 3H), 3.18-3.08 (m, 2H), 2.74-2.61 (m, 5H), 2.19-2.11 (m, 1H), 2.09-1.98 (m, 1H), 1.19 (ddd, J=2.4, 4.0, 6.6 Hz, 12H). $^{31}$P NMR (162 MHz, CD$_3$CN) δ=149.77 (s), 149.63 (br s).

Example 54. Long-Term Efficacy of siNA in an AAV-HBV Mouse Model

Figure 13:
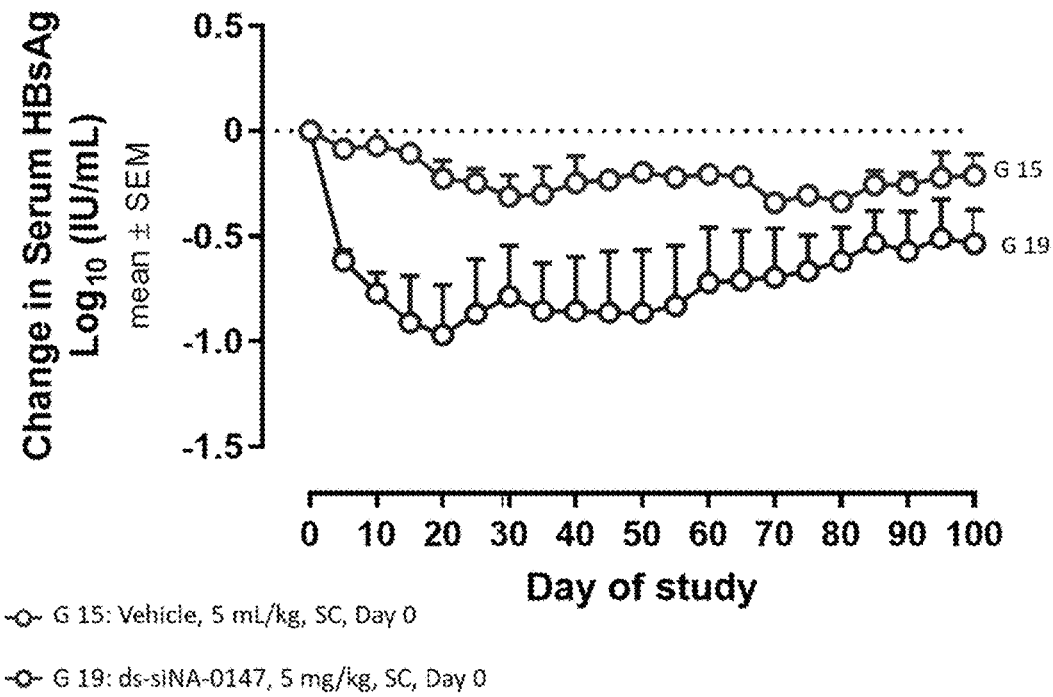
FIG. 13 shows a graph of the change in serum HBsAg from AAV-HBV mice treated with vehicle (G 15) or ds-siNA-0147 (G 19).

AAV/HBV is a recombinant AAV carrying replicable HBV genome. Taking advantage of the highly hepatotropic feature of genotype 8 AAV, the HBV genome can be efficiently delivered to the mouse liver cells. Infection of immune competent mouse with AAV/HBV can result in long term HBV viremia, which mimics chronic HBV infection in patients. The AAV/HBV model can be used to evaluate the in vivo activity of various types of anti-HBV agents. Mice were infected with AAV-HBV on day −28 of the study. AAV-HBV mice were subcutaneously injected with a single dose of 5 mL/kg of vehicle or 5 mg/kg of ds-siNA-0147 on day 0. Serial blood collections were usually taken every 5 days on day 0, 5, 10, and 15, etc. until the termination of the study. Serum HBV S antigen (HBsAg) was assayed through ELISA. FIG. 13 shows a graph of the change in serum HBsAg from AAV-HBV mice treated with vehicle (G 15) or ds-siNA-0147 (G 19). As shown in FIG. 13, ds-siNA-0147 was effective in reducing serum HBsAg levels and the reduction in serum HBsAg levels was observed for the duration of the study (i.e., 100 days). Thus, FIG. 13 demonstrates that ds-siNA-0147 is effective and durable after a single dose of 5 mg/kg.

| ds-siNA ID | Strand | Sequence | SEQ ID NO: |
|---|---|---|---|
| ds-siNA-0147 | Sense | 5'-mGpsmUpsmGmGfUmGfGfAfCm UmUmCmUmCmUmCmAmAmU-p-ps2- GalNAc4-3' | 438 |
|  | Antisense | 3'-mApsmGpsmCmAmCfCmAfCmCm UmGmAmAmGmAfGmAmGmUpsfUpsm A-5' | 501 |

Example 55. Deuterated Vinyl Phosphonate Improves Potency of siNA

This example investigates whether a deuterated vinyl phosphonate improves potency of siNA in an AAV-HBV mouse. AAV-HBV mice were subcutaneously injected with vehicle, ds-siNA-0109 (e.g., siNA without a deuterated vinyl phosphonate), or ds-siNA-0172 (e.g., siNA with a deuterated vinyl phosphonate). AAV-HBV mice were subcutaneously injected with a single dose of 5 mL/kg of vehicle or 5 mg/kg of ds-siNA-0149 or ds-siNA-0172 at day 0. Serial blood collections were usually taken every 5 days on day 0, 5, 10, and 15, etc. until the termination of the study. Serum HBV S antigen (HBsAg) was assayed through ELISA.

Figure 14:
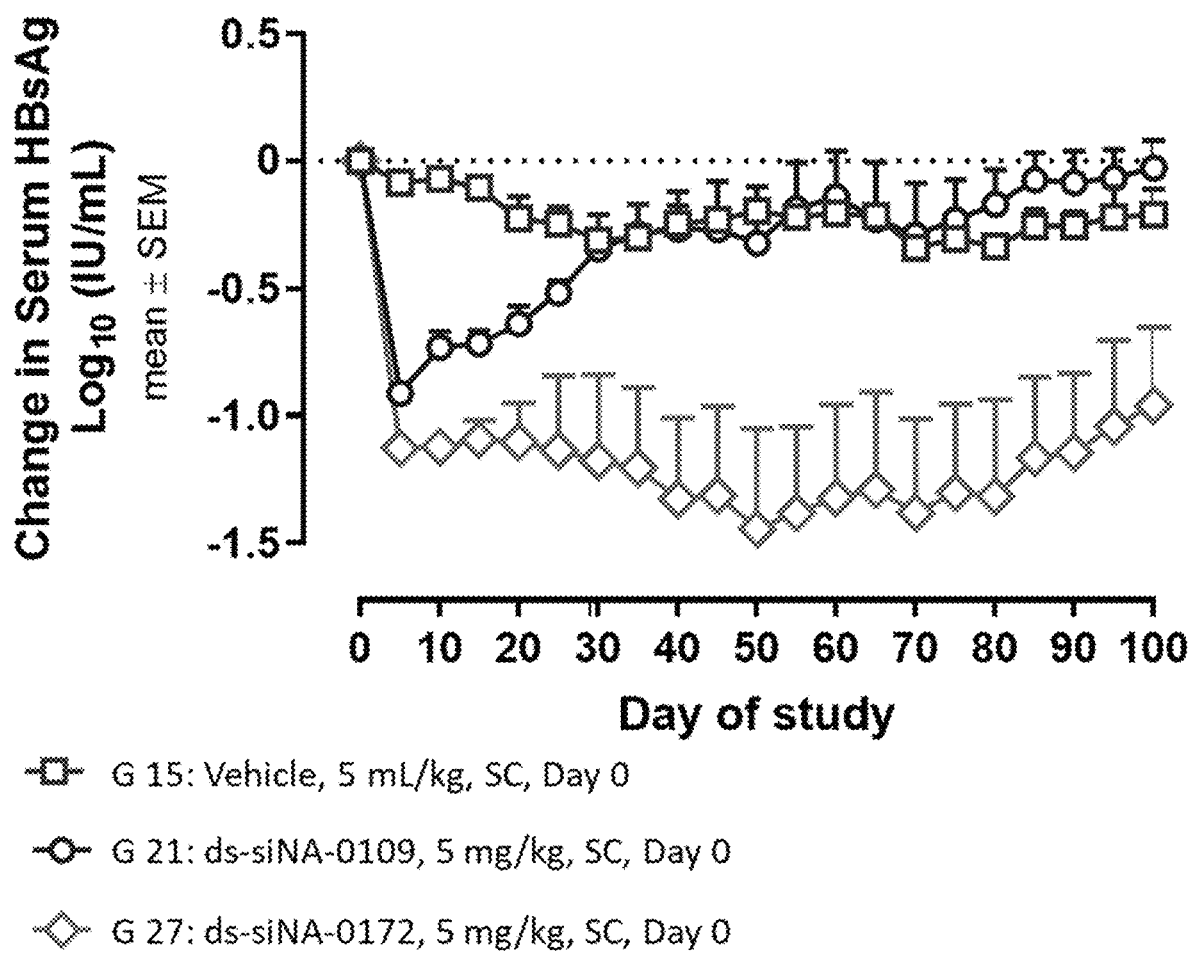
FIG. 14 shows a graph of the change in serum HBsAg from AAV-HBV mice treated with vehicle (G 15, square), ds-siNA-0109 (G 21, circle), or ds-siNA-0172 (G 27, diamond).

As shown in FIG. 14, siNA molecules having 2'-fluoro nucleotides at positions 5 and 7-9 from the 5' end of the sense strand and 2'-fluoro nucleotides at positions 2, 5, 8, 14, and 17 from the 5' end of the antisense strand resulted in greater than a 0.5-log reduction in HBsAg, with the greatest reduction in HBsAg found in mice treated with the deuterated vinylphosphonate siNA (ds-siNA-0172). In addition, the duration of the reduction in serum HBsAg levels was significantly longer for the deuterated vinylphosphonate siNA (ds-siNA-0172). Thus, FIG. 14 demonstrates that the presence of a deuterated vinyl phosphonate improves potency and durability of the siNA.

| ds-siNA ID | Strand | Sequence | SEQ ID NO: |
|---|---|---|---|
| ds-siNA-0109 | Sense | 5'-mCpsmCpsmGmUfGmUfGfCfAmCmUmUmCmGmCmUmUmCmAp-ps2-GalNAc4 | 424 |
| | Antisense | 3'-mCpsmUpsmGmGfCmAmCfAmCmGmUmGmAfAmGmCfGmAmApsfGpsmU-5' | 485 |
| ds-siNA-0119 | Sense | 5'-mGpsmCpsmUmGfCmUmAmUfGfCfCmUmCfAmUmCmUmUfCmUmU-p-ps2-GalNAc4 | 430 |
| | Antisense | 3'-mGpsmApsmCmGmAmCmGmAmUfAmCmGmGmAmGmUmAmGmAmAmGpsfApsmA-5' | 595 |

| ds-siNA ID | Strand | Sequence | SEQ ID NO: |
|---|---|---|---|
| ds-siNA-0109 | Sense | 5'-mCpsmCpsmGmUfGmUfGfCfAmCmUmUmCmGmCmUmUmCmAp-ps2-GalNAc4 | 424 |
| | Antisense | 3'-mCpsmUpsmGmGfCmAmCfAmCmGmUmGmAfAmGmCfGmAmApsfGpsmU-5' | 485 |
| ds-siNA-0172 | Sense | 5'-mCpsmCpsmGmUfGmUfGfCfAmCmUmUmCmGmCmUmUmCmA-p-ps2-GalNAc4-3' | 424 |
| | Antisense | 3'-mCpsmUpsmGmGfCmAmCfAmCmGmUmGmAfAmGmCfGmAmApsfGpsd2vd3U-5' | 536 | d2vd3U =

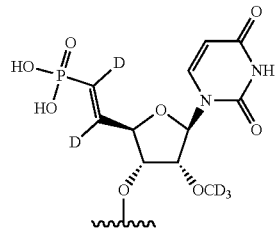

Example 56. Comparison of siNAs

Figure 15:
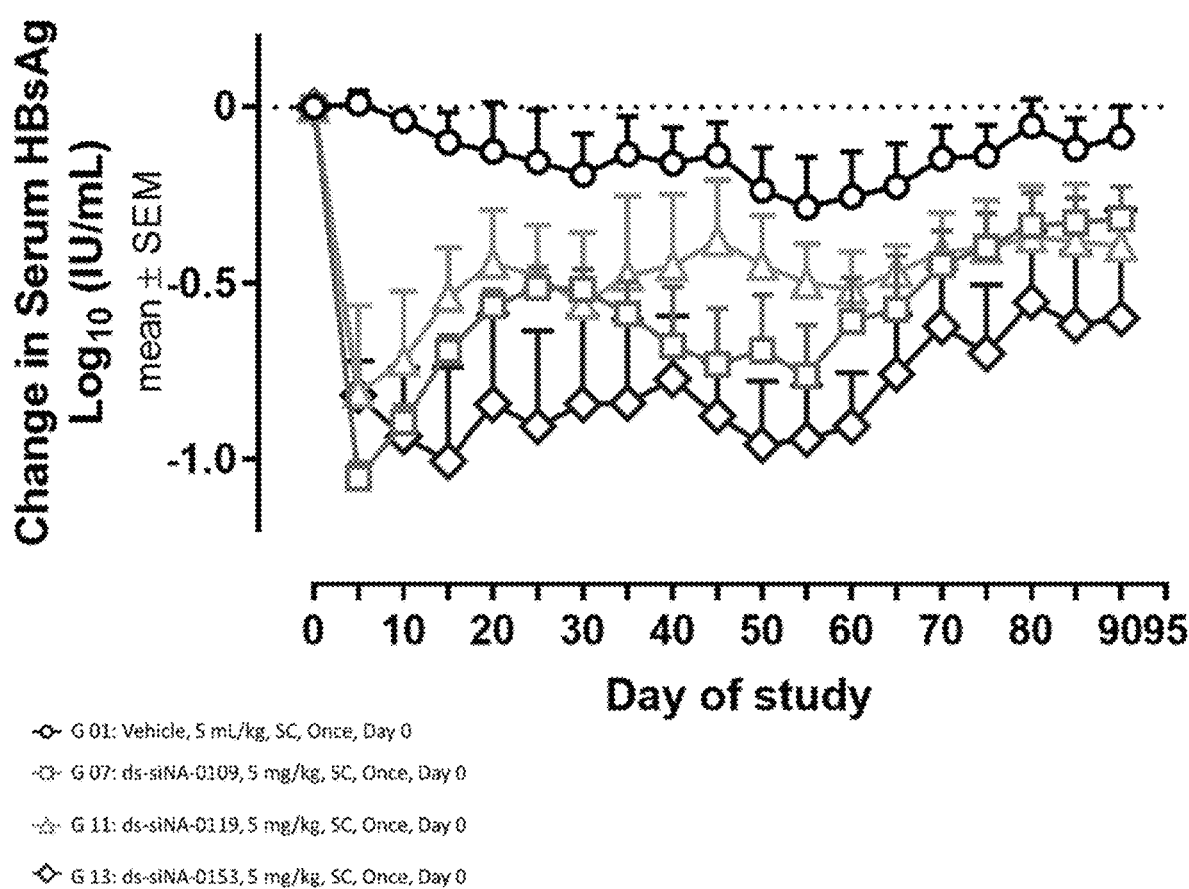
FIG. 15 shows a graph of the change in serum HBsAg from AAV-HBV mice treated with vehicle (G 01, circle), ds-siNA-0109 (G 07, square), ds-siNA-0119 (G 11, triangle), or ds-siNA-0153 (G 13, diamond).

AAV/HBV is a recombinant AAV carrying replicable HBV genome. Taking advantage of the highly hepatotropic feature of genotype 8 AAV, the HBV genome can be efficiently delivered to the mouse liver cells. Infection of immune competent mouse with AAV/HBV can result in long term HBV viremia, which mimics chronic HBV infection in patients. The AAV/HBV model can be used to evaluate the in vivo activity of various types of anti-HBV agents. Mice were infected with AAV-HBV on day −28 of the study. AAV-HBV mice were subcutaneously injected with a single dose of 5 mL/kg of vehicle or 5 mg/kg of ds-siNA-0109, ds-siNA-0119, or ds-siNA-0153 on day 0. Serial blood collections were usually taken every 5 days on day 0, 5, 10, and 15, etc. until the termination of the study. Serum HBV S antigen (HBsAg) was assayed through ELISA. FIG. 15 shows a graph of the change in serum HBsAg from AAV-HBV mice treated with vehicle (G 01, circle), ds-siNA-0109 (G 07, square), ds-siNA-0119 (G11, triangle), or ds-siNA-0153 (G13, diamond). As shown in FIG. 14, all three ds-siNAs were effective in reducing serum HBsAg levels and the reduction in serum HBsAg levels was observed for the duration of the study (i.e., 100 days), with the best potency and durability observed for ds-siNA-0153. Thus, FIG. 15 demonstrates that ds-siNA-0109, ds-siNA-0119, and ds-siNA-0153 were effective and durable after a single dose of 5 mg/kg.

-continued

| ds-siNA ID | Strand | Sequence | SEQ ID NO: |
|---|---|---|---|
| ds-siNA-0153 | Sense | 5'-mUpsmGpsfUmGmCmAfCfUfUmCmGfCmUmUmCmAfCmCmU-p-ps2-GalNAc4-3' | 441 |
| | Antisense | 3'-mGpsmCpsmAfCmAmCmGfUmGmAmAfGmCmGmAfAmGmUmGpsfGpsmA-5 | 526 |

Example 57. Efficacy of a Combination Therapy in AAV-HBV Mouse Model

This example investigates the efficacy of a combination therapy comprising an antisense oligonucleotide (ASO 1, 5' GalNAc4-ps-GalNAc4-ps-GalNAc4-po-mA-po-lnGpslnApslnTpslnApslnApsApsAps(5OH)CpsGps(5m)Cps(5m)CpsGps(5m)CpslnApslnG pslnApscp(5m)C-3' (SEQ ID NO: 534)) and a ds-siNA-0147 for treating HBV in an AAV-HBV mouse model.

AAV-HBV mice were subcutaneously injected with (a) 5 mL/kg of vehicle, three times a week, on days 0, 7, and 14 (G 01); (b) 5 mg/kg of ASO 1 on a weekly basis, on days 0, 7, and 14 (G 20); (c) a single dose of 5 mg/kg of ds-siNA-0147 on day 0 (G 24); or (d) a combination of ASO 1 and ds-siNA-0147, wherein ASO 1 was administered at a dose of 5 mg/kg on a weekly basis, on days 0, 7, and 14; and ds-siNA-0160 was administered as a single dose of 5 mg/kg at day 0 (G25). Serial blood collections were usually taken every 5 days on day 0, 5, 10, and 15, etc. until the termination of the study. Serum HBV S antigen (HBsAg) was assayed through ELISA. FIG. 16 shows a graph of the change in serum HBsAg from AAV-HBV mice treated with vehicle (G 01, circle), ASO 1 (G 20, square), ds-siNA-0147 (G 24, diamond), or a combination of ds-siNA-0147 and ASO 1 (G 25, triangle). As shown in FIG. 16, treatment with ASO 1, ds-siNA-0147, or a combination of ASO 1 and ds-siNA-0147 resulted in a reduction in serum, with the greatest reduction observed in mice treated with the combination of ASO 1 and ds-siNA-0147.

| ds-siNA ID | Strand | Sequence | SEQ ID NO: |
|---|---|---|---|
| ds-siNA-0147 | Sense | 5'-mGpsmUpsmGmGfUmGfGfAf CmUmUmCmUmCmUmCmAmAmU-p-ps2-GalNAc4-3' | 438 |
| | Antisense | 3'-mApsmGpsmCmAmCfCmAfCm CmUmGmAmAmGmAfGmAmGmUpsf UpsmA-5' | 501 |

Example 58. Efficacy of a Combination Therapy in AAV-HBV Mouse Model

This example investigates the efficacy of a combination therapy comprising an antisense oligonucleotide (ASO 1, 5' GalNAc4-ps-GalNAc4-ps-GalNAc4-po-mA-po-lnGpslnApslnTpslnApslnApsApsAps(5OH)CpsGps(5m) Cps(5m)CpsGps(5m)CpslnApslnG pslnApscp(5m)C-3' (SEQ ID NO: 534)) and a ds-siNA-0109 for treating HBV in an AAV-HBV mouse model.

AAV-HBV mice were subcutaneously injected with (a) 5 mL/kg of vehicle, three times a week, on days 0, 7, and 14 (G 01); (b) 5 mg/kg of ASO 1 on a weekly basis, on days 0, 7, and 14 (G 20); (c) a single dose of 5 mg/kg of ds-siNA-0109 on day 0 (G 26); or (d) a combination of ASO 1 and ds-siNA-0109, wherein ASO 1 was administered at a dose of 5 mg/kg on a weekly basis, on days 0, 7, and 14; and ds-siNA-0160 was administered as a single dose of 5 mg/kg at day 0 (G27). Serial blood collections were usually taken every 5 days on day 0, 5, 10, and 15, etc. until the termination of the study. Serum HBV S antigen (HBsAg) was assayed through ELISA. FIG. 17 shows a graph of the change in serum HBsAg from AAV-HBV mice treated with vehicle (G 01, circle), ASO 1 (G 20, square), ds-siNA-0109 (G 26, diamond), or a combination of ds-siNA-0109 and ASO 1 (G 27, triangle). As shown in FIG. 17, treatment with ASO 1, ds-siNA-0109, or a combination of ASO 1 and ds-siNA-0109 resulted in a reduction in serum, with the greatest reduction observed in mice treated with the combination of ASO 1 and ds-siNA-0109.

| ds-siNA ID | Strand | Sequence | SEQ ID NO: |
|---|---|---|---|
| ds-siNA-0109 | Sense | 5'-mCpsmCpsmGmUfGmUfGfCf AmCmUmUmCmGmCmUmUmCmAp-ps2-GalNAc4 | 424 |
| | Antisense | 3'-mCpsmUpsmGmGfCmAmCfAm CmGmUmGmAfAmGmCfGmAmApsf GpsmU-5' | 485 |

Example 59. Role of 2'-Fluoro Mimics on siNA Activity

This example investigates the role of 2'-fluoro mimics, f4P and f2P monomers, on siNA activity. The f4P monomer was produced as described in Example 42. The f2P monomer was produced as described in Example 45.

The activity of ds-siNA-0173, ds-siNA-0174, and ds-siNA-0175 was assayed using an in vitro HBsAg secretion assay with HepG2.2.15 cells. Generally, HepG2.2.15 cells were maintained in DMEM medium with 10% fetal bovine serum (FBS) and 1% penicillin/streptomycin, 1% Glutamine, 1% non-essential amino acids, 1% Sodium Pyruvate and 250 ug/ml G418. Cells were maintained at 37° C. in a 5% $CO^2$ atmosphere. For HBsAg release assay, an assay medium was made that DMEM with 5% FBS, 1% penicillin/streptomycin, 1% Glutamine and 1% DMSO. The day before the assay, HepG2.2.15 cells were trypsinized and washed with Assay Medium once, then spun at 250 g×5 min, resuspended with Assay Medium. The resuspended cells were seeded at 50,000/well in assay medium in collagen coated 96 well plates. On the next day, siRNA was diluted with Opti-MEM, 9-pt, 3-fold dilution and dilute Lipofectamine RNAiMAX (Invitrogen) according manufacturer's manual. siRNA dilution and RNAiMAX dilution were mixed and incubated at room temperature for 5 minutes. 15 µl of the siRNA/RNAiMax mixture was added each well of the collagen coated 96 well plate. The plates were placed in a 37° C., 5% $CO^2$ incubator for 4 days. After incubation, the supernatant was harvested and measured for HBsAg with ELISA kit (Diasino). The cell viability was measured with CellTiter-Glo (Promega). The EC50, the concentration of the drug required for reducing HBsAg secretion by 50% in relation to the untreated cell control, was calculated using the Prism Graphpad. The CC50, the concentration of the drug required for reducing cell viability by 50% in relation to the untreated cell control, was calculated with the same software. The EC50 and CC50 values are shown in Table 11.

TABLE 11

| | | siNA Activity | | | |
|---|---|---|---|---|---|
| ds-siNA ID | Strand | Sequence | SEQ ID NO: | EC50 (nM)* | CC50 (nM) |
| ds-siNA-0173 | Sense | 5'-mGpsmUpsmGmGfUmGfGfAfC mUmUmCmUmCmUmCmAmAmU | 438 | C | >1 |
| | Antisense | 3'-mApsmGpsmCmAmCfCmA fCmCmUmGmAmAmGmAfGmAmG mUpsf4PpsmA-5' | 537 | | |

TABLE 11-continued

| ds-siNA ID | Strand | Sequence | SEQ ID NO: | EC50 (nM)* | CC50 (nM) |
|---|---|---|---|---|---|
| ds-siNA-0174 | Sense | 5'-mGpsmUpsmGmGfUmGfGfAfCmUmUmCmUmCmUmCmAmAmU | 438 | A | >1 |
| | Antisense | 3'-mApsmGpsmCmAmCfCmAf2PmCmUmGmAmAmGmAfGmAmGmUpsfUpsmA-5' | 538 | | |
| ds-siNA-0175 (control) | Sense | 5'-mGpsmUpsmGmGfUmGfGfAfCmUmUmCmUmCmUmCmAmAmU | 438 | B | >1 |
| | Antisense | 5'-mApsfUpsmUmGmAfGmAmGmAmAmGmUmCfCmAfCmCmAmCpsmGpsmA-3' | 501 | | |

*A = EC50 < 0.2 nM; B = 0.2 nM < EC50 < 0.1 nm; C = EC50 > 0.1 nm f4P =

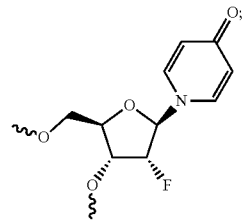

f2P =

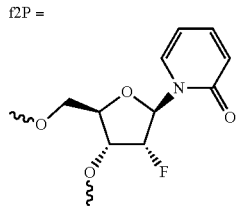

Example 60. Role of 2'-Fluoro Mimics on siNA Activity

This example investigates the role of 2'-fluoro mimics, f4P, f2P, and fx monomers, on siNA activity of GalNAc4 conjugated siNAs. The f4P monomer was produced as described in Example 42. The f2P monomer was produced as described in Example 45. The fx monomer was produced as described in Example 41.

| ds-siNA ID | Strand | Sequence | SEQ ID NO: |
|---|---|---|---|
| ds-siNA-0176 | Sense | 5'-mGpsmUpsmGmGfUmGfGfAfCmUmUmCmUmCmUmCmUmCmAmAmU-p-(PS)2-GalNAc4 | 438 |
| | Antisense | 3'-mApsmGpsmCmAmCfCmAfCmCmUmGmAmAmGmAfGmAmGmUpsf4PpsmA-5' | 537 |
| ds-siNA-0177 | Sense | 5'-mGpsmUpsmGmGfUmGfGfAfCmUmUmCmUmCmUmCmUmCmAmAmU-p-(PS)2-GalNAc4 | 438 |
| | Antisense | 3'-mApsmGpsmCmAmCfCmAf2PmCmUmGmAmAmGmAfGmAmGmUpsfUpsmA-5' | 538 |
| ds-siNA-0178 | Sense | 5'-mGpsmUpsmGmGfUmGfGfAfCmUmUmCmUmCmUmCmUmCmAmAmU-p-(PS)2-GalNAc4 | 438 |
| | Antisense | 3'-mApsmGpsmCmAmCfCmAfXmCmUmGmAmAmGmAfGmAmGmUpsfUpsmA-5' | 539 |
| ds-siNA-0147 | Sense | 5'-mGpsmUpsmGmGfUmGfGfAfCmUmUmCmUmCmUmCmUmCmAmAmU-p-ps2-GalNAc4 | 438 |
| | Antisense | 3'-mApsmGpsmCmAmCfCmAfCmCmUmGmAmAmGmAfGmAmGmUpsfUpsmA-5' | 501 | f4P =

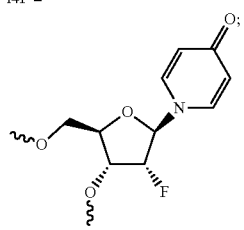

-continued

| ds-siNA ID | Strand | Sequence | SEQ ID NO: |
|---|---|---|---| f2P =

[chemical structure of 2'-fluoro pyridinone nucleoside]

fX =

[chemical structure of 2'-fluoro aminoquinazolinone nucleoside]

The activity of ds-siNA-017, ds-siNA-017, ds-siNA-017, and ds-siNA-0147 can be assayed using in vitro or in vivo methods. An exemplary in vitro assay can be performed as follows:

*Homo sapiens* HepG2.2.15 cells are cultured in Dulbecco's Modified Eagle's Medium (DMEM) (ATCC 30-2002) supplemented to also contain 10% fetal calf serum (FCS). Cells were incubated at 37° C. in an atmosphere with 5% CO2 in a humidified incubator. For transfection of HepG2.2.15 cells with HBV targeting siRNAs, cells are seeded at a density of 15000 cells/well in 96-well regular tissue culture plates. Transfection of cells is carried out using RNAiMAX (Invitrogen/Life Technologies) according to the manufacturer's instructions. Dose-response experiments are done with oligo concentrations of 40, 20, 10, 5, 2.5, 1.25, 0.625, 0.3125, 0.15625 and 0.07813 nM. For each HBV targeting siRNA treatment (e.g., ds-siNA-0176, ds-siNA-0177, ds-siNA-0178, or ds-siNA-0147), four wells are transfected in parallel, and individual data points were collected from each well. After 24 h of incubation with siRNA, media is removed, and cells are lysed and analyzed with a QuantiGene2.0 branched DNA (bDNA) probe set specific for HBV genotype D (also called Hepatitis B virus subtype ayw, complete genome of 3182 base-pairs) as present in cell line HepG2.2.15.

For each well, the HBV on-target mRNA levels is normalized to the GAPDH mRNA level. The activity of the HBV targeting ds-siNAs can be expressed as EC50, 50% reduction of normalized HBV RNA level from no drug control. The cytotoxicity of the HBV targeting ds-siRNAs can be expressed by CC50 of 50% reduction of GAPDH mRNA from no drug control.

The AAV/HBV model can be used to evaluate the in vivo activity of the siRNA treatment (e.g., ds-siNA-0173, ds-siNA-0174, ds-siNA-0175, and ds-siNA-0147). Mice are infected with AAV-HBV on day −28 of the study. AAV-HBV mice are subcutaneously injected with a single dose of 5 mL/kg of vehicle or 5 mg/kg of ds-siNA-0173, ds-siNA-0174, ds-siNA-0175, or ds-siNA-0147 on day 0. Serial blood collections can be taken every 5 days on day 0, 5, 10, and 15, etc. until the termination of the study. Serum HBV S antigen (HBsAg) can be assayed through ELISA.

EXEMPLARY EMBODIMENTS

Exemplary Embodiments are Provided Below:

1. A short interfering nucleic acid (siNA) molecule comprising:
   (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence:
      (i) is 15 to 30 nucleotides in length; and
      (ii) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 3, 5, 7, 8, 9, 10, 11, 12, 14, 17, and/or 19 from the 5' end of the first nucleotide sequence is a 2'-fluoro nucleotide; and
   (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence:
      (i) is 15 to 30 nucleotides in length; and
      (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide.

2. A short interfering nucleic acid (siNA) molecule comprising:
   (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence:
      (i) is 15 to 30 nucleotides in length; and
      (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence:
  (i) is 15 to 30 nucleotides in length; and
  (ii) comprises 15 or more modified nucleotides independently selected from a 2'-O-methyl nucleotide and a 2'-fluoro nucleotide, wherein at least one modified nucleotide is a 2'-O-methyl nucleotide and the nucleotide at position 2, 5, 6, 8, 10, 14, 16, 17, and/or 18 from the 5' end of the second nucleotide sequence is a 2'-fluoro nucleotide.

3. The siNA of embodiment 1 or 2, wherein the first nucleotide sequence comprises 16, 17, 18, 19, 20, 21, 22, 23, or more modified nucleotides independently selected from a 2'-O-methyl nucleotide and a 2'-fluoro nucleotide.

4. The siNA of embodiment 1 or 2, wherein 70%, 75%, 80%, 85%, 90%, 95% or 100% of the nucleotides in the first nucleotide sequence are modified nucleotides independently selected from a 2'-O-methyl nucleotide and a 2'-fluoro nucleotide.

5. The siNA of any one of embodiments 1-4, wherein at least 2, 3, 4, 5, or 6 modified nucleotides of the first nucleotide sequence are 2'-fluoro nucleotides.

6. The siNA of any one of embodiments 1-5, wherein no more than 10, 9, 8, 7, 6, 5, 4, 3, or 2 modified nucleotides of the first nucleotide sequence are 2'-fluoro nucleotides.

7. The siNA of any one of embodiments 1-6, wherein at least 10, 11, 12, 13, 14, 15, 16, 17, 18, 19, 20, 21, or 22 modified nucleotides of the first nucleotide sequence are 2'-O-methyl nucleotides.

8. The siNA of any one of embodiments 1-7, wherein no more than 25, 24, 23, 22, 21, 20, 19, 18, 17, 16, 15, 14, 13, 12, 11, 10, 9, 8, 7, 6, 5, 4, 3, or 2 modified nucleotides of the first nucleotide sequence are 2'-O-methyl nucleotides.

9. The siRNA of any one of embodiments 1-8, wherein the second nucleotide sequence comprises 16, 17, 18, 19, 20, 21, 22, 23, or more modified nucleotides independently selected from a 2'-O-methyl nucleotide and a 2'-fluoro nucleotide.

10. The siNA of any one of embodiments 1-9, wherein 70%, 75%, 80%, 85%, 90%, 95% or 100% of the nucleotides in the second nucleotide sequence are modified nucleotides independently selected from a 2'-O-methyl nucleotide and a 2'-fluoro nucleotide.

11. The siNA of any one of embodiments 1-10, wherein at least 2, 3, 4, 5, or 6 modified nucleotides of the second nucleotide sequence are 2'-fluoro nucleotides.

12. The siNA of any one of embodiments 1-11, wherein less than or equal to 10, 9, 8, 7, 6, 5, 4, 3, or 2 modified nucleotides of the second nucleotide sequence are 2'-fluoro nucleotides.

13. The siNA of any one of embodiments 1-12, wherein at least 10, 11, 12, 13, 14, 15, 16, 17, 18, 19, 20, 21, or 22 modified nucleotides of the second nucleotide sequence are 2'-O-methyl nucleotides.

14. The siNA of any one of embodiments 1-12, wherein less than or equal to 25, 24, 23, 22, 21, 20, 19, 18, 17, 16, 15, 14, 13, 12, 11, 10, 9, 8, 7, 6, 5, 4, 3, or 2 modified nucleotides of the second nucleotide sequence are 2'-O-methyl nucleotides.

15. A short interfering nucleic acid (siNA) molecule comprising:
  (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence:
    (i) is 15 to 30 nucleotides in length;
    (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and
    (iii) comprises 1 or more phosphorothioate internucleoside linkage; and
  (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence:
    (i) is 15 to 30 nucleotides in length;
    (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and
    (iii) comprises 1 or more phosphorothioate internucleoside linkage.

16. A short interfering nucleic acid (siNA) molecule comprising:
  (a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence:
    (i) is 15 to 30 nucleotides in length; and
    (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide; and
  (b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence:
    (i) is 15 to 30 nucleotides in length; and
    (ii) comprises 15 or more modified nucleotides independently selected from a 2'-O-methyl nucleotide and a 2'-fluoro nucleotide, wherein at least one modified nucleotide is a 2'-O-methyl nucleotide and at least one modified nucleotide is a 2'-fluoro nucleotide,
  wherein the siNA further comprises a phosphorylation blocker, a galactosamine, or 5'-stabilized end cap.

17. The siNA according to any preceding embodiment, wherein at least 1, 2, 3, 4, 5, 6, or 7 nucleotides at position 3, 5, 7, 8, 9, 10, 11, 12, and/or 17 from the 5' end of the first nucleotide sequence is a 2'-fluoro nucleotide.

18. The siNA according to any preceding embodiment, wherein the nucleotide at position 3 from the 5' end of the first nucleotide sequence is a 2'-fluoro nucleotide.

19. The siNA according to any preceding embodiment, wherein the nucleotide at position 5 from the 5' end of the first nucleotide sequence is a 2'-fluoro nucleotide.

20. The siNA according to any preceding embodiment, wherein the nucleotide at position 7 from the 5' end of the first nucleotide sequence is a 2'-fluoro nucleotide.

21. The siNA according to any preceding embodiment, wherein the nucleotide at position 8 from the 5' end of the first nucleotide sequence is a 2'-fluoro nucleotide.

22. The siNA according to any preceding embodiment, wherein the nucleotide at position 9 from the 5' end of the first nucleotide sequence is a 2'-fluoro nucleotide.
23. The siNA according to any preceding embodiment, wherein the nucleotide at position 12 from the 5' end of the first nucleotide sequence is a 2'-fluoro nucleotide.
24. The siNA according to any preceding embodiment, wherein the nucleotide at position 17 from the 5' end of the first nucleotide sequence is a 2'-fluoro nucleotide.
25. The siNA according to any preceding embodiment, wherein the nucleotide at position 10 from the 5' end of the first nucleotide sequence is a 2'-fluoro nucleotide.
26. The siNA according to any preceding embodiment, wherein the nucleotide at position 11 from the 5' end of the first nucleotide sequence is a 2'-fluoro nucleotide.
27. The siNA according to any preceding embodiment, wherein at least 1, 2, 3, 4, 5, 6, 7, 8, or 9 nucleotides at position 2, 5, 6, 8, 10, 14, 16, 17, and/or 18 from the 5' end of the second nucleotide sequence is a 2'-fluoro nucleotide.
28. The siNA according to any preceding embodiment, wherein the nucleotide at position 2 from the 5' end of the second nucleotide sequence is a 2'-fluoro nucleotide.
29. The siNA according to any preceding embodiment, wherein the nucleotide at position 5 from the 5' end of the second nucleotide sequence is a 2'-fluoro nucleotide.
30. The siNA according to any preceding embodiment, wherein the nucleotide at position 6 from the 5' end of the second nucleotide sequence is a 2'-fluoro nucleotide.
31. The siNA according to any preceding embodiment, wherein the nucleotide at position 8 from the 5' end of the second nucleotide sequence is a 2'-fluoro nucleotide.
32. The siNA according to any preceding embodiment, wherein the nucleotide at position 10 from the 5' end of the second nucleotide sequence is a 2'-fluoro nucleotide.
33. The siNA according to any preceding embodiment, wherein the nucleotide at position 14 from the 5' end of the second nucleotide sequence is a 2'-fluoro nucleotide.
34. The siNA according to any preceding embodiment, wherein the nucleotides at position 16 from the 5' end of the second nucleotide sequence is a 2'-fluoro nucleotide.
35. The siNA according to any preceding embodiment, wherein the nucleotide at position 17 from the 5' end of the second nucleotide sequence is a 2'-fluoro nucleotide.
36. The siNA according to any preceding embodiment, wherein the nucleotide at position 18 from the 5' end of the second nucleotide sequence is a 2'-fluoro nucleotide.
37. The siNA according to any preceding embodiment, wherein the nucleotides in the second nucleotide sequence are arranged in an alternating 1:3 modification pattern, and wherein 1 nucleotide is a 2'-fluoro nucleotide and 3 nucleotides are 2'-O-methyl nucleotides.
38. The siNA of embodiment 37, wherein the alternating 1:3 modification pattern occurs 2-5 times.
39. The siNA according to embodiment 37 or 38, wherein at least two of the alternating 1:3 modification pattern occur consecutively.
40. The siNA according to any of embodiments 37-39, wherein at least two of the alternating 1:3 modification pattern occurs nonconsecutively.
41. The siNA according to any of claims 37-40, wherein at least 1, 2, 3, 4, or 5 alternating 1:3 modification pattern begins at nucleotide position 2, 6, 10, 14, and/or 18 from the 5' end of the antisense strand.
42. The siNA according to any of claims 37-41, wherein at least one alternating 1:3 modification pattern begins at nucleotide position 2 from the 5' end of the antisense strand.
43. The siNA according to any of claims 37-42, wherein at least one alternating 1:3 modification pattern begins at nucleotide position 6 from the 5' end of the antisense strand.
44. The siNA according to any of claims 37-43, wherein at least one alternating 1:3 modification pattern begins at nucleotide position 10 from the 5' end of the antisense strand.
45. The siNA according to any of claims 37-44, wherein at least one alternating 1:3 modification pattern begins at nucleotide position 14 from the 5' end of the antisense strand.
46. The siNA according to any of claims 37-45, wherein at least one alternating 1:3 modification pattern begins at nucleotide position 18 from the 5' end of the antisense strand.
47. The siNA according to any one of embodiments 1-37, wherein the nucleotides in the second nucleotide sequence are arranged in an alternating 1:2 modification pattern, and wherein 1 nucleotide is a 2'-fluoro nucleotide and 2 nucleotides are 2'-O-methyl nucleotides.
48. The siNA of embodiment 47, wherein the alternating 1:2 modification pattern occurs 2-5 times.
49. The siNA according to embodiment 47 or 48, wherein at least two of the alternating 1:2 modification pattern occurs consecutively.
50. The siNA according to any of embodiments 47-49, wherein at least two of the alternating 1:2 modification pattern occurs nonconsecutively.
51. The siNA according to any of claims 47-50, wherein at least 1, 2, 3, 4, or 5 alternating 1:2 modification pattern begins at nucleotide position 2, 5, 8, 14, and/or 17 from the 5' end of the antisense strand.
52. The siNA according to any of claims 47-51, wherein at least one alternating 1:2 modification pattern begins at nucleotide position 2 from the 5' end of the antisense strand.
53. The siNA according to any of claims 47-52, wherein at least one alternating 1:2 modification pattern begins at nucleotide position 5 from the 5' end of the antisense strand.
54. The siNA according to any of claims 47-53, wherein at least one alternating 1:2 modification pattern begins at nucleotide position 8 from the 5' end of the antisense strand.
55. The siNA according to any of claims 47-54, wherein at least one alternating 1:2 modification pattern begins at nucleotide position 14 from the 5' end of the antisense strand.
56. The siNA according to any of claims 47-55, wherein at least one alternating 1:2 modification pattern begins at nucleotide position 17 from the 5' end of the antisense strand.
57. A short interfering nucleic acid (siNA) molecule represented by Formula (VIII):

$$5'-A_n^1 B_n^2 A_n^3 B_n^4 A_n^5 B_n^6 A_n^7 B_n^8 A_n^9-3'$$

$$3'-C_q^1 A_q^2 B_q^3 A_q^4 B_q^5 A_q^6 B_q^7 A_q^8 B_q^9 A_q^{10} B_q^{11} A_q^{12}-5'$$

wherein:
the top strand is a sense strand comprising a first nucleotide sequence that is at least about 60%, 65%, 70%, 75%, 80%, 85%, 90%, 95%, or 100% identical to an RNA corresponding to a target gene, wherein the first nucleotide sequence comprises 15 to 30 nucleotides;
the bottom strand is an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence comprises 15 to 30 nucleotides;

each A is independently a 2'-O-methyl nucleotide or a nucleotide comprising a 5'-stabilized end cap or a phosphorylation blocker;
B is a 2'-fluoro nucleotide;
C represents overhanging nucleotides and is a 2'-O-methyl nucleotide;
$n^1 = 1-4$ nucleotides in length;
each $n^2$, $n^6$, $n^8$, $q^3$, $q^5$, $q^7$, $q^9$, $q^{11}$, and $q^{12}$ is independently 0-1 nucleotides in length;
each $n^3$ and $n^4$ is independently 1-3 nucleotides in length;
$n^5$ is 1-10 nucleotides in length;
$n^7$ is 0-4 nucleotides in length;
each $n^9$, $q^1$, and $q^2$ is independently 0-2 nucleotides in length;
$q^4$ is 0-3 nucleotides in length;
$q^6$ is 0-5 nucleotides in length;
$q^8$ is 2-7 nucleotides in length; and
$q^{10}$ is 2-11 nucleotides in length.

58. A short interfering nucleic acid (siNA) molecule represented by Formula (IX):

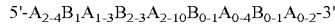
$$5'\text{-}A_{2\text{-}4}B_1A_{1\text{-}3}B_{2\text{-}3}A_{2\text{-}10}B_{0\text{-}1}A_{0\text{-}4}B_{0\text{-}1}A_{0\text{-}2}\text{-}3'$$

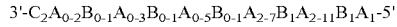
$$3'\text{-}C_2A_{0\text{-}2}B_{0\text{-}1}A_{0\text{-}3}B_{0\text{-}1}A_{0\text{-}5}B_{0\text{-}1}A_{2\text{-}7}B_1A_{2\text{-}11}B_1A_1\text{-}5'$$

wherein:
the top strand is a sense strand comprising a first nucleotide sequence that is at least about 60%, 65%, 70%, 75%, 80%, 85%, 90%, 95%, or 100% identical to an RNA corresponding to a target gene, wherein the first nucleotide sequence comprises 15 to 30 nucleotides;
the bottom strand is an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence comprises 15 to 30 nucleotides;
each A is independently a 2'-O-methyl nucleotide or a nucleotide comprising a 5'-stabilized end cap or a phosphorylation blocker;
B is a 2'-fluoro nucleotide;
C represents overhanging nucleotides and is a 2'-O-methyl nucleotide.

59. A short interfering nucleic acid (siNA) molecule comprising
   (a) a sense strand comprising a first nucleotide sequence consisting of 17 to 23 nucleotides, wherein 2'-fluoro nucleotides are at positions 3, 7-9, 12, and 17 from the 5' end of the first nucleotide sequence, and wherein 2'-O-methyl nucleotides are at positions 1, 2, 4-6, 10, 11, and 13-16 from the 5' end of the first nucleotide sequence; and
   (b) an antisense strand comprising a second nucleotide sequence consisting of 17 to 23 nucleotides, wherein 2'-fluoro nucleotides are at positions 2 and 14 from the 5' end of the second nucleotide sequence, and wherein 2'-O-methyl nucleotides are at positions 1, 3-13, and 15-17 from the 5' end of the second nucleotide sequence.

60. The siNA molecule of embodiment 59, wherein the first nucleotide sequence consists of 19 nucleotides.

61. The siNA molecule of embodiment 60, wherein 2'-O-methyl nucleotides are at positions 18 and 19 from the 5' end of the first nucleotide sequence.

62. The siNA molecule according to any one of embodiments 59-61, wherein the second nucleotide sequence consists of 21 nucleotides.

63. The siNA molecule of embodiment 62, wherein 2'-O-methyl nucleotides are at positions 18-21 from the 5' end of the second nucleotide sequence.

64. A short interfering nucleic acid (siNA) molecule comprising
   (a) a sense strand comprising a first nucleotide sequence consisting of 17 to 23 nucleotides, wherein 2'-fluoro nucleotides are at positions 3, 7, 8, and 17 from the 5' end of the first nucleotide sequence, and wherein 2'-O-methyl nucleotides are at positions 1, 2, 4-6, and 9-16 from the 5' end of the first nucleotide sequence; and
   (b) an antisense strand comprising a second nucleotide sequence consisting of 17 to 23 nucleotides, wherein 2'-fluoro nucleotides are at positions 2 and 14 from the 5' end of the first nucleotide sequence; and wherein 2'-O-methyl nucleotides are at positions 1, 3-13, and 15-17 from the 5' end of the first nucleotide sequence.

65. The siNA molecule of embodiment 64, wherein the first nucleotide sequence consists of 19 nucleotides.

66. The siNA molecule of embodiment 65, wherein 2'-O-methyl nucleotides are at positions 18 and 19 from the 5' end of the first nucleotide sequence.

67. The siNA molecule according to any one of embodiments 64-66, wherein the second nucleotide sequence consists of 21 nucleotides.

68. The siNA molecule of embodiment 67, wherein 2'-O-methyl nucleotides are at positions 18-21 from the 5' end of the second nucleotide sequence.

69. A short interfering nucleic acid (siNA) molecule comprising
   (a) a sense strand comprising a first nucleotide sequence consisting of 17 to 23 nucleotides, wherein 2'-fluoro nucleotides are at positions 3, 7-9, 12 and 17 from the 5' end of the first nucleotide sequence, and wherein 2'-O-methyl nucleotides are at positions 1, 2, 4-6, 10, 11, and 13-16 from the 5' end of the first nucleotide sequence; and
   (b) an antisense strand comprising a second nucleotide sequence consisting of 17 to 23 nucleotides, wherein the nucleotides in the second nucleotide sequence are arranged in an alternating 1:3 modification pattern, and wherein 1 nucleotide is a 2'-fluoro nucleotide and 3 nucleotides are 2'-O-methyl nucleotides.

70. The siNA molecule of embodiment 69, wherein the first nucleotide sequence consists of 19 nucleotides.

71. The siNA molecule of embodiment 70, wherein 2'-O-methyl nucleotides are at positions 18 and 19 from the 5' end of the first nucleotide sequence.

72. The siNA molecule according to any one of embodiments 69-71, wherein the second nucleotide sequence consists of 21 nucleotides.

73. The siNA molecule of embodiment 72, wherein 2'-O-methyl nucleotides are at positions 19-21 from the 5' end of the second nucleotide sequence.

74. The siRNA molecule according to any one of embodiments 69-73, wherein the alternating 1:3 modification pattern occurs 2-5 times.

75. The siRNA molecule according to any one of embodiments 69-74, wherein at least two of the alternating 1:3 modification pattern occur consecutively.

76. The siRNA molecule according to any one of embodiments 69-75, wherein at least two of the alternating 1:3 modification pattern occurs nonconsecutively.

77. The siNA according to any one of embodiments 69-76, wherein at least 1, 2, 3, 4, or 5 alternating 1:3 modification pattern begins at nucleotide position 2, 6, 10, 14, and/or 18 from the 5' end of the antisense strand.

78. The siNA according to any one of embodiments 69-77, wherein at least one alternating 1:3 modification pattern begins at nucleotide position 2 from the 5' end of the antisense strand.

79. The siNA according to any one of embodiments 69-78, wherein at least one alternating 1:3 modification pattern begins at nucleotide position 6 from the 5' end of the antisense strand.

80. The siNA according to any one of embodiments 69-79, wherein at least one alternating 1:3 modification pattern begins at nucleotide position 10 from the 5' end of the antisense strand.

81. The siNA according to any one of embodiments 69-80, wherein at least one alternating 1:3 modification pattern begins at nucleotide position 14 from the 5' end of the antisense strand.

82. The siNA according to any one of embodiments 69-81, wherein at least one alternating 1:3 modification pattern begins at nucleotide position 18 from the 5' end of the antisense strand.

83. A short interfering nucleic acid (siNA) molecule comprising
(a) a sense strand comprising a first nucleotide sequence consisting of 17 to 23 nucleotides, wherein 2'-fluoro nucleotides are at positions 5 and 7-9 from the 5' end of the first nucleotide sequence, and wherein 2'-O-methyl nucleotides are at positions 1-4, 6, and 10-17 from the 5' end of the first nucleotide sequence; and
(b) an antisense strand comprising a second nucleotide sequence consisting of 17 to 23 nucleotides, wherein the nucleotides in the second nucleotide sequence are arranged in an alternating 1:3 modification pattern, and wherein 1 nucleotide is a 2'-fluoro nucleotide and 3 nucleotides are 2'-O-methyl nucleotides.

84. The siNA molecule of embodiment 83, wherein the first nucleotide sequence consists of 19 nucleotides.

85. The siNA molecule of embodiment 84, wherein 2'-O-methyl nucleotides are at positions 18 and 19 from the 5' end of the first nucleotide sequence.

86. The siNA molecule according to any one of embodiments 83-85, wherein the second nucleotide sequence consists of 21 nucleotides.

87. The siNA molecule of embodiment 86, wherein 2'-O-methyl nucleotides are at positions 19-21 from the 5' end of the second nucleotide sequence.

88. The siRNA molecule according to any one of embodiments 83-87, wherein the alternating 1:3 modification pattern occurs 2-5 times.

89. The siRNA molecule according to any one of embodiments 83-88, wherein at least two of the alternating 1:3 modification pattern occur consecutively.

90. The siRNA molecule according to any one of embodiments 83-89, wherein at least two of the alternating 1:3 modification pattern occurs nonconsecutively.

91. The siNA according to any one of embodiments 83-90, wherein at least 1, 2, 3, 4, or 5 alternating 1:3 modification pattern begins at nucleotide position 2, 6, 10, 14, and/or 18 from the 5' end of the antisense strand.

92. The siNA according to any one of embodiments 83-91, wherein at least one alternating 1:3 modification pattern begins at nucleotide position 2 from the 5' end of the antisense strand.

93. The siNA according to any one of embodiments 83-92, wherein at least one alternating 1:3 modification pattern begins at nucleotide position 6 from the 5' end of the antisense strand.

94. The siNA according to any one of embodiments 83-93, wherein at least one alternating 1:3 modification pattern begins at nucleotide position 10 from the 5' end of the antisense strand.

95. The siNA according to any one of embodiments 83-94, wherein at least one alternating 1:3 modification pattern begins at nucleotide position 14 from the 5' end of the antisense strand.

96. The siNA according to any one of embodiments 83-95, wherein at least one alternating 1:3 modification pattern begins at nucleotide position 18 from the 5' end of the antisense strand.

97. A short interfering nucleic acid (siNA) molecule comprising
(a) a sense strand comprising a first nucleotide sequence consisting of 17 to 23 nucleotides, wherein 2'-fluoro nucleotides are at positions 5 and 7-9 from the 5' end of the first nucleotide sequence, and wherein 2'-O-methyl nucleotides are at positions 1-4, 6, and 10-17 from the 5' end of the first nucleotide sequence; and
(b) an antisense strand comprising a second nucleotide sequence consisting of 17 to 23 nucleotides, wherein the nucleotides in the second nucleotide sequence are arranged in an alternating 1:2 modification pattern, and wherein 1 nucleotide is a 2'-fluoro nucleotide and 2 nucleotides are 2'-O-methyl nucleotides.

98. The siNA molecule of embodiment 97, wherein the first nucleotide sequence consists of 19 nucleotides.

99. The siNA molecule of embodiment 98, wherein 2'-O-methyl nucleotides are at positions 18 and 19 from the 5' end of the first nucleotide sequence.

100. The siNA molecule according to any one of embodiments 97-99, wherein the second nucleotide sequence consists of 21 nucleotides.

101. The siNA molecule of embodiment 100, wherein 2'-O-methyl nucleotides are at positions 18-21 from the 5' end of the second nucleotide sequence.

102. The siRNA molecule according to any one of embodiments 97-101, wherein the alternating 1:2 modification pattern occurs 2-5 times.

103. The siRNA molecule according to any one of embodiments 97-102, wherein at least two of the alternating 1:2 modification pattern occur consecutively.

104. The siRNA molecule according to any one of embodiments 97-103, wherein at least two of the alternating 1:2 modification pattern occurs nonconsecutively.

105. The siNA according to any one of embodiments 97-104, wherein at least 1, 2, 3, 4, or 5 alternating 1:2 modification pattern begins at nucleotide position 2, 5, 8, 14, and/or 17 from the 5' end of the antisense strand.

106. The siNA according to any one of embodiments 97-105, wherein at least one alternating 1:2 modification pattern begins at nucleotide position 2 from the 5' end of the antisense strand.

107. The siNA according to any one of embodiments 97-106, wherein at least one alternating 1:2 modification pattern begins at nucleotide position 5 from the 5' end of the antisense strand.

108. The siNA according to any one of embodiments 97-107, wherein at least one alternating 1:2 modification pattern begins at nucleotide position 8 from the 5' end of the antisense strand.

109. The siNA according to any one of embodiments 74-85, wherein at least one alternating 1:2 modification pattern begins at nucleotide position 14 from the 5' end of the antisense strand.

110. The siNA according to any one of embodiments 97-109, wherein at least one alternating 1:2 modification pattern begins at nucleotide position 17 from the 5' end of the antisense strand.

111. A short interfering nucleic acid (siNA) molecule comprising
(a) a sense strand comprising a first nucleotide sequence consisting of 17 to 23 nucleotides, wherein 2'-fluoro nucleotides are at positions 5 and 7-9 from the 5' end of the first nucleotide sequence, and wherein 2'-O-methyl nucleotides are at positions 1-4, 6, and 10-17 from the 5' end of the first nucleotide sequence; and
(b) an antisense strand comprising a second nucleotide sequence consisting of 17 to 23 nucleotides, wherein 2'-fluoro nucleotides are at positions 2, 6, 14, and 16 from the 5' end of the second nucleotide sequence, and wherein 2'-O-methyl nucleotides are at positions 1, 3-5, 7-13, 15, and 17 from the 5' end the second nucleotide sequence.

112. The siNA molecule of embodiment 111, wherein the first nucleotide sequence consists of 19 nucleotides.

113. The siNA molecule of embodiment 112, wherein 2'-O-methyl nucleotides are at positions 18 and 19 from the 5' end of the first nucleotide sequence.

114. The siNA molecule according to any one of embodiments 111-113, wherein the second nucleotide sequence consists of 21 nucleotides.

115. The siNA molecule of embodiment 114, wherein 2'-O-methyl nucleotides are at positions 18-21 from the 5' end of the second nucleotide sequence.

116. A short interfering nucleic acid (siNA) molecule comprising:
(a) a sense strand comprising a first nucleotide sequence consisting of 17 to 23 nucleotides, wherein 2'-fluoro nucleotides are at positions 5, 9-11, and 14 from the 5' end of the first nucleotide sequence, and wherein 2'-O-methyl nucleotides are at positions 1-4, 6-8, and 12-17 from the 5' end of the first nucleotide sequence; and
(b) an antisense strand comprising a second nucleotide sequence consisting of 17 to 23 nucleotides, wherein 2'-fluoro nucleotides are at positions 2 and 14 from the 5' end of the second nucleotide sequence, and wherein 2'-O-methyl nucleotides are at positions 1, 3-13, and 15-17 from the 5' end the second nucleotide sequence.

117. The siNA molecule of embodiment 116, wherein the first nucleotide sequence consists of 21 nucleotides.

118. The siNA molecule of embodiment 117, wherein 2'-O-methyl nucleotides are at positions 18-21 from the 5' end of the first nucleotide sequence.

119. The siNA molecule according to any one of embodiments 116-118, wherein the second nucleotide sequence consists of 23 nucleotides.

120. The siNA molecule of embodiment 119, wherein 2'-O-methyl nucleotides are at positions 18-23 from the 5' end of the second nucleotide sequence.

121. The siNA according to any preceding embodiment, wherein the sense strand further comprises TT sequence adjacent to the first nucleotide sequence.

122. The siNA according to any preceding embodiment, wherein the sense strand further comprises at least 1, 2, 3, 4, 5, 6, 7, 8, 9, 10, 11, 12, 13, 14, 15 or more phosphorothioate internucleoside linkages.

123. The siNA of embodiment 122, wherein at least one phosphorothioate internucleoside linkage is between the nucleotides at positions 1 and 2 from the 5' end of the first nucleotide sequence.

124. The siNA of embodiment 122 or 123, wherein at least one phosphorothioate internucleoside linkage is between the nucleotides at positions 2 and 3 from the 5' end of the first nucleotide sequence.

125. The siNA according to any preceding embodiment, wherein the antisense strand further comprises TT sequence adjacent to the second nucleotide sequence.

126. The siNA according to any preceding embodiment, wherein the antisense strand further comprises at least 1, 2, 3, 4, 5, 6, 7, 8, 9, 10, 11, 12, 13, 14, 15 or more phosphorothioate internucleoside linkages.

127. The siNA of embodiment 126, wherein at least one phosphorothioate internucleoside linkage is between the nucleotides at positions 1 and 2 from the 5' end of the second nucleotide sequence.

128. The siNA of embodiment 126 or 127, wherein at least one phosphorothioate internucleoside linkage is between the nucleotides at positions 2 and 3 from the 5' end of the second nucleotide sequence.

129. The siNA of any one of embodiments 126-128, wherein at least one phosphorothioate internucleoside linkage is between the nucleotides at positions 1 and 2 from the 3' end of the second nucleotide sequence.

130. The siNA of any one of embodiments 126-129, wherein at least one phosphorothioate internucleoside linkage is between the nucleotides at positions 2 and 3 from the 3' end of the second nucleotide sequence.

131. The siNA according to any preceding embodiment, wherein the first nucleotide from the 5' end of the first nucleotide sequence comprises a 5' stabilizing end cap.

132. The siNA according to any preceding embodiment, wherein the first nucleotide from the 5' end of the second nucleotide sequence comprises a 5' stabilizing end cap.

133. The siNA according to any preceding embodiment, wherein the first nucleotide from the 5' end of the first nucleotide sequence comprises a phosphorylation blocker.

134. The siNA according to any preceding embodiment, wherein the first nucleotide from the 5' end of the second nucleotide sequence comprises a phosphorylation blocker.

135. The siNA according to any preceding embodiment, wherein the first nucleotide sequence or second nucleotide sequence comprises at least one modified nucleotide selected from

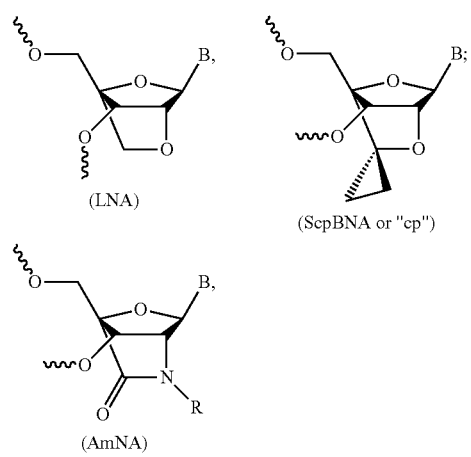

where R is H or alkyl (or AmNA(N-Me)) when R is alkyl);

315

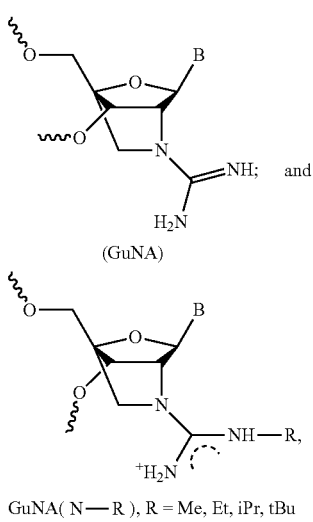

(GuNA)

GuNA( N—R ), R = Me, Et, iPr, tBu wherein B is a nucleobase.

136. A short-interfering nucleic acid (siNA) molecule comprising:
   (a) a phosphorylation blocker of Formula (IV):

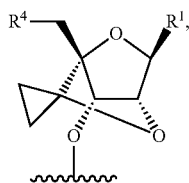

wherein
$R^1$ is a nucleobase,
$R^4$ is —O—$R^{30}$ or —$NR^{31}R^{32}$,
$R^{30}$ is $C_1$-$C_8$ substituted or unsubstituted alkyl; and
$R^{31}$ and $R^{32}$ together with the nitrogen to which they are attached form a substituted
or unsubstituted heterocyclic ring; and
   (b) a short interfering nucleic acid (siNA).

137. A short-interfering nucleic acid (siNA) molecule comprising:
   (a) a 5'-stabilized end cap of Formula (Ia):

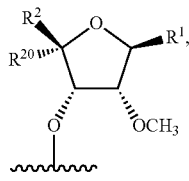

wherein
$R^1$ is a nucleobase, aryl, heteroaryl, or H,
$R^2$ is

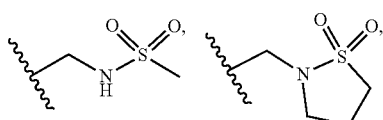

316

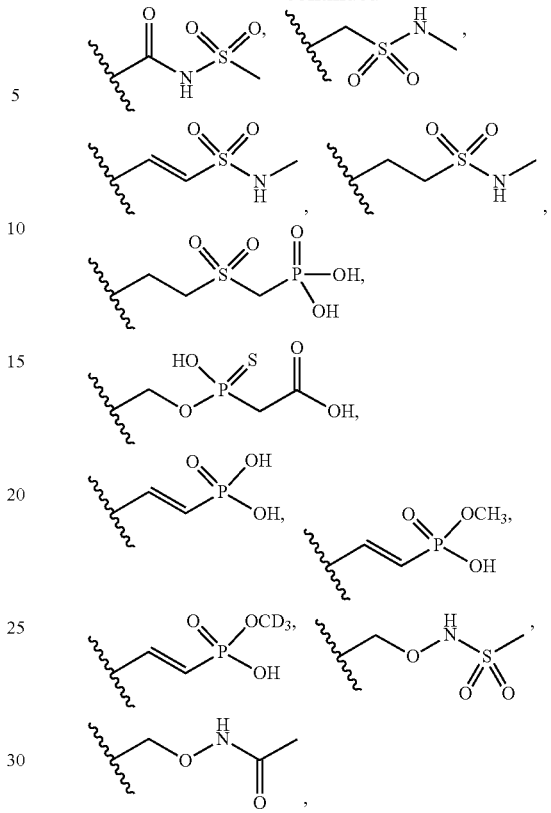

—CH=CD-Z, —CD=CH—Z, —CD=CD-Z, —($CR^{21}R^{22})_n$—Z, or —($C_2$-$C_6$ alkenylene)-Z and $R^{20}$ is hydrogen; or $R^2$ and $R^{20}$ together form a 3- to 7-membered carbocyclic ring substituted with —($CR^{21}R^{22})_n$—Z or —($C_2$-$C_6$ alkenylene)-Z;

n is 1, 2, 3, or 4;

Z is —$ONR^{23}R^{24}$, —OP(O)OH($CH_2)_m CO_2 R^{23}$, —OP(S)OH($CH_2)_m CO_2 R^{23}$, —P(O)(OH)$_2$, —P(O)(OH)(OCH$_3$), —P(O)(OH)(OCD$_3$), —SO$_2$(CH$_2)_m$P(O)(OH)$_2$, —SO$_2$NR$^{23}$R$^{25}$, —NR$^{23}$R$^{24}$, $R^{21}$ and $R^{22}$ are independently hydrogen or $C_1$-$C_6$ alkyl;
$R^{21}$ and $R^{22}$ together form an oxo group;
$R^{23}$ is hydrogen or $C_1$-$C_6$ alkyl;
$R^{24}$ is —SO$_2$R$^{25}$ or —C(O)R$^{25}$; or
$R^{23}$ and $R^{24}$ together with the nitrogen to which they are attached form a substituted or unsubstituted heterocyclic ring;
$R^{25}$ is $C_1$-$C_6$ alkyl; and
m is 1, 2, 3, or 4; and (b) a short interfering nucleic acid (siNA).

138. A short-interfering nucleic acid (siNA) molecule comprising:
   (a) a 5'-stabilized end cap of Formula (Ib):

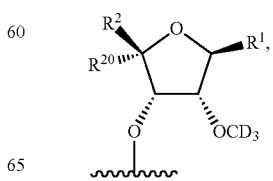

wherein
R¹ is a nucleobase, aryl, heteroaryl, or H,
R² is

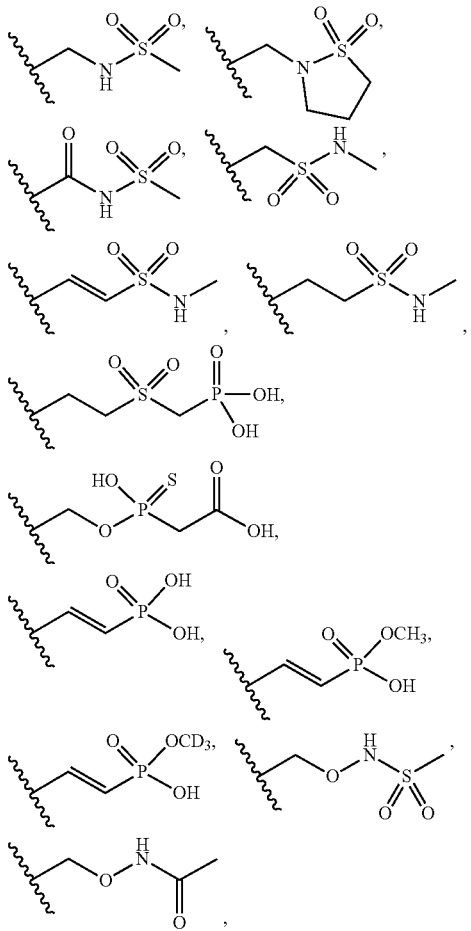

—CH=CD-Z, —CD=CH—Z, —CD=CD-Z, —(CR²¹ R²²)$_n$—Z, or —(C$_2$-C$_6$ alkenylene)-Z and R²⁰ is hydrogen; or R² and R²⁰ together form a 3- to 7-membered carbocyclic ring substituted with —(CR²¹R²²)$_n$—Z or —(C$_2$-C$_6$ alkenylene)-Z;

n is 1, 2, 3, or 4;

Z is —ONR²³R²⁴, —OP(O)OH(CH$_2$)$_m$CO$_2$R²³, —OP(S)OH(CH$_2$)$_m$CO$_2$R²³, —P(O)(OH)$_2$, —P(O)(OH)(OCH$_3$), —P(O)(OH)(OCD$_3$), —SO$_2$(CH$_2$)$_m$P(O)(OH)$_2$, —SO$_2$NR²³R²⁵, —NR²³R²⁴,

R²¹ and R²² are independently hydrogen or C$_1$-C$_6$ alkyl;

R²¹ and R²² together form an oxo group;

R²³ is hydrogen or C$_1$-C$_6$ alkyl;

R²⁴ is —SO$_2$R²⁵ or —C(O)R²⁵; or

R²³ and R²⁴ together with the nitrogen to which they are attached form a substituted or unsubstituted heterocyclic ring;

R²⁵ is C$_1$-C$_6$ alkyl; and m is 1, 2, 3, or 4; and (b) a short interfering nucleic acid (siNA).

139. A short-interfering nucleic acid (siNA) molecule comprising:

(a) a 5'-stabilized end cap selected from the group consisting of Formula (1) to Formula (15), Formula (9X) to Formula (12X), and Formula (9Y) to Formula (12Y):

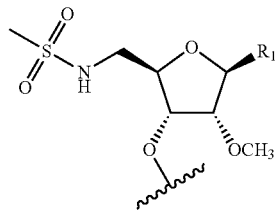

Formula (1)

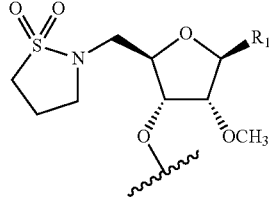

Formula (2)

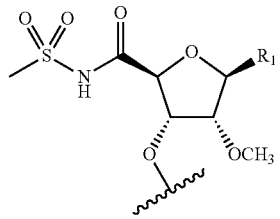

Formula (3)

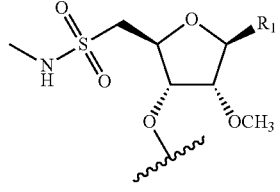

Formula (4)

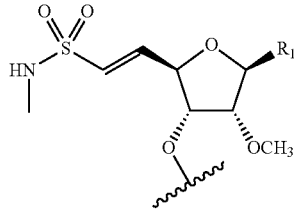

(Formula (5))

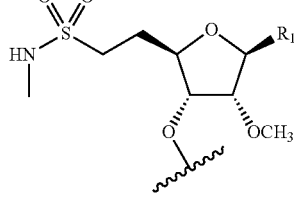

Formula (6)

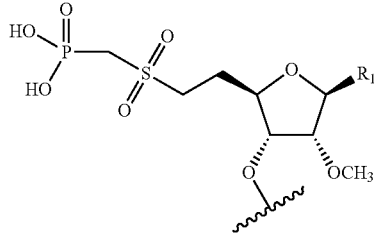

Formula (7)

Formula (8)
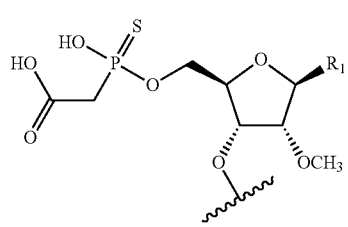
Formula (9)
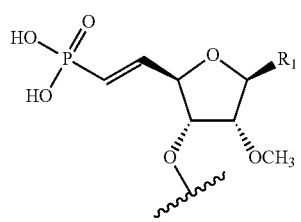
Formula (9X)
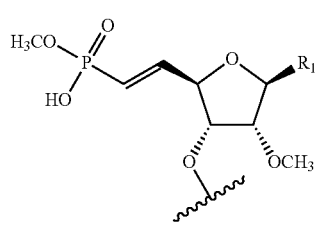
Formula (9Y)
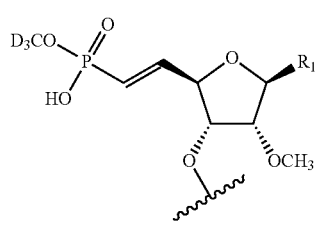
Formula (10)
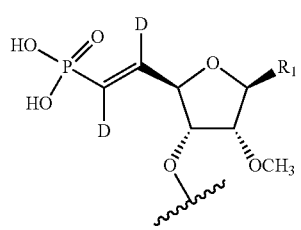
Formula (10X)
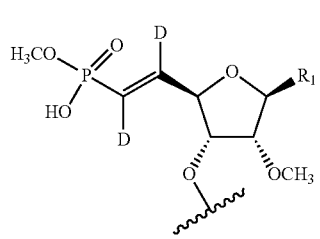
Formula (10Y)
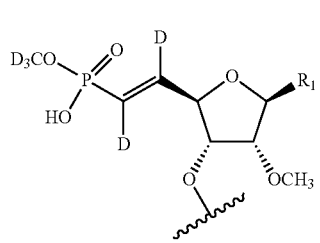
Formula (11)
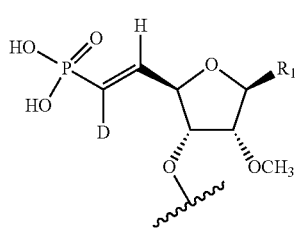
Formula (11X)
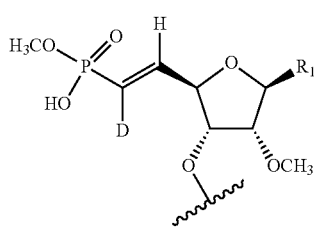
Formula (11Y)
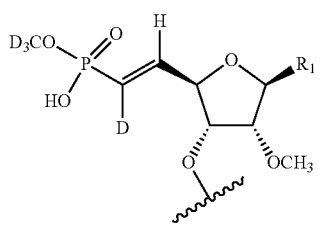
Formula (12)
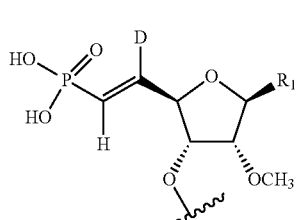
Formula (12X)
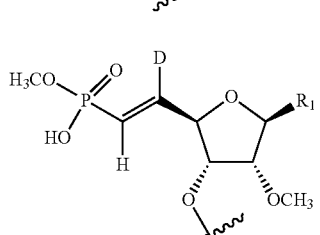
Formula (12Y)
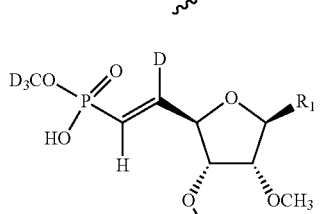
Formula (13)
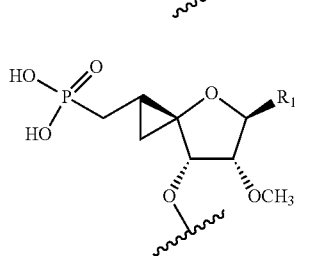

Formula (14)

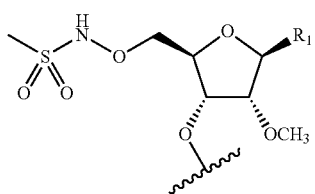

Formula (15)

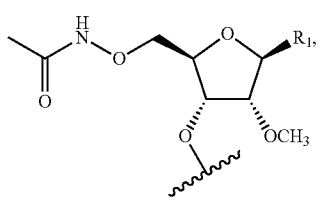

wherein R¹ is a nucleobase, aryl, heteroaryl, or H; and
(b) a short interfering nucleic acid (siNA).

140. A short-interfering nucleic acid (siNA) molecule comprising:
(a) a 5'-stabilized end cap selected from the group consisting of Formulas (1A)-(15A), Formulas (9B)-(12B), Formulas (9AX)-(12AX), Formulas (9AY)-(12AY), Formulas (9BX)-(12BX), and Formulas (9BY)-(12BY):

Formula (1A)

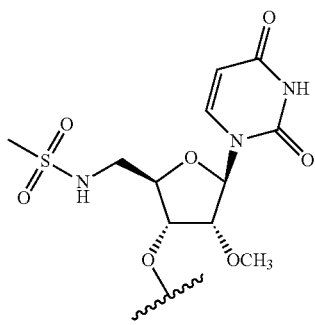

Formula (2A)

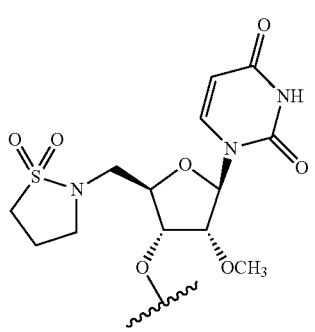

Formula (3A)

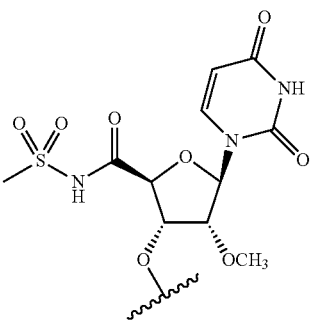

Formula (4A)

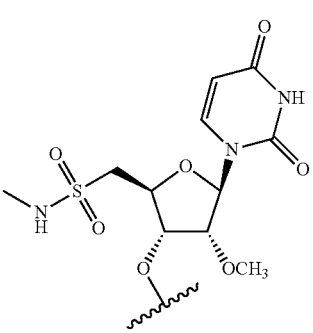

Formula (5A)

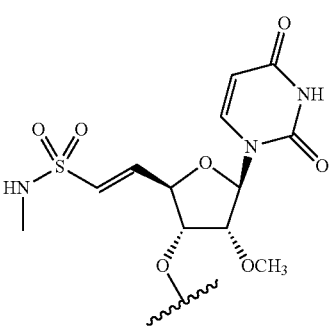

Formula (6A)

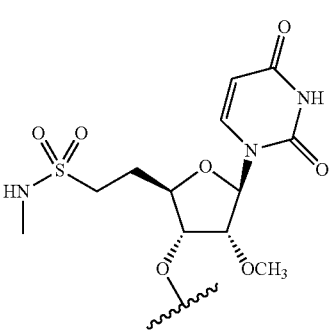

Formula (7A)

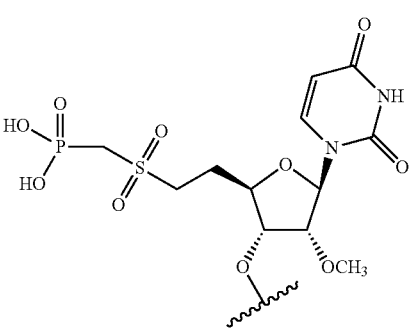

Formula (8A)
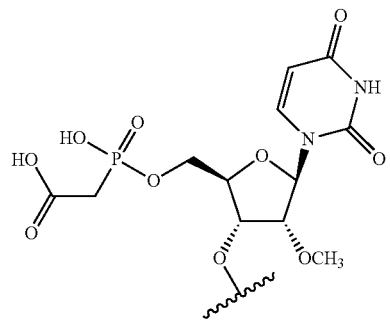
Formula (9A)
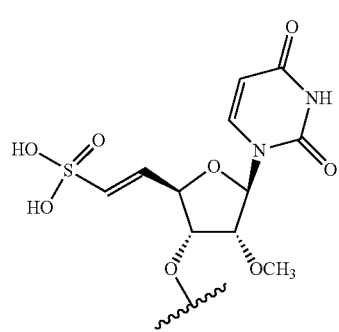
Formula (9AX)
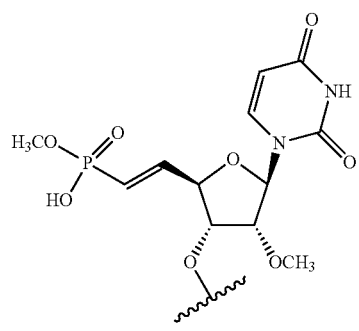
Formula (9AY)
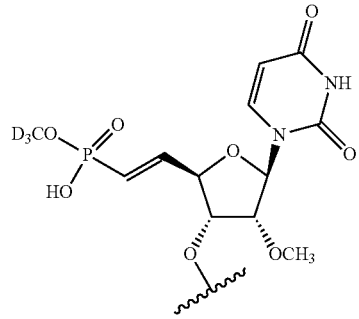
Formula (9B)
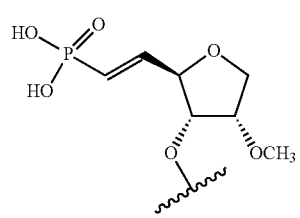
Formula (9BX)
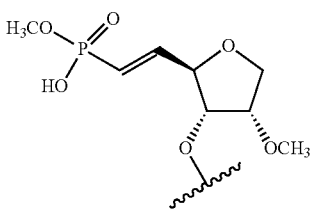
Formula (9BY)
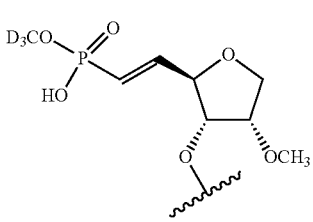
Formula (10A)
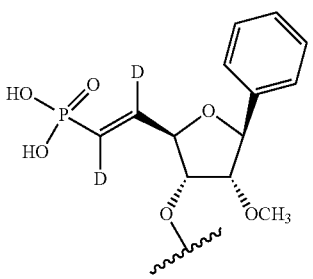
Formula (10AX)
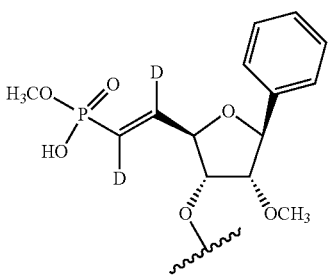
Formula (10AY)
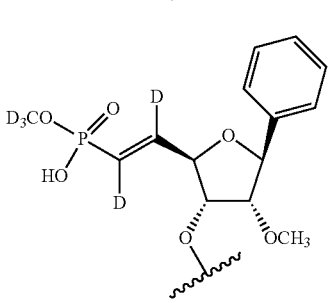
Formula (10B)
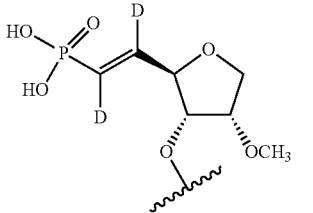

Formula (10BX)
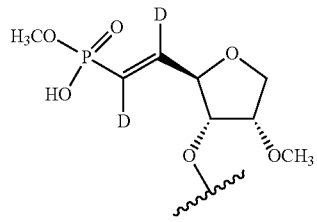
Formula (10BY)
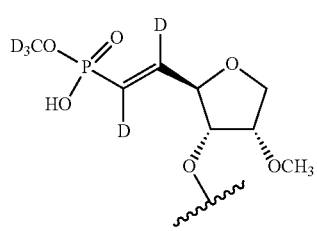
Formula (11A)
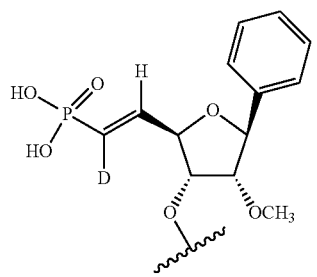
Formula (11AX)
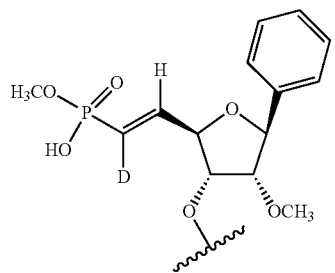
Formula (11AY)
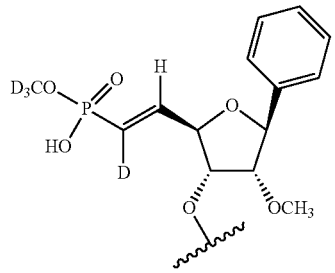
Formula 11B)
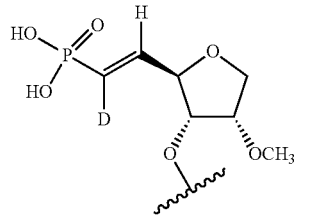
Formula (11BX)
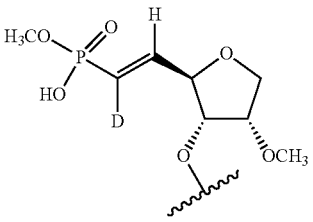
Formula (11BY)
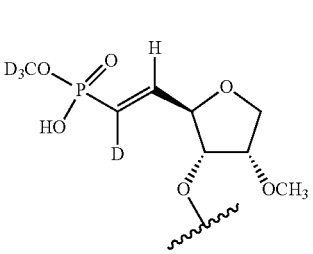
Formula (12A)
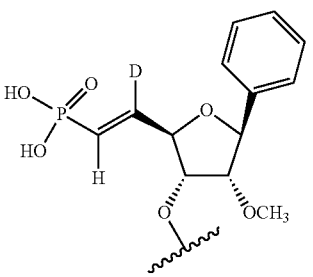
Formula (12AX)
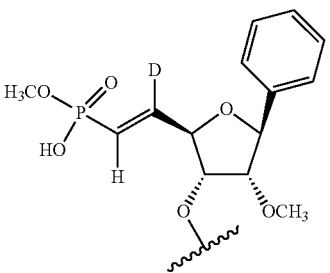
Formula (12AY)
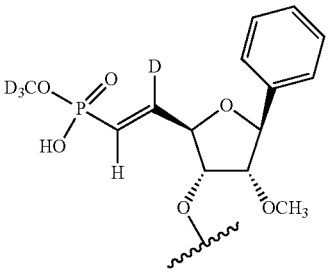
Formula (12B)
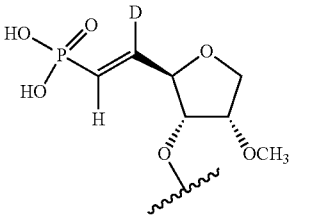

-continued

Formula (12BX)
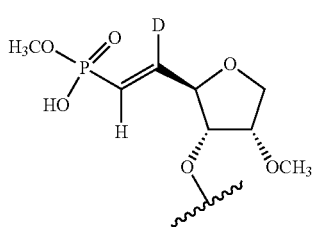

Formula (12BY)
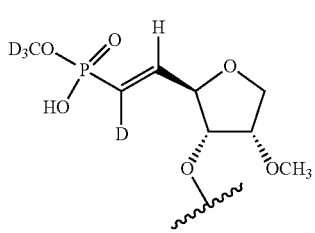

Formula (13A)
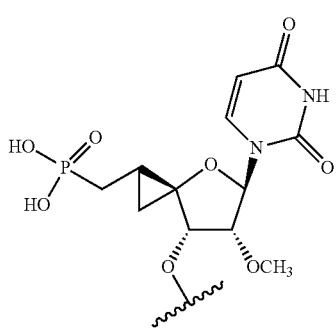

Formula (14A)
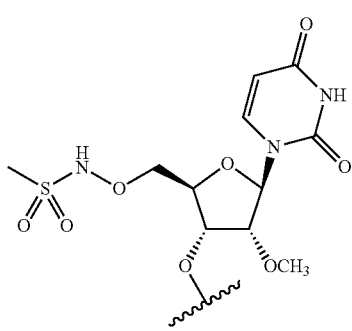

Formula (15A)
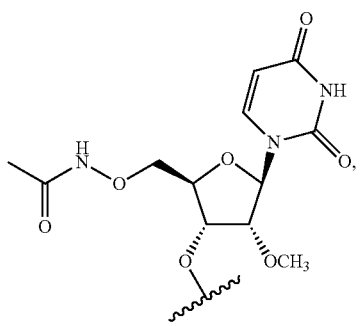

and
(b) a short interfering nucleic acid (siNA).

141. The siNA molecule according to any one of embodiments 136-140, wherein the siNA comprises the sense strand of any one of embodiments 1-135.

142. The siNA molecule according to any one of embodiments 136-141, wherein the siNA comprises the antisense strand of any one of embodiments 1-135.

143. A short interfering nucleic acid (siNA) molecule comprising:
(a) a sense strand comprising a first nucleotide sequence that is at least about 60%, 65%, 70%, 75%, 80%, 85%, 90%, 95%, or 100% identical to an RNA corresponding to a target gene, wherein the first nucleotide sequence comprises a nucleotide sequence of any one SEQ ID NOs: 1-56, 103-158, and 205-260; and
(b) an antisense strand comprising a second nucleotide sequence that is at least about 60%, 65%, 70%, 75%, 80%, 85%, 90%, 95%, or 100% complementary to the RNA corresponding to the target gene, wherein the second nucleotide sequence comprises a nucleotide sequence of any one of SEQ ID NOs: 57-102, 159-204, and 261-306.

144. A interfering nucleic acid (siNA) molecule comprising:
(a) a sense strand comprising a nucleotide sequence of any one of SEQ ID NOs: 307-362 and 415-444; and
(b) an antisense strand comprising a nucleotide sequence of any one of SEQ ID NOs: 363-409, 445-533, and 536-539.

145. The siNA according to any one of embodiments 1-132, 135, and 137-144, wherein the siNA further comprises a phosphorylation blocker.

146. The siNA according to any one of embodiments 16, 133, 134, and 145, wherein the phosphorylation blocker has the structure of Formula (IV):

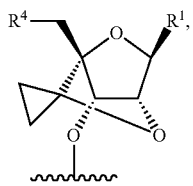

wherein
R$^1$ is a nucleobase,
R$^4$ is —O—R$^{30}$ or —NR$^{31}$R$^{32}$, R$^{30}$ is C$_1$-C$_8$ substituted or unsubstituted alkyl; and
R$^{31}$ and R$^{32}$ together with the nitrogen to which they are attached form a substituted or unsubstituted heterocyclic ring.

147. The siNA of embodiment 136 or 146, wherein R$^4$ is —OCH$_3$ or —N(CH$_2$CH$_2$)$_2$O.

148. The siNA according to any one of embodiments 16, 133, 134, 136, and 145-147, wherein the phosphorylation blocker is attached to the 5' end of the sense strand.

149. The siNA of embodiment 148, wherein the phosphorylation blocker is attached to the 5' end of the sense strand via one or more linkers independently selected from a phosphodiester linker, phosphorothioate linker, and phosphorodithioate linker.

150. The siNA according to any one of embodiments 16, 133, 134, 136, and 145-147, wherein the phosphorylation blocker is attached to the 3' end of the sense strand.

151. The siNA of embodiment 150, wherein the phosphorylation blocker is attached to the 3' end of the sense strand via one or more linkers independently selected from a phosphodiester linker, phosphorothioate linker, and phosphorodithioate linker.

152. The siNA according to any one of embodiments 16, 133, 134, 136, and 145-147, wherein the phosphorylation blocker is attached to the 5' end of the antisense strand.

153. The siNA of embodiment 152, wherein the phosphorylation blocker is attached to the 5' end of the antisense strand via one or more linkers independently selected from a phosphodiester linker, phosphorothioate linker, and phosphorodithioate linker.

154. The siNA according to any one of embodiments 16, 133, 134, 136, and 144-147, wherein the phosphorylation blocker is attached to the 3' end of the antisense strand.

155. The siNA of embodiment 154, wherein the phosphorylation blocker is attached to the 3' end of the antisense strand via one or more linkers independently selected from a phosphodiester linker, phosphorothioate linker, and phosphorodithioate linker.

156. The siNA according to any preceding embodiment, wherein the siNA further comprises a galactosamine.

157. The siNA of embodiment 16 or 156, wherein the galactosamine is N-acetylgalactosamine (GalNAc) of Formula (VII):

each R is independently H;
each Y is independently selected from —O—P(=O)(SH)—, —O—P(=O)(O)—, —O—P(=O)(OH)—, and —O—P(S)S—;
Z is H or a second protecting group;
either L is a linker or L and Y in combination are a linker; and
A is H, OH, a third protecting group, an activated group, or an oligonucleotide.

159. The siNA of embodiment 158, wherein A is an oligonucleotide.

160. The siNA of embodiment 158, wherein A is 1-2 oligonucleotides.

161. The siNA of any one of embodiments 158-160, wherein the oligonucleotide is dTdT.

162. The siNA according to any one of embodiments 16 and 156-161, wherein the galactosamine is attached to the 3' end of the sense strand.

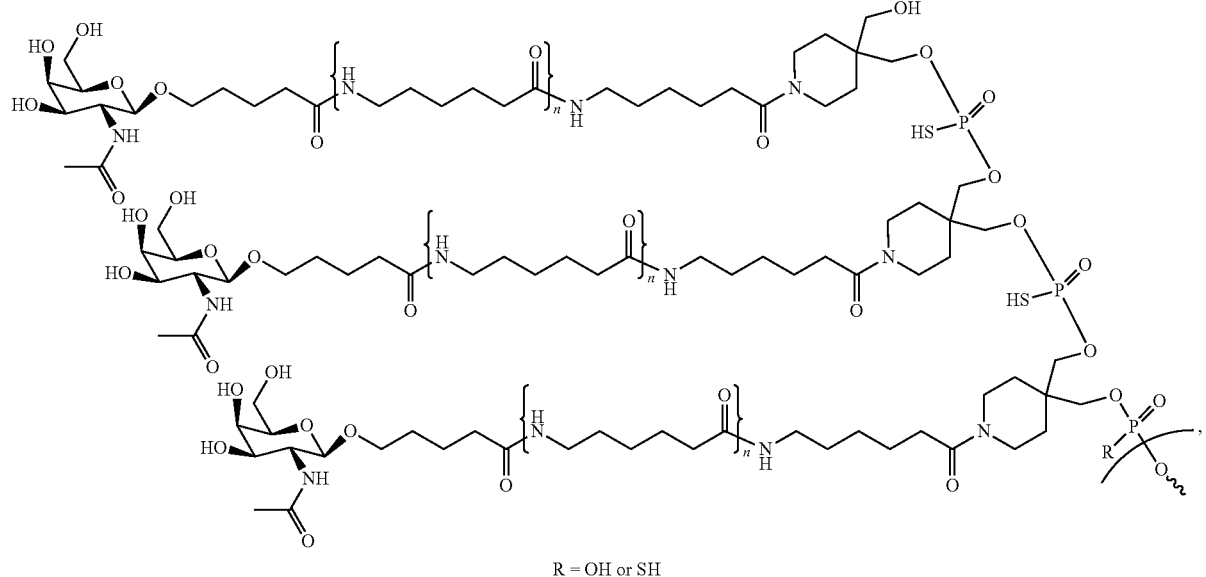

R = OH or SH wherein each n is independently 1 or 2.

158. The siNA of embodiment 16 or 156, wherein the galactosamine is N-acetylgalactosamine (GalNAc) of Formula (VI):

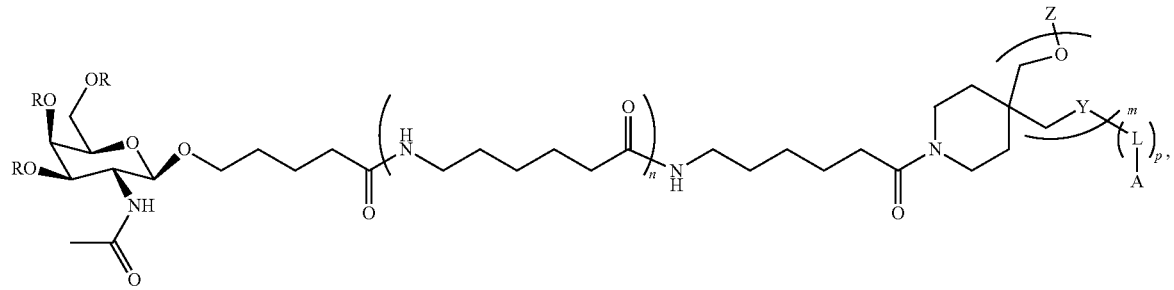

wherein
m is 1, 2, 3, 4, or 5;
each n is independently 1 or 2;
p is 0 or 1;

163. The siNA of embodiment 162, wherein the galactosamine is attached to the 3' end of the sense strand via one or more linkers independently selected from a phosphodiester linker, phosphorothioate linker, or phosphorodithioate linker.

164. The siNA according to any one of embodiments 16 and 156-161, wherein the galactosamine is attached to the 5' end of the sense strand.
165. The siNA of embodiment 164, wherein the galactosamine is attached to the 5' end of the sense strand via one or more linkers independently selected from a phosphodiester linker, phosphorothioate linker, or phosphorodithioate linker.
166. The siNA according to any one of embodiments 16 and 156-161, wherein the galactosamine is attached to the 3' end of the antisense strand.
167. The siNA of embodiment 166, wherein the galactosamine is attached to the 3' end of the antisense strand via one or more linkers independently selected from a phosphodiester linker, phosphorothioate linker, or phosphorodithioate linker.
168. The siNA according to any one of embodiments 16 and 156-161, wherein the galactosamine is attached to the 5' end of the antisense strand.
169. The siNA of embodiment 168, wherein the galactosamine is attached to the 5' end of the antisense strand via one or more linkers independently selected from a phosphodiester linker, phosphorothioate linker, or phosphorodithioate linker.
170. The siNA according to any one of embodiments 1-130, 133-136, and 139-169, wherein the siNA further comprises a 5'-stabilized end cap.
171. The siNA according to any one of embodiments 16, 131, 132, and 170, wherein the 5'-stabilized end cap is a 5' vinyl phosphonate or deuterated 5' vinyl phosphonate.
172. The siNA according to any one of embodiments 16, 131, 132, and 170, wherein the 5'-stabilized end cap has the structure of Formula (Ia):

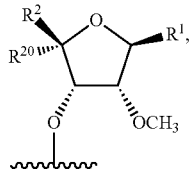

wherein
R$^1$ is a nucleobase, aryl, heteroaryl, or H,
R$^2$ is

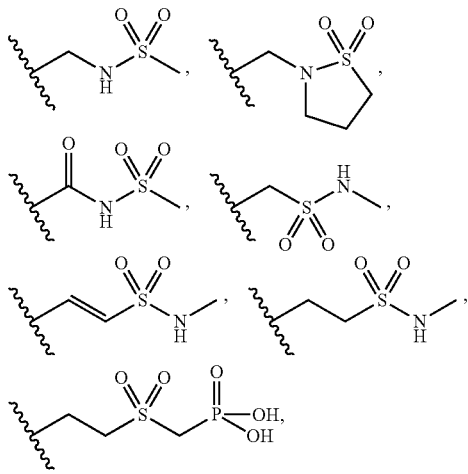

-continued

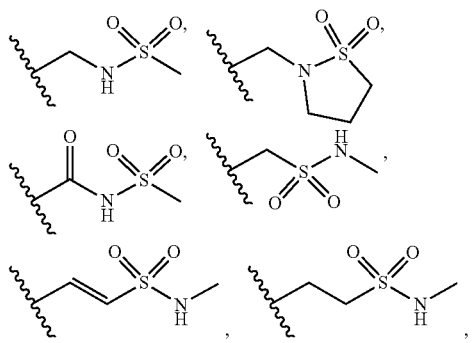

—CH=CD-Z, —CD=CH—Z, —CD=CD-Z, —(CR$^{21}$R$^{22}$)$_n$—Z, or —(C$_2$-C$_6$ alkenylene)-Z and R$^{20}$ is hydrogen;
or
R$^2$ and R$^{20}$ together form a 3- to 7-membered carbocyclic ring substituted with —(CR$^{21}$R$^{22}$)$_n$—Z or —(C$_2$-C$_6$ alkenylene)-Z;
n is 1, 2, 3, or 4;
Z is —ONR$^{23}$R$^{24}$, —OP(O)OH(CH$_2$)$_m$CO$_2$R$^{23}$, —OP(S)OH(CH$_2$)$_m$CO$_2$R$^{23}$, —P(O)(OH)$_2$, —P(O)(OH)(OCH$_3$), —P(O)(OH)(OCD$_3$), —SO$_2$(CH$_2$)$_m$P(O)(OH)$_2$, —SO$_2$NR$^{23}$R$^{25}$, —NR$^{23}$R$^{24}$, or —NR$^{23}$SO$_2$R$^{24}$;
R$^{21}$ and R$^{22}$ either are independently hydrogen or C$_1$-C$_6$ alkyl, or R$^{21}$ and R$^{22}$ together form an oxo group;
R$^{23}$ is hydrogen or C$_1$-C$_6$ alkyl;
R$^{24}$ is —SO$_2$R$^{25}$ or —C(O)R$^{25}$; or
R$^{23}$ and R$^{24}$ together with the nitrogen to which they are attached form a substituted or unsubstituted heterocyclic ring;
R$^{25}$ is C$_1$-C$_6$ alkyl; and
m is 1, 2, 3, or 4.
173. The siNA according to any one of embodiments 131, 132, and 170, wherein the 5'-stabilized end cap has the structure of Formula (Ib):

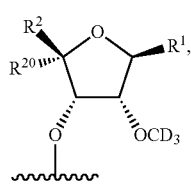

wherein
R$^1$ is a nucleobase, aryl, heteroaryl, or H,
R$^2$ is

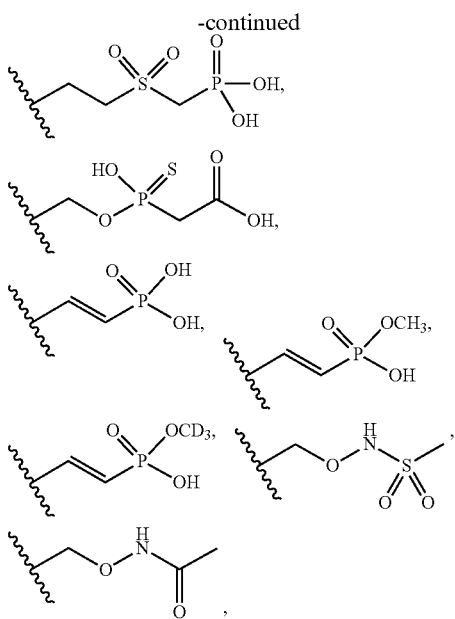

—CH=CD-Z, —CD=CH—Z, —CD=CD-Z, —(CR²¹R²²)ₙ—Z, or —(C₂-C₆ alkenylene)-Z and $R^{20}$ is hydrogen; or $R^2$ and $R^{20}$ together form a 3- to 7-membered carbocyclic ring substituted with —(CR²¹R²²)ₙ—Z or —(C₂-C₆ alkenylene)-Z;

n is 1, 2, 3, or 4;

Z is —ONR²³R²⁴, —OP(O)OH(CH₂)ₘCO₂R²³, —OP(S)OH(CH₂)ₘCO₂R²³, —P(O)(OH)₂, —P(O)(OH)(OCH₃), —P(O)(OH)(OCD₃), —SO₂(CH₂)ₘP(O)(OH)₂, —SO₂NR²³R²⁵, —NR²³R²⁴, or —NR²³SO₂R²⁴;

$R^{21}$ and $R^{22}$ either are independently hydrogen or $C_1$-$C_6$ alkyl, or $R^{21}$ and $R^{22}$ together form an oxo group;

$R^{23}$ is hydrogen or $C_1$-$C_6$ alkyl;

$R^{24}$ is —SO₂R²⁵ or —C(O)R²⁵; or $R^{23}$ and $R^{24}$ together with the nitrogen to which they are attached form a substituted or unsubstituted heterocyclic ring;

$R^{25}$ is $C_1$-$C_6$ alkyl; and m is 1, 2, 3, or 4.

174. The siNA of embodiment 172 or 173, wherein $R^1$ is an aryl.

175. The siNA of embodiment 174, wherein the aryl is a phenyl.

176. The siNA according to any one of embodiments 16, 131, 132, and 170, wherein the 5'-stabilized end cap is selected from the group consisting of Formula (1) to Formula (15), Formula (9X) to Formula (12X), and Formula (9Y) to Formula (12Y):

Formula (1)

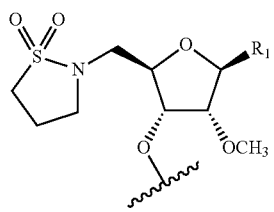

Formula (2)

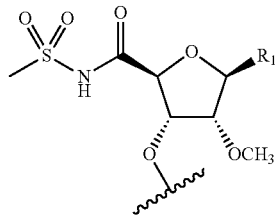

Formula (3)

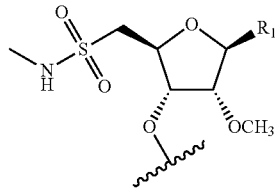

Formula (4)

(Formula (5))

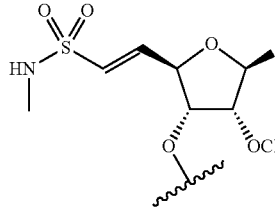

Formula (6)

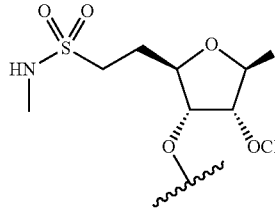

Formula (7)

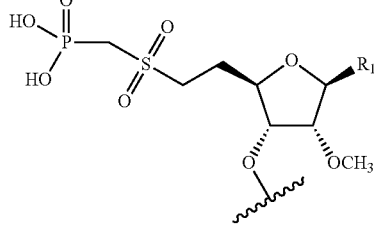

Formula (8)

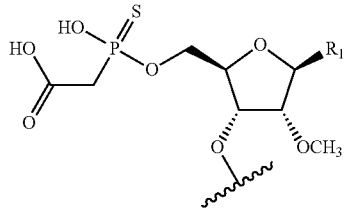

Formula (9)
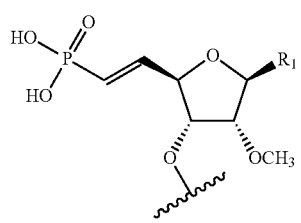
Formula (9X)
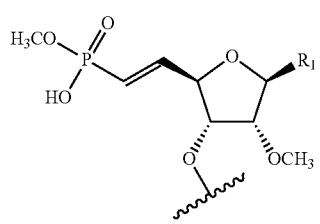
Formula (9Y)
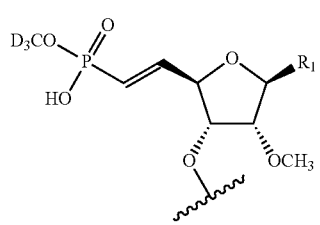
Formula (10)
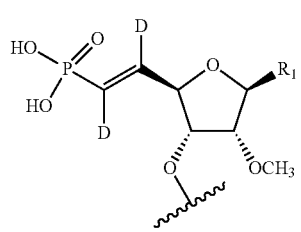
Formula (10X)
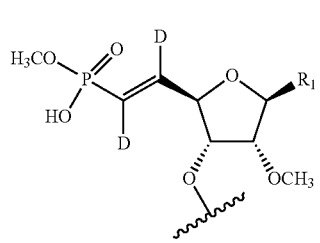
Formula (10Y)
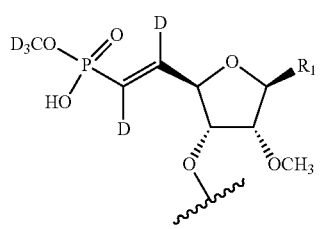
Formula (11)
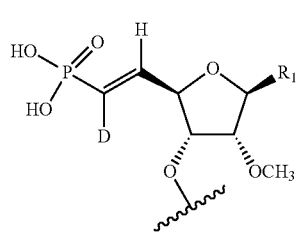
Formula (11X)
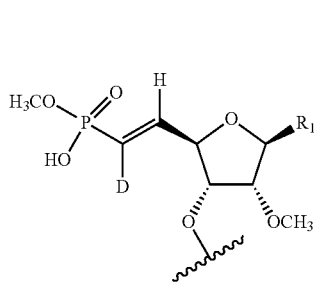
Formula (11Y)
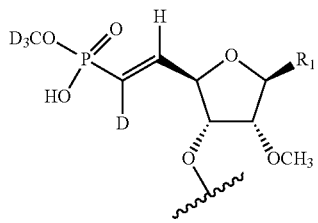
Formula (12)
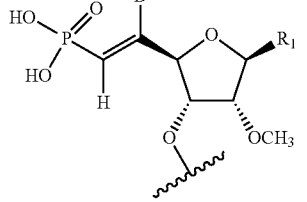
Formula (12X)
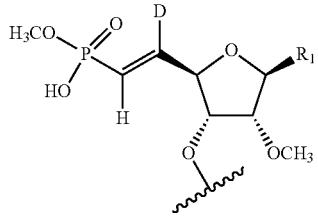
Formula (12Y)
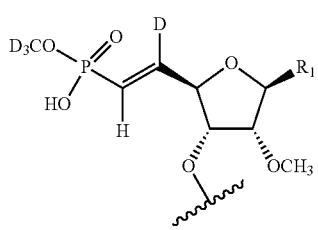
Formula (13)
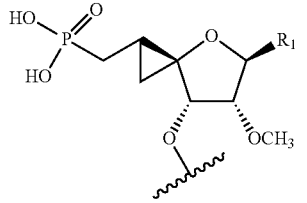
Formula (14)
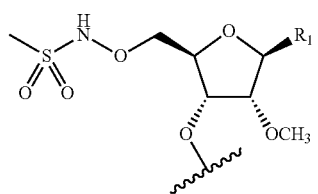

-continued
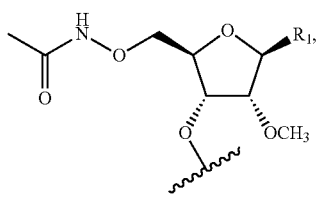
Formula (15)
wherein R¹ is a nucleobase, aryl, heteroaryl, or H.
177. The siNA according to any one of embodiments 16, 131, 132, and 170, wherein the 5'-stabilized end cap is selected from the group consisting of Formulas (1A)-(15A), Formulas (9B)-(12B), Formulas (9AX)-(12AX), Formulas (9AY)-(12AY), Formulas (9BX)-(12BX), and Formulas (9BY)-(12BY):
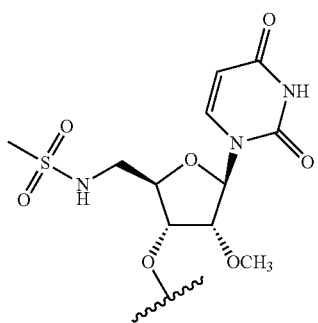
Formula (1A)
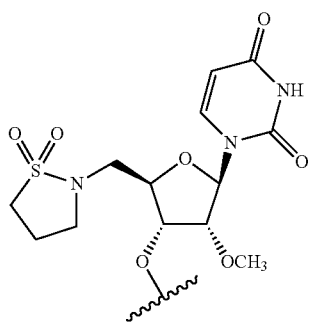
Formula (2A)
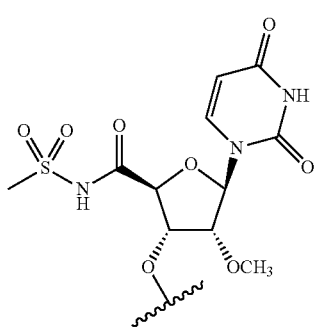
Formula (3A)
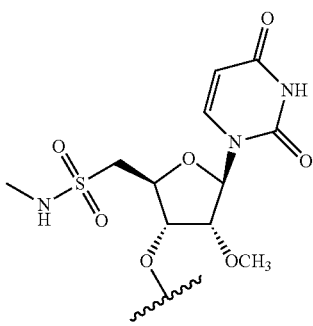
Formula (4A)
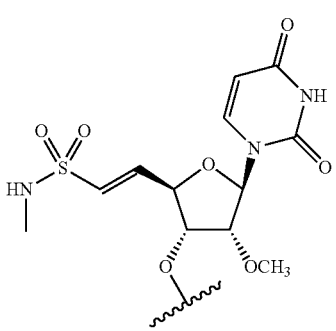
Formula (5A)
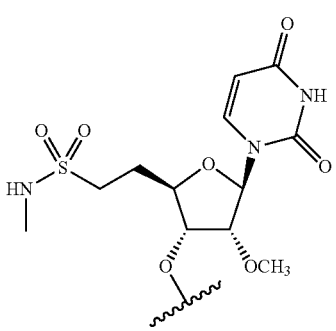
Formula (6A)
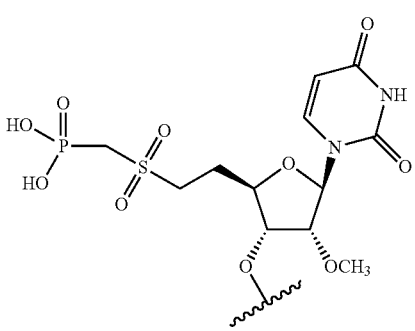
Formula (7A)
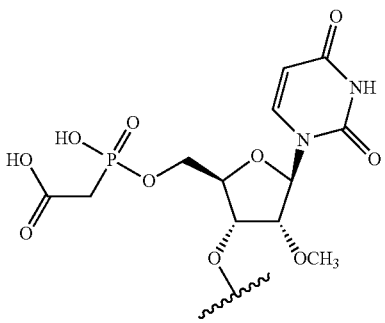
Formula (8A)

Formula (9A)
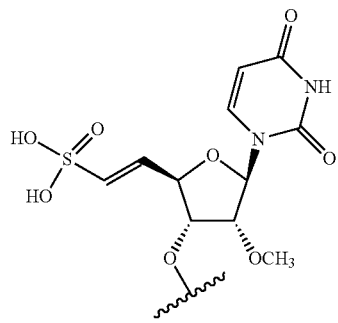
Formula (10A)
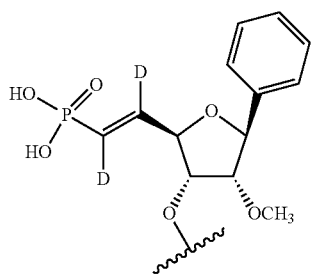
Formula (9AX)
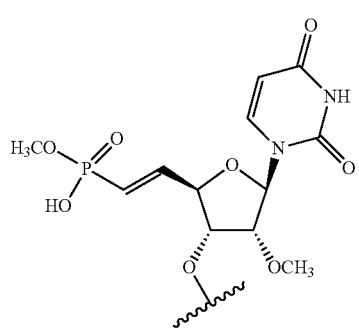
Formula (10AX)
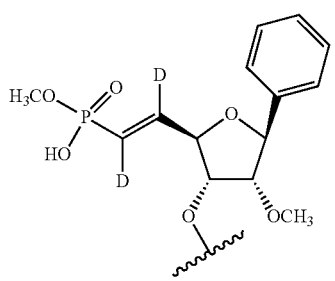
Formula (9AY)
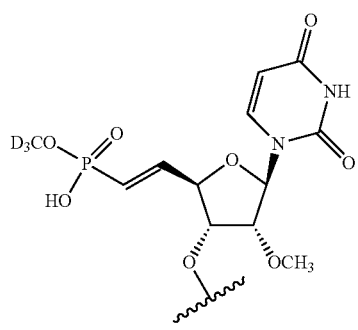
Formula (10AY)
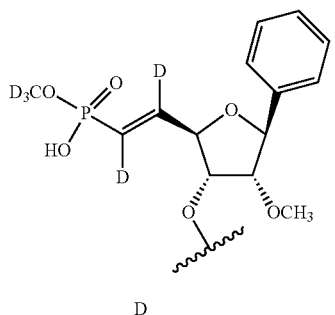
Formula (9B)
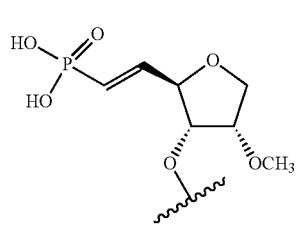
Formula (10B)
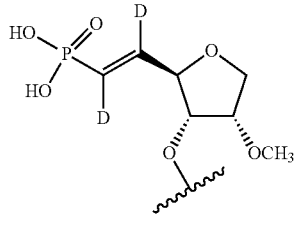
Formula (9BX)
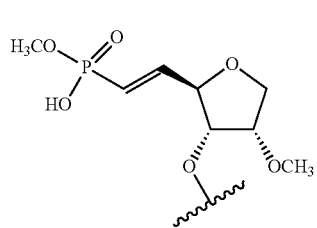
Formula (10BX)
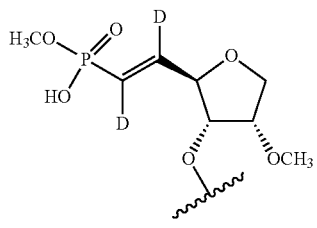
Formula (9BY)
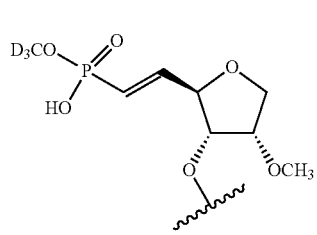
Formula (10BY)
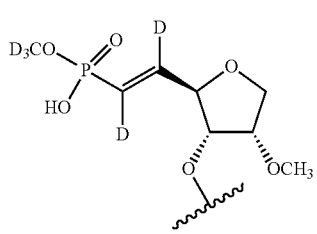

-continued
Formula (11A)
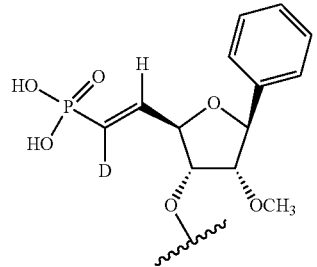
Formula (11AX)
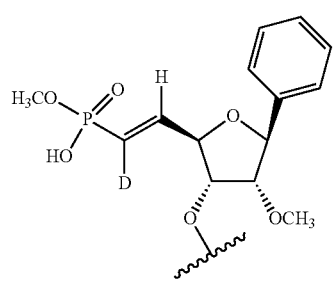
Formula (11AY)
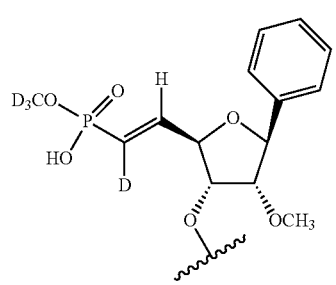
Formula (11B)
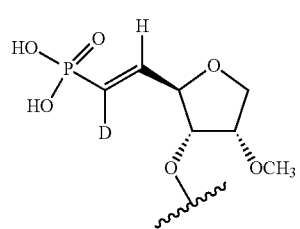
Formula (11BX)
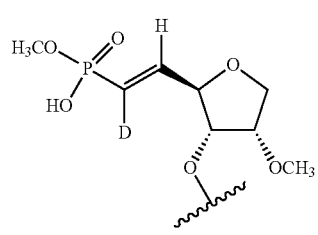
Formula (11BY)
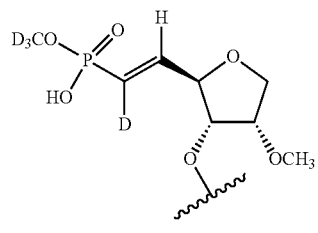
-continued
Formula (12A)
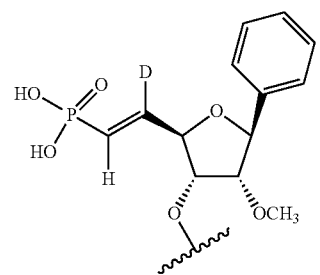
Formula (12AX)
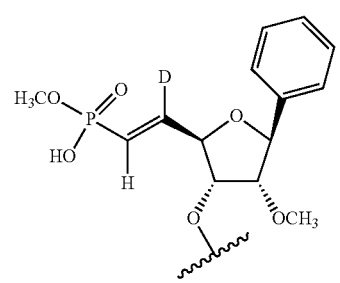
Formula (12AY)
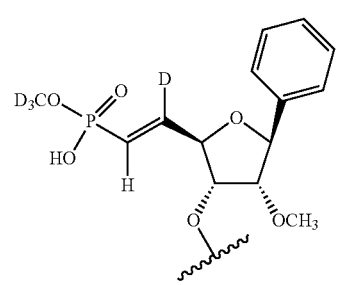
Formula (12B)
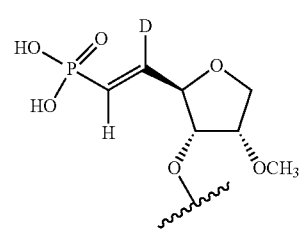
Formula (12BX)
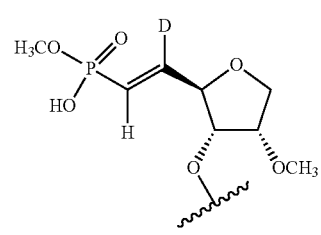
Formula (12BY)
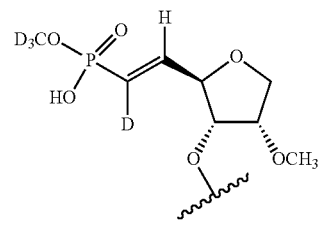

Formula (13A)

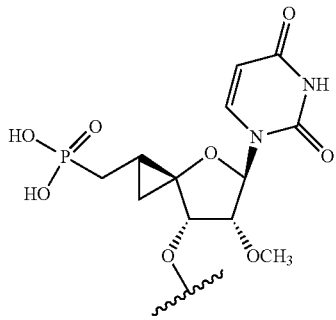

Formula (14A)

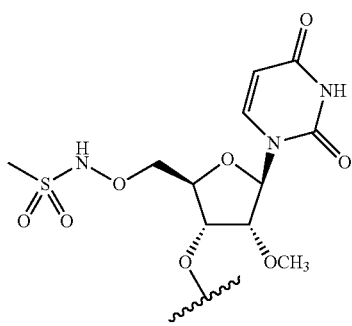

Formula (15A)

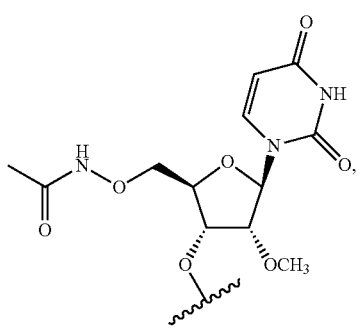

178. The siNA according to any one of embodiments 131, 132, and 170, wherein the 5′-stabilized end cap has the structure of Formula (Ic):

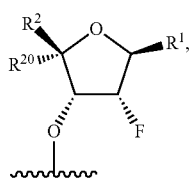

wherein
$R^1$ is a nucleobase, aryl, heteroaryl, or H,
$R^2$ is

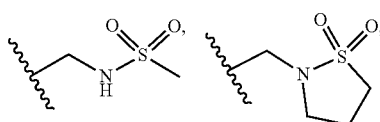

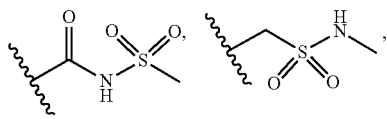

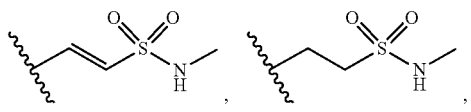

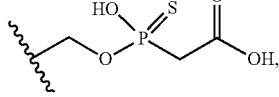

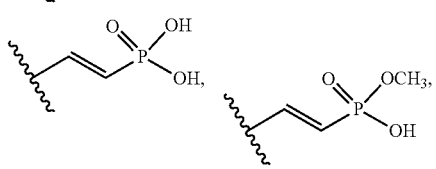

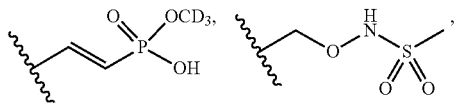

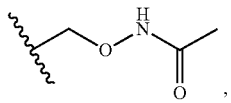

—CH=CD-Z, —CD=CH—Z, —CD=CD-Z, —(CR$^{21}$R$^{22}$)$_n$—Z, or —(C$_2$-C$_6$ alkenylene)-Z and R$^{20}$ is hydrogen; or $R^2$ and $R^{20}$ together form a 3- to 7-membered carbocyclic ring substituted with —(CR$^{21}$R$^{22}$)$_n$—Z or —(C$_2$-C$_6$ alkenylene)-Z;

n is 1, 2, 3, or 4;

Z is —ONR$^{23}$R$^{24}$, —OP(O)OH(CH$_2$)$_m$CO$_2$R$^{23}$, —OP(S)OH(CH$_2$)$_m$CO$_2$R$^{23}$, —P(O)(OH)$_2$, —P(O)(OH)(OCH$_3$), —P(O)(OH)(OCD$_3$), —SO$_2$(CH$_2$)$_m$P(O)(OH)$_2$, —SO$_2$NR$^{23}$R$^{25}$, —NR$^{23}$R$^{24}$, or —NR$^{23}$SO$_2$R$^{24}$;

R$^{21}$ and R$^{22}$ either are independently hydrogen or C$_1$-C$_6$ alkyl, or R$^{21}$ and R$^{22}$ together form an oxo group;

R$^{23}$ is hydrogen or C$_1$-C$_6$ alkyl;

R$^{24}$ is —SO$_2$R$^{25}$ or —C(O)R$^{25}$; or

R$^{23}$ and R$^{24}$ together with the nitrogen to which they are attached form a substituted or unsubstituted heterocyclic ring;

R$^{25}$ is C$_1$-C$_6$ alkyl; and m is 1, 2, 3, or 4.

179. The siNA of embodiment 178, wherein R$^1$ is an aryl.

180. The siNA of embodiment 179, wherein the aryl is a phenyl.

181. The siNA according to any one of embodiments 16, 131, 132, and 170, wherein the 5′-stabilized end cap is selected from the group consisting of Formula (21) to Formula (35):

Formula (21)
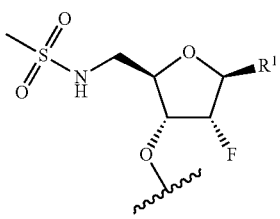
Formula (22)
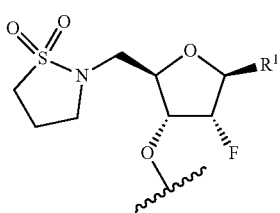
Formula (23)
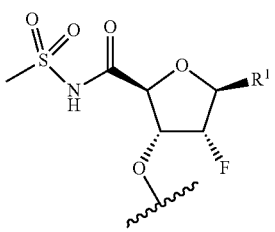
Formula (24)
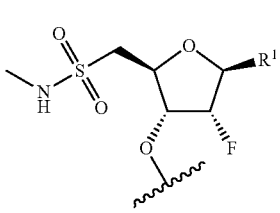
Formula (25)
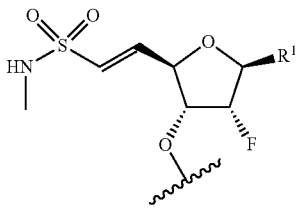
Formula (26)
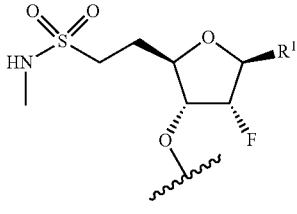
Formula (27)
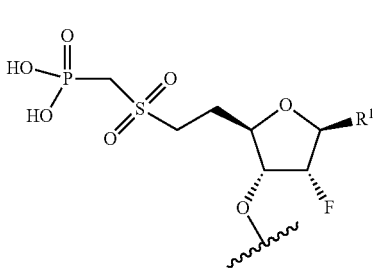
-continued
Formula (28)
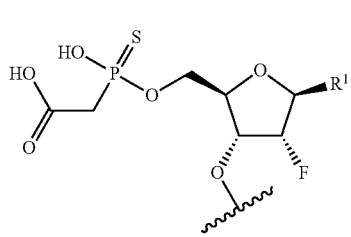
Formula (29)
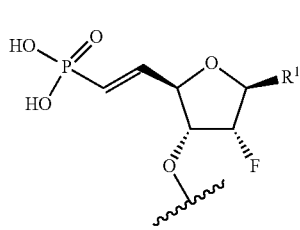
Formula (30)
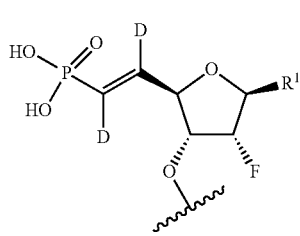
Formula (31)
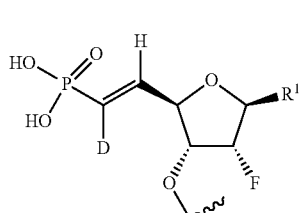
Formula (32)
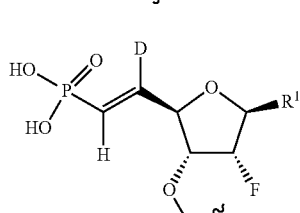
Formula (33)
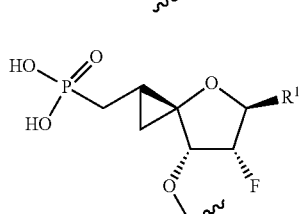
Formula (34)
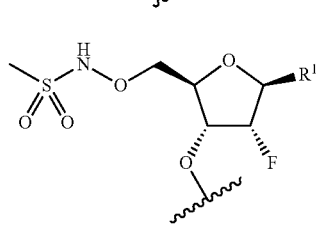

Formula (35)
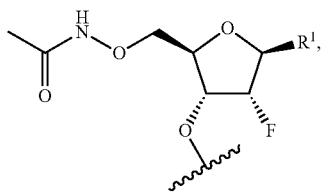
wherein R¹ is a nucleobase, aryl, heteroaryl, or H.
182. The siNA according to any one of embodiments 16, 131, 132, and 170, wherein the 5'-stabilized end cap is selected from the group consisting of Formulas (21A)-(35A), Formulas (29B)-(32B), Formulas (29AX)-(32AX), Formulas (29AY)-(32AY), Formulas (29BX)-(32BX), and Formulas (29BY)-(32BY):
Formula (21A)
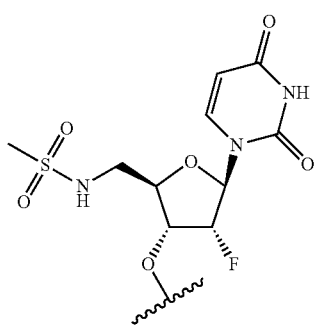
Formula (22A)
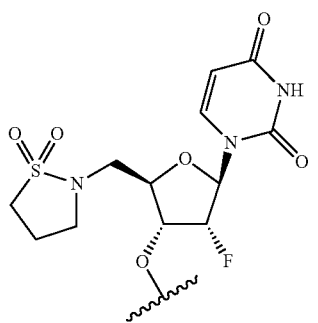
Formula (23A)
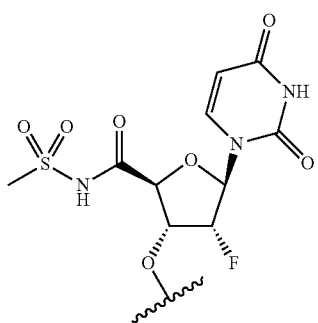
Formula (24A)
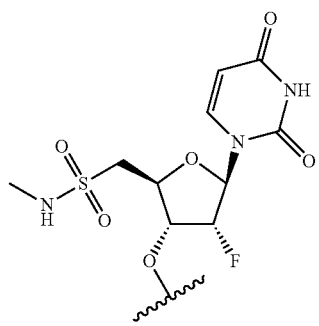
Formula (25A)
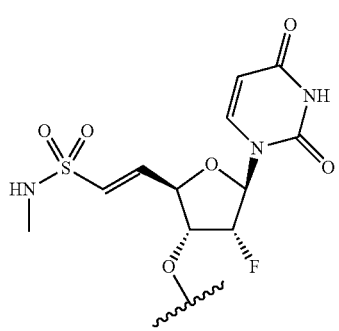
Formula (26A)
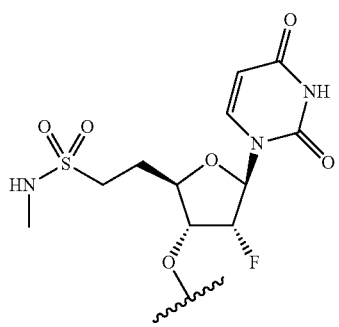
Formula (27A)
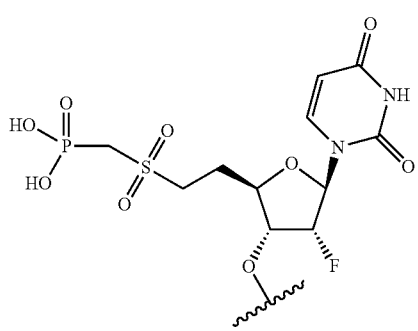
Formula (28A)
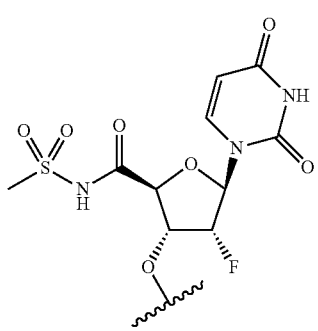

Formula (29A)
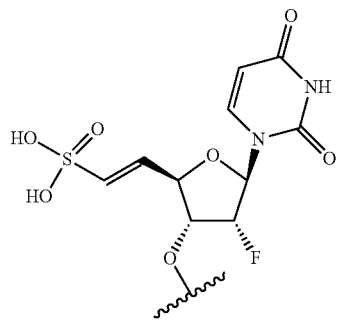
Formula (30A)
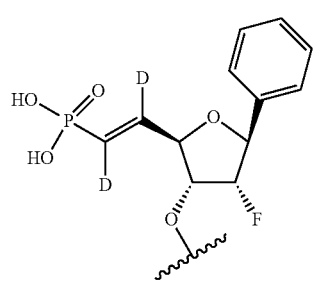
Formula (29AX)
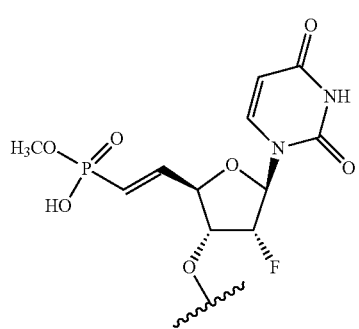
Formula (30AX)
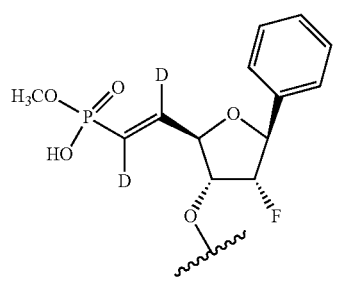
Formula (29AY)
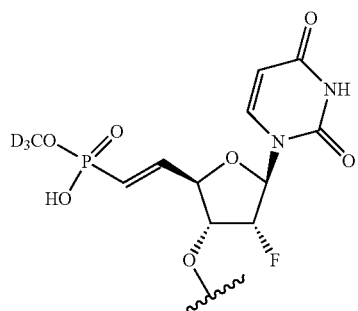
Formula (30AY)
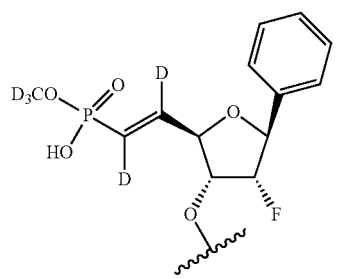
Formula (29B)
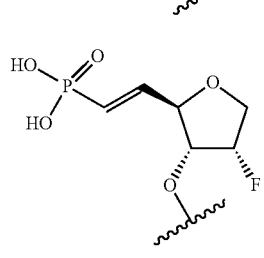
Formula (30B)
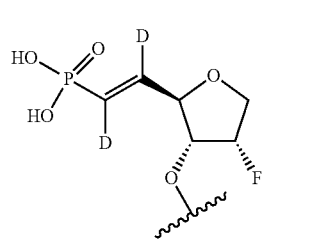
Formula (29BX)
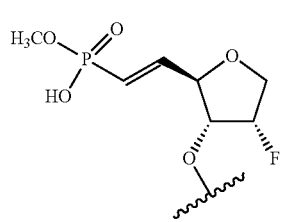
Formula (30BX)
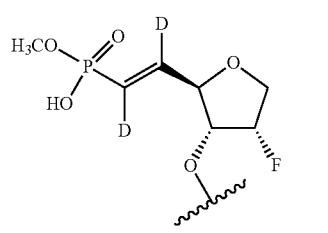
Formula (29BY)
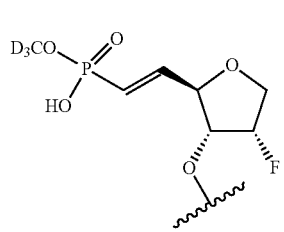
Formula (30BY)
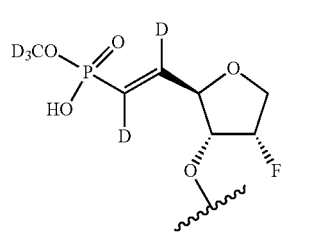

| | |
|---|---|
| Formula (31A) 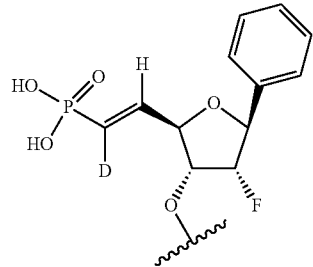 | Formula (32A) 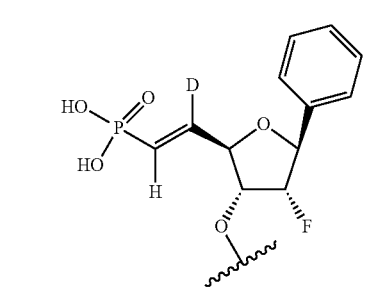 |
| Formula (31AX) 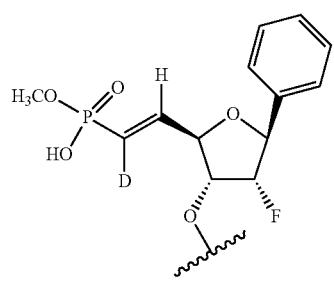 | Formula (32AX) 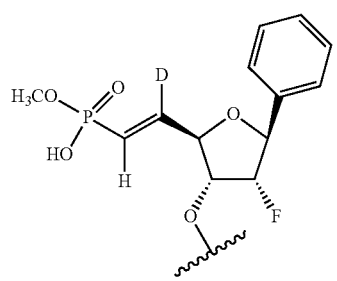 |
| Formula (31AY) 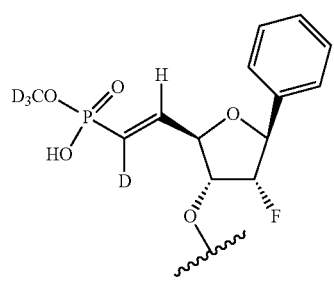 | Formula (32AY) 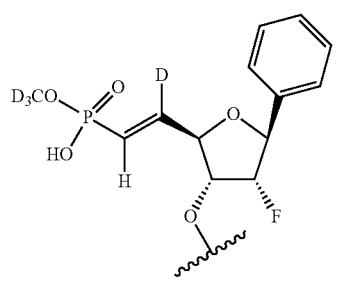 |
| Formula (31B) 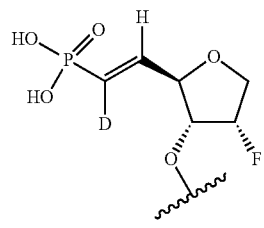 | Formula (32B) 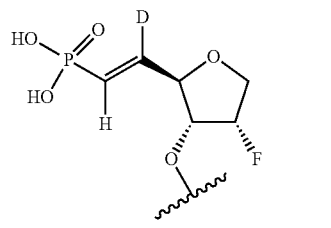 |
| Formula (31BX) 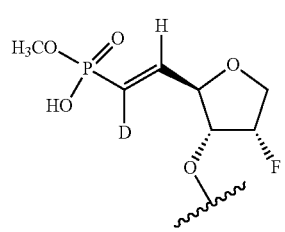 | Formula (32BX) 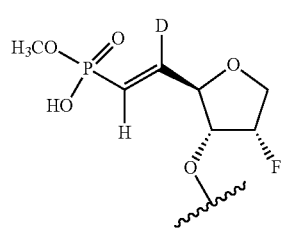 |
| Formula (31BY) 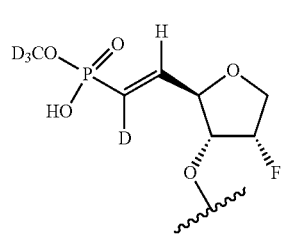 | Formula (32BY) 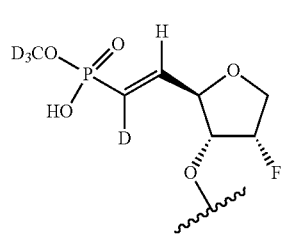 |

Formula (33A)
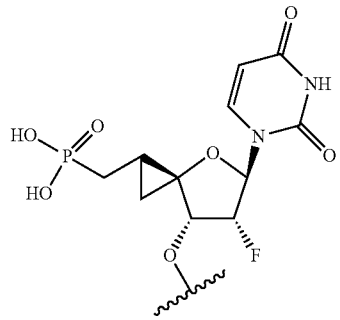

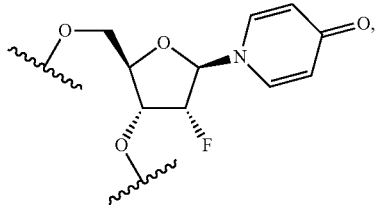

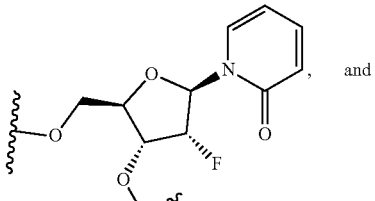

Formula (34A)
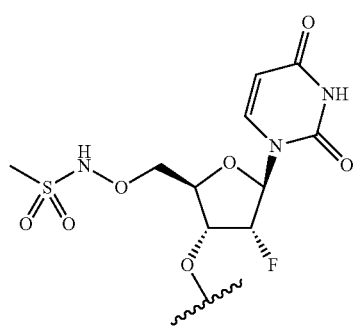

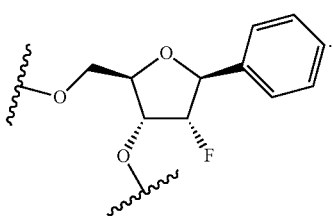

Formula (35A)
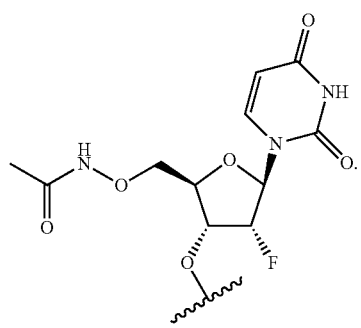

185. The siNA according to any one of embodiments 1-182, wherein the first nucleotide sequence comprises at least one thermally destabilizing nucleotide selected from:

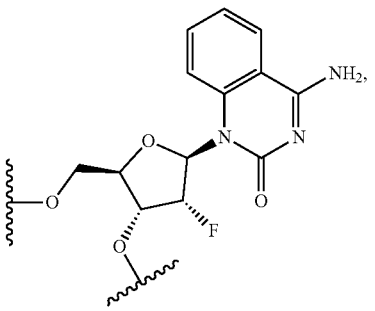

183. The siNA according to any one of embodiments 1-182, wherein the antisense strand comprises at least one thermally destabilizing nucleotide selected from:

184. The siNA according to any one of embodiments 1-182, wherein the sense strand comprises at least one thermally destabilizing nucleotide selected from:

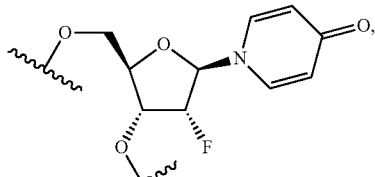

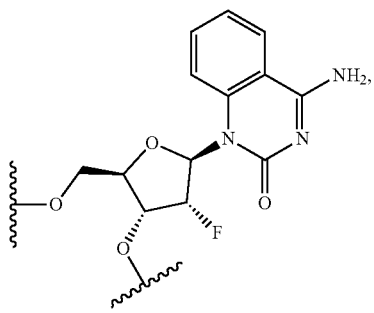

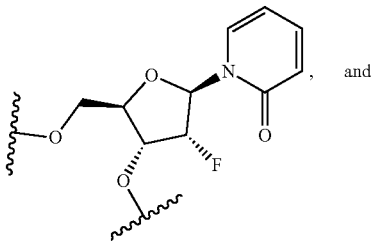

-continued

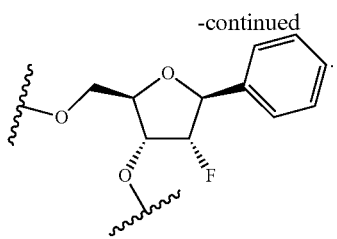

186. The siNA according to any one of embodiments 1-182, wherein the second nucleotide sequence comprises at least one thermally destabilizing nucleotide selected from:

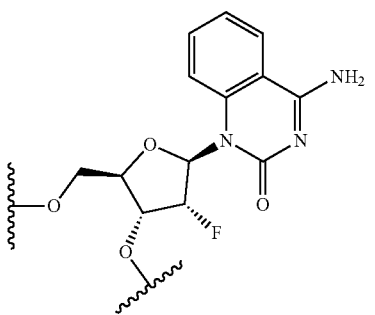

,

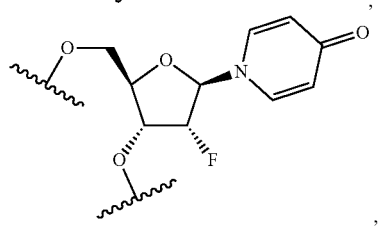

,

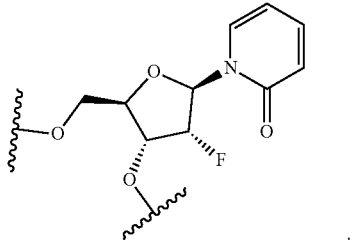

, and

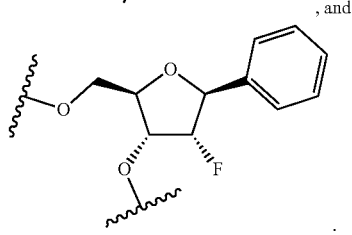

.

187. The siNA according to any one of embodiments 16, 131, 132, and 170-186, wherein the 5'-stabilized end cap is attached to the 5' end of the antisense strand.
188. The siNA of embodiment 187, wherein the 5'-stabilized end cap is attached to the 5' end of the antisense strand via one or more linkers independently selected from a phosphodiester linker, phosphorothioate linker, or phosphorodithioate linker.
189. The siNA according to any one of embodiments 16, 131, 132, and 170-186, wherein the 5'-stabilized end cap is attached to the 5' end of the sense strand.
190. The siNA of embodiment 189, wherein the 5'-stabilized end cap is attached to the 5' end of the sense strand via one or more linkers independently selected from a phosphodiester linker, phosphorothioate linker, or phosphorodithioate linker.
191. The siNA according to any preceding embodiment, wherein the target gene is a viral gene.
192. The siNA of embodiment 191, wherein the viral gene is from a DNA virus.
193. The siNA of embodiment 192, wherein the DNA virus is a double-stranded DNA (dsDNA) virus.
194. The siNA of embodiment 193, wherein the dsDNA virus is a hepadnavirus.
195. The siNA of embodiment 194, wherein the hepadnavirus is a hepatitis B virus (HBV).
196. The siNA of embodiment 195, wherein the HBV is selected from HBV genotypes A-J.
197. The siNA of embodiment 195 or 196, wherein the target gene is selected from the S gene or X gene of the HBV.
198. The siNA according to any one of embodiments 1-197, wherein the second nucleotide sequence is at least about 60%, 65%, 70%, 75%, 80%, 85%, 90%, 95%, or 100% complementary to 15 to 30 nucleotides within positions 200-720 or 1100-1700 of SEQ ID NO: 410.
199. The siNA according to any one of embodiments 1-197, wherein the second nucleotide sequence is at least about 60%, 65%, 70%, 75%, 80%, 85%, 90%, 95%, or 100% complementary to 15 to 30 nucleotides within positions 200-280, 300-445, 460-510, 650-720, 1170-1220, 1250-1300, or 1550-1630 of SEQ ID NO: 410.
200. The siNA according to any one of embodiments 1-197, wherein the second nucleotide sequence is at least about 60%, 65%, 70%, 75%, 80%, 85%, 90%, 95%, or 100% complementary to 15 to 30 nucleotides within positions 200-230, 250-280, 300-330, 370-400, 405-445, 460-500, 670-700, 1180-1210, 1260-1295, 1520-1550, or 1570-1610 of SEQ ID NO: 410.
201. The siNA according to any one of embodiments 1-197, wherein the second nucleotide sequence is at least about 60%, 65%, 70%, 75%, 80%, 85%, 90%, 95%, or 100% complementary to 15 to 30 nucleotides starting at position 203, 206, 254, 305, 375, 409, 412, 415, 416, 419, 462, 466, 467, 674, 676, 1182, 1262, 1263, 1268, 1526, 1577, 1578, 1580, 1581, 1583, or 1584 of SEQ ID NO: 410.
202. The siNA according to any one of embodiments 1-201, wherein the first nucleotide sequence is at least about 60%, 65%, 70%, 75%, 80%, 85%, 90%, 95%, or 100% identical to 15 to 30 nucleotides within positions 200-720 or 1100-1700 of SEQ ID NO: 410.
203. The siNA according to any one of embodiments 1-201, wherein the first nucleotide sequence is at least about 60%, 65%, 70%, 75%, 80%, 85%, 90%, 95%, or 100% identical to 15 to 30 nucleotides within positions 200-280, 300-445, 460-510, 650-720, 1170-1220, 1250-1300, or 1550-1630 of SEQ ID NO: 410.
204. The siNA according to any one of embodiments 1-201, wherein the first nucleotide sequence is at least about 60%, 65%, 70%, 75%, 80%, 85%, 90%, 95%, or 100% identical to 15 to 30 nucleotides within positions 200-230, 250-280, 300-330, 370-400, 405-445, 460-500, 670-700, 1180-1210, 1260-1295, 1520-1550, or 1570-1610 of SEQ ID NO: 410.
205. The siNA according to any one of embodiments 1-201, wherein the first nucleotide sequence is at least about 60%, 65%, 70%, 75%, 80%, 85%, 90%, 95%, or 100% identical to 15 to 30 nucleotides starting at position 203, 206, 254, 305, 375, 409, 412, 415, 416, 419, 462, 466, 467, 674, 676, 1182, 1262, 1263, 1268, 1526, 1577, 1578, 1580, 1581, 1583, or 1584 of SEQ ID NO: 410.

206. The siNA according to any preceding embodiment, wherein the first nucleotide sequence comprises a nucleotide sequence of any one SEQ ID NOs: 1-56, 103-158, and 205-260.
207. The siNA according to any preceding embodiment, wherein the second nucleotide sequence comprises a nucleotide sequence of any one of SEQ ID NOs: 57-102, 159-204, and 261-306.
208. The siNA according to any preceding embodiment, wherein the sense strand comprises a nucleotide sequence of any one of SEQ ID NOs: 307-362 and 415-444.
209. The siNA according to any preceding embodiment, wherein the antisense strand comprises a nucleotide sequence of any one of SEQ ID NOs: 363-409, 445-533, and 536-539.
210. The siNA according to any preceding embodiment, wherein at least one end of the siNA is a blunt end.
211. The siNA according to any preceding embodiment, wherein at least one end of the siNA comprises an overhang, wherein the overhang comprises at least one nucleotide.
212. The siNA according to any one of embodiments 1-209, wherein both ends of the siNA comprise an overhang, wherein the overhang comprises at least one nucleotide.
213. The siNA according to any preceding embodiment, wherein the siNA is selected from ds-siNA-001 to ds-siNA-0178.
214. The siNA according to any preceding embodiment, wherein at least one 2'-fluoro nucleotide or 2'-O-methyl nucleotide is a 2'-fluoro or 2-O-methyl nucleotide mimic of Formula (V):

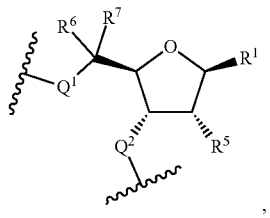

wherein
  $R^1$ is independently a nucleobase, aryl, heteroaryl, or H,
  $Q^1$ and $Q^2$ are independently S or O,
  $R^5$ is independently —$OCD_3$, —F, or —$OCH_3$, and
  $R^6$ and $R^7$ are independently H, D, or $CD_3$.
215. The siNA of embodiment 214, wherein the 2'-fluoro or 2'-O-methyl nucleotide mimic is a nucleotide mimic of Formula (16)-Formula (20):

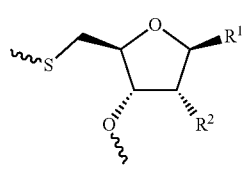

Formula (16)

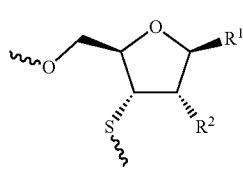

Formula (17)

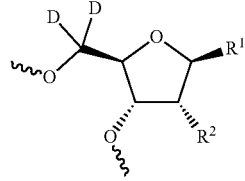

Formula (18)

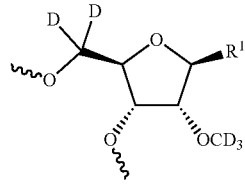

Formula (19)

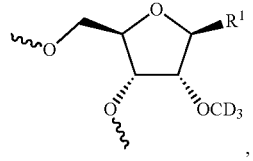

Formula (20)

wherein $R^1$ is a nucleobase and $R^2$ is independently F or —$OCH_3$.
216. The siNA according to any preceding embodiment, wherein at least one 2'-fluoro nucleotide is a 2'-fluoro nucleotide mimic.
217. The siNA according to embodiment 216, wherein at least one 2'-fluoro nucleotide on the antisense strand or the second nucleotide sequence is a 2'-fluoro nucleotide mimic.
218. The siNA according to embodiment 216 or 217, wherein the nucleotide at position 2 from the 5' end of the antisense strand or the second nucleotide sequence is a 2'-fluoro nucleotide mimic.
219. The siNA according to any one of embodiments 216-218, wherein the nucleotide at position 5 from the 5' end of the antisense strand or the second nucleotide sequence is a 2'-fluoro nucleotide mimic.
220. The siNA according to any one of embodiments 216-219, wherein the nucleotide at position 6 from the 5' end of the antisense strand or the second nucleotide sequence is a 2'-fluoro nucleotide mimic.
221. The siNA according any one of embodiments 216-220, wherein the nucleotide at position 8 from the 5' end of the antisense strand or the second nucleotide sequence is a 2'-fluoro nucleotide mimic.
222. The siNA according to any one of embodiments 216-221, wherein the nucleotide at position 10 from the 5' end of the antisense strand or the second nucleotide sequence is a 2'-fluoro nucleotide mimic.
223. The siNA according to any one of embodiments 216-222, wherein the nucleotide at position 14 from the 5' end of the antisense strand or the second nucleotide sequence is a 2'-fluoro nucleotide mimic.
224. The siNA according to any one of embodiments 216-223, wherein the nucleotide at position 16 from the 5' end of the antisense strand or the second nucleotide sequence is a 2'-fluoro nucleotide mimic.
225. The siNA according to any one of embodiments 216-224, wherein the nucleotide at position 17 from the 5' end of the antisense strand or the second nucleotide sequence is a 2'-fluoro nucleotide mimic.
226. The siNA according to any one of embodiments 216-225, wherein at least one 2'-fluoro nucleotide on the sense strand or the first nucleotide sequence is a 2'-fluoro nucleotide mimic.

227. The siNA according to any one of embodiments 216-226, wherein the nucleotide at position 3 from the 5' end of the sense strand or the first nucleotide sequence is a 2'-fluoro nucleotide mimic.

228. The siNA according to any one of embodiments 216-227, wherein the nucleotide at position 5 from the 5' end of the sense strand or the first nucleotide sequence is a 2'-fluoro nucleotide mimic.

229. The siNA according to any one of embodiments 216-228, wherein the nucleotide at position 7 from the 5' end of the sense strand or the first nucleotide sequence is a 2'-fluoro nucleotide mimic.

230. The siNA according to any one of embodiments 216-229, wherein the nucleotide at position 8 from the 5' end of the sense strand or the first nucleotide sequence is a 2'-fluoro nucleotide mimic.

231. The siNA according to any one of embodiments 216-230, wherein the nucleotide at position 9 from the 5' end of the sense strand or the first nucleotide sequence is a 2'-fluoro nucleotide mimic.

232. The siNA according to any one of embodiments 216-231, wherein the nucleotide at position 10 from the 5' end of the sense strand or the first nucleotide sequence is a 2'-fluoro nucleotide mimic.

233. The siNA according to any one of embodiments 216-232, wherein the nucleotide at position 11 from the 5' end of the sense strand or the first nucleotide sequence is a 2'-fluoro nucleotide mimic.

234. The siNA according to any one of embodiments 216-233, wherein the nucleotide at position 12 from the 5' end of the sense strand or the first nucleotide sequence is a 2'-fluoro nucleotide mimic.

235. The siNA according to any one of embodiments 216-234, wherein the nucleotide at position 14 from the 5' end of the sense strand or the first nucleotide sequence is a 2'-fluoro nucleotide mimic.

236. The siNA according to any one of embodiments 216-235, wherein the nucleotide at position 17 from the 5' end of the sense strand or the first nucleotide sequence is a 2'-fluoro nucleotide mimic.

237. The siNA according to any one of embodiments 216-236, wherein at least 1, 2, 3, 4, 5, 6, or more 2'-fluoro nucleotide mimics is a f4P nucleotide

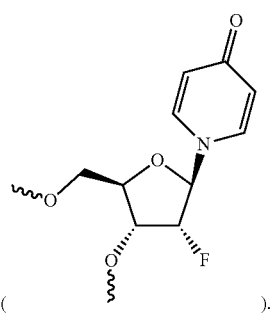

238. The siNA according to any one of embodiments 216-237, wherein less than or equal to 10, 9, 8, 7, 6, 5, 4, 3, or 2 2'-fluoro nucleotide mimics is a f4P nucleotide

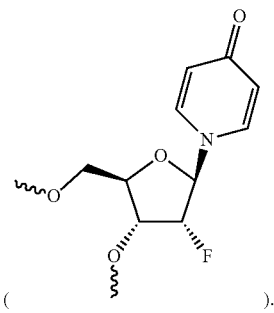

239. The siNA according to any one of embodiments 216-238, wherein 1, 2, 3, 4, 5, 6, or more 2'-fluoro nucleotide mimics is a f2P nucleotide

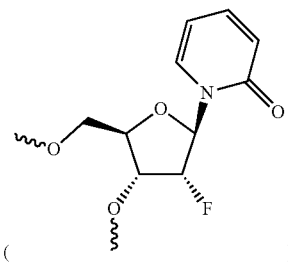

240. The siNA according to any one of embodiments 216-239, wherein less than or equal to 10, 9, 8, 7, 6, 5, 4, 3, or 2 2'-fluoro nucleotide mimics is a f2P nucleotide

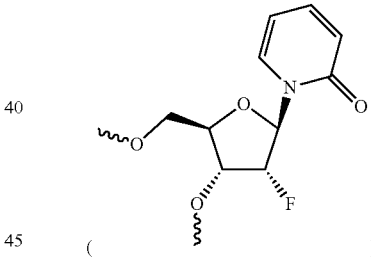

241. The siNA according to any one of embodiments 216-240, wherein 1, 2, 3, 4, 5, 6, or more 2'-fluoro nucleotide mimics is a fX nucleotide

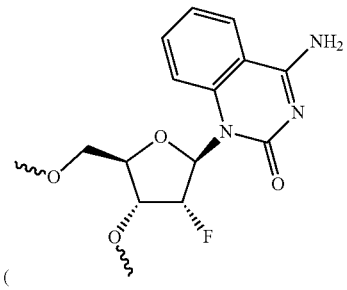

242. The siNA according to any one of embodiments 216-241, wherein less than or equal to 10, 9, 8, 7, 6, 5, 4, 3, or 2 2'-fluoro nucleotide mimics is a fX nucleotide

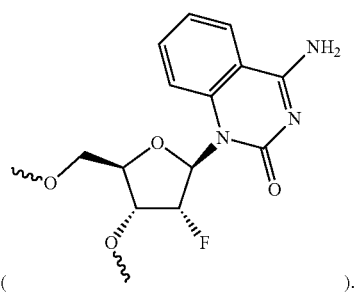

( ).

243. The siNA according to any preceding embodiment, wherein the first nucleotide from the 5' end of the sense strand or first nucleotide sequence is a d2vd3 nucleotide

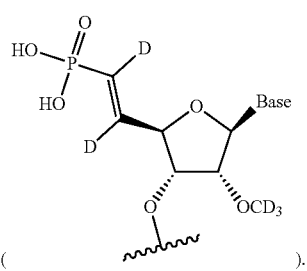

( ).

244. The siNA according to any preceding embodiment, wherein the first nucleotide from the 3' end of the sense strand or first nucleotide sequence is a d2vd3 nucleotide

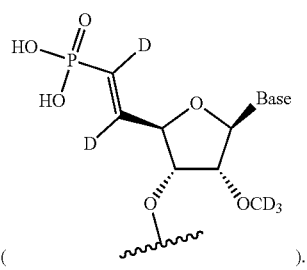

( ).

245. The siNA according to any preceding embodiment, wherein the first nucleotide from the 5' end of the antisense strand or second nucleotide sequence is a d2vd3 nucleotide

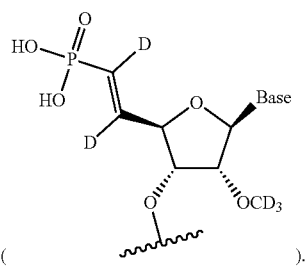

( ).

246. The siNA according to any preceding embodiment, wherein the first nucleotide from the 3' end of the antisense strand or second nucleotide sequence is a d2vd3 nucleotide

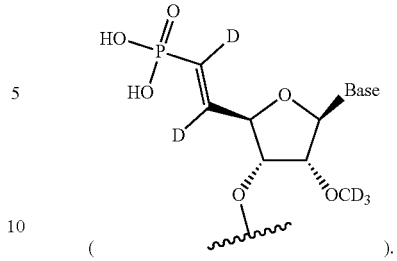

( ).

247. A composition comprising the siNA according to any one of embodiments 1-246.
248. A composition comprising 2, 3, 4, 5, 6, 7, 8, 9, 10 or more siNAs according to any one of embodiments 1-246.
249. The composition of embodiment 248, wherein at least 1, 2, 3, 4, 5, or more siNAs target an S gene of HBV.
250. The composition of embodiment 248 or 249, wherein at least 1, 2, 3, 4, 5, or more siNAs target an X gene of HBV.
251. The composition according to any one of embodiments 247-250, further comprising an additional HBV treatment agent.
252. The composition of embodiment 251, wherein the additional HBV treatment agent is selected from a nucleotide analog, nucleoside analog, a capsid assembly modulator (CAM), a recombinant interferon, an entry inhibitor, a small molecule immunomodulator and oligonucleotide therapy.
253. The composition of embodiment 252, wherein the oligonucleotide therapy is an additional siNA.
254. The composition of embodiment 253, wherein the additional siNA is selected from any of ds-siNA-001 to ds-siNA-0178.
255. The composition of embodiment 252, wherein the oligonucleotide therapy is an antisense oligonucleotide (ASO), NAPs, or STOPS™
256. The composition of embodiment 255, wherein the ASO is ASO 1 or ASO 2.
257. The composition of embodiment 251 or 252, wherein the additional HBV treatment agent is selected from HBV STOPS™ ALG-010133, HBV CAM ALG-000184, ASO 1, recombinant interferon alpha 2b, IFN-a, PEG-IFN-a-2a, lamivudine, telbivudine, adefovir dipivoxil, clevudine, entecavir, tenofovir alafenamide, tenofovir disoproxil, NVR3-778, BAY41-4109, JNJ-632, JNJ-3989 (ARO-HBV), RG6004, GSK3228836, REP-2139, REP-2165, AB-729, VIR-2218, RG6346 (DCR-HBVS), JNJ-6379, GLS4, ABI-HO731, JNJ-440, NZ-4, RG7907, EDP-514, AB-423, AB-506, ABI-H03733 and ABI-H2158.
258. A method of treating a disease in a subject in need thereof, comprising administering to the subject the siNA according to any one of embodiments 1-246.
259. A method of treating a disease in a subject in need thereof, comprising administering to the subject the composition according to any one of embodiments 247-257.
260. The method of embodiment 258 or 259, wherein the disease is a viral disease.
261. The method of embodiment 260, wherein the viral disease is caused by a DNA virus.
262. The method of embodiment 261, wherein the DNA virus is a double stranded DNA (dsDNA) virus.
263. The method of embodiment 262, wherein the dsDNA virus is a hepadnavirus.
264. The method of embodiment 263, wherein the hepadnavirus is a hepatitis B virus (HBV).

265. The method of embodiment 264, wherein the HBV is selected from HBV genotypes A-J.
266. The method of any of embodiments 258-265, further comprising administering an additional HBV treatment agent.
267. The method of embodiment 266, wherein the siNA or the composition and the additional HBV treatment agent are administered concurrently.
268. The method of embodiment 266, wherein the siNA or the composition and the additional HBV treatment agent are administered sequentially.
269. The method of embodiment 266, wherein the siNA or the composition is administered prior to administering the additional HBV treatment agent.
270. The method of embodiment 266, wherein the siNA or the composition is administered after administering the additional HBV treatment agent.
271. The method of any one of embodiments 266-270, wherein the additional HBV treatment agent is selected from a nucleotide analog, nucleoside analog, a capsid assembly modulator (CAM), a recombinant interferon, an entry inhibitor, a small molecule immunomodulator and oligonucleotide therapy.
272. The method of embodiment 271, wherein the oligonucleotide therapy is an additional siNA.
273. The method of embodiment 272, wherein the additional siNA is selected from any of ds-siNA-001 to ds-siNA-0178.
274. The method of embodiment 271, wherein the oligonucleotide therapy is an antisense oligonucleotide (ASO), NAPs, or STOPs.
275. The method of embodiment 274, wherein the ASO is ASO 1 or ASO 2.
276. The method of embodiment 270 or 271, wherein the additional HBV treatment agent is selected from HBV STOPS™ ALG-010133, HBV CAM ALG-000184, ASO 1, recombinant interferon alpha 2b, IFN-a, PEG-IFN-a-2a, lamivudine, telbivudine, adefovir dipivoxil, clevudine, entecavir, tenofovir alafenamide, tenofovir disoproxil, NVR3-778, BAY41-4109, JNJ-632, JNJ-3989 (ARO-HBV), RG6004, GSK3228836, REP-2139, REP-2165, AB-729, VIR-2218, RG6346 (DCR-HBVS), JNJ-6379, GLS4, ABI-HO731, JNJ-440, NZ-4, RG7907, EDP-514, AB-423, AB-506, ABI-H03733 and ABI-H2158.
277. The method of embodiment 258 or 259, wherein the disease is a liver disease.
278. The method of embodiment 277, wherein the liver disease is a nonalcoholic fatty liver disease (NAFLD) or hepatocellular carcinoma (HCC).
279. The method of embodiment 278, wherein the NAFLD is nonalcoholic steatohepatitis (NASH).
280. The method of any of embodiments 277-279 further comprising administering to the subject a liver disease treatment agent.
281. The method of embodiment 280, wherein the liver disease treatment agent is selected from a peroxisome proliferator-activator receptor (PPAR) agonist, farnesoid X receptor (FXR) agonist, lipid-altering agent, and incretin-based therapy.
282. The method of embodiment 281, wherein the PPAR agonist is selected from a PPARα agonist, dual PPARα/δ agonist, PPARγ agonist, and dual PPARα/γ agonist.
283. The method of embodiment 282, wherein the dual PPARα agonist is a fibrate.
284. The method of embodiment 282, wherein the PPARα/δ agonist is elafibranor.
285. The method of embodiment 282, wherein the PPARγ agonist is a thiazolidinedione (TZD).
286. The method of embodiment 282, wherein TZD is pioglitazone.
287. The method of embodiment 282, wherein the dual PPARα/γ agonist is saroglitazar.
288. The method of embodiment 281, wherein the FXR agonist is obeticholic acis (OCA).
289. The method of embodiment 281, wherein the lipid-altering agent is aramchol.
290. The method of embodiment 281, wherein the incretin-based therapy is a glucagon-like peptide 1 (GLP-1) receptor agonist or dipeptidyl peptidase 4 (DPP-4) inhibitor.
291. The method of embodiment 290, wherein the GLP-1 receptor agonist is exenatide or liraglutide.
292. The method of embodiment 290, wherein the DPP-4 inhibitor is sitagliptin or vildagliptin.
293. The method of any one of embodiments 280-292, wherein the siNA or composition and the liver disease treatment agent are administered concurrently.
294. The method of any one of embodiments 280-292, wherein the siNA or composition and the liver disease treatment agent are administered sequentially.
295. The method of any one of embodiments 280-292, wherein the siNA or composition is administered prior to administering the liver disease treatment agent.
296. The method of any one of embodiments 280-292, wherein the siNA or composition is administered after administering the liver disease treatment agent.
297. The method of any of one embodiments 258-296, wherein the siNA or the composition is administered at a dose of at least 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg 14 mg/kg, or 15 mg/kg.
298. The method of any of one embodiments 258-296, wherein the siNA or the composition is administered at a dose of between 0.5 mg/kg to 50 mg/kg, 0.5 mg/kg to 40 mg/kg 0.5 mg/kg to 30 mg/kg, 1 mg/kg to 50 mg/kg, 1 mg/kg to 40 mg/kg, 1 mg/kg to 30 mg/kg, 1 mg/kg to 20 mg/kg, 3 mg/kg to 50 mg/kg, 3 mg/kg to 40 mg/kg, 3 mg/kg to 30 mg/kg, 3 mg/kg to 20 mg/kg, 3 mg/kg to 15 mg/kg, 3 mg/kg to 10 mg/kg, 4 mg/kg to 50 mg/kg, 4 mg/kg to 40 mg/kg, 4 mg/kg to 30 mg/kg, 4 mg/kg to 20 mg/kg, 4 mg/kg to 15 mg/kg, 4 mg/kg to 10 mg/kg, 5 mg/kg to 50 mg/kg, 5 mg/kg to 40 mg/kg, 5 mg/kg to 30 mg/kg, 5 mg/kg to 20 mg/kg, 5 mg/kg to 15 mg/kg, or 5 mg/kg to 10 mg/kg.
299. The method of any of one embodiments 258-298, wherein the siNA or the composition is administered at least 1, 2, 3, 4, 5, 6, 7, 8, 9, or 10 times.
300. The method of any of one embodiments 258-298, wherein the siNA or the composition is administered at least 1, 2, 3, 4, 5, 6, 7, 8, 9, or 10 times a day, at least 1, 2, 3, 4, 5, 6, 7, 8, 9, or 10 times a week, or at least 1, 2, 3, 4, 5, 6, 7, 8, 9, or 10 times a month.
301. The method of any of one embodiments 258-300, wherein the siNA or the composition are administered at least once every 1, 2, 3, 4, 5, 6, 7, 8, 9, 10, 11, 12, 13, 14, 15, 16, 17, 18, 19, 20, or 21 days.
302. The method of any of one embodiments 258-301, wherein the siNA or the composition is administered for a period of at least 1, 2, 3, 4, 5, 6, 7, 8, 9, 10, 11, 12, 13, 14, 15, 16, 17, 18, 19, 20, or 21 days, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 51, 52, 53, 54, or 55 weeks.
303. The method of any of one embodiments 258-302, wherein the siNA or the composition is administered at a single dose of 5 mg/kg.

304. The method of any of one embodiments 258-302, wherein the siNA or the composition is administered at a single dose of 10 mg/kg.

305. The method of any of one embodiments 258-302, wherein the siNA or the composition is administered at three doses of 10 mg/kg once a week.

306. The method of any of one embodiments 258-302, wherein the siNA or the composition is administered at three doses of 10 mg/kg once every three days.

307. The method of any of one embodiments 258-302, wherein the siNA or the composition is administered at five doses of 10 mg/kg once every three days.

308. The method of any of one embodiments 258-302, wherein the siNA or the composition is administered at six doses of ranging from 1 mg/kg to 15 mg/kg, 1 mg/kg to 10 mg/kg, 2 mg/kg to 15 mg/kg, 2 mg/kg to 10 mg/kg, 3 mg/kg to 15 mg/kg, or 3 mg/kg to 10 mg/kg.

309. The method of embodiment 308, wherein the first dose and second dose are administered at least 3 days apart.

310. The method of embodiment 308 or 309, wherein the second dose and third dose are administered at least 4 days apart.

311. The method of any one of embodiments 308-310, wherein the third dose and fourth dose, fourth dose and fifth dose, or fifth dose and sixth dose are administered at least 7 days apart.

312. The method of any one of embodiments 258-311, wherein the siNA or the composition are administered in a particle or viral vector.

313. The method of embodiment 312, wherein the viral vector is a vector of adenovirus, adeno-associated virus (AAV), alphavirus, flavivirus, herpes simplex virus, lentivirus, measles virus, picornavirus, poxvirus, retrovirus, or rhabdovirus.

314. The method of embodiment 312, wherein the viral vector is a recombinant viral vector.

315. The method according to any one of embodiments 312-314, wherein the viral vector is selected from AAVrh.74, AAVrh.10, AAVrh.20, AAV-1, AAV-2, AAV-3, AAV-4, AAV-5, AAV-6, AAV-7, AAV-8, AAV-9, AAV-10, AAV-11, AAV-12 and AAV-13.

316. The method according to any one of embodiments 258-315, wherein the siNA or the composition is administered systemically.

317. The method according to any one of embodiments 258-315, wherein the siNA or the composition is administered locally.

318. The method according to any one of embodiments 258-317, wherein the siNA or the composition is administered intravenously, subcutaneously, or intramuscularly.

319. Use of the siNA according to any one of embodiments 1-246 or the composition according to any one of embodiments 247-257 in the manufacture of a medicament for treating a disease.

320. The use of embodiment 319, wherein the disease is a viral disease.

321. The use of embodiment 320, wherein the viral disease is caused by a DNA virus.

322. The use of embodiment 321, wherein the DNA virus is a double stranded DNA (dsDNA virus).

323. The use of embodiment 321, wherein the dsDNA virus is a hepadnavirus.

324. The use of embodiment 323, wherein the hepadnavirus is a hepatitis B virus (HBV).

325. The use of embodiment 324, wherein the HBV is selected from HBV genotypes A-J.

326. The use of any of one of embodiments 319-325, further comprising an additional HBV treatment agent in the manufacture of the medicament.

327. The use of embodiment 326, wherein the additional HBV treatment agent is selected from a nucleotide analog, nucleoside analog, a capsid assembly modulator (CAM), a recombinant interferon, an entry inhibitor, a small molecule immunomodulator and oligonucleotide therapy.

328. The use of embodiment 327, wherein the oligonucleotide therapy is an additional siNA.

329. The use of embodiment 328, wherein the additional siNA is selected from any of ds-siNA-001 to ds-siNA-0178.

330. The use of embodiment 327, wherein the oligonucleotide therapy is an antisense oligonucleotide (ASO), NAPs, or STOPs.

331. The use of embodiment 330, wherein the ASO is ASO 1 or ASO2.

332. The use of embodiment 326 or 327, wherein the additional HBV treatment agent is selected from HBV STOPS™ ALG-010133, HBV CAM ALG-000184, ASO 1, recombinant interferon alpha 2b, IFN-a, PEG-IFN-a-2a, lamivudine, telbivudine, adefovir dipivoxil, clevudine, entecavir, tenofovir alafenamide, tenofovir disoproxil, NVR3-778, BAY41-4109, JNJ-632, JNJ-3989 (ARO-HBV), RG6004, GSK3228836, REP-2139, REP-2165, AB-729, VIR-2218, RG6346 (DCR-HBVS), JNJ-6379, GLS4, ABI-H0731, JNJ-440, NZ-4, RG7907, EDP-514, AB-423, AB-506, ABI-H03733 and ABI-H2158.

333. The use of embodiment 319, wherein the disease is a liver disease.

334. The use of embodiment 333, wherein the liver disease is a nonalcoholic fatty liver disease (NAFLD) or hepatocellular carcinoma (HCC).

335. The use of embodiment 334, wherein the NAFLD is nonalcoholic steatohepatitis (NASH).

336. The use of any of embodiments 333-335, further comprising a liver disease treatment agent in the manufacture of the medicament.

337. The use of embodiment 336, wherein the liver disease treatment agent is selected from a peroxisome proliferator-activator receptor (PPAR) agonist, farnesoid X receptor (FXR) agonist, lipid-altering agent, and incretin-based therapy.

338. The use of embodiment 337, wherein the PPAR agonist is selected from a PPARα agonist, dual PPARα/δ agonist, PPARγ agonist, and dual PPARα/γ agonist.

339. The use of embodiment 338, wherein the dual PPARα agonist is a fibrate.

340. The use of embodiment 338, wherein the PPARα/δ agonist is elafibranor.

341. The use of embodiment 338, wherein the PPARγ agonist is a thiazolidinedione (TZD).

342. The use of embodiment 341, wherein TZD is pioglitazone.

343. The use of embodiment 338, wherein the dual PPARα/γ agonist is saroglitazar.

344. The use of embodiment 337, wherein the FXR agonist is obeticholic acis (OCA).

345. The use of embodiment 337, wherein the lipid-altering agent is aramchol.

346. The use of embodiment 337, wherein the incretin-based therapy is a glucagon-like peptide 1 (GLP-1) receptor agonist or dipeptidyl peptidase 4 (DPP-4) inhibitor.

347. The use of embodiment 346, wherein the GLP-1 receptor agonist is exenatide or liraglutide.

348. The use of embodiment 346, wherein the DPP-4 inhibitor is sitagliptin or vildagliptin.

349. The siNA according to any one of embodiments 1-246 for use as a medicament.
350. The composition according to any one of embodiments 247-257 for use as a medicament.
351. The siNA according to any one of embodiments 1-246 for use in the treatment of a disease.
352. The siNA of embodiment 351, wherein the disease is a viral disease.
353. The siNA of embodiment 352, wherein the viral disease is caused by a DNA virus.
354. The siNA of embodiment 353, wherein the DNA virus is a double stranded DNA (dsDNA virus).
355. The siNA of embodiment 354, wherein the dsDNA virus is a hepadnavirus.
356. The siNA of embodiment 355, wherein the hepadnavirus is a hepatitis B virus (HBV).
357. The siNA of embodiment 356, wherein the HBV is selected from HBV genotypes A-J.
358. The siNA of embodiment 351, wherein the disease is a liver disease.
359. The siNA of embodiment 358, wherein the liver disease is a nonalcoholic fatty liver disease (NAFLD) or hepatocellular carcinoma (HCC).
360. The siNA of embodiment 359, wherein the NAFLD is nonalcoholic steatohepatitis (NASH).
361. The composition according to any one of embodiments 247-257, for use in the treatment of a disease.
362. The composition of embodiment 361, wherein the disease is a viral disease.
363. The composition of embodiment 362, wherein the viral disease is caused by a DNA virus.
364. The composition of embodiment 363, wherein the DNA virus is a double stranded DNA (dsDNA virus).
365. The composition of embodiment 364, wherein the dsDNA virus is a hepadnavirus.
366. The composition of embodiment 365, wherein the hepadnavirus is a hepatitis B virus (HBV).
367. The composition of embodiment 366, wherein the disease is a liver disease.
368. The composition of embodiment 367, wherein the liver disease is a nonalcoholic fatty liver disease (NAFLD) or hepatocellular carcinoma (HCC).
369. The composition of embodiment 368, wherein the NAFLD is nonalcoholic steatohepatitis (NASH).

Tables

TABLE 1

Non-modified Nucleotide Sequences

| SEQ ID NO. | First Nucleotide Sequence (5'-3') | SEQ ID NO. | Second Nucleotide Sequence (5'-3') |
|---|---|---|---|
| 1 | ACCGUGUGCACUUCGCUUC | 57 | GAAGCGAAGUGCACACGGUCC |
| 2 | ACCGUGUGCACUUCGCUUC | 58 | GAAGCGAAGUGCACACGGU |
| 3 | ACUUCGCUUCACCUCUGCA | 59 | UGCAGAGGUGAAGCGAAGUGC |
| 4 | AGUGUUUGCUGACGCAACC | 60 | GGUUGCGUCAGCAAACACUUG |
| 5 | CAGGCGGGGUUUUUCUUGU | 61 | ACAAGAAAAACCCCGCCUGUA |
| 6 | CAGGCGGGGUUUUUCUUGU | 62 | ACAAGAAAAACCCCGCCUG |
| 7 | CAGUUUACUAGUGCCAUUU | 63 | AAAUGGCACUAGUAAACUGAG |
| 8 | CAGUUUACUAGUGCCAUUU | 64 | AAAUGGCACUAGUAAACUG |
| 9 | CAUCCUGCUGCUAUGCCUC | 65 | GAGGCAUAGCAGCAGGAUGAA |
| 10 | CAUCCUGCUGCUAUGCCUCAU | 66 | AUGAGGCAUAGCAGCAGGAUGAA |
| 11 | CAUCCUGCUGCUAUGCCUC | 67 | GAGGCAUAGCAGCAGGAUG |
| 12 | CCGUGUGCACUUCGCUUCA | 68 | UGAAGCGAAGUGCACACGGUC |
| 13 | CCGUGUGCACUUCGCUUCA | 69 | UGAAGCGAAGUGCACACGG |
| 14 | CCUGCUGCUAUGCCUCAUCUU | 70 | AAGAUGAGGCAUAGCAGCAGGAU |
| 15 | CUCAGUUUACUAGUGCCAU | 71 | AUGGCACUAGUAAACUGAGCC |
| 16 | CUCAGUUUACUAGUGCCAU | 71 | AUGGCACUAGUAAACUGAGCC |
| 17 | CUCAGUUUACUAGUGCCAU | 71 | AUGGCACUAGUAAACUGAGCC |
| 18 | CUCAGUUUACUAGUGCCAU | 72 | AUGGCACUAGUAAACUGAG |
| 19 | CUCAGUUUACUAGUGCCAU | 72 | AUGGCACUAGUAAACUGAG |
| 20 | CUGCUAUGCCUCAUCUUCU | 73 | AGAAGAUGAGGCAUAGCAGCA |
| 21 | CUGCUAUGCCUCAUCUUCU | 73 | AGAAGAUGAGGCAUAGCAGCA |
| 22 | CUGCUAUGCCUCAUCUUCU | 74 | AGAAGAUGAGGCAUAGCAG |

TABLE 1-continued

| | Non-modified Nucleotide Sequences | | |
|---|---|---|---|
| SEQ ID NO. | First Nucleotide Sequence (5'-3') | SEQ ID NO. | Second Nucleotide Sequence (5'-3') |
| 23 | CUGCUAUGCCUCAUCUUCU | 74 | AGAAGAUGAGGCAUAGCAG |
| 24 | CUGCUGCUAUGCCUCAUCU | 75 | AGAUGAGGCAUAGCAGCAGGA |
| 25 | CUGCUGCUAUGCCUCAUCU | 76 | AGAUGAGGCAUAGCAGCAG |
| 26 | CUGCUGCUAUGCCUCAUCU | 76 | AGAUGAGGCAUAGCAGCAG |
| 27 | CUUCGCUUCACCUCUGCACGU | 77 | ACGUGCAGAGGUGAAGCGAAGUG |
| 28 | GCACUUCGCUUCACCUCUGCA | 78 | UGCAGAGGUGAAGCGAAGUGCAC |
| 29 | GCCGAUCCAUACUGCGGAA | 79 | UUCCGCAGUAUGGAUCGGCAG |
| 30 | GCCGGGUUUUUCUUGUUGA | 80 | UUCCGCAGUAUGGAUCGGC |
| 31 | GCGGGGUUUUUCUUGUUGA | 81 | UCAACAAGAAAAACCCCGCCU |
| 32 | GCGGGGUUUUUCUUGUUGA | 81 | UCAACAAGAAAAACCCCGCCU |
| 33 | GCGGGGUUUUUCUUGUUGA | 82 | UCAACAAGAAAAACCCCGC |
| 34 | GCGGGGUUUUUCUUGUUGA | 82 | UCAACAAGAAAAACCCCGC |
| 35 | GCUGCUAUGCCUCAUCUUCUU | 83 | AAGAAGAUGAGGCAUAGCAGCAG |
| 36 | GGAUGUGUCUGCGGCGUUUUA | 84 | UAAAACGCCGCAGACACAUCCAG |
| 37 | GGCCAAAAUUCGCAGUCCC | 85 | GGGACUGCGAAUUUUGGCCAA |
| 38 | GGCGCACCUCUCUUUACGC | 86 | GCGUAAAGAGAGGUGCGCCCC |
| 39 | GUAUGUUGCCCGUUUGUCC | 87 | GGACAAACGGGCAACAUACCU |
| 40 | GUGGUGGACUUCUCUCAAU | 88 | AUUGAGAAGUCCACCACGA |
| 41 | GUGUGCACUUCGCUUCACC | 89 | GGUGAAGCGAAGUGCACACGG |
| 42 | GUUGCCCGUUUGUCCUCUA | 90 | UAGAGGACAAACGGGCAACAU |
| 43 | GUUGCCCGUUUGUCCUCUA | 91 | UAGAGGACAAACGGGCAAC |
| 44 | UCCAUACUGCGGAACUCCU | 92 | AGGAGUUCCGCAGUAUGGAUC |
| 45 | UCCAUACUGCGGAACUCCU | 93 | AGGAGUUCCGCAGUAUGGA |
| 46 | UCGUGGUGGACUUCUCUCAAU | 94 | AUUGAGAAGUCCACCACGAGU |
| 47 | UGCACUUCGCUUCACCUCU | 95 | AGAGGUGAAGCGAAGUGCACA |
| 48 | UGCCGAUCCAUACUGCGGA | 96 | UCCGCAGUAUGGAUCGGCAGA |
| 49 | UGCCGAUCCAUACUGCGGA | 97 | UCCGCAGUAUGGAUCGGCA |
| 50 | UGCUAUGCCUCAUCUUCUU | 98 | AAGAAGAUGAGGCAUAGCAGC |
| 51 | UGUGCACUUCGCUUCACCU | 99 | AGGUGAAGCGAAGUGCACACG |
| 52 | UGUGCACUUCGCUUCACCU | 99 | AGGUGAAGCGAAGUGCACACG |
| 53 | UGUGCACUUCGCUUCACCU | 100 | AGGUGAAGCGAAGUGCACA |
| 54 | UGUGCACUUCGCUUCACCU | 100 | AGGUGAAGCGAAGUGCACA |
| 55 | UUGCCCGUUUGUCCUCUAA | 101 | UUAGAGGACAAACGGGCAACA |
| 56 | UUGCCCGUUUGUCCUCUAA | 102 | UUAGAGGACAAACGGGCAA |

TABLE 2

2'-OMe and 2'-F Modified Nucleotide Sequences

| SEQ ID NO. | First Nucleotide Sequence (5'-3') | SEQ ID NO. | Second Nucleotide Sequence (5'-3') |
|---|---|---|---|
| 103 | mAmCfCmGmUmGfUfGfCmAmCfUmUmCmGmCfUmUmC | 159 | mGfAmAmGmCmGmAmAmGmUmGmCmAfCmAmCmGmUmCmC |
| 104 | mAmCfCmGmUmGfUfGfCmAmCfUmUmCmGmCfUmUmC | 160 | mGfAmAmGmCmGmAmAmGmUmGmCmAfCmAmCmGmU |
| 105 | mAmCfUmUmCmGfCfUfUmCmAfCmCmUmCmUfGmCmA | 161 | mUfGmCmAmGmAmGmGmUmGmAmAmGfCmGmAmAmGmUmGmC |
| 106 | mAmGfUmGmUmUfUfGfCmUmGfAmCmGmCmAfAmCmC | 162 | mGfGmUmUmGmCmGmUmCmAmGmCmAfAmAmCmAmCmUmUmG |
| 107 | mCmAfGmCmGmGfGfGfGmUmUfUmUmUmCmUfUmGmU | 163 | mAfCmAmAmGmAmAmAmAmAmCmCmCfCmGmCmCmUmGmUmA |
| 108 | mCmAfGmCmGmGfGfGfGmUmUfUmUmUmCmUfUmGmU | 164 | mAfCmAmAmGmAmAmAmAmAmCmCmCfCmGmCmCmUmG |
| 109 | mCmAfGmUmUmUfAfCfUmAmGfUmGmCmCmAfUmUmU | 165 | mAfAmAmUmGmGmCmAmCmUmAmGmUfAmAmAmCmUmGmAmG |
| 110 | mCmAfGmUmUmUfAfCfUmAmGfUmGmCmCmAfUmUmU | 166 | mAfAmAmUmGmGmCmAmCmUmAmGmUfAmAmAmCmUmG |
| 111 | mCmAfUmCmCmUfGfCfUmGmCfUmAmUmGmCfCmUmC | 167 | mGfAmGmCmAmUmAmGmCmAmGmCfAmGmAmUmGmAmA |
| 112 | mCmAmUmCmCmUfGmCfUfGfCmUmAmUmGmCmCmUmCmAmU | 168 | mAfUmGmAmGfGmCmAmUmAmGmCmAfGmCfAmGmAmUmGmAmA |
| 113 | mCmAfUmCmCmUfGfCfUmGmCfUmAmUmGmCfCmUmC | 169 | mGfAmGmCmAmUmAmGmCmAmGmCfAmGmAmUmG |
| 114 | mCmCfGmUmGmUfGfCfAmCmUfUmCmGmCmUfUmCmA | 170 | mUfGmAmAmGmCmGmAmAmGmUmGmCfAmCmAmCmGmUmC |
| 115 | mCmCfGmUmGmUfGfCfAmCmUfUmCmGmCmUfUmCmA | 171 | mUfGmAmAmGmCmGmAmAmGmUmGmCfAmCmAmCmGmG |
| 116 | mCmCmUmGmCmUfGmCfUfAfUmGmCmCmUmCmAmUmCmUmU | 172 | mAfAmGmAmUfGmAmGmGmCmAmUmAfGmCfAmGmCmAmGmGmAmU |
| 117 | mCmUfCmAmGmUfUfUfAmCmUfAmGmUmGmCfCmAmU | 173 | mAfUmGmGmCmAmCmUmAmGmUmAmAfAmCmUmGmAmGmCmC |
| 118 | mCmUmCmAmGmUfUmUmAmCmUmAmGmUmGmCmCmAmU | 173 | mAfUmGmGmCmAmCmUmAmGmUmAmAfAmCmUmGmAmGmCmC |
| 119 | mCmUfCmAmGmUfUfUmAmCmUmAmGmUmGmCfCmAmU | 173 | mAfUmGmGmCmAmCmUmAmGmUmAmAfAmCmUmGmAmGmCmC |
| 120 | mCmUfCmAmGmUfUfUfAmCmUfAmGmUmGmCfCmAmU | 174 | mAfUmGmGmCmAmCmUmAmGmUmAmAfAmCmUmGmAmG |
| 121 | mCmUfCmAmGmUfUfUmAmCmUmAmGmUmGmCfCmAmU | 174 | mAfUmGmGmCmAmCmUmAmGmUmAmAfAmCmUmGmAmG |
| 122 | mCmUfGmCmUmAfUfGfCmCmUfCmAmUmCmUfUmCmU | 175 | mAfGmAmAmGmAmUmGmAmGmGmCmAfUmAmGmCmAmGmCmA |
| 123 | mCmUfGmCmUmAfUfGmCmCmUmCmAmUmCmUfUmCmU | 175 | mAfGmAmAmGmAmUmGmAmGmGmCmAfUmAmGmCmAmGmCmA |
| 124 | mCmUfGmCmUmAfUfGfCmCmUfCmAmUmCmUfUmCmU | 176 | mAfGmAmAmGmAmUmGmAmGmGmCmAfUmAmGmCmAmG |
| 125 | mCmUfGmCmUmAfUfGmCmCmUmCmAmUmCmUfUmCmU | 176 | mAfGmAmAmGmAmUmGmAmGmGmCmAfUmAmGmCmAmG |
| 126 | mCmUfGmCmUmGfCfUfAmUmGfCmCmUmCmAfUmCmU | 177 | mAfGmAmUmGmAmGmGmCmAmUmAmGfCmAmGmCmAmGmGmA |
| 127 | mCmUfGmCmUmGfCfUfAmUmGfCmCmUmCmAfUmCmU | 178 | mAfGmAmUmGmAmGmGmCmAmUmAmGfCmAmGmCmAmG |

TABLE 2-continued

2'-OMe and 2'-F Modified Nucleotide Sequences

| SEQ ID NO. | First Nucleotide Sequence (5'-3') | SEQ ID NO. | Second Nucleotide Sequence (5'-3') |
|---|---|---|---|
| 128 | mCmUfGmCmUmGfCfUmAmUm GmCmCmUmCmAfUmCmU | 178 | mAfGmAmUmGmAmGmGmCmAmUm AmGfCmAmGmCmAmG |
| 129 | mCmUmUmCmGmCfUmUfCfAf CmCmUmCmUmGmCmAmCmGmU | 179 | mAfCmGmUmGfCmAmGmAmGmGm UmGfAmAfGmCmGmAmAmGmUmG |
| 130 | mGmCmAmCmUmUfCmGfCfUf UmCmAmCmCmUmCmUmGmCmA | 180 | mUfGmCmAmGfAmGmGmUmGmAm AmGfCmGfAmAmGmUmGmCmAmC |
| 131 | mGmCfCmGmAmUfCfCfAmU mAfCmUmGmCmGfGmAmA | 181 | mUfUmCmCmGmCmCmAmGmUmAmUm GmGfAmUmCmGmCmGmCmAmG |
| 132 | mGmCfCmGmGmGfUfUfUmUm UfCmUmUmGmUfUmGmA | 182 | mUfUmCmCmGmCmCmAmGmUmAmUm GmGfAmUmCmGmGmC |
| 133 | mGmCfGmGmGmGfUfUfUmUm UfCmUmUmGmUfUmGmA | 183 | mUfCmAmAmCmAmAmGmAmAmAm AmAfCmCmCmCmGmCmCmU |
| 134 | mGmCfGmGmGmGfUfUmUmUm UmCmUmUmGmUfUmGmA | 183 | mUfCmAmAmCmAmAmGmAmAmAm AmAfCmCmCmCmGmCmCmU |
| 135 | mGmCfGmGmGmGfUfUfUmUm UfCmUmUmGmUfUmGmA | 184 | mUfCmAmAmCmAmAmGmAmAmAm AmAfCmCmCmCmGmC |
| 136 | mGmCfGmGmGmGfUfUmUmUm UmCmUmUmGmUfUmGmA | 184 | mUfCmAmAmCmAmAmGmAmAmAm AmAfCmCmCmCmGmC |
| 137 | mGmCmUmGmCmUfAmUfUfGfCf CmUmCmAmUmCmUmCmUmU | 185 | mAfAmGmAmAfGmAmUmGmAmGm GmCfAmUfAmGmCmAmGmCmAmG |
| 138 | mGmGmAmUmGmUfGmUfCfUf GmCmGmGmCmGmUmUmUmA | 186 | mUfAmAmAmAfCmGmCmCmGmCm AmGfAmCfAmCmAmUmCmCmAmG |
| 139 | mGmGfCmCmAmAfAfAfUmUm CfGmCmAmGmUfCmCmC | 187 | mGfGmGmAmCmUmGmCmGmAmAm UmUfUmGmGmCmCmAmA |
| 140 | mGmGfCmGmCmAfCfCfUmCm UfCmUmUmUmAfCmGmC | 188 | mGfCmGmUmAmAmAmGmAmGmAm GmGfUmGmCmGmCmCmC |
| 141 | mGmAmUfAmUmGmUfUfGfCmCm CfGmUmUmUmGfUmCmC | 189 | mGfGmAmCmAmAmAmCmGmGmGm CmAfAmCmAmUmAmCmU |
| 142 | mGmUfGmGmUmGfGfAfCmUm UfCmUmCmUmCfAmAmU | 190 | mAfUmUmGmAmGmAmGmAmAmGm UmCfCmAmCmCmAmCmGmA |
| 143 | mGmUfGmUmGmCfAfCfUmU mCfGmCmUmUmCfAmCmC | 191 | mGfGmUmGmAmAmGmCmGmAmAm GmUfGmCmAmCmAmCmG |
| 144 | mGmUfUmGmCmCfCfGfUmU mUfGmUmCmCmUfCmUmA | 192 | mUfAmGmAmGmGmAmCmAmAmAm CmGfGmGmCmAmAmCmAmU |
| 145 | mGmUfUmGmCmCfCfGfUmUm UfGmUmCmCmUfCmUmA | 193 | mUfAmGmAmGmGmAmCmAmAmAmAm CmGfGmGmCmAmAmC |
| 146 | mUmCfCmAmUmAfCfUfGmCm GfGmAmAmCmUfCmCmU | 194 | mAfGmGmAmGmUmUmCmCmGmCm AmGfUmAmUmGmGmAmUmC |
| 147 | mUmCfCmAmUmAfCfUfGmCm GfGmAmAmCmUfCmCmU | 195 | mAfGmGmAmGmUmUmCmCmGmCm AmGfUmAmUmGmGmA |
| 148 | mUmCmGmUmGmGfUmGfGfAf CmUmUmCmUmCmUmCmAmAmU | 196 | mAfUmUmGmAfGmAmGmAmAmGm UmCfCmAfCmCmAmCmGmAmGmU |
| 149 | mUmGfCmAmCmUfUfCfGmCm UfUmCmAmCmCfUmCmU | 197 | mAfGmAmGmGmUmGmAmAmGmCm GmAfAmGmUmGmCmAmCmA |
| 150 | mUmGfCmCmGmAfUfCfCmAm UfAmCmUmGmCfGmGmA | 198 | mUfCmCmGmCmAmGmUmAmUmGm GmAfUmCmGmGmCmAmGmA |
| 151 | mUmGfCmCmGmAfUfCfCmAm UfAmCmUmGmCfGmGmA | 199 | mUfCmCmGmCmAmGmUmAmUmGm GmAfUmCmGmGmCmA |
| 152 | mUmGfCmUmAmUfGfCfCmUm CfAmUmCmUmUfCmUmU | 200 | mAfAmGmAmAmGmAmUmGmAmGm GmCfAmUmAmGmCmAmGmC |

TABLE 2-continued

2'-OMe and 2'-F Modified Nucleotide Sequences

| SEQ ID NO. | First Nucleotide Sequence (5'-3') | SEQ ID NO. | Second Nucleotide Sequence (5'-3') |
|---|---|---|---|
| 153 | mUmGfUmGmCmAfCfUfUmCm GfCmUmUmCmAfCmCmU | 201 | mAfGmGmUmGmAmAmGmCmGmAm AmGfUmGmCmAmCmAmCmG |
| 154 | mUmGfUmGmCmAfCfUmUmCm GmCmUmUmCmAfCmCmU | 201 | mAfGmGmUmGmAmAmGmCmGmAm AmGfUmGmCmAmCmAmCmG |
| 155 | mUmGfUmGmCmAfCfUfUmCm GfCmUmUmCmAfCmCmU | 202 | mAfGmGmUmGmAmAmGmCmGmAm AmGfUmGmCmAmCmA |
| 156 | mUmGfUmGmCmAfCfUmUmCm GmCmUmUmCmAfCmCmU | 202 | mAfGmGmUmGmAmAmGmCmGmAm AmGfUmGmCmAmCmA |
| 157 | mUmUfGmCmCmCfGfUmUmUm GmUmCmCmUmCfUmAmA | 203 | mUfUmAmGmAmGmGmAmCmAmAm AmCfGmGmCmAmAmCmA |
| 158 | mUmUfGmCmCmCfGfUfUmUm GfUmCmCmUmCfUmAmA | 204 | mUfUmAmGmAmGmGmAmCmAmAm AmCfGmGmCmAmA | mX = 2'-O-methyl nucleotide; fX = 2'-fluoro nucleotide

TABLE 3

2'-O-methyl and 2'-fluoro Modified Nucleotide Sequences with Phosphorothioate Linkages

| SEQ ID NO. | First Nucleotide Sequence (5'-3') | SEQ ID NO. | Second Nucleotide Sequence (5'-3') |
|---|---|---|---|
| 205 | mApsmCpsfCmGmUmGfUfGfC mAmCfUmUmCmGmCfUmUmC | 261 | mGpsfApsmAmGmCmGmAmAmGm UmGmCmAfCmAmCmGmGmUpsmC psmC |
| 206 | mApsmCpsfCmGmUmGfUfGfC mAmCfUmUmCmGmCfUmUmC | 262 | mGpsfApsmAmGmCmGmAmAmGm UmGmCmAfCmAmCmGmGmU |
| 207 | mApsmCpsfUmUmCmGfCfUfU mCmAfCmCmUmCmUfGmCmA | 263 | mUpsfGpsmCmAmGmAmGmGmUm GmAmAmGfCmGmAmAmGmUpsmG psmC |
| 208 | mApsmGpsfUmGmUmUfUfGfC mUmGfAmCmGmCmAfAmCmC | 264 | mGpsfGpsmUmUmGmCmGmUmCm AmGmCmAfAmAmCmAmCmUpsmU psmG |
| 209 | mCpsmApsfGmGmCmGfGfGfG mUmUfUmUmUmCmUfUmGmU | 265 | mApsfCpsmAmAmGmAmAmAmAm AmCmCmCfCmGmCmCmUmGpsmU psmA |
| 210 | mCpsmApsfGmGmCmGfGfGfG mUmUfUmUmUmCmUfUmGmU | 266 | mApsfCpsmAmAmGmAmAmAmAm AmAmCmCmCfCmGmCmCmUmG |
| 211 | mCpsmApsfGmUmUmUfAfCfU mAmGfUmGmCmCmAfUmUmU | 267 | mApsfApsmAmUmGmGmCmAmCm UmAmGmUfAmAmAmCmUmGpsmA psmG |
| 212 | mCpsmApsfGmUmUmUfAfCfU mAmGfUmGmCmCmAfUmUmU | 268 | mApsfApsmAmUmGmGmCmAmCm UmAmGmUfAmAmAmCmUmG |
| 213 | mCpsmApsfUmCmCmUfGfCfU mGmCfUmAmUmGmCfCmUmC | 269 | mGpsfApsmGmGmCmAmUmAmGm CmAmGmCfAmGmGmAmUmGpsmA psmA |
| 214 | mCpsmApsmUmCmCmUfGmCf UfGfCmUmAmUmGmCmCmUmCm AmU | 270 | mApsfUpsmGmAmGmGfGmCmAmUm AmGmCmAfGmCfAmGmGmAmUmG psmApsmA |
| 215 | mCpsmApsfUmCmCmUfGfCfU mGmCfUmAmUmGmCfCmUmC | 271 | mGpsfApsmGmGmCmAmUmAmGm CmAmGmCfAmGmGmAmUmG |
| 216 | mCpsmCpsfGmUmGmUfGfCfA mCmUfUmCmGmCmUfUmCmA | 272 | mUpsfGpsmAmAmGmCmGmAmAm GmUmGmCfAmCmAmCmGmGpsmU psmC |

TABLE 3-continued

2'-O-methyl and 2'-fluoro Modified Nucleotide
Sequences with Phosphorothioate Linkages

| SEQ ID NO. | First Nucleotide Sequence (5'-3') | SEQ ID NO. | Second Nucleotide Sequence (5'-3') |
|---|---|---|---|
| 217 | mCpsmCpsfGmUmGmUfGfCfAmCmUfUmCmCmUfUmCmA | 273 | mUpsfGpsmAmAmCmGmAmAmGmUmGmCfAmCmAmCmGmG |
| 218 | mCpsmCpsmUmGmCmUfGmCfUfAfUmGmCmCmUmCmAmUmCmUmU | 274 | mApsfApsmGmAmUfGmAmGmGmCmAmUmAfGmCfAmGmCmAmGmGpsmApsmU |
| 219 | mCpsmUpsfCmAmGmUfUfUfAmCmUfAmGmUmGmCfCmAmU | 275 | mApsfUpsmGmGmCmAmCmUmAmGmUmAmAfAmCmUmGmAmGpsmCpsmC |
| 220 | mCpsmUpsmCmAmGmUfUmUmAmCmUmAmGmUmGmCmCmAmU | 275 | mApsfUpsmGmGmCmAmCmUmAmGmUmAmAfAmCmUmGmAmGpsmCpsmC |
| 221 | mCpsmUpsfCmAmGmUfUfUmAmCmUmAmGmUmGmCfCmAmU | 275 | mApsfUpsmGmGmCmAmCmUmAmGmUmAmAfAmCmUmGmAmGpsmCpsmC |
| 222 | mCpsmUpsfCmAmGmUfUfUfAmCmUfAmGmUmGmCfCmAmU | 276 | mApsfUpsmGmGmCmAmCmUmAmGmUmAmAfAmCmUmGmAmG |
| 223 | mCpsmUpsfCmAmGmUfUfUmAmCmUmAmGmUmGmCfCmAmU | 276 | mApsfUpsmGmGmCmAmCmUmAmGmUmAmAfAmCmUmGmAmG |
| 224 | mCpsmUpsfGmCmUmAfUfGfCmCmUfCmAmUmCmUfUmCmU | 277 | mApsfGpsmAmAmGmAmUmGmAmGmGmCmAfUmAmGmCmAmGpsmCpsmA |
| 225 | mCpsmUpsfGmCmUmAfUfGmCmCmUmCmAmUmCmUfUmCmU | 277 | mApsfGpsmAmAmGmAmUmGmAmGmGmCmAfUmAmGmCmAmGpsmCpsmA |
| 226 | mCpsmUpsfGmCmUmAfUfGfCmCmUfCmAmUmCmUfUmCmU | 278 | mApsfGpsmAmAmGmAmUmGmAmGmGmCmAfUmAmGmCmAmG |
| 227 | mCpsmUpsfGmCmUmAfUfGmCmCmUmCmAmUmCmUfUmCmU | 278 | mApsfGpsmAmAmGmAmUmGmAmGmGmCmAfUmAmGmCmAmG |
| 228 | mCpsmUpsfGmCmUmGfCfUfAmUmGfCmCmUmCmAfUmCmU | 279 | mApsfGpsmAmUmGmAmGmGmCmAmUmAmGfCmAmGmCmAmGpsmGpsmA |
| 229 | mCpsmUpsfGmCmUmGfCfUfAmUmGfCmCmUmCmAfUmCmU | 280 | mApsfGpsmAmUmGmAmGmGmCmAmUmAmGfCmAmGmCmAmG |
| 230 | mCpsmUpsfGmCmUmGfCfUmAmUmGmCmCmUmCmAfUmCmU | 280 | mApsfGpsmAmUmGmAmGmGmCmAmUmAmGfCmAmGmCmAmG |
| 231 | mCpsmUpsmUmCmGmCfUmUfCfAfCmCmUmCmUmGmCmAmCmGmU | 281 | mApsfCpsmGmUmGfCmAmGmAmGmGmUmGfAmAfGmCmGmAmAmGpsmUpsmG |
| 232 | mGpsmCpsmAmCmUmUfCmGfCfUfUmCmAmCmCmUmCmUmGmCmA | 282 | mUpsfGpsmCmAmGfAmGmGmUmGmAmAmGfCmGfAmAmGmUmGmCpsmApsmC |
| 233 | mGpsmCpsfCmGmAmUfCfCfAmUmAfCmUmGmCmGfGmAmA | 283 | mUpsfUpsmCmCmGmCmAmGmUmAmUmGmGfAmUmCmGmGmCpsmApsmG |
| 234 | mGpsmCpsfCmGmGmGfUfUfUmUmUfCmUmUmGmUfUmGmA | 284 | mUpsfUpsmCmCmGmCmAmGmUmAmUmGmGfAmUmCmGmGmC |
| 235 | mGpsmCpsfGmGmGmGfUfUfUmUmUfCmUmUmGmUfUmGmA | 285 | mUpsfCpsmAmAmCmAmAmGmAmAmAmAfCmCmCmCmGmCpsmU |
| 236 | mGpsmCpsfGmGmGmGfUfUmUmUmCmUmUmGmUfUmGmA | 285 | mUpsfCpsmAmAmCmAmAmGmAmAmAmAfCmCmCmCmGmCpsmU |

TABLE 3-continued

2'-O-methyl and 2'-fluoro Modified Nucleotide
Sequences with Phosphorothioate Linkages

| SEQ ID NO. | First Nucleotide Sequence (5'-3') | SEQ ID NO. | Second Nucleotide Sequence (5'-3') |
|---|---|---|---|
| 237 | mGpsmCpsfGmGmGmGfUfUfUmUmUfCmUmUmGmUfUmGmA | 286 | mUpsfCpsmAmAmCmAmAmGmAmAmAmAmAfCmCmCmCmGmC |
| 238 | mGpsmCpsfGmGmGmGfUfUmUmUmUmCmUmUmGmUfUmGmA | 286 | mUpsfCmAmAmCmAmAmGmAmAmAmAmAfCmCmCmCmGmC |
| 239 | mGpsmCpsmUmGmCmUfAmUfGfCfCmUmCmAmUmCmUmUmCmUmU | 287 | mApsfApsmGmAmAfGmAmUmGmAmGmGmCfAmUfAmGmCmAmGmCpsmApsmG |
| 240 | mGpsmGpsmAmUmGmUfGmUfCfUfGmCmGmCmGmUmUmUmUmA | 288 | mUpsfApsmAmAmAfCmGmCmCmGmCmAmGfAmCfAmCmAmUmCmCpsmApsmG |
| 241 | mGpsmGpsfCmCmAmAfAfAfUmUmCfGmCmAmGmUfCmCmC | 289 | mGpsfGpsmGmAmCmUmGmCmGmAmAmUfUmGmCmCpsmApsmA |
| 242 | mGpsmGpsfCmGmCmAfCfCfUmCmUmCmUmUmUmAfCmGmC | 290 | mGpsfCpsmGmUmAmAmAmGmAmGmAmGmGfUmGmCmGmCmCpsmCpsmC |
| 243 | mGpsmUpsfAmUmGmUfUfGfCmCmCfGmUmUmUmGfUmCmC | 291 | mGpsfGpsmAmCmAmAmAmCmGmGmGmCmAfAmCmAmUmAmCpsmCpsmU |
| 244 | mGpsmUpsfGmGmUmGfGfAfCmUmUfCmUmCmUmCfAmAmU | 292 | mApsfUpsmUmGmAmGmAmGmAmAmGmUmCfCmAmCmCmAmCpsmGpsmA |
| 245 | mGpsmUpsfGmUmGmCfAfCfUmUmCfGmCmUmUmCfAmCmC | 293 | mGpsfGpsmUmGmAmAmGmCmGmAmAmGmUfGmCmAmCmAmCpsmGpsmG |
| 246 | mGpsmUpsfUmGmCmCfCfGfUmUmUfGmUmCmCmUfCmUmA | 294 | mUpsfApsmGmAmGmGmAmCmAmAmCmGfGmGmCmAmAmCpsmApsmU |
| 247 | mGpsmUpsfUmGmCmCfCfGfUmUmUfGmUmCmCmUfCmUmA | 295 | mUpsfApsmGmAmGmGmAmCmAmAmAmCmGfGmGmCmAmAmC |
| 248 | mUpsmCpsfCmAmUmAfCfUfGmCmGfGmAmAmCmUfCmCmU | 296 | mApsfGpsmGmAmGmUmUmCmCmGmCmAmGfUmAmUmGmGmApsmUpsmC |
| 249 | mUpsmCpsfCmAmUmAfCfUfGmCmGfGmAmAmCmUfCmCmU | 297 | mApsfGpsmGmAmGmUmUmCmCmGmCmAmGfUmAmUmGmGmA |
| 250 | mUpsmCpsmGmUmGmGfUmGfGfAfCmUmUmCmUmCmUmCmAmAmU | 298 | mApsfUpsmUmGmAfGmAmGmAmAmGmUmCfCmAfCmCmAmCmGmApsmGpsmU |
| 251 | mUpsmGpsfCmAmCmUfUfCfGmCmUfUmCmAmCmCfUmCmU | 299 | mApsfGpsmAmGmGmUmGmAmAmGmCmGmAfAmGmUmGmCmApsmCpsmA |
| 252 | mUpsmGpsfCmCmGmAfUfCfCmAmUfAmCmUmGmCfGmGmA | 300 | mUpsfCpsmCmGmCmAmGmUmAmUmGmGmAfUmCmGmGmCmApsmGpsmA |
| 253 | mUpsmGpsfCmCmGmAfUfCfCmAmUfAmCmUmGmCfGmGmA | 301 | mUpsfCpsmCmGmCmAmGmUmAmUmGmGmAfUmCmGmGmCmA |
| 254 | mUpsmGpsfCmUmAmUfGfCfCmUmCfAmUmCmUmUfCmUmU | 302 | mApsfApsmGmAmAmGmAmUmGmAmGmGmCfAmUfAmGmCmApsmGpsmC |
| 255 | mUpsmGpsfUmGmCmAfCfUfUmCmGfCmUmUmCmAfCmCmU | 303 | mApsfGpsmGmUmGmAmAmGmCmGmAmAmGfUmGmCmAmCmApsmCpsmG |

TABLE 3-continued

2'-O-methyl and 2'-fluoro Modified Nucleotide Sequences with Phosphorothioate Linkages

| SEQ ID NO. | First Nucleotide Sequence (5'-3') | SEQ ID NO. | Second Nucleotide Sequence (5'-3') |
|---|---|---|---|
| 256 | mUpsmGpsfUmGmCmAfCfUmU mCmGmCmUmUmCmAfCmCmU | 303 | mApsfGpsmGmUmGmAmAmGmCm GmAmAmGfUmGmCmAmCmApsmC psmG |
| 257 | mUpsmGpsfUmGmCmAfCfUfU mCmGfCmUmUmCmAfCmCmU | 304 | mApsfGpsmGmUmGmAmAmGmCm GmAmAmGfUmGmCmAmCmA |
| 258 | mUpsmGpsfUmGmCmAfCfUmU mCmGmCmUmUmCmAfCmCmU | 304 | mApsfGpsmGmUmGmAmAmGmCm GmAmAmGfUmGmCmAmCmA |
| 259 | mUpsmUpsfGmCmCmCfGfUmU mUmGmUmCmCmUmCfUmAmA | 305 | mUpsfUpsmAmAmAmGmGmAmCm AmAmAmCfGmGmCmAmApsmC psmA |
| 260 | mUpsmUpsfGmCmCmCfGfUfU mUmGfUmCmCmUmCfUmAmA | 306 | mUpsfUpsmAmAmAmGmGmAmCm AmAmAmCfGmGmCmAmA | mX = 2'-O-methyl nucleotide; fX = 2'-fluoro nucleotide; ps = phosphorothioate linkage

TABLE 4 siNA Sequences

| SEQ ID NO. | Sense Sequence (5'-3') | SEQ ID NO. | Antisense Sequence (5'-3') |
|---|---|---|---|
| 307 | mApsmCpsfCmGmUmGfUfGfC mAmCfUmUmCmGmCfUmUmC | 363 | mGpsfApsmAmGmCmGmAmAmGmU mGmCmAfCmAmCmGmGmUpsmCps mC |
| 308 | mApsmCpsfCmGmUmGfUfGfC mAmCfUmUmCmGmCfUmUmC TT | 364 | mGpsfApsmAmGmCmGmAmAmGmU mGmCmAfCmAmCmGmGmUpsTpsT |
| 309 | mApsmCpsfUmUmCmGfCfUfU mCmAfCmCmUmCmUfGmCmA | 365 | mUpsfGpsmCmAmGmAmGmGmUmG mAmAmGfCmGmAmAmGmUpsmGps mC |
| 310 | mApsmGpsfUmGmUmUfUfGfC mUmGfAmCmGmCmAfAmCmC | 366 | mGpsfGpsmUmUmGmCmGmUmCmA mGmCmAfAmAmCmAmCmUpsmUps mG |
| 311 | mCpsmApsfGmGmCmGfGfGfG mUmUfUmUmUmUmCmUfUmGm U | 367 | mApsfCpsmAmAmGmAmAmAmAmA mCmCmCfCmGmCmCmUmGpsmUps mA |
| 312 | mCpsmApsfGmGmCmGfGfGfG mUmUfUmUmUmUmCmUfUmGm UTT | 368 | mApsfCpsmAmAmGmAmAmAmAmA mAmCmCmCfCmGmCmCmUmGpsTp sT |
| 313 | mCpsmApsfGmUmUmUfAfCfU mAmGfUmGmCmCmAfUmUmUm U | 369 | mApsfApsmAmUmGmGmCmAmCmU mAmGmUfAmAmAmCmUmGpsmAps mG |
| 314 | mCpsmApsfGmUmUmUfAfCfU mAmGfUmGmCmCmAfUmUmUm UTT | 370 | mApsfApsmAmUmGmGmCmAmCmU mAmGmUfAmAmAmCmUmGpsTpsT |
| 315 | mCpsmApsfUmCmCmUfGfCfU mGmCfUmAmUmGmCfCmUmC | 371 | mGpsfApsmGmGmCmAmUmAmGmC mAmGmCfAmGmGmAmUmGpsmAps mA |
| 316 | mCpsmApsmUmCmCmUfGmCf UfGfCmUmAmUmGmCmCmUm CmAmU | 372 | mApsfUpsmGmAmGfGmCmAmUmA mGmCmAfGmCfAmGmGmAmUmGps mApsmA |
| 317 | mCpsmApsfUmCmCmUfGfCfU mGmCfUmAmUmGmCfCmUmC TT | 373 | mGpsfApsmGmGmCmAmUmAmGmC mAmGmCfAmGmGmAmUmGpsTpsT |
| 318 | mCpsmCpsfGmUmGmUfGfCfA mCmUfUmCmGmCmUfUmCmA | 374 | mUpsfGpsmAmAmGmCmGmAmAmG mUmGmCfAmCmAmCmGmGpsmUps mC |
| 319 | mCpsmCpsfGmUmGmUfGfCfA mCmUfUmCmGmCmUfUmCmA TT | 375 | mUpsfGpsmAmAmGmCmGmAmAmG mUmGmCfAmCmAmCmGmGpsTpsT |
| 320 | mCpsmCpsmUmGmCmUfGmCf UfAfUmGmCmCmUmUmCmAmUm CmUmU | 376 | mApsfApsmGmAmUfGmAmGmGmC mAmUmAfGmCfAmGmCmAmGmGps mApsmU |
| 321 | mCpsmUpsfCmAmGmUfUfUfA mCmUfAmGmUmGmCfCmAmU | 377 | mApsfUpsmGmGmCmAmCmUmAmG mUmAmAfAmCmUmGmAmGpsmCps mC |

TABLE 4-continued siNA Sequences

| SEQ ID NO. | Sense Sequence (5'-3') | SEQ ID NO. | Antisense Sequence (5'-3') |
|---|---|---|---|
| 322 | mCpsmUpsmCmAmGmUfUmU mAmCmUmAmGmUmGmCmC mAmU | 377 | mApsfUpsmGmGmCmAmCmUmAmG mUmAmAfAmCmUmGmAmGpsmCps mC |
| 323 | mCpsmUpsfCmAmGmUfUfUmA mCmUmAmGmUmGmCfCmAm U | 377 | mApsfUpsmGmGmCmAmCmUmAmG mUmAmAfAmCmUmGmAmGpsmCps mC |
| 324 | mCpsmUpsfCmAmGmUfUfUfA mCmUfAmGmUmGmCfCmAmU TT | 378 | mApsfUpsmGmGmCmAmCmUmAmG mUmAmAfAmCmUmGmAmGpsTpsT |
| 325 | mCpsmUpsfCmAmGmUfUfUmA mCmUmAmGmUmGmCfCmAm UTT | 378 | mApsfUpsmGmGmCmAmCmUmAmG mUmAmAfAmCmUmGmAmGpsTpsT |
| 326 | mCpsmUpsfGmCmUmAfUfGfC mCmUfCmAmUmCmUfUmCmU | 379 | mApsfGpsmAmAmGmAmUmGmAmG mGmCmAfUmAmGmCmAmGpsmCps mA |
| 327 | mCpsmUpsfGmCmUmAfUfGmC mCmUmCmAmUmCmUfUmCm U | 379 | mApsfGpsmAmAmGmAmUmGmAmG mGmCmAfUmAmGmCmAmGpsmCps mA |
| 328 | mCpsmUpsfGmCmUmAfUfGfC mCmUfCmAmUmCmUfUmCmU TT | 380 | mApsfGpsmAmAmGmAmUmGmAmG mGmCmAfUmAmGmCmAmGpsTpsT |
| 329 | mCpsmUpsfGmCmUmAfUfGmC mCmUmCmAmUmCmUfUmCm UTT | 380 | mApsfGpsmAmAmGmAmUmGmAmG mGmCmAfUmAmGmCmAmGpsTpsT |
| 330 | mCpsmUpsfGmCmUmGfCfUfA mUmGfCmCmUmCmAfUmCmU | 381 | mApsfGpsmAmUmGmAmGmGmCmA mUmAmGfCmAmGmCmAmGpsmGps mA |
| 331 | mCpsmUpsfGmCmUmGfCfUfA mUmGfCmCmUmCmAfUmCmU TT | 382 | mApsfGpsmAmUmGmAmGmGmCmA mUmAmGfCmAmGmCmAmGpsTpsT |
| 332 | mCpsmUpsfGmCmUmGfCfUmA mUmGmCmCmUmCmAfUmCm UTT | 383 | mApsfGpsmAmUmGmAmGmGmCmA mUmAmGfCmAmGmCmAmGpsTpsT |
| 333 | mCpsmUpsmUmCmGmCfUmUf CfAfCmCmUmCmUmGmCmAm CmGmU | 384 | mApsfCpsmGmUmGfCmAmGmAmG mGmUmGfAmAfGmCmGmAmAmGp smUpsmG |
| 334 | mGpsmCpsmAmCmUmUfCmGf CfUfUmCmAmCmCmUmCmUm GmCmA | 385 | mUpsfGpsmCmAmGfAmGmGmUmG mAmAmGfCmGfAmAmGmUmGmCps mApsmC |
| 335 | mGpsmCpsfCmGmAmUfCfCfA mUmAfCmUmGmCmGfGmAm A | 386 | mUpsfUpsmCmCmGmCmAmGmUmA mUmGmGfAmUmCmGmGmCpsmAps mG |
| 336 | mGpsmCpsfCmGmGmGfUfUfU mUmUfC mUmUmGmUfUmGm ATT | 387 | mUpsfUpsmCmCmGmCmAmGmUmA mUmGmGfAmUmCmGmGmCpsTpsT |
| 337 | mGpsmCpsfGmGmGmGfUfUfU mUmUfC mUmUmGmUfUmGm A | 388 | mUpsfCpsmAmAmCmAmAmGmAmA mAmAmAfCmCmCmCmGmCpsmCps mU |
| 338 | mGpsmCpsfGmGmGmGfUfUmU mUmUmCmUmUmGmUfUmGm A | 388 | mUpsfCpsmAmAmCmAmAmGmAmA mAmAmAfCmCmCmCmGmCpsmCps mU |
| 339 | mGpsmCpsfGmGmGmGfUfUfU mUmUfCmUmUmGmUfUmGm ATT | 389 | mUpsfCpsmAmAmCmAmAmGmAmA mAmAmAfCmCmCmCmGmCpsTpsT |
| 340 | mGpsmCpsfGmGmGmGfUfUmU mUmUmCmUmUmGmUfUmGm ATT | 389 | mUpsfCmAmAmCmAmAmGmAmAm AmAmAfCmCmCmCmGmCpsTpsT |
| 341 | mGpsmCpsmUmGmCmUfAmUf GfCfCmUmCmAmUmCmUmUm CmUmU | 390 | mApsfApsmGmAmAfGmAmUmGmA mGmGmCfAmUfAmGmCmAmGmCps mApsmG |
| 342 | mGpsmGpsmAmUmGmUfGmUf CfUfGmCmGmCmGmUmUm UmUmA | 391 | mUpsfApsmAmAmAfCmGmCmCmG mCmAmAfCmAfCmAmUmCmCps mApsmG |
| 343 | mGpsmGpsfCmCmAmAfAfAfU mUmCfGmCmAmGmUfCmCmC | 392 | mGpsGpsmGmAmCmUmGmCmGmA mAmUmUfUmUmGmGmCmCpsmAps mA |
| 344 | mGpsmGpsfCmGmCmAfCfCfU mCmUfCmUmUmUmAfCmGmC | 393 | mGpsCpsmGmUmAmAmAmGmAmG mAmGmGfUmGmCmGmCmCpsmCps mC |
| 345 | mGpsmUpsfAmUmGmUfUfGfC mCmCfGmUmUmUmGfUmCmC | 394 | mGpsfGpsmAmCmAmAmAmCmGmG mGmCmAfAmCmAmUmAmCpsmCps mU |
| 346 | mGpsmUpsfGmGmUmGfGfAfC mUmUfCmUmCmUmCfAmAmU | 395 | mApsfUpsmUmGmAmGmAmGmAmA mGmUmCfCmAmCmCmAmCpsmGps mA |

TABLE 4-continued

| SEQ ID NO. | Sense Sequence (5'-3') | SEQ ID NO. | Antisense Sequence (5'-3') |
|---|---|---|---|
| 347 | mGpsmUpsfGmUmGmCfAfCfUmUmCfGmCmUmUmCfAmCmC | 396 | mGpsfGpsmUmGmAmAmGmCmGmAmAmGmUfGmCmAmCmAmCpsmGpsmG |
| 348 | mGpsmUpsfUmGmCmCfCfGfUmUmUfGmUmCmCmUfCmUmA | 397 | mUpsfApsmGmAmGmGmAmCmAmAmAmCmGfGmGmCmAmAmCpsmApsmU |
| 349 | mGpsmUpsfUmGmCmCfCfGfUmUmUfGmUmCmCmUfCmUmATT | 398 | mUpsfApsmGmAmGmGmAmCmAmAmAmCmGfGmGmCmAmAmCpsTpsT |
| 350 | mUpsmCpsfCmAmUmAfCfUfGmCmGfGmAmAmCmUfCmCmU | 399 | mApsfGpsmGmAmGmUmUmCmCmGmCmAmGfUmAmUmGmGmApsmUpsmC |
| 351 | mUpsmCpsfCmAmUmAfCfUfGmCmGfGmAmAmCmUfCmCmUTT | 400 | mApsfGpsmGmAmGmUmUmCmCmGmCmAmGfUmAmUmGmGmApsTpsT |
| 352 | mUpsmCpsmGmUmGmGfUmGfGfAfCmUmUmCmUmCmUmCmAmAmU | 401 | mApsfUpsmUmGmAfGmAmGmAmAmGmUmCfCmAfCmCmAmCmGmApsmGpsmU |
| 353 | mUpsmGpsfCmAmCmUfUfCfGmCmUfUmCmAmCmCfUmCmU | 402 | mApsfGpsmAmGmGmUmGmAmAmGmCmGmAfAmGmUmGmCmApsmCpsmA |
| 354 | mUpsmGpsfCmCmGmAfUfCfCmAmUfAmCmUmGmCfGmGmA | 403 | mUpsfCpsmCmGmCmAmGmUmAmUmGmGmAfUmCmGmGmCmApsmGpsmA |
| 355 | mUpsmGpsfCmCmGmAfUfCfCmAmUfAmCmUmGmCfGmGmATT | 404 | mUpsfCpsmCmGmCmAmGmUmAmUmGmGmAfUmCmGmGmCmApsTpsT |
| 356 | mUpsmGpsfCmUmAmUfGfCfCmUmCfAmUmCmUmUfCmUmU | 405 | mApsfApsmGmAmAmGmAmUmGmAmGmGmCfAmUmAmGmCmApsmGpsmC |
| 357 | mUpsmGpsfUmGmCmAfCfUfUmCmGfCmUmUmCmAfCmCmU | 406 | mApsfGpsmGmUmGmAmAmGmCmGmAmAmGfUmGmCmAmCmApsmCpsmG |
| 358 | mUpsmGpsfUmGmCmAfCfUmUmCmGmCmUmUmCmAfCmCmU | 406 | mApsfGpsmGmUmGmAmAmGmCmGmAmAmGfUmGmCmAmCmApsmCpsmG |
| 359 | mUpsmGpsfUmGmCmAfCfUfUmCmGfCmUmUmCmAfCmCmUTT | 407 | mApsfGpsmGmUmGmAmAmGmCmGmAmAmGfUmGmCmAmCmApsTpsT |
| 360 | mUpsmGpsfUmGmCmAfCfUmUmCmGmCmUmUmCmAfCmCmUTT | 407 | mApsfGpsmGmUmGmAmAmGmCmGmAmAmGfUmGmCmAmCmApsTpsT |
| 361 | mUpsmUpsfGmCmCmCfGfUmUmUmGmUmCmCmUmCfUmAmA | 408 | mUpsfUpsmAmGmAmGmGmAmCmAmAmAmCfGmGmGmCmAmApsmCpsmA |
| 362 | mUpsmUpsfGmCmCmCfGfUfUmUmGfUmCmCmUmCfUmAmATT | 409 | mUpsfUpsmAmGmAmGmGmAmCmAmAmAmCmGfGmGmCmAmApsTpsT |
| 415 | 5dcd3Cps5dcd3CpsfG5dcd3UmG5dcd3UfG5dfCfA5dcd3C5dcd3U5dfU5dcd3CmG5dcd3C5dcd3U5dfU5dcd3CmA | 445 | 5dcd3UpsfGpsmAmAmG5dcd3CmGmAmAmG5dcd3UmG5dcd3CfA5dcd3CmA5dcd3CmGmGps5dcd3Ups5dcd3U |
| 415 | 5dcd3Cps5dcd3CpsfG5dcd3UmG5dcd3UfG5dfCfA5dcd3C5dcd3U5dfU5dcd3CmG5dcd3C5dcd3U5dfU5dcd3CmA | 446 | 5dcd3UpsfGpsmAmAmGmCmGmAmAmGmUmGmCfAmCmAmCmGmGps5dcd3Ups5dcd3U |
| 415 | 5dcd3Cps5dcd3CpsfG5dcd3UmG5dcd3UfG5dfCfA5dcd3C5dcd3U5dfU5dcd3CmG5dcd3C5dcd3U5dfU5dcd3CmA | 447 | mUpsfGpsmAmAmGmCmGmAmAmGmUmGmCfAmCmAmCmGmGpsmUpsmU |
| 416 | fCpsmCpsfGmUfGmUfGmCfAmCfUmUfCmGfCmUfUmCfA | 448 | mUpsfGpsmAfAmGfCmGfAmAfGmUmGmCfAmCfAmCfGmGpsmUpsmC |
| 416 | fCpsmCpsfGmUfGmUfGmCfAmCfUmUfCmGfCmUfUmCfA | 449 | vmUpsfGpsmAfAmGfCmGfAmAfGmUmGmCfAmCfAmCfGmGpsmUpsmC |
| 416 | fCpsmCpsfGmUfGmUfGmCfAmCfUmUfCmGfCmUfUmCfA | 450 | mUpsfGpsmAfAmGfCmGfAmAfGmUfGmCfAmCfAmCfGmGpsmUpsmC |
| 416 | fCpsmCpsfGmUfGmUfGmCfAmCfUmUfCmGfCmUfUmCfA | 451 | vmUpsfGpsmAfAmGfCmGfAmAfGmUfGmCfAmCfAmCfGmGpsmUpsmC |
| 417 | fCpsmUpsfGmCfUmAfUmGfCmCfUmCfAmUfCmUfUmCfU | 452 | mApsfGpsmAfAmGfAmUfGmAfGmGfCmAfUmAfGmCfAmGpsmUpsmU |
| 417 | fCpsmUpsfGmCfUmAfUmGfCmCfUmCfAmUfCmUfUmCfU | 452 | mApsfGpsmAfAmGfAmUfGmAfGmGfCmAfUmAfGmCfAmGpsmUpsmU |
| 417 | fCpsmUpsfGmCfUmAfUmGfCmCfUmCfAmUfCmUfUmCfU | 452 | mApsfGpsmAfAmGfAmUfGmAfGmGfCmAfUmAfGmCfAmGpsmUpsmU |

TABLE 4-continued siNA Sequences

| SEQ ID NO. | Sense Sequence (5'-3') | SEQ ID NO. | Antisense Sequence (5'-3') |
|---|---|---|---|
| 417 | fCpsmUpsfGmCfUmAfUmGfCmCfUmCfAmUfCmUfUmCfU | 452 | mApsfGpsmAfAmGfAmUfGmAfGmGfCmAfUmAfGmCfAmGpsmUpsmU |
| 418 | fGpsmUpsfGmGfUmGfGfAfCmUfUmCfUmCfUmCfAmAfU | 453 | mApsfUpsmUfGmAfGmAfGmAfAmGmUmCfCmAfCmCfAmCpsmGpsmA |
| 418 | fGpsmUpsfGmGfUmGfGfAfCmUfUmCfUmCfUmCfAmAfU | 454 | vmApsfUpsmUfGmAfGmAfGmAfAmGmUmCfCmAfCmCfAmCpsmGpsmA |
| 419 | fGpsmUpsfGmGfUmGfGmAfCmUfUmCfUmCfUmCfAmAfU | 455 | mApsfUpsmUfGmAfGmAfGmAfAmGfUmCfCmAfCmCfAmCpsmGpsmA |
| 419 | fGpsmUpsfGmGfUmGfGmAfCmUfUmCfUmCfUmCfAmAfU | 456 | vmApsfUpsmUfGmAfGmAfGmAfAmGfUmCfCmAfCmCfAmCpsmGpsmA |
| 420 | mCpsmCpsfGmUfGmUfGfCfAmCmUmUmCmGmCmUmUmCmA | 457 | mUpsfGpsmAmAmGfCmGmAmAmGmUmGmCfAmCfAmCmGmGpsmUpsmC |
| 421 | mCpsmCpsfGmUmGmUfGfCfAmAmUfUmCmGmCmUfUmCmA | 458 | mUpsfGpsmAmAmGmCmGmAmAmGmUmGmCfAmCmAmCmGmGpsmUpsmC |
| 422 | mCpsmCpsfGmUmGmUfGfCfAmCmUfUmCmGmCmUfUmCmA | 459 | mUpsfGpsmAmAmGmCmGmAmAmGmUmGmCfAmCmAmCmGmGpsmU3smU |
| 423 | mCpsmCpsfGmUmGmUfGfCfAmCmUfUmCmGmCmUfUmCmA | 460 | mUpsfGpsmAmAmGmCmGmAmAmGmUmGmCfAmCmAmCmGmG5smU5smU |
| 423 | mCpsmCpsfGmUmGmUfGfCfAmCmUfUmCmGmCmUfUmCmA | 461 | mUpsfGpsmAmAmGmCmGmAmAmGmUmGmCfAmCmAmCmGmGpsmU5smU |
| 423 | mCpsmCpsfGmUmGmUfGfCfAmCmUfUmCmGmCmUfUmCmA | 458 | mUpsfGpsmAmAmGmCmGmAmAmGmUmGmCfAmCmAmCmGmGpsmUpsmC |
| 423 | mCpsmCpsfGmUmGmUfGfCfAmCmUfUmCmGmCmUfUmCmA | 458 | mUpsfGpsmAmAmGmCmGmAmAmGmUmGmCfAmCmAmCmGmGpsmUpsmC |
| 423 | mCpsmCpsfGmUmGmUfGfCfAmCmUfUmCmGmCmUfUmCmA | 458 | mUpsfGpsmAmAmGmCmGmAmAmGmUmGmCfAmCmAmCmGmGpsmUpsmC |
| 423 | mCpsmCpsfGmUmGmUfGfCfAmCmUfUmCmGmCmUfUmCmA | 462 | vmUpsfGpsmAmAmGmCmGmAmAmGmUmGmCfAmCmAmCmGmGpsmUpsmC |
| 423 | mCpsmCpsfGmUmGmUfGfCfAmCmUfUmCmGmCmUfUmCmA | 463 | vmUpsfGpsmAmAmGmCmGmAmAmGmUmGmCfAmCmAmCmGmGpsTpsT |
| 423 | mCpsmCpsfGmUmGmUfGfCfAmCmUfUmCmGmCmUfUmCmA | 447 | mUpsfGpsmAmAmGmCmGmAmAmGmUmGmCfAmCmAmCmGmGpsmUpsmU |
| 423 | mCpsmCpsfGmUmGmUfGfCfAmCmUfUmCmGmCmUfUmCmA | 458 | mUpsfGpsmAmAmGmCmGmAmAmGmUmGmCfAmCmAmCmGmGpsmUpsmC |
| 423 | mCpsmCpsfGmUmGmUfGfCfAmCmUfUmCmGmCmUfUmCmA | 457 | mUpsfGpsmAmAmGfCmGmAmAmGmUmGmCfAmCfAmCmGmGpsmUpsmC |
| 423 | mCpsmCpsfGmUmGmUfGfCfAmCmUfUmCmGmCmUfUmCmA | 464 | mUpsfGpsmAmAmGfCmGmAmAfGmUmGmCfAmCmAmCfGmGpsmUpsmC |
| 423 | mCpsmCpsfGmUmGmUfGfCfAmCmUfUmCmGmCmUfUmCmA | 465 | vmBpsfGpsmAmAmGmCmGmAmAmGmUmGmCfAmCmAmCmGmGpsmUpsmC |
| 423 | mCpsmCpsfGmUmGmUfGfCfAmCmUfUmCmGmCmUfUmCmA | 466 | mesnmUpsfGpsmAmAmGmCmGmAmAmGmUmGmCfAmCmAmCmGmGpsmUpsmC |
| 423 | mCpsmCpsfGmUmGmUfGfCfAmCmUfUmCmGmCmUfUmCmA | 467 | cmUpsfGpsmAmAmGmCmGmAmAmGmUmGmCfAmCmAmCmGmGpsmUpsmC |
| 423 | mCpsmCpsfGmUmGmUfGfCfAmCmUfUmCmGmCmUfUmCmA | 468 | mesnomUpsfGpsmAmAmGmCmGmAmAmGmUmGmCfAmCmAmCmGmGpsmUpsmC |
| 423 | mCpsmCpsfGmUmGmUfGfCfAmCmUfUmCmGmCmUfUmCmA | 469 | mUpsfGpsmAmAmGfCmGmAmAmGmUmGmCfAmCmAmCmGmGpsmUpsmC |
| 423 | mCpsmCpsfGmUmGmUfGfCfAmCmUfUmCmGmCmUfUmCmA | 470 | mUpsfGpsmAmAmGmCmGmAmAmGfUmGmCfAmCmAmCmGmGpsmUpsmC |
| 423 | mCpsmCpsfGmUmGmUfGfCfAmCmUfUmCmGmCmUfUmCmA | 471 | mUpsfGpsmAmAmGmCmGmAmAmGmUfGmCfAmCmAmCmGmGpsmUpsmC |
| 423 | mCpsmCpsfGmUmGmUfGfCfAmCmUfUmCmGmCmUfUmCmA | 472 | mUpsfGpsmAmAmGmCmGmAmAmGmUmGmCfAmCfAmCmGmGpsmUpsmC |

TABLE 4-continued siNA Sequences

| SEQ ID NO. | Sense Sequence (5'-3') | SEQ ID NO. | Antisense Sequence (5'-3') |
|---|---|---|---|
| 423 | mCpsmCpsfGmUmGmUfGfCfAmCmUfUmCmGmCmUfUmCmA | 473 | mUpsfGpsmAmAmGmCmGmAmAmGmUmGmCfAmCmAfCmGmGpsmUpsmC |
| 423 | mCpsmCpsfGmUmGmUfGfCfAmCmUfUmCmGmCmUfUmCmA | 474 | mUpsfGpsmAmAmGmCmGmAmAmGmUmGmCfAmCmAmCfGmGpsmUpsmC |
| 423 | mCpsmCpsfGmUmGmUfGfCfAmCmUfUmCmGmCmUfUmCmA | 475 | mUpsfGpsmAmAmGmCmGmAmAmGmUmGmCfAmCmAmCmGfGpsmUpsmC |
| 423 | mCpsmCpsfGmUmGmUfGfCfAmCmUfUmCmGmCmUfUmCmA | 476 | mUpsfGpsmAfAmGmCmGmAmAmGmUmGmCfAmCmAmCmGmGpsmUpsmC |
| 423 | mCpsmCpsfGmUmGmUfGfCfAmCmUfUmCmGmCmUfUmCmA | 477 | mUpsfGpsmAmAfGmCmGmAmAmGmUmGmCfAmCmAmCmGmGpsmUpsmC |
| 423 | mCpsmCpsfGmUmGmUfGfCfAmCmUfUmCmGmCmUfUmCmA | 478 | mUpsfGpsmAmAmGmCfGmAmAmGmUmGmCfAmCmAmCmGmGpsmUpsmC |
| 423 | mCpsmCpsfGmUmGmUfGfCfAmCmUfUmCmGmCmUfUmCmA | 479 | mUpsfGpsmAmAmGmCmGfAmAmGmUmGmCfAmCmAmCmGmGpsmUpsmC |
| 423 | mCpsmCpsfGmUmGmUfGfCfAmCmUfUmCmGmCmUfUmCmA | 480 | mUpsfGpsmAmAmGmCmGmAfAmGmUmGmCfAmCmAmCmGmGpsmUpsmC |
| 423 | mCpsmCpsfGmUmGmUfGfCfAmCmUfUmCmGmCmUfUmCmA | 481 | mUpsfGpsmAmAmGmCmGmAmAfGmUmGmCfAmCmAmCmGmGpsmUpsmC |
| 423 | mCpsmCpsfGmUmGmUfGfCfAmCmUfUmCmGmCmUfUmCmA | 482 | d2vmUpsfGpsmAmAmGmCmGmAmAmGmUmGmCfAmCmAmCmGmGpsmUpsmC |
| 423 | mCpsmCpsfGmUmGmUfGfCfAmCmUmUmCmGmCmUfUmCmA | 483 | mUpsfGpsmAfAmGfCmGfAmAmGmUmGmCfAmCmAmCmGmGpsmUpsmC |
| 423 | mCpsmCpsfGmUmGmUfGfCfCmCmUfUmCmGmCmUfUmCmA | 458 | mUpsfGpsmAmAmGmCmGmAmAmGmUmGmCfAmCmAmCmGmGpsmUpsmC |
| 423 | mCpsmCpsfGmUmGmUfGfCmAmCmUmUmCmGmCmUfUmCmA | 458 | mUpsfGpsmAmAmGmCmGmAmAmGmUmGmCfAmCmAmCmGmGpsmUpsmC |
| 424 | mCpsmCpsmGmUfGmUfGfCfAmCmUmUmCmGmCmUmUmCmA | 457 | mUpsfGpsmAmAmGfCmGmAmAmGmUmGmCfAmCfAmCmGmGpsmUpsmC |
| 424 | mCpsmCpsmGmUfGmUfGfCfAmCmUmUmCmGmCmUmUmCmA | 484 | mUpsfGpsmAmAmGfCmGfAfAmGmUmGmCfAmCfAmCmGmGpsmUpsmC |
| 424 | mCpsmCpsmGmUfGmUfGfCfAmCmUmUmCmGmCmUmUmCmA | 485 | mUpsfGpsmAmAfGmCmGfAmAmGmUmGmCfAmCmAfCmGmGpsmUpsmC |
| 425 | mCpsmUpsmGmCfUmAfUfGfCmCmUmCmAmUmCmUmUmCmU | 486 | mApsfGpsmAmAmGfAmUmGmAfGmGmCmAfUmAmGmCfAmGpsmCpsmA |
| 425 | mCpsmUpsmGmCfUmAfUfGfCmCmUmCmAmUmCmUmUmCmU | 487 | mApsfGpsmAmAmGfAmUmGmAmGmGmCmAfUmAfGmCmAmGpsmCpsmA |
| 425 | mCpsmUpsmGmCfUmAfUfGfCmCmUmCmAmUmCmUmUmCmU | 488 | mApsfGpsmAmAfGmAmUfGmAmGmGmCmAfUmAmGfCmAmGpsmCpsmA |
| 426 | mCpsmUpsmGmCfUmAfUmGfCmCmUfCmAmUmCmUfUmCmU | 489 | mApsfGpsmAmAmGmAmUmGmAmGmGmCmAfUmAmGmCmAmGpsmCpsmA |
| 427 | mGpsmCpsfGmGmGmGfUfUfUmUmUfCmUmUmGmUfUmGmA | 490 | vmUpsfCpsmAmAmCmAmAmGmAmAmAmAfCmCmCmCmGmCpsmCpsmU |
| 428 | mGpsmCpsfGmGmGmGfUmUmUmUmUmCmUmUmGmUfUmGmA | 491 | mUpsfCpsmAmAmCmAmAmGmAmAmAmAfCmCmCmCmGmCpsmCpsmU |
| 429 | mGpsmCpsmGmGfGmGfUfUfUmUmUmCmUmUmGmUmUmGmA | 492 | mUpsfCpsmAmAmCfAmAmGmAfAmAmAfCmCmCmCfGmCpsmCpsmU |
| 429 | mGpsmCpsmGmGfGmGfUfUfUmUmUmCmUmUmGmUmUmGmA | 493 | mUpsfCpsmAmAmCfAmAmGmAmAmAmAfCmCfCmCmGmCpsmCpsmU |
| 429 | mGpsmCpsmGmGfGmGfUfUfUmUmUmCmUmUmGmUmUmGmA | 494 | mUpsfCpsmAmAfCmAmAfGmAmAmAmAfCmCmCfCmGmCpsmCpsmU |

TABLE 4-continued siNA Sequences

| SEQ ID NO. | Sense Sequence (5'-3') | SEQ ID NO. | Antisense Sequence (5'-3') |
|---|---|---|---|
| 430 | mGpsmCpsmUmGfCmUmAmUf GfCfCmUmCfAmUmCmUmUfC mUmU | 495 | mApsfApsmGmAmAmGmAmUmGmA mGmGmCfAmUmAmGmCmAmGmCp smApsmG |
| 430 | mGpsmCpsmUmGfCmUmAmUf GfCfCmUmCfAmUmCmUmUfC mUmU | 496 | mApsfApsmGmAmAfGmAmUmGmA mGmGmCfAmUfAmGmCmAmGmCps mApsmG |
| 431 | mGpsmCpsmUmGmCmUfAmUf GfCfCmUmCmAmUfCmUmUfC mUmU | 497 | mApsfApsmGmAmAfGmAfUfGmAm GmGmCfAmUfAmGmCmAmGmCpsm ApsmG |
| 432 | mGpsmCpsmUmGmCmUfAmUf GfCfCmUmCmAmUmCmUmUm CmUmU | 498 | vmApsfApsmGmAmAfGmAmUmGmA mGmGmCfAmUfAmGmCmAmGmCps mApsmG |
| 432 | mGpsmCpsmUmGmCmUfAmUf GfCfCmUmCmAmUmCmUmUm CmUmU | 500 | d2vmApsfApsmGmAmAfGmAmUmG mAmGmGmCfAmUfAmGmCmAmGm CpsmApsmG |
| 433 | mGpsmUpsfGmGfUmGfGfAfCm UmUmCmUmCmUmCmAmAm U | 501 | mApsfUpsmGmAfGmAmGmAmA mGmUmCfCmAfCmCmAmCpsmGpsm A |
| 434 | mGpsmUpsfGmGmUmGfGfAfA mUmUfCmUmCmUmCfAmAmU | 502 | mApsfUpsmUmGmAmGmAmGmAmA mGmGmUmCfCmAmCmCmAmCpsmGps mA |
| 435 | mGpsmUpsfGmGmUmGfGfAfC mGmUfCmUmCmUmCfAmAmU | 502 | mApsfUpsmUmGmAmGmAmGmAmA mGmGmUmCfCmAmCmCmAmCpsmGps mA |
| 435 | mGpsmUpsfGmGmUmGfGfAfC mUmUfCmUmCmUmCfAmAmU | 503 | vmApsfUpsmUmGmAmGmAmGmAm AmGmUmCfCmAmCmCmAmCpsmGp smA |
| 435 | mGpsmUpsfGmGmUmGfGfAfC mUmUfCmUmCmUmCfAmAmU | 501 | mApsfUpsmUmGmAfGmAmGmAmA mGmUmCfCmAfCmCmAmCpsmGpsm A |
| 435 | mGpsmUpsfGmGmUmGfGfAfC mUmUfCmUmCmUmCfAmAmU | 504 | mApsfUpsmUmGmAfGmAmGmAfAm GmUmCfCmAmCmCfAmCpsmGpsmA |
| 435 | mGpsmUpsfGmGmUmGfGfAfC mUmUfCmUmCmUmCfAmAmU | 505 | vmNpsfUpsmUmGmAmGmAmGmAm AmGmUmCfCmAmCmCmAmCpsmGp smA |
| 435 | mGpsmUpsfGmGmUmGfGfAfC mUmUfCmUmCmUmCfAmAmU | 506 | vmUpsfUpsmUmGmAmGmAmGmAm AmGmUmCfCmAmCmCmAmCpsmGp smA |
| 435 | mGpsmUpsfGmGmUmGfGfAfC mUmUfCmUmCmUmCfAmAmU | 507 | cmUpsfUpsmUmGmAmGmAmGmAm AmGmUmCfCmAmCmCmAmCpsmGp smA |
| 435 | mGpsmUpsfGmGmUmGfGfAfC mUmUfCmUmCmUmCfAmAmU | 508 | mesnmUpsfUpsmUmGmAmGmAmGm AmAmGmUmCfCmAmCmCmAmCps mGpsmA |
| 435 | mGpsmUpsfGmGmUmGfGfAfC mUmUfCmUmCmUmCfAmAmU | 509 | mesnomUpsfUpsmUmGmAmGmAmG mAmAmGmUmCfCmAmCmCmAmCp smGpsmA |
| 435 | mGpsmUpsfGmGmUmGfGfAfC mUmUfCmUmCmUmCfAmAmU | 510 | mApsfUpsmUmGmAfGmAmGmAmA mGmUmCfCmAmCmCmAmCpsmGps mA |
| 435 | mGpsmUpsfGmGmUmGfGfAfC mUmUfCmUmCmUmCfAmAmU | 511 | mApsfUpsmUfGmAmGmAmGmAmA mGmUmCfCmAmCmCmAmCpsmGps mA |
| 435 | mGpsmUpsfGmGmUmGfGfAfC mUmUfCmUmCmUmCfAmAmU | 512 | mApsfUpsmUmGfAmGmAmGmAmA mGmUmCfCmAmCmCmAmCpsmGps mA |
| 435 | mGpsmUpsfGmGmUmGfGfAfC mUmUfCmUmCmUmCfAmAmU | 513 | mApsfUpsmUmGmAmGfAmGmAmA mGmUmCfCmAmCmCmAmCpsmGps mA |
| 435 | mGpsmUpsfGmGmUmGfGfAfC mUmUfCmUmCmUmCfAmAmU | 514 | mApsfUpsmUmGmAmGmAmGfAmA mGmUmCfCmAmCmCmAmCpsmGps mA |
| 435 | mGpsmUpsfGmGmUmGfGfAfC mUmUfCmUmCmUmCfAmAmU | 515 | mApsfUpsmUmGmAmGmAmGmAfA mGmUmCfCmAmCmCmAmCpsmGps mA |
| 435 | mGpsmUpsfGmGmUmGfGfAfC mUmUfCmUmCmUmCfAmAmU | 516 | mApsfUpsmUmGmAmGmAmGmAmA mGmUmCfCmAfCmCmAmCpsmGpsm A |
| 435 | mGpsmUpsfGmGmUmGfGfAfC mUmUfCmUmCmUmCfAmAmU | 517 | mApsfUpsmUmGmAmGmAmGmAmA mGmUmCfCmAmCmCfAmCpsmGpsm A |
| 435 | mGpsmUpsfGmGmUmGfGfAfC mUmUfCmUmCmUmCfAmAmU | 518 | mApsfUpsmUmGmAmGmAmGmAmA mGmUmCfCmAmCmCmAfCpsmGpsm A |

TABLE 4-continued siNA Sequences

| SEQ ID NO. | Sense Sequence (5'-3') | SEQ ID NO. | Antisense Sequence (5'-3') |
|---|---|---|---|
| 435 | mGpsmUpsfGmGmUmGfGfAfCmUmUfCmUmCmUmCfAmAmU | 519 | d2vmApsfUpsmUmGmAmGmAmGmAmAmGmUmCfCmAmCmCmAmCpsmGpsmA |
| 436 | mGpsmUpsfGmGmUmGfGfAfCmUmUmCmUmCmUmCfUmAmU | 520 | mApsfUpsmUfGmAfGmAfGmAmAmGmUmCfCmAmCmCmAmCpsmGpsmA |
| 437 | mGpsmUpsfGmGmUmGfGfAmCmUmUmCmUmCmUmCfAmAmU | 502 | mApsfUpsmUmGmAmGmAmGmAmAmGmUmCfCmAmCmCmAmCpsmGpsmA |
| 438 | mGpsmUpsmGmGfUmGfGfAfCmUmUmCmUmCmUmCmAmAmU | 501 | mApsfUpsmUmGmAfGmAmGmAmAmGmUmCfCmAfCmCmAmCpsmGpsmA |
| 438 | mGpsmUpsmGmGfUmGfGfAfCmUmUmCmUmCmUmCmAmAmU | 521 | mApsfUpsmUmGmAfGmAfGfAmAmGmUmCfCmAfCmCmAmCpsmGpsmA |
| 438 | mGpsmUpsmGmGfUmGfGfAfCmUmUmCmUmCmUmCmAmAmU | 522 | mApsfUpsmUmGfAmGmAfGmAmAmGmUmCfCmAmCfCmAmCpsmGpsmA |
| 439 | mUpsmCpsmGmUmGmGfUmGfGfAfCmUmUmCmUmCmUmCmAmAmU | 523 | vmApsfUpsmUmGmAfGmAmGmAmAmGmUmCfCmAfCmCmAmCmGmApsmGpsmU |
| 440 | mUpsmGpsfCmCmGmAfUfCfCmAmUfAmCmUmGmCfGmGmA | 524 | vmUpsfCpsmCmGmCmAmGmUmAmUmGmAfUmCmGmGmCmApsmGpsmA |
| 441 | mUpsmGpsfUmGmCmAfCfUfUmCmGfCmUmUmCmAfCmCmU | 525 | vmApsfGpsmGmUmGmAmAmGmCmGmAmAmGfUmGmCmAmCmApsmCpsmG |
| 441 | mUpsmGpsfUmGmCmAfCfUfUmCmGfCmUmUmCmAfCmCmU | 526 | mApsfGpsmGmUmGfAmAmGmCfGmAmAmGfUmGmCmAfCmApsmCpsmG |
| 441 | mUpsmGpsfUmGmCmAfCfUfUmCmGfCmUmUmCmAfCmCmU | 527 | mApsfGpsmGmUmGfAmAmGmCmGmAmAmGfUmGfCmAmCmApsmCpsmG |
| 442 | mUpsmGpsfUmGmCmAfCfUmUmCmGmCmUmUmCmAfCmCmU | 525 | vmApsfGpsmGmUmGmAmAmGmCmGmAmAmGfUmGmCmAmCmApsmCpsmG |
| 442 | mUpsmGpsfUmGmCmAfCfUmUmCmGmCmUmUmCmAfCmCmU | 528 | vmApsfGpsmGmUmGmAmAmGmCmGmAmAmGfUmGmCmAmCmApsTpsT |
| 442 | mUpsmGpsfUmGmCmAfCfUmUmCmGmCmUmUmCmAfCmCmU | 529 | d2vmApsfGpsmGmUmGmAmAmGmCmGmAmAmGfUmGmCmAmCmApsmCpsmG |
| 443 | unCpsmCpsfGmUmGmUfGfCfAmCmUfUmCmGmCmUfUmCmA | 458 | mUpsfGpsmAmAmGmCmGmAmAmGmUmGmCfAmCmAmCmGmGpsmUpsmC |
| 444 | unGpsmUpsfGmGmUmGfGfAfCmUmUfCmUmCmUmCfAmAmU | 502 | mApsfUpsmUmGmAmGmAmGmAmAmGmUmCfCmAmCmCmAmCpsmGpsmA |
| 423 | mCpsmCpsfGmUmGmUfGfCfAmCmUfUmCmGmCmUfUmCmA | 458 | mUpsfGpsmAmAmGmCmGmAmAmGmUmGmCfAmCmAmCmGmGpsmUpsmC |
| 224 | mCpsmUpsfGmCmUmAfUfGfCmCmUfCmAmUmCmUfUmCmU | 489 | mApsfGpsmAmAmGmAmUmGmAmGmGmCmAfUmAmGmCmAmGpsmCpsmA |
| 236 | mGpsmCpsfGmGmGmGfUfUmUmUmCmUmUmGmUfUmGmA | 491 | mUpsfCpsmAmAmCmAmAmGmAmAmAmAfCmCmCmCmGmCpsmCpsmU |
| 432 | mGpsmCpsmUmGmCmUfAmUfGfCfCmUmCmAmUmCmUmUmCmUmU | 496 | mApsfApsmGmAmAfGmAmUmGmAmGmGmCfAmUfAmGmCmAmGmCpsmApsmG |
| 435 | mGpsmUpsfGmGmUmGfGfAfCmUmUfCmUmCmUmCfAmAmU | 502 | mApsfUpsmUmGmAmGmAmGmAmAmGmUmCfCmAmCmCmAmCpsmGpsmA |
| 442 | mUpsmGpsfUmGmCmAfCfUmUmCmGmCmUmUmCmAfCmCmU | 530 | mApsfGpsmGmUmGmAmAmGmCmGmAmAmGfUmGmCmAmCmApsmCpsmG |
| 439 | mUpsmCpsmGmUmGmGfUmGfGfAfCmUmUmCmUmCmUmCmAmAmU | 531 | mApsfUpsmUmGmAfGmAmGmAmAmGmUmCfCmAfCmCmAmCmGmApsmGpsmU |
| 423 | mCpsmCpsfGmUmGmUfGfCfAmCmUfUmCmGmCmUfUmCmA | 532 | mUpsfGpsmAmAmGmCmGmAmAmGmUmGmCfAmCmAmCmGmGpsTpsT |
| 441 | mUpsmGpsfUmGmCmAfCfUfUmCmGfCmUmUmCmAfCmCmU | 530 | mApsfGpsmGmUmGmAmAmGmCmGmAmAmGfUmGmCmAmCmApsmCpsmG |

TABLE 4-continued siNA Sequences

| SEQ ID NO. | Sense Sequence (5'-3') | SEQ ID NO. | Antisense Sequence (5'-3') |
|---|---|---|---|
| 442 | mUpsmGpsfUmGmCmAfCfUmUmCmGmCmUmUmCmAfCmCmU | 533 | mApsfGpsmGmUmGmAmAmGmCmGmAmAmGfUmGmCmAmCmApsTpsT |
| 424 | mCpsmCpsmGmUfGmUfGfCfAmCmUmUmCmGmCmUmUmCmA | 536 | d2vd3UpsfGpsmAmAfGmCmGfAmAmGmUmGmCfAmCmAfCmGmGpsmUpsmC |
| 438 | mGpsmUpsmGmGfUmGfGfAfCmUmUmCmUmCmUmCmAmAmU | 537 | mApsf4PpsmUmGmAfGmAmGmAmAmGmUmCfCmAfCmCmAmCpsmGpsmA |
| 438 | mGpsmUpsmGmGfUmGfGfAfCmUmUmCmUmCmUmCmAmAmU | 538 | mApsfUpsmUmGmAfGmAmGmAmAmGmUmCf2PmAfCmCmAmCpsmGpsmA |
| 438 | mGpsmUpsmGmGfUmGfGfAfCmUmUmCmUmCmUmCmAmAmU | 599 | mApsfUpsmUmGmAfGmAmGmAmAmGmUmCfCmAfXmCmAmCpsmGpsmA | mX = 2'-O-methyl nucleotide;
fX = 2'-fluoro nucleotide;
5dcd3X = nucleotide of Formula 17;
5dfX = nucleotide of Formula 16;
vX = 5' vinyl phosphonate nucleotide;
d2vX = deuterated 5' vinyl phosphonate nucleotide;
vmX = 5' vinyl phosphonate, 2'-O-methylnucleotide;
vmB =

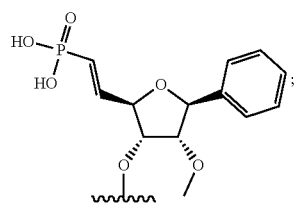 [SMILES: *O[C@H]1[C@@H](OC)[C@H](c2ccccc2)O[C@@H]1/C=C/P(=O)(O)O]

vmN =

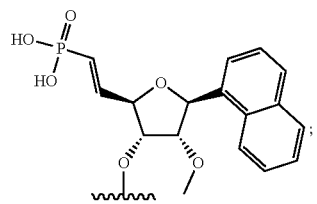 [SMILES: *O[C@H]1[C@@H](OC)[C@H](c2cccc3ccccc23)O[C@@H]1/C=C/P(=O)(O)O]

VmU =

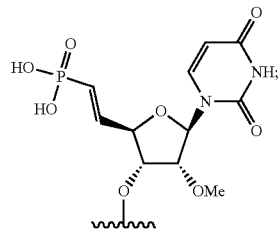 [SMILES: *O[C@H]1[C@@H](OC)[C@H](n2ccc(=O)[nH]c2=O)O[C@@H]1/C=C/P(=O)(O)O]

cmU =

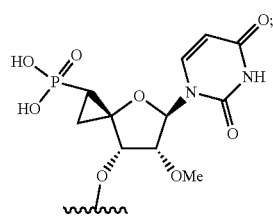

mesnmU =

US 11,549,110 B2
397                                                          398
TABLE 4-continued
siNA Sequences
| SEQ ID NO. | Sense Sequence (5'-3') | SEQ ID NO. | Antisense Sequence (5'-3') |
|---|---|---|---|
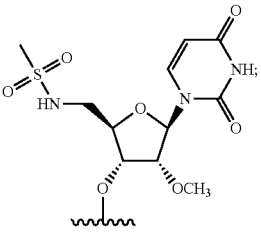 [SMILES: *O[C@H]1[C@@H](OC)[C@H](n2ccc(=O)[nH]c2=O)O[C@@H]1CNS(C)(=O)=O]
mesnomU =
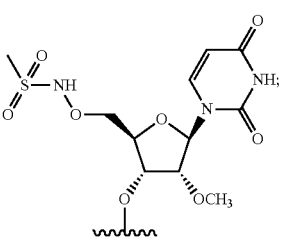 [SMILES: *O[C@H]1[C@@H](OC)[C@H](n2ccc(=O)[nH]c2=O)O[C@@H]1CONS(C)(=O)=O]
d2vmU =
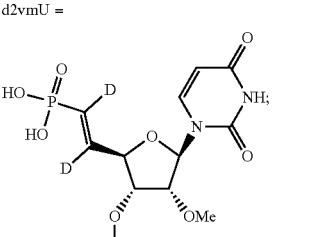
d2vmA =
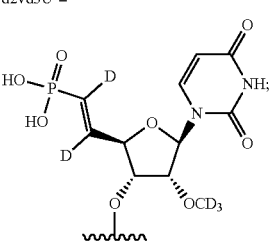
d2vd3U =
f4P =
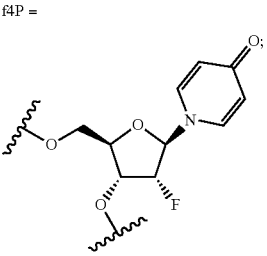
f2P =

TABLE 4-continued siNA Sequences

| SEQ ID NO. | Sense Sequence (5'-3') | SEQ ID NO. | Antisense Sequence (5'-3') |
|---|---|---|---|

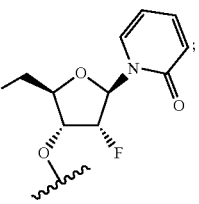

fX =

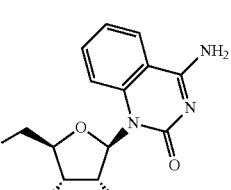

ps = phosphorothioate linkage

TABLE 5

| SEQ ID NO: | Description | Sequence+ |
|---|---|---|
| 410 | Hepatitis B virus (Genbank Accession No. U95551.1) | aattccacaacctttcaccaaactctgcaagatcccagagtgagaggcctgtatttccctgctggtgg ctccagttcaggagcagtaaaccctgttccgactactgcctctcccttatcgtcaatcttctcgaggatt ggggaccctgcgctgaacatggagaacatcacatcaggattcctaggacccctctcgtgttacagg cggggttttcttgttgacaagaatcctcacaataccgcagagtctagactcgtggtggacttctctca atttctaggggaactaccgtgtgtcttggccaaaattcgcagtccccaacctccaatcactcacca acctcctgtcctccaacttgtcctggttatcgctggatgtgtctgcggcgttttatcatcttcctcttcatc ctgctgctatgcctcatcttcttgttggttcttctggactatcaaggtatgttgcccgtttgtcctctaattc caggatcctcaaccaccagcacgggaccatgccgaacctgcatgactactgctcaaggaacctcta tgtatccctcctgttgctgtaccaaaccttcggacggaaattgcacctgtattcccatcccatcatcctg ggctttcggaaaattcctatgggagtgggcctcagcccgtttctcctggctcagtttactagtgccattt gttcagtggttcgtagggcttccccccactgtttggctttcagtatatggatgatgtggtattgggggc caagtctgtacagcatcttgagtccctttttaccgctgttaccaattttcttttgtctttgggtatacatttaa accctaacaaaacaaagagatggggttactctctgaatttatgggttatgtcattggaagttatgggtc cttgccacaagaacacatcatacaaaaaatcaaagaatgttttagaaaacttcctattaacaggcctat tgattggaaagtatgtcaacgaattgtgggtcttttgggttttgctgccccatttacacaatgtggttatc ctgcgttaatgcccttgtatgcatgtattcaatctaagcaggctttcactttctcgccaacttacaaggcc tttctgtgtaaacaatacctgaaccttTACcccgttcccggcaacggccaggtctgtgccaagtgttt gctgacgcaaccccactggctggggcttggtcatgggccatcagcgcgtgcgtggaaccttttcg gctccctctgccgatccatactgcggaactcctagccgcttgttttgctcgcacagggtctggagcaaa cattatcgggactgataactctgttgtcctctcccgcaaatatacatcgtatccatggctgctaggctgt gctgccaactggatcctgcgcgggacgtccttttgtttacgtcccgtcggcgctgaatcctgcggacg accatctgggggtgcgcttgggactctctcgtcccccttctccgtctgccgttccgaccgaccacgggg cgcacctctattacgcggactccccgtctgtgccttctcatctgccggaccgtgtgcacttcgcttca cctctgcacgtcgcatggagaccaccgtgaacgcccaccgaatgttgcccaaggtcttacataaga ggactatggactctctgcaatgtcaacgaccgaccttgaggcatacttcaaagactgtttgtttaaag actggggaggagttggggggaggagattagattaaaggtetttgtactaggaggctgtaggcataaatt ggtctgcgcaccagcaccatgcaacttttcaccctctgcctaatcatctcttgttcatgtcctactgttca agcctccaagctgtgccttgggtggctttggggcatggacatcgaccttataaagaatttggagcta ctgtggagttactctcgttfttgccttctgacttctttccttcagtacgagatcttctagataccgcctcag ctctgtatcgggaagccttagagtctcctgagcattgttcacctcaccatactgcactcaggcaagca attctttgctggggggaactaatgactctagctacctgggtgggtgttaatttggaagatccagcatct agagacctagtagtcagttatgtcaacactaatatgggcctaaagttcaggcaactcttgtggtttcac atttcttgtctcacttttggaagagaaaccgttatagagtatttggtgtctttcggagtgtggattcgcact cctccagatatagaccaccaaatgcccctatcctatcaacacttccggaaactactgttgttagacga cgaggcaggtccccctagaagaagaactccctcgcctcgcagacgaaggtctcaatcgccgcgtcg cagaagatctcaatctcgggaacctcaatgttagtattccttggactcataaggtggggaacttactg gtctttattcttctactgtacctgtctttaatcctccattggaaaacaccatcttttcctaatatacatttacacc aagacattatcaaaaaatgtgaacagtttgtaggcccacttacagttaatgagaaaagaagattgcaa ttgattatgcctgctagtttattccaaaggttaccaaatattttaccattggataagggtattaaaccttat tatccagaacatctagttaatcattacttccaaactagacactattt acacactctatggaaggcgggta tattatataagagagaaacaacacatagcgcctcattttgtgggtcaccatattcttgggaacaagatc tacagcatggggcagaatctttccaccagcaatcctctgggattctttcccgaccaccagttggatcc agccttcagagcaaacacagcaaatccagattgggacttcaatcccaacaaggacacctggccag

TABLE 5-continued

| SEQ ID NO: | Description | Sequence+ |
|---|---|---|
| | | acgccaacaaggtaggagctggagcattcgggctgggtttcaccccaccgcacggaggccttttg gggtggagccctcaggctcagggcatactacaaactttgccagcaaatccgcctcctgcctccacc aatcgccagacaggaaggcagcctaccccgctgtctccaccttttgagaaacactcatcctcaggcc atgcagtgg |
| 411 | MCJ mRNA (GenBank Accession No. NM_013238.3) | agtcactgccgccggcgccttgagtctccgggccgccttgccatggctgcccgtggtgtcatcgctc cagttggcgagagtttgcgctacgctgagtacttgcagccctcggccaaacggccagacgccgac gtcgaccagcagagactggtaagaagtttgatagctgtaggactgggtgttgcagctcttgcatttgc aggtcgctacgcatttcggatctggaaacctctagaacaagttatcacagaaactgcaaagaagattt caactcctagcttttcatcctactataaaggaggatttgaacagaaaatgagtaggcgagaagctggt cttattttaggtgtaagcccatctgctggcaaggctaagattagaacagctcataggagagtcatgatt ttgaatcacccagatataaaggtggatctccttacgctagcagccaaaataaatgaagcaaaagacttgct agaaacaaccaccaaacattgatgcttaaggaccacactgaaggaaaaaaaagaggggactccg aaaaaaaaaaagccctgcaaaatattctaaaacatggtcttcttaattttctatatggattgaccacag tcttatcttccaccattaagctgtataacaataaaatgttaatagtcttgcttttttattatcttttaaagatctc cttaaattctataactgatctttttcttattttgtttgtgacattcatacattttaagattttttgttatgttctgaa ttcccccctacacacacacacacacacacacacacacacacgtgcaaaaaatatgatcaagaatgc aattgggattgtgagcaatgagtagacctcttattgtttatatttgtaccctcattgtcaattttttttttagg gaatttgggactctgcctatataaggtgttttaaatgtcttgagaacaagcactggctgatacctcttgg agatatgatctgaaatgtaatggaatttattaaatggtgtttagtaaagtaggggttaaggacttgttaaa gaaccccactatctctgagacccctatagccaaagcatgaggacttggagagctactaaaatgattca ggtttacaaaatgagccctgtgaggaaaggttgagagaagtctgaggagtttgtatttaattatagtctt ccagtactgtatattcattcattactccattctcacaaatatttattgaccccttttgatgtgcaaggcactatc gtgcgtcccctgagagttgcaagtatgaagcagtcatggatcatgaaccaaaggaacttatatgtag aggaaggataaatcacaaatagtgaatactgttagatacagatgatatattttaaaagttcaaaggaag aaaagaatgtgttaaacactgcatgagagaggaggaataagtggcatagagctaggcttagaaaaga aaaatattccgataccatatgattggtgaggtaagtgttattctgagatgagaattagcagaaatagat atatcaatcggagtgattagagtgcagggtttctggaaagcaaggtttggacagagtggtcatcaaa ggccagccctgtgacttacactgcattaaattaatttcttagaacatagtccctgatcattatcactttact attccaaaggtgagagaacagattcagatagagtgccagcattgtttcccagtattccttttacaaatctt gggttcattccaggtaaactgaaactactgcattgtttctatcttaaaatacttttttagatatcctagatgcat cttcaacttctaacattctgtagtttaggagttctcaaccttggcattattgacatgttaggccaaataatt tttttttgtgggaggtctcttgtgcgttttagatgattagcaataatccctgacctgttatctactaaagact agtcgtttctcatcagttgtgacaacaaaaatggttccagatattgccaaatgccctttagaggacagt aatcgcccccagttgagaaccatttcagtaaaactttaattactatttttttcttttggtttataaaataatgat cctgaattaaattgatggaaccttgaagtcgataaaatatatttcttgctttaaagtccccatacgtgtcct actaattttctcatgcttttagtgttttcactttttctcctgttatccttgtacctaagaatgccatcccaatccc cagatgtccacctgcccaaagtctaggcatagctgaaggccaagctaaaatgtatccctcttttttctgg tacatgcagcaaaagtaatatgaattatcagcttctgagagcaggcattgtatctgtcttgtttggtgtt acattggcacccaataaatatttgttgagtgaatgaataaattcccatagcactttattcttcacatggta cataactataggggctatagcttggtaccttgtgaagcaactcttggtgtaacataccttatttctcatac taaaatgcaagaaccttagagcaaggatcttgccattcatctttgtaacctctttactctggagcacttg catttagcaggcatcataaagtttttacgtaccaagaaaatgttgctgtttttctgaatactatgcatcaaaa aatgttaccactaattttttaaagctctgctaaggaatattggggcaccctcagatgcaccttttaattgat gtcatattttcctaatccatacttttattcatgagaatttgagtcaccccagcattagcttggaatttccttatt tcccatttgcttttgcaggtgccttggagtcagatctggttttgaatactatcttcctgttatgtgatcttgg gcagttacttaattttctagtcaataacccgtatctataaaatagagaaaataatcctacacaccgggg cctgttgtggggcggggagaggggggagggatcgcatttggagatatactaatgtaaatgacaagt taattggtgcagcacaccaacatggctcatgtctacatatgtaacaaacctgcacgttgtgcacatgtg ccctagaacttaaagtataataaaaagaaattttaaaaaatcctgtcaaataaggttatagtagagaata aggatgtgtaaagcatttagtcacgtaaatgcttaaaaaaatgtaattttacttctttcactgcctcattta attagttttatctttaataataaccttggattcagggtaaagtttcagttatgtcccagtaatcatttattttacc ctcgaatctgcaatttggatagaacatggtggggacagctcgtctctattccttgcagcattaacagg ctggaggcaccacttctctggccagcaagttgggcctggttgttggctgagagcctcagttccttct gcacaggttcctcttttacataggcttctcaacagggctactagagcatcgtcaccatagcagctgtctt ataacagagagtggtcggtctgagagacaaaaaatggaagctgccaaattgttctgggtctggaaa ctgtcagggcatcacttgtgccatattcagttggcctaagaattacagagcctgcctcgattcaaagg gagaggatagagaggactgaaggaatcagtgctcatctttaatatgcagcaggacaggtttgggatt ttttttccccctttgagtctgtgaaggcattacttaagaacaaagtcaggcatgtataattgaactacagtt acttgaaatataagcccagaaagtttcagataataaatacaactattttttctgctgttacccttgtacctaa agatgccatcctaatccccagatctccacaactatacctacatagtagaaggttaaaatgtatccctctt tttctggtcatccagcaaaagtaatatcatgaattatgagctctctgagagcaaggatcatatcagtct tgtttattgttgcagtgaacaagtacagttgcagatattcaggagtaattatctaaatggcagtaggctt ataaaactgaattttcaccagccacaccctccccccaactccttatctgtaaaaagcttatttgagtggt tacctgtcttcagtaaagattgcgcttgcatatttgctgtcattgcatattctgcttaattaagctctgttga tattgcagtttctgtgcatacttacatcttagatgcaatctgagggcctaggaaggcctttttaaaaataa aacaattccgattgcagagaaagtgtaagtcaaggacagttaattcaaggggaacatagaaagctat ttagattttagttgatggtgccagtcttcagcgtaaagtcaaaagtggagggaagtttagtaaggaaa aaatgttgggcttggaatacattgtttagtcttcaaagcacttttacttttttatgaaatatatttttagacattca gcaaatattgaatacttactatatcaggcagtaaagatataaattcattcttaaaatgtgcaacatgttca aactgaaaaaaatacattcttaaacaggaaacttttttccttcatactttttaattaacaagacatataaga gttgcattaatgggcgtgcttatgattgatcacccagcagcatcattagaaataatatattttattcatgt gcagaaatcttttggttgtcctggggaaccttgaacacagaaaagagcttttattgataaggtaattga acacacttgacatattagcttaatatggtttaataccatttgtgggagaagatgaatcagccaggctctt acgtcaagaatatgaagtttctcttgagtcaaccaacttaagatgagctacggagactgcagtgaaaa gttaaatatccaagtacaccagccaatttcacacagtggaaccatgctgtcctcgggcacctgcac ctcgcccaacagtcatcaactagatggaggctcctggctgcaaggaggattgatgggaatgagta aatgtgtcagcatagtccgtcccttctaatggaaaagcaacccaaagagcaaatcctattaatggctg |

TABLE 5-continued

| SEQ ID NO: | Description | Sequence+ |
|---|---|---|
|  |  | gatcagtatcatctacttgtcaaaaacattccatgaattatgagtcaaaattttatttatggtggcattaca cacattaagagatgaggacttctgttagcataattattagctggaaaagttgagaaggttctctggact cattttttataggtggaacctaagtgatctggataattgcccaccagcaaaattgctgggcatggtgga caaagaaaatgttccttctaatgattttttatgagctgagtagctattgttcccagctgagtgctcttttcct cttttttattgttgctgagcaaaagaatttataaaaagctcttcttttgtattaaaaaccctgctcaatgaa atgcaagttcattaagtaatcttcatttctcttcctgccataataacccttcccctctctgttcgattcaaca gtatctagcagcactgctccaaattttaagtctgaacagactatattacatagatgtagagaaatactca atcttcagcattaagagggagcttaatttcacacgggtggaatatgatcactcaggctagatgttggc cataaatttcaaattagtatctcaacttagcagggggggatcaacagtggcaaacttcaattatgacagg ataaaaatcacatagagatattggttcaatatggacatctaaactataatgctaaaagccaataattaga ataagttcattttaagaaaagcattaataatattagctaacgtttagtacctgtgccaaacattctacctat gttaccttgattttcatagccagcctaagaggtactattatgtatcccattttacaggttaagaaacagg ctcagaggagtttaggatcttttccaagattacatagccagtaagtggtggcactaggaaccaaattc agactctgaatcgcatgctgtttatattatattgcactcattctaaatatgtgggaatcagaatgaaggg gcttgtatgacttttggctcatttttttgatgcatgtgacctgggattataaatgtgaaattaggtttacgaa aggatccagtgtcattgtgcatcatgggcaaggagtacctaatctctttaattcttccctggaagcttac gatgtccatccaagtgcacatagcaaaagttctgttgtaaagtttagcagagtgactttctttgactcag agtgatgacggaggaagcttgataagattttatctgaaatgttcatggacaagagctttcaaggaga acatccagagcaaggttctgaagacagctcatgaaggtgaagcagcagacctggcacaagaaatg aagagagagctcagtgtattaaagatgaaaacaagaaaaccgaatatattgaaaggagcagagag gcaatgaaaacaagacaactgaaatgaggtaacttgcagcaattgaaagggaatttcagtactttat agaattcttaaaaattgtttcctgctgttttattttcaattttgaacagggttatttgtccatgccatactttttt gccaaattccaaaattgtgtatagttctatagttgtctggtggagtcaatggaacttagttaccagtcta agaatgtgtctttgagattgtccagttaattctctatttccagtagctgtaataaatggtgaaaaggtttct gactcctggagaaagtttctaactccttatgactaatattcataacagacttgtgagttcttgaacatgg atacacctatatgcaagagtgtattccaaagctaactcagtgatctttccatttatctattcttggattagt ggtgcctttgctctttccttctgtaaatgtgaatagttaagagttgactgcagaagtgtttacacttggct tccatgcctctggaatgtttgtgcttggtggtgagatgtgagactatatttgtatagtctgcatctctcag gctgccccagaatgttgtacagtgcagtgctgaagaaagcagcaggtacacacagaaatgcagcc tttcctggttaaccctgcttggatctgagttacactttgtttcctgacttcttgggacttaggtaatcagttt gccttctactctatctcattttgtactcgcttacatactacattcttgtttgggctttcgtttcttcttgtaagc agagattttttaaaatccaatatgtgaaaatacggatgcactacaattaaataaataaaatgctgttgtgt ttgttttgctttaaaattgtaaaggataaacaataagatagttttatctatgtggttttcccgatgcagttaa aataaaacctaatctgctaaaattgaa |
| 412 | TAZ (GenBank Accession No. NM_000116.5) | gctttccggcggttgcaccgggccggggtgccagcgcccgccttcccgtttcctcccgttccgcag cgcgcccacggcctgtgaccccgcgaccgctccccagtgacgagagagcggggccgggcgc tgctccggcctgacctgcgaagggacctcggtccagtcccctgttgcgccgcgccccgtccgtcc gtgcgcgggccagtcaggggccagtgtctcgagcggtcgaggtcgcagacctagaggcgcccc acaggccggccgggcgctgggagcgccggccgcgggccgggtggggatgcctctgacgt gaagtggccgttcccgcggtgccgccgctcacctggaccctggccagcagcgtcgtcatggct tggtgggcacctacagctgcttctggaccaagtacatgaaccacctgaccgtgcacaacagggag gtgctgtacgagctcatcgagaagcgaggcccggccacgcccctcatcaccgtgtccaatcacca gtcctgcatggacgaccctcatctctgggggatcctgaaactccgccacatctgtgaacctgaagttg atgcgttggaccccctgcagctgcagacatctgcttcaccaaggagctacactcccacttcttcagctt gggcaagtgtgtgcctgtgtgccgaggagcagaattttttccaagcagagaatgagggaaaggtg ttctagacacaggcaggcacatgccaggtgctggaaaaagaagagagaaaggagatggcgtcta ccagaaggggatggacttcattttggagaagctcaaccatggggactggtgcatatcttcccagaa gggaaagtgaacatgagttccgaattcctgcgtttcaagtggggaatcgggcgcctgattgctgagt gtcatctcaaccccatcatcctgccccctgtggcatgtcggaatgaatgacgtccttcctaacagtccg ccctacttccccgctttggacagaaaatcactgtgctgatcgggaagcccttcagtgccctgcctgt actcgagcggctccgggcggagaacaagtcggctgtggagatgcggaaagccctgacggacttc attcaagaggaattccagcatctgaagactcaggcagagcagctccacaaccaccctccagcctgg gagataggccttgcttgctgcctctggattcttggcccgcacagagctggggctgagggatggact gatgctttagctcaaacgtggcttttagacagatttgttcatagaccctctcaagtgccctctccgagc tggtaggcattccagctcctccgtgcttcctcagttacacaaaggacctcagctgcttctcccacttgg ccaagcagggaggaagaagcttaggcaggggctctctttccttcttgccttcagatgttctctcccagg ggctggcttcaggagggagcatagaaggcaggtgagcaaccagttggctaggggagcagggg cccaccagagctgtggagagggaccctaagactcctcggcctggctcctacccaccgcccttgc cgaaccaggagctgctcactacctcctcagggatggccgttggccacgtcttccttctgcctgagctt cccccccaccacaggcccttcctcaggcaaggtctggcctcaggtgggccgcaggcgggaaaa gcagccctggccagaagtcaagcccagccacgtgggagcctagagtgagggcctgaggtctggc tgcttgcccccatgctggcgccaacaactctccatccttctgcctctcaacatcacttgaatcctagg gcctgggttttcatgttttttgaaacagaaccataaagcatatgtgttggctgttgtaaaa |
| 413 | ANGPTL3 (GenBank Accession No. NM_014495.4) | agaagaaaacagttccacgttgcttgaaattgaaaatcaagataaaaatgttcacaattaagctccttc ttttttattgttcctctagttatttcctccagaattgatcaagacaattcatcatttgattctctatctccagag ccaaaatcaagatttgctatgttagacgatgtaaaaattttagccaatggcctccttcagttgggacatg gtcttaaagactttgtccataagacgaagggccaaattaatgacatatttcaaaaactcaacatatttga tcagtcttttttatgatctatccgctcaaaccagtgaaatcaaagaagaagaaaaggaactgagaaga actacatatataaactacaagtcaaaaatgaagaggtaaagaatatgtcacttgaactcaactcaaaactt gaaagcctcctagaagaaaaaattctacttcaacaaaaagtgaaatatttagaagagcaactaactaa cttaattcaaaatcaacctgaaactccagaacacccagaagtaactcacttaaaacttttgtagaaaa acaagataatagcatcaaagaccttctccagacgtggaagaccaatataaacaattaaaccaacag catagtcaaataaaagaaatagaaaatcagctcagaaggactagtattcaagaacccacagaaattt ctctatcttccaagccaagagcaccaagaactactcccttcttcagttgaatgaaataagaaatgtaa aacatgatggcattcctgctgaatgtaccaccatttataacagaggtgaacatacaagtggcatgtat gccatcagacccagcaactctcaagttttcatgtctactgtgatgtatatcaggtagtccatggacatt aattcaacatcgaatagatggatcacaaaacttcaatgaaacgtgggagaactacaaatatggttttg |

TABLE 5-continued

| SEQ ID NO: | Description | Sequence+ |
|---|---|---|
| | | ggaggcttgatggagaattttggttgggcctagagaagatatactccatagtgaagcaatctaattat gttttacgaattgagttggaagactggaaagacaacaaacattatattgaatattcttttacttgggaaa tcacgaaaccaactatacgctacatctagttgcgattactggcaatgtccccaatgcaatcccggaaa acaaagatttggtgttttctacttgggatcacaaagcaaaaggacacttcaactgtccagagggttatt caggaggctggtggtggcatgatgagtgtggagaaaacaacctaaatggtaaatataacaaaccaa gagcaaaatctaagccagagaggagaagaggattatcttggaagtctcaaaatggaaggttatactc tataaaatcaaccaaaatgttgatccatccaacagattcagaaagctttgaatgaactgaggcaaattt aaaaggcaataatttaaacattaacctcattccaagttaatgtggtctaataatctggtattaaatccttaa gagaaagcttgagaaatagattttttttatcttaaagtcactgtctatttaagattaaacatacaatcacat aaccttaaagaataccgtttacatttctcaatcaaaattcttataatactatttgttttaaattttgtgatgtg ggaatcaattttagatggtcacaatctagattataatcaataggtgaacttattaaataacttttctaaata aaaaatttagagacttttattttaaaaggcatcatatgagctaatatcacaactttcccagtttaaaaaact agtactcttgttaaaactctaaacttgactaaatacagaggactggtaattgtacagttcttaaatgttgt agtattaatttcaaaactaaaaatcgtcagcacagagtatgtgtaaaaatctgtaatacaaattttaaac tgatgcttcattttgctacaaaataatttggagtaaatgtttgatatgatttatttatgaaacctaatgaagc agaattaaatactgtattaaaataagttcgctgtctttaaacaaatggagatgactactaagtcacattg acttaacatgaggtatcactatacctatttgttaaaatatatactgtatacattttatatattttaacactta atactatgaaaacaaataattgtaaaggaatcttgtcagattacagtaagaatgaacatatttgtggcat cgagttaaagttttatatttcccctaaatatgctgtgattctaatacattcgtgtaggttttcaagtagaaat aaacctcgtaacaagttactgaacgtttaaacagcctgacaagcatgtatatatgtttaaaattcaataa acaaagacccagtccctaaattatagaaattttaaattattcttgcatgttttatcgacatcacaacagatcc ctaaatccctaaatcccctaaagattagatacaaatttttttaccacagtatccacttgtcagaattttattttaa atatgattttttaaaactgccagtaagaaatttttaaattaaaccatttgttaaaggatatagtgcccaagt tatatggtgacctaccttgtcaatacttagcattatgtatttcaaattatccaatatacatgtcatatatattt ttatatgtcacatatataaaagatatgtatgatctatgtgaatcctaagtaaatatttttgttccagaaaagt acaaaataataaaggtaaaaataatctataattttcaggaccacagactaagctgtcgaaattaacgct gattttttttagggccagaataccaaaatggctcctctcttccccccaaaattggacaatttcaaatgcaaa ataattcattatttaatatatgagttgcttcctctatttggtttcc |
| 414 | DGAT2 (GenBank Accession No. NM_001253891.1) | tgccccgttgtgaggtgataaagtgttgcgctccgggacgccagcgccgcggctgccgcctctgct ggggtctaggctgtttctctcgcgccaccactggccgccggccgcagctccaggtgtcctagccgc ccagcctcgacgccgtcccgggaccctgtgctctgcgcgaagccctggccccgggggccggg gcatgggccaggggcgcggggtgaagcggcttcccgcggggccgtgactgggcgggcttcagc catgaagaccctcatagccgcctactccggggtcctgcgcggcgagcgtcaggccgaggctgac cggagccagcgctctcacggaggacctgcgctgtcgcgcgagggtctgggagatggggagtg gcctgcagtgccatcctcatgtacatattctgcactgattgctggctcatcgctgtgctctacttcacttg gctggtgtttgactggaacacacccaagaaagtggcaggaggtcacagtgggtccgaaactggg ctgtgtggcgctactttcgagactactttcccatccagctggtgaagacacacaacctgctgaccacc aggaactatatctttggataccaccccccatggtatcatgggcctgggtgccttctgcaacttcagcac agaggccacagaagtgagcaagaagttcccaggcatacggccttacctggctacactggcaggca acttccgaatgcctgtgttgagggagtacctgatgtctggaggtatctgccctgtcagccgggacac catagactatttgcttcaaagaatgggagtggcaatgctatcatcgtggtcggggtgcggctg agtctctgagctccatgcctggcaagaatgcagtcaccctgcggaaccgcaagggctttgtgaaact ggccctgcgtcatggagctgacctggttcccatctactcctttggagagaatgaagtgtacaagcag gtgatcttcgaggagggctcctggggccgatggtccagaagaagttccagaaatacattggtttcg ccccatgcatcttccatgtcgaggcctcttctcctccgacacctgggggctggtgccctactccaag cccatcaccactgttgtgggagagcccatcaccatccccaagctggagcacccaacccagcaaga catcgacctgtaccacaccatgtacatggaggccctggtgaagctcttcgacaagcacaagaccaa gttcggcctccccggagactgaggtcctggaggtgaactgagccagccttcggggccaattccctg gaggaaccagctgcaaatcacttttttgctctgtaaattttggaagtgtcatgggtgtctgtgggttattta aaagaaattataacaatttgctaaaccattacaatgttaggtcttttttaagaaggaaaaagtcagtattt caagttctttcacttccagcttgccctgttctaggtggtggctaaatctgggcctaatctgggtggctca gctaacctctcttcttccctttcctgaagtgacaaaaggaaactcagtcttcttggggaaagaaggattgcc attagtgacttggaccagttagatgattcacttttttgcccctagggatgagaggcgaaagccacttctc atacaagcccctttattgccactaccccacgctcgtcgtagtcctgaaactgcaggaccagtttctctgc caaggggaggagttggagagcacagttgccccgttgtgtgagggcagtagtaggcatctggaatg ctccagtttgatctcccttctgccacccctacctcacccctagtcactcatatcggagcctggactggc ctccaggatgaggatgggggtggcaatgacaccctgcaggggaaaggactgccccccatgcacc attgcaggagggatgccgccaccatgagctaggtggagtaactggttttcttgggtggctgatgac atggatgcagcacagactcagccttggcctggacacatgcttactggtggcctcagtttaccttccc cagatcctagattctggatgtgaggaagagatccctcttcagaaggggcctggccttctgagcagca gattagttccaaagcaggtggcccccgaacccaagcctcacttttctgtgccttcctgaggggggttg ggccggggaggaaacccaaccctctcctgtgtgttctgttatctcttgatgagatcattgcaccatgtc agactttgtatatgccttgaaaatatatgaaagtgagaatcctctaaaaaaaaaaaa |
| 596 | HBV Genbank Accession No. KC315400.1 | ctccaccacttttccaccaaactcttcaagatcccagagtcaggggccctgtactttcctgctggtggctc aagttccggaacagtaaaccctgctccgactactgcctctcccatatcgtcaatcttctcgaggactg gggacccgtaccgaatatggagagcaccacatcaggattcctaggacccctgctcgtgttacagg cggggttttcttgttgacaagaatcctcacaataccacagagtctagactcgtggtggacttctctca attttctagggggagcacccacgtgtcctggccaaaatttgcagtccccaacctccaatcactcacca acctcttgtcctccaatttgtcctggttatcgctggatgtgtctgcggcgttttatcatcttcctcttcatcc tgctgctatgcctcatcttcttgttggttcttctggactaccaaggtatgttgcccgtttgtcctctacttcc aggaacatcaactaccagcaccggaccatgcaaaacctgcacaactactgctcaagggacctctat gtttccctcatgttgctgtacaaaacctacggacggaaactgcacctgtattcccatcccatcatcttgg gctttcgcaaaatacctatgggagtgggcctcagtccgtttctcttggctcagtttactagtgccatttgt tcagtggttcgtagggattccccactgtctggctttcagttatatggatgatgtggtttgggggcca agtctgtacaacatcttgagtcccttttataccgctgttaccaattttcttttatctttgggtatacatttaaac cctcacaaaacaaaaagatggggatattcccttaacttcatgggatatgtaattgggagttggggcac tttgcctcaggaacatatgtacaaaaaatcaagcaatgtttaggaaacttcctgtaaacaggcctatt |

TABLE 5-continued

| SEQ ID NO: | Description | Sequence+ |
|---|---|---|
| | | gattggaaagtatgtcaacraattgtgggtcttttggggtttgccgccccttcacgcaatgtggatatc<br>ctgctttaatgcctttatatgcatgtatacaagctaagcaggcttttactttctcgccaacttacaaggcct<br>ttctgtgtaaacaatatctgaacctttaccccgttgctcggcaacggtcaggtctttgccaagtgtttgct<br>gacgcaaccccactggttggggcttggccataggccatcagcgcatgcgtggaacctttgtggct<br>cctctgccgatccatactgcggaactcctagcagcttgttttgctcgcagccggtctggagcaaaact<br>tatcggcaccgacaactctgttgtcctctctcggaaatacacctcctttccatggctgctaggatgtgct<br>gccaactggatcctgcgcgggacgtcctttgtctacgtcccgtcggcgctgaatcccgcggacgac<br>ccatctcggggccgtttgggactctaccgtccccttctgcgtctgccgttccgcccgaccacggggc<br>gcacctctctttacgcggtctccccgtctgtgccttctcatctgccggaccgtgtgcacttcgcttcacc<br>tctgcacgtcgcatggagaccaccgtgaacgcccacgggaacctgcccaaggtcttgcataagag<br>gactcttggactttcagcaatgtcaacgaccgaccttgaggcatacttcaaagactgtgtgtttactga<br>gtgggaggagttgggggaggaggttaggttaaaggtctttgtactaggaggctgtaggcataaattg<br>gtgtgttcaccagcaccatgcaacttttcacctctgcctaatcatctcatgttcatgtcctactgttcaag<br>cctccaagctgtgccttgggtggctttggggcatggacattgacccgtataaagaatttggagctct<br>gtggagttactctattttttgccttctgacttctttccttctattcgagatctcctcgacaccgcctctgctct<br>gtatcgggaggcctagagtctccggaacattgttcacctcaccatacggcactcaggcaagcaatt<br>ctgtgttggggtgagttaatgaatctagccacctgggtgggaagtaatttggaagatccagcatcca<br>gggaattagtagtcagctatgtcaacgttaatatgggcctaaaaatcagacaactattgtggtttcaca<br>tttcctgtcttactttttgggagagaaactgttcttgaatatttggtgtcttttggagtgtggattcgcactcc<br>tcctgcatatagaccacaaaatgcccctatcttatcaacacttccggaaactactgttgttagacgaag<br>aggcaggtcccctagaagaagaactccctcgcctcgcagacgaaggtctcaatcgccgcgtcgca<br>gaagatctcaatctcgggaatctcaatgttagtattccttggacacataaggtgggaaactttacggg<br>gctttattcttctacggtaccttgctttaatcctaaatggcaaactccttctttcctgacattcatttgcag<br>gaggacattgttgatagatgtaagcaatttgtggggccccttacagtaaatgaaaacaggagacttaa<br>attaattatgcctgctaggttttatcccaatgttactaaatatttgcccttagataaagggatcaaaccgta<br>ttatccagagtatgtagttaatcattacttccagacgcgacattatttacacactctttggaaggcgggg<br>atcttatataaaagagagtccacacgtagcgcctcattttgcgggtcaccatattcttgggaacaagat<br>ctacagcatgggaggttggtcttccaaacctcgaaaaggcatggggacaaatctttctgtccccaatc<br>ccctgggattcttccccgatcatcagttggaccctgcattcaaagccaactcagaaaatccagattgg<br>gacctcaacccacacaaggacaactggccggacgccaacaaggtgggagtgggagcattcggg<br>ccaggtgttcaccctcctcatgggggactgttggggtggagccctcaggctcagggcatattcaca<br>acagtgccagcagctcctcctcctgcctccaccaatcggcagtcaggaaggcagcctactcccttct<br>ctccacctctaagagacactcatcctcaggccatgcagtggaa |
| 534 | ASO 1 | GalNAc4-ps-GalNAc4-ps-GalNAc4-po-mA-po-<br>lnGpslnApslnTpslnApsApsAps(5OH)CpsGps(5m)Cps(5m)Cps<br>Gps(5m)CpslnApslnGpslnApscp(5m)C |
| 535 | ASO 2 | mA-po-<br>lnGpslnApslnTpslnApsApsAps(5OH)CpsGps(5m)Cps(5m)Cps<br>Gps(5m)CpslnApslnGpslnApscp(5m)C |

+ln = Locked nucleic acid (LNA) =

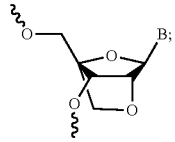

lnA = Locked nucleic acid (LNA) A;
ln(5m)C = ln(5m)C = Locked nucleic acid (LNA)-5 methyl C;
lnG = Locked nucleic acid (LNA) G;
lnT = Locked nucleic acid (LNA) T;
(5m)C = 5 methyl C;
cp = scp = cyclopropyl;
cpC = scpC = cyclopropyl C;
scp(5m)C = cyclopropyl-5 methyl C;
(5OH)C =

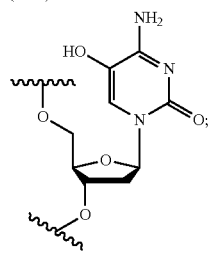

po = phosphodiester linkage;
ps = phosphorothioate linkage

TABLE 6 siNA Activity

| ds-siNA ID | Sense Strand SEQ ID NO. | Antisense Strand SEQ ID NO. | HepG2.2.15 in vitro EC50* | HepG2.2.15 in vitro CC50 (nM) |
|---|---|---|---|---|
| ds-siNA-001 | 307 | 363 | A | >40 |
| ds-siNA-002 | 308 | 364 | A | >40 |
| ds-siNA-003 | 309 | 365 | B | >40 |
| ds-siNA-004 | 310 | 366 | B | >40 |
| ds-siNA-005 | 311 | 367 | B | >40 |
| ds-siNA-006 | 312 | 368 | C | >40 |
| ds-siNA-007 | 313 | 369 | A | >40 |
| ds-siNA-008 | 314 | 370 | A | >40 |
| ds-siNA-009 | 315 | 371 | B | >40 |
| ds-siNA-010 | 316 | 372 | A | >40 |
| ds-siNA-011 | 317 | 373 | B | >40 |
| ds-siNA-012 | 318 | 374 | A | >40 |
| ds-siNA-013 | 319 | 375 | A | >40 |
| ds-siNA-014 | 320 | 376 | B | >40 |
| ds-siNA-015 | 321 | 377 | A | >40 |
| ds-siNA-016 | 322 | 377 | C | >40 |
| ds-siNA-017 | 323 | 377 | A | >40 |
| ds-siNA-018 | 324 | 378 | A | >40 |
| ds-siNA-019 | 325 | 378 | A | >40 |
| ds-siNA-020 | 326 | 379 | A | >40 |
| ds-siNA-021 | 327 | 379 | B | >40 |
| ds-siNA-022 | 328 | 380 | A | >40 |
| ds-siNA-023 | 329 | 380 | B | >40 |
| ds-siNA-024 | 330 | 381 | A | >40 |
| ds-siNA-025 | 331 | 382 | A | >40 |
| ds-siNA-026 | 332 | 383 | C | >40 |
| ds-siNA-027 | 333 | 384 | A | >40 |
| ds-siNA-028 | 334 | 385 | B | >40 |
| ds-siNA-029 | 335 | 386 | A | >40 |
| ds-siNA-030 | 336 | 387 | C | >40 |
| ds-siNA-031 | 337 | 388 | A | >40 |
| ds-siNA-032 | 338 | 388 | C | >40 |
| ds-siNA-033 | 339 | 389 | B | >40 |
| ds-siNA-034 | 340 | 389 | C | >40 |
| ds-siNA-035 | 341 | 390 | A | >40 |
| ds-siNA-036 | 342 | 391 | A | >40 |
| ds-siNA-037 | 343 | 392 | B | >40 |
| ds-siNA-038 | 344 | 393 | A | >40 |
| ds-siNA-039 | 345 | 394 | A | >40 |
| ds-siNA-040 | 346 | 395 | A | >40 |
| ds-siNA-041 | 347 | 396 | C | >40 |
| ds-siNA-042 | 348 | 397 | A | >40 |
| ds-siNA-043 | 349 | 398 | B | >40 |
| ds-siNA-044 | 350 | 399 | A | >40 |
| ds-siNA-045 | 351 | 400 | A | >40 |
| ds-siNA-046 | 352 | 401 | A | >40 |
| ds-siNA-047 | 353 | 402 | A | >40 |
| ds-siNA-048 | 354 | 403 | A | >40 |
| ds-siNA-049 | 355 | 404 | B | >40 |
| ds-siNA-050 | 356 | 405 | A | >40 |
| ds-siNA-051 | 357 | 406 | A | >40 |
| ds-siNA-052 | 358 | 406 | A | >40 |
| ds-siNA-053 | 359 | 407 | A | >40 |
| ds-siNA-054 | 360 | 407 | A | >40 |
| ds-siNA-055 | 361 | 408 | A | >40 |
| ds-siNA-056 | 362 | 409 | A | >40 |
| ds-siNA-0164 | 423 | 482 | | |

*A = EC50 < 0.5 nM; B = 0.5 nM < EC50 < 1; C = EC50 > 1 nm

TABLE 10 siNA Activity

| ds-siNA ID | Sense Strand SEQ ID NO | 3' Ligand Monomer⁺ | Antisense Strand SEQ ID NO | HepG2.2.15 EC50* | HepG2.2.15 CC50 (nM) | Max HBsAg Knock Down (Log$_{10}$)** |
|---|---|---|---|---|---|---|
| ds-siNA-057 | 415 | p-(PS)2-GalNac4 | 445 | ND | ND | X |
| ds-siNA-058 | 415 | p-(PS)2-GalNac4 | 446 | ND | ND | X |
| ds-siNA-059 | 415 | p-(PS)2-GalNac4 | 447 | ND | ND | Y |

TABLE 10-continued siNA Activity

| ds-siNA ID | Sense Strand SEQ ID NO | 3' Ligand Monomer+ | Antisense Strand SEQ ID NO | HepG2.2.15 EC50* | HepG2.2.15 CC50 (nM) | Max HBsAg Knock Down (Log$_{10}$)** |
|---|---|---|---|---|---|---|
| ds-siNA-060 | 416 | p-(PS)2-GalNac4 | 448 | ND | ND | Y |
| ds-siNA-061 | 416 | p-(PS)2-GalNac4 | 449 | ND | ND | Y |
| ds-siNA-062 | 416 | p-(PS)2-GalNac4 | 450 | ND | ND | Y |
| ds-siNA-063 | 416 | p-(PS)2-GalNac4 | 451 | ND | ND | X |
| ds-siNA-064 | 417 | 5'-GalNAc4-(PS)2-p-TEG-p | 452 | ND | ND | Y |
| ds-siNA-065 | 417 | 5'-GalNAc4-(PS)2-p-HEG-p | 452 | ND | ND | Y |
| ds-siNA-066 | 417 | 5'-GalNAc4-(PS)2-p-(HEG-p)2 | 452 | ND | ND | Y |
| ds-siNA-067 | 417 | 5'-GalNAc4-(PS)2-p-(HEG-p)2 | 452 | ND | ND | Z |
| ds-siNA-068 | 418 | p-(PS)2-GalNac4 | 453 | ND | ND | Y |
| ds-siNA-069 | 418 | p-(PS)2-GalNac4 | 454 | ND | ND | Y |
| ds-siNA-070 | 419 | p-(PS)2-GalNac4 | 455 | ND | ND | Y |
| ds-siNA-071 | 419 | p-(PS)2-GalNac4 | 456 | ND | ND | Y |
| ds-siNA-072 | 420 | p-(PS)2-GalNac4 | 457 | ND | ND | X |
| ds-siNA-073 | 421 | p-(PS)2-GalNac4 | 458 | ND | ND | X |
| ds-siNA-074 | 422 | p-(PS)2-GalNac4 | 459 | ND | ND | Y |
| ds-siNA-075 | 423 | p-(PS)2-GalNac4 | 460 | ND | ND | Y |
| ds-siNA-076 | 423 | p-(PS)2-GalNac4 | 461 | ND | ND | Y |
| ds-siNA-077 | 423 | 5'-GalNAc4-(PS)2-p-TEG-p | 458 | ND | ND | Y |
| ds-siNA-078 | 423 | 5'-GalNAc4-(PS)2-p-HEG-p | 458 | ND | ND | X |
| ds-siNA-079 | 423 | 5'-GalNAc4-(PS)2-p-(HEG-p)2 | 458 | ND | ND | Y |
| ds-siNA-080 | 423 | p-(PS)2-GalNac4 | 462 | ND | ND | X |
| ds-siNA-081 | 423 | p-(PS)2-GalNac4 | 463 | ND | ND | X |
| ds-siNA-082 | 423 | p-(PS)2-GalNac4 | 447 | ND | ND | X |
| ds-siNA-083 | 423 | 5'-GalNAc4-(PS)2-p-(HEG-p)2 | 458 | ND | ND | Z |
| ds-siNA-084 | 423 | p-(PS)2-GalNac4 | 457 | ND | ND | X |
| ds-siNA-085 | 423 | p-(PS)2-GalNac4 | 464 | ND | ND | X |
| ds-siNA-086 | 423 | p-(PS)2-GalNac4 | 465 | ND | ND | X |
| ds-siNA-087 | 423 | p-(PS)2-GalNac4 | 466 | ND | ND | Y |
| ds-siNA-088 | 423 | p-(PS)2-GalNac4 | 467 | ND | ND | Z |
| ds-siNA-089 | 423 | p-(PS)2-GalNac4 | 468 | ND | ND | Z |
| ds-siNA-090 | 423 | p-(PS)2-GalNac4 | 469 | B | >1000 | X |
| ds-siNA-091 | 423 | p-(PS)2-GalNac4 | 470 | C | >1000 | ND |
| ds-siNA-092 | 423 | p-(PS)2-GalNac4 | 471 | B | >1000 | ND |
| ds-siNA-093 | 423 | p-(PS)2-GalNac4 | 472 | B | >1000 | ND |
| ds-siNA-094 | 423 | p-(PS)2-GalNac4 | 473 | B | >1000 | ND |
| ds-siNA-095 | 423 | p-(PS)2-GalNac4 | 474 | C | >1000 | ND |
| ds-siNA-096 | 423 | p-(PS)2-GalNac4 | 475 | B | >1000 | ND |
| ds-siNA-097 | 423 | p-(PS)2-GalNac4 | 476 | B | >1000 | ND |
| ds-siNA-098 | 423 | p-(PS)2-GalNac4 | 477 | A | >1000 | ND |
| ds-siNA-099 | 423 | p-(PS)2-GalNac4 | 478 | B | >1000 | ND |
| ds-siNA-0100 | 423 | p-(PS)2-GalNac4 | 479 | B | >1000 | ND |
| ds-siNA-0101 | 423 | p-(PS)2-GalNac4 | 480 | B | >1000 | ND |
| ds-siNA-0102 | 423 | p-(PS)2-GalNac4 | 481 | A | >1000 | ND |
| ds-siNA-0103 | 423 | p-(PS)2-GalNac4 | 482 | ND | ND | ND |
| ds-siNA-0104 | 423 | p-(PS)2-GalNac4 | 483 | ND | ND | ND |
| ds-siNA-0105 | 423 | p-(PS)2-GalNac4 | 458 | ND | ND | Z |
| ds-siNA-0106 | 423 | p-(PS)2-GalNac4 | 458 | ND | ND | Y |
| ds-siNA-0107 | 424 | p-(PS)2-GalNac4 | 457 | ND | ND | X |
| ds-siNA-0108 | 424 | p-(PS)2-GalNac4 | 484 | ND | ND | X |
| ds-siNA-0109 | 424 | p-(PS)2-GalNac4 | 485 | ND | ND | X |
| ds-siNA-0110 | 425 | p-(PS)2-GalNac4 | 486 | ND | ND | ND |
| ds-siNA-0111 | 425 | p-(PS)2-GalNac4 | 487 | ND | ND | ND |
| ds-siNA-0112 | 425 | p-(PS)2-GalNac4 | 488 | ND | ND | ND |
| ds-siNA-0113 | 426 | p-(PS)2-GalNac4 | 489 | ND | ND | ND |
| ds-siNA-0114 | 427 | p-(PS)2-GalNac4 | 490 | ND | ND | X |
| ds-siNA-0115 | 428 | p-(PS)2-GalNac4 | 491 | ND | ND | Y |
| ds-siNA-0116 | 429 | p-(PS)2-GalNac4 | 492 | ND | ND | ND |
| ds-siNA-0117 | 429 | p-(PS)2-GalNac4 | 493 | ND | ND | ND |
| ds-siNA-0118 | 429 | p-(PS)2-GalNac4 | 494 | ND | ND | ND |
| ds-siNA-0119 | 430 | p-(PS)2-GalNac4 | 495 | ND | ND | X |
| ds-siNA-0120 | 430 | p-(PS)2-GalNac4 | 496 | ND | ND | ND |
| ds-siNA-0121 | 431 | p-(PS)2-GalNac4 | 497 | ND | ND | Y |
| ds-siNA-0122 | 432 | p-(PS)2-GalNac4 | 498 | ND | ND | ND |
| ds-siNA-0123 | 432 | p-(PS)2-GalNac4 | 500 | ND | ND | ND |
| ds-siNA-0124 | 433 | p-(PS)2-GalNac4 | 501 | ND | ND | ND |

TABLE 10-continued siNA Activity

| ds-siNA ID | Sense Strand SEQ ID NO | 3' Ligand Monomer+ | Antisense Strand SEQ ID NO | HepG2.2.15 EC50* | HepG2.2.15 CC50 (nM) | Max HBsAg Knock Down ($Log_{10}$)** |
|---|---|---|---|---|---|---|
| ds-siNA-0125 | 434 | p-(PS)2-GalNac4 | 502 | ND | ND | Y |
| ds-siNA-0126 | 435 | p-(PS)2-GalNac4 | 502 | ND | ND | Y |
| ds-siNA-0127 | 435 | p-(PS)2-GalNac4 | 503 | ND | ND | X |
| ds-siNA-0128 | 435 | p-(PS)2-GalNac4 | 501 | ND | ND | X |
| ds-siNA-0129 | 435 | p-(PS)2-GalNac4 | 504 | ND | ND | Y |
| ds-siNA-0130 | 435 | p-(PS)2-GalNac4 | 505 | ND | ND | Z |
| ds-siNA-0131 | 435 | p-(PS)2-GalNac4 | 506 | ND | ND | Y |
| ds-siNA-0132 | 435 | p-(PS)2-GalNac4 | 507 | ND | ND | Z |
| ds-siNA-0133 | 435 | p-(PS)2-GalNac4 | 508 | ND | ND | Z |
| ds-siNA-0134 | 435 | p-(PS)2-GalNac4 | 509 | ND | ND | Z |
| ds-siNA-0135 | 435 | p-(PS)2-GalNac4 | 510 | ND | ND | Y |
| ds-siNA-0136 | 435 | p-(PS)2-GalNac4 | 511 | B | >1000 | ND |
| ds-siNA-0137 | 435 | p-(PS)2-GalNac4 | 512 | B | >1000 | ND |
| ds-siNA-0138 | 435 | p-(PS)2-GalNac4 | 513 | A | >1000 | ND |
| ds-siNA-0139 | 435 | p-(PS)2-GalNac4 | 514 | B | >1000 | ND |
| ds-siNA-0140 | 435 | p-(PS)2-GalNac4 | 515 | C | >1000 | ND |
| ds-siNA-0141 | 435 | p-(PS)2-GalNac4 | 516 | A | >1000 | ND |
| ds-siNA-0142 | 435 | p-(PS)2-GalNac4 | 517 | C | >1000 | ND |
| ds-siNA-0143 | 435 | p-(PS)2-GalNac4 | 518 | C | >1000 | ND |
| ds-siNA-0144 | 435 | p-(PS)2-GalNac4 | 519 | ND | ND | ND |
| ds-siNA-0145 | 436 | p-(PS)2-GalNac4 | 520 | ND | ND | ND |
| ds-siNA-0146 | 437 | p-(PS)2-GalNac4 | 502 | ND | ND | Y |
| ds-siNA-0147 | 438 | p-(PS)2-GalNac4 | 501 | ND | ND | X |
| ds-siNA-0148 | 438 | p-(PS)2-GalNac4 | 521 | ND | ND | X |
| ds-siNA-0149 | 438 | p-(PS)2-GalNac4 | 522 | ND | ND | X |
| ds-siNA-0150 | 439 | p-(PS)2-GalNac4 | 523 | ND | ND | X |
| ds-siNA-0151 | 440 | p-(PS)2-GalNac4 | 524 | ND | ND | Y |
| ds-siNA-0152 | 441 | p-(PS)2-GalNac4 | 525 | ND | ND | Y |
| ds-siNA-0153 | 441 | p-(PS)2-GalNac4 | 526 | ND | ND | X |
| ds-siNA-0154 | 441 | p-(PS)2-GalNac4 | 527 | ND | ND | ND |
| ds-siNA-0155 | 442 | p-(PS)2-GalNac4 | 525 | ND | ND | X |
| ds-siNA-0156 | 442 | p-(PS)2-GalNac4 | 528 | ND | ND | Y |
| ds-siNA-0157 | 442 | p-(PS)2-GalNac4 | 529 | ND | ND | ND |
| ds-siNA-0158 | 443 | p-(PS)2-GalNac4 | 458 | ND | ND | Y |
| ds-siNA-0159 | 444 | p-(PS)2-GalNac4 | 502 | ND | ND | Y |
| ds-siNA-0160 | 423 | p-(PS)2-GalNac4 | 458 | ND | ND | ND |
| ds-siNA-0161 | 533 | p-(PS)2-GalNac4 | 489 | ND | ND | ND |
| ds-siNA-0162 | 534 | p-(PS)2-GalNac4 | 491 | ND | ND | ND |
| ds-siNA-0163 | 432 | p-(PS)2-GalNac4 | 496 | ND | ND | ND |
| ds-siNA-0165 | 435 | p-(PS)2-GalNac4 | 502 | ND | ND | ND |
| ds-siNA-0166 | 442 | p-(PS)2-GalNac4 | 530 | ND | ND | ND |
| ds-siNA-0167 | 427 | p-(PS)2-GalNAc4 | 491 | ND | ND | ND |
| ds-siNA-0168 | 439 | p-(PS)2-GalNac4 | 531 | ND | ND | ND |
| ds-siNA-0169 | 423 | p-(PS)2-GalNac4 | 532 | ND | ND | ND |
| ds-siNA-0170 | 441 | p-(PS)2-GalNAc4 | 530 | ND | ND | ND |
| ds-siNA-0171 | 442 | p-(PS)2-GalNAc4 | 533 | ND | ND | ND |
| ds-siNA-0172 | 424 | p-(PS)2-GalNac4 | 536 | A | >1 | ND |
| ds-siNA-0173 | 438 | None | 537 | | | |
| ds-siNA-0174 | 438 | None | 538 | | | |
| ds-siNA-0175 | 438 | None | 501 | | | |
| ds-siNA-0176 | 438 | p-(PS)2-GalNAc4 | 537 | | | |
| ds-siNA-0177 | 438 | p-(PS)2-GalNAc4 | 538 | | | |
| ds-siNA-0178 | 438 | p-(PS)2-GalNAc4 | 539 | | | |

+Ligand monomers are attached to the 3' end of the sense strand, unless the ligand monomer is annotated with 5', in which the ligand monomer is attached to the 5' end of the sense strand.
Linkers are represented as p-(PS)2, (PS)2-p-TEG-p, (PS)2-p-HEG-p, or (PS)2-p-(HEG-p)2.
*For EC50, A = EC50 ≤5 nM; B = 5 nM < EC50 <10; C = EC50 ≥10.
**For Max HBsAg knock down, X ≥1 $log_{10}$ reduction in HBsAg, Y is 0.5 –1 $log_{10}$ reduction in HBsAg, and Z is <0.5 $log_{10}$ reduction in HBsAg.

What is claimed is:

1. A double stranded short interfering nucleic acid (siNA) comprising:
   (a) a sense strand comprising 19-21 nucleotides in a nucleic acid sequence that is at least 80% identical to SEQ ID NO: 40, wherein 15 or more of the nucleotides are modified nucleotides independently selected from a 2'-O-methyl nucleotide and a 2'-fluoro nucleotide, and wherein at least 11 of the modified nucleotides are a 2'-O-methyl nucleotide and at least 4 of the modified nucleotides are a 2'-fluoro nucleotide; and
   (b) an antisense strand comprising 19-21 nucleotides in a nucleic acid sequence that is at least 80% complementary to SEQ ID NO: 40, wherein 15 or more of the nucleotides are modified nucleotides independently selected from a 2'-O-methyl nucleotide and a 2'-fluoro nucleotide, and wherein at least 11 of the modified nucleotides are a 2'-O-methyl nucleotide and 4 to 6 of the modified nucleotides are a 2'-fluoro nucleotide.

2. The double stranded siNA of claim 1, wherein:
   (a) the nucleotide(s) at position 3, 5, 7, 8, 9, 10, 11, 12, 14, 17, or 19 from the 5' end of the sense strand is a 2'-fluoro nucleotide; and
   (b) the nucleotide(s) at position 2, 5, 6, 8, 10, 14, 16, 17, or 18 from the 5' end of the antisense strand is a 2'-fluoro nucleotide.

3. The double stranded siNA of claim 1, wherein the sense strand comprises SEQ ID NO: 438 or SEQ ID NO: 435, and the antisense strand comprises any one of SEQ ID NOs: 501-519, SEQ ID NO: 537, SEQ ID NO: 538, or SEQ ID NO: 539.

4. A double stranded short interfering nucleic acid (siNA) comprising:
   (a) a sense strand comprising 19 nucleotides, wherein 2'-fluoro nucleotides are at positions 5 and 7-9 from the 5' end of the sense strand, and wherein 2'-O-methyl nucleotides are at positions 1-4, 6, and 10-19 from the 5' end of the sense strand; and (b) an antisense strand comprising 21 nucleotides, wherein 2'-fluoro nucleotides are at positions 2, 6, 14, and 16 from the 5' end of the antisense strand, and wherein 2'-O-methyl nucleotides are at positions 1, 3-5, 7-13, 15, and 17-21 from the 5' end of the antisense strand.

5. The double stranded siNA of claim 4 further comprising (i) the nucleotides at positions 1 and 2 and positions 2 and 3 from the 5' end of the sense strand are connected by phosphorothioate internucleoside linkages; and (ii) the nucleotides at positions 1 and 2; positions 2 and 3; positions 19 and 20; and positions 20 and 21 from the 5' end of the antisense strand are connected by phosphorothioate internucleoside linkages.

6. The double stranded siNA of claim 4 further comprising a conjugated moiety attached to the sense strand.

7. The double stranded siNA of claim 6, wherein the conjugated moiety is a galactosamine.

8. The double stranded siNA of claim 6, wherein the conjugated moiety is N-acetylgalactosamine (GalNAc).

9. The double stranded siNA of claim 4, wherein the sense strand comprises SEQ ID NO: 438, and the antisense strand comprises any one of SEQ ID NO: 501, SEQ ID NO: 537, SEQ ID NO: 538, or SEQ ID NO: 539.

10. The double stranded siNA of claim 4, wherein the sense strand is at least 80% identical to SEQ ID NO: 40 and the antisense strand is at least 80% complementary to SEQ ID NO: 40.

11. The double stranded siNA of claim 4, wherein the sense strand or the antisense strand comprises at least one overhang consisting of 1 or 2 nucleotides.

12. The double stranded siNA of claim 4, wherein both the sense strand and the antisense strand each independently comprise an overhang consisting of 1 or 2 nucleotides, wherein the overhang on the sense strand and the overhang on the antisense strand are on opposite ends of the double stranded siNA.

13. A short interfering nucleic acid (siNA) molecule comprising:
  (a) a sense strand comprising a nucleic acid sequence consisting of SEQ ID NO: 438 or SEQ ID NO: 435, and
  (b) an antisense strand comprising a nucleic acid sequence consisting of any one of SEQ ID NO: 501, SEQ ID NO: 505, SEQ ID NO: 506, SEQ ID NO: 537, SEQ ID NO: 538, and SEQ ID NO: 539.

14. The double stranded siNA of claim 9, wherein the senses strand comprises SEQ ID NO: 438 and the antisense comprises SEQ ID NO: 501.

15. The double stranded siNA of claim 9, wherein the senses strand comprises SEQ ID NO: 438 and the antisense comprises any one of SEQ ID NO: 537-539.

16. A double stranded short interfering nucleic acid (siNA) comprising:

(a) a sense strand of
                                                (SEQ ID NO: 438)
5'-mGpsmUpsmGmGfUmGfGfAfCmUmUmCmUmCmUmCmAmAmU-p- ps2-GalNAc-3' and an antisense strand of
                                                (SEQ ID NO: 501)
5'-mApsfUpsmUmGmAfGmAfGmAmAmGmUmCfCmAfCmCmAmCpsm GpsmA-3';

(b) a sense strand of
                                                (SEQ ID NO: 438)
5'-mGpsmUpsmGmGfUmGfGfAfCmUmUmCmUmCmUmCmAmAmU-p- ps2-GalNAc-3' and an antisense strand of
                                                (SEQ ID NO: 521)
5'-mApsfUpsmUmGmAfGmAfGfAmAmGmUmCfCmAfCmCmAmCpsm GpsmA-3';

(c) a sense strand of
                                                (SEQ ID NO: 438)
5'-mGpsmUpsmGmGfUmGfGfAfCmUmUmCmUmCmUmCmAmAmU-p- ps2-GalNAc-3' and an antisense strand of
                                                (SEQ ID NO: 522)
5'-mApsfUpsmUmGfAmGmAfGmAmAmGmUmCfCmAmCfCmAmCpsm GpsmA-3';

(d) a sense strand of
                                                (SEQ ID NO: 438)
5'-mGpsmUpsmGmGfUmGfGfAfCmUmUmCmUmCmUmCmAmAmUp-ps2-GalNAc-3' and an antisense strand of
                                                (SEQ ID NO: 537)
5'-mApsf4PpsmUmGmAfGmAmGmAmAmGmUmCfCmAfCmCmAmCp smGpsmA-3';

(e) a sense strand of
                                                (SEQ ID NO: 438)
5'-mGpsmUpsmGmGfUmGfGfAfCmUmUmCmUmCmUmCmAmAmUp-ps2-GalNAc-3' and an antisense strand of
                                                (SEQ ID NO: 538)
5'-mApsfUpsmUmGmAfGmAmGmAmAmGmUmCf2PmAfCmCmAmCp smGpsmA-3';
or (f) a sense strand of
                                                (SEQ ID NO: 438)
5'-mGpsmUpsmGmGfUmGfGfAfCmUmUmCmUmCmUmCmAmAmU-p- ps2-GalNAc-3' and an antisense strand of
                                                (SEQ ID NO: 539)
5'-mApsfUpsmUmGmAfGmAmGmAmAmGmUmCfCmAfXmCmAmCpsm GpsmA-3', wherein fX is

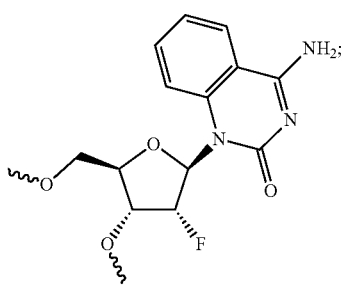

wherein GalNAc comprises a structure of Formula (VII):

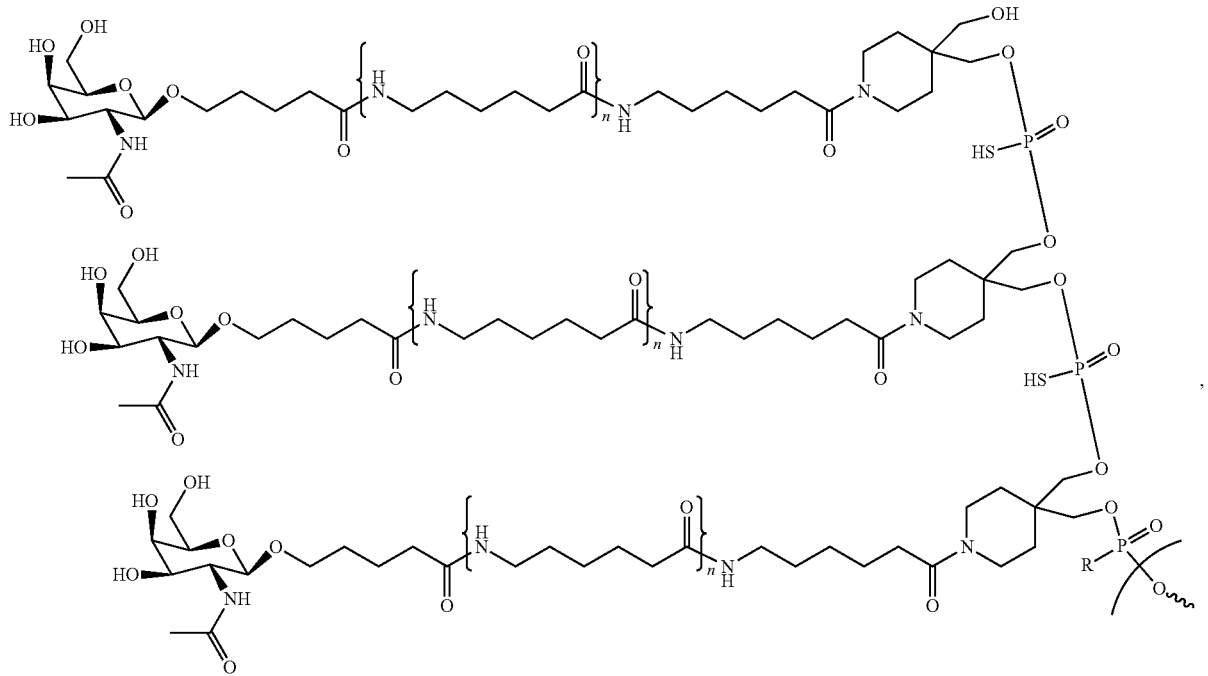

wherein n is 1, and R is OH.

17. The double stranded siNA of claim 16, comprising a sense strand of 5'-mGpsmUpsmGmGfUmGfGfAfCmU-mUmCmUmCmUmCmAmAmU-p-ps2-GalNAc-3' (SEQ ID NO: 438) and an antisense strand of 5'-mApsfUps-mUmGmAfGmAmGmAmAmGmUmCfCmAfCmCmAm-CpsmGpsmA-3' (SEQ ID NO: 501).

18. The double stranded siNA of claim 16, comprising a sense strand of 5'-mGpsmUpsmGmGfUmGfGfAfCmU-mUmCmUmCmUmCmAmAmU-p-ps2-GalNAc-3' (SEQ ID NO: 438) and an antisense strand of 5'-mApsfUps-mUmGmAfGmAfGfAmAmGmUmCfCmAfCmCmAm-CpsmGpsmA-3' (SEQ ID NO: 521).

19. The double stranded siNA of claim 16, comprising a sense strand of 5'-mGpsmUpsmGmGfUmGfGfAfCmU-mUmCmUmCmUmCmAmAmU-p-ps2-GalNAc-3' (SEQ ID NO: 438) and an antisense strand of 5'-mApsfUps-mUmGfAmGmAfGmAmAmGmUmCfCmAmCfCmAm-CpsmGpsmA-3' (SEQ ID NO: 522).

20. The double stranded siNA of claim 16, comprising a sense strand of 5'-mGpsmUpsmGmGfUmGfGfAfCmU-mUmCmUmCmUmCmAmAmU-p-ps2-GalNAc-3' (SEQ ID NO: 438) and an antisense strand of 5'-mApsf4PpsmUmGmAfGmAmGmAmAmGmUmCfCm AfCmCmAmCpsmGpsmA-3' (SEQ ID NO: 537).

21. The double stranded siNA of claim 16, comprising a sense strand of 5'-mGpsmUpsmGmGfUmGfGfAfCmU-mUmCmUmCmUmCmAmAmU-p-ps2-GalNAc-3' (SEQ ID NO: 438) and an antisense strand of 5'-mApsfUpsmUmGmAfGmAmGmAmAmGmUmCf2Pm AfCmCmAmCpsmGpsmA-3' (SEQ ID NO: 538).

22. The double stranded siNA of claim 16, comprising a sense strand of 5'-mGpsmUpsmGmGfUmGfGfAfCmU-mUmCmUmCmUmCmAmAmU-p-ps2-GalNAc-3' (SEQ ID NO: 438) and an antisense strand of 5'-mApsfUps-mUmGmAfGmAmGmAmAmGmUmCfCmAfXmCmAm-CpsmGpsmA-3' (SEQ ID NO: 539), wherein fX is

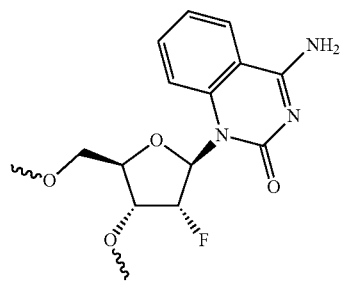

23. The double stranded siNA of claim 9 further comprising a galactosamine attached to the sense strand.

24. The double stranded siNA of claim 9 further comprising a N-acetylgalactosamine (GalNAc) attached to the 3' of the sense strand.

25. The double stranded siNA of claim 24, wherein the GalNAc comprises a structure of Formula (VII):

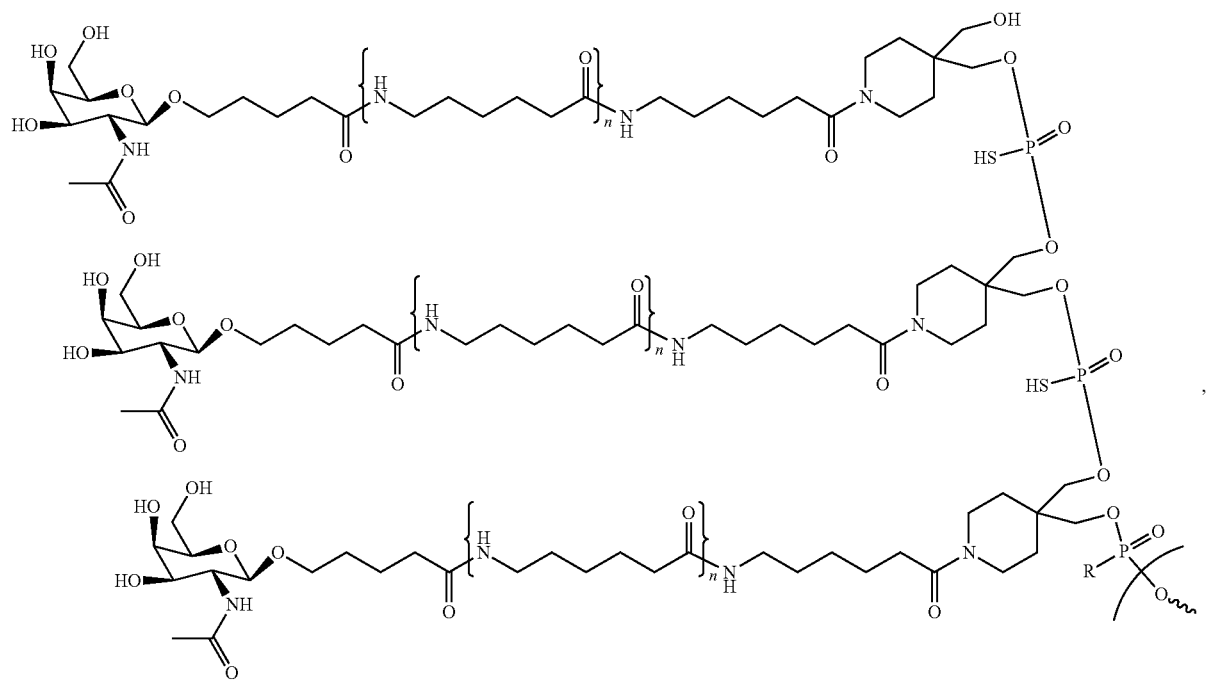
wherein n is 1, and R is OH.
26. The siNA molecule of claim 13 further comprising a galactosamine attached to the sense strand.
27. The siNA molecule of claim 13 further comprising a N-acetylgalactosamine (GalNAc) attached to the 3' of the sense strand.
28. The siNA molecule of claim 27, wherein the GalNAc comprises a structure of Formula (VII):
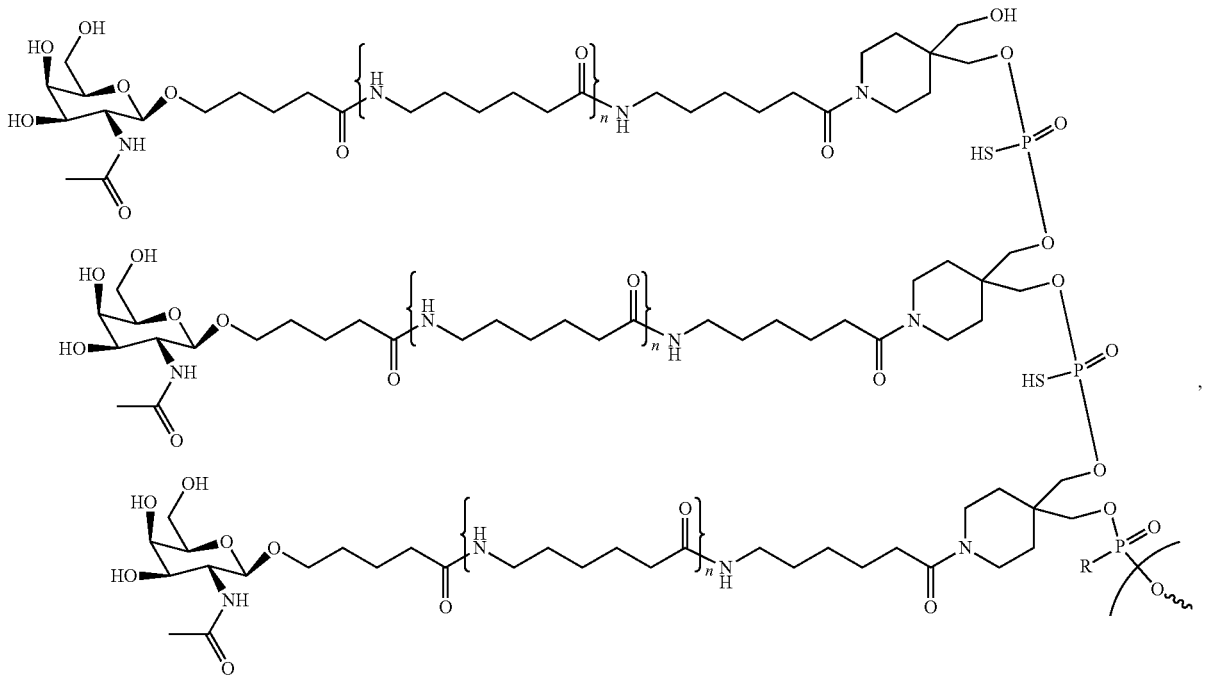
wherein n is 1, and R is OH.

29. The double stranded siNA of claim 14 further comprising a N-acetylgalactosamine (GalNAc) attached to the 3' of the sense strand.
30. The double stranded siNA of claim 29, wherein the GalNAc comprises a structure of Formula (VII):
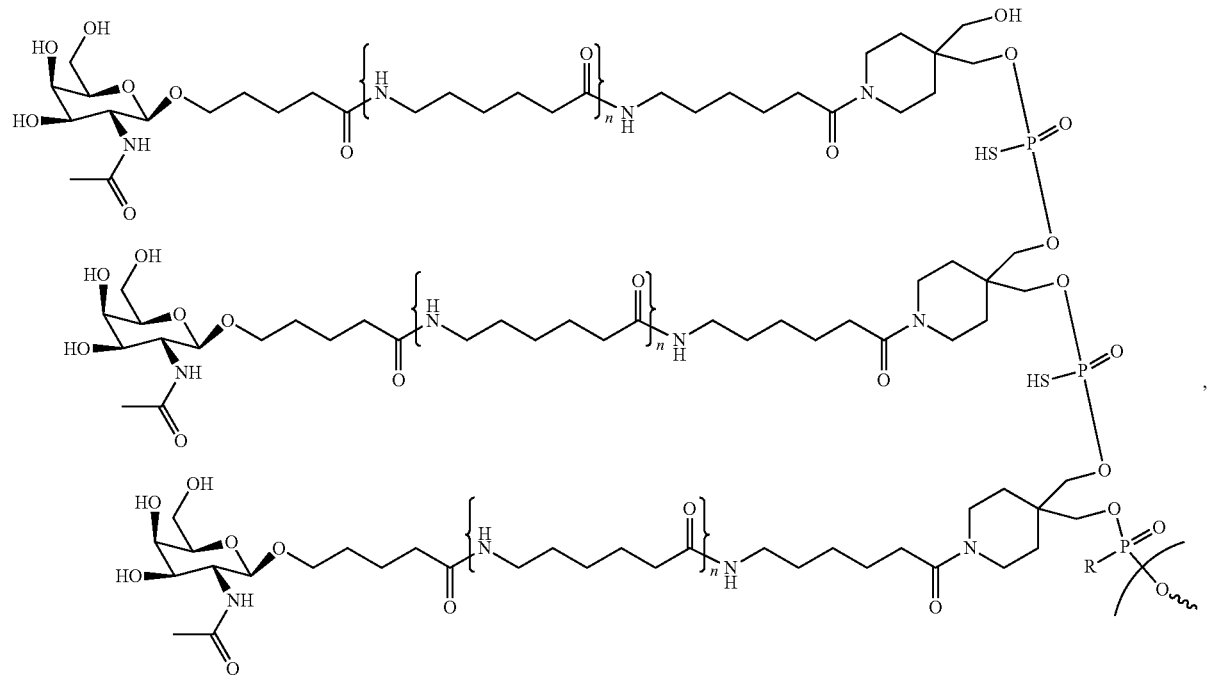
wherein n is 1, and R is OH.
* * * * *

SEQUENCE LISTING

<160> NUMBER OF SEQ ID NOS: 618

<210> SEQ ID NO 1
<211> LENGTH: 19
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 1
accgugugca cuucgcuuc                                                        19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
accgugugca cuucgcuuc                                                        19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
acuucgcuuc accucugca                                                        19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
aguguuugcu gacgcaacc                                                        19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
caggcggggu uuucuugu                                                         19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
caggcggggu uuucuugu                                                         19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 7
caguuuacua gugccauuu                                              19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
caguuuacua gugccauuu                                              19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cauccugcug cuaugccuc                                              19

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
cauccugcug cuaugccuca u                                           21

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
cauccugcug cuaugccuc                                              19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ccgugugcac uucgcuuca                                              19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 13
ccgugugcac uucgcuuca                                                19

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ccugcugcua ugccucaucu u                                             21

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
cucaguuuac uagugccau                                                19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
cucaguuuac uagugccau                                                19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
cucaguuuac uagugccau                                                19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
cucaguuuac uagugccau                                                19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 19
cucaguuuac uagugccau                                            19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cugcuaugcc ucaucuucu                                            19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
cugcuaugcc ucaucuucu                                            19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cugcuaugcc ucaucuucu                                            19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
cugcuaugcc ucaucuucu                                            19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
cugcugcuau gccucaucu                                            19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
```
cugcugcuau gccucaucu                                                19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
cugcugcuau gccucaucu                                                19

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
cuucgcuuca ccucugcacg u                                             21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gcacuucgcu ucaccucugc a                                             21

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gccgauccau acugcggaa                                                19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gccggguuuu ucuuguuga                                                19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31

-continued gcggggutttt ucuuguuga                                                19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32 gcggggutttt ucuuguuga                                                19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33 gcggggutttt ucuuguuga                                                19

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34 gcggggutttt ucuuguuga                                                19

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
gcugcuaugc cucaucuucu u                                              21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ggaugugucu gcggcguuuu a                                              21

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ggccaaaauu cgcagucccc                                                19

```
<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ggcgcaccuc ucuuuacgc                                                19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
guauguugcc cguuugucc                                                19

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
gugguggacu ucucucaau                                                19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gugugcacuu cgcuucacc                                                19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
guugcccguu uguccucua                                                19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
guugcccguu uguccucua                                                19
```

```
<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
uccauacugc ggaacuccu                                                    19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
uccauacugc ggaacuccu                                                    19

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ucguggugga cuucucucaa u                                                 21

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
ugcacuucgc uucaccucu                                                    19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ugccgaucca uacugcgga                                                    19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ugccgaucca uacugcgga                                                    19
```

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 50
ugcuaugccu caucuucuu                                                    19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 51
ugugcacuuc gcuucaccu                                                    19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 52
ugugcacuuc gcuucaccu                                                    19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 53
ugugcacuuc gcuucaccu                                                    19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 54
ugugcacuuc gcuucaccu                                                    19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 55
uugcccguuu guccucuaa                                                    19

<210> SEQ ID NO 56

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
uugcccguuu guccucuaa                                                    19

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
gaagcgaagu gcacacgguc c                                                 21

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gaagcgaagu gcacacggu                                                    19

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
ugcagaggug aagcgaagug c                                                 21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
gguugcguca gcaaacacuu g                                                 21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
acaagaaaaa ccccgccugu a                                                 21

<210> SEQ ID NO 62
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
acaagaaaaa accccgccug                                                    20

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
aaauggcacu aguaaacuga g                                                  21

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
aaauggcacu aguaaacug                                                     19

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
gaggcauagc agcaggauga a                                                  21

<210> SEQ ID NO 66
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
augaggcaua gcagcaggau gaa                                                23

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
gaggcauagc agcaggaug                                                     19

<210> SEQ ID NO 68
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 68
ugaagcgaag ugcacacggu c                                              21

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
ugaagcgaag ugcacacgg                                                 19

<210> SEQ ID NO 70
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
aagaugaggc auagcagcag gau                                            23

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
auggcacuag uaaacugagc c                                              21

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
auggcacuag uaaacugag                                                 19

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
agaagaugag gcauagcagc a                                              21

<210> SEQ ID NO 74
<211> LENGTH: 19
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 74
agaagaugag gcauagcag                                                        19

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
agaugaggca uagcagcagg a                                                     21

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
agaugaggca uagcagcag                                                        19

<210> SEQ ID NO 77
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
acgugcagag gugaagcgaa gug                                                   23

<210> SEQ ID NO 78
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
ugcagaggug aagcgaagug cac                                                   23

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
uuccgcagua uggaucggca g                                                     21

<210> SEQ ID NO 80
<211> LENGTH: 19
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 80
uuccgcagua uggaucggc                                                        19

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
ucaacaagaa aaccccgcc u                                                      21

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
ucaacaagaa aaccccgc                                                         19

<210> SEQ ID NO 83
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
aagaagauga ggcauagcag cag                                                   23

<210> SEQ ID NO 84
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
uaaaacgccg cagacacauc cag                                                   23

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
gggacugcga auuuuggcca a                                                     21

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 86
gcguaaagag aggugcgccc c                                        21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
ggacaaacgg gcaacauacc u                                        21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
auugagagaa guccaccacg a                                        21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ggugaagcga agugcacacg g                                        21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
uagaggacaa acgggcaaca u                                        21

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
uagaggacaa acgggcaac                                           19

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 92
aggaguuccg caguauggau c					21

<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
aggaguuccg caguaugga					19

<210> SEQ ID NO 94
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
auugagagaa guccaccacg agu					23

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
agaggugaag cgaagugcac a					21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
uccgcaguau ggaucggcag a					21

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
uccgcaguau ggaucggca					19

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
aagaagauga ggcauagcag c                                              21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
aggugaagcg aagugcacac g                                              21

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
aggugaagcg aagugcaca                                                 19

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
uuagaggaca aacgggcaac a                                              21

<210> SEQ ID NO 102
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
uuagaggaca aacgggcaa                                                 19

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
accgugugca cuucgcuuc                                                 19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
accgugugca cuucgcuuc                                              19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
acuucgcuuc accucugca                                              19

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
aguguuugcu gacgcaacc                                              19

<210> SEQ ID NO 107
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107 caggcgggu uuucuugu                                                19

<210> SEQ ID NO 108
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108 caggcgggu uuucuugu                                                19

<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
caguuuacua gugccauuu                                              19

<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110

```
caguuuacua gugccauuu                                          19
```

<210> SEQ ID NO 111
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111

```
cauccugcug cuaugccuc                                          19
```

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112

```
cauccugcug cuaugccuca u                                       21
```

<210> SEQ ID NO 113
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113

```
cauccugcug cuaugccuc                                          19
```

<210> SEQ ID NO 114
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114

```
ccgugugcac uucgcuuca                                          19
```

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115

```
ccgugugcac uucgcuuca                                          19
```

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116

```
ccugcugcua ugccucaucu u                                       21
```

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
cucaguuuac uagugccau                                                19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
cucaguuuac uagugccau                                                19

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
cucaguuuac uagugccau                                                19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
cucaguuuac uagugccau                                                19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
cucaguuuac uagugccau                                                19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
cugcuaugcc ucaucuucu                                                19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
cugcuaugcc ucaucuucu                                                  19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
cugcuaugcc ucaucuucu                                                  19

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
cugcuaugcc ucaucuucu                                                  19

<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
cugcugcuau gccucaucu                                                  19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
cugcugcuau gccucaucu                                                  19

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
cugcugcuau gccucaucu                                                  19

```
<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
cuucgcuuca ccucugcacg u                                              21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
gcacuucgcu ucaccucugc a                                              21

<210> SEQ ID NO 131
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
gccgauccau acugcggaa                                                 19

<210> SEQ ID NO 132
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
gccggguuuu ucuuguuga                                                 19

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133 gcggguuuu ucuuguuga                                                  19

<210> SEQ ID NO 134
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134 gcggggguuuu ucuuguuga                                                19

<210> SEQ ID NO 135
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
gcgggguuuu ucuuguuga                                                    19

<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136 gcggguuuu ucuuguuga                                                     19

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
gcugcuaugc cucaucuucu u                                                 21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
ggaugugucu gcggcguuuu a                                                 21

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
ggccaaaauu cgcagucccc                                                   19

<210> SEQ ID NO 140
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
ggcgcaccuc ucuuuacgc                                                    19

<210> SEQ ID NO 141
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
guauguugcc cguuugucc                                                  19

<210> SEQ ID NO 142
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
gugguggacu ucucucaau                                                  19

<210> SEQ ID NO 143
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
gugugcacuu cgcuucacc                                                  19

<210> SEQ ID NO 144
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
guugcccguu uguccucua                                                  19

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
guugcccguu uguccucua                                                  19

<210> SEQ ID NO 146
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
uccauacugc ggaacuccu                                                  19

<210> SEQ ID NO 147
<211> LENGTH: 19
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 147
uccauacugc ggaacuccu                                                   19

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
ucguggugga cuucucucaa u                                                21

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
ugcacuucgc uucaccucu                                                   19

<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
ugccgaucca uacugcgga                                                   19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
ugccgaucca uacugcgga                                                   19

<210> SEQ ID NO 152
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
ugcuaugccu caucuucuu                                                   19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
ugugcacuuc gcuucaccu                                                    19

<210> SEQ ID NO 154
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
ugugcacuuc gcuucaccu                                                    19

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
ugugcacuuc gcuucaccu                                                    19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
ugugcacuuc gcuucaccu                                                    19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
uugcccguuu guccucuaa                                                    19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
uugcccguuu guccucuaa                                                    19

<210> SEQ ID NO 159
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 159
gaagcgaagu gcacacgguc c                                              21

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
gaagcgaagu gcacacggu                                                 19

<210> SEQ ID NO 161
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
ugcagaggug aagcgaagug c                                              21

<210> SEQ ID NO 162
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
gguugcguca gcaaacacuu g                                              21

<210> SEQ ID NO 163
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
acaagaaaaa ccccgccugu a                                              21

<210> SEQ ID NO 164
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
acaagaaaaa accccgccug                                                20

<210> SEQ ID NO 165
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 165
aaauggcacu aguaaacuga g                                              21

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
aaauggcacu aguaaacug                                                 19

<210> SEQ ID NO 167
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
gaggcauagc agcaggauga a                                              21

<210> SEQ ID NO 168
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
augaggcaua gcagcaggau gaa                                            23

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
gaggcauagc agcaggaug                                                 19

<210> SEQ ID NO 170
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
ugaagcgaag ugcacacggu c                                              21

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 171
ugaagcgaag ugcacacgg                                                19

<210> SEQ ID NO 172
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
aagaugaggc auagcagcag gau                                           23

<210> SEQ ID NO 173
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
auggcacuag uaaacugagc c                                             21

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
auggcacuag uaaacugag                                                19

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
agaagaugag gcauagcagc a                                             21

<210> SEQ ID NO 176
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
agaagaugag gcauagcag                                                19

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 177
agaugaggca uagcagcagg a                                              21

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
agaugaggca uagcagcag                                                 19

<210> SEQ ID NO 179
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
acgugcagag gugaagcgaa gug                                            23

<210> SEQ ID NO 180
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
ugcagaggug aagcgaagug cac                                            23

<210> SEQ ID NO 181
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
uuccgcagua uggaucggca g                                              21

<210> SEQ ID NO 182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
uuccgcagua uggaucggc                                                 19

<210> SEQ ID NO 183
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
```
ucaacaagaa aaaccccgcc u                                          21

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
ucaacaagaa aaaccccgc                                             19

<210> SEQ ID NO 185
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
aagaagauga ggcauagcag cag                                        23

<210> SEQ ID NO 186
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
uaaaacgccg cagacacauc cag                                        23

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
gggacugcga auuuuggcca a                                          21

<210> SEQ ID NO 188
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
gcguaaagag aggugcgccc c                                          21

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189

-continued

```
ggacaaacgg gcaacauacc u                                              21

<210> SEQ ID NO 190
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
auugagagaa guccaccacg a                                              21

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
ggugaagcga agugcacacg g                                              21

<210> SEQ ID NO 192
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
uagaggacaa acgggcaaca u                                              21

<210> SEQ ID NO 193
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
uagaggacaa acgggcaac                                                 19

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
aggaguuccg caguauggau c                                              21

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
aggaguuccg caguaugga                                                 19
```

<210> SEQ ID NO 196
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
auugagagaa guccaccacg agu                                          23

<210> SEQ ID NO 197
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
agaggugaag cgaagugcac a                                            21

<210> SEQ ID NO 198
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
uccgcaguau ggaucggcag a                                            21

<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
uccgcaguau ggaucggca                                               19

<210> SEQ ID NO 200
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
aagaagauga ggcauagcag c                                            21

<210> SEQ ID NO 201
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
aggugaagcg aagugcacac g                                            21

```
<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
aggugaagcg aagugcaca                                                   19

<210> SEQ ID NO 203
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
uuagaggaca aacgggcaac a                                                21

<210> SEQ ID NO 204
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
uuagaggaca aacgggcaa                                                   19

<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
accgugugca cuucgcuuc                                                   19

<210> SEQ ID NO 206
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
accgugugca cuucgcuuc                                                   19

<210> SEQ ID NO 207
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
acuucgcuuc accucugca                                                   19
```

```
<210> SEQ ID NO 208
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
aguguuugcu gacgcaacc                                               19

<210> SEQ ID NO 209
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
caggcggggu uuucuugu                                                19

<210> SEQ ID NO 210
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
caggcggggu uuucuugu                                                19

<210> SEQ ID NO 211
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
caguuuacua gugccauuu                                               19

<210> SEQ ID NO 212
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
caguuuacua gugccauuu                                               19

<210> SEQ ID NO 213
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
cauccugcug cuaugccuc                                               19

<210> SEQ ID NO 214
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
cauccugcug cuaugccuca u                                             21

<210> SEQ ID NO 215
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
cauccugcug cuaugccuc                                                19

<210> SEQ ID NO 216
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
ccgugugcac uucgcuuca                                                19

<210> SEQ ID NO 217
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
ccgugugcac uucgcuuca                                                19

<210> SEQ ID NO 218
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
ccugcugcua ugccucaucu u                                             21

<210> SEQ ID NO 219
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
cucaguuuac uagugccau                                                19

<210> SEQ ID NO 220
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
cucaguuuac uagugccau                                                 19

<210> SEQ ID NO 221
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
cucaguuuac uagugccau                                                 19

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
cucaguuuac uagugccau                                                 19

<210> SEQ ID NO 223
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
cucaguuuac uagugccau                                                 19

<210> SEQ ID NO 224
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
cugcuaugcc ucaucuucu                                                 19

<210> SEQ ID NO 225
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
cugcuaugcc ucaucuucu                                                 19

<210> SEQ ID NO 226
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 226
cugcuaugcc ucaucuucu                                                    19

<210> SEQ ID NO 227
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
cugcuaugcc ucaucuucu                                                    19

<210> SEQ ID NO 228
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
cugcugcuau gccucaucu                                                    19

<210> SEQ ID NO 229
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
cugcugcuau gccucaucu                                                    19

<210> SEQ ID NO 230
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
cugcugcuau gccucaucu                                                    19

<210> SEQ ID NO 231
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
cuucgcuuca ccucugcacg u                                                 21

<210> SEQ ID NO 232
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 232
gcacuucgcu ucaccucugc a                                                  21

<210> SEQ ID NO 233
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
gccgauccau acugcggaa                                                     19

<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
gccggguuuu ucuuguuga                                                     19

<210> SEQ ID NO 235
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235 gcggggu uuu ucuuguuga                                                    19

<210> SEQ ID NO 236
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236 gcggggu uuu ucuuguuga                                                    19

<210> SEQ ID NO 237
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237 gcggggu uuu ucuuguuga                                                    19

<210> SEQ ID NO 238
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 238
gcgggguuuu ucuuguuga                                                    19

<210> SEQ ID NO 239
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
gcugcuaugc cucaucuucu u                                                 21

<210> SEQ ID NO 240
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
ggaugugucu gcggcguuuu a                                                 21

<210> SEQ ID NO 241
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
ggccaaaauu cgcagucccc                                                   19

<210> SEQ ID NO 242
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
ggcgcaccuc ucuuuacgc                                                    19

<210> SEQ ID NO 243
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
guauguugcc cguuugucc                                                    19

<210> SEQ ID NO 244
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 244
gugguggacu ucucucaau                                                19

<210> SEQ ID NO 245
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
gugugcacuu cgcuucacc                                                19

<210> SEQ ID NO 246
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
guugcccguu uguccucua                                                19

<210> SEQ ID NO 247
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
guugcccguu uguccucua                                                19

<210> SEQ ID NO 248
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
uccauacugc ggaacuccu                                                19

<210> SEQ ID NO 249
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
uccauacugc ggaacuccu                                                19

<210> SEQ ID NO 250
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
ucguggugga cuucucucaa u                                              21

<210> SEQ ID NO 251
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
ugcacuucgc uucaccucu                                                 19

<210> SEQ ID NO 252
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
ugccgaucca uacugcgga                                                 19

<210> SEQ ID NO 253
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
ugccgaucca uacugcgga                                                 19

<210> SEQ ID NO 254
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
ugcuaugccu caucuucuu                                                 19

<210> SEQ ID NO 255
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
ugugcacuuc gcuucaccu                                                 19

<210> SEQ ID NO 256
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 256
ugugcacuuc gcuucaccu                                                    19

<210> SEQ ID NO 257
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
ugugcacuuc gcuucaccu                                                    19

<210> SEQ ID NO 258
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
ugugcacuuc gcuucaccu                                                    19

<210> SEQ ID NO 259
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
uugcccguuu guccucuaa                                                    19

<210> SEQ ID NO 260
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
uugcccguuu guccucuaa                                                    19

<210> SEQ ID NO 261
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
gaagcgaagu gcacacgguc c                                                 21

<210> SEQ ID NO 262
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
```

```
gaagcgaagu gcacacggu                                                    19

<210> SEQ ID NO 263
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
ugcagaggug aagcgaagug c                                                 21

<210> SEQ ID NO 264
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
gguugcguca gcaaacacuu g                                                 21

<210> SEQ ID NO 265
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
acaagaaaaa ccccgccugu a                                                 21

<210> SEQ ID NO 266
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
acaagaaaaa accccgccug                                                   20

<210> SEQ ID NO 267
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
aaauggcacu aguaaacuga g                                                 21

<210> SEQ ID NO 268
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
```
aaauggcacu aguaaacug                                              19

<210> SEQ ID NO 269
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
gaggcauagc agcaggauga a                                           21

<210> SEQ ID NO 270
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
augaggcaua gcagcaggau gaa                                         23

<210> SEQ ID NO 271
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
gaggcauagc agcaggaug                                              19

<210> SEQ ID NO 272
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
ugaagcgaag ugcacacggu c                                           21

<210> SEQ ID NO 273
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
ugaagcgaag ugcacacgg                                              19

<210> SEQ ID NO 274
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
aagaugaggc auagcagcag gau                                         23

```
<210> SEQ ID NO 275
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
auggcacuag uaaacugagc c                                              21

<210> SEQ ID NO 276
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
auggcacuag uaaacugag                                                 19

<210> SEQ ID NO 277
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
agaagaugag gcauagcagc a                                              21

<210> SEQ ID NO 278
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
agaagaugag gcauagcag                                                 19

<210> SEQ ID NO 279
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
agaugaggca uagcagcagg a                                              21

<210> SEQ ID NO 280
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
agaugaggca uagcagcag                                                 19
```

<210> SEQ ID NO 281
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
acgugcagag gugaagcgaa gug                                          23

<210> SEQ ID NO 282
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
ugcagaggug aagcgaagug cac                                          23

<210> SEQ ID NO 283
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
uuccgcagua uggaucggca g                                            21

<210> SEQ ID NO 284
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
uuccgcagua uggaucggc                                               19

<210> SEQ ID NO 285
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
ucaacaagaa aaccccgcc u                                             21

<210> SEQ ID NO 286
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
ucaacaagaa aaccccgc                                                19

-continued

<210> SEQ ID NO 287
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
aagaagauga ggcauagcag cag                                              23

<210> SEQ ID NO 288
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
uaaaacgccg cagacacauc cag                                              23

<210> SEQ ID NO 289
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
gggacugcga auuuuggcca a                                                21

<210> SEQ ID NO 290
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
gcguaaagag aggugcgccc c                                                21

<210> SEQ ID NO 291
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
ggacaaacgg gcaacauacc u                                                21

<210> SEQ ID NO 292
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
auugagagaa guccaccacg a                                                21

<210> SEQ ID NO 293

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
ggugaagcga agugcacacg g                                                 21

<210> SEQ ID NO 294
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
uagaggacaa acgggcaaca u                                                 21

<210> SEQ ID NO 295
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
uagaggacaa acgggcaac                                                    19

<210> SEQ ID NO 296
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
aggaguuccg caguauggau c                                                 21

<210> SEQ ID NO 297
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
aggaguuccg caguaugga                                                    19

<210> SEQ ID NO 298
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
auugagagaa guccaccacg agu                                               23

<210> SEQ ID NO 299
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
agaggugaag cgaagugcac a                                           21

<210> SEQ ID NO 300
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
uccgcaguau ggaucggcag a                                           21

<210> SEQ ID NO 301
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
uccgcaguau ggaucggca                                              19

<210> SEQ ID NO 302
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
aagaagauga ggcauagcag c                                           21

<210> SEQ ID NO 303
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
aggugaagcg aagugcacac g                                           21

<210> SEQ ID NO 304
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
aggugaagcg aagugcaca                                              19

<210> SEQ ID NO 305
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 305
uuagaggaca aacgggcaac a                                              21

<210> SEQ ID NO 306
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
uuagaggaca aacgggcaa                                                 19

<210> SEQ ID NO 307
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
accgugugca cuucgcuuc                                                 19

<210> SEQ ID NO 308
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 308
accgugugca cuucgcuuct t                                              21

<210> SEQ ID NO 309
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
acuucgcuuc accucugca                                                 19

<210> SEQ ID NO 310
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
aguguuugcu gacgcaacc                                                 19

<210> SEQ ID NO 311
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
caggcggggu uuucuugu                                                       19

<210> SEQ ID NO 312
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 312
caggcggggu uuucuugut t                                                    21

<210> SEQ ID NO 313
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
caguuuacua gugccauuu                                                      19

<210> SEQ ID NO 314
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 314
caguuuacua gugccauuut t                                                   21

<210> SEQ ID NO 315
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
cauccugcug cuaugccuc                                                      19

<210> SEQ ID NO 316
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
```
cauccugcug cuaugccuca u                                              21

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 317
cauccugcug cuaugccuct t                                              21

<210> SEQ ID NO 318
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
ccgugugcac uucgcuuca                                                 19

<210> SEQ ID NO 319
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 319
ccgugugcac uucgcuucat t                                              21

<210> SEQ ID NO 320
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
ccugcugcua ugccucaucu u                                              21

<210> SEQ ID NO 321
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
cucaguuuac uagugccau                                                 19

<210> SEQ ID NO 322
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 322
cucaguuuac uagugccau                                                    19

<210> SEQ ID NO 323
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
cucaguuuac uagugccau                                                    19

<210> SEQ ID NO 324
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 324
cucaguuuac uagugccaut t                                                 21

<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 325
cucaguuuac uagugccaut t                                                 21

<210> SEQ ID NO 326
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
cugcuaugcc ucaucuucu                                                    19

<210> SEQ ID NO 327
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
cugcuaugcc ucaucuucu                                                    19
```

<210> SEQ ID NO 328
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 328
cugcuaugcc ucaucuucut t                                          21

<210> SEQ ID NO 329
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 329
cugcuaugcc ucaucuucut t                                          21

<210> SEQ ID NO 330
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 330
cugcugcuau gccucaucu                                             19

<210> SEQ ID NO 331
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 331
cugcugcuau gccucaucut t                                          21

<210> SEQ ID NO 332
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 332
cugcugcuau gccucaucut t                                          21

<210> SEQ ID NO 333

-continued

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
cuucgcuuca ccucugcacg u                                              21

<210> SEQ ID NO 334
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
gcacuucgcu ucaccucugc a                                              21

<210> SEQ ID NO 335
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
gccgauccau acugcggaa                                                 19

<210> SEQ ID NO 336
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 336
gccggguuuu ucuuguugat t                                              21

<210> SEQ ID NO 337
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337 gcggguuuu ucuuguuga                                                  19

<210> SEQ ID NO 338
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338 gcggguuuu ucuuguuga                                                  19
```

<210> SEQ ID NO 339
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 339
gcgggguuuu ucuuguugat t                                              21

<210> SEQ ID NO 340
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 340
gcgggguuuu ucuuguugat t                                              21

<210> SEQ ID NO 341
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
gcugcuaugc cucaucuucu u                                              21

<210> SEQ ID NO 342
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
ggaugugucu gcggcguuuu a                                              21

<210> SEQ ID NO 343
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
ggccaaaauu cgcagaccc                                                 19

<210> SEQ ID NO 344
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 344
ggcgcaccuc ucuuuacgc                                                 19

<210> SEQ ID NO 345
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
guauguugcc cguuugucc                                                 19

<210> SEQ ID NO 346
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
gugguggacu ucucucaau                                                 19

<210> SEQ ID NO 347
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
gugugcacuu cgcuucacc                                                 19

<210> SEQ ID NO 348
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
guugcccguu uguccucua                                                 19

<210> SEQ ID NO 349
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 349
guugcccguu uguccucuat t                                              21

<210> SEQ ID NO 350
<211> LENGTH: 19
<212> TYPE: RNA
<213> ORGANISM: Artificial Sequence
<220> FEATURE:
```

<223> OTHER INFORMATION: Description of Artificial Sequence: Synthetic
    oligonucleotide

<400> SEQUENCE: 350
uccauacugc ggaacuccu                                                19

<210> SEQ ID NO 351
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 351
uccauacugc ggaacuccut t                                             21

<210> SEQ ID NO 352
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 352
ucguggugga cuucucucaa u                                             21

<210> SEQ ID NO 353
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 353
ugcacuucgc uucaccucu                                                19

<210> SEQ ID NO 354
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 354
ugccgaucca uacugcgga                                                19

<210> SEQ ID NO 355
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 355
ugccgaucca uacugcggat t                                             21

```
<210> SEQ ID NO 356
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
ugcuaugccu caucuucuu                                                       19

<210> SEQ ID NO 357
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
ugugcacuuc gcuucaccu                                                       19

<210> SEQ ID NO 358
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
ugugcacuuc gcuucaccu                                                       19

<210> SEQ ID NO 359
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 359
ugugcacuuc gcuucaccut t                                                    21

<210> SEQ ID NO 360
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 360
ugugcacuuc gcuucaccut t                                                    21

<210> SEQ ID NO 361
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 361
uugcccguuu guccucuaa                                                19

<210> SEQ ID NO 362
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 362
uugcccguuu guccucuaat t                                             21

<210> SEQ ID NO 363
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
gaagcgaagu gcacacgguc c                                             21

<210> SEQ ID NO 364
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 364
gaagcgaagu gcacacggut t                                             21

<210> SEQ ID NO 365
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
ugcagaggug aagcgaagug c                                             21

<210> SEQ ID NO 366
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
gguugcguca gcaaacacuu g                                             21

<210> SEQ ID NO 367
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 367
acaagaaaaa ccccgccugu a                                              21

<210> SEQ ID NO 368
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 368
acaagaaaaa accccgccug tt                                             22

<210> SEQ ID NO 369
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
aaauggcacu aguaaacuga g                                              21

<210> SEQ ID NO 370
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 370
aaauggcacu aguaaacugt t                                              21

<210> SEQ ID NO 371
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
gaggcauagc agcaggauga a                                              21

<210> SEQ ID NO 372
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
augaggcaua gcagcaggau gaa                                            23
```

<210> SEQ ID NO 373
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 373
gaggcauagc agcaggaugt t                                              21

<210> SEQ ID NO 374
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
ugaagcgaag ugcacacggu c                                              21

<210> SEQ ID NO 375
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 375
ugaagcgaag ugcacacggt t                                              21

<210> SEQ ID NO 376
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
aagaugaggc auagcagcag gau                                            23

<210> SEQ ID NO 377
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
auggcacuag uaaacugagc c                                              21

<210> SEQ ID NO 378
<211> LENGTH: 21
<212> TYPE: DNA
<213> ORGANISM: Artificial Sequence
<220> FEATURE:
<223> OTHER INFORMATION: Description of Artificial Sequence: Synthetic

```
              oligonucleotide
<220> FEATURE:
<223> OTHER INFORMATION: Description of Combined DNA/RNA Molecule:
      Synthetic oligonucleotide

<400> SEQUENCE: 378
auggcacuag uaaacugagt t                                             21

<210> SEQ ID NO 379
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
agaagaugag gcauagcagc a                                             21

<210> SEQ ID NO 380
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 380
agaagaugag gcauagcagt t                                             21

<210> SEQ ID NO 381
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
agaugaggca uagcagcagg a                                             21

<210> SEQ ID NO 382
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 382
agaugaggca uagcagcagt t                                             21

<210> SEQ ID NO 383
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 383
agaugaggca uagcagcagt t                                              21

<210> SEQ ID NO 384
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
acgugcagag gugaagcgaa gug                                            23

<210> SEQ ID NO 385
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
ugcagaggug aagcgaagug cac                                            23

<210> SEQ ID NO 386
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
uuccgcagua uggaucggca g                                              21

<210> SEQ ID NO 387
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 387
uuccgcagua uggaucggct t                                              21

<210> SEQ ID NO 388
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
ucaacaagaa aaccccgcc u                                               21

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 389
ucaacaagaa aaaccccgct t                                          21

<210> SEQ ID NO 390
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
aagaagauga ggcauagcag cag                                        23

<210> SEQ ID NO 391
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
uaaaacgccg cagacacauc cag                                        23

<210> SEQ ID NO 392
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
gggacugcga auuuuggcca a                                          21

<210> SEQ ID NO 393
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
gcguaaagag aggugcgccc c                                          21

<210> SEQ ID NO 394
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
ggacaaacgg gcaacauacc u                                          21

<210> SEQ ID NO 395
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 395
auugagagaa guccaccacg a                                              21

<210> SEQ ID NO 396
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
ggugaagcga agugcacacg g                                              21

<210> SEQ ID NO 397
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
uagaggacaa acgggcaaca u                                              21

<210> SEQ ID NO 398
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 398
uagaggacaa acgggcaact t                                              21

<210> SEQ ID NO 399
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
aggaguuccg caguauggau c                                              21

<210> SEQ ID NO 400
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 400
aggaguuccg caguauggat t                                              21
```

<210> SEQ ID NO 401
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
auugagagaa guccaccacg agu                                              23

<210> SEQ ID NO 402
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
agaggugaag cgaagugcac a                                                21

<210> SEQ ID NO 403
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
uccgcaguau ggaucggcag a                                                21

<210> SEQ ID NO 404
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 404
uccgcaguau ggaucggcat t                                                21

<210> SEQ ID NO 405
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
aagaagauga ggcauagcag c                                                21

<210> SEQ ID NO 406
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
aggugaagcg aagugcacac g                                           21

<210> SEQ ID NO 407
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 407
aggugaagcg aagugcacat t                                           21

<210> SEQ ID NO 408
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
uuagaggaca aacgggcaac a                                           21

<210> SEQ ID NO 409
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 409
uuagaggaca aacgggcaat t                                           21

<210> SEQ ID NO 410
<211> LENGTH: 3182
<212> TYPE: DNA
<213> ORGANISM: Hepatitis B virus

<400> SEQUENCE: 410
aattccacaa cctttcacca aactctgcaa gatcccagag tgagaggcct gtatttccct    60
gctggtggct ccagttcagg agcagtaaac cctgttccga ctactgcctc tcccttatcg   120
tcaatcttct cgaggattgg ggaccctgcg ctgaacatgg agaacatcac atcaggattc   180
ctaggacccc ttctcgtgtt acaggcgggg ttttcttgt tgacaagaat cctcacaata   240
ccgcagagtc tagactcgtg gtggacttct ctcaattttc taggggggaac taccgtgtgt   300 cttggccaaa attcgcagtc cccaacctcc aatcactcac caacctcctg tcctccaact   360
tgtcctggtt atcgctggat gtgtctgcgg cgttttatca tcttcctctt catcctgctg   420
ctatgcctca tcttcttgtt ggttcttctg gactatcaag gtatgttgcc cgtttgtcct   480
ctaattccag gatcctcaac caccagcacg ggaccatgcc gaacctgcat gactactgct   540
caaggaacct ctatgtatcc ctcctgttgc tgtaccaaac cttcggacgg aaattgcacc   600
tgtattccca tccatcatc ctgggctttc ggaaaattcc tatgggagtg ggcctcagcc   660
cgtttctcct ggctcagttt actagtgcca tttgttcagt ggttcgtagg gctttccccc   720

```
actgtttggc tttcagttat atggatgatg tggtattggg ggccaagtct gtacagcatc    780
ttgagtccct ttttaccgct gttaccaatt ttcttttgtc tttgggtata catttaaacc    840
ctaacaaaac aaagagatgg ggttactctc tgaattttat gggttatgtc attggaagtt    900
atgggtcctt gccacaagaa cacatcatac aaaaaatcaa agaatgtttt agaaaacttc    960
ctattaacag gcctattgat tggaaagtat gtcaacgaat gtgggtctt ttgggttttg    1020 ctgccccatt tacacaatgt ggttatcctg cgttaatgcc cttgtatgca tgtattcaat    1080
ctaagcaggc tttcactttc tcgccaactt acaaggcctt tctgtgtaaa caatacctga    1140
acctttaccc cgttgcccgg caacggccag gtctgtgcca gtgtttgct gacgcaaccc     1200 ccactggctg gggcttggtc atgggccatc agcgcgtgcg tggaacctttt cggctcctc    1260 tgccgatcca tactgcggaa ctcctagccg cttgttttgc tcgcagcagg tctggagcaa    1320
acattatcgg gactgataac tctgttgtcc tctcccgcaa atatacatcg tatccatggc    1380
tgctaggctg tgctgccaac tggatcctgc gcgggacgtc ctttgtttac gtcccgtcgg    1440
cgctgaatcc tgcggacgac ccttctcggg gtcgcttggg actctctcgt ccccttctcc    1500
gtctgccgtt ccgaccgacc acggggcgca cctctcttta cgcggactcc ccgtctgtgc    1560
cttctcatct gccggaccgt gtgcacttcg cttcacctct gcacgtcgca tggagaccac    1620
cgtgaacgcc caccgaatgt tgcccaaggt cttacataag aggactcttg gactctctgc    1680
aatgtcaacg accgaccttg aggcatactt caaagactgt ttgtttaaag actgggagga    1740
gttgggggag gagattagat taaaggtctt tgtactagga ggctgtaggc ataaattggt    1800
ctgcgcacca gcaccatgca acttttttcac ctctgcctaa tcatctcttg ttcatgtcct    1860
actgttcaag cctccaagct gtgccttggg tggctttggg gcatggacat cgacccttat    1920
aaagaatttg gagctactgt ggagttactc tcgttttttgc cttctgactt ctttccttca    1980
gtacgagatc ttctagatac cgcctcagct ctgtatcggg aagcttaga gtctcctgag     2040 cattgttcac ctcaccatac tgcactcagg caagcaattc tttgctgggg gaactaatg     2100 actctagcta cctgggtggg tgttaatttg gaagatccag catctagaga cctagtagtc    2160
agttatgtca acactaatat gggcctaaag ttcaggcaac tcttgtggtt tcacatttct    2220
tgtctcactt ttggaagaga aaccgttata gagtatttgg tgtctttcgg agtgtggatt    2280
cgcactcctc cagcttatag accaccaaat gcccctatcc tatcaacact tccggaaact    2340
actgttgtta gacgacgagg caggtcccct agaagaagaa ctccctcgcc tcgcagacga    2400
aggtctcaat cgccgcgtcg cagaagatct caatctcggg aacctcaatg ttagtattcc    2460
ttggactcat aaggtgggga actttactgg tctttattct tctactgtac ctgtctttaa    2520
tcctcattgg aaaacaccat cttttcctaa tatacattta caccaagaca ttatcaaaaa    2580
atgtgaacag tttgtaggcc cacttacagt taatgagaaa agaagattgc aattgattat    2640
gcctgctagg ttttatccaa aggttaccaa atatttacca ttggataagg gtattaaacc    2700
ttattatcca gaacatctag ttaatcatta cttccaaact agacactatt tacacactct    2760
atggaaggcg ggtatattat ataagagaga acaacacat agcgcctcat tttgtgggtc    2820
accatattct tgggaacaag atctacagca tggggcagaa tctttccacc agcaatcctc    2880
tgggattctt tcccgaccac cagttggatc cagccttcag agcaaacaca gcaaatccag    2940
attgggactt caatcccaac aaggacacct ggccagacgc caacaaggta ggagctggag    3000
cattcgggct gggtttcacc ccaccgcacg gaggcctttt ggggtggagc cctcaggctc    3060
agggcatact acaaactttg ccagcaaatc cgcctcctgc ctccaccaat cgccagacag    3120
```

```
gaaggcagcc tacccogctg tctccacctt tgagaaacac tcatcctcag gccatgcagt    3180
gg                                                                   3182

<210> SEQ ID NO 411
<211> LENGTH: 7459
<212> TYPE: DNA
<213> ORGANISM: Homo sapiens

<400> SEQUENCE: 411
agtcactgcc gcggcgcctt gagtctccgg gccgccttgc catggctgcc cgtggtgtca      60
tcgctccagt tggcgagagt ttgcgctacg ctgagtactt gcagccctcg gccaaacggc     120
cagacgccga cgtcgaccag cagagactgg taagaagttt gatagctgta ggactgggtg     180
ttgcagctct tgcatttgca ggtcgctacg catttcggat ctggaaacct ctagaacaag     240
ttatcacaga aactgcaaag aagatttcaa ctcctagctt ttcatcctac tataaaggag     300
gatttgaaca gaaaatgagt aggcgagaag ctggtcttat tttaggtgta agcccatctg     360
ctggcaaggc taagattaga acagctcata ggagagtcat gattttgaat cacccagata     420
aaggtggatc tccttacgta gcagccaaaa taaatgaagc aaaagacttg ctagaaacaa     480
ccaccaaaca ttgatgctta aggaccacac tgaaggaaaa aaaagaggg gacttcgaaa      540 aaaaaaaag ccctgcaaaa tattctaaaa catggtcttc ttaattttct atatggattg      600
accacagtct tatcttccac cattaagctg tataacaata aatgttaat agtcttgctt      660 tttattatct tttaaagatc tccttaaatt ctataactga tctttttct tattttgttt      720 gtgacattca tacatttta agattttgt tatgttctga attccccct acacacacac        780 acacacacac acacacacac acgtgcaaaa aatatgatca agaatgcaat tgggatttgt     840
gagcaatgag tagacctctt attgtttata tttgtaccct cattgtcaat ttttttttag     900
ggaatttggg actctgccta tataaggtgt tttaaatgtc ttgagaacaa gcactggctg     960
atacctcttg gagatatgat ctgaaatgta atggaattta ttaaatggtg tttagtaaag    1020
taggggttaa ggacttgtta aagaaccca ctatctctga daccctatag ccaaagcatg     1080
aggacttgga gagctactaa aatgattcag gtttacaaaa tgagcccgt gaggaaaggt     1140 tgagagaagt ctgaggagtt tgtatttaat tatagtcttc cagtactgta tattcattca    1200
ttactcattc tacaaatatt tattgacccc ttttgatgtg caaggcacta tcgtgcgtcc    1260
cctgagagtt gcaagtatga agcagtcatg gatcatgaac caaaggaact tatatgtaga    1320
ggaaggataa atcacaaata gtgaatactg ttagatacag atgatatatt ttaaaagttc    1380
aaaggaagaa aagaatgtgt taaacactgc atgagaggag gaataagtgg catagagcta    1440
ggctttagaa aagaaaaata ttccgatacc atatgattgg tgaggtaagt gttattctga    1500
gatgagaatt agcagaaata gatatatcaa tcggagtgat tagagtgcag ggtttctgga    1560
aagcaaggtt tggacagagt ggtcatcaaa ggccagccct gtgacttaca ctgcattaaa    1620
ttaatttctt agaacatagt ccctgatcat tatcacttta ctattccaaa ggtgagagaa    1680
cagattcaga tagagtgcca gcattgtttc ccagtattcc tttacaaatc ttgggttcat    1740
tccaggtaaa ctgaactact gcattgtttc tatcttaaaa tactttttag atatcctaga    1800
tgcatctttc aacttctaac attctgtagt ttaggagttc tcaaccttgg cattattgac    1860
atgttaggcc aaataatttt ttttgtggga ggtctcttgt gcgttttaga tgattagcaa    1920
taatccctga cctgttatct actaaagact agtcgtttct catcagttgt gacaacaaaa    1980
```

```
atggttccag atattgccaa atgcccttta gaggacagta atcgccccca gttgagaacc    2040
atttcagtaa aactttaatt actattttt cttttggttt ataaataat gatcctgaat      2100
taaattgatg gaaccttgaa gtcgataaaa tatatttctt gctttaaagt ccccatacgt    2160
gtcctactaa ttttctcatg ctttagtgtt ttcactttc tcctgttatc cttgtaccta     2220
agaatgccat cccaatcccc agatgtccac ctgcccaaag tctaggcata gctgaaggcc    2280
aagctaaaat gtatccctct ttttctggta catgcagcaa aagtaatatg aattatcagc    2340
tttctgagag caggcattgt atctgtcttg tttggtgtta cattggcacc caataaatat    2400
ttgttgagtg aatgaataaa ttcccatagc actttattct tcacatggta cataactata    2460
ggggctatag cttggtacct tgtgaagcaa ctcttggtgt aacatacctt atttctcata    2520
ctaaaatgca agaaccttta gagcaaggat cttgccattc atctttgtaa cctctttact    2580
ctggagcact tgcatttagc aggcatcata agttttacg taccaagaaa atgttgctgt     2640
tttctgaata ctatgcatca aaaaatgtta ccactaattt ttaaagctct gctaaggaat    2700
attgggcac cctcagatgc accttttaat tgatgtcata ttttcctaat ccatacttta    2760
ttcatgagaa tttgagtcac cccagcatta gcttggaatt tccttatttc ccatttgctt   2820
tgcaggtgcc ttggagtcag atctggtttt gaatactatc ttcctgttat gtgatcttgg   2880
gcagttactt aattttctag tcaataaccc gtatctataa aatagagaaa ataatcctac    2940
acaccgggc ctgttgtggg gcggggagag ggggaggga tcgcatttgg agatatacta     3000
atgtaaatga caagttaatt ggtgcagcac accaacatgg ctcatgtcta catatgtaac    3060
aaacctgcac gttgtgcaca tgtgccctag aacttaaagt ataataaaaa gaaattttaa    3120
aaaatcctgt caaataaggt tatagtagag aataaggatg tgtaaagcat ttagtcacgt    3180
aaatgcttaa aaaaatgtaa ttttacttc tttcactgcc tcatttaatt agttttatct    3240
ttaataatac cttggattca gggtaaagtt tcagttatgt cccagtaatc atttatttta    3300
ccctcgaatc tgcaatttgg atagaacatg gtggggacag ctcgtctcta ttccttgcag    3360
cattaacagg ctggaggcac cacttctctg gccagcaagt tgggcctggt tgttggctga    3420
gagcctcagt tcctttctgc acaggttcct ctttacatag gcttctcaac agggctacta   3480
gagcatcgtc accatagcag ctgtcttata acagagagtg gtcggtctga gagacaaaaa    3540
atggaagctg ccaaattgtt ctgggtctgg aaactgtcag ggcatcactt gtgccatatt    3600
cagttggcct aagaattaca gagcctgcct cgattcaaag ggagaggata gagaggactg    3660
aaggaatcag tgctcatctt taatatgcag caggacaggt ttgggatttt ttttccccct    3720
tgagtctgtg aaggcattac ttaagaacaa agtcaggcat gtataattga actacagtta    3780
cttgaaatat aagcccagaa agtttcgat aataaataca actattttc tgctgttacc     3840
cttgtaccta aagatgccat cctaatcccc agatctccac aactatacct acatagtaga    3900
aggtaaaaat gtatccctct ttttctggtg catccagcaa aagtaatatc atgaattatg    3960
agctctctga gagcaaggat catatcagtc ttgtttattg ttgcagtgaa caagtacagt    4020
tgcagatatt caggagtaat tatctaaatg gcagtaggct tataaaactg aattttcacc    4080
agccacaccc tcccccaac tccttatctg taaaaagctt atttgagtgg ttacctgtct    4140
tcagtaaaga ttgcgcttgc atatttgctg tcattgcata ttctgcttaa ttaagctctg    4200
ttgatattgc agtttctgtg catacttaca tcttagatgc aatctgaggg cctaggaagg    4260
ccttttaaaa ataaaacaat tccgattgca gagaaagtgt aagtcaagga cagttaattc    4320
aaggggaaca tagaaagcta tttagatttt agttgatggt gccagtcttc agcgtaaagt    4380
```

```
caaaagtgga gggaagttta gtaaggaaaa aatgttgggc ttggaataca ttgtttagtc    4440
ttcaaagcac tttactttt atgaaatata ttttagacat tcagcaaata ttgaatactt    4500
actatatcag gcagtaaaga tataaattca ttcttaaaat gtgcaacatg ttcaaactga    4560
aaaaaataca ttcttaaaca ggaaactttt tccttcatac tttttaatta acaagacata    4620
taagagttgc attaatgggc gtgcttatga ttgatcaccc agcagcatca ttagaaataa    4680
tatattttat tcatgtgcag aaatcttttg gttgtcctgg ggaaccttga acacagaaaa    4740
gagcttttat tgataaggta attgaacaca cttgacaatt agcttaatat ggtttaatac    4800
catttgtggg agaagatgaa tcagccaggc tctttacgtc aagaatatga agtttctctt    4860
gagtcaacca acttaagatg agctacggag actgcagtga aaagttaaat atccaagtac    4920
accagccaat ttcacacagt ggaaccatgc tgtcctcggg caccctgcac ctcgcccaac    4980
agtcatcaac tagatggagg ctcctggctg caaggaggat ttgatgggaa tgagtaaatg    5040
tgtcagcata gtccgtccct tctaatggaa aagcaaccca aagagcaaat cctattaatg    5100
gctggatcag tatcatctac ttgtcaaaaa cattccatga attatgagtc aaaattttat    5160
ttatggtggc attacacaca ttaagagatg aggacttctg ttagcataat ttattagctg    5220
gaaaagttga gaaggttctc tggactcatt tttataggtg gaacctaagt gatctggata    5280
attgcccacc agcaaaattg ctgggcatgg tggacaaaga aaatgttcct tctaatgatt    5340
ttttatgagc tgagtagcta ttgttcccag ctgagtgctc ttttcctctt tttattgttg    5400
ctgagcaaaa gaatttataa aaagctcttt cttttgtatt aaaaaccctg ctcaattgaa    5460
atgcaagttc attaagtaat cttcatttct cttcctgcca taataaccct ttccctctct    5520
gttcgattca acagtatcta gcagcactgc tccaaatttt aagtctgaac agactatatt    5580
acatagatgt agagaaatac tcaatcttca gcattaagag ggagcttaat ttcacacggg    5640
tggaatatga tcactcaggc tagatgttgg ccataaattt caaattagta tctcaactta    5700 gcaggggga tcaacagtgg caaacttcaa ttatgacagg ataaaaatca catagagata    5760
ttggttcaat atggacatct aaactataat gctaaaagcc aataattaga ataagttcat    5820
tttaagaaaa gcattaataa tattagctaa cgtttagtac ctgtgccaaa cattctacct    5880
atgttacctt gattttcata gccagcctaa gaggtactat tatgtatccc cattttacag    5940
gttaagaaac aggctcagag gagtttagga tcttttccaa gattacatag ccagtaagtg    6000
gtggcactag gaaccaaatt cagactctga atcgcatgct gtttatatta tattgcactc    6060
attctaaata tgtgggaatc agaatgaagg ggcttgtatg acttttggct cattttttga    6120
tgcatgtgac ctgggattat aaatgtgaaa ttaggtttac gaaaggatcc agtgtcattg    6180
tgcatcatgg gcaaggagta cctaatctct ttaattcttc cctggaagct tacgatgtcc    6240
atccaagtgc acatagcaaa agttctgttg taaagtttag cagagtgact ttctttgact    6300
cagagtgatg acgaggaag ctttgataag attttatctg aaatgttcat ggacaagagc    6360
tttcaaggag aacatccaga gcaaggttct gaagacagct catgaaggtg aagcagcaga    6420
cctggcacaa gaaatgaaga gagagctcag tgtattaaag atgaaaacaa gaaaaccgaa    6480
tatattgaaa ggagcagaga ggcaatgaaa acaagacaac tgaaatgagg taacttgcag    6540
caattgaaag ggaatttcag tactttata gaattcttaa aaattgtttc ctgctgttta    6600
ttttcaattt tgaacagggt tatttgtcca tgccatactt ttttgccaa attccaaaat    6660 tgtgtatagt tctatagttg tctggtggag tcaatggaac tttagttacc agtctaagaa    6720
```

```
tgtgtctttg agattgtcca gttaattctc tatttccagt agctgtaata aatggtgaaa    6780
aggtttctga ctcctggaga aagtttctaa ctccttatga ctaatattca taacagactt    6840
gtgagttcct tgaacatgga tacacctata tgcaagagtg tattccaaag ctaactcagt    6900
gatctttcca tttatctatt cttggattag tggtgccttt gctctttcct tctgtaaatg    6960
tgaatagtta agagttgact gcagaagtgt ttacactttg gcttccatgc ctctggaatg    7020
tttgtgcttt ggtggtgaga tgtgagacta tatttgtata gtctgcatct ctcaggctgc    7080
cccagaatgt tgtacagtgc agtgctgaag aaagcagcag gtacacacag aaatgcagcc    7140
tttcctggtt aaccctgctt ggatctgagt tacactttgt ttcctgactt cttgggactt    7200
aggtaatcag tttgccttct actctatctc attttgtact cgcttacata ctacattctt    7260
gtttgggctt tcgtttcttc ttgtaagcag agattttta aaatccaata tgtgaaaata    7320
cggatgcact acaattaaat aaataaaatg ctgttgtgtt tgttttgctt taaaattgta    7380
aaggataaac aataagatag ttttatctat gtggttttcc cgatgcagtt aaaataaaac    7440
ctaatctgct aaaattgaa                                                 7459
```

<210> SEQ ID NO 412  
<211> LENGTH: 1906  
<212> TYPE: DNA  
<213> ORGANISM: Homo sapiens

<400> SEQUENCE: 412

```
gctttccggc ggttgcaccg ggccggggtg ccagcgcccg ccttcccgtt tcctcccgtt      60
ccgcagcgcg cccacggcct gtgaccccgg cgaccgctcc ccagtgacga gagagcgggg    120
ccgggcgctg ctccggcctg acctgcgaag ggacctcggt ccagtcccct gttgcgccgc    180
gcccccgtcc gtccgtgcgc gggccagtca ggggccagtg tctcgagcgg tcgaggtcgc    240
agacctagag gcgcccccaca ggccggcccg gggcgctggg agcgccggcc gcgggccggg    300
tggggatgcc tctgcacgtg aagtggccgt tccccgcggt gccgccgctc acctggaccc    360
tggccagcag cgtcgtcatg ggcttggtgg gcacctacag ctgcttctgg accaagtaca    420
tgaaccacct gaccgtgcac aacagggagg tgctgtacga gctcatcgag aagcgaggcc    480
cggccacgcc cctcatcacc gtgtccaatc accagtcctg catggacgac cctcatctct    540 ggggatcct gaaactccgc cacatctgga acctgaagtt gatgcgttgg acccctgcag    600
ctgcagacat ctgcttcacc aaggagctac actcccactt cttcagcttg ggcaagtgtg    660
tgcctgtgtg ccgaggagca gaattttttcc aagcagagaa tgaggggaaa ggtgttctag    720
acacaggcag gcacatgcca ggtgctggaa aaagaagaga gaaggagat ggcgtctacc    780 agaaggggat ggacttcatt ttggagaagc tcaaccatgg ggactgggtg catatcttcc    840
cagaagggaa agtgaacatg agttccgaat tcctgcgttt caagtgggga atcgggcgcc    900
tgattgctga gtgtcatctc aaccccatca tcctgccccc gtggcatgtc ggaatgaatg    960
acgtccttcc taacagtccg ccctacttcc cccgctttgg acagaaaatc actgtgctga   1020
tcgggaagcc cttcagtgcc ctgcctgtac tcgagcggct ccgggcggag aacaagtcgg   1080
ctgtggagat gcggaaagcc ctgacggact tcattcaaga ggaattccag catctgaaga   1140
ctcaggcaga gcagctccac aaccacctcc agcctgggag ataggccttg cttgctgcct   1200
tctggattct tggcccgcac agagctgggg ctgagggatg gactgatgct tttagctcaa   1260
acgtggcttt tagacagatt tgttcataga ccctctcaag tgccctctcc gagctggtag   1320
gcattccagc tcctccgtgc ttcctcagtt acacaaagga cctcagctgc ttctcccact   1380
```

| | |
|---|---:|
| tggccaagca gggaggaaga agcttaggca gggctctctt tccttcttgc cttcagatgt | 1440 |
| tctctcccag gggctggctt caggagggag catagaaggc aggtgagcaa ccagttggct | 1500 |
| aggggagcag ggggcccacc agagctgtgg agagggacc ctaagactcc tcggcctggc | 1560 |
| tcctacccac cgcccttgcc gaaccaggag ctgctcacta cctcctcagg gatggccgtt | 1620 |
| ggccacgtct tccttctgcc tgagcttccc ccccaccaca ggccctttcc tcaggcaagg | 1680 |
| tctggcctca ggtgggccgc aggcgggaaa agcagcccct tggccagaagt caagcccagc | 1740 |
| cacgtggagc ctagagtgag ggcctgaggt ctggctgctt gcccccatgc tggcgccaac | 1800 |
| aacttctcca tcctttctgc ctctcaacat cacttgaatc ctagggcctg ggttttcatg | 1860 |
| tttttgaaac agaaccataa agcatatgtg ttggcttgtt gtaaaa | 1906 |

<210> SEQ ID NO 413
<211> LENGTH: 2926
<212> TYPE: DNA
<213> ORGANISM: Homo sapiens

<400> SEQUENCE: 413

| | |
|---|---:|
| agaagaaaac agttccacgt tgcttgaaat tgaaaatcaa gataaaaatg ttcacaatta | 60 |
| agctccttct ttttattgtt cctctagtta tttcctccag aattgatcaa gacaattcat | 120 |
| catttgattc tctatctcca gagccaaaat caagatttgc tatgttagac gatgtaaaaa | 180 |
| ttttagccaa tggcctcctt cagttgggac atggtcttaa agactttgtc cataagacga | 240 |
| agggccaaat taatgacata tttcaaaaac tcaacatatt tgatcagtct ttttatgatc | 300 |
| tatcgctgca aaccagtgaa atcaaagaag aagaaaagga actgagaaga actacatata | 360 |
| aactacaagt caaaaatgaa gaggtaaaga atatgtcact tgaactcaac tcaaaacttg | 420 |
| aaagcctcct agaagaaaaa attctacttc aacaaaaagt gaaatattta gaagagcaac | 480 |
| taactaactt aattcaaaat caacctgaaa ctccagaaca cccagaagta acttcactta | 540 |
| aaacttttgt agaaaaacaa gataatagca tcaaagacct tctccagacc gtggaagacc | 600 |
| aatataaaca attaaaccaa cagcatagtc aaataaaaga aatagaaaat cagctcagaa | 660 |
| ggactagtat tcaagaaccc acagaaattt ctctatcttc caagccaaga gcaccaagaa | 720 |
| ctactccctt tcttcagttg aatgaaataa gaaatgtaaa acatgatggc attcctgctg | 780 |
| aatgtaccac catttataac agaggtgaac atacaagtgg catgtatgcc atcagaccca | 840 |
| gcaactctca agttttttcat gtctactgtg atgttatatc aggtagtcca tggacattaa | 900 |
| ttcaacatcg aatagatgga tcacaaaact tcaatgaaac gtgggagaac tacaaatatg | 960 |
| gttttgggag gcttgatgga gaattttggt tgggcctaga aagatatac tccatagtga | 1020 |
| agcaatctaa ttatgtttta cgaattgagt tggaagactg gaaagacaac aaacattata | 1080 |
| ttgaatattc ttttttacttg ggaaatcacg aaaccaacta tacgctacat ctagttgcga | 1140 |
| ttactggcaa tgtccccaat gcaatcccgg aaaacaaaga tttggtgttt tctacttggg | 1200 |
| atcacaaagc aaaaggacac ttcaactgtc cagagggtta ttcaggaggc tggtggtggc | 1260 |
| atgatgagtg tggagaaaac aacctaaatg gtaaatataa caaaccaaga gcaaatctaa | 1320 |
| agccagagag gagaagagga ttatcttgga gtctcaaaa tggaaggtta tactctataa | 1380 |
| aatcaaccaa aatgttgatc catccaacag attcagaaag ctttgaatga actgaggcaa | 1440 |
| atttaaaagg caataattta aacattaacc tcattccaag ttaatgtggt ctaataatct | 1500 |
| ggtattaaat cctaagagaa agcttgagaa atagattttt ttttatctta aagtcactgt | 1560 |

| | |
|---|---|
| ctatttaaga ttaaacatac aatcacataa ccttaaagaa taccgtttac atttctcaat | 1620 |
| caaaattctt ataatactat ttgttttaaa ttttgtgatg tgggaatcaa ttttagatgg | 1680 |
| tcacaatcta gattataatc aataggtgaa cttattaaat aacttttcta aataaaaaat | 1740 |
| ttagagactt ttattttaaa aggcatcata tgagctaata tcacaacttt cccagtttaa | 1800 |
| aaaactagta ctcttgttaa aactctaaac ttgactaaat acagaggact ggtaattgta | 1860 |
| cagttcttaa atgttgtagt attaatttca aaactaaaaa tcgtcagcac agagtatgtg | 1920 |
| taaaaatctg taatacaaat ttttaaactg atgcttcatt ttgctacaaa ataatttgga | 1980 |
| gtaaatgttt gatatgattt atttatgaaa cctaatgaag cagaattaaa tactgtatta | 2040 |
| aaataagttc gctgtcttta aacaaatgga gatgactact aagtcacatt gactttaaca | 2100 |
| tgaggtatca ctataccta tttgttaaaa tatatactgt atacatttta tatattttaa | 2160 |
| cacttaatac tatgaaaaca aataattgta aaggaatctt gtcagattac agtaagaatg | 2220 |
| aacatatttg tggcatcgag ttaaagttta tatttcccct aaatatgctg tgattctaat | 2280 |
| acattcgtgt aggttttcaa gtagaaataa acctcgtaac aagttactga acgtttaaac | 2340 |
| agcctgacaa gcatgtatat atgtttaaaa ttcaataaac aaagacccag tccctaaatt | 2400 |
| atagaaattt aaattattct tgcatgttta tcgacatcac aacagatccc taaatcccta | 2460 |
| aatccctaaa gattagatac aaattttta ccacagtatc acttgtcaga atttattttt | 2520 |
| aaatatgatt ttttaaaact gccagtaaga aattttaaat taaacccatt tgttaaagga | 2580 |
| tatagtgccc aagttatatg gtgacctacc tttgtcaata cttagcatta tgtatttcaa | 2640 |
| attatccaat atacatgtca tatatatttt tatatgtcac atatataaaa gatatgtatg | 2700 |
| atctatgtga atcctaagta aatattttgt tccagaaaag tacaaaataa taaggtaaa | 2760 |
| aataatctat aattttcagg accacagact aagctgtcga aattaacgct gattttttta | 2820 |
| gggccagaat accaaaatgg ctcctctctt cccccaaaat tggacaattt caaatgcaaa | 2880 |
| ataattcatt atttaatata tgagttgctt cctctatttg gtttcc | 2926 |

<210> SEQ ID NO 414
<211> LENGTH: 2336
<212> TYPE: DNA
<213> ORGANISM: Homo sapiens

<400> SEQUENCE: 414

| | |
|---|---|
| tgccccgttg tgaggtgata aagtgttgcg ctccgggacg ccagcgccgc ggctgccgcc | 60 |
| tctgctgggg tctaggctgt ttctctcgcg ccaccactgg ccgccggccg cagctccagg | 120 |
| tgtcctagcc gcccagcctc gacgccgtcc cgggacccct gtgctctgcg cgaagccctg | 180 |
| gccccggggg ccggggcatg gccaggggc gcggggtgaa gcggcttccc gcggggccgt | 240 |
| gactgggcgg gcttcagcca tgaagaccct catagccgcc tactccgggg tcctgcgcgg | 300 |
| cgagcgtcag gccgaggctg accggagcca gcgctctcac ggaggacctg cgctgtcgcg | 360 |
| cgagggtct gggagatggg gagtggcctg cagtgccatc ctcatgtaca tattctgcac | 420 |
| tgattgctgg ctcatcgctg tgctctactt cacttggctg gtgtttgact ggaacacacc | 480 |
| caagaaaggt ggcaggaggt cacagtgggt ccgaaactgg gctgtgtggc gctactttcg | 540 |
| agactacttt cccatccagc tggtgaagac acacaacctg ctgaccacca ggaactatat | 600 |
| ctttggatac caccccccatg gtatcatggg cctgggtgcc ttctgcaact tcagcacaga | 660 |
| ggccacagaa gtgagcaaga agttcccagg catacgggcct tacctggcta cactggcagg | 720 |
| caacttccga atgcctgtgt tgagggagta cctgatgtct ggaggtatct gccctgtcag | 780 |

```
ccgggacacc atagactatt tgctttcaaa gaatgggagt ggcaatgcta tcatcatcgt      840 ggtcggggt  gcggctgagt ctctgagctc catgcctggc aagaatgcag tcaccctgcg      900
gaaccgcaag ggctttgtga aactggccct gcgtcatgga gctgacctgg ttcccatcta      960
ctcctttgga gagaatgaag tgtacaagca ggtgatcttc gaggagggct cctggggccg     1020
atgggtccag aagaagttcc agaaatacat tggtttcgcc ccatgcatct tccatggtcg     1080
aggcctcttc tcctccgaca cctgggggct ggtgccctac tccaagccca tcaccactgt     1140
tgtgggagag cccatcacca tccccaagct ggagcaccca acccagcaag acatcgacct     1200
gtaccacacc atgtacatgg aggccctggt gaagctcttc gacaagcaca agaccaagtt     1260
cggcctcccg gagactgagg tcctggaggt gaactgagcc agccttcggg gccaattccc     1320
tggaggaacc agctgcaaat cacttttttg ctctgtaaat ttggaagtgt catgggtgtc     1380
tgtgggttat ttaaaagaaa ttataacaat tttgctaaac cattacaatg ttaggtcttt     1440
tttaagaagg aaaaagtcag tatttcaagt tctttcactt ccagcttgcc ctgttctagg     1500
tggtggctaa atctgggcct aatctgggtg gctcagctaa cctctcttct tcccttcctg     1560
aagtgacaaa ggaaactcag tcttcttggg gaagaaggat tgccattagt gacttggacc     1620
agttagatga ttcactttt  gcccctaggg atgagaggcg aaagccactt ctcatacaag     1680
cccctttatt gccactaccc cacgctcgtc tagtcctgaa actgcaggac cagtttctct     1740
gccaagggga ggagttggag agcacagttg ccccgttgtg tgagggcagt agtaggcatc     1800
tggaatgctc cagtttgatc tcccttctgc caccctacc  tcaccctag  tcactcatat     1860 cggagcctgg actggcctcc aggatgagga tgggggtggc aatgacaccc tgcagggaa      1920 aggactgccc cccatgcacc attgcaggga ggatgccgcc accatgagct aggtggagta     1980
actggttttt cttgggtggc tgatgacatg gatgcagcac agactcagcc ttggcctgga     2040
gcacatgctt actggtggcc tcagtttacc ttccccagat cctagattct ggatgtgagg     2100
aagagatccc tcttcagaag gggcctggcc ttctgagcag cagattagtt ccaaagcagg     2160
tggcccccga acccaagcct cactttctgt tgccttcctg agggggttgg gccggggagg     2220
aaacccaacc ctctcctgtg tgttctgtta tctcttgatg agatcattgc accatgtcag     2280
acttttgtat atgccttgaa aataaatgaa agtgagaatc tctaaaaaa  aaaaaa        2336
```

<210> SEQ ID NO 415
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 415
ccgugugcac uucgcuuca         19

<210> SEQ ID NO 416
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 416
ccgugugcac uucgcuuca         19

```
<210> SEQ ID NO 417
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
cugcuaugcc ucaucuucu                                                      19

<210> SEQ ID NO 418
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
gugguggacu ucucucaau                                                      19

<210> SEQ ID NO 419
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
gugguggacu ucucucaau                                                      19

<210> SEQ ID NO 420
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
ccgugugcac uucgcuuca                                                      19

<210> SEQ ID NO 421
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
ccgugugcaa uucgcuuca                                                      19

<210> SEQ ID NO 422
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
ccgugugcac uucgcuuca                                                      19
```

```
<210> SEQ ID NO 423
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
ccgugugcac uucgcuuca                                                19

<210> SEQ ID NO 424
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
ccgugugcac uucgcuuca                                                19

<210> SEQ ID NO 425
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
cugcuaugcc ucaucuucu                                                19

<210> SEQ ID NO 426
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
cugcuaugcc ucaucuucu                                                19

<210> SEQ ID NO 427
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
gcgggguuuu ucuuguuga                                                19

<210> SEQ ID NO 428
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
gcgggguuuu ucuuguuga                                                19

<210> SEQ ID NO 429
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
gcgggguuuu ucuuguuga                                                     19

<210> SEQ ID NO 430
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
gcugcuaugc cucaucuucu u                                                  21

<210> SEQ ID NO 431
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
gcugcuaugc cucaucuucu u                                                  21

<210> SEQ ID NO 432
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
gcugcuaugc cucaucuucu u                                                  21

<210> SEQ ID NO 433
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
gugguggacu ucucucaau                                                     19

<210> SEQ ID NO 434
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
gugguggaau ucucucaau                                                     19

<210> SEQ ID NO 435
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
gugguggacu ucucucaau                                                    19

<210> SEQ ID NO 436
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
gugguggacu ucucucuau                                                    19

<210> SEQ ID NO 437
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
gugguggacu ucucucaau                                                    19

<210> SEQ ID NO 438
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
gugguggacu ucucucaau                                                    19

<210> SEQ ID NO 439
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
ucguggugga cuucucucaa u                                                 21

<210> SEQ ID NO 440
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
ugccgaucca uacugcgga                                                    19

<210> SEQ ID NO 441
<211> LENGTH: 19
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 441
ugugcacuuc gcuucaccu                                              19

<210> SEQ ID NO 442
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 442
ugugcacuuc gcuucaccu                                              19

<210> SEQ ID NO 443
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 443
ccgugugcac uucgcuuca                                              19

<210> SEQ ID NO 444
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 444
gugguggacu ucucucaau                                              19

<210> SEQ ID NO 445
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 445
ugaagcgaag ugcacacggu u                                           21

<210> SEQ ID NO 446
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 446
ugaagcgaag ugcacacggu u                                           21

<210> SEQ ID NO 447
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 447
ugaagcgaag ugcacacggu u                                              21

<210> SEQ ID NO 448
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
ugaagcgaag ugcacacggu c                                              21

<210> SEQ ID NO 449
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
ugaagcgaag ugcacacggu c                                              21

<210> SEQ ID NO 450
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
ugaagcgaag ugcacacggu c                                              21

<210> SEQ ID NO 451
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
ugaagcgaag ugcacacggu c                                              21

<210> SEQ ID NO 452
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
agaagaugag gcauagcagu u                                              21

<210> SEQ ID NO 453
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 453
auugagagaa guccaccacg a                                              21

<210> SEQ ID NO 454
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
auugagagaa guccaccacg a                                              21

<210> SEQ ID NO 455
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
auugagagaa guccaccacg a                                              21

<210> SEQ ID NO 456
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
auugagagaa guccaccacg a                                              21

<210> SEQ ID NO 457
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
ugaagcgaag ugcacacggu c                                              21

<210> SEQ ID NO 458
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
ugaagcgaag ugcacacggu c                                              21

<210> SEQ ID NO 459
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 459
ugaagcgaag ugcacacggu u                                              21

<210> SEQ ID NO 460
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
ugaagcgaag ugcacacggu u                                              21

<210> SEQ ID NO 461
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
ugaagcgaag ugcacacggu u                                              21

<210> SEQ ID NO 462
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
ugaagcgaag ugcacacggu c                                              21

<210> SEQ ID NO 463
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 463
ugaagcgaag ugcacacggt t                                              21

<210> SEQ ID NO 464
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
ugaagcgaag ugcacacggu c                                              21

<210> SEQ ID NO 465
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 465
bgaagcgaag ugcacacggu c                                              21

<210> SEQ ID NO 466
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
ugaagcgaag ugcacacggu c                                              21

<210> SEQ ID NO 467
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 467
ugaagcgaag ugcacacggu c                                              21

<210> SEQ ID NO 468
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 468
ugaagcgaag ugcacacggu c                                              21

<210> SEQ ID NO 469
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
ugaagcgaag ugcacacggu c                                              21

<210> SEQ ID NO 470
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
ugaagcgaag ugcacacggu c                                              21

<210> SEQ ID NO 471
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 471
ugaagcgaag ugcacacggu c                                             21

<210> SEQ ID NO 472
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
ugaagcgaag ugcacacggu c                                             21

<210> SEQ ID NO 473
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
ugaagcgaag ugcacacggu c                                             21

<210> SEQ ID NO 474
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
ugaagcgaag ugcacacggu c                                             21

<210> SEQ ID NO 475
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
ugaagcgaag ugcacacggu c                                             21

<210> SEQ ID NO 476
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
ugaagcgaag ugcacacggu c                                             21

<210> SEQ ID NO 477
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 477
ugaagcgaag ugcacacggu c                                              21

<210> SEQ ID NO 478
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
ugaagcgaag ugcacacggu c                                              21

<210> SEQ ID NO 479
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
ugaagcgaag ugcacacggu c                                              21

<210> SEQ ID NO 480
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
ugaagcgaag ugcacacggu c                                              21

<210> SEQ ID NO 481
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
ugaagcgaag ugcacacggu c                                              21

<210> SEQ ID NO 482
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
ugaagcgaag ugcacacggu c                                              21

<210> SEQ ID NO 483
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
ugaagcgaag ugcacacggu c                                              21

<210> SEQ ID NO 484
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
ugaagcgaag ugcacacggu c                                              21

<210> SEQ ID NO 485
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
ugaagcgaag ugcacacggu c                                              21

<210> SEQ ID NO 486
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
agaagaugag gcauagcagc a                                              21

<210> SEQ ID NO 487
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
agaagaugag gcauagcagc a                                              21

<210> SEQ ID NO 488
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
agaagaugag gcauagcagc a                                              21

<210> SEQ ID NO 489
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 489
agaagaugag gcauagcagc a                                              21

<210> SEQ ID NO 490
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
ucaacaagaa aaccccgcc u                                               21

<210> SEQ ID NO 491
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 491
ucaacaagaa aaccccgcc u                                               21

<210> SEQ ID NO 492
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492
ucaacaagaa aaccccgcc u                                               21

<210> SEQ ID NO 493
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
ucaacaagaa aaccccgcc u                                               21

<210> SEQ ID NO 494
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
ucaacaagaa aaccccgcc u                                               21

<210> SEQ ID NO 495
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
```

```
aagaagauga ggcauagcag cag                                              23

<210> SEQ ID NO 496
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
aagaagauga ggcauagcag cag                                              23

<210> SEQ ID NO 497
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 497
aagaagauga ggcauagcag cag                                              23

<210> SEQ ID NO 498
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
aagaagauga ggcauagcag cag                                              23

<210> SEQ ID NO 499

<400> SEQUENCE: 499

000

<210> SEQ ID NO 500
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
aagaagauga ggcauagcag cag                                              23

<210> SEQ ID NO 501
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
auugagagaa guccaccacg a                                                21

<210> SEQ ID NO 502
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 502
auugagagaa guccaccacg a                                              21

<210> SEQ ID NO 503
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 503
auugagagaa guccaccacg a                                              21

<210> SEQ ID NO 504
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
auugagagaa guccaccacg a                                              21

<210> SEQ ID NO 505
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other

<400> SEQUENCE: 505
nuugagagaa guccaccacg a                                              21

<210> SEQ ID NO 506
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
uuugagagaa guccaccacg a                                              21

<210> SEQ ID NO 507
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
uuugagagaa guccaccacg a                                              21
```

```
<210> SEQ ID NO 508
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508
uuugagagaa guccaccacg a                                                   21

<210> SEQ ID NO 509
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509
uuugagagaa guccaccacg a                                                   21

<210> SEQ ID NO 510
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
auugagagaa guccaccacg a                                                   21

<210> SEQ ID NO 511
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
auugagagaa guccaccacg a                                                   21

<210> SEQ ID NO 512
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
auugagagaa guccaccacg a                                                   21

<210> SEQ ID NO 513
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
auugagagaa guccaccacg a                                                   21

<210> SEQ ID NO 514
```

```
<210> SEQ ID NO 514
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
auugagagaa guccaccacg a                                              21

<210> SEQ ID NO 515
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
auugagagaa guccaccacg a                                              21

<210> SEQ ID NO 516
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
auugagagaa guccaccacg a                                              21

<210> SEQ ID NO 517
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
auugagagaa guccaccacg a                                              21

<210> SEQ ID NO 518
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
auugagagaa guccaccacg a                                              21

<210> SEQ ID NO 519
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
auugagagaa guccaccacg a                                              21

<210> SEQ ID NO 520
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
auugagagaa guccaccacg a                                              21

<210> SEQ ID NO 521
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 521
auugagagaa guccaccacg a                                              21

<210> SEQ ID NO 522
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
auugagagaa guccaccacg a                                              21

<210> SEQ ID NO 523
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
auugagagaa guccaccacg agu                                            23

<210> SEQ ID NO 524
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
uccgcaguau ggaucggcag a                                              21

<210> SEQ ID NO 525
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
aggugaagcg aagugcacac g                                              21

<210> SEQ ID NO 526
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 526
aggugaagcg aagugcacac g                                          21

<210> SEQ ID NO 527
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
aggugaagcg aagugcacac g                                          21

<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 528
aggugaagcg aagugcacat t                                          21

<210> SEQ ID NO 529
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
aggugaagcg aagugcacac g                                          21

<210> SEQ ID NO 530
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
aggugaagcg aagugcacac g                                          21

<210> SEQ ID NO 531
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
auugagagaa guccaccacg agu                                        23

<210> SEQ ID NO 532
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 532
ugaagcgaag ugcacacggt t                                              21

<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 533
aggugaagcg aagugcacat t                                              21

<210> SEQ ID NO 534
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
agataaaacg ccgcagac                                                  18

<210> SEQ ID NO 535
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
agataaaacg ccgcagac                                                  18

<210> SEQ ID NO 536
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536
ugaagcgaag ugcacacggu c                                              21

<210> SEQ ID NO 537
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (2)..(2)
<223> OTHER INFORMATION: a, c, u, g, unknown or other

<400> SEQUENCE: 537
anugagagaa guccaccacg a                                              21

<210> SEQ ID NO 538
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: a, c, u, g, unknown or other

<400> SEQUENCE: 538
auugagagaa gucnaccacg a                                              21

<210> SEQ ID NO 539
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: a, c, u, g, unknown or other

<400> SEQUENCE: 539
auugagagaa gucnaccacg a                                              21

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545
```

```
<400> SEQUENCE: 545
000

<210> SEQ ID NO 546
<400> SEQUENCE: 546
000

<210> SEQ ID NO 547
<400> SEQUENCE: 547
000

<210> SEQ ID NO 548
<400> SEQUENCE: 548
000

<210> SEQ ID NO 549
<400> SEQUENCE: 549
000

<210> SEQ ID NO 550
<400> SEQUENCE: 550
000

<210> SEQ ID NO 551
<400> SEQUENCE: 551
000

<210> SEQ ID NO 552
<400> SEQUENCE: 552
000

<210> SEQ ID NO 553
<400> SEQUENCE: 553
000

<210> SEQ ID NO 554
<400> SEQUENCE: 554
000

<210> SEQ ID NO 555
<400> SEQUENCE: 555
000

<210> SEQ ID NO 556
<400> SEQUENCE: 556
```

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591
<400> SEQUENCE: 591

000

<210> SEQ ID NO 592
<400> SEQUENCE: 592

000

<210> SEQ ID NO 593
<400> SEQUENCE: 593

000

<210> SEQ ID NO 594
<400> SEQUENCE: 594

000

<210> SEQ ID NO 595
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 595
aagaagauga ggcauagcag cag                                            23

<210> SEQ ID NO 596
<211> LENGTH: 3215
<212> TYPE: DNA
<213> ORGANISM: Hepatitis B virus

<400> SEQUENCE: 596
ctccaccact ttccaccaaa ctcttcaaga tcccagagtc agggccctgt actttcctgc     60
tggtggctca agttccggaa cagtaaaccc tgctccgact actgcctctc ccatatcgtc    120
aatcttctcg aggactgggg accctgtacc gaatatggag agcaccacat caggattcct    180
aggacccctg ctcgtgttac aggcggggtt tttcttgttg acaagaatcc tcacaatacc    240
acagagtcta gactcgtggt ggacttctct caatttttcta gggggagcac ccacgtgtcc    300
tggccaaaat tgcagtccc caacctccaa tcactcacca acctcttgtc ctccaatttg    360
tcctggttat cgctggatgt gtctgcggcg ttttatcatc ttcctcttca tcctgctgct    420
atgcctcatc ttcttgttgg ttcttctgga ctaccaaggt atgttgcccg tttgtcctct    480
acttccagga acatcaacta ccagcaccgg accatgcaaa acctgcacaa ctactgctca    540
agggacctct atgtttccct catgttgctg tacaaaacct acggacggaa actgcacctg    600
tattcccatc ccatcatctt gggctttcgc aaaataccta tgggagtggg cctcagtccg    660
tttctcttgg ctcagtttac tagtgccatt tgttcagtgg ttcgtagggc tttcccccac    720
tgtctggctt tcagttatat ggatgatgtg gttttggggg ccaagtctgt acaacatctt    780
gagtcccttt ataccgctgt taccaatttt ctttttatctt tgggtataca tttaaaccct    840

```
cacaaaacaa aaagatgggg atattccctt aacttcatgg gatatgtaat tgggagttgg      900
ggcactttgc ctcaggaaca tattgtacaa aaaatcaagc aatgttttag gaaacttcct      960
gtaaacaggc ctattgattg gaaagtatgt caacraattg tgggtctttt ggggtttgcc     1020
gccccttcca cgcaatgtgg atatcctgct ttaatgcctt tatatgcatg tatacaagct     1080
aagcaggctt ttactttctc gccaacttac aaggcctttc tgtgtaaaca atatctgaac     1140
cttaccccg ttgctcggca acggtcaggt ctttgccaag tgtttgctga cgcaaccccc      1200
actggttggg gcttggccat aggccatcag cgcatgcgtg gaacctttgt ggctcctctg     1260
ccgatccata ctgcggaact cctagcagct tgttttgctc gcagccggtc tggagcaaaa     1320
cttatcggca ccgacaactc tgttgtcctc tctcggaaat acacctcctt tccatggctg     1380
ctaggatgtg ctgccaactg gatcctgcgc gggacgtcct ttgtctacgt cccgtcggcg     1440
ctgaatcccg cggacgaccc atctcggggc cgtttgggac tctaccgtcc ccttctgcgt     1500
ctgccgttcc gcccgaccac ggggcgcacc tctctttacg cggtctcccc gtctgtgcct     1560
tctcatctgc cggaccgtgt gcacttcgct tcacctctgc acgtcgcatg gagaccaccg     1620
tgaacgccca cgggaacctg cccaaggtct tgcataagag gactcttgga ctttcagcaa     1680
tgtcaacgac cgaccttgag gcatacttca aagactgtgt gtttactgag tgggaggagt     1740
tgggggagga ggttaggtta aaggtctttg tactaggagg ctgtaggcat aaattggtgt     1800
gttcaccagc accatgcaac ttttttcacct ctgcctaatc atctcatgtt catgtcctac     1860
tgttcaagcc tccaagctgt gccttgggtg gctttgggc atggacattg acccgtataa      1920
agaatttgga gcttctgtgg agttactctc ttttttgcct tctgacttct ttccttctat     1980
tcgagatctc ctcgacaccg cctctgctct gtatcgggag ccttagagt ctccggaaca      2040
ttgttcacct caccatacgg cactcaggca agcaattctg tgttggggtg agttaatgaa     2100
tctagccacc tgggtgggaa gtaaatttgga agatccagca tccagggaat tagtagtcag    2160
ctatgtcaac gttaatatgg gcctaaaaat cagacaacta ttgtggtttc acatttcctg     2220
tcttactttt gggagagaaa ctgttcttga atatttggtg tcttttggag tgtggattcg     2280
cactcctcct gcatatagac cacaaaatgc ccctatctta tcaacacttc cggaaactac     2340
tgttgttaga cgaagaggca ggtccctag aagaagaact ccctcgcctc gcagacgaag      2400
gtctcaatcg ccgcgtcgca gaagatctca atctcggaa tctcaatgtt agtattcctt      2460
ggacacataa ggtgggaaac tttacggggc tttattcttc tacggtacct tgctttaatc     2520
ctaaatggca aactccttct tttcctgaca ttcatttgca ggaggacatt gttgatagat     2580
gtaagcaatt tgtggggccc cttacagtaa atgaaaacag gagacttaaa ttaattatgc     2640
ctgctaggtt ttatcccaat gttactaaat atttgccctt agataaaggg atcaaaccgt     2700
attatccaga gtatgtagtt aatcattact ccagacgcg acattattta cacactcttt      2760
ggaaggcggg gatcttatat aaaagagagt ccacacgtag cgcctcattt tgcgggtcac     2820
catattcttg ggaacaagat ctacagcatg ggaggttggt cttccaaacc tcgaaaaggc     2880
atggggacaa atctttctgt ccccaatccc ctgggattct tccccgatca tcagttggac     2940
cctgcattca aagccaactc agaaaatcca gattgggacc tcaacccaca caaggacaac     3000
tggccggacg ccaacaaggt gggagtggga gcattcgggc cagggttcac ccctcctcat     3060
ggggactgt tggggtggag ccctcaggct caggcatat tcacaacagt gccagcagct       3120
cctcctcctg cctccaccaa tcggcagtca ggaaggcagc ctactcccctt ctctccacct    3180
```

```
ctaagagaca ctcatcctca ggccatgcag tggaa                              3215
```

<210> SEQ ID NO 597
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 597

```
ccgugugccc uucgcuuca                                                19
```

<210> SEQ ID NO 598
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598

```
gugguggacg ucucucaau                                                19
```

<210> SEQ ID NO 599
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: a, c, u, g, unknown or other

<400> SEQUENCE: 599

```
auugagagaa guccancacg a                                             21
```

<210> SEQ ID NO 600
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 600

```
ccgugugcac uucgcuuca                                                19
```

<210> SEQ ID NO 601
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601

```
gugguggacu ucucucaau                                                19
```

<210> SEQ ID NO 602
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 602
gcugcuaugc cucaucuucu u                                              21

<210> SEQ ID NO 603
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603
ugugcacuuc gcuucaccu                                                 19

<210> SEQ ID NO 604
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604
ccgugugcac uucgcuuca                                                 19

<210> SEQ ID NO 605
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 605
ugaagcgaag ugcacacggu c                                              21

<210> SEQ ID NO 606
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
gcugcuaugc cucaucuucu u                                              21

<210> SEQ ID NO 607
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 607
gugguggacu ucucucaau                                                 19

<210> SEQ ID NO 608
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 608
auugagagaa guccaccacg a                                                    21

<210> SEQ ID NO 609
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 609
ugugcacuuc gcuucaccu                                                       19

<210> SEQ ID NO 610
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 610
aggugaagcg aagugcacac g                                                    21

<210> SEQ ID NO 611
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 611 gcggguuuu ucuuguuga                                                        19

<210> SEQ ID NO 612
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 612 gcggguuuu ucuuguuga                                                        19

<210> SEQ ID NO 613
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
ucguggugga cuucucucaa u                                                    21

<210> SEQ ID NO 614
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 614
```

```
cugcuaugcc ucaucuucu                                              19

<210> SEQ ID NO 615
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 615
ugugcacuuc gcuucaccu                                              19

<210> SEQ ID NO 616
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 616
ccgugugcac uucgcuuca                                              19

<210> SEQ ID NO 617
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 617
gugguggacu ucucucaau                                              19

<210> SEQ ID NO 618
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
ucguggugga cuucucucaa u                                           21
```